(12) United States Patent
Jafar-nejad

(10) Patent No.: US 11,078,486 B2
(45) Date of Patent: Aug. 3, 2021

(54) COMPOUNDS AND METHODS FOR REDUCING ATXN2 EXPRESSION

(71) Applicant: Ionis Pharmaceuticals, Inc., Carlsbad, CA (US)

(72) Inventor: Paymaan Jafar-nejad, Carlsbad, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 16/522,133

(22) Filed: Jul. 25, 2019

(65) Prior Publication Data

US 2020/0056179 A1 Feb. 20, 2020

Related U.S. Application Data

(60) Provisional application No. 62/703,240, filed on Jul. 25, 2018.

(51) Int. Cl.
*C12N 15/113* (2010.01)
*A61K 47/02* (2006.01)
*A61K 47/46* (2006.01)

(52) U.S. Cl.
CPC ............ *C12N 15/113* (2013.01); *A61K 47/02* (2013.01); *A61K 47/46* (2013.01); *C12N 2310/14* (2013.01); *C12N 2310/315* (2013.01); *C12N 2310/322* (2013.01); *C12N 2310/341* (2013.01); *C12N 2310/346* (2013.01); *C12N 2310/351* (2013.01)

(58) Field of Classification Search
CPC .............. C12N 15/113; C12N 2310/14; C12N 2310/315; C12N 2310/322; C12N 2310/341; C12N 2310/346; C12N 2310/351
See application file for complete search history.

(56) References Cited

U.S. PATENT DOCUMENTS

| | | |
|---|---|---|
| 3,687,808 A | 8/1972 | Merigan et al. |
| 4,415,732 A | 11/1983 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,725,677 A | 2/1988 | Koster et al. |
| 4,845,205 A | 7/1989 | Huynh Dinh et al. |
| 4,973,679 A | 11/1990 | Caruthers et al. |
| 4,981,957 A | 1/1991 | Lebleu et al. |
| 5,013,830 A | 5/1991 | Ohtsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,036 E | 8/1992 | McGeehan |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,220,007 A | 6/1993 | Pederson et al. |
| 5,223,618 A | 6/1993 | Cook et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |
| 5,185,444 A | 12/1993 | Summerton et al. |
| 5,276,019 A | 1/1994 | Cohen et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,378,825 A | 1/1995 | Cook et al. |

(Continued)

FOREIGN PATENT DOCUMENTS

| | | |
|---|---|---|
| EP | 0878543 A1 | 11/1998 |
| EP | 1752536 A1 | 2/2007 |

(Continued)

OTHER PUBLICATIONS

Albaek et al., "Analogues of a Locked Nucleic Acid with Three-Carbon 2',4'-Linkages: Aynthesis by Ring-Closing Metathesis and Influence on Nucleic Acid Duplex Stability and Structure" J. Org. Chem. (2006) 71: 7731-7740.

Ataxin-2 Wikipedia. Downloaded on Jul. 16, 2018 from http://en.wikipedia.org/wiki/Ataxin-2.

Becker et al., "Therapeutic reduction of ataxin-2 extends lifespan and reduces pathology in TDP-43 mice." Nature (2017) online Apr. 12, 2017, pp. 1-17.

Bezprozvanny et al., "Therapeutic prospects for spinocerebellar ataxia type 2 and 3." Drugs Future (2009) 34(12):1-17.

(Continued)

*Primary Examiner* — Brian Whiteman
(74) *Attorney, Agent, or Firm* — McNeill Baur PLLC

(57) ABSTRACT

Provided are compounds, methods, and pharmaceutical compositions for reducing the amount or activity of ATXN2 RNA in a cell or animal, and in certain instances reducing the amount of Ataxin-2 protein in a cell or animal. Such compounds, methods, and pharmaceutical compositions are useful to ameliorate at least one symptom or hallmark of a neurodegenerative disease. Such symptoms and hallmarks include ataxia, neuropathy, and aggregate formation. Such neurodegenerative diseases include spinocerebellar ataxia type 2 (SCA2), amyotrophic lateral sclerosis (ALS), and parkinsonism.

36 Claims, No Drawings
Specification includes a Sequence Listing.

(56) References Cited

U.S. PATENT DOCUMENTS

| | | |
|---|---|---|
| 5,386,023 A | 1/1995 | Sanghvi et al. |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Sumerton et al. |
| 5,405,939 A | 4/1995 | Suhadolnik et al. |
| 5,432,272 A | 7/1995 | Benner |
| 5,434,257 A | 7/1995 | Matteucci |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmelner et al. |
| 5,457,191 A | 10/1995 | Cook et al. |
| 5,459,255 A | 10/1995 | Cook et al. |
| 5,466,677 A | 11/1995 | Baxter et al. |
| 5,466,786 A | 11/1995 | Burh et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,508,270 A | 4/1996 | Baxter et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Mistura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,587,470 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bishofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci |
| 5,652,355 A | 7/1997 | Metelev et al. |
| 5,652,356 A | 7/1997 | Agrawal |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,698,685 A | 12/1997 | Summerton et al. |
| 5,700,920 A | 12/1997 | Altmann et al. |
| 5,700,922 A | 12/1997 | Cook |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,847 A | 8/1998 | Burh et al. |
| 5,801,154 A | 9/1998 | Baracchini et al. |
| 5,808,027 A | 9/1998 | Cook et al. |
| 5,811,534 A | 9/1998 | Cook et al. |
| 5,830,653 A | 11/1998 | Froehler et al. |
| 5,859,221 A | 1/1999 | Cook et al. |
| 5,948,903 A | 9/1999 | Cook et al. |
| 5,994,517 A | 11/1999 | Ts'O |
| 6,005,087 A | 12/1999 | Cook et al. |
| 6,005,096 A | 12/1999 | Matteucci et al. |
| 6,166,199 A | 12/2000 | Cook et al. |
| 6,268,490 B1 | 7/2001 | Imanishi et al. |
| 6,300,319 B1 | 10/2001 | Manoharan |
| 6,426,220 B1 | 7/2002 | Bennett et al. |
| 6,525,191 B1 | 2/2003 | Ramasamy |
| 6,531,584 B1 | 3/2003 | Cook et al. |
| 6,582,908 B2 | 6/2003 | Fodor et al. |
| 6,600,032 B1 | 7/2003 | Manoharan et al. |
| 6,660,720 B2 | 12/2003 | Manoharan |
| 6,670,461 B1 | 12/2003 | Wengel et al. |
| 6,673,535 B1 | 1/2004 | Pulst |
| 6,770,748 B2 | 8/2004 | Imanishi et al. |
| 6,794,499 B2 | 9/2004 | Wengel et al. |
| 6,844,431 B1 | 1/2005 | Pulst |
| 7,015,315 B1 | 3/2006 | Cook et al. |
| 7,034,133 B2 | 4/2006 | Wengel et al. |
| 7,053,207 B2 | 5/2006 | Wengel et al. |
| 7,101,993 B1 | 9/2006 | Cook et al. |
| 7,262,177 B2 | 8/2007 | Ts'o et al. |
| 7,374,927 B2 | 5/2008 | Palma et al. |
| 7,399,845 B2 | 7/2008 | Seth et al. |
| 7,427,672 B2 | 9/2008 | Imanishi et al. |
| 7,491,805 B2 | 2/2009 | Vargeese et al. |
| 7,547,684 B2 | 6/2009 | Seth et al. |
| 7,569,686 B1 | 8/2009 | Bhat et al. |
| 7,572,582 B2 | 8/2009 | Wengel et al. |
| 7,666,854 B2 | 2/2010 | Seth et al. |
| 7,696,345 B2 | 4/2010 | Allerson et al. |
| 7,723,509 B2 | 5/2010 | Manoharan et al. |
| 7,741,457 B2 | 6/2010 | Swayze et al. |
| 7,750,131 B2 | 7/2010 | Seth et al. |
| 7,875,733 B2 | 1/2011 | Bhat et al. |
| 7,888,497 B2 | 2/2011 | Bentwich et al. |
| 7,939,677 B2 | 5/2011 | Bhat et al. |
| 8,022,193 B2 | 9/2011 | Swayze et al. |
| 8,030,467 B2 | 10/2011 | Seth et al. |
| 8,034,909 B2 | 10/2011 | Wengel et al. |
| 8,080,644 B2 | 12/2011 | Wengel et al. |
| 8,088,746 B2 | 1/2012 | Seth et al. |
| 8,088,904 B2 | 1/2012 | Swayze et al. |
| 8,106,022 B2 | 1/2012 | Manoharan et al. |
| 8,124,745 B2 | 2/2012 | Allerson et al. |
| 8,153,365 B2 | 4/2012 | Wengel et al. |
| 8,268,980 B2 | 9/2012 | Seth et al. |
| 8,278,283 B2 | 10/2012 | Seth et al. |
| 8,278,425 B2 | 10/2012 | Prakash et al. |
| 8,278,426 B2 | 10/2012 | Seth et al. |
| 8,501,805 B2 | 4/2013 | Seth et al. |
| 8,440,803 B2 | 5/2013 | Swayze et al. |
| 8,530,640 B2 | 9/2013 | Seth et al. |
| 8,546,556 B2 | 10/2013 | Seth et al. |
| RE44,779 E | 2/2014 | Imanishi et al. |
| 8,728,736 B2 | 5/2014 | Leamon et al. |
| 8,796,437 B2 | 8/2014 | Swayze et al. |
| 8,828,956 B2 | 9/2014 | Manoharan et al. |
| 9,005,906 B2 | 4/2015 | Swayze et al. |
| 9,012,421 B2 | 4/2015 | Migawa et al. |
| 9,127,276 B2 | 8/2015 | Prakash et al. |
| 9,290,760 B2 | 3/2016 | Rajeev et al. |
| 10,006,027 B2 | 6/2018 | Bennett et al. |
| 10,308,934 B2 | 6/2019 | Freier |
| 10,533,178 B2 | 1/2020 | Bennett et al. |
| 2001/0053519 A1 | 12/2001 | Fodor et al. |
| 2003/0158403 A1 | 8/2003 | Manoharan et al. |
| 2003/0175906 A1 | 9/2003 | Manoharan et al. |
| 2003/0228597 A1 | 12/2003 | Cowsert et al. |

(56) References Cited

U.S. PATENT DOCUMENTS

| | | |
|---|---|---|
| 2004/0171570 A1 | 9/2004 | Allerson et al. |
| 2004/0220132 A1 | 11/2004 | Kaemmerer |
| 2005/0026164 A1 | 2/2005 | Zhou |
| 2005/0042646 A1 | 2/2005 | Davidson et al. |
| 2005/0100885 A1 | 5/2005 | Crooke et al. |
| 2005/0130923 A1 | 6/2005 | Bhat et al. |
| 2005/0209178 A1 | 9/2005 | Pulst |
| 2005/0244851 A1 | 11/2005 | Blume et al. |
| 2005/0255487 A1 | 11/2005 | Khvorova et al. |
| 2006/0148740 A1 | 7/2006 | Platenburg |
| 2006/0270727 A1 | 11/2006 | Melander et al. |
| 2007/0031844 A1 | 2/2007 | Khvorova et al. |
| 2007/0224624 A1 | 9/2007 | Pulst |
| 2008/0039618 A1 | 2/2008 | Allerson et al. |
| 2008/0113351 A1 | 5/2008 | Naito et al. |
| 2010/0190837 A1 | 7/2010 | Migawa et al. |
| 2010/0197762 A1 | 8/2010 | Swayze et al. |
| 2011/0054005 A1 | 3/2011 | Naito et al. |
| 2011/0142789 A1 | 6/2011 | Gitler et al. |
| 2013/0130378 A1 | 5/2013 | Manoharan et al. |
| 2013/0172399 A1 | 7/2013 | Corey et al. |
| 2013/0203836 A1 | 8/2013 | Rajeev et al. |
| 2013/0225659 A1 | 8/2013 | Bennett et al. |
| 2014/0107330 A1 | 4/2014 | Freier et al. |
| 2014/0303238 A1 | 10/2014 | Linsley et al. |
| 2015/0018540 A1 | 1/2015 | Prakash et al. |
| 2015/0141320 A1 | 5/2015 | Krieg et al. |
| 2015/0184153 A1 | 7/2015 | Freier et al. |
| 2015/0191727 A1 | 7/2015 | Migawa et al. |
| 2015/0259679 A1 | 9/2015 | Bennett et al. |
| 2015/0267195 A1 | 9/2015 | Seth et al. |
| 2015/0275212 A1 | 10/2015 | Albaek et al. |
| 2016/0053254 A1 | 2/2016 | Kimpe et al. |
| 2017/0175113 A1 | 6/2017 | Bennett et al. |
| 2017/0175114 A1 | 6/2017 | Freier et al. |
| 2019/0002887 A1 | 1/2019 | Ionis Pharmaceuticals Inc |
| 2019/0017047 A1 | 1/2019 | Bennett et al. |
| 2020/0056179 A1 | 2/2020 | Freier et al. |
| 2020/0087661 A1 | 3/2020 | Freier |

FOREIGN PATENT DOCUMENTS

| | | |
|---|---|---|
| EP | 2399611 A2 | 12/2011 |
| WO | WO 2017/015555 | 1/1917 |
| WO | WO 2017/117496 | 7/1917 |
| WO | WO 2020/023737 | 1/1920 |
| WO | WO 1997/42314 | 11/1997 |
| WO | WO 1999/014226 | 3/1999 |
| WO | WO 2004/003201 | 1/2004 |
| WO | WO 2004/047872 | 6/2004 |
| WO | WO 2004/070062 | 8/2004 |
| WO | WO 2004/106356 | 12/2004 |
| WO | WO 2005/116204 | 12/2005 |
| WO | WO 2005/116212 | 12/2005 |
| WO | WO 2006/021814 | 3/2006 |
| WO | WO 2006/131925 | 12/2006 |
| WO | WO 2007/106407 | 9/2007 |
| WO | WO 2007/134181 | 11/2007 |
| WO | WO 2008/101157 | 8/2008 |
| WO | WO 2008/109379 | 9/2008 |
| WO | WO 2008/109450 | 9/2008 |
| WO | WO 2008/152636 | 12/2008 |
| WO | WO 2009/046141 | 4/2009 |
| WO | WO 2010/014592 | 2/2010 |
| WO | WO 2011/006121 | 1/2011 |
| WO | 2011073326 A2 | 6/2011 |
| WO | WO 2011/097641 | 8/2011 |
| WO | WO 2011/133876 | 10/2011 |
| WO | WO 2012/012467 | 1/2012 |
| WO | WO 2012/079578 | 6/2012 |
| WO | WO 2012/149438 | 11/2012 |
| WO | WO 2013/081864 | 6/2013 |
| WO | WO 2013/162363 | 10/2013 |
| WO | WO 2013/173645 | 11/2013 |
| WO | WO 2014/179620 | 11/2014 |
| WO | WO 2015/002971 | 1/2015 |
| WO | WO 2015/072438 | 5/2015 |
| WO | WO 2015/143245 | 9/2015 |
| WO | WO 2015/143246 | 9/2015 |

OTHER PUBLICATIONS

Braasch et al., "Novel Antisense and Peptide Nucleic Acid Strategies for Controlling Gene Expression" Biochemistry (2002) 41: 4503-4510.

Branch et al., "A good antisense molecule is hard to find," TIBS (1998) 23:45-50.

Burke et al., "Huntingtin and DRPLA proteins selectively interact with the enzyme GADPH." Nat. Med. (1996) 2(3):347-350.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Ciosk et al., "ATX-2, the C. elegans ortholog of ataxin 2, functions in translational regulation in the germline." Development (2004) 131(19):4831-4841.

Corrado et al., "ATXN-2 CAG repeat expansions are interrupted in ALS patients." Hum. Genet. (2011) 130(4):575-580.

Crooke, ST., et al., "Antisense Drug Technology" Second Edition, CRC Press (2008) Chapters 1-28.

Crooke et al., "Pharmacokinetic Properties of Several Novel Oligonucleotide Analogs in mice" J. Pharmacol. Exp. Ther. (1996) 277: 923-937.

Deleavy et al., "Designing chemically modified oligonucleotides for targeted gene silencing" Chem Biol (2012) 19(8): 937-954.

Duvick et al., "SCA1-like disease in mice expressing wild-type ataxin-1 with a serine to aspartic acid replacement at residue 776." Neuron (2010) 67(6): 929-935.

Egli, et al., "Synthesis, improved antisense activity and structural rationale for the divergent RNA affinities of 3'-fluoro hexitol nucleic acid (FHNA and Ara-FHNA) modified oligonucleotides." J Am Chem (2011) 133(41):16642-16649.

Elden et al., "Ataxin-2 intermediate-length polyglutamine expansions are associated with increased risk for ALS." Nature (2010) 466: 1069-1075.

European partial search report for 15765851.9 dated Oct. 25, 2017.
Extended Ep Search Report for 15765851.9 dated Jan. 30, 2018.

Evers et al., "Targeting Several CAG Expansion Diseases by a Single Antisense Oligonucleotide" PLoS One (2011) 6(9): e24308.

Freier et al., "The ups and downs of nucleic acid duplex stability: structure-stability studies on chemically-modified DNA:RNA duplexes" Nucleic Acids Research (1997) 25(22): 4429-4443.

Frieden et al., "Expanding the design horizon of antisense oligonucleotides with alpha-L-LNA" Nucleic Acids Research (2003) 21: 6365-6372.

Gautschi et al. "Activity of a Novel bcl-2/bcl-xL-Bispecific Antisense Oligonucleotide Against Tumors of Diverse Histologic Origins" J. Natl. Cancer Inst. (2001) 93:463-471.

GenBank: NM_002973.3, Homo sapiens ataxin 2 (ATXN2), transcript variant 1, mRNA, NCBI Accession No. NM_002973 (2015) (retrieved from the internet Jun. 28, 2017: https://www.ncbi.nlm.nih.gov/nuccore/171543894/).

GenBank: NT_009775.17 (truncated from nucleotides 2465000 to 2616000) Homo sapiens chromosome 12 genomic contig, GRCh37.p13 Primary Assembly (2013) (retrieved from the internet Jun. 28, 2017: https://www.ncbi.nlm.nih.gov/nuccore/NT_009775.17?report—genbank).

GenBank: BX410018.2, BX410018 *Homo sapiens*Fetal Brain *Homo sapiens* cDNA clone CS0DF030YB075-Prime, mRNA sequence; (2003) (retrieved from the internet Jun. 28, 2017: https://www.ncbi.nlm.nih.gov/nucest/BX410018.2).

Heuvel et al., "Taking a risk: a therapeutic focus on ataxin-2 in amyotrophic lateral sclerosis?" Trends Mol Med (2014) 20(1): 25-35.

Huynh et al., "Expression of ataxin-2 in brains from normal individuals and patients with Alzheimer's disease and spinocerebellar ataxia 2." Ann. Neurol. (1999) 45: 232-241.

(56) References Cited

OTHER PUBLICATIONS

Huynh et al., "Expansion of the polyQ repeat in ataxin-2 alters its Golgi localization, disrupts the Golgi complex and causes cell death." Hum. Mol. Genet. (2003) 12: 1485-1496.
International Search Report for application PCT/US2015/021607 dated Jun. 29, 2015.
International Search Report for application PCT/US2015/021608 dated Jul. 1, 2015.
International Search Report for application PCT/US2016/069406 dated Mar. 31, 2017.
Kabanov et al., "A new class of antivirals: antisense oligonucleotides combined with a hydrophobic substituent effectively inhibit influenza virus reproduction and synthesis of virus-specific proteins in MDCK cells" FEBS Lett. (1990) 259:327-330.
Kim et al., "Importance of low-range CAG expansion and CAA interruption in SCA2 Parkinsonism." Arch. Neurol. (2007) 64(10): 1510-1518.
Koshy et al., "Spinocerebellar ataxia type-1 and spinobulbar muscular atrophy gene products interact with glyceraldehyde-3-phosphate dehydrogenase" Hum. Mol. Genet. (1996) 5(9): 1311-1318.
Koshkin et al., "LNA 9Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition" Tetrahedron (1998) 54: 3607-3630.
Kumar et al., "The First Analogues of LNA (Locked Nucleic Acids): Phosphorothioate-LNA and 2'-Thio-LNA" Bioorg. Med. Chem. Lett. (1998) 8: 2219-2222.
Kumar et al., "Design, synthesis, biophysical and primer extension studies of novel acyclic butyl nucleic acid (BuNA)" Org. Biomol. Chem. (2013) 11: 5853-5865.
Lajoie et al., "Formation and toxicity of soluble polyglutamine oligomers in living cells." PLoS One (2010) 5(12): e15245 1-15.
Letsinger et al., "Cholesteryl-conjugated oligonucleotides: Synthesis, properties, and activity as inhibitors of replication of human immunodeficiency virus in cell culture" Proc. Natl. Acad. Sci. USA (1989) 86: 6553-6556.
Leumann, "DNA Analogues: From Supramolecular Principles to Biological Properties" CJ. Bioorg. & Med. Chem. (2002) 10: 841-854.
Lou Gehrig's Disease (ALS): Prevention | Florida Hospital. Downloaded on Jul. 16, 2018 from https://www.floridahospital.com/lou-gehrigs-disease-als/prevention-lou-gehrigs-disease-als.
Lovett-Racke et al., Therapeutic Potential of Small Interfering RNA for Central Nervous System Diseases. Archives of Neurobiology (2005) 62:1810-1813.
Magana et al., "Spinocerebellar ataxia type 2: clinical presentation, molecular mechanisms, and therapeutic perspectives" Mol Neurobiol (2013) 47(1): 90-104.
Maher et al., "Comparative hybrid arrest by tandem antisense oligodeoxyribonucleotides or oligodeoxyribonucleoside methylphosphonates in a cell-free system" Nuc. Acid. Res. (1988) 16(8):3341-3358.
Manoharan et al., "Chemical Modifications to Improve Uptake and Bioavailability of Antisense Oligonucleotides" Ann. N.Y. Acad. Sci. (1992) 660: 306-309.
Manoharan et al., "Introduction of a Lipophilic Thioether Tether in the Minor Groove of Nucleic Acids for Antisense Applications" Bioorg. Med. Chem. Lett. (1993) 3(12):2765-2770.
Manoharan et al., "Cholic Acid-Oligonucleotide Conjugates for Antisense Applications" Bioorg. Med. Chem. Lett. (1994) 4:1053-1060.
Manoharan et al., "Lipidic Nucleic Acids" Tetrahedron Lett. (1995) 36(21):3651-3654.
Manoharan et al., "Oligonucleotide Conjugates: Alteration of the Pharmacokinetic Properties of Antisense Agents" Nucleosides & Nucleotides (1995) 14(3-5): 969-973.

Mishra et al., "Improved leishmanicidal effect of phosphorotioate antisense oligonucleotides by LDL-mediated delivery" Biochim. Biophys. Acta (1995) 1264:229-237.
New England Biolabs 1998/99 Catalog (cover page and pp. 121 and 284).
Nishina et al., "Chimeric Antisense Oligonucleotide Conjugated to alpha-Tocopherol" Molecular Therapy Nucleic Acids (2015) 4:e220.
Nishina et al., "Efficient in Vivo Delivery of siRNA to the liver by Conjugation of alpha-Tocopherol." Molecular Therapy (2008) 16(4): 734-740.
Nonhoff et al., "Ataxin-2 interacts with the Dead/H-box RNA helicase DDX6 and interferes with P-bodies and stress granules." Mol. Biol. Cell (2007) 18(4):1385-1396.
Nonis et al., "Ataxin-2 associates with the endocytosis complex and affects EGF receptor trafficking" Cell Signal (2008) 20(10):1725-1739.
Oberhauser et al., "Effective incorporation of 2'-O-methyl-oligoribonucleotides into liposomes and enhanced cell association through modifications with thiocholesterol" Nucl. Acids Res. (1992) 20(3):533-538.
Oka et al., "An Oxazaphospholidine Approach for the Stereocontrolled Synthesis of Oligonucleoside Phosphorothioates" J. Am. Chem. Soc. (2003) 125:8307-8317.
Parkinson's Disease—Symptoms and causes—Mayo Clinic. Downnloaded on Jul. 16, 2018 from https://www.mayoclinic.org/diseases-conditions/parkinsons-disease/symptoms-causes/syc-20376055.
Pulst S.M. (ed.) "Inherited Ataxias: An Introduction" Genetics of Movement Disorders. Elsevier, Inc., Amsterdam, published Oct. 3, 2002, pp. 19-34.
Pulst S.M., "Rare mendelian diseases: pathways to therapy development" Oral presentation, American Academy of Neurology Annual Meeting, Philadelphia, PA, Apr. 29, 2014.
Ramachandran, P. "RNA interference therapy for the Spinocerebellar ataxias." Thesis, May 2014, University of Iowa, pp. 1-140.
Reynolds et al., "Rational siRNA design for RNA interference" Nature Biotechnology (2004) 22(3):326-330.
Ross et al., "Ataxin-2 repeat-length variation and neurodegeneration." Hum. Mol. Genet. (2011) 20(16): 3207-3212.
Saison-Behmoaras et al., "Short modified antisense oligonucleotides directed against Ha-ras point mutation induce selective cleavage of the mRNA and inhibit T24 cells proliferation" EMBO J. (1991) 10(5):1111-1118.
Sanghvi et al., "Heterocyclic Base Modifications in Nucleic Acids and Their Applications in Antisense Oligonucleotides" Antisense Research and Applications (1993) pp. 273-288.
Sanghvi et al., "Carbohydrate Modifications in Antisense Research" ACS Symposium Series 580; Chapters 3 and 4, 40-65.
Satterfield et al., "Ataxin-2 and its *Drosophila homolog*, ATX2, physically assemble with polyribosomes." Hum. Mol. Genet. (2006) 15(16):2523-2532.
Scoles et al., "Antisense oligonucleotides for the treatment of spinocerebellar ataxia type 2 (SCA2)" AAN Annual Meeting abstract published online Feb. 26, 2015; Neurology (2015) 82(Meeting Abstracts): S32.002.
Scoles et al., "Antisense oligonucleotide therapy for spinocerebellar ataxia type 2." Nature (2017) 544: 362-366.
Scoles et al, Antisense oligonucleotides for the treatment of spinocerebellar ataxia type 2 (SCA2), 5th Ataxia Investigators Meeting (AIM) meeting abstract presented Mar. 20, 2014.
Scoles et al., "ETS1 regulates the expression of ATXN2" Human Mol Genetics (2012) 21(23): 5048-65.
Scoles et al., "Treatment of Spinocerebellar Ataxia Type 2 (SCA2) with MOE Antisense Oligonucleotides." AAN Annual Meeting abstract published online Feb. 26, 2014; Neurology (2014) 82(10 Supplement): S47.006.
Scoles et al., "ATXN2 Is Regulated by a Promoter Associated Antisense Long Noncoding RNA (lncRNA)" Neurology (2013) 80: P05030.
Seth et al., "Short Antisense Oligonucleotides with Novel 2'-4' Conformationally Restricted Nucleoside Analogues Show Improved Potency Without Increased Toxicity in Animals " J Med Chem (2009) 52:10-13.

(56) References Cited

OTHER PUBLICATIONS

Shea et al., "Synthesis, hybridization properties and antiviral activity of lipid-oligodeoxynucleotide conjugates" Nucl. Acids Res. (1990) 18(13):3777-3783.

Shen et al., "Research on (CAG)n mutation detection of Spinocerebellar ataxia type 2" Chinese J Int Med (2000) 39(4): 259-261.

Shibata et al., "A novel protein with RNA-binding motifs interacts with ataxin-2." Hum. Mol. Genet. (2000) 9(9): 1303-1313.

Singh et al., "LNA (locked nucleic acids): synthesis and high-affinity nucleic acid recognition" Chem. Commun. (1998) 455-456.

Singh et al., "Synthesis of 2'-amino-LNA: A novel conformationally restricted high-affinity oligonucleotide analogue with a handle" J. Org. Chem. (1998) 63: 10035-10039.

Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.

Svinarchuk et al., "Inhibition of HIV proliferation in MT-4 cells by antisense oligonucleotide conjugated to lipophilic groups" Biochimie (1993) 75:49-54.

Van Damme et al., "Expanded ATXN2 CAG repeat size in ALS identifies genetic overlap between ALS and SCA2." Neurology (2011) 76(24):2066-2072.

Wan et al., "Synthesis, biophysical properties and biological activity of second generation antisense oligonucleotides containing chiral phosphorothioate linkages." Nucleic Acids Research (2014) 42(22): 13456-13468.

Woolf et al. "Specificity of antisense oligonucleotides in vivo" PNAS (1992) 89:7305-7309.

Yamanaka et al., "Transcription factor sequestration by polyglutamine proteins." Methods Mol. Biol. (2010) 648:215-229.

Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.

Zhang et al., "Stress Granule Assembly Disrupts Nucleocytoplasmic Transport" Cell (2018) 173:1-14.

International Search Report for application PCT/US2019/043424 dated Jan. 7, 2020.

Keiser et al., "RNAi prevents and reverses phenotypes induced by mutant human ataxin-1" Ann Neurol (2016) 80: 754-765.

Zangemeister-Wittke et al., "A novel bispecific antisense oligonucleotide inhibiting both bcl-2 and bcl-xL expression efficiently induces apoptosis in tumor cells" Clin Cancer Res (2000) 6: 2547-2555.

Elden et al., "Ataxin-2 localization in ALS and FTLD-TDP and TDP-43 localization in SCA2," Nature, 2010, 466:1069-1075 (Supplementary Information).

Chiu et al., "Age-Dependent Penetrance of Disease in a Transgenic Mouse Model of Familial Amyotrophic Lateral Sclerosis," Mol and Cell Neurosci, 1995, 6:349-362.

Frey et al., "Early and Selective Loss of Neuromuscular Synapse Subtypes with Low Sprouting Competence in Motoneuron Diseases," J Neurosci, 2000, 20(7):2534-2542.

Grunweller et al. "Comparison of different antisense strategies in mammalian cells using locked nucleic acids, 2'-O-methyl RNA, phosphorothioates and small interfering RNA" Nucl Ac Res (2003) 31: 185-193.

Gurney et al., "Motor Neuron Degeneration in Mice that Express a Human Cu,ZN Superoxide Dismutase Mutation," Science, 2004, 264:1772-1775.

Ito et al., "Treatment with edaravone, initiated at symptom onset, slows motor decline and decreases SOD1 deposition in ALS mice," Experimental Neurology, 2008, 213:448-455.

Philips et al., "Rodent Models of Amyotrophic Lateral Sclerosis," Curr Protoc Pharmacol, 2015, 69: 1-21.

Pun et al., "Selective Vulnerability and Pruning of Phasic Motoneuron Axons in Motoneuron Disease Alleviated by CTNF," Nat Neurosci, 2006, 9:408-419.

Takei et al., "Edaravone and its Clinical Development for Amyotrophic Lateral Sclerosis," Amyotrophic Lateral Sclerosis and Frontotemporal Degeneration, 2017, 18:5-10.

Van Blitterswijk et al., "Ataxin-2 as potential disease modifier in C9ORF72 expansion carriers" Neurobiology of Aging (2014) 35: e13-e17.

COMPOUNDS AND METHODS FOR REDUCING ATXN2 EXPRESSION

SEQUENCE LISTING

The present application is being filed along with a Sequence Listing in electronic format. The Sequence Listing is provided as a file entitled BIOL0321USSEQ_ST25.txt, created on Jul. 24, 2019, which is 847 KB in size. The information in the electronic format of the sequence listing is incorporated herein by reference in its entirety.

FIELD

Provided are compounds, methods, and pharmaceutical compositions for reducing the amount or activity of ATXN2 RNA in a cell or animal, and in certain instances reducing the amount of Ataxin-2 protein in a cell or animal. Such compounds, methods, and pharmaceutical compositions are useful to ameliorate at least one symptom or hallmark of a neurodegenerative disease. Such symptoms and hallmarks include ataxia, neuropathy, and aggregate formation. Such neurodegenerative diseases include spinocerebellar ataxia type 2 (SCA2), amyotrophic lateral sclerosis (ALS), and parkinsonism.

BACKGROUND

Spinocerebellar ataxia type 2 (SCA2) is an autosomal dominant neurodegenerative disease characterized by progressive functional and cell loss of neurons in the cerebellum, brain stem and spinal cord. The cause of SCA2 is CAG expansion in the ATXN2 gene resulting in polyglutamine (polyQ) expansion in the ataxin-2 protein. Patients with SCA2 are characterized by progressive cerebellar ataxia, slow saccadic eye movements and other neurologic features such as neuropathy (Pulst, S. M. (ed.), *Genetics of Movement Disorders*. Elsevier, Inc., Amsterdam, 2003, pp. 19-34.). Moderate CAG expansion in the ATXN2 gene is also associated with parkinsonism or amyotrophic lateral sclerosis (ALS) indistinguishable from the idiopathic forms of these diseases (Kim et al., *Arch. Neurol.,* 2007, 64: 1510-1518; Ross et al., *Hum. Mol. Genet.,* 2011, 20: 3207-3212; Corrado et al., *Hum. Genet.,* 2011, 130: 575-580; Elden et al., *Nature,* 2010, 466: 1069-1075; Van Damme et al., *Neurology,* 2011, 76: 2066-2072).

The pathogenic functions of polyQ disease proteins that occur with polyQ expansion may be attributed to the gain of toxicity associated with the development of intranuclear inclusion bodies or with soluble toxic oligomers (Lajoie et al., *PLoS One,* 2011, 5: e15245). While SCA2 patient brains are characterized by loss of Purkinje cells, SCA2 Purkinje cells lack inclusion bodies indicating polyQ-expanded ataxin-2 may cause toxicity that is unrelated to inclusion body formation (Huynh et al., *Ann. Neurol.,* 1999, 45: 232-241). Functions gained in polyQ-expanded ataxin-2 may include anomalous accumulation in Golgi bodies (Huynh et al., *Hum. Mol. Genet.,* 2003, 12: 1485-1496), gain-of-normal functions (Duvick et al., *Neuron,* 2010, 67: 929-935) and sequestering of transcription factors (TFs) and glyceraldehyde-3-phosphate dehydrogenase like for other polyQ proteins (Yamanaka et al., *Methods Mol. Biol.,* 2010: 648, 215-229; Koshy et al., *Hum. Mol. Genet.,* 1996, 5: 1311-1318; Burke et al., *Nat. Med.,* 1996, 2: 347-350). Some normal functions of ataxin-2 have been characterized. Ataxin-2 is present in stress granules and P-bodies suggesting functions in sequestering mRNAs and protein translation regulation during stress (Nonhoff et al., *Mol. Biol. Cell,* 2007, 18: 1385-1396). Ataxin-2 overexpression interfered with the P-body assembly, while underexpression interfered with stress granule assembly (Nonhoff et al., *Mol. Biol. Cell,* 2007, 18: 1385-1396). Interactions with polyA-binding protein 1, the RNA splicing factor A2BP1/Fox1 and polyribosomes further support roles for ataxin-2 in RNA metabolism (Shibata et al., *Hum. Mol. Genet.,* 2000, 9: 1303-1313; Ciosk et al., Development, 2004, 131: 4831-4841; Satterfield et al., *Hum. Mol. Genet.,* 2006, 15: 2523-2532). Ataxin-2 is a regulator of EGF receptor internalization and signaling by the way of its interactions with SRC kinase and the endocytic protein CIN85 (Nonis et al., *Cell Signal.,* 2008, 20: 1725-1739). Ataxin-2 also interacts with the ALS-related protein TDP-43 in an RNA-dependent manner and familial and sporadic ALS associates with the occurrence of long normal CAG repeat expansion ATXN2 (Elden et al., *Nature,* 2010, 466: 1069-1075; Van Damme et al., *Neurology,* 2011, 76: 2066-2072).

Currently there is a lack of acceptable options for treating such neurodegenerative diseases. It is therefore an object herein to provide methods for the treatment of such diseases.

SUMMARY OF THE INVENTION

Provided herein are compounds, methods, and pharmaceutical compositions for reducing the amount or activity of ATXN2 RNA, and in certain embodiments reducing the amount of Ataxin-2 protein in a cell or animal. In certain embodiments, the animal has a neurodegenerative disease. In certain embodiments, the animal has spinocerebellar ataxia type 2 (SCA2), amyotrophic lateral sclerosis (ALS), or parkinsonism. In certain embodiments, compounds useful for reducing expression of ATXN2 RNA are oligomeric compounds. In certain embodiments, the oligomeric compound comprises a modified oligonucleotide.

Also provided are methods useful for ameliorating at least one symptom or hallmark of a neurodegenerative disease. In certain embodiments, the neurodegenerative disease is SCA2, ALS, or parkinsonism. In certain embodiments symptoms and hallmarks include ataxia, neuropathy, and aggregate formation. In certain embodiments, amelioration of these symptoms results in improved motor function, reduced neuropathy, and reduction in number of aggregates.

DETAILED DESCRIPTION OF THE INVENTION

It is to be understood that both the foregoing general description and the following detailed description are exemplary and explanatory only and are not restrictive. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated-by-reference for the portions of the document discussed herein, as well as in their entirety.

DEFINITIONS

Unless specific definitions are provided, the nomenclature used in connection with, and the procedures and techniques of, analytical chemistry, synthetic organic chemistry, and medicinal and pharmaceutical chemistry described herein are those well known and commonly used in the art. Where permitted, all patents, applications, published applications and other publications and other data referred to throughout in the disclosure are incorporated by reference herein in their entirety.

Unless otherwise indicated, the following terms have the following meanings:

As used herein, "2'-deoxynucleoside" means a nucleoside comprising a 2'-H(H) deoxyribosy sugar moiety, as found in naturally occurring deoxyribonucleic acids (DNA). In certain embodiments, a 2'-deoxynucleoside may comprise a modified nucleobase or may comprise an RNA nucleobase (uracil).

As used herein, "2'-substituted nucleoside" means a nucleoside comprising a 2'-substituted sugar moiety. As used herein, "2'-substituted" in reference to a sugar moiety means a sugar moiety comprising at least one 2'-substituent group other than H or OH.

As used herein, "5-methyl cytosine" means a cytosine modified with a methyl group attached to the 5 position. A 5-methyl cytosine is a modified nucleobase.

As used herein, "administering" means providing a pharmaceutical agent to an animal.

As used herein, "animal" means a human or non-human animal.

As used herein, "antisense activity" means any detectable and/or measurable change attributable to the hybridization of an antisense compound to its target nucleic acid. In certain embodiments, antisense activity is a decrease in the amount or expression of a target nucleic acid or protein encoded by such target nucleic acid compared to target nucleic acid levels or target protein levels in the absence of the antisense compound.

As used herein, "antisense compound" means an oligomeric compound capable of achieving at least one antisense activity.

As used herein, "ameliorate" in reference to a treatment means improvement in at least one symptom relative to the same symptom in the absence of the treatment. In certain embodiments, amelioration is the reduction in the severity or frequency of a symptom or the delayed onset or slowing of progression in the severity or frequency of a symptom. In certain embodiments, the symptom or hallmark is ataxia, neuropathy, and aggregate formation. In certain embodiments, amelioration of these symptoms results in improved motor function, reduced neuropathy, or reduction in number of aggregates.

As used herein, "bicyclic nucleoside" or "BNA" means a nucleoside comprising a bicyclic sugar moiety.

As used herein, "bicyclic sugar" or "bicyclic sugar moiety" means a modified sugar moiety comprising two rings, wherein the second ring is formed via a bridge connecting two of the atoms in the first ring thereby forming a bicyclic structure. In certain embodiments, the first ring of the bicyclic sugar moiety is a furanosyl moiety. In certain embodiments, the bicyclic sugar moiety does not comprise a furanosyl moiety.

As used herein, "cleavable moiety" means a bond or group of atoms that is cleaved under physiological conditions, for example, inside a cell, an animal, or a human.

As used herein, "complementary" in reference to an oligonucleotide means that at least 70% of the nucleobases of the oligonucleotide or one or more regions thereof and the nucleobases of another nucleic acid or one or more regions thereof are capable of hydrogen bonding with one another when the nucleobase sequence of the oligonucleotide and the other nucleic acid are aligned in opposing directions. Complementary nucleobases means nucleobases that are capable of forming hydrogen bonds with one another. Complementary nucleobase pairs include adenine (A) and thymine (T), adenine (A) and uracil (U), cytosine (C) and guanine (G), 5-methyl cytosine (mC) and guanine (G). Complementary oligonucleotides and/or nucleic acids need not have nucleobase complementarity at each nucleoside. Rather, some mismatches are tolerated. As used herein, "fully complementary" or "100% complementary" in reference to oligonucleotides means that oligonucleotides are complementary to another oligonucleotide or nucleic acid at each nucleoside of the oligonucleotide.

As used herein, "conjugate group" means a group of atoms that is directly attached to an oligonucleotide. Conjugate groups include a conjugate moiety and a conjugate linker that attaches the conjugate moiety to the oligonucleotide.

As used herein, "conjugate linker" means a single bond or a group of atoms comprising at least one bond that connects a conjugate moiety to an oligonucleotide.

As used herein, "conjugate moiety" means a group of atoms that is attached to an oligonucleotide via a conjugate linker.

As used herein, "contiguous" in the context of an oligonucleotide refers to nucleosides, nucleobases, sugar moieties, or internucleoside linkages that are immediately adjacent to each other. For example, "contiguous nucleobases" means nucleobases that are immediately adjacent to each other in a sequence.

As used herein, "constrained ethyl" or "cEt" or "cEt modified sugar" means a β-D ribosyl bicyclic sugar moiety wherein the second ring of the bicyclic sugar is formed via a bridge connecting the 4'-carbon and the 2'-carbon of the β-D ribosyl sugar moiety, wherein the bridge has the formula 4'-CH(CH$_3$)—O-2', and wherein the methyl group of the bridge is in the S configuration.

As used herein, "cEt nucleoside" means a nucleoside comprising cEt modified sugar.

As used herein, "chirally enriched population" means a plurality of molecules of identical molecular formula, wherein the number or percentage of molecules within the population that contain a particular stereochemical configuration at a particular chiral center is greater than the number or percentage of molecules expected to contain the same particular stereochemical configuration at the same particular chiral center within the population if the particular chiral center were stereorandom. Chirally enriched populations of molecules having multiple chiral centers within each molecule may contain one or more stereorandom chiral centers. In certain embodiments, the molecules are modified oligonucleotides. In certain embodiments, the molecules are compounds comprising modified oligonucleotides.

As used herein, "gapmer" means a modified oligonucleotide comprising an internal region having a plurality of nucleosides that support RNase H cleavage positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings." Unless otherwise indicated, "gapmer" refers to a sugar motif. Unless otherwise indicated, the sugar moieties of the nucleosides of the gap of a gapmer are unmodified 2'-deoxyribosyl. Thus, the term "MOE gapmer" indicates a gapmer having a sugar motif of 2'-MOE nucleosides in both wings and a gap of 2'-deoxynucleosides. Unless otherwise indicated, a MOE gapmer may comprise one or more modified internucleoside linkages and/or modified nucleobases and such modifications do not necessarily follow the gapmer pattern of the sugar modifications.

As used herein, "hotspot region" is a range of nucleobases on a target nucleic acid amenable to oligomeric compound-mediated reduction of the amount or activity of the target nucleic acid.

As used herein, "hybridization" means the pairing or annealing of complementary oligonucleotides and/or nucleic acids. While not limited to a particular mechanism, the most common mechanism of hybridization involves hydrogen bonding, which may be Watson-Crick, Hoogsteen or reversed Hoogsteen hydrogen bonding, between complementary nucleobases.

As used herein, the term "internucleoside linkage" is the covalent linkage between adjacent nucleosides in an oligonucleotide. As used herein "modified internucleoside linkage" means any internucleoside linkage other than a phosphodiester internucleoside linkage. "Phosphorothioate internucleoside linkage" is a modified internucleoside linkage in which one of the non-bridging oxygen atoms of a phosphodiester internucleoside linkage is replaced with a sulfur atom.

As used herein, "linker-nucleoside" means a nucleoside that links, either directly or indirectly, an oligonucleotide to a conjugate moiety. Linker-nucleosides are located within the conjugate linker of an oligomeric compound. Linker-nucleosides are not considered part of the oligonucleotide portion of an oligomeric compound even if they are contiguous with the oligonucleotide.

As used herein, "non-bicyclic modified sugar moiety" means a modified sugar moiety that comprises a modification, such as a substituent, that does not form a bridge between two atoms of the sugar to form a second ring.

As used herein, "mismatch" or "non-complementary" means a nucleobase of a first oligonucleotide that is not complementary with the corresponding nucleobase of a second oligonucleotide or target nucleic acid when the first and second oligonucleotide are aligned.

As used herein, "MOE" means methoxyethyl. "2'-MOE" or "2'-MOE modified sugar" means a 2'-OCH$_2$CH$_2$OCH$_3$ group in place of the 2'-OH group of a ribosyl sugar moiety. As used herein, "2'-MOE nucleoside" means a nucleoside comprising a 2'-MOE modified sugar.

As used herein, "motif" means the pattern of unmodified and/or modified sugar moieties, nucleobases, and/or internucleoside linkages, in an oligonucleotide.

As used herein, "neurodegenerative disease" means a condition marked by progressive loss of function or structure, including loss of motor function and death of neurons. In certain embodiments, the neurodegenerative disease is spinocerebellar ataxia type 2 (SCA2), amyotrophic lateral sclerosis (ALS), or parkinsonism.

As used herein, "nucleobase" means an unmodified nucleobase or a modified nucleobase. As used herein an "unmodified nucleobase" is adenine (A), thymine (T), cytosine (C), uracil (U), or guanine (G). As used herein, a "modified nucleobase" is a group of atoms other than unmodified A, T, C, U, or G capable of pairing with at least one unmodified nucleobase. A "5-methyl cytosine" is a modified nucleobase. A universal base is a modified nucleobase that can pair with any one of the five unmodified nucleobases. As used herein, "nucleobase sequence" means the order of contiguous nucleobases in a nucleic acid or oligonucleotide independent of any sugar or internucleoside linkage modification.

As used herein, "nucleoside" means a compound comprising a nucleobase and a sugar moiety. The nucleobase and sugar moiety are each, independently, unmodified or modified. As used herein, "modified nucleoside" means a nucleoside comprising a modified nucleobase and/or a modified sugar moiety. Modified nucleosides include abasic nucleosides, which lack a nucleobase. "Linked nucleosides" are nucleosides that are connected in a contiguous sequence (i.e., no additional nucleosides are presented between those that are linked).

As used herein, "oligomeric compound" means an oligonucleotide and optionally one or more additional features, such as a conjugate group or terminal group. An oligomeric compound may be paired with a second oligomeric compound that is complementary to the first oligomeric compound or may be unpaired. A "singled-stranded oligomeric compound" is an unpaired oligomeric compound. The term "oligomeric duplex" means a duplex formed by two oligomeric compounds having complementary nucleobase sequences. Each oligomeric compound of an oligomeric duplex may be referred to as a "duplexed oligomeric compound."

As used herein, "oligonucleotide" means a strand of linked nucleosides connected via internucleoside linkages, wherein each nucleoside and internucleoside linkage may be modified or unmodified. Unless otherwise indicated, oligonucleotides consist of 8-50 linked nucleosides. As used herein, "modified oligonucleotide" means an oligonucleotide, wherein at least one nucleoside or internucleoside linkage is modified. As used herein, "unmodified oligonucleotide" means an oligonucleotide that does not comprise any nucleoside modifications or internucleoside modifications.

As used herein, "pharmaceutically acceptable carrier or diluent" means any substance suitable for use in administering to an animal. Certain such carriers enable pharmaceutical compositions to be formulated as, for example, tablets, pills, dragees, capsules, liquids, gels, syrups, slurries, suspension and lozenges for the oral ingestion by a subject. In certain embodiments, a pharmaceutically acceptable carrier or diluent is sterile water, sterile saline, sterile buffer solution or sterile artificial cerebrospinal fluid.

As used herein "pharmaceutically acceptable salts" means physiologically and pharmaceutically acceptable salts of compounds. Pharmaceutically acceptable salts retain the desired biological activity of the parent compound and do not impart undesired toxicological effects thereto.

As used herein "pharmaceutical composition" means a mixture of substances suitable for administering to a subject. For example, a pharmaceutical composition may comprise an oligomeric compound and a sterile aqueous solution. In certain embodiments, a pharmaceutical composition shows activity in free uptake assay in certain cell lines.

As used herein "prodrug" means a therapeutic agent in a form outside the body that is converted to a different form within an animal or cells thereof. Typically conversion of a prodrug within the animal is facilitated by the action of an enzymes (e.g., endogenous or viral enzyme) or chemicals present in cells or tissues and/or by physiologic conditions.

As used herein, "reducing or inhibiting the amount or activity" refers to a reduction or blockade of the transcriptional expression or activity relative to the transcriptional expression or activity in an untreated or control sample and does not necessarily indicate a total elimination of transcriptional expression or activity.

As used herein, "RNAi compound" means an antisense compound that acts, at least in part, through RISC or Ago2 to modulate a target nucleic acid and/or protein encoded by a target nucleic acid. RNAi compounds include, but are not limited to double-stranded siRNA, single-stranded RNA (ssRNA), and microRNA, including microRNA mimics. In certain embodiments, an RNAi compound modulates the amount, activity, and/or splicing of a target nucleic acid. The term RNAi compound excludes antisense compounds that act through RNase H.

As used herein, "self-complementary" in reference to an oligonucleotide means an oligonucleotide that at least partially hybridizes to itself.

As used herein, "standard cell assay" means the assay described in Example 3 and reasonable variations thereof.

As used herein, "standard in vivo assay" means the experiment described in Example 15 and reasonable variations thereof.

As used herein, "stereorandom chiral center" in the context of a population of molecules of identical molecular formula means a chiral center having a random stereochemical configuration. For example, in a population of molecules comprising a stereorandom chiral center, the number of molecules having the (S) configuration of the stereorandom chiral center may be but is not necessarily the same as the number of molecules having the (R) configuration of the stereorandom chiral center. The stereochemical configuration of a chiral center is considered random when it is the results of a synthetic method that is not designed to control the stereochemical configuration. In certain embodiments, a stereorandom chiral center is a stereorandom phosphorothioate internucleoside linkage.

As used herein, "sugar moiety" means an unmodified sugar moiety or a modified sugar moiety. As used herein, "unmodified sugar moiety" means a 2'-OH(H) ribosyl moiety, as found in RNA (an "unmodified RNA sugar moiety"), or a 2'-H(H) deoxyribosyl moiety, as found in DNA (an "unmodified DNA sugar moiety"). Unmodified sugar moieties have one hydrogen at each of the 1', 3', and 4' positions, an oxygen at the 3' position, and two hydrogens at the 5' position. As used herein, "modified sugar moiety" or "modified sugar" means a modified furanosyl sugar moiety or a sugar surrogate.

As used herein, "sugar surrogate" means a modified sugar moiety having other than a furanosyl moiety that can link a nucleobase to another group, such as an internucleoside linkage, conjugate group, or terminal group in an oligonucleotide. Modified nucleosides comprising sugar surrogates can be incorporated into one or more positions within an oligonucleotide and such oligonucleotides are capable of hybridizing to complementary oligomeric compounds or target nucleic acids.

As used herein, "target nucleic acid" and "target RNA" mean a nucleic acid that an antisense compound is designed to affect.

As used herein, "target region" means a portion of a target nucleic acid to which an oligomeric compound is designed to hybridize.

As used herein, "terminal group" means a chemical group or group of atoms that is covalently linked to a terminus of an oligonucleotide.

As used herein, "therapeutically effective amount" means an amount of a pharmaceutical agent that provides a therapeutic benefit to an animal. For example, a therapeutically effective amount improves a symptom of a disease.

CERTAIN EMBODIMENTS

The present disclosure provides the following non-limiting numbered embodiments:

Embodiment 1

An oligomeric compound, comprising a modified oligonucleotide consisting of 12-50 linked nucleosides wherein the nucleobase sequence of the modified oligonucleotide is at least 90% complementary to an equal length portion of an ATXN2 nucleic acid, and wherein the modified oligonucleotide comprises at least one modification selected from a modified sugar, a sugar surrogate, and a modified internucleoside linkage.

Embodiment 2

An oligomeric compound comprising a modified oligonucleotide consisting of 12-50 linked nucleosides and having a nucleobase sequence comprising at least 12, at least 13, at least 14, at least 15, at least 16, at least 17, at least 18, at least 19, or at least 20 contiguous nucleobases of any of the nucleobase sequences of SEQ ID NOS: 30-3319.

Embodiment 3

An oligomeric compound comprising a modified oligonucleotide consisting of 12-50 linked nucleosides and having a nucleobase sequence comprising a portion of at least 8, at least 9, at least 10, at least 11, at least 12, at least 13, at least 14, at least 15, at least 16, at least 17, at least 18, at least 19, or at least 20 contiguous nucleobases, wherein the portion is complementary to:

an equal length portion of nucleobases 2,455-2,483 of SEQ ID NO: 1;
an equal length portion of nucleobases 4,393-4,424 of SEQ ID NO: 1;
an equal length portion of nucleobases 4,413-4,437 of SEQ ID NO: 1;
an equal length portion of nucleobases 4,525-4,554 of SEQ ID NO: 2;
an equal length portion of nucleobases 4,748-4,771 of SEQ ID NO: 2;
an equal length portion of nucleobases 9,927-9,954 of SEQ ID NO: 2;
an equal length portion of nucleobases 10,345-10,368 of SEQ ID NO: 2;
an equal length portion of nucleobases 17,153-17,182 of SEQ ID NO: 2;
an equal length portion of nucleobases 18,680-18,702 of SEQ ID NO: 2;
an equal length portion of nucleobases 23,251-23,276 of SEQ ID NO: 2;
an equal length portion of nucleobases 28,081-28,105 of SEQ ID NO: 2;
an equal length portion of nucleobases 28,491-28,526 of SEQ ID NO: 2;

an equal length portion of nucleobases 28,885-28,912 of SEQ ID NO: 2;

an equal length portion of nucleobases 32,328-32,352 of SEQ ID NO: 2;

an equal length portion of nucleobases 32,796-32,824 of SEQ ID NO: 2;

an equal length portion of nucleobases 32,809-32,838 of SEQ ID NO: 2;

an equal length portion of nucleobases 36,308-36,334 of SEQ ID NO: 2;

an equal length portion of nucleobases 36,845-36,872 of SEQ ID NO: 2;

an equal length portion of nucleobases 49,147-49,173 of SEQ ID NO: 2;

an equal length portion of nucleobases 57,469-57,494 of SEQ ID NO: 2;

an equal length portion of nucleobases 82,848-82,874 of SEQ ID NO: 2;

an equal length portion of nucleobases 83,784-83,813 of SEQ ID NO: 2;

an equal length portion of nucleobases 84,743-84,782 of SEQ ID NO: 2;

an equal length portion of nucleobases 84,813-84,839 of SEQ ID NO: 2;

an equal length portion of nucleobases 85,051-85,076 of SEQ ID NO: 2;

an equal length portion of nucleobases 97,618-97,643 of SEQ ID NO: 2;

an equal length portion of nucleobases 119,023-119,048 of SEQ ID NO: 2;

an equal length portion of nucleobases 132,161-132,195 of SEQ ID NO: 2;

an equal length portion of nucleobases 139,271-139,303 of SEQ ID NO: 2; or an equal length portion of nucleobases 1,075-1,146 of SEQ ID NO: 1.

Embodiment 4

The oligomeric compound of any one of embodiments 1-3, wherein the modified oligonucleotide has a nucleobase sequence that is at least 80%, at least 85%, at least 90%, at least 95%, or 100% complementary to any of the nucleobase sequences of SEQ ID NO: 1 or SEQ ID NO: 2, when measured across the entire nucleobase sequence of the modified oligonucleotide.

Embodiment 5

The oligomeric compound of any of embodiments 1-4, wherein the modified oligonucleotide comprises at least one modified nucleoside.

Embodiment 6

The oligomeric compound of embodiment 5, wherein the modified oligonucleotide comprises at least one modified nucleoside comprising a modified sugar moiety.

Embodiment 7

The oligomeric compound of embodiment 6, wherein the modified oligonucleotide comprises at least one modified nucleoside comprising a bicyclic sugar moiety.

Embodiment 8

The oligomeric compound of embodiment 7, wherein the modified oligonucleotide comprises at least one modified nucleoside comprising a bicyclic sugar moiety having a 2'-4' bridge, wherein the 2'-4' bridge is selected from —O—CH2-; and —O—CH(CH3)—.

Embodiment 9

The oligomeric compound of any of embodiments 5-8, wherein the modified oligonucleotide comprises at least one modified nucleoside comprising a non-bicyclic modified sugar moiety.

Embodiment 10

The oligomeric compound of embodiment 9, wherein the modified oligonucleotide comprises at least one modified nucleoside comprising a non-bicyclic modified sugar moiety comprising a 2'-MOE modified sugar or 2'-OMe modified sugar.

Embodiment 11

The oligomeric compound of any of embodiments 5-10, wherein the modified oligonucleotide comprises at least one modified nucleoside comprising a sugar surrogate.

Embodiment 12

The oligomeric compound of embodiment 11, wherein the modified oligonucleotide comprises at least one modified nucleoside comprising a sugar surrogate selected from morpholino and PNA.

Embodiment 13

The oligomeric compound of any of embodiments 1-12, wherein the modified oligonucleotide has a sugar motif comprising:

a 5'-region consisting of 1-5 linked 5'-region nucleosides;

a central region consisting of 6-10 linked central region nucleosides; and a 3'-region consisting of 1-5 linked 3'-region nucleosides; wherein each of the 5'-region nucleosides and each of the 3'-region nucleosides comprises a modified sugar moiety and each of the central region nucleosides comprises an unmodified 2'-deoxyribosyl sugar moiety.

Embodiment 14

The oligomeric compound of any of embodiments 1-13, wherein the modified oligonucleotide comprises at least one modified internucleoside linkage.

Embodiment 15

The oligomeric compound of embodiment 14, wherein each internucleoside linkage of the modified oligonucleotide is a modified internucleoside linkage.

Embodiment 16

The oligomeric compound of embodiment 14 or 15 wherein at least one internucleoside linkage is a phosphorothioate internucleoside linkage.

Embodiment 17

The oligomeric compound of embodiment 14 or 16 wherein the modified oligonucleotide comprises at least one phosphodiester internucleoside linkage.

Embodiment 18

The oligomeric compound of any of embodiments 14, 16, or 17, wherein each internucleoside linkage is either a phosphodiester internucleoside linkage or a phosphorothioate internucleoside linkage.

Embodiment 19

The oligomeric compound of any of embodiments 1-18, wherein the modified oligonucleotide comprises at least one modified nucleobase.

Embodiment 20

The oligomeric compound of embodiment 19, wherein the modified nucleobase is a 5-methyl cytosine.

Embodiment 21

The oligomeric compound of any of embodiments 1-20, wherein the modified oligonucleotide consists of 12-30, 12-22, 12-20, 14-20, 15-25, 16-20, 18-22 or 18-20 linked nucleosides.

Embodiment 22

The oligomeric compound of any of embodiments 1-21, wherein the modified oligonucleotide consists of 18 or 20 linked nucleosides.

Embodiment 23

The oligomeric compound of any of embodiments 1-22 consisting of the modified oligonucleotide.

Embodiment 24

The oligomeric compound of any of embodiments 1-22 comprising a conjugate group comprising a conjugate moiety and a conjugate linker.

Embodiment 25

The oligomeric compound of embodiment 24, wherein the conjugate group comprises a GalNAc cluster comprising 1-3 GalNAc ligands.

Embodiment 26

The oligomeric compound of embodiment 24 or 25, wherein the conjugate linker consists of a single bond.

Embodiment 27

The oligomeric compound of embodiment 25, wherein the conjugate linker is cleavable.

Embodiment 28

The oligomeric compound of embodiment 27, wherein the conjugate linker comprises 1-3 linker-nucleosides.

Embodiment 29

The oligomeric compound of any of embodiments 24-28, wherein the conjugate group is attached to the modified oligonucleotide at the 5'-end of the modified oligonucleotide.

Embodiment 30

The oligomeric compound of any of embodiments 24-28, wherein the conjugate group is attached to the modified oligonucleotide at the 3'-end of the modified oligonucleotide.

Embodiment 31

The oligomeric compound of any of embodiments 1-30 comprising a terminal group.

Embodiment 32

The oligomeric compound of any of embodiments 1-31 wherein the oligomeric compound is a singled-stranded oligomeric compound.

Embodiment 33

The oligomeric compound of any of embodiments 1-27 or 29-31, wherein the oligomeric compound does not comprise linker-nucleosides.

Embodiment 34

An oligomeric duplex comprising an oligomeric compound of any of embodiments 1-31 or 33.

Embodiment 35

An antisense compound comprising or consisting of an oligomeric compound of any of embodiments 1-33 or an oligomeric duplex of embodiment 34.

Embodiment 36

A pharmaceutical composition comprising an oligomeric compound of any of embodiments 1-33 or an oligomeric duplex of embodiment 34 and a pharmaceutically acceptable carrier or diluent.

Embodiment 37
A modified oligonucleotide according to the following formula:
(SEQ ID NO: 1714)
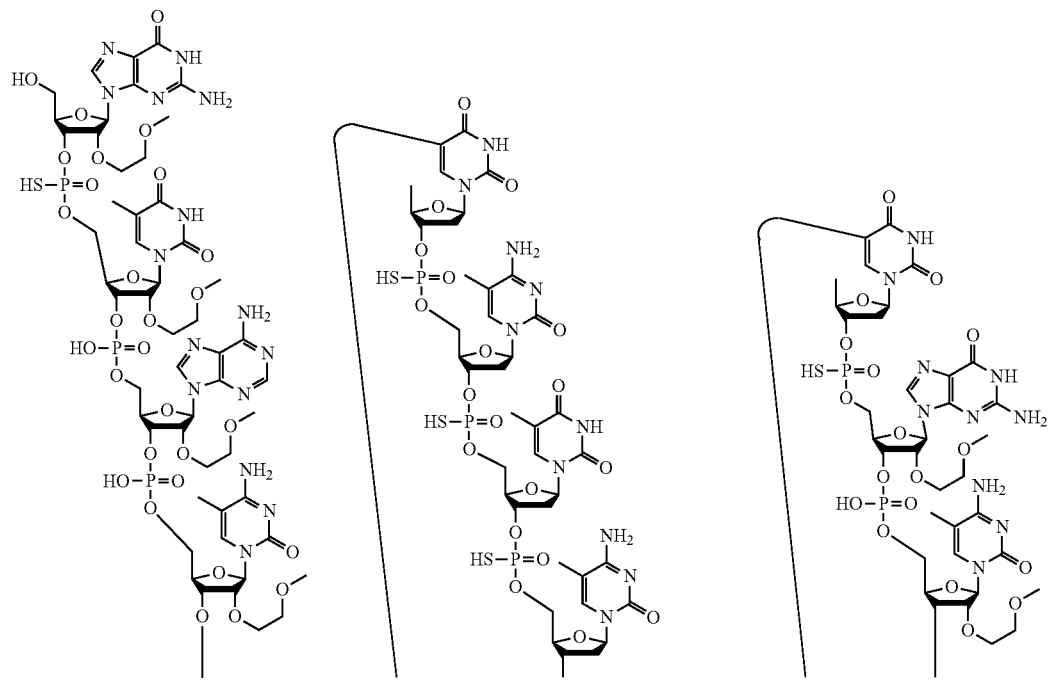
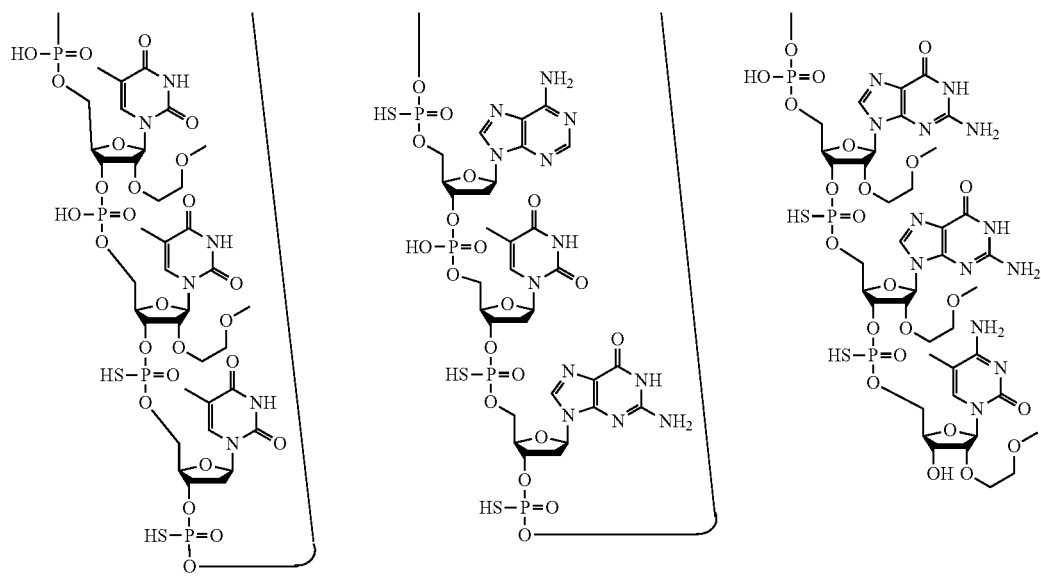
or a salt thereof.

Embodiment 38
A modified oligonucleotide according to the following formula:
(SEQ ID NO: 1255)
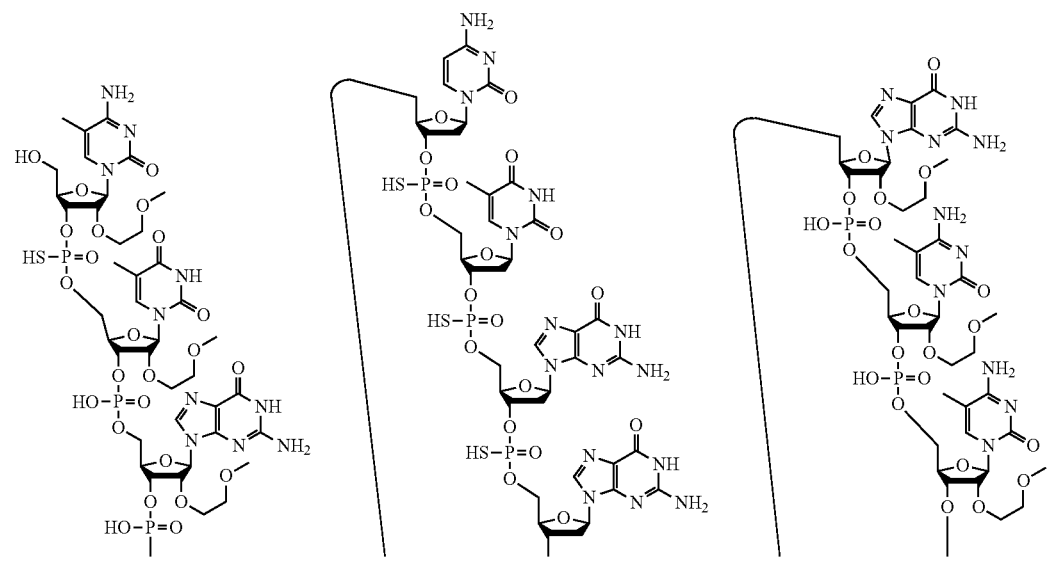
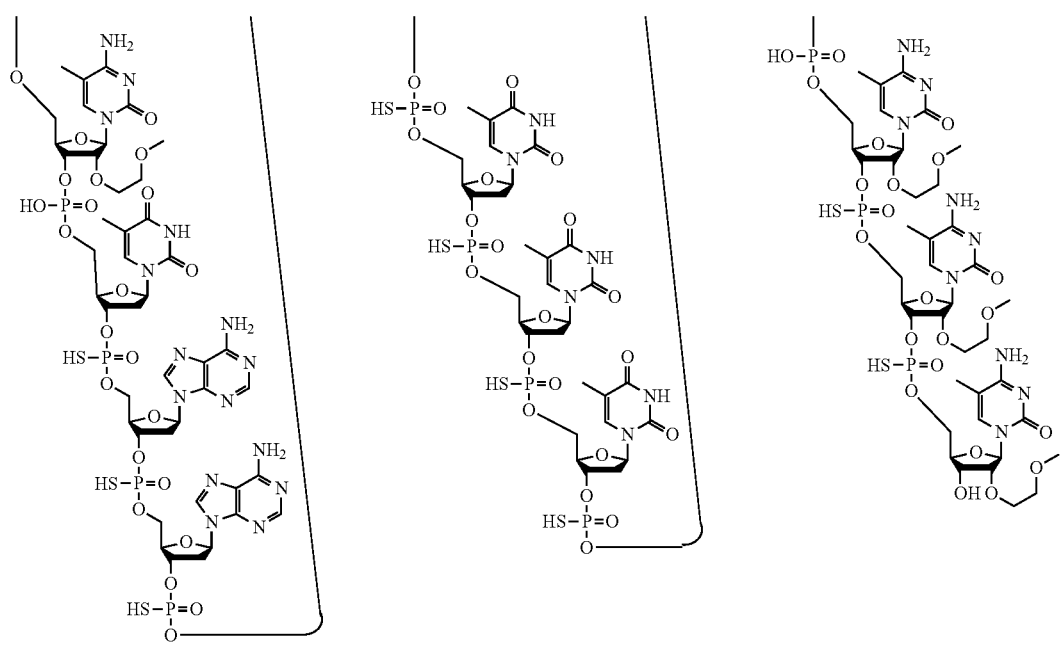
or a salt thereof.

Embodiment 39
A modified oligonucleotide according to the following formula:
(SEQ ID NO: 1185)
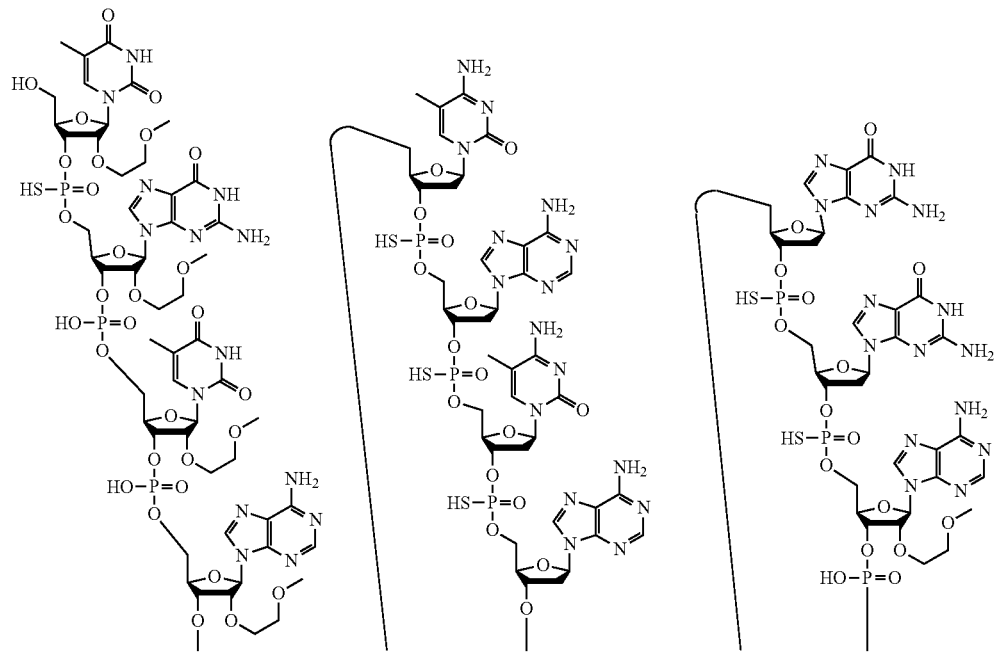
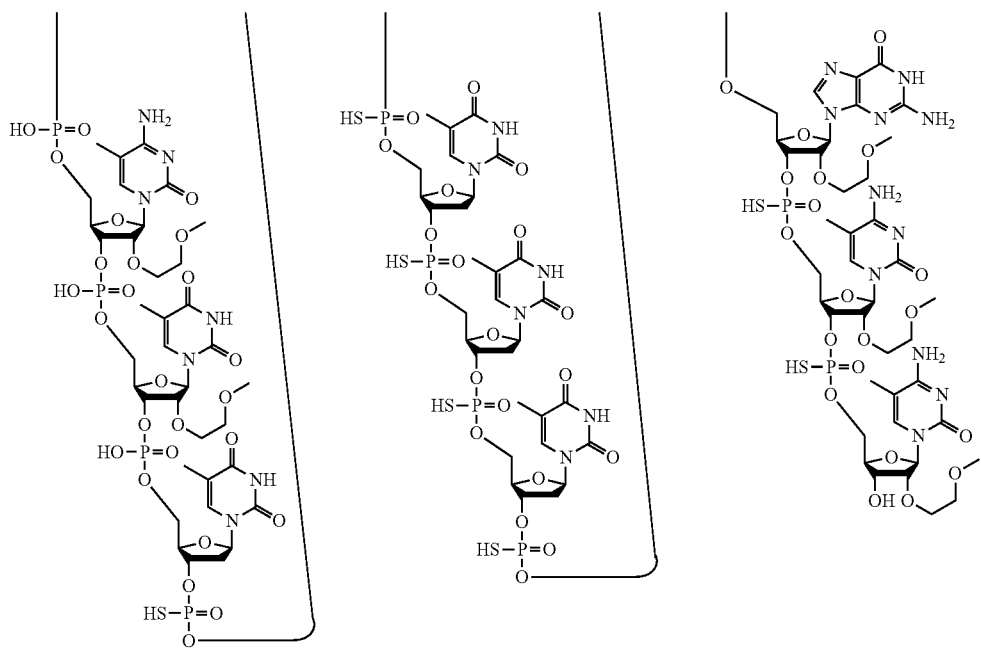
or a salt thereof.

Embodiment 40
A modified oligonucleotide according to the following formula:
(SEQ ID NO: 3235)
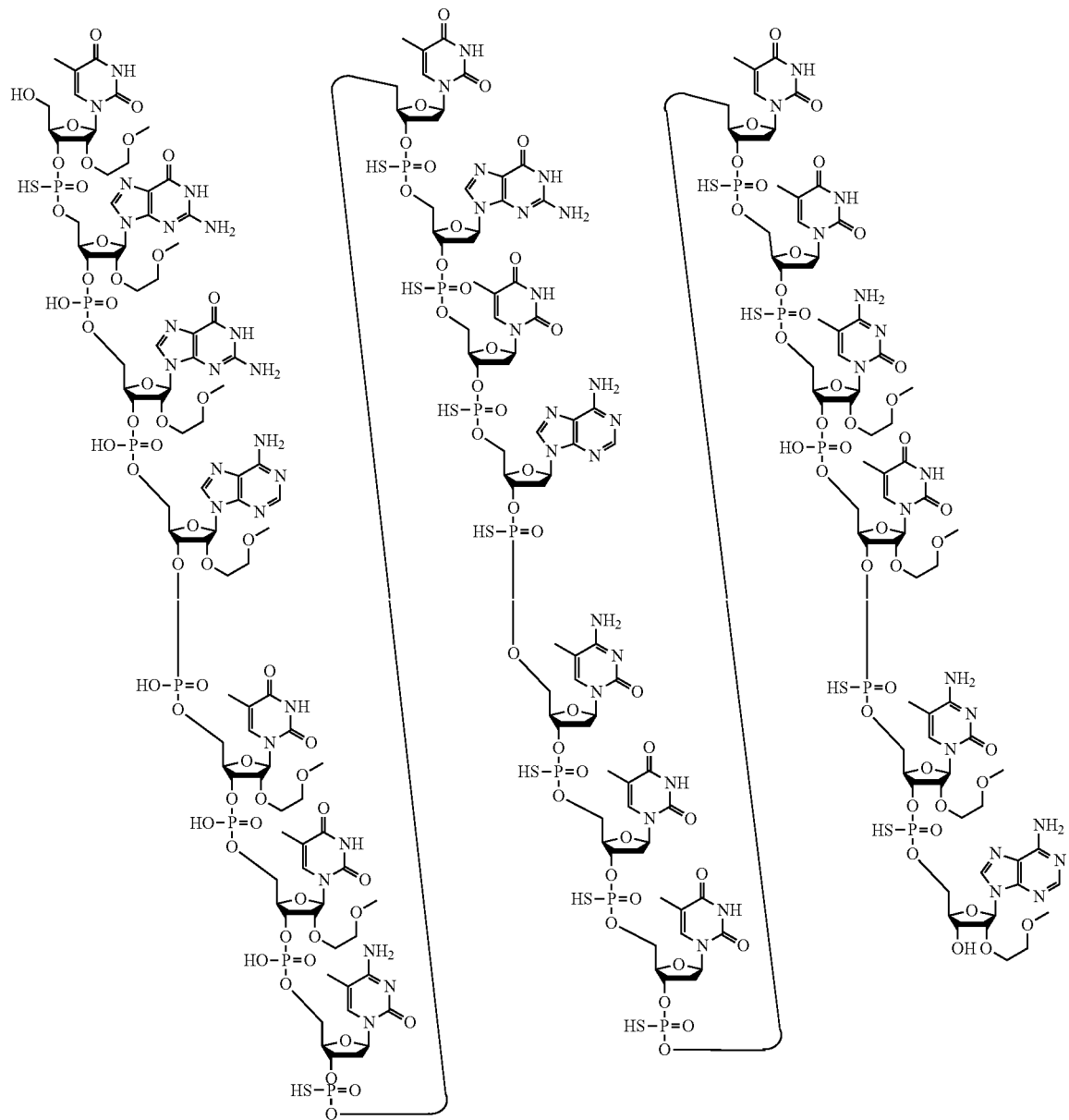
or a salt thereof.
Embodiment 41
A modified oligonucleotide according to the following formula:

(SEQ ID NO: 158)
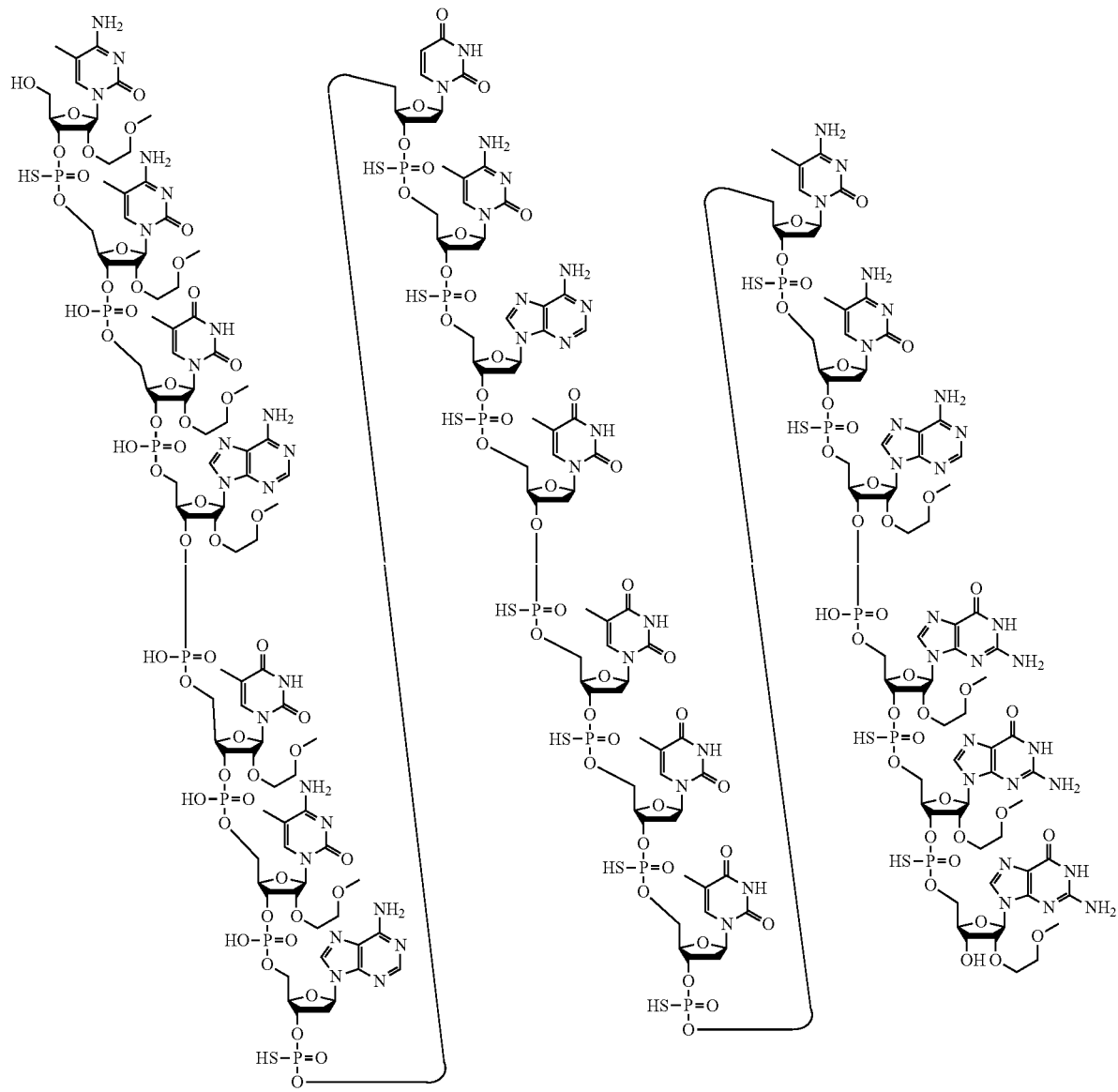
or a salt thereof.
Embodiment 42
A modified oligonucleotide according to the following formula:

SEQ ID NO: 2544
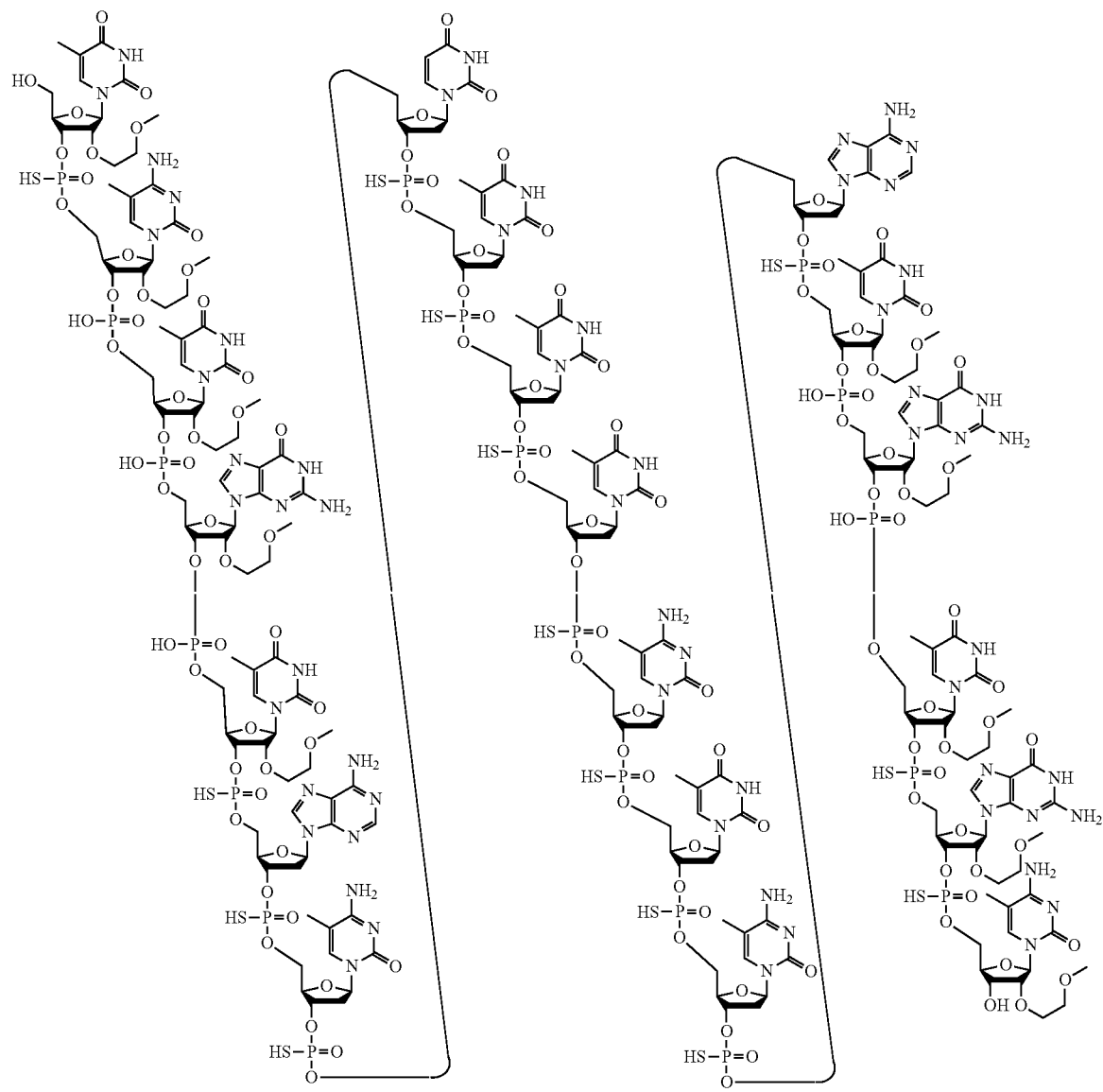
or a salt thereof.
Embodiment 43
The modified oligonucleotide of any of embodiments 37-42, which is a sodium salt of the formula.
Embodiment 44
A modified oligonucleotide according to the following formula:

SEQ ID NO: 1714
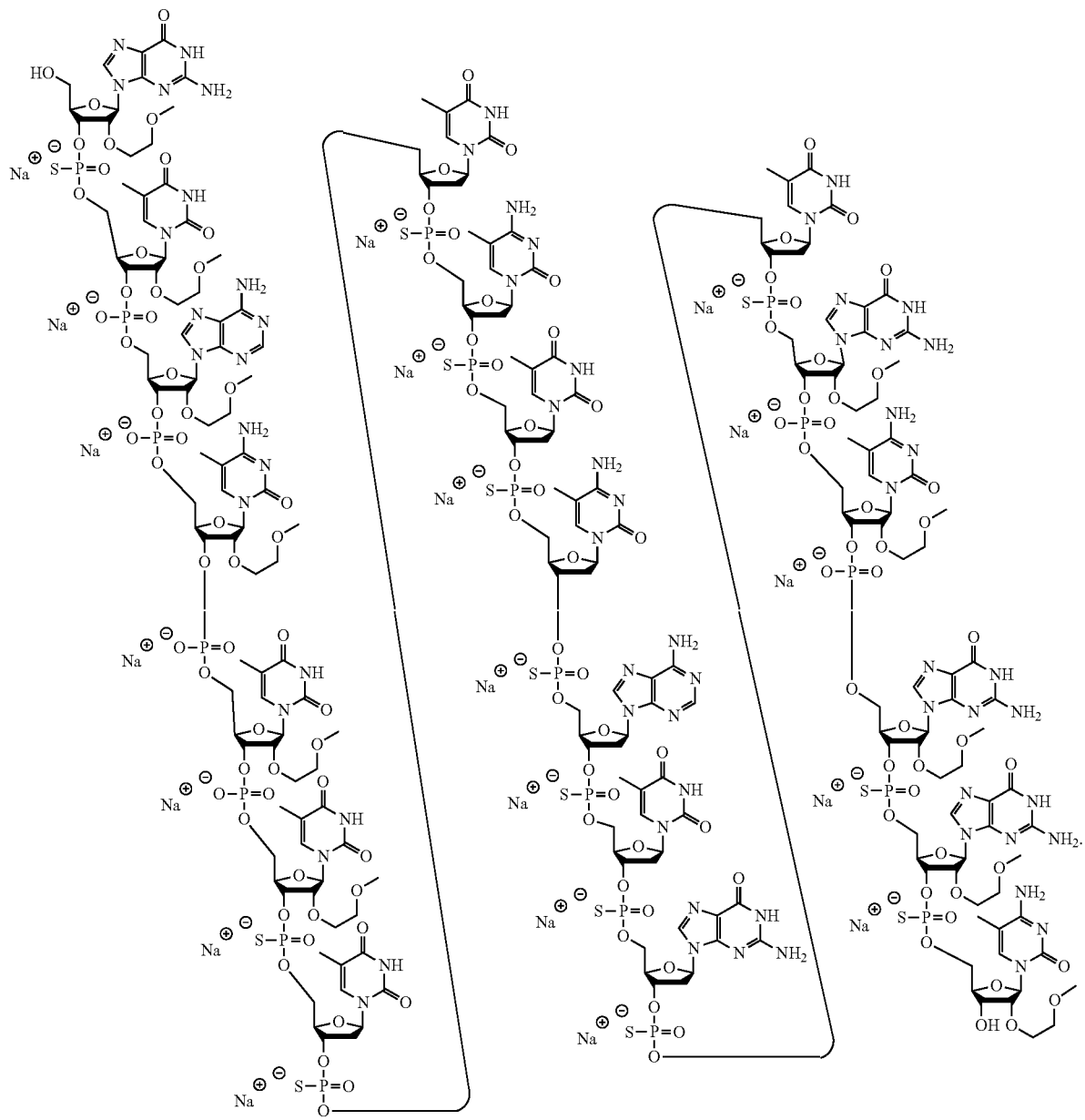
Embodiment 45
A modified oligonucleotide according to the following formula:

SEQ ID NO: 1255
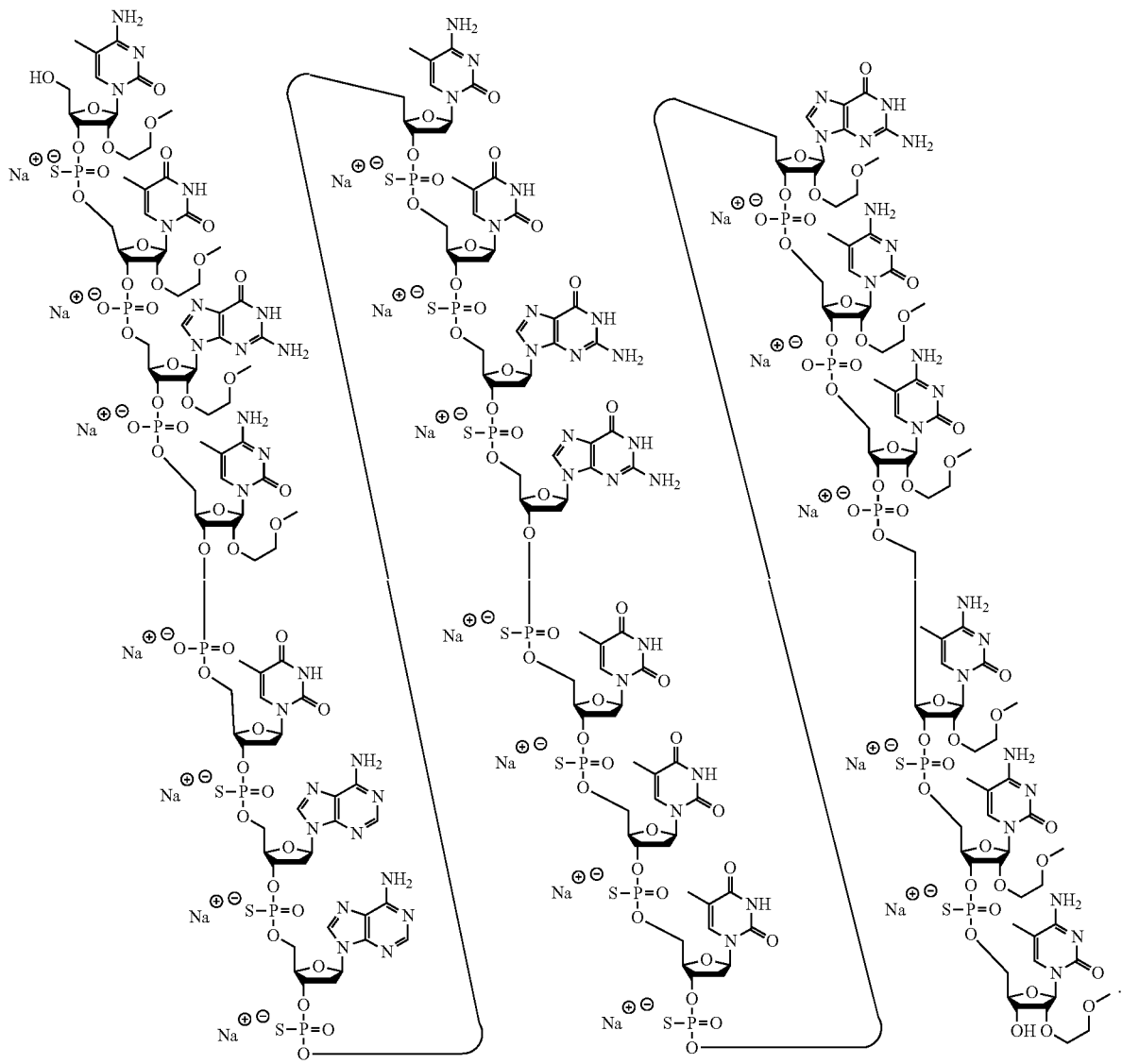
Embodiment 46
A modified oligonucleotide according to the following formula:

SEQ ID NO: 1185
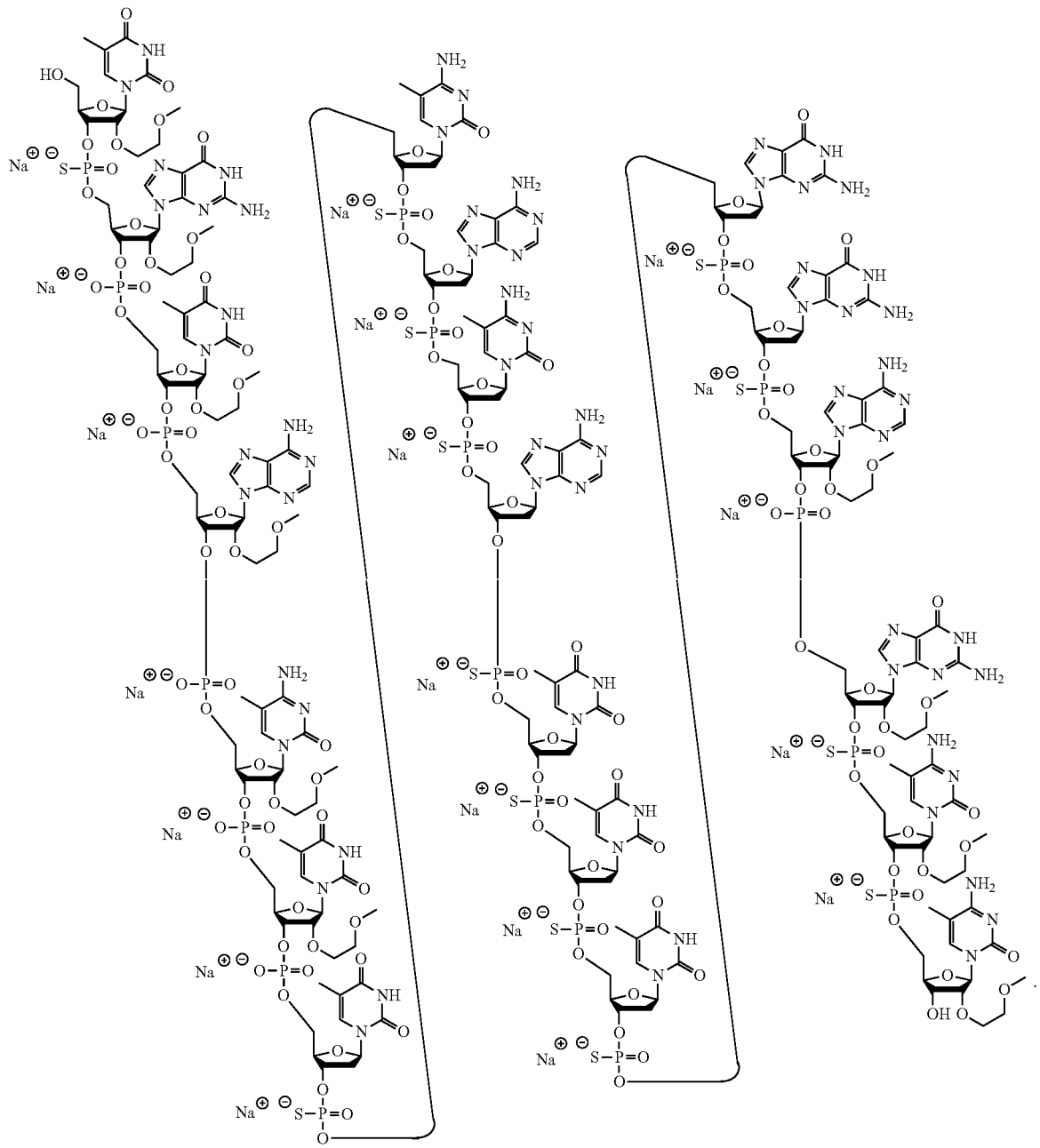
Embodiment 47
A modified oligonucleotide according to the following formula:

SEQ ID NO: 3235
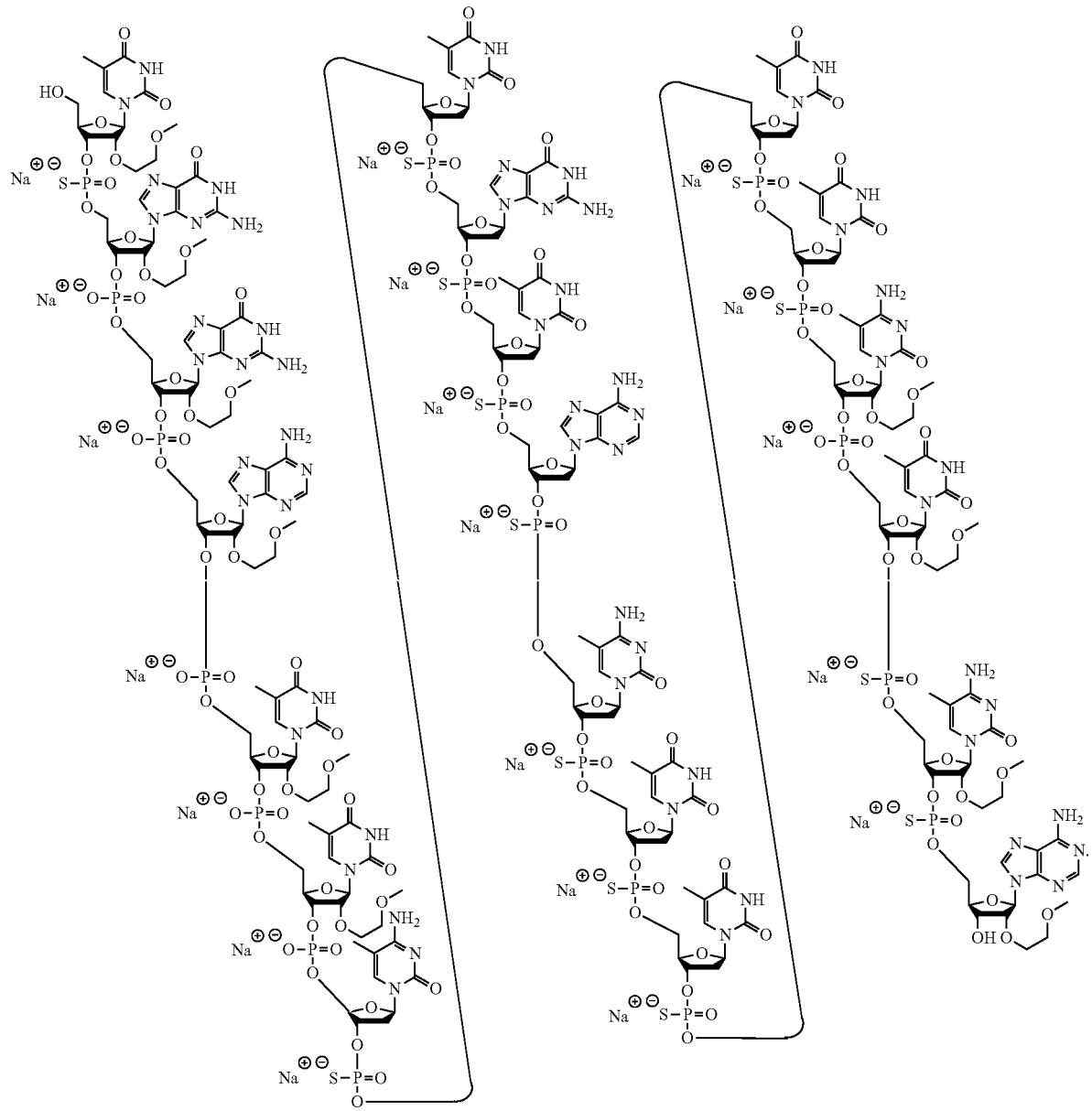
Embodiment 48
A modified oligonucleotide according to the following formula:

SEQ ID NO: 158
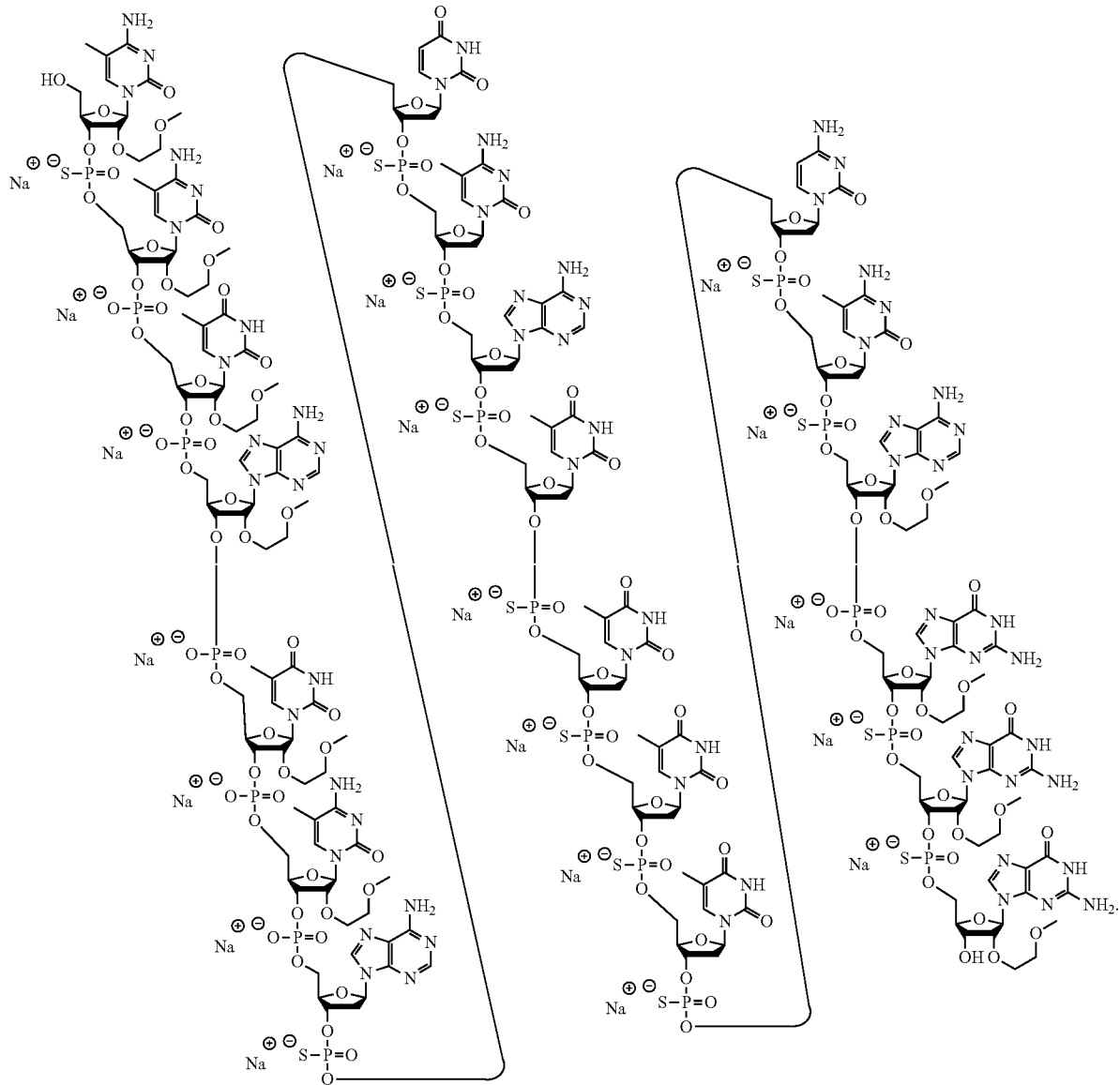
Embodiment 49
50
A modified oligonucleotide according to the following formula:

SEQ ID NO: 2544

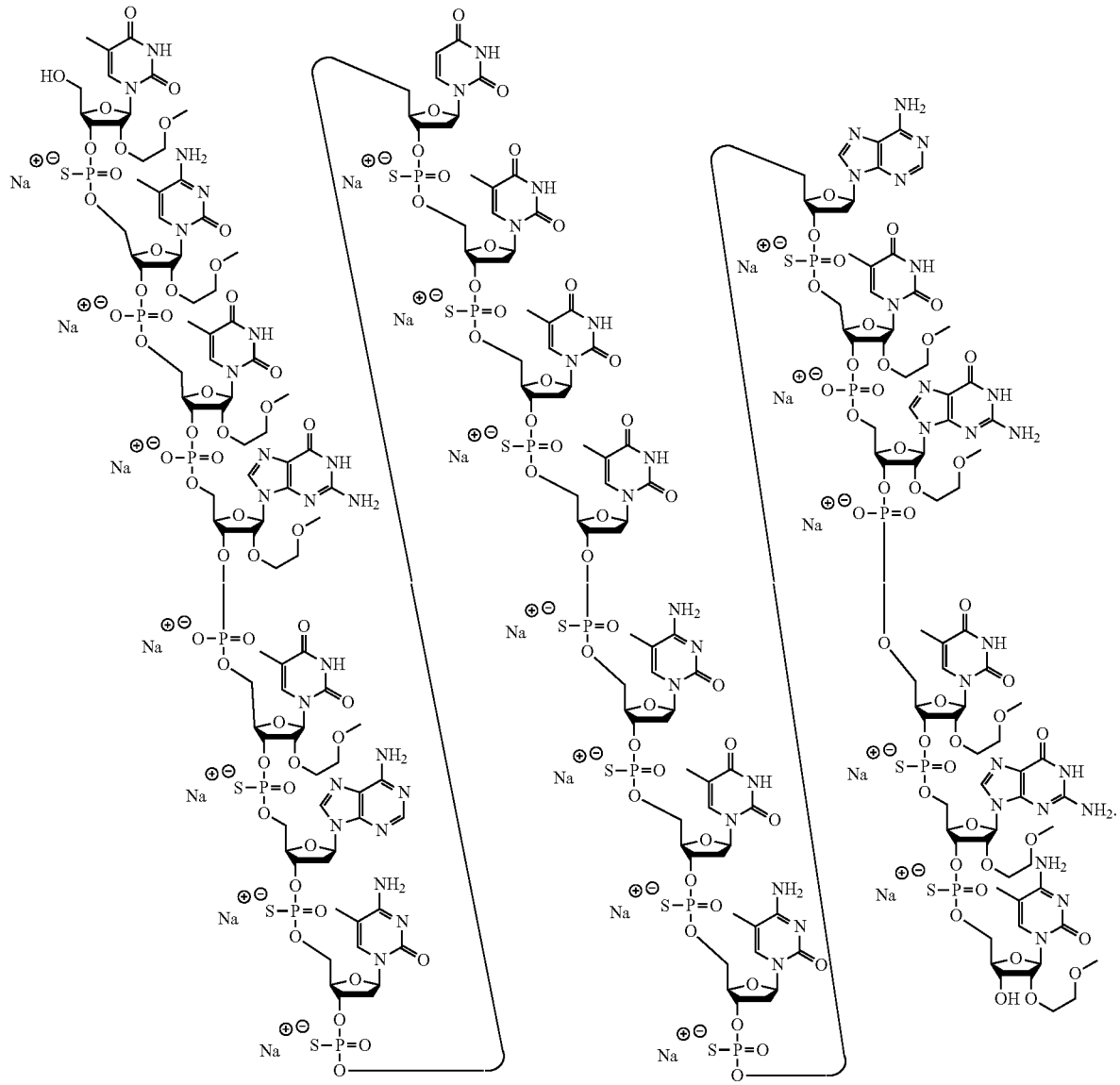

Embodiment 50

A chirally enriched population of the modified oligonucleotide of any of embodiments 37-49 wherein the population is enriched for modified oligonucleotides comprising at least one particular phosphorothioate internucleoside linkage having a particular stereochemical configuration.

Embodiment 51

The chirally enriched population of embodiment 50, wherein the population is enriched for modified oligonucleotides comprising at least one particular phosphorothioate internucleoside linkage having the (Sp) configuration.

Embodiment 52

The chirally enriched population of embodiment 50 or 51, wherein the population is enriched for modified oligonucleotides comprising at least one particular phosphorothioate internucleoside linkage having the (Rp) configuration.

Embodiment 53

The chirally enriched population of embodiment 50, wherein the population is enriched for modified oligonucleotides having a particular, independently selected stereochemical configuration at each phosphorothioate internucleoside linkage Embodiment 54

The chirally enriched population of embodiment 53, wherein the population is enriched for modified oligonucleotides having the (Sp) configuration at each phosphorothioate internucleoside linkage.

Embodiment 55

The chirally enriched population of embodiment 53, wherein the population is enriched for modified oligonucleotides having the (Rp) configuration at each phosphorothioate internucleoside linkage.

Embodiment 56

The chirally enriched population of embodiment 50 or embodiment 53 wherein the population is enriched for modified oligonucleotides having at least 3 contiguous phosphorothioate internucleoside linkages in the Sp-Sp-Rp configuration, in the 5' to 3' direction.

Embodiment 57

A population of modified oligonucleotides of any of embodiments 37-49, wherein all of the phosphorothioate internucleoside linkages of the modified oligonucleotide are stereorandom.

Embodiment 58

A pharmaceutical composition comprising the modified oligonucleotide of any of embodiments 37-49 and a pharmaceutically acceptable diluent or carrier.

Embodiment 59

The pharmaceutical composition of embodiment 58, wherein the pharmaceutically acceptable diluent is artificial cerebrospinal fluid.

Embodiment 60

The pharmaceutical composition of embodiment 59, wherein the pharmaceutical composition consists essentially of the modified oligonucleotide and artificial cerebrospinal fluid.

Embodiment 61

A method comprising administering to an animal a pharmaceutical composition of any of embodiments 36 or 58-60.

Embodiment 62

A method of treating a disease associated with ATXN2 comprising administering to an individual having or at risk for developing a disease associated with ATXN2 a therapeutically effective amount of a pharmaceutical composition according to any of embodiments 36 or 58-60; and thereby treating the disease associated with ATXN2.

Embodiment 63

The method of embodiment 62, wherein the disease associated with ATXN2 is a neurodegenerative disease.

Embodiment 64

The method of embodiment 63, wherein the neurodegenerative disease is any of spinocerebellar ataxia type 2 (SCA2), amyotrophic lateral sclerosis (ALS), and parkinsonism.

Embodiment 65

The method of embodiment 64, wherein at least one symptom or hallmark of the neurodegenerative disease is ameliorated.

Embodiment 66

The method of embodiment 65, wherein the symptom or hallmark is any of ataxia, neuropathy, and aggregate formation.

Embodiment 67

An oligomeric compound comprising a modified oligonucleotide according to the following formula:
Ges Teo Aeo mCeo Teo Tds Tds Tds mCds Tds mCds Ads Tds Gds Tds Geo mCeo Ges Ges mCe (SEQ ID NO: 1714); wherein,
  A=an adenine nucleobase,
  mC=a 5'-methyl cytosine nucleobase,
  G=a guanine nucleobase,
  T=a thymine nucleobase,
  e=a 2'-MOE modified sugar,
  d=a 2'-deoxyribose sugar,
  s=a phosphorothioate internucleoside linkage, and
  o=a phosphodiester internucleoside linkage.

Embodiment 68

An oligomeric compound comprising a modified oligonucleotide according to the following formula: mCes Teo Geo mCeo Tds Ads Ads mCds Tds Gds Gds Tds Tds Tds Geo mCeo mCeo mCes Tes Te (SEQ ID NO: 1255); wherein,
  A=an adenine nucleobase,
  mC=a 5'-methyl cytosine nucleobase,
  G=a guanine nucleobase,
  T=a thymine nucleobase,
  e=a 2'-MOE modified sugar,
  d=a 2'-deoxyribose sugar,
  s=a phosphorothioate internucleoside linkage, and
  o=a phosphodiester internucleoside linkage.

Embodiment 69

An oligomeric compound comprising a modified oligonucleotide according to the following formula: Tes Geo Teo Aeo mCeo Teo Tds mCds Ads mCds Ads Tds Tds Tds Gds Gds Aeo Ges mCes mCe (SEQ ID NO: 1185); wherein,
  A=an adenine nucleobase,
  mC=a 5'-methyl cytosine nucleobase,
  G=a guanine nucleobase,
  T=a thymine nucleobase,
  e=a 2'-MOE modified sugar,
  d=a 2'-deoxyribose sugar,
  s=a phosphorothioate internucleoside linkage, and
  o=a phosphodiester internucleoside linkage.

Embodiment 70

An oligomeric compound comprising a modified oligonucleotide according to the following formula: Tes Geo Geo Aeo Teo Teo mCds Tds Gds Tds Ads mCds Tds Tds Tds Tds mCeo Tes mCes Ae (SEQ ID NO: 3235); wherein,
  A=an adenine nucleobase,
  mC=a 5'-methyl cytosine nucleobase, G=a guanine nucleobase,
T=a thymine nucleobase,
e=a 2'-MOE modified sugar,
d=a 2'-deoxyribose sugar,
s=a phosphorothioate internucleoside linkage, and
o=a phosphodiester internucleoside linkage.

Embodiment 71

An oligomeric compound comprising a modified oligonucleotide according to the following formula: mCes mCeo Teo Aeo Teo mCeo Ads Tds mCds Ads Tds Tds Tds Tds mCds mCds Aeo Ges Ges Ge (SEQ ID NO: 158); wherein,
A=an adenine nucleobase,
mC=a 5'-methyl cytosine nucleobase,
G=a guanine nucleobase,
T=a thymine nucleobase,
e=a 2'-MOE modified sugar,
d=a 2'-deoxyribose sugar,
s=a phosphorothioate internucleoside linkage, and
o=a phosphodiester internucleoside linkage.

Embodiment 72

An oligomeric compound comprising a modified oligonucleotide according to the following formula: Tes mCeo Teo Geo Tes Ads mCds Tds Tds Tds Tds mCds Tds mCds Ads Teo Geo Tes Ges mCe (SEQ ID NO: 2544); wherein,
A=an adenine nucleobase,
mC=a 5'-methyl cytosine nucleobase,
G=a guanine nucleobase,
T=a thymine nucleobase,
e=a 2'-MOE modified sugar,
d=a 2'-deoxyribose sugar,
s=a phosphorothioate internucleoside linkage, and
o=a phosphodiester internucleoside linkage.

Embodiment 73

The oligomeric compound of embodiment 3, wherein the modified oligonucleotide is an RNAi compound.

Embodiment 74

The oligomeric compound of embodiment 73, wherein the RNAi compound is an ssRNA or an siRNA.

I. Certain Oligonucleotides

In certain embodiments, provided herein are oligomeric compounds comprising oligonucleotides, which consist of linked nucleosides. Oligonucleotides may be unmodified oligonucleotides (RNA or DNA) or may be modified oligonucleotides. Modified oligonucleotides comprise at least one modification relative to unmodified RNA or DNA. That is, modified oligonucleotides comprise at least one modified nucleoside (comprising a modified sugar moiety and/or a modified nucleobase) and/or at least one modified internucleoside linkage.

A. Certain Modified Nucleosides

Modified nucleosides comprise a modified sugar moiety or a modified nucleobase or both a modifed sugar moiety and a modified nucleobase.

1. Certain Sugar Moieties

In certain embodiments, modified sugar moieties are non-bicyclic modified sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of other types of modified sugar moieties.

In certain embodiments, modified sugar moieties are non-bicyclic modified sugar moieties comprising a furanosyl ring with one or more substituent groups none of which bridges two atoms of the furanosyl ring to form a bicyclic structure. Such non bridging substituents may be at any position of the furanosyl, including but not limited to substituents at the 2', 4', and/or 5' positions. In certain embodiments one or more non-bridging substituent of non-bicyclic modified sugar moieties is branched. Examples of 2'-substituent groups suitable for non-bicyclic modified sugar moieties include but are not limited to: 2'-F, 2'-OCH$_3$ ("OMe" or "O-methyl"), and 2'-O(CH$_2$)$_2$OCH$_3$ ("MOE"). In certain embodiments, 2'-substituent groups are selected from among: halo, allyl, amino, azido, SH, CN, OCN, CF$_3$, OCF$_3$, O—C$_1$-C$_{10}$ alkoxy, O—C$_1$-C$_{10}$ substituted alkoxy, O—C$_1$-C$_{10}$ alkyl, O—C$_1$-C$_{10}$ substituted alkyl, S-alkyl, N(R$_m$)-alkyl, O-alkenyl, S-alkenyl, N(R$_m$)-alkenyl, O-alkynyl, S-alkynyl, N(R$_m$)-alkynyl, O-alkylenyl-O-alkyl, alkynyl, alkaryl, aralkyl, O-alkaryl, O-aralkyl, O(CH$_2$)$_2$SCH$_3$, O(CH$_2$)$_2$ON(R$_m$)(R$_n$) or OCH$_2$C(=O)—N(R$_m$)(R$_n$), where each R$_m$ and R$_n$ is, independently, H, an amino protecting group, or substituted or unsubstituted C$_1$-C$_{10}$ alkyl, and the 2'-substituent groups described in Cook et al., U.S. Pat. No. 6,531,584; Cook et al., U.S. Pat. No. 5,859,221; and Cook et al., U.S. Pat. No. 6,005,087. Certain embodiments of these 2'-substituent groups can be further substituted with one or more substituent groups independently selected from among: hydroxyl, amino, alkoxy, carboxy, benzyl, phenyl, nitro (NO$_2$), thiol, thioalkoxy, thioalkyl, halogen, alkyl, aryl, alkenyl and alkynyl. Examples of 4'-substituent groups suitable for non-bicyclic modified sugar moieties include but are not limited to alkoxy (e.g., methoxy), alkyl, and those described in Manoharan et al., WO 2015/106128. Examples of 5'-substituent groups suitable for non-bicyclic modified sugar moieties include but are not limited to: 5-methyl (R or S), 5'-vinyl, and 5'-methoxy. In certain embodiments, non-bicyclic modified sugar moieties comprise more than one non-bridging sugar substituent, for example, 2'-F-5'-methyl sugar moieties and the modified sugar moieties and modified nucleosides described in Migawa et al., WO 2008/101157 and Rajeev et al., US2013/0203836.

In certain embodiments, a 2'-substituted non-bicyclic modified nucleoside comprises a sugar moiety comprising a non-bridging 2'-substituent group selected from: F, NH$_2$, N$_3$, OCF$_3$, OCH$_3$, O(CH$_2$)$_3$NH$_2$, CH$_2$CH=CH$_2$, OCH$_2$CH=CH$_2$, OCH$_2$CH$_2$OCH$_3$, O(CH$_2$)$_2$SCH$_3$, O(CH$_2$)$_2$ON(R$_m$)(R$_n$), O(CH$_2$)$_2$O(CH$_2$)$_2$N(CH$_3$)$_2$, and N-substituted acetamide (OCH$_2$C(=O)—N(R$_m$)(R$_n$)), where each R$_m$ and R$_n$ is, independently, H, an amino protecting group, or substituted or unsubstituted C$_1$-C$_{10}$ alkyl.

In certain embodiments, a 2'-substituted nucleoside non-bicyclic modified nucleoside comprises a sugar moiety comprising a non-bridging 2'-substituent group selected from: F, OCF$_3$, OCH$_3$, OCH$_2$CH$_2$OCH$_3$, O(CH$_2$)$_2$SCH$_3$, O(CH$_2$)$_2$ON(CH$_3$)$_2$, O(CH$_2$)$_2$O(CH$_2$)$_2$N(CH$_3$)$_2$, and OCH$_2$C(=O)—N(H)CH$_3$ ("NMA").

In certain embodiments, a 2'-substituted non-bicyclic modified nucleoside comprises a sugar moiety comprising a non-bridging 2'-substituent group selected from: F, OCH$_3$, and OCH$_2$CH$_2$OCH$_3$.

Certain modified sugar moieties comprise a substituent that bridges two atoms of the furanosyl ring to form a second ring, resulting in a bicyclic sugar moiety. In certain such embodiments, the bicyclic sugar moiety comprises a bridge between the 4' and the 2' furanose ring atoms. Examples of such 4' to 2' bridging sugar substituents include but are not limited to: 4'-CH$_2$-2', 4'-(CH$_2$)$_2$-2', 4'-(CH$_2$)$_3$-2', 4'-CH$_2$—O-2' ("LNA"), 4'-CH$_2$—S-2', 4'-(CH$_2$)$_2$—O-2' ("ENA"), 4'-CH(CH$_3$)—O-2' (referred to as "constrained ethyl" or "cEt"), 4'-CH$_2$—O—CH$_2$-2', 4'-CH$_2$—N(R)-2', 4'-CH(CH$_2$OCH$_3$)—O-2' ("constrained MOE" or "cMOE") and analogs thereof (see, e.g., Seth et al., U.S. Pat. No. 7,399,845, Bhat et al., U.S. Pat. No. 7,569,686, Swayze et al., U.S. Pat. No. 7,741,457, and Swayze et al., U.S. Pat. No. 8,022,193), 4'-C(CH$_3$)(CH$_3$)—O-2' and analogs thereof (see, e.g., Seth et al., U.S. Pat. No. 8,278,283), 4'-CH$_2$—N(OCH$_3$)-2' and analogs thereof (see, e.g., Prakash et al., U.S. Pat. No. 8,278,425), 4'-CH$_2$—O—N(CH$_3$)-2' (see, e.g., Allerson et al., U.S. Pat. No. 7,696,345 and Allerson et al., U.S. Pat. No. 8,124,745), 4'-CH$_2$—C(H)(CH$_3$)-2' (see, e.g., Zhou, et al., J. Org. Chem., 2009, 74, 118-134), 4'-CH$_2$—C(=CH$_2$)-2' and analogs thereof (see e.g., Seth et al., U.S. Pat. No. 8,278,426), 4'-C(R$_a$R$_b$)—N(R)—O-2', 4'-C(R$_a$R$_b$)—O—N(R)-2', 4'-CH$_2$—O—N(R)-2', and 4'-CH$_2$—N(R)—O- 2', wherein each R, R$_a$, and R$_b$ is, independently, H, a protecting group, or C$_1$-C$_{12}$ alkyl (see, e.g. Imanishi et al., U.S. Pat. No. 7,427,672).

In certain embodiments, such 4' to 2' bridges independently comprise from 1 to 4 linked groups independently selected from: —[C(R$_a$)(R$_b$)]$_n$—, —[C(R$_a$)(R$_b$)]$_n$—O—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl, or a protecting group.

Additional bicyclic sugar moieties are known in the art, see, for example: Freier et al., *Nucleic Acids Research*, 1997, 25(22), 4429-4443, Albaek et al., *J. Org. Chem.*, 2006, 71, 7731-7740, Singh et al., *Chem. Commun.*, 1998, 4, 455-456; Koshkin et al., *Tetrahedron*, 1998, 54, 3607-3630; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 2007, 129, 8362-8379; Wengel et a., U.S. Pat. No. 7,053,207; Imanishi et al., U.S. Pat. No. 6,268,490; Imanishi et al. U.S. Pat. No. 6,770,748; Imanishi et al., U.S. Pat. No. RE44,779; Wengel et al., U.S. Pat. No. 6,794,499; Wengel et al., U.S. Pat. No. 6,670,461; Wengel et al., U.S. Pat. No. 7,034,133; Wengel et al., U.S. Pat. No. 8,080,644; Wengel et al., U.S. Pat. No. 8,034,909; Wengel et al., U.S. Pat. No. 8,153,365; Wengel et al., U.S. Pat. No. 7,572,582; and Ramasamy et al., U.S. Pat. No. 6,525,191; Torsten et al., WO 2004/106356; Wengel et al., WO 1999/014226; Seth et al., WO 2007/134181; Seth et al., U.S. Pat. No. 7,547,684; Seth et al., U.S. Pat. No. 7,666,854; Seth et al., U.S. Pat. No. 8,088,746; Seth et al., U.S. Pat. No. 7,750,131; Seth et al., U.S. Pat. No. 8,030,467; Seth et al., U.S. Pat. No. 8,268,980; Seth et al., U.S. Pat. No. 8,546,556; Seth et al., U.S. Pat. No. 8,530,640; Migawa et al., U.S. Pat. No. 9,012,421; Seth et al., U.S. Pat. No. 8,501,805; and U.S. Patent Publication Nos. Allerson et al., US2008/0039618 and Migawa et al., US2015/0191727.

In certain embodiments, bicyclic sugar moieties and nucleosides incorporating such bicyclic sugar moieties are further defined by isomeric configuration. For example, an LNA nucleoside (described herein) may be in the α-L configuration or in the β-D configuration.

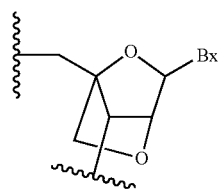

LNA (β-D-configuration)
bridge = 4'-CH$_2$—O-2'

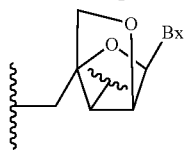

α-L-LNA (α-L-configuration)
bridge = 4'-CH$_2$—O-2'

α-L-methyleneoxy (4'-CH$_2$—O-2') or α-L-LNA bicyclic nucleosides have been incorporated into oligonucleotides that showed antisense activity (Frieden et al., *Nucleic Acids Research*, 2003, 21, 6365-6372). Herein, general descriptions of bicyclic nucleosides include both isomeric configurations. When the positions of specific bicyclic nucleosides (e.g., LNA or cEt) are identified in exemplified embodiments herein, they are in the β-D configuration, unless otherwise specified.

In certain embodiments, modified sugar moieties comprise one or more non-bridging sugar substituent and one or more bridging sugar substituent (e.g., 5'-substituted and 4'-2' bridged sugars).

In certain embodiments, modified sugar moieties are sugar surrogates. In certain such embodiments, the oxygen atom of the sugar moiety is replaced, e.g., with a sulfur, carbon or nitrogen atom. In certain such embodiments, such modified sugar moieties also comprise bridging and/or non-bridging substituents as described herein. For example, certain sugar surrogates comprise a 4'-sulfur atom and a substitution at the 2'-position (see, e.g., Bhat et al., U.S. Pat. No. 7,875,733 and Bhat et al., U.S. Pat. No. 7,939,677) and/or the 5' position.

In certain embodiments, sugar surrogates comprise rings having other than 5 atoms. For example, in certain embodiments, a sugar surrogate comprises a six-membered tetrahydropyran ("THP"). Such tetrahydropyrans may be further modified or substituted. Nucleosides comprising such modified tetrahydropyrans include but are not limited to hexitol nucleic acid ("HNA"), anitol nucleic acid ("ANA"), manitol nucleic acid ("MNA") (see, e.g., Leumann, C J. *Bioorg. & Med. Chem.* 2002, 10, 841-854), fluoro HNA:

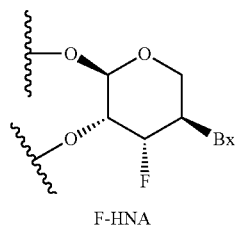

F-HNA ("F-HNA", see e.g. Swayze et al., U.S. Pat. No. 8,088,904; Swayze et al., U.S. Pat. No. 8,440,803; Swayze et al., U.S. Pat. No. 8,796,437; and Swayze et al., U.S. Pat. No. 9,005,906; F-HNA can also be referred to as a F-THP or 3'-fluoro tetrahydropyran), and nucleosides comprising additional modified THP compounds having the formula:

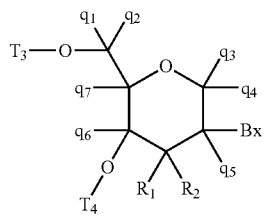

wherein, independently, for each of said modified THP nucleoside:

Bx is a nucleobase moiety;

$T_3$ and $T_4$ are each, independently, an internucleoside linking group linking the modified THP nucleoside to the remainder of an oligonucleotide or one of $T_3$ and $T_4$ is an internucleoside linking group linking the modified THP nucleoside to the remainder of an oligonucleotide and the other of $T_3$ and $T_4$ is H, a hydroxyl protecting group, a linked conjugate group, or a 5' or 3'-terminal group;

$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, modified THP nucleosides are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, modified THP nucleosides are provided wherein one of $R_1$ and $R_2$ is F. In certain embodiments, $R_1$ is F and $R_2$ is H, in certain embodiments, $R_1$ is methoxy and $R_2$ is H, and in certain embodiments, $R_1$ is methoxyethoxy and $R_2$ is H.

In certain embodiments, sugar surrogates comprise rings having more than 5 atoms and more than one heteroatom. For example, nucleosides comprising morpholino sugar moieties and their use in oligonucleotides have been reported (see, e.g., Braasch et al., Biochemistry, 2002, 41, 4503-4510 and Summerton et al., U.S. Pat. No. 5,698,685; Summerton et al., U.S. Pat. No. 5,166,315; Summerton et al., U.S. Pat. No. 5,185,444; and Summerton et al., U.S. Pat. No. 5,034,506). As used here, the term "morpholino" means a sugar surrogate having the following structure:

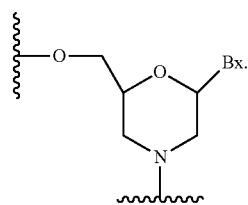

In certain embodiments, morpholinos may be modified, for example by adding or altering various substituent groups from the above morpholino structure. Such sugar surrogates are referred to herein as "modifed morpholinos."

In certain embodiments, sugar surrogates comprise acyclic moieites. Examples of nucleosides and oligonucleotides comprising such acyclic sugar surrogates include but are not limited to: peptide nucleic acid ("PNA"), acyclic butyl nucleic acid (see, e.g., Kumar et al., Org. Biomol. Chem., 2013, 11, 5853-5865), and nucleosides and oligonucleotides described in Manoharan et al., WO2011/133876.

Many other bicyclic and tricyclic sugar and sugar surrogate ring systems are known in the art that can be used in modified nucleosides.

2. Certain Modified Nucleobases

In certain embodiments, modified oligonucleotides comprise one or more nucleoside comprising an unmodified nucleobase. In certain embodiments, modified oligonucleotides comprise one or more nucleoside comprising a modified nucleobase. In certain embodiments, modified oligonucleotides comprise one or more nucleoside that does not comprise a nucleobase, referred to as an abasic nucleoside.

In certain embodiments, modified nucleobases are selected from: 5-substituted pyrimidines, 6-azapyrimidines, alkyl or alkynyl substituted pyrimidines, alkyl substituted purines, and N-2, N-6 and O-6 substituted purines. In certain embodiments, modified nucleobases are selected from: 2-aminopropyladenine, 5-hydroxymethyl cytosine, xanthine, hypoxanthine, 2-aminoadenine, 6-N-methylguanine, 6-N-methyladenine, 2-propyladenine 2-thiouracil, 2-thiothymine and 2-thiocytosine, 5-propynyl (—C≡C—CH$_3$) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp). Modified nucleobases may also include those in which the purine or pyrimidine base is replaced with other heterocycles, for example 7-deazaadenine, 7-deazaguanosine, 2-aminopyridine and 2-pyridone. Further nucleobases include those disclosed in Merigan et al., U.S. Pat. No. 3,687,808, those disclosed in i The Concise Encyclopedia Of Polymer Science And Engineering, Kroschwitz, J. I., Ed., John Wiley & Sons, 1990, 858-859; Englisch et al., Angewandte Chemie, International Edition, 1991, 30, 613; Sanghvi, Y. S., Chapter 15, Antisense Research and Applications, Crooke, S. T. and Lebleu, B., Eds., CRC Press, 1993, 273-288; and those disclosed in Chapters 6 and 15, *Antisense Drug Technology*, Crooke S. T., Ed., CRC Press, 2008, 163-166 and 442-443.

Publications that teach the preparation of certain of the above noted modified nucleobases as well as other modified nucleobases include without limitation, Manohara et al., US2003/0158403; Manoharan et al., US2003/0175906; Dinh et al., U.S. Pat. No. 4,845,205; Spielvogel et al., U.S. Pat. No. 5,130,302; Rogers et al., U.S. Pat. No. 5,134,066; Bischofberger et al., U.S. Pat. No. 5,175,273; Urdea et al., U.S. Pat. No. 5,367,066; Benner et al., U.S. Pat. No. 5,432,272; Matteucci et al., U.S. Pat. No. 5,434,257; Gmeiner et al., U.S. Pat. No. 5,457,187; Cook et al., U.S. Pat. No. 5,459,255; Froehler et al., U.S. Pat. No. 5,484,908; Matteucci et al., U.S. Pat. No. 5,502,177; Hawkins et al., U.S. Pat. No. 5,525,711; Haralambidis et al., U.S. Pat. No. 5,552,540; Cook et al., U.S. Pat. No. 5,587,469; Froehler et al., U.S. Pat. No. 5,594,121; Switzer et al., U.S. Pat. No. 5,596,091; Cook et al., U.S. Pat. No. 5,614,617; Froehler et al., U.S. Pat. No. 5,645,985; Cook et al., U.S. Pat. No. 5,681,941; Cook et al., U.S. Pat. No. 5,811,534; Cook et al., U.S. Pat. No. 5,750,692; Cook et al., U.S. Pat. No. 5,948,903; Cook et al., U.S. Pat. No. 5,587,470; Cook et al., U.S. Pat. No. 5,457,191; Matteucci et al., U.S. Pat. No. 5,763,588; Froehler et al., U.S. Pat. No. 5,830,653; Cook et al., U.S. Pat. No. 5,808,027; Cook et al., U.S. Pat. No. 6,166,199; and Matteucci et al., U.S. Pat. No. 6,005,096.

3. Certain Modified Internucleoside Linkages

In certain embodiments, nucleosides of modified oligonucleotides may be linked together using any internucleoside linkage. The two main classes of internucleoside linking groups are defined by the presence or absence of a phosphorus atom. Representative phosphorus-containing internucleoside linkages include but are not limited to phosphates, which contain a phosphodiester bond ("P=O") (also referred to as unmodified or naturally occurring linkages), phosphotriesters, methylphosphonates, phosphoramidates, and phosphorothioates ("P=S"), and phosphorodithioates ("HS—P=S"). Representative non-phosphorus containing internucleoside linking groups include but are not limited to methylenemethylimino (—CH$_2$—N(CH$_3$)—O—CH$_2$—), thiodiester, thionocarbamate (—O—C(=O)(NH)—S—); siloxane (—O—SiH$_2$—O—); and N,N'-dimethylhydrazine (—CH$_2$—N(CH$_3$)—N(CH$_3$)—). Modified internucleoside linkages, compared to naturally occurring phosphate linkages, can be used to alter, typically increase, nuclease resistance of the oligonucleotide. In certain embodiments, internucleoside linkages having a chiral atom can be prepared as a racemic mixture, or as separate enantiomers. Methods of preparation of phosphorous-containing and non-phosphorous-containing internucleoside linkages are well known to those skilled in the art.

Representative internucleoside linkages having a chiral center include but are not limited to alkylphosphonates and phosphorothioates. Modified oligonucleotides comprising internucleoside linkages having a chiral center can be prepared as populations of modified oligonucleotides comprising stereorandom internucleoside linkages, or as populations of modified oligonucleotides comprising phosphorothioate linkages in particular stereochemical configurations. In certain embodiments, populations of modified oligonucleotides comprise phosphorothioate internucleoside linkages wherein all of the phosphorothioate internucleoside linkages are stereorandom. Such modified oligonucleotides can be generated using synthetic methods that result in random selection of the stereochemical configuration of each phosphorothioate linkage. Nonetheless, as is well understood by those of skill in the art, each individual phosphorothioate of each individual oligonucleotide molecule has a defined stereoconfiguration. In certain embodiments, populations of modified oligonucleotides are enriched for modified oligonucleotides comprising one or more particular phosphorothioate internucleoside linkages in a particular, independently selected stereochemical configuration. In certain embodiments, the particular configuration of the particular phosphorothioate linkage is present in at least 65% of the molecules in the population. In certain embodiments, the particular configuration of the particular phosphorothioate linkage is present in at least 70% of the molecules in the population. In certain embodiments, the particular configuration of the particular phosphorothioate linkage is present in at least 80% of the molecules in the population. In certain embodiments, the particular configuration of the particular phosphorothioate linkage is present in at least 90% of the molecules in the population. In certain embodiments, the particular configuration of the particular phosphorothioate linkage is present in at least 99% of the molecules in the population. Such chirally enriched populations of modified oligonucleotides can be generated using synthetic methods known in the art, e.g., methods described in Oka et al., *JACS* 125, 8307 (2003), Wan et al. *Nuc. Acid. Res.* 42, 13456 (2014), and WO 2017/015555. In certain embodiments, a population of modified oligonucleotides is enriched for modified oligonucleotides having at least one indicated phosphorothioate in the (Sp) configuration. In certain embodiments, a population of modified oligonucleotides is enriched for modified oligonucleotides having at least one phosphorothioate in the (Rp) configuration. In certain embodiments, modified oligonucleotides comprising (Rp) and/or (Sp) phosphorothioates comprise one or more of the following formulas, respectively, wherein "B" indicates a nucleobase:

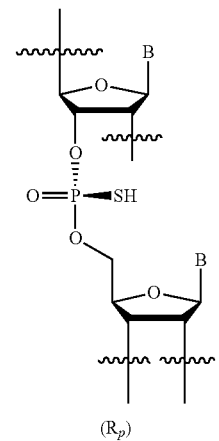

(R$_p$)

-continued

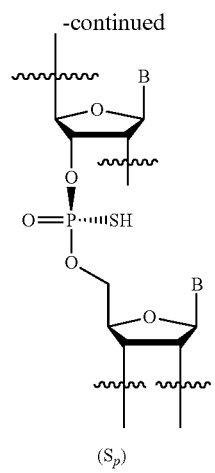

($S_p$)

Unless otherwise indicated, chiral internucleoside linkages of modified oligonucleotides described herein can be stereorandom or in a particular stereochemical configuration.

Neutral internucleoside linkages include, without limitation, phosphotriesters, methylphosphonates, MMI (3'-$CH_2$—N($CH_3$)—O-5'), amide-3 (3'-$CH_2$—C(=O)—N(H)-5'), amide-4 (3'-$CH_2$—N(H)—C(=O)-5'), formacetal (3'-O—$CH_2$—O-5'), methoxypropyl, and thioformacetal (3'-S—$CH_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

B. Certain Motifs

In certain embodiments, modified oligonucleotides comprise one or more modified nucleosides comprising a modified sugar moiety. In certain embodiments, modified oligonucleotides comprise one or more modified nucleosides comprising a modified nucleobase. In certain embodiments, modified oligonucleotides comprise one or more modified internucleoside linkage. In such embodiments, the modified, unmodified, and differently modified sugar moieties, nucleobases, and/or internucleoside linkages of a modified oligonucleotide define a pattern or motif. In certain embodiments, the patterns of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the sequence of nucleobases).

1. Certain Sugar Motifs

In certain embodiments, oligonucleotides comprise one or more type of modified sugar and/or unmodified sugar moiety arranged along the oligonucleotide or region thereof in a defined pattern or sugar motif. In certain instances, such sugar motifs include but are not limited to any of the sugar modifications discussed herein.

In certain embodiments, modified oligonucleotides comprise or consist of a region having a gapmer motif, which is defined by two external regions or "wings" and a central or internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap (i.e., the wing/gap junction). In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric gapmer). In certain embodiments, the sugar motif of the 5'-wing differs from the sugar motif of the 3'-wing (asymmetric gapmer).

In certain embodiments, the wings of a gapmer comprise 1-5 nucleosides. In certain embodiments, each nucleoside of each wing of a gapmer is a modified nucleoside. In certain embodiments, at least one nucleoside of each wing of a gapmer is a modified nucleoside. In certain embodiments, at least two nucleosides of each wing of a gapmer are modified nucleosides. In certain embodiments, at least three nucleosides of each wing of a gapmer are modified nucleosides. In certain embodiments, at least four nucleosides of each wing of a gapmer are modified nucleosides.

In certain embodiments, the gap of a gapmer comprises 7-12 nucleosides. In certain embodiments, each nucleoside of the gap of a gapmer is an unmodified 2'-deoxy nucleoside. In certain embodiments, at least one nucleoside of the gap of a gapmer is a modified nucleoside.

In certain embodiments, the gapmer is a deoxy gapmer. In certain embodiments, the nucleosides on the gap side of each wing/gap junction are unmodified 2'-deoxy nucleosides and the nucleosides on the wing sides of each wing/gap junction are modified nucleosides. In certain embodiments, each nucleoside of the gap is an unmodified 2'-deoxy nucleoside. In certain embodiments, each nucleoside of each wing of a gapmer is a modified nucleoside.

In certain embodiments, modified oligonucleotides comprise or consist of a region having a fully modified sugar motif. In such embodiments, each nucleoside of the fully modified region of the modified oligonucleotide comprises a modified sugar moiety. In certain embodiments, each nucleoside of the entire modified oligonucleotide comprises a modified sugar moiety. In certain embodiments, modified oligonucleotides comprise or consist of a region having a fully modified sugar motif, wherein each nucleoside within the fully modified region comprises the same modified sugar moiety, referred to herein as a uniformly modified sugar motif. In certain embodiments, a fully modified oligonucleotide is a uniformly modified oligonucleotide. In certain embodiments, each nucleoside of a uniformly modified comprises the same 2'-modification.

Herein, the lengths (number of nucleosides) of the three regions of a gapmer may be provided using the notation [# of nucleosides in the 5'-wing]-[# of nucleosides in the gap]-[# of nucleosides in the 3'-wing]. Thus, a 5-10-5 gapmer consists of 5 linked nucleosides in each wing and 10 linked nucleosides in the gap. Where such nomenclature is followed by a specific modification, that modification is the modification in each sugar moiety of each wing and the gap nucleosides comprise unmodified deoxynucleosides sugars. Thus, a 5-10-5 MOE gapmer consists of 5 linked MOE modified nucleosides in the 5'-wing, 10 linked deoxynucleosides in the gap, and 5 linked MOE nucleosides in the 3'-wing.

In certain embodiments, modified oligonucleotides are 5-10-5 MOE gapmers. In certain embodiments, modified oligonucleotides are 3-10-3 BNA gapmers. In certain embodiments, modified oligonucleotides are 3-10-3 cEt gapmers. In certain embodiments, modified oligonucleotides are 3-10-3 LNA gapmers.

2. Certain Nucleobase Motifs

In certain embodiments, oligonucleotides comprise modified and/or unmodified nucleobases arranged along the oligonucleotide or region thereof in a defined pattern or motif. In certain embodiments, each nucleobase is modified. In certain embodiments, none of the nucleobases are modified. In certain embodiments, each purine or each pyrimidine is modified. In certain embodiments, each adenine is modified. In certain embodiments, each guanine is modified. In certain embodiments, each thymine is modified. In certain embodiments, each uracil is modified. In certain embodiments, each cytosine is modified. In certain embodiments, some or all of the cytosine nucleobases in a modified oligonucleotide are 5-methyl cytosines. In certain embodiments, all of the cytosine nucleobases are 5-methyl cytosines and all of the other nucleobases of the modified oligonucleotide are unmodified nucleobases.

In certain embodiments, modified oligonucleotides comprise a block of modified nucleobases. In certain such embodiments, the block is at the 3'-end of the oligonucleotide. In certain embodiments the block is within 3 nucleosides of the 3'-end of the oligonucleotide. In certain embodiments, the block is at the 5'-end of the oligonucleotide. In certain embodiments the block is within 3 nucleosides of the 5'-end of the oligonucleotide.

In certain embodiments, oligonucleotides having a gapmer motif comprise a nucleoside comprising a modified nucleobase. In certain such embodiments, one nucleoside comprising a modified nucleobase is in the central gap of an oligonucleotide having a gapmer motif. In certain such embodiments, the sugar moiety of said nucleoside is a 2'-deoxyribosyl moiety. In certain embodiments, the modified nucleobase is selected from: a 2-thiopyrimidine and a 5-propynepyrimidine.

3. Certain Internucleoside Linkage Motifs

In certain embodiments, oligonucleotides comprise modified and/or unmodified internucleoside linkages arranged along the oligonucleotide or region thereof in a defined pattern or motif. In certain embodiments, each internucleoside linking group is a phosphodiester internucleoside linkage (P=O). In certain embodiments, each internucleoside linking group of a modified oligonucleotide is a phosphorothioate internucleoside linkage (P=S). In certain embodiments, each internucleoside linkage of a modified oligonucleotide is independently selected from a phosphorothioate internucleoside linkage and phosphodiester internucleoside linkage. In certain embodiments, each phosphorothioate internucleoside linkage is independently selected from a stereorandom phosphorothioate, a (Sp) phosphorothioate, and a (Rp) phosphorothioate. In certain embodiments, the sugar motif of a modified oligonucleotide is a gapmer and the internucleoside linkages within the gap are all modified. In certain such embodiments, some or all of the internucleoside linkages in the wings are unmodified phosphodiester internucleoside linkages. In certain embodiments, the terminal internucleoside linkages are modified. In certain embodiments, the sugar motif of a modified oligonucleotide is a gapmer, and the internucleoside linkage motif comprises at least one phosphodiester internucleoside linkage in at least one wing, wherein the at least one phosphodiester linkage is not a terminal internucleoside linkage, and the remaining internucleoside linkages are phosphorothioate internucleoside linkages. In certain such embodiments, all of the phosphorothioate linkages are stereorandom. In certain embodiments, all of the phosphorothioate linkages in the wings are (Sp) phosphorothioates, and the gap comprises at least one Sp, Sp, Rp motif. In certain embodiments, populations of modified oligonucleotides are enriched for modified oligonucleotides comprising such internucleoside linkage motifs.

C. Certain Lengths

It is possible to increase or decrease the length of an oligonucleotide without eliminating activity. For example, in Woolf et al. (Proc. Natl. Acad. Sci. USA 89:7305-7309, 1992), a series of oligonucleotides 13-25 nucleobases in length were tested for their ability to induce cleavage of a target RNA in an oocyte injection model. Oligonucleotides 25 nucleobases in length with 8 or 11 mismatch bases near the ends of the oligonucleotides were able to direct specific cleavage of the target mRNA, albeit to a lesser extent than the oligonucleotides that contained no mismatches. Similarly, target specific cleavage was achieved using 13 nucleobase oligonucleotides, including those with 1 or 3 mismatches.

In certain embodiments, oligonucleotides (including modified oligonucleotides) can have any of a variety of ranges of lengths. In certain embodiments, oligonucleotides consist of X to Y linked nucleosides, where X represents the fewest number of nucleosides in the range and Y represents the largest number nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, oligonucleotides consist of 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides D. Certain Modified Oligonucleotides In certain embodiments, the above modifications (sugar, nucleobase, internucleoside linkage) are incorporated into a modified oligonucleotide. In certain embodiments, modified oligonucleotides are characterized by their modification motifs and overall lengths. In certain embodiments, such parameters are each independent of one another. Thus, unless otherwise indicated, each internucleoside linkage of an oligonucleotide having a gapmer sugar motif may be modified or unmodified and may or may not follow the gapmer modification pattern of the sugar modifications. For example, the internucleoside linkages within the wing regions of a sugar gapmer may be the same or different from one another and may be the same or different from the internucleoside linkages of the gap region of the sugar motif. Likewise, such sugar gapmer oligonucleotides may comprise one or more modified nucleobase independent of the gapmer pattern of the sugar modifications. Unless otherwise indicated, all modifications are independent of nucleobase sequence.

E. Certain Populations of Modified Oligonucleotides

Populations of modified oligonucleotides in which all of the modified oligonucleotides of the population have the same molecular formula can be stereorandom populations or chirally enriched populations. All of the chiral centers of all of the modified oligonucleotides are stereorandom in a stereorandom population. In a chirally enriched population, at least one particular chiral center is not stereorandom in the modified oligonucleotides of the population. In certain embodiments, the modified oligonucleotides of a chirally enriched population are enriched for β-D ribosyl sugar moieties, and all of the phosphorothioate internucleoside linkages are stereorandom. In certain embodiments, the modified oligonucleotides of a chirally enriched population are enriched for both β-D ribosyl sugar moieties and at least one, particular phosphorothioate internucleoside linkage in a particular stereochemical configuration.

F. Nucleobase Sequence

In certain embodiments, oligonucleotides (unmodified or modified oligonucleotides) are further described by their nucleobase sequence. In certain embodiments oligonucleotides have a nucleobase sequence that is complementary to a second oligonucleotide or an identified reference nucleic acid, such as a target nucleic acid. In certain such embodiments, a region of an oligonucleotide has a nucleobase sequence that is complementary to a second oligonucleotide or an identified reference nucleic acid, such as a target nucleic acid. In certain embodiments, the nucleobase sequence of a region or entire length of an oligonucleotide is at least 50%, at least 60%, at least 70%, at least 80%, at least 85%, at least 90%, at least 95%, or 100% complementary to the second oligonucleotide or nucleic acid, such as a target nucleic acid.

II. Certain Oligomeric Compounds

In certain embodiments, provided herein are oligomeric compounds, which consist of an oligonucleotide (modified or unmodified) and optionally one or more conjugate groups and/or terminal groups. Conjugate groups consist of one or more conjugate moiety and a conjugate linker which links the conjugate moiety to the oligonucleotide. Conjugate groups may be attached to either or both ends of an oligonucleotide and/or at any internal position. In certain embodiments, conjugate groups are attached to the 2'-position of a nucleoside of a modified oligonucleotide. In certain embodiments, conjugate groups that are attached to either or both ends of an oligonucleotide are terminal groups. In certain such embodiments, conjugate groups or terminal groups are attached at the 3' and/or 5'-end of oligonucleotides. In certain such embodiments, conjugate groups (or terminal groups) are attached at the 3'-end of oligonucleotides. In certain embodiments, conjugate groups are attached near the 3'-end of oligonucleotides. In certain embodiments, conjugate groups (or terminal groups) are attached at the 5'-end of oligonucleotides. In certain embodiments, conjugate groups are attached near the 5'-end of oligonucleotides.

Examples of terminal groups include but are not limited to conjugate groups, capping groups, phosphate moieties, protecting groups, modified or unmodified nucleosides, and two or more nucleosides that are independently modified or unmodified.

A. Certain Conjugate Groups

In certain embodiments, oligonucleotides are covalently attached to one or more conjugate groups. In certain embodiments, conjugate groups modify one or more properties of the attached oligonucleotide, including but not limited to pharmacodynamics, pharmacokinetics, stability, binding, absorption, tissue distribution, cellular distribution, cellular uptake, charge and clearance. In certain embodiments, conjugate groups impart a new property on the attached oligonucleotide, e.g., fluorophores or reporter groups that enable detection of the oligonucleotide. Certain conjugate groups and conjugate moieties have been described previously, for example: cholesterol moiety (Letsinger et al., Proc. Natl. Acad. Sci. USA, 1989, 86, 6553-6556), cholic acid (Manoharan et al., Bioorg. Med. Chem. Lett., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Lett., 1993, 3, 2765-2770), a thiocholesterol (Oberhauser et al., Nucl. Acids Res., 1992, 20, 533-538), an aliphatic chain, e g., do-decan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid a palmityl moiety (Mishra et al., Biochim. Biophys. Acta, 1995, 1264, 229-237), an octadecylamine or hexylamino-carbonyl-oxycholesterol moiety (Crooke et al., J. Pharmacol. Exp. Ther., 1996, 277, 923-937), a tocopherol group (Nishina et al., Molecular Therapy Nucleic Acids, 2015, 4, e220; and Nishina et al., Molecular Therapy, 2008, 16, 734-740), or a GalNAc cluster (e.g., WO2014/179620).

1. Conjugate Moieties

Conjugate moieties include, without limitation, intercalators, reporter molecules, polyamines, polyamides, peptides, carbohydrates, vitamin moieties, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins, fluorophores, and dyes.

In certain embodiments, a conjugate moiety comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, fingolimod, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

2. Conjugate Linkers

Conjugate moieties are attached to oligonucleotides through conjugate linkers. In certain oligomeric compounds, the conjugate linker is a single chemical bond (i.e., the conjugate moiety is attached directly to an oligonucleotide through a single bond). In certain embodiments, the conjugate linker comprises a chain structure, such as a hydrocarbyl chain, or an oligomer of repeating units such as ethylene glycol, nucleosides, or amino acid units.

In certain embodiments, a conjugate linker comprises one or more groups selected from alkyl, amino, oxo, amide, disulfide, polyethylene glycol, ether, thioether, and hydroxylamino. In certain such embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus moiety. In certain embodiments, the conjugate linker comprises at least one phosphate group. In certain embodiments, the conjugate linker includes at least one neutral linking group.

In certain embodiments, conjugate linkers, including the conjugate linkers described above, are bifunctional linking moieties, e.g., those known in the art to be useful for attaching conjugate groups to parent compounds, such as the oligonucleotides provided herein. In general, a bifunctional linking moiety comprises at least two functional groups. One of the functional groups is selected to react with to a particular site on a parent compound and the other is selected to react with to a conjugate group. Examples of functional groups used in a bifunctional linking moiety include but are not limited to electrophiles for reacting with nucleophilic groups and nucleophiles for reacting with electrophilic groups. In certain embodiments, bifunctional linking moieties comprise one or more groups selected from amino, hydroxyl, carboxylic acid, thiol, alkyl, alkenyl, and alkynyl.

Examples of conjugate linkers include but are not limited to pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other conjugate linkers include but are not limited to substituted or unsubstituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, conjugate linkers comprise 1-10 linker-nucleosides. In certain embodiments, conjugate linkers comprise 2-5 linker-nucleosides. In certain embodiments, conjugate linkers comprise exactly 3 linker-nucleosides. In certain embodiments, conjugate linkers comprise the TCA motif. In certain embodiments, such linker-nucleosides are modified nucleosides. In certain embodiments such linker-nucleosides comprise a modified sugar moiety. In certain embodiments, linker-nucleosides are unmodified. In certain embodiments, linker-nucleosides comprise an optionally protected heterocyclic base selected from a purine, substituted purine, pyrimidine or substituted pyrimidine. In certain embodiments, a cleavable moiety is a nucleoside selected from uracil, thymine, cytosine, 4-N-benzoylcytosine, 5-methyl cytosine, 4-N-benzoyl-5-methyl cytosine, adenine, 6-N-benzoyladenine, guanine and 2-N-isobutyrylguanine. It is typically desirable for linker-nucleosides to be cleaved from the oligomeric compound after it reaches a target tissue. Accordingly, linker-nucleosides are typically linked to one another and to the remainder of the oligomeric compound through cleavable bonds. In certain embodiments, such cleavable bonds are phosphodiester bonds.

Herein, linker-nucleosides are not considered to be part of the oligonucleotide. Accordingly, in embodiments in which an oligomeric compound comprises an oligonucleotide consisting of a specified number or range of linked nucleosides and/or a specified percent complementarity to a reference nucleic acid and the oligomeric compound also comprises a conjugate group comprising a conjugate linker comprising linker-nucleosides, those linker-nucleosides are not counted toward the length of the oligonucleotide and are not used in determining the percent complementarity of the oligonucleotide for the reference nucleic acid. For example, an oligomeric compound may comprise (1) a modified oligonucleotide consisting of 8-30 nucleosides and (2) a conjugate group comprising 1-10 linker-nucleosides that are contiguous with the nucleosides of the modified oligonucleotide. The total number of contiguous linked nucleosides in such an oligomeric compound is more than 30. Alternatively, an oligomeric compound may comprise a modified oligonucleotide consisting of 8-30 nucleosides and no conjugate group. The total number of contiguous linked nucleosides in such an oligomeric compound is no more than 30. Unless otherwise indicated conjugate linkers comprise no more than 10 linker-nucleosides. In certain embodiments, conjugate linkers comprise no more than 5 linker-nucleosides. In certain embodiments, conjugate linkers comprise no more than 3 linker-nucleosides. In certain embodiments, conjugate linkers comprise no more than 2 linker-nucleosides. In certain embodiments, conjugate linkers comprise no more than 1 linker-nucleoside.

In certain embodiments, it is desirable for a conjugate group to be cleaved from the oligonucleotide. For example, in certain circumstances oligomeric compounds comprising a particular conjugate moiety are better taken up by a particular cell type, but once the oligomeric compound has been taken up, it is desirable that the conjugate group be cleaved to release the unconjugated or parent oligonucleotide. Thus, certain conjugate linkers may comprise one or more cleavable moieties. In certain embodiments, a cleavable moiety is a cleavable bond. In certain embodiments, a cleavable moiety is a group of atoms comprising at least one cleavable bond. In certain embodiments, a cleavable moiety comprises a group of atoms having one, two, three, four, or more than four cleavable bonds. In certain embodiments, a cleavable moiety is selectively cleaved inside a cell or subcellular compartment, such as a lysosome. In certain embodiments, a cleavable moiety is selectively cleaved by endogenous enzymes, such as nucleases.

In certain embodiments, a cleavable bond is selected from among: an amide, an ester, an ether, one or both esters of a phosphodiester, a phosphate ester, a carbamate, or a disulfide. In certain embodiments, a cleavable bond is one or both of the esters of a phosphodiester. In certain embodiments, a cleavable moiety comprises a phosphate or phosphodiester. In certain embodiments, the cleavable moiety is a phosphate linkage between an oligonucleotide and a conjugate moiety or conjugate group.

In certain embodiments, a cleavable moiety comprises or consists of one or more linker-nucleosides. In certain such embodiments, the one or more linker-nucleosides are linked to one another and/or to the remainder of the oligomeric compound through cleavable bonds. In certain embodiments, such cleavable bonds are unmodified phosphodiester bonds. In certain embodiments, a cleavable moiety is 2'-deoxy nucleoside that is attached to either the 3' or 5'-terminal nucleoside of an oligonucleotide by a phosphate internucleoside linkage and covalently attached to the remainder of the conjugate linker or conjugate moiety by a phosphate or phosphorothioate linkage. In certain such embodiments, the cleavable moiety is 2'-deoxyadenosine.

B. Certain Terminal Groups

In certain embodiments, oligomeric compounds comprise one or more terminal groups. In certain such embodiments, oligomeric compounds comprise a stabilized 5'-phosphate. Stabilized 5'-phosphates include, but are not limited to 5'-phosphanates, including, but not limited to 5'-vinylphosphonates. In certain embodiments, terminal groups comprise one or more abasic nucleosides and/or inverted nucleosides. In certain embodiments, terminal groups comprise one or more 2'-linked nucleosides. In certain such embodiments, the 2'-linked nucleoside is an abasic nucleoside.

III. Oligomeric Duplexes

In certain embodiments, oligomeric compounds described herein comprise an oligonucleotide, having a nucleobase sequence complementary to that of a target nucleic acid. In certain embodiments, an oligomeric compound is paired with a second oligomeric compound to form an oligomeric duplex. Such oligomeric duplexes comprise a first oligomeric compound having a region complementary to a target nucleic acid and a second oligomeric compound having a region complementary to the first oligomeric compound. In certain embodiments, the first oligomeric compound of an oligomeric duplex comprises or consists of (1) a modified or unmodified oligonucleotide and optionally a conjugate group and (2) a second modified or unmodified oligonucleotide and optionally a conjugate group. Either or both oligomeric compounds of an oligomeric duplex may comprise a conjugate group. The oligonucleotides of each oligomeric compound of an oligomeric duplex may include non-complementary overhanging nucleosides.

IV. Antisense Activity

In certain embodiments, oligomeric compounds and oligomeric duplexes are capable of hybridizing to a target nucleic acid, resulting in at least one antisense activity; such oligomeric compounds and oligomeric duplexes are antisense compounds. In certain embodiments, antisense compounds have antisense activity when they reduce or inhibit the amount or activity of a target nucleic acid by 25% or more in the standard cell assay. In certain embodiments, antisense compounds selectively affect one or more target nucleic acid. Such antisense compounds comprise a nucleobase sequence that hybridizes to one or more target nucleic acid, resulting in one or more desired antisense activity and does not hybridize to one or more non-target nucleic acid or does not hybridize to one or more non-target nucleic acid in such a way that results in significant undesired antisense activity.

In certain antisense activities, hybridization of an antisense compound to a target nucleic acid results in recruitment of a protein that cleaves the target nucleic acid. For example, certain antisense compounds result in RNase H mediated cleavage of the target nucleic acid. RNase H is a cellular endonuclease that cleaves the RNA strand of an RNA:DNA duplex. The DNA in such an RNA:DNA duplex need not be unmodified DNA. In certain embodiments, described herein are antisense compounds that are sufficiently "DNA-like" to elicit RNase H activity. In certain embodiments, one or more non-DNA-like nucleoside in the gap of a gapmer is tolerated.

In certain antisense activities, an antisense compound or a portion of an antisense compound is loaded into an RNA-induced silencing complex (RISC), ultimately resulting in cleavage of the target nucleic acid. For example, certain antisense compounds result in cleavage of the target nucleic acid by Argonaute. Antisense compounds that are loaded into RISC are RNAi compounds. RNAi compounds may be double-stranded (siRNA) or single-stranded (ssRNA).

In certain embodiments, hybridization of an antisense compound to a target nucleic acid does not result in recruitment of a protein that cleaves that target nucleic acid. In certain embodiments, hybridization of the antisense compound to the target nucleic acid results in alteration of splicing of the target nucleic acid. In certain embodiments, hybridization of an antisense compound to a target nucleic acid results in inhibition of a binding interaction between the target nucleic acid and a protein or other nucleic acid. In certain embodiments, hybridization of an antisense compound to a target nucleic acid results in alteration of translation of the target nucleic acid.

Antisense activities may be observed directly or indirectly. In certain embodiments, observation or detection of an antisense activity involves observation or detection of a change in an amount of a target nucleic acid or protein encoded by such target nucleic acid, a change in the ratio of splice variants of a nucleic acid or protein and/or a phenotypic change in a cell or animal.

V. Certain Target Nucleic Acids

In certain embodiments, oligomeric compounds comprise or consist of an oligonucleotide comprising a region that is complementary to a target nucleic acid. In certain embodiments, the target nucleic acid is an endogenous RNA molecule. In certain embodiments, the target nucleic acid encodes a protein. In certain such embodiments, the target nucleic acid is selected from: a mature mRNA and a pre-mRNA, including intronic, exonic and untranslated regions. In certain embodiments, the target RNA is a mature mRNA. In certain embodiments, the target nucleic acid is a pre-mRNA. In certain such embodiments, the target region is entirely within an intron. In certain embodiments, the target region spans an intron/exon junction. In certain embodiments, the target region is at least 50% within an intron. In certain embodiments, the target nucleic acid is the RNA transcriptional product of a retrogene. In certain embodiments, the target nucleic acid is a non-coding RNA. In certain such embodiments, the target non-coding RNA is selected from: a long non-coding RNA, a short non-coding RNA, an intronic RNA molecule.

A. Complementarity/Mismatches to the Target Nucleic Acid

It is possible to introduce mismatch bases without eliminating activity. For example, Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo. Maher and Dolnick (Nuc. Acid. Res. 16:3341-3358, 1988) tested a series of tandem 14 nucleobase oligonucleotides, and a 28 and 42 nucleobase oligonucleotides comprised of the sequence of two or three of the tandem oligonucleotides, respectively, for their ability to arrest translation of human DHFR in a rabbit reticulocyte assay. Each of the three 14 nucleobase oligonucleotides alone was able to inhibit translation, albeit at a more modest level than the 28 or 42 nucleobase oligonucleotides.

In certain embodiments, oligonucleotides are complementary to the target nucleic acid over the entire length of the oligonucleotide. In certain embodiments, oligonucleotides are 99%, 95%, 90%, 85%, or 80% complementary to the target nucleic acid. In certain embodiments, oligonucleotides are at least 80% complementary to the target nucleic acid over the entire length of the oligonucleotide and comprise a region that is 100% or fully complementary to a target nucleic acid. In certain embodiments, the region of full complementarity is from 6 to 20, 10 to 18, or 18 to 20 nucleobases in length.

In certain embodiments, oligonucleotides comprise one or more mismatched nucleobases relative to the target nucleic acid. In certain embodiments, antisense activity against the target is reduced by such mismatch, but activity against a non-target is reduced by a greater amount. Thus, in certain embodiments selectivity of the oligonucleotide is improved. In certain embodiments, the mismatch is specifically positioned within an oligonucleotide having a gapmer motif. In certain embodiments, the mismatch is at position 1, 2, 3, 4, 5, 6, 7, or 8 from the 5'-end of the gap region. In certain embodiments, the mismatch is at position 9, 8, 7, 6, 5, 4, 3, 2, 1 from the 3'-end of the gap region. In certain embodiments, the mismatch is at position 1, 2, 3, or 4 from the 5'-end of the wing region. In certain embodiments, the mismatch is at position 4, 3, 2, or 1 from the 3'-end of the wing region.

B. ATXN2

In certain embodiments, oligomeric compounds comprise or consist of an oligonucleotide comprising a region that is complementary to a target nucleic acid, wherein the target nucleic acid is ATXN2. In certain embodiments, ATXN2 nucleic acid has the sequence set forth in SEQ ID NO: 1 (GENBANK Accession No: NM_002973.3) and SEQ ID NO: 2 (the complement of GENBANK Accession No: NT_009775.17 truncated from nucleotides 2465000 to 2616000).

In certain embodiments, contacting a cell with an oligomeric compound complementary to SEQ ID NO: 1 or SEQ ID NO: 2 reduces the amount of ATXN2 mRNA, and in certain embodiments reduces the amount of Ataxin-2 protein. In certain embodiments, the oligomeric compound consists of a modified oligonucleotide. In certain embodiments, contacting a cell with an oligomeric compound complementary to SEQ ID NO: 1 or SEQ ID NO: 2 ameliorates one or more symptom or hallmark of a neurodegenerative disease. In certain embodiments, the oligomeric compound consists of a modified oligonucleotide. In certain embodiments, the symptom or hallmark is ataxia, neuropathy, or aggregate formation. In certain embodiments, contacting a cell with a modified oligonucleotide complementary to SEQ ID NO: 1 or SEQ ID NO: 2 results in improved motor function, reduced neuropathy, and reduction in number of aggregates. In certain embodiments, the oligomeric compound consists of a modified oligonucleotide.

C. Certain Target Nucleic Acids in Certain Tissues

In certain embodiments, oligomeric compounds comprise or consist of an oligonucleotide comprising a region that is complementary to a target nucleic acid, wherein the target nucleic acid is expressed in a pharmacologically relevant tissue. In certain embodiments, the pharmacologically relevant tissues are the cells and tissues that comprise the central nervous system (CNS). Such tissues include brain tissues, such as, cortex, spinal cord, hippocampus, pons, cerebellum, substantia nigra, red nucleus, medulla, thalamus, and dorsal root ganglia.

VI. Certain Pharmaceutical Compositions

In certain embodiments, described herein are pharmaceutical compositions comprising one or more oligomeric compounds. In certain embodiments, the one or more oligomeric compounds each consists of a modified oligonucleotide. In certain embodiments, the pharmaceutical composition comprises a pharmaceutically acceptable diluent or carrier. In certain embodiments, a pharmaceutical composition comprises or consists of a sterile saline solution and one or more oligomeric compound. In certain embodiments, the sterile saline is pharmaceutical grade saline. In certain embodiments, a pharmaceutical composition comprises or consists of one or more oligomeric compound and sterile water. In certain embodiments, the sterile water is pharmaceutical grade water. In certain embodiments, a pharmaceutical composition comprises or consists of one or more oligomeric compound and phosphate-buffered saline (PBS). In certain embodiments, the sterile PBS is pharmaceutical grade PBS. In certain embodiments, a pharmaceutical composition comprises or consists of one or more oligomeric compound and artificial cerebrospinal fluid. In certain embodiments, the artificial cerebrospinal fluid is pharmaceutical grade.

In certain embodiments, a pharmaceutical composition comprises a modified oligonucleotide and artificial cerebrospinal fluid. In certain embodiments, a pharmaceutical composition consists of a modified oligonucleotide and artificial cerebrospinal fluid. In certain embodiments, a pharmaceutical composition consists essentially of a modified oligonucleotide and artificial cerebrospinal fluid. In certain embodiments, the artificial cerebrospinal fluid is pharmaceutical grade.

In certain embodiments, pharmaceutical compositions comprise one or more oligomeric compound and one or more excipients. In certain embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, oligomeric compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

In certain embodiments, pharmaceutical compositions comprising an oligomeric compound encompass any pharmaceutically acceptable salts of the oligomeric compound, esters of the oligomeric compound, or salts of such esters. In certain embodiments, pharmaceutical compositions comprising oligomeric compounds comprising one or more oligonucleotide, upon administration to an animal, including a human, are capable of providing (directly or indirectly) the biologically active metabolite or residue thereof. Accordingly, for example, the disclosure is also drawn to pharmaceutically acceptable salts of oligomeric compounds, prodrugs, pharmaceutically acceptable salts of such prodrugs, and other bioequivalents. Suitable pharmaceutically acceptable salts include, but are not limited to, sodium and potassium salts. In certain embodiments, prodrugs comprise one or more conjugate group attached to an oligonucleotide, wherein the conjugate group is cleaved by endogenous nucleases within the body.

Lipid moieties have been used in nucleic acid therapies in a variety of methods. In certain such methods, the nucleic acid, such as an oligomeric compound, is introduced into preformed liposomes or lipoplexes made of mixtures of cationic lipids and neutral lipids. In certain methods, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions comprise a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, pharmaceutical compositions comprise one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, pharmaceutical compositions comprise a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, pharmaceutical compositions are prepared for oral administration. In certain embodiments, pharmaceutical compositions are prepared for buccal administration. In certain embodiments, a pharmaceutical composition is prepared for administration by injection (e.g., intravenous, subcutaneous, intramuscular, intrathecal (IT), intracerebroventricular (ICV), etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes.

Under certain conditions, certain compounds disclosed herein act as acids. Although such compounds may be drawn or described in protonated (free acid) form, in ionized (anion) form, or ionized and in association with a cation (salt) form, aqueous solutions of such compounds exist in equilibrium among such forms. For example, a phosphate linkage of an oligonucleotide in aqueous solution exists in equilibrium among free acid, anion, and salt forms. Unless otherwise indicated, compounds described herein are intended to include all such forms. Moreover, certain oligonucleotides have several such linkages, each of which is in equilibrium. Thus, oligonucleotides in solution exist in an ensemble of forms at multiple positions all at equilibrium. The term "oligonucleotide" is intended to include all such forms. Drawn structures necessarily depict a single form. Nevertheless, unless otherwise indicated, such drawings are likewise intended to include corresponding forms. Herein, a structure depicting the free acid of a compound followed by the term "or salts thereof" expressly includes all such forms that may be fully or partially protonated/de-protonated/in association with a cation. In certain instances, one or more specific cation is identified.

In certain embodiments, oligomeric compounds disclosed herein are in aqueous solution with sodium. In certain embodiments, oligomeric compounds are in aqueous solution with potassium. In certain embodiments, oligomeric compounds are in artificial CSF. In certain embodiments, oligomeric compounds are in PBS. In certain embodiments, oligomeric compounds are in water. In certain such embodiments, the pH of the solution is adjusted with NaOH and/or HCl to achieve a desired pH.

VII. Certain Compositions

1. Compound No: 874218

Compound No: 874218 may be characterized as a 5-10-5 MOE gapmer, having a sequence of (from 5' to 3') GTACTTTTCTCATGTGCGGC (incorporated herein as SEQ ID NO: 1714), wherein each of nucleosides 1-5 and 16-20 (from 5' to 3') comprise a 2'-MOE modification and each of nucleosides 6-15 are 2'-deoxynucleosides, wherein the internucleoside linkages between nucleosides 2 to 3, 3 to 4, 4 to 5, 5 to 6, 16 to 17, and 17 to 18 are phosphodiester internucleoside linkages and the internucleoside linkages between nucleosides 1 to 2, 6 to 7, 7 to 8, 8 to 9, 9 to 10, 10 to 11, 11 to 12, 12 to 13, 13 to 14, 14 to 15, 15 to 16, 18 to 19, and 19 to 20 are phosphorothioate internucleoside linkages, and wherein each cytosine is a 5-methyl cytosine.

Compound No: 780241 may be characterized by the following chemical notation: Ges Teo Aeo mCeo Teo Tds Tds Tds mCds Tds mCds Ads Tds Gds Tds Geo mCeo Ges Ges mCe; wherein, A=an adenine nucleobase,
mC=a 5-methyl cytosine nucleobase,
G=a guanine nucleobase,
T=a thymine nucleobase,
e=a 2'-MOE modified sugar,
d=a 2'-deoxyribose sugar,
s=a phosphorothioate internucleoside linkage, and
o=a phosphodiester internucleoside linkage.

Compound No: 874218 may be represented by the following chemical structure:

SEQ ID NO: 1714
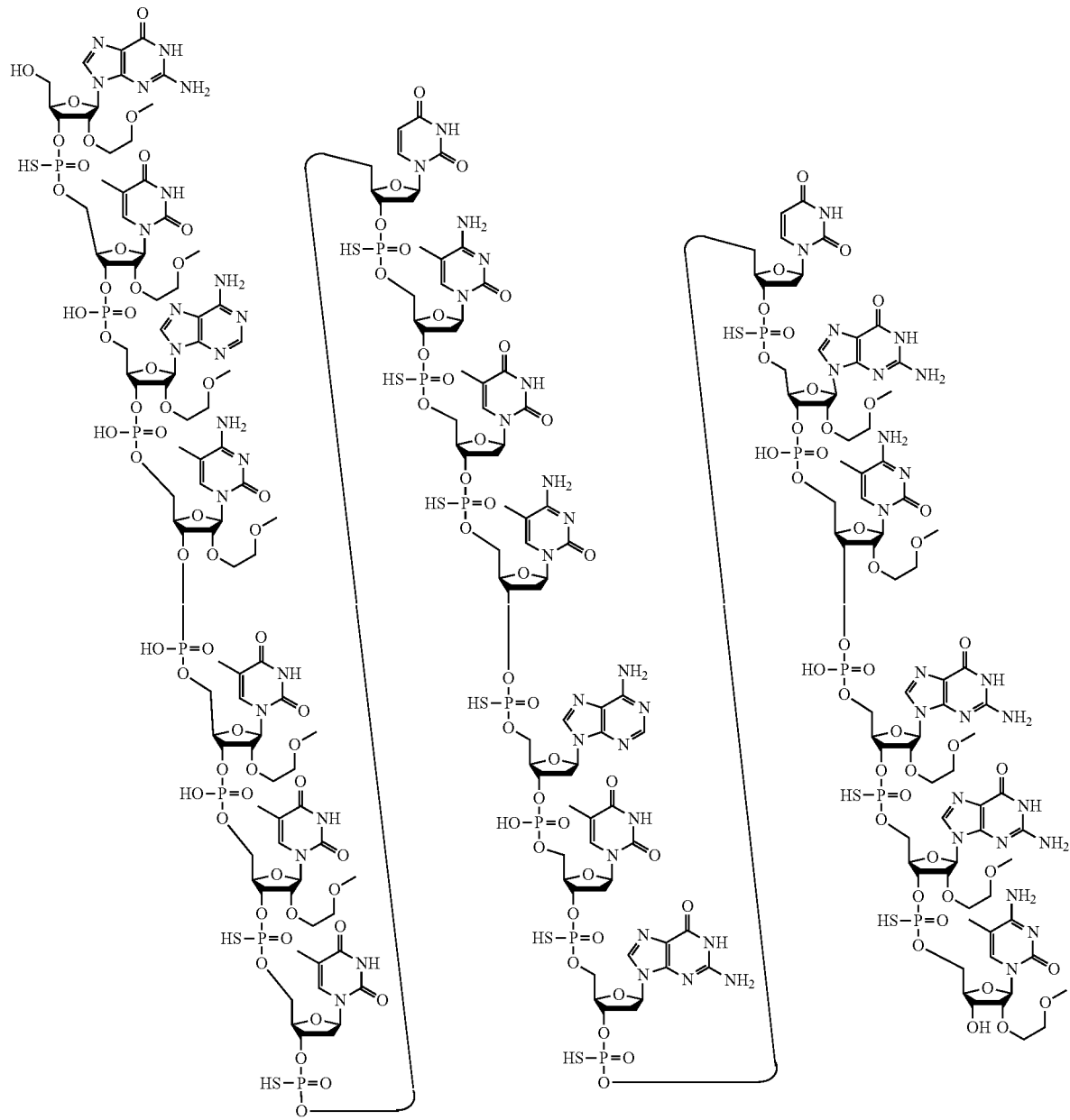
Structure 1. Compound No. 874218
In certain embodiments, the sodium salt of Compound No: 874218 may be represented by the following chemical structure:

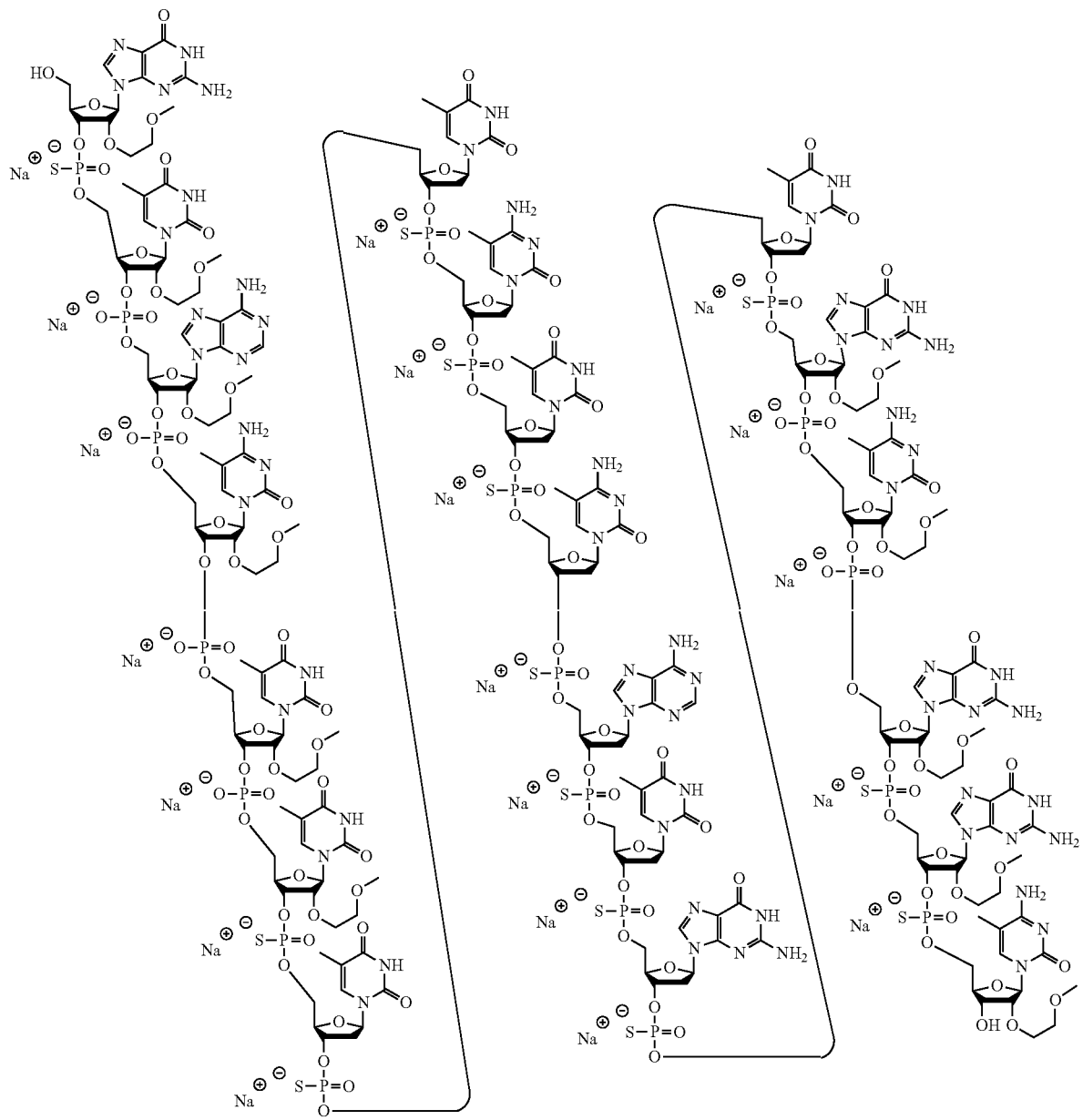

Structure 2. The Sodium Salt of Compound No. 874218

2. Compound No: 1008854

Compound No: 1008854 may be characterized as a 4-10-6 MOE gapmer, having a sequence of (from 5' to 3') CTGCTAACTGGTTTGCCCTT (incorporated herein as SEQ ID NO: 1255), wherein each of nucleosides 1-4 and 15-20 (from 5' to 3') comprise a 2'-MOE modification and each of nucleosides 5-14 are 2'-deoxynucleosides, wherein the internucleoside linkages between nucleosides 2 to 3, 3 to 4, 4 to 5, 15 to 16, 16 to 17, 17 to 18 are phosphodiester internucleoside linkages and the internucleoside linkages between nucleosides 1 to 2, 5 to 6, 6 to 7, 7 to 8, 8 to 9, 9 to 10, 10 to 11, 11 to 12, 12 to 13, 13 to 14, 14 to 15, 18 to 19, and 19 to 20 are phosphorothioate internucleoside linkages, and wherein each cytosine is a 5-methyl cytosine.

Compound No: 1008854 may be characterized by the following chemical notation: mCes Teo Geo mCeo Tds Ads Ads mCds Tds Gds Gds Tds Tds Tds Geo mCeo mCeo mCes Tes Te; wherein, A=an adenine nucleobase, mC=a 5-methyl cytosine nucleobase, G=a guanine nucleobase, T=a thymine nucleobase, e=a 2'-MOE modified sugar, d=a 2'-deoxyribose sugar, s=a phosphorothioate internucleoside linkage, and o=a phosphodiester internucleoside linkage.

Compound No: 1008854 may be represented by the following chemical structure:

SEQ ID NO: 1255
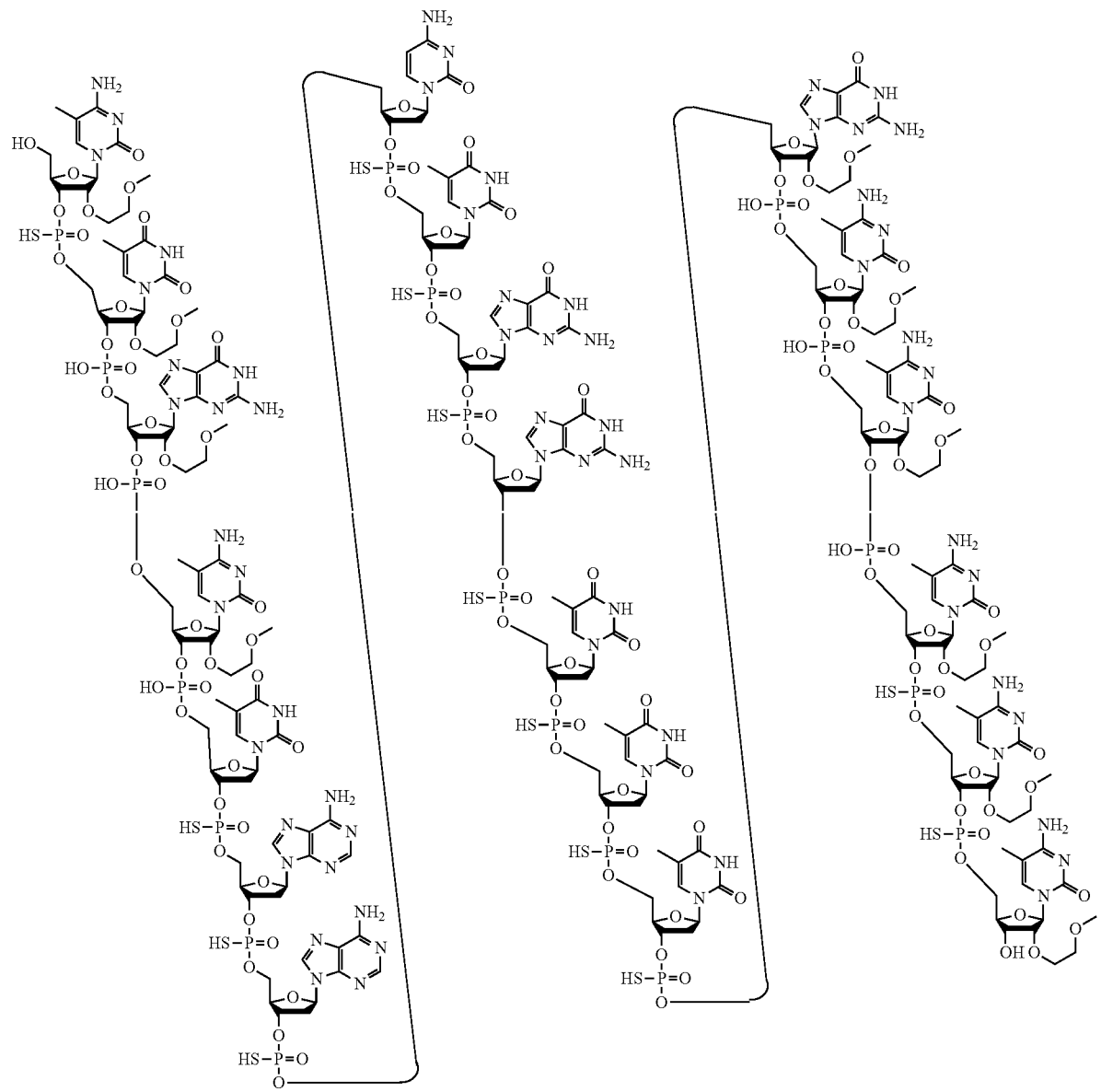
Structure 3. Compound No. 1008854
In certain embodiments, the sodium salt of Compound No: 1008854 may be represented by the following chemical structure:

SEQ ID NO: 1255

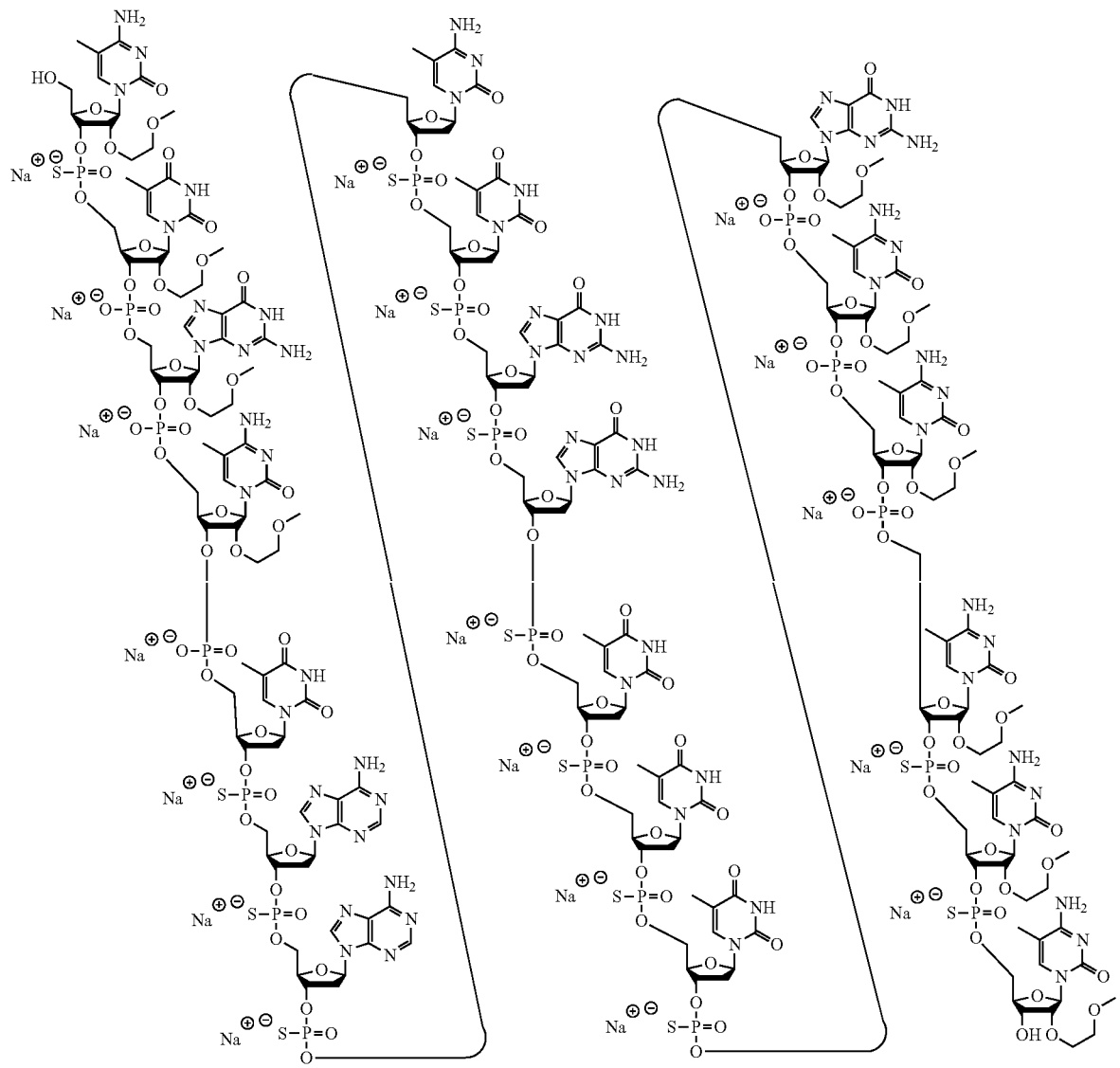

Structure 4. Sodium Salt of Compound No. 1008854

3. Compound No: 1008862

Compound No: 1008862 may be characterized as a 6-10-4 MOE gapmer, having a sequence of (from 5' to 3') TGTACTTCACATTTGGAGCC (incorporated herein as SEQ ID NO: 1185), wherein each of nucleosides 1-6 and 17-20 (from 5' to 3') comprise a 2'-MOE modification and each of nucleosides 7-16 are 2'-deoxynucleosides, wherein the internucleoside linkages between nucleosides 2 to 3, 3 to 4, 4 to 5, 5 to 6, 6 to 7, and 17 to 18 are phosphodiester internucleoside linkages and the internucleoside linkages between nucleosides 1 to 2, 7 to 8, 8 to 9, 9 to 10, 10 to 11, 11 to 12, 12 to 13, 13 to 14, 14 to 15, 15 to 16, 16 to 17, 18 to 19, and 19 to 20 are phosphorothioate internucleoside linkages, and wherein each cytosine is a 5-methyl cytosine.

Compound No: 1008862 may be characterized by the following chemical notation: Tes Geo Teo Aeo mCeo Teo Tds mCds Ads mCds Ads Tds Tds Tds Gds Gds Aeo Ges mCes mCe; wherein, A=an adenine nucleobase,
mC=a 5-methyl cytosine nucleobase,
G=a guanine nucleobase,
T=a thymine nucleobase,
e=a 2'-MOE modified sugar,
d=a 2'-deoxyribose sugar,
s=a phosphorothioate internucleoside linkage, and
o=a phosphodiester internucleoside linkage.

Compound No: 1008862 may be represented by the following chemical structure:

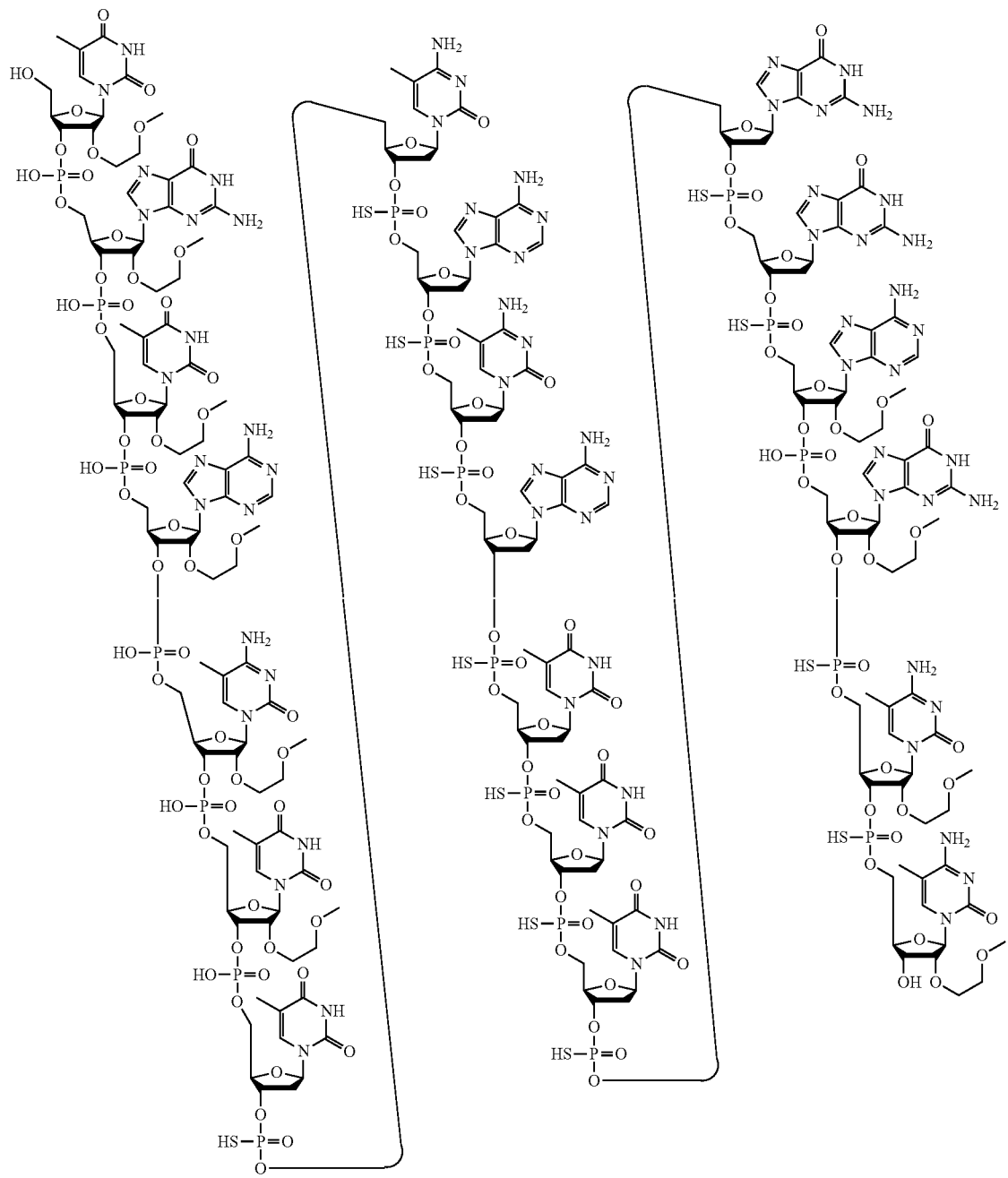
Structure 5. Compound No. 1008862
In certain embodiments, the sodium salt of Compound No: 1008862 may be represented by the following chemical structure:

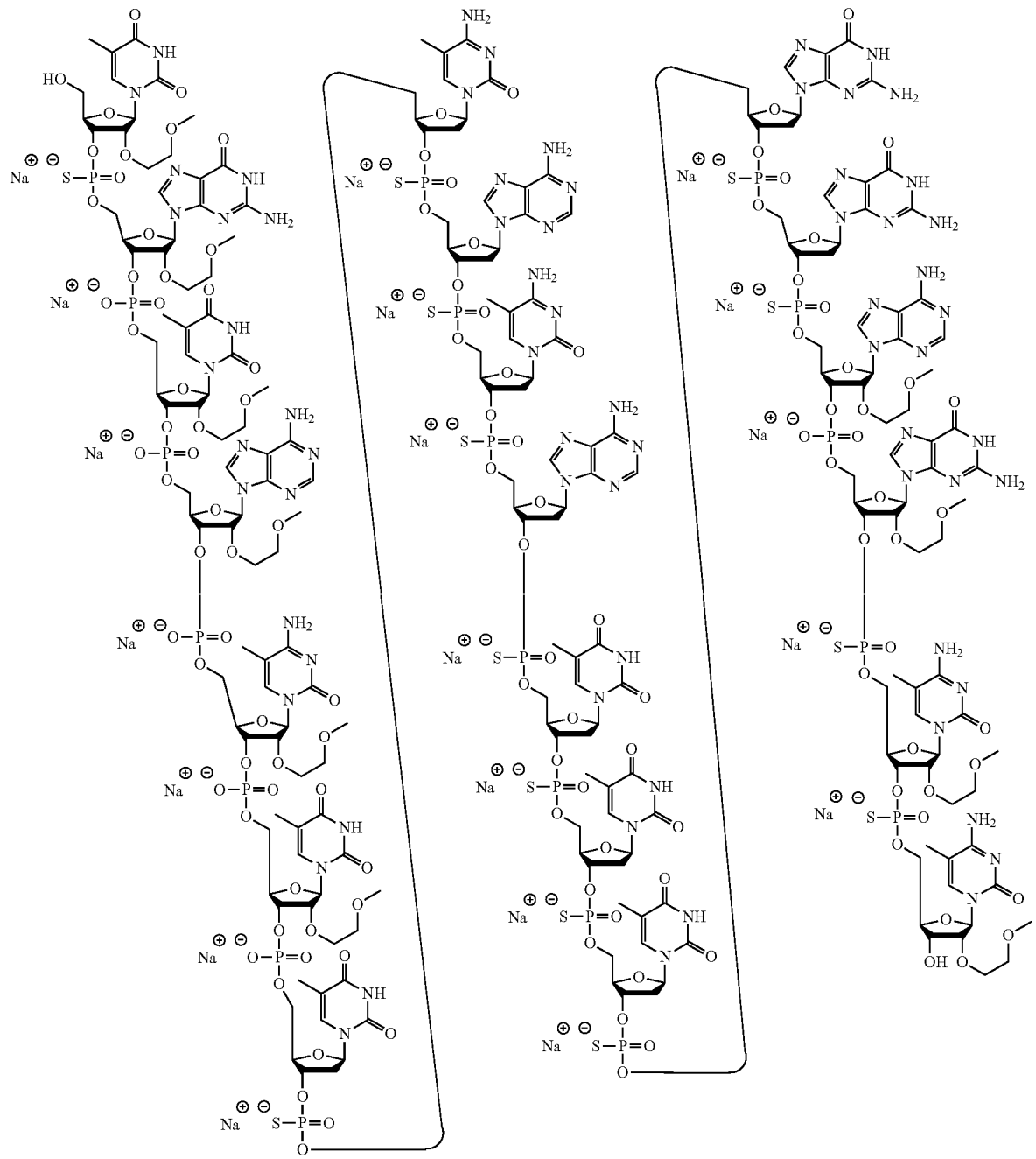

(SEQ ID NO:1185)

Structure 6. The Sodium Salt of Compound No. 1008862

4. Compound No: 1008870

Compound No: 1008870 may be characterized as a 6-10-4 MOE gapmer, having a sequence of (from 5' to 3') TGGAT-TCTGTACTTTTCTCA (incorporated herein as SEQ ID NO: 3235), wherein each of nucleosides 1-6 and 17-20 (from 5' to 3') comprise a 2'-MOE modification and each of nucleosides 7-16 are 2'-deoxynucleosides, wherein the internucleoside linkages between nucleosides 2 to 3, 3 to 4, 4 to 5, 5 to 6, 6 to 7, and 17 to 18, are phosphodiester internucleoside linkages and the internucleoside linkages between nucleosides 1 to 2, 7 to 8, 8 to 9, 9 to 10, 10 to 11, 11 to 12, 12 to 13, 13 to 14, 14 to 15, 15 to 16, 16 to 17, 18 to 19, and 19 to 20 are phosphorothioate internucleoside linkages, and wherein each cytosine is a 5-methyl cytosine.

Compound No: 1008870 may be characterized by the following chemical notation: Tes Geo Geo Aeo Teo Teo mCds Tds Gds Tds Ads mCds Tds Tds Tds Tds mCeo Tes mCes Ae; wherein, A=an adenine nucleobase,
mC=a 5-methyl cytosine nucleobase,
G=a guanine nucleobase,
T=a thymine nucleobase,
e=a 2'-MOE modified sugar, d=a 2'-deoxyribose sugar,
s=a phosphorothioate internucleoside linkage, and
o=a phosphodiester internucleoside linkage.
Compound No: 1008870 may be represented by the following chemical structure:
In certain embodiments, the sodium salt of Compound No: 1008870 may be represented by the following chemical structure:
SEQ ID NO: 3235
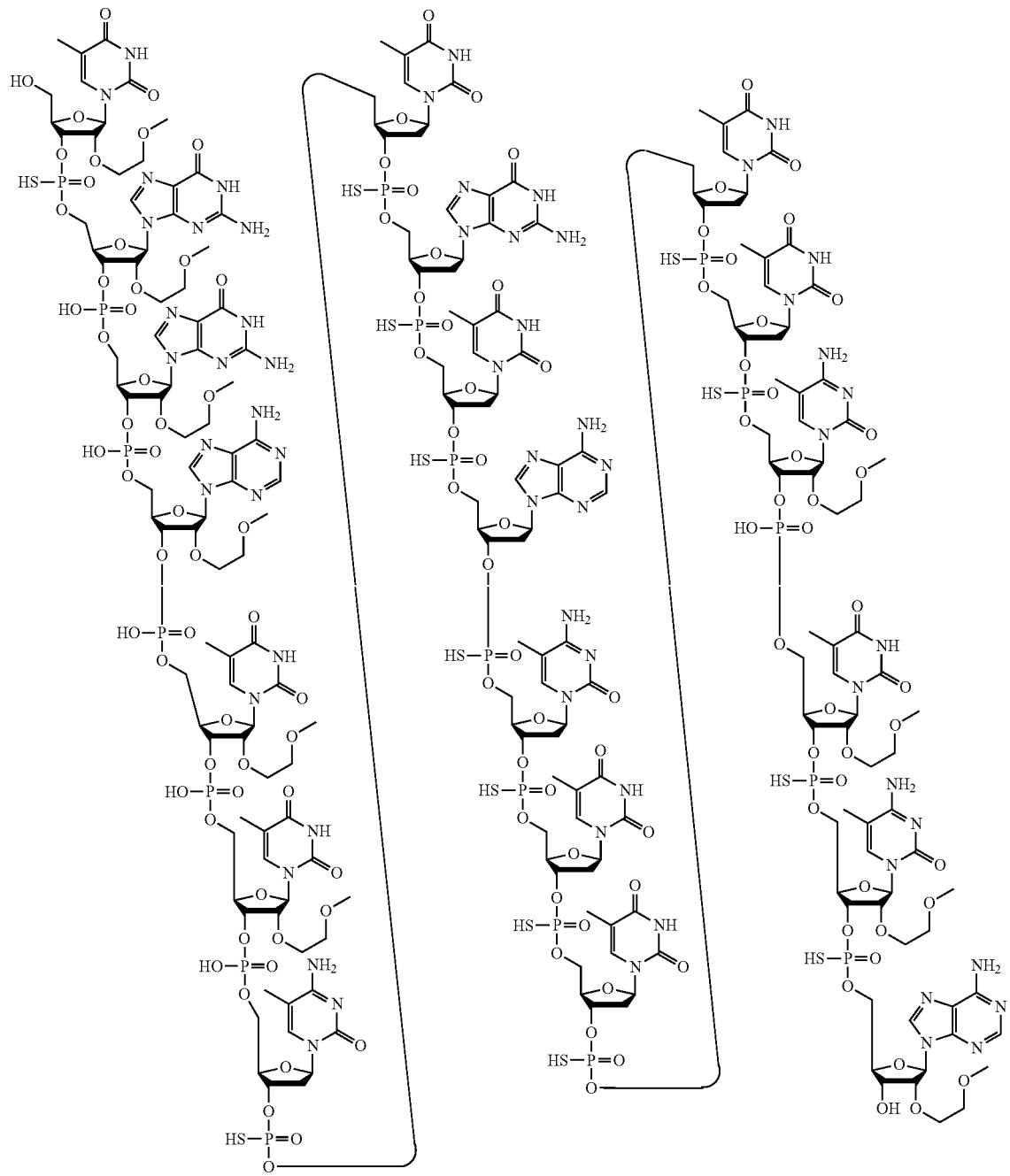
Structure 7. Compound No. 1008870

SEQ ID NO: 3235

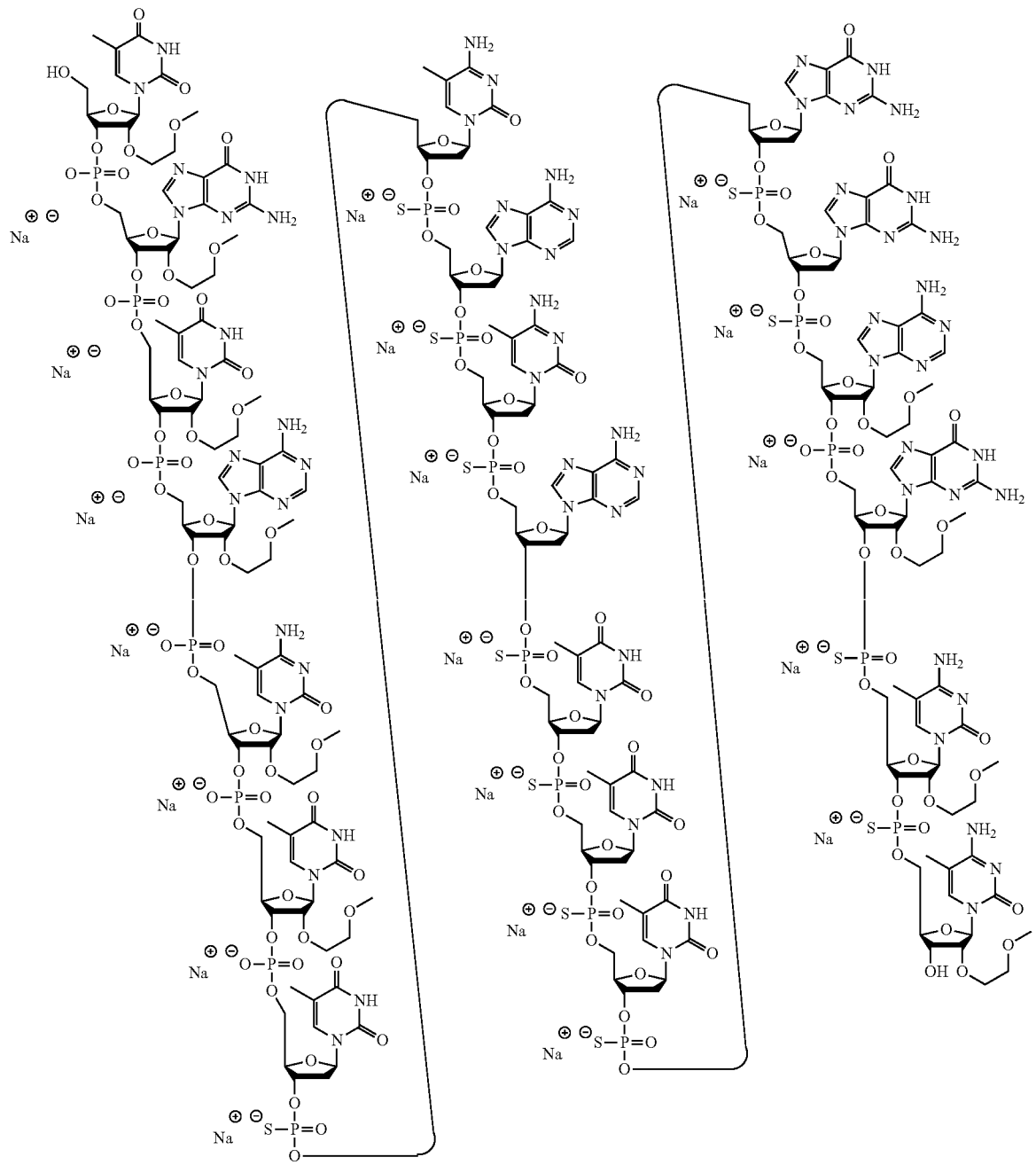

Structure 8. The Sodium salt of Compound No. 1008870
5. Compound No: 1008874

Compound No: 1008874 may be characterized as a 6-10-4 MOE gapmer, having a sequence of (from 5' to 3') CCTAT-CATCATTTTCCAGGG (incorporated herein as SEQ ID NO: 158), wherein each of nucleosides 1-6 and 17-20 (from 5' to 3') comprise a 2'-MOE modification and each of nucleosides 7-16 are 2'-deoxynucleosides, wherein the internucleoside linkages between nucleosides 2 to 3, 3 to 4, 4 to 5, 5 to 6, 6 to 7, and 17 to 18 are phosphodiester internucleoside linkages and the internucleoside linkages between nucleosides 1 to 2, 7 to 8, 8 to 9, 9 to 10, 10 to 11, 11 to 12, 12 to 13, 13 to 14, 14 to 15, 15 to 16, 16 to 17, 18 to 19, and 19 to 20 are phosphorothioate internucleoside linkages, and wherein each cytosine is a 5-methyl cytosine.

Compound No: 1008874 may be characterized by the following chemical notation: mCes mCeo Teo Aeo Teo mCeo Ads Tds mCds Ads Tds Tds Tds Tds mCds mCds Aeo Ges Ges Ge; wherein, A=an adenine nucleobase,
mC=a 5-methyl cytosine nucleobase,
G=a guanine nucleobase,
T=a thymine nucleobase,
e=a 2'-MOE modified sugar,
d=a 2'-deoxyribose sugar,
s=a phosphorothioate internucleoside linkage, and o=a phosphodiester internucleoside linkage.
Compound No: 1008874 may be represented by the following chemical structure:
In certain embodiments, the sodium salt of Compound No: 1008874 may be represented by the following chemical structure:
SEQ ID NO: 158
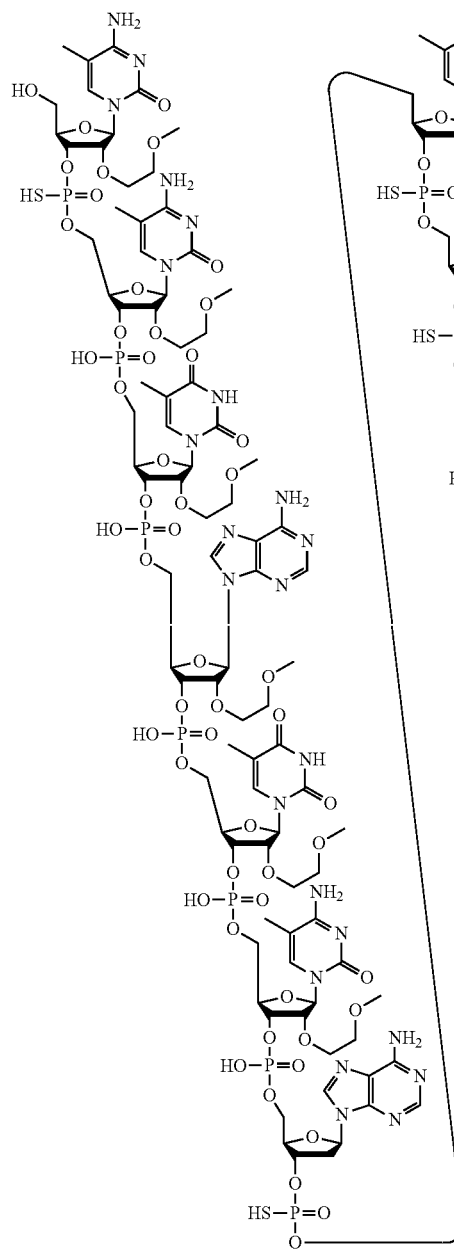
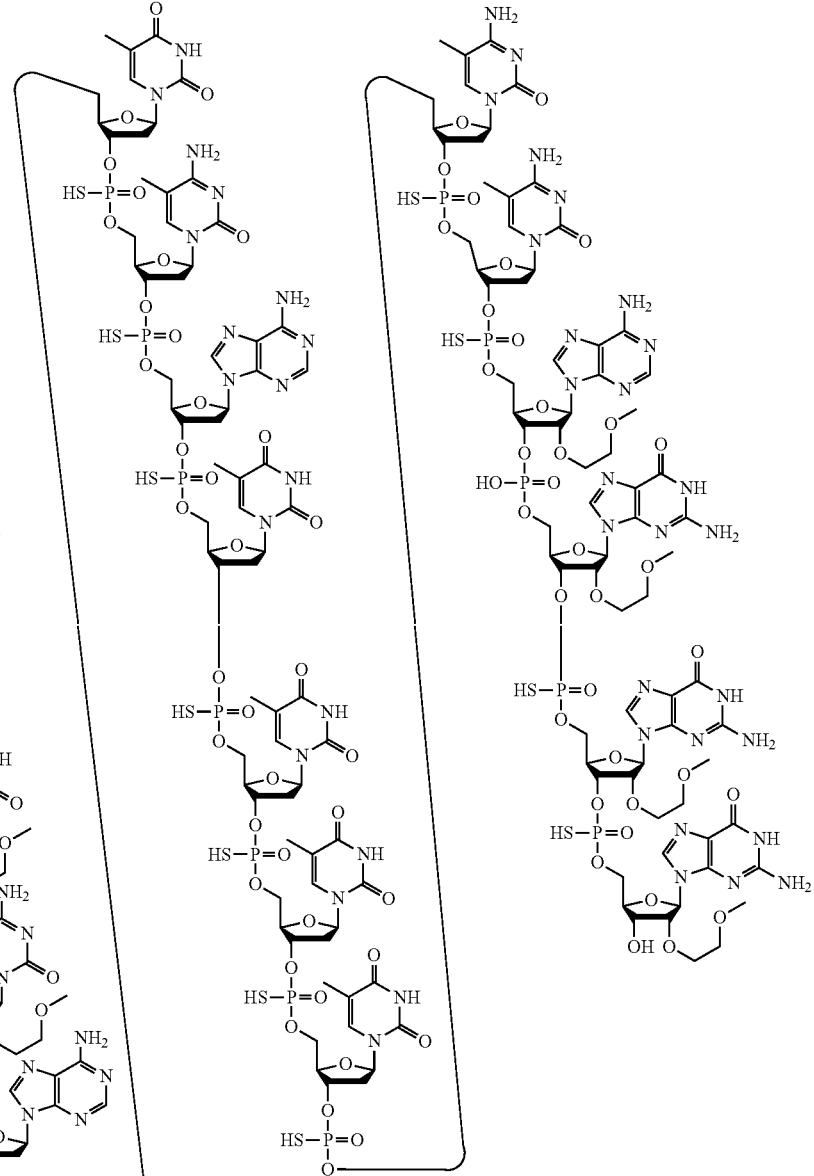
Structure 9. Compound No. 1008874

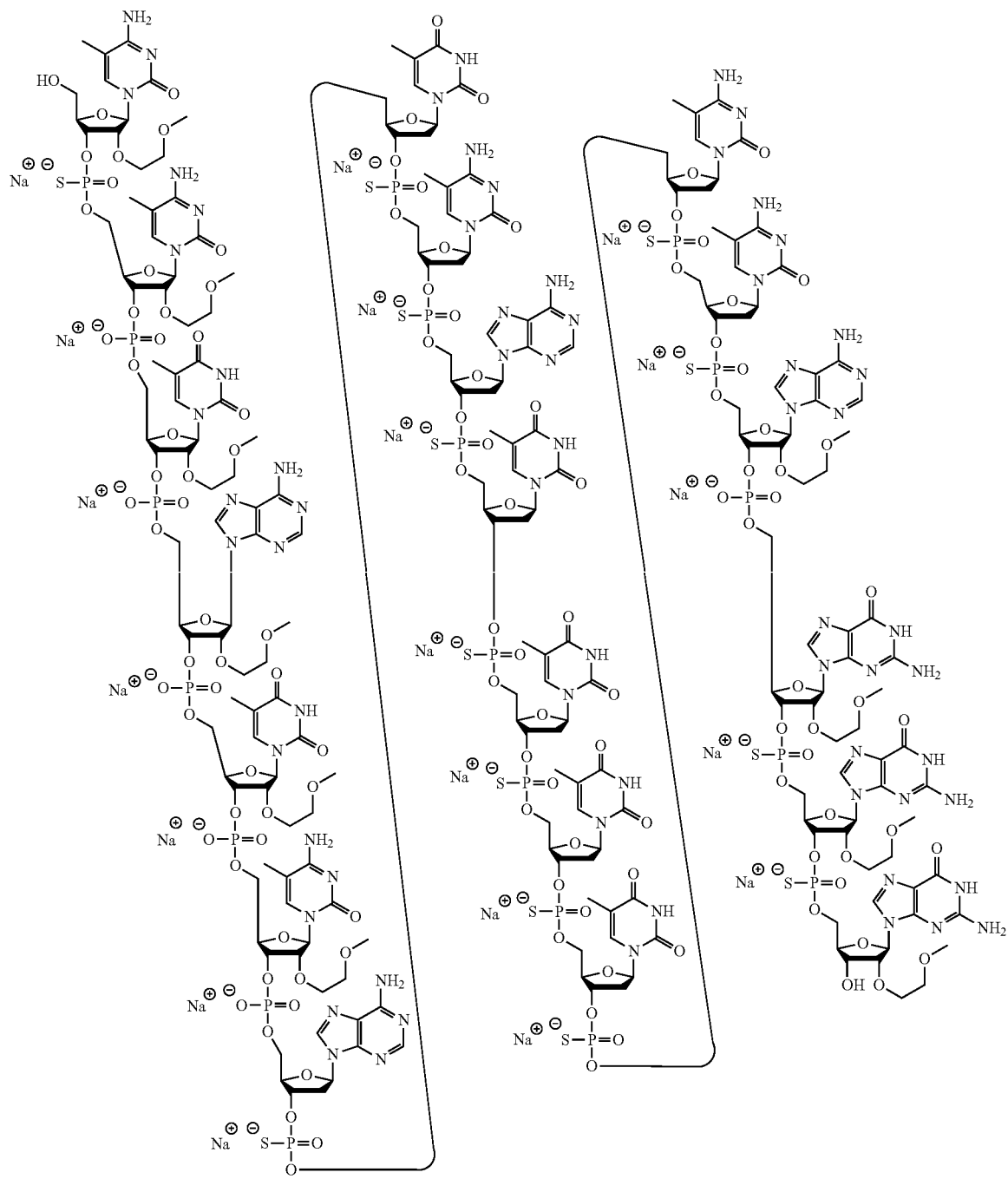

SEQ ID NO: 158

Structure 10. Sodium Salt of Compound No. 1008874

6. Compound No: 1008910

Compound No: 1008910 may be characterized as a 5-10-5 MOE gapmer, having a sequence of (from 5' to 3') TCTGTACTTTTCTCATGTGC (incorporated herein as SEQ ID NO: 2544), wherein each of nucleosides 1-5 and 16-20 (from 5' to 3') comprise a 2'-MOE modification and each of nucleosides 6-15 are 2'-deoxynucleosides, wherein the internucleoside linkages between nucleosides 2 to 3, 3 to 4, 4 to 5, 16 to 17, and 17 to 18 are phosphodiester internucleoside linkages and the internucleoside linkages between nucleosides 1 to 2, 5 to 6, 6 to 7, 7 to 8, 8 to 9, 9 to 10, 10 to 11, 11 to 12, 12 to 13, 13 to 14, 14 to 15, 15 to 16, 18 to 19, and 19 to 20 are phosphorothioate internucleoside linkages, and wherein each cytosine is a 5-methyl cytosine.

Compound No: 1008910 may be characterized by the following chemical notation: Tes mCeo Teo Geo Tes Ads mCds Tds Tds Tds Tds mCds Tds mCds Ads Teo Geo Tes Ges mCe; wherein, A=an adenine nucleobase, mC=a 5-methyl cytosine nucleobase, G=a guanine nucleobase,
T=a thymine nucleobase,
e=a 2'-MOE modified sugar,
d=a 2'-deoxyribose sugar,
s=a phosphorothioate internucleoside linkage, and
o=a phosphodiester internucleoside linkage.

Compound No: 1008910 may be represented by the following chemical structure:

In certain embodiments, the sodium salt of Compound No: 1008910 may be represented by the following chemical structure:

SEQ ID NO: 2544

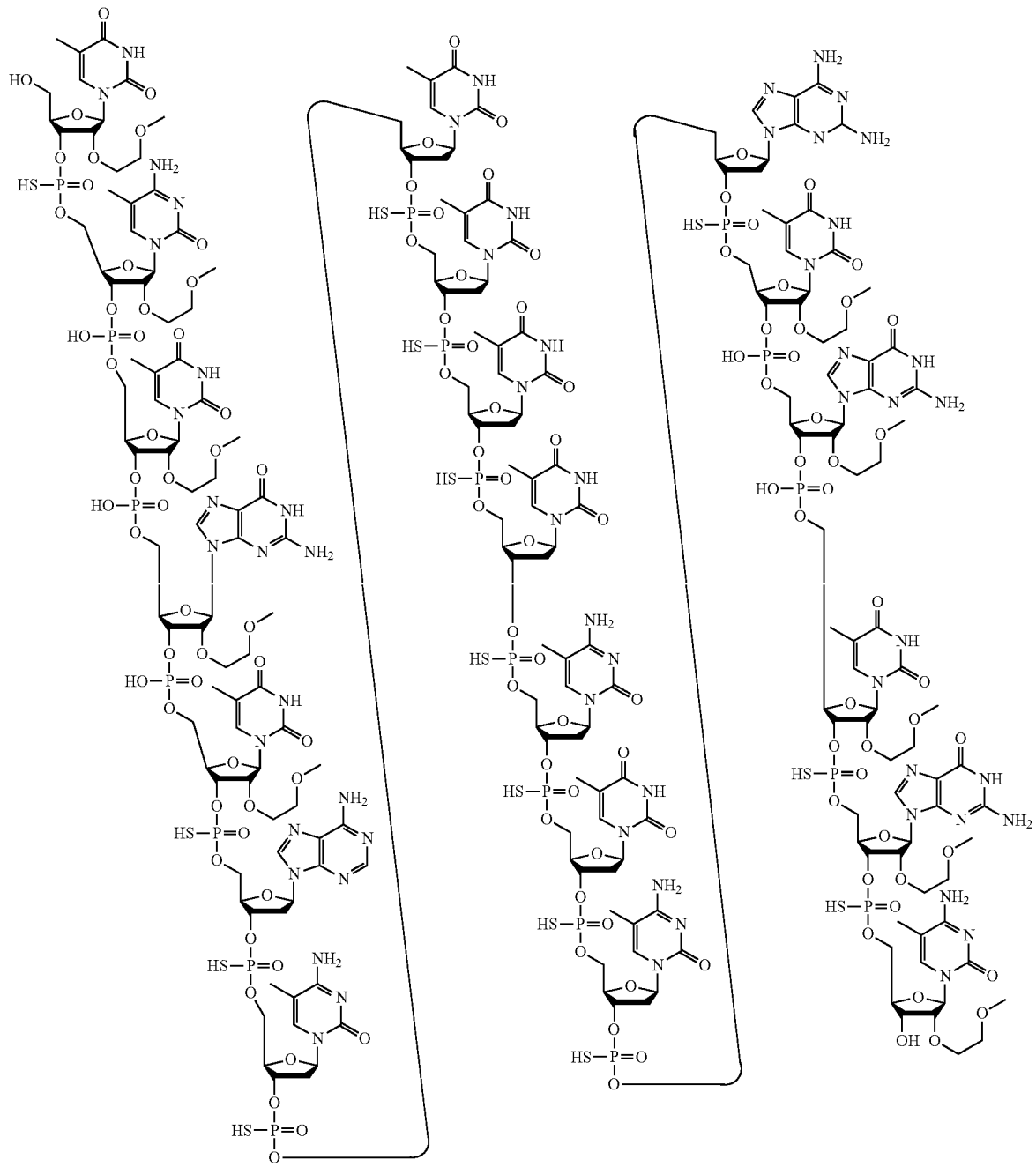

Structure 11. Compound No. 1008910

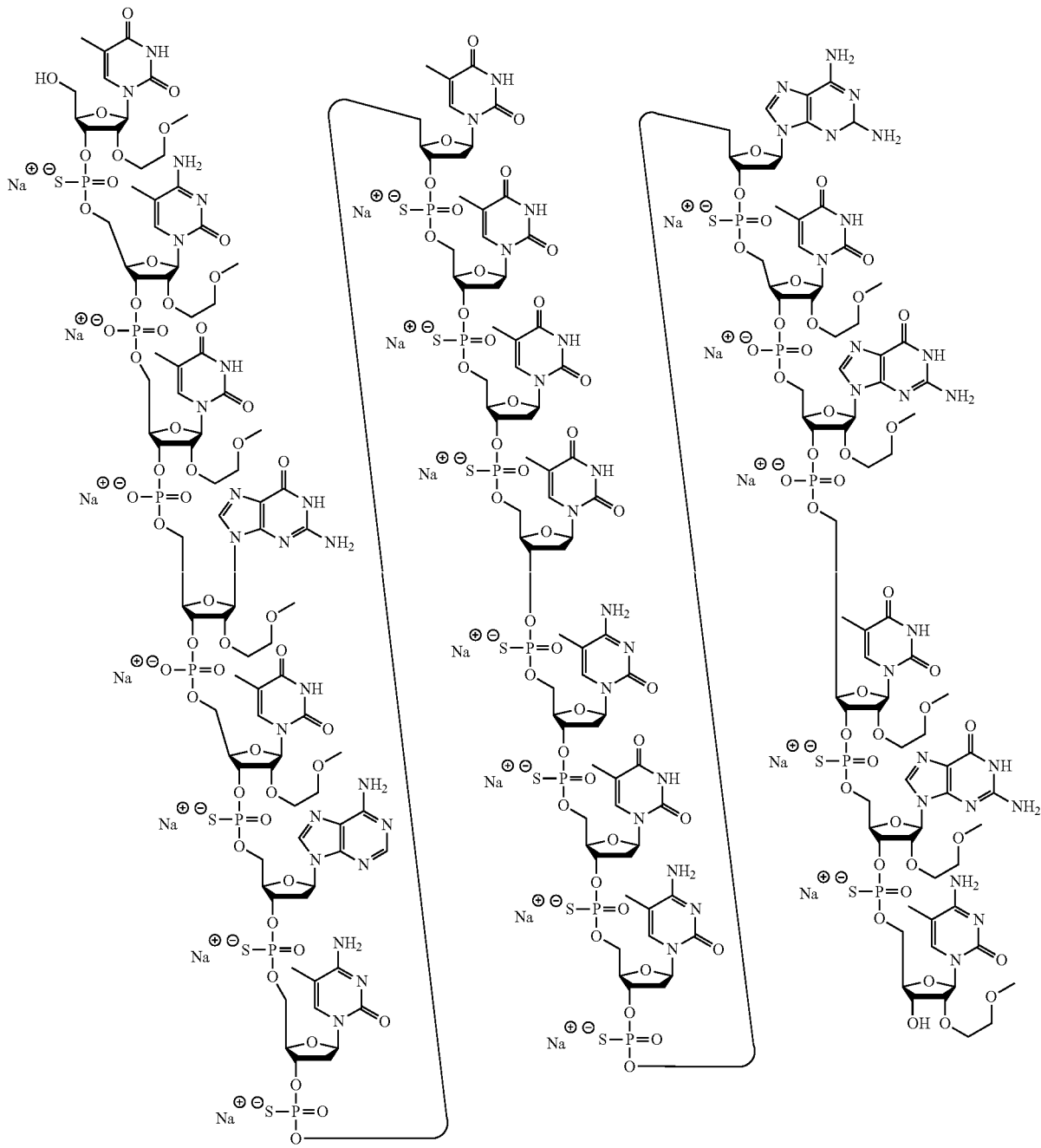

Structure 12. The Sodium Salt of Compound No. 1008910

VIII. Certain Comparator Compositions

In certain embodiments, Compound No. 564122, which was previously described in WO 2015/143246 and in Scoles et al., Nature, 2017, 544(7650):362-366 (both of which are incorporated herein by reference) is a comparator compound. Compound No. 564122 is a 5-10-5 MOE gapmer, having a sequence from (from 5' to 3') TGCATAGATTC-CATCAAAAG (incorporated herein as SEQ ID NO: 67), wherein each cytosine is a 5-methylcytosine, each internucleoside linkage is a phosphorothioate internucleoside linkage, and each of nucleosides 1-5 and 16-20 comprise a 2'-OCH$_2$CH$_2$OCH$_3$ group.

In certain embodiments, Compound No. 564127, which was previously described in WO 2015/143246 and in Scoles, 2017 is a comparator compound. Compound No. 564127 is a 5-10-5 MOE gapmer, having a sequence from (from 5' to 3') CTCTCCATTATTTCTTCACG (incorporated herein as SEQ ID NO: 33), wherein each cytosine is a 5-methylcytosine, each internucleoside linkage is a phosphorothioate internucleoside linkage, and each of nucleosides 1-5 and 16-20 comprise a 2'-OCH$_2$CH$_2$OCH$_3$ group.

In certain embodiments, Compound No. 564133, which was previously described in WO 2015/143246 and in Scoles, 2017 is a comparator compound. Compound No. 564133 is a 5-10-5 MOE gapmer, having a sequence from (from 5' to 3') GCTAACTGGTTTGCCCTTGC (incorporated herein as SEQ ID NO: 32), wherein each cytosine is a 5-methylcytosine, each internucleoside linkage is a phosphorothioate internucleoside linkage, and each of nucleosides 1-5 and 16-20 comprise a 2'-OCH$_2$CH$_2$OCH$_3$ group.

In certain embodiments, Compound No. 564143, which was previously described in WO 2015/143246 and in Scoles, 2017 is a comparator compound. Compound No. 564143 is a 5-10-5 MOE gapmer, having a sequence from (from 5' to 3') GGAGCTGGAGAACCATGAGC (incorporated herein as SEQ ID NO: 188), wherein each cytosine is a 5-methylcytosine, each internucleoside linkage is a phosphorothioate internucleoside linkage, and each of nucleosides 1-5 and 16-20 comprise a 2'-OCH$_2$CH$_2$OCH$_3$ group.

In certain embodiments, Compound No. 564150, which was previously described in WO 2015/143246 and in Scoles, 2017 is a comparator compound. Compound No. 564150 is a 5-10-5 MOE gapmer, having a sequence from (from 5' to 3') CTGGTACAGTTGCTGCTGCT (incorporated herein as SEQ ID NO: 330), wherein each cytosine is a 5-methylcytosine, each internucleoside linkage is a phosphorothioate internucleoside linkage, and each of nucleosides 1-5 and 16-20 comprise a 2'-OCH$_2$CH$_2$OCH$_3$ group.

In certain embodiments, Compound No. 564188, which was previously described in WO 2015/143246 and in Scoles, 2017 is a comparator compound. Compound No. 564188 is a 5-10-5 MOE gapmer, having a sequence from (from 5' to 3') CCCAAAGGGTTAATTAGGAT (incorporated herein as SEQ ID NO: 2901), wherein each cytosine is a 5-methylcytosine, each internucleoside linkage is a phosphorothioate internucleoside linkage, and each of nucleosides 1-5 and 16-20 comprise a 2'-OCH$_2$CH$_2$OCH$_3$ group.

In certain embodiments, Compound No. 564210, which was previously described in WO 2015/143246 and in Scoles, 2017 is a comparator compound. Compound No. 564210 is a 5-10-5 MOE gapmer, having a sequence from (from 5' to 3') CCCATACGCGGTGAATTCTG (incorporated herein as SEQ ID NO: 112), wherein each cytosine is a 5-methylcytosine, each internucleoside linkage is a phosphorothioate internucleoside linkage, and each of nucleosides 1-5 and 16-20 comprise a 2'-OCH$_2$CH$_2$OCH$_3$ group.

In certain embodiments, Compound No. 564216, which was previously described in WO 2015/143246 and in Scoles, 2017 is a comparator compound. Compound No. 564216 is a 5-10-5 MOE gapmer, having a sequence from (from 5' to 3') GTGGGATACAAATTCTAGGC (incorporated herein as SEQ ID NO: 190), wherein each cytosine is a 5-methylcytosine, each internucleoside linkage is a phosphorothioate internucleoside linkage, and each of nucleosides 1-5 and 16-20 comprise a 2'-OCH$_2$CH$_2$OCH$_3$ group.

In certain embodiments, compounds described herein are superior relative to compounds described in WO 2015/143246 and in Scoles, 2017 because they demonstrate one or more improved properties.

Compound 874218

For example, as provided in Example 13 (hereinbelow), Compound 874218 demonstrated a functional observational battery (FOB) score of 1.00 in wild-type mice whereas each of Comparator Compounds Nos: 564122, 564127, 564133, 564143, 564150, 564188, 564210, and 564216 demonstrated a FOB score of 7.00. Therefore, Compound 874218 is demonstrably more tolerable than each of Comparator Compounds Nos: 564122, 564127, 564133, 564143, 564150, 564188, 564210, and 564216 in this assay.

Compound 1008854

For example, as provided in Example 13 (hereinbelow), Compound 1008854 demonstrated a functional observational battery (FOB) score of 1.00 in wild-type mice whereas each of Comparator Compounds Nos: 564122, 564127, 564133, 564143, 564150, 564188, 564210, and 564216 demonstrated a FOB score of 7.00. Therefore, Compound 1008854 is demonstrably more tolerable than each of Comparator Compounds Nos: 564122, 564127, 564133, 564143, 564150, 564188, 564210, and 564216 in this assay.

Compound 1008862

For example, as provided in Example 13 (hereinbelow), Compound 1008862 demonstrated a functional observational battery (FOB) score of 2.50 in wild-type mice whereas each of Comparator Compounds Nos: 564122, 564127, 564133, 564143, 564150, 564188, 564210, and 564216 demonstrated a FOB score of 7.00. Therefore, Compound 1008862 is demonstrably more tolerable than each of Comparator Compounds Nos: 564122, 564127, 564133, 564143, 564150, 564188, 564210, and 564216 in this assay.

Compound 1008870

For example, as provided in Example 13 (hereinbelow), Compound 1008870 demonstrated a functional observational battery (FOB) score of 1.00 in wild-type mice whereas each of Comparator Compounds Nos: 564122, 564127, 564133, 564143, 564150, 564188, 564210, and 564216 demonstrated a FOB score of 7.00. Therefore, Compound 1008870 is demonstrably more tolerable than each of Comparator Compounds Nos: 564122, 564127, 564133, 564143, 564150, 564188, 564210, and 564216 in this assay.

Compound 1008874

For example, as provided in Example 13 (hereinbelow), Compound 1008874 demonstrated a functional observational battery (FOB) score of 1.25 in wild-type mice whereas each of Comparator Compounds Nos: 564122, 564127, 564133, 564143, 564150, 564188, 564210, and 564216 demonstrated a FOB score of 7.00. Therefore, Compound 1008874 is demonstrably more tolerable than each of Comparator Compounds Nos: 564122, 564127, 564133, 564143, 564150, 564188, 564210, and 564216 in this assay.

Compound 1008910

For example, as provided in Example 13 (hereinbelow), Compound 1008910 demonstrated a functional observational battery (FOB) score of 0.00 in wild-type mice whereas each of Comparator Compounds Nos: 564122, 564127, 564133, 564143, 564150, 564188, 564210, and 564216 demonstrated a FOB score of 7.00. Therefore, Compound 1008910 is demonstrably more tolerable than each of Comparator Compounds Nos: 564122, 564127, 564133, 564143, 564150, 564188, 564210, and 564216 in this assay.

IX. Certain Hotspot Regions

1. Nucleobases 2,455-2,483 of SEQ ID NO: 1

In certain embodiments, nucleobases 2,455-2,483 of SEQ ID NO: 1 comprise a hotspot region. In certain embodiments, modified oligonucleotides are complementary to nucleobases 2,455-2,483 of SEQ ID NO: 1. In certain embodiments, modified oligonucleotides are 20 nucleobases in length. In certain embodiments, modified oligonucleotides are gapmers. In certain embodiments, the gapmers are 5-10-5 MOE gapmers. In certain embodiments, the internucleoside linkages of the modified oligonucleotides are phosphodiester ("o") and phosphorothioate ("s") internucleoside linkages. In certain embodiments, the phosphodiester ("o") and phosphorothioate ("s") internucleoside linkages are arranged in order from 5' to 3': soooossssssssssssooss.

The nucleobase sequences of SEQ ID Nos: 286, 287, 1113, 1188, 1260, 1336, 1412, 2391, 2468, and 3002 are complementary to nucleobases 2,455-2,483 of SEQ ID NO: 1.

In certain embodiments, modified oligonucleotides complementary to nucleobases 2,455-2,483 of SEQ ID NO: 1 achieve at least 67% reduction of ATXN2 RNA in vitro in the standard cell assay.

2. Nucleobases 4,393-4,424 of SEQ ID NO: 1

In certain embodiments, nucleobases 4,393-4,424 of SEQ ID NO: 1 comprise a hotspot region. In certain embodiments, modified oligonucleotides are complementary to nucleobases 4,393-4,424 of SEQ ID NO: 1. In certain embodiments, modified oligonucleotides are 20 nucleobases in length. In certain embodiments, modified oligonucleotides are gapmers. In certain embodiments, the gapmers are 5-10-5 MOE gapmers. In certain embodiments, the internucleoside linkages of the modified oligonucleotides are phosphodiester ("o") and phosphorothioate ("s") internucleoside linkages. In certain embodiments, the phosphodiester ("o") and phosphorothioate ("s") internucleoside linkages are arranged in order from 5' to 3': sooooossssssssssooss.

The nucleobase sequences of SEQ ID Nos: 1945, 2020, 2316, 2392, 2469, 2546, 2623, 2697, 2926, 3003, 3080, and 3157 are complementary to nucleobases 4,393-4,424 of SEQ ID NO: 1.

In certain embodiments, modified oligonucleotides complementary to nucleobases 4,393-4,424 of SEQ ID NO: 1 achieve at least 64% reduction of ATXN2 RNA in vitro in the standard cell assay.

3. Nucleobases 4,413-4,437 of SEQ ID NO: 1

In certain embodiments, nucleobases 4,413-4,437 of SEQ ID NO: 1 comprise a hotspot region. In certain embodiments, modified oligonucleotides are complementary to nucleobases 4,413-4,437 of SEQ ID NO: 1. In certain embodiments, modified oligonucleotides are 20 nucleobases in length. In certain embodiments, modified oligonucleotides are gapmers. In certain embodiments, the gapmers are 5-10-5 MOE gapmers. In certain embodiments, the internucleoside linkages of the modified oligonucleotides are phosphodiester ("o") and phosphorothioate ("s") internucleoside linkages. In certain embodiments, the phosphodiester ("o") and phosphorothioate ("s") internucleoside linkages are arranged in order from 5' to 3': sooooossssssssssooss.

The nucleobase sequences of SEQ ID Nos: 2247, 2317, 2393, 2470, 2927, and 3004 are complementary to nucleobases 4,413-4,437 of SEQ ID NO: 1.

In certain embodiments, modified oligonucleotides complementary to nucleobases 4,413-4,437 of SEQ ID NO: 1 achieve at least 68% reduction of ATXN2 RNA in vitro in the standard cell assay.

4. Nucleobases 4,525-4,554 of SEQ ID NO: 2 In certain embodiments, nucleobases 4,525-4,554 of SEQ ID NO: 2 comprise a hotspot region. In certain embodiments, modified oligonucleotides are complementary to nucleobases 4,525-4,554 of SEQ ID NO: 2. In certain embodiments, modified oligonucleotides are 20 nucleobases in length. In certain embodiments, modified oligonucleotides are gapmers. In certain embodiments, the gapmers are 5-10-5 MOE gapmers. In certain embodiments, the internucleoside linkages of the modified oligonucleotides are phosphodiester ("o") and phosphorothioate ("s") internucleoside linkages. In certain embodiments, the phosphodiester ("o") and phosphorothioate ("s") internucleoside linkages are arranged in order from 5' to 3': sooooossssssssssooss.

The nucleobase sequences of SEQ ID Nos: 1948, 2319, 2549, 2625, 2701, 2777, 2853, 2929, 3006, 3083, and 3160 are complementary to nucleobases 4,525-4,554 of SEQ ID NO: 2.

In certain embodiments, modified oligonucleotides complementary to nucleobases 4,525-4,554 of SEQ ID NO: 2 achieve at least 79% reduction of ATXN2 RNA in vitro in the standard cell assay.

5. Nucleobases 4,748-4,771 of SEQ ID NO: 2

In certain embodiments, nucleobases 4,748-4,771 of SEQ ID NO: 2 comprise a hotspot region. In certain embodiments, modified oligonucleotides are complementary to nucleobases 4,748-4,771 of SEQ ID NO: 2. In certain embodiments, modified oligonucleotides are 20 nucleobases in length. In certain embodiments, modified oligonucleotides are gapmers. In certain embodiments, the gapmers are 5-10-5 MOE gapmers. In certain embodiments, the internucleoside linkages of the modified oligonucleotides are phosphodiester ("o") and phosphorothioate ("s") internucleoside linkages. In certain embodiments, the phosphodiester ("o") and phosphorothioate ("s") internucleoside linkages are arranged in order from 5' to 3': soooosssssssssooss.

The nucleobase sequences of SEQ ID Nos: 2175, 2626, 2702, 2778, and 3161 are complementary to nucleobases 4,748-4,771 of SEQ ID NO: 2.

In certain embodiments, modified oligonucleotides complementary to nucleobases 4,748-4,771 of SEQ ID NO: 2 achieve at least 70% reduction of ATXN2 RNA in vitro in the standard cell assay.

6. Nucleobases 9,927-9,954 of SEQ ID NO: 2

In certain embodiments, nucleobases 9,927-9,954 of SEQ ID NO: 2 comprise a hotspot region. In certain embodiments, modified oligonucleotides are complementary to nucleobases 9,927-9,954 of SEQ ID NO: 2. In certain embodiments, modified oligonucleotides are 20 nucleobases in length. In certain embodiments, modified oligonucleotides are gapmers. In certain embodiments, the gapmers are 5-10-5 MOE gapmers. In certain embodiments, the internucleoside linkages of the modified oligonucleotides are phosphodiester ("o") and phosphorothioate ("s") internucleoside linkages. In certain embodiments, the phosphodiester ("o") and phosphorothioate ("s") internucleoside linkages are arranged in order from 5' to 3': sooosssssssssooss.

The nucleobase sequences of SEQ ID Nos: 2177, 2399, 2476, 2553, 2629, 2705, 3010, 3087, and 3164 are complementary to nucleobases 9,927-9,954 of SEQ ID NO: 2.

In certain embodiments, modified oligonucleotides complementary to nucleobases 9,927-9,954 of SEQ ID NO: 2 achieve at least 62% reduction of ATXN2 RNA in vitro in the standard cell assay. 7. Nucleobases 10,345-10,368 of SEQ ID NO: 2

In certain embodiments, nucleobases 10,345-10,368 of SEQ ID NO: 2 comprise a hotspot region. In certain embodiments, modified oligonucleotides are complementary to nucleobases 10,345-10,368 of SEQ ID NO: 2. In certain embodiments, modified oligonucleotides are 20 nucleobases in length. In certain embodiments, modified oligonucleotides are gapmers. In certain embodiments, the gapmers are 5-10-5 MOE gapmers. In certain embodiments, the internucleoside linkages of the modified oligonucleotides are phosphodiester ("o") and phosphorothioate ("s") internucleoside linkages. In certain embodiments, the phosphodiester ("o") and phosphorothioate ("s") internucleoside linkages are arranged in order from 5' to 3': sooooosssssssssooss.

The nucleobase sequences of SEQ ID Nos: 2323, 2400, 2477, 2933, and 3011 are complementary to nucleobases 10,345-10,368 of SEQ ID NO: 2.

In certain embodiments, modified oligonucleotides complementary to nucleobases 10,345-10,368 of SEQ ID NO: 2 achieve at least 87% reduction of ATXN2 RNA in vitro in the standard cell assay.

8. Nucleobases 17,153-17,182 of SEQ ID NO: 2

In certain embodiments, nucleobases 17,153-17,182 of SEQ ID NO: 2 comprise a hotspot region. In certain embodiments, modified oligonucleotides are complementary to nucleobases 17,153-17,182 of SEQ ID NO: 2. In certain embodiments, modified oligonucleotides are 20 nucleobases in length. In certain embodiments, modified oligonucleotides are gapmers. In certain embodiments, the gapmers are 5-10-5 MOE gapmers. In certain embodiments, the internucleoside linkages of the modified oligonucleotides are phosphodiester ("o") and phosphorothioate ("s") internucleoside linkages. In certain embodiments, the phosphodiester ("o") and phosphorothioate ("s") internucleoside linkages are arranged in order from 5' to 3': soooosssssssssssooss.

The nucleobase sequences of SEQ ID Nos: 973, 2479, 2556, 2632, 2708, 2784, 2860, 2936, 3013, 3090, and 3167 are complementary to nucleobases 17,153-17,182 of SEQ ID NO: 2.

In certain embodiments, modified oligonucleotides complementary to nucleobases 17,153-17,182 of SEQ ID NO: 2 achieve at least 68% reduction of ATXN2 RNA in vitro in the standard cell assay. 9. Nucleobases 18,680-18,702 of SEQ ID NO: 2

In certain embodiments, nucleobases 18,680-18,702 of SEQ ID NO: 2 comprise a hotspot region. In certain embodiments, modified oligonucleotides are complementary to nucleobases 18,680-18,702 of SEQ ID NO: 2. In certain embodiments, modified oligonucleotides are 20 nucleobases in length. In certain embodiments, modified oligonucleotides are gapmers. In certain embodiments, the gapmers are 5-10-5 MOE gapmers. In certain embodiments, the internucleoside linkages of the modified oligonucleotides are phosphodiester ("o") and phosphorothioate ("s") internucleoside linkages. In certain embodiments, the phosphodiester ("o") and phosphorothioate ("s") internucleoside linkages are arranged in order from 5' to 3': soooosssssssssssooss.

The nucleobase sequences of SEQ ID Nos: 2256, 2557, 3014, and 3091 are complementary to nucleobases 18,680-18,702 of SEQ ID NO: 2.

In certain embodiments, modified oligonucleotides complementary to nucleobases 18,680-18,702 of SEQ ID NO: 2 achieve at least 65% reduction of ATXN2 RNA in vitro in the standard cell assay.

10. Nucleobases 23,251-23,276 of SEQ ID NO: 2

In certain embodiments, nucleobases 23,251-23,276 of SEQ ID NO: 2 comprise a hotspot region. In certain embodiments, modified oligonucleotides are complementary to nucleobases 23,251-23,276 of SEQ ID NO: 2. In certain embodiments, modified oligonucleotides are 20 nucleobases in length. In certain embodiments, modified oligonucleotides are gapmers. In certain embodiments, the gapmers are 5-10-5 MOE gapmers. In certain embodiments, the internucleoside linkages of the modified oligonucleotides are phosphodiester ("o") and phosphorothioate ("s") internucleoside linkages. In certain embodiments, the phosphodiester ("o") and phosphorothioate ("s") internucleoside linkages are arranged in order from 5' to 3': soooosssssssssssooss.

The nucleobase sequences of SEQ ID Nos: 1805, 2635, 2711, 2787, 2863, 2939, and 3170 are complementary to nucleobases 23,251-23,276 of SEQ ID NO: 2.

In certain embodiments, modified oligonucleotides complementary to nucleobases 23,251-23,276 of SEQ ID NO: 2 achieve at least 64% reduction of ATXN2 RNA in vitro in the standard cell assay.

11. Nucleobases 28,081-28,105 of SEQ ID NO: 2

In certain embodiments, nucleobases 28,081-28,105 of SEQ ID NO: 2 comprise a hotspot region. In certain embodiments, modified oligonucleotides are complementary to nucleobases 28,081-28,105 of SEQ ID NO: 2. In certain embodiments, modified oligonucleotides are 20 nucleobases in length. In certain embodiments, modified oligonucleotides are gapmers. In certain embodiments, the gapmers are 5-10-5 MOE gapmers. In certain embodiments, the internucleoside linkages of the modified oligonucleotides are phosphodiester ("o") and phosphorothioate ("s") internucleoside linkages. In certain embodiments, the phosphodiester ("o") and phosphorothioate ("s") internucleoside linkages are arranged in order from 5' to 3': sooooosssssssssssooss.

The nucleobase sequences of SEQ ID Nos: 2259, 2331, 2713, 2789, 2865, and 2941 are complementary to nucleobases 28,081-28,105 of SEQ ID NO: 2.

In certain embodiments, modified oligonucleotides complementary to nucleobases 28,081-28,105 of SEQ ID NO: 2 achieve at least 62% reduction of ATXN2 RNA in vitro in the standard cell assay.

12. Nucleobases 28,491-28,526 of SEQ ID NO: 2

In certain embodiments, nucleobases 28,491-28,526 of SEQ ID NO: 2 comprise a hotspot region. In certain embodiments, modified oligonucleotides are complementary to nucleobases 28,491-28,526 of SEQ ID NO: 2. In certain embodiments, modified oligonucleotides are 20 nucleobases in length. In certain embodiments, modified oligonucleotides are gapmers. In certain embodiments, the gapmers are 5-10-5 MOE gapmers. In certain embodiments, the internucleoside linkages of the modified oligonucleotides are phosphodiester ("o") and phosphorothioate ("s") internucleoside linkages. In certain embodiments, the phosphodiester ("o") and phosphorothioate ("s") internucleoside linkages are arranged in order from 5' to 3': sooooosssssssssssooss.

The nucleobase sequences of SEQ ID Nos: 669, 746, 2562, 2638, 2714, 2790, 2866, 3019, 3096, and 3173 are complementary to nucleobases 28,491-28,526 of SEQ ID NO: 2.

In certain embodiments, modified oligonucleotides complementary to nucleobases 28,491-28,526 of SEQ ID NO: 2 achieve at least 67% reduction of ATXN2 RNA in vitro in the standard cell assay.

13. Nucleobases 28,885-28,912 of SEQ ID NO: 2

In certain embodiments, nucleobases 28,885-28,912 of SEQ ID NO: 2 comprise a hotspot region. In certain embodiments, modified oligonucleotides are complementary to nucleobases 28,885-28,912 of SEQ ID NO: 2. In certain embodiments, modified oligonucleotides are 20 nucleobases in length. In certain embodiments, modified oligonucleotides are gapmers. In certain embodiments, the gapmers are 5-10-5 MOE gapmers. In certain embodiments, the internucleoside linkages of the modified oligonucleotides are phosphodiester ("o") and phosphorothioate ("s") internucleoside linkages. In certain embodiments, the phosphodiester ("o") and phosphorothioate ("s") internucleoside linkages are arranged in order from 5' to 3': soooosssssssssssooss.

The nucleobase sequences of SEQ ID Nos: 977, 2486, 2563, 2639, 2715, 2791, 3020, 3097, and 3174 are complementary to nucleobases 28,885-28,912 of SEQ ID NO: 2.

In certain embodiments, modified oligonucleotides complementary to nucleobases 28,885-28,912 of SEQ ID NO: 2 achieve at least 75% reduction of ATXN2 RNA in vitro in the standard cell assay.

14. Nucleobases 32,328-32,352 of SEQ ID NO: 2

In certain embodiments, nucleobases 32,328-32,352 of SEQ ID NO: 2 comprise a hotspot region. In certain embodiments, modified oligonucleotides are complementary to nucleobases 32,328-32,352 of SEQ ID NO: 2. In certain embodiments, modified oligonucleotides are 20 nucleobases in length. In certain embodiments, modified oligonucleotides are gapmers. In certain embodiments, the gapmers are 5-10-5 MOE gapmers. In certain embodiments, the internucleoside linkages of the modified oligonucleotides are phosphodiester ("o") and phosphorothioate ("s") internucleoside linkages. In certain embodiments, the phosphodiester ("o") and phosphorothioate ("s") internucleoside linkages are arranged in order from 5' to 3': soooosssssssssooss.

The nucleobase sequences of SEQ ID Nos: 2109, 2334, 2411, 2488, 2565, and 3022 are complementary to nucleobases 32,328-32,352 of SEQ ID NO: 2.

In certain embodiments, modified oligonucleotides complementary to nucleobases 32,328-32,352 of SEQ ID NO: 2 achieve at least 66% reduction of ATXN2 RNA in vitro in the standard cell assay.

15. Nucleobases 32,796-32,824 of SEQ ID NO: 2

In certain embodiments, nucleobases 32,796-32,824 of SEQ ID NO: 2 comprise a hotspot region. In certain embodiments, modified oligonucleotides are complementary to nucleobases 32,796-32,824 of SEQ ID NO: 2. In certain embodiments, modified oligonucleotides are 20 nucleobases in length. In certain embodiments, modified oligonucleotides are gapmers. In certain embodiments, the gapmers are 5-10-5 MOE gapmers. In certain embodiments, the internucleoside linkages of the modified oligonucleotides are phosphodiester ("o") and phosphorothioate ("s") internucleoside linkages. In certain embodiments, the phosphodiester ("o") and phosphorothioate ("s") internucleoside linkages are arranged in order from 5' to 3': soooosssssssssooss.

The nucleobase sequences of SEQ ID Nos: 902, 2335, 2412, 2489, 2566, 2869, 2945, 3023, 3100, and 3177 are complementary to nucleobases 32,796-32,824 of SEQ ID NO: 2.

In certain embodiments, modified oligonucleotides complementary to nucleobases 32,796-32,824 of SEQ ID NO: 2 achieve at least 72% reduction of ATXN2 RNA in vitro in the standard cell assay.

16. Nucleobases 32,809-32,838 of SEQ ID NO: 2

In certain embodiments, nucleobases 32,809-32,838 of SEQ ID NO: 2 comprise a hotspot region. In certain embodiments, modified oligonucleotides are complementary to nucleobases 32,809-32,838 of SEQ ID NO: 2. In certain embodiments, modified oligonucleotides are 20 nucleobases in length. In certain embodiments, modified oligonucleotides are gapmers. In certain embodiments, the gapmers are 5-10-5 MOE gapmers. In certain embodiments, the internucleoside linkages of the modified oligonucleotides are phosphodiester ("o") and phosphorothioate ("s") internucleoside linkages. In certain embodiments, the phosphodiester ("o") and phosphorothioate ("s") internucleoside linkages are arranged in order from 5' to 3': soooosssssssssooss.

The nucleobase sequences of SEQ ID Nos: 979, 2336, 2413, 2490, 2567, 2643, 2870, 2946, 3024, 3101, and 3178 are complementary to nucleobases 32,809-32,838 of SEQ ID NO: 2.

In certain embodiments, modified oligonucleotides complementary to nucleobases 32,809-32,838 of SEQ ID NO: 2 achieve at least 60% reduction of ATXN2 RNA in vitro in the standard cell assay.

17. Nucleobases 36,308-36,334 of SEQ ID NO: 2

In certain embodiments, nucleobases 36,308-36,334 of SEQ ID NO: 2 comprise a hotspot region. In certain embodiments, modified oligonucleotides are complementary to nucleobases 36,308-36,334 of SEQ ID NO: 2. In certain embodiments, modified oligonucleotides are 20 nucleobases in length. In certain embodiments, modified oligonucleotides are gapmers. In certain embodiments, the gapmers are 5-10-5 MOE gapmers. In certain embodiments, the internucleoside linkages of the modified oligonucleotides are phosphodiester ("o") and phosphorothioate ("s") internucleoside linkages. In certain embodiments, the phosphodiester ("o") and phosphorothioate ("s") internucleoside linkages are arranged in order from 5' to 3': soooosssssssssooss.

The nucleobase sequences of SEQ ID Nos: 1280, 2338, 2415, 2644, 2720, 2796, 2872, and 2948 are complementary to nucleobases 36,308-36,334 of SEQ ID NO: 2.

In certain embodiments, modified oligonucleotides complementary to nucleobases 36,308-36,334 of SEQ ID NO: 2 achieve at least 69% reduction of ATXN2 RNA in vitro in the standard cell assay.

18. Nucleobases 36,845-36,872 of SEQ ID NO: 2

In certain embodiments, nucleobases 36,845-36,872 of SEQ ID NO: 2 comprise a hotspot region. In certain embodiments, modified oligonucleotides are complementary to nucleobases 36,845-36,872 of SEQ ID NO: 2. In certain embodiments, modified oligonucleotides are 20 nucleobases in length. In certain embodiments, modified oligonucleotides are gapmers. In certain embodiments, the gapmers are 5-10-5 MOE gapmers. In certain embodiments, the internucleoside linkages of the modified oligonucleotides are phosphodiester ("o") and phosphorothioate ("s") internucleoside linkages. In certain embodiments, the phosphodiester ("o") and phosphorothioate ("s") internucleoside linkages are arranged in order from 5' to 3': soooosssssssssooss.

The nucleobase sequences of SEQ ID Nos: 2035, 2339, 2645, 2721, 2797, 2873, 2949, 3103, and 3180 are complementary to nucleobases 36,845-36,872 of SEQ ID NO: 2.

In certain embodiments, modified oligonucleotides complementary to nucleobases 36,845-36,872 of SEQ ID NO: 2 achieve at least 63% reduction of ATXN2 RNA in vitro in the standard cell assay.

19. Nucleobases 49,147-49,173 of SEQ ID NO: 2

In certain embodiments, nucleobases 49,147-49,173 of SEQ ID NO: 2 comprise a hotspot region. In certain embodiments, modified oligonucleotides are complementary to nucleobases 49,147-49,173 of SEQ ID NO: 2. In certain embodiments, modified oligonucleotides are 20 nucleobases in length. In certain embodiments, modified oligonucleotides are gapmers. In certain embodiments, the gapmers are 5-10-5 MOE gapmers. In certain embodiments, the internucleoside linkages of the modified oligonucleotides are phosphodiester ("o") and phosphorothioate ("s") internucleoside linkages. In certain embodiments, the phosphodiester ("o") and phosphorothioate ("s") internucleoside linkages are arranged in order from 5' to 3': soooosssssssssooss.

The nucleobase sequences of SEQ ID Nos: 1439, 2575, 2651, 2727, 2803, 3032, 3109, and 3186 are complementary to nucleobases 49,147-49,173 of SEQ ID NO: 2.

In certain embodiments, modified oligonucleotides complementary to nucleobases 49,147-49,173 of SEQ ID NO: 2 achieve at least 69% reduction of ATXN2 RNA in vitro in the standard cell assay.

20. Nucleobases 57,469-57,494 of SEQ ID NO: 2

In certain embodiments, nucleobases 57,469-57,494 of SEQ ID NO: 2 comprise a hotspot region. In certain embodiments, modified oligonucleotides are complementary to nucleobases 57,469-57,494 of SEQ ID NO: 2. In certain embodiments, modified oligonucleotides are 20 nucleobases in length. In certain embodiments, modified oligonucleotides are gapmers. In certain embodiments, the gapmers are 5-10-5 MOE gapmers. In certain embodiments, the internucleoside linkages of the modified oligonucleotides are phosphodiester ("o") and phosphorothioate ("s") internucleoside linkages. In certain embodiments, the phosphodiester ("o") and phosphorothioate ("s") internucleoside linkages are arranged in order from 5' to 3': soooosssssssssooss.

The nucleobase sequences of SEQ ID Nos: 2045, 2121, 2426, 2503, 2580, 3037, and 3114 are complementary to nucleobases 57,469-57,494 of SEQ ID NO: 2.

In certain embodiments, modified oligonucleotides complementary to nucleobases 57,469-57,494 of SEQ ID NO: 2 achieve at least 49% reduction of ATXN2 RNA in vitro in the standard cell assay.

21. Nucleobases 82,848-82,874 of SEQ ID NO: 2

In certain embodiments, nucleobases 82,848-82,874 of SEQ ID NO: 2 comprise a hotspot region. In certain embodiments, modified oligonucleotides are complementary to nucleobases 82,848-82,874 of SEQ ID NO: 2. In certain embodiments, modified oligonucleotides are 20 nucleobases in length. In certain embodiments, modified oligonucleotides are gapmers. In certain embodiments, the gapmers are 5-10-5 MOE gapmers. In certain embodiments, the internucleoside linkages of the modified oligonucleotides are phosphodiester ("o") and phosphorothioate ("s") internucleoside linkages. In certain embodiments, the phosphodiester ("o") and phosphorothioate ("s") internucleoside linkages are arranged in order from 5' to 3': soooosssssssssooss.

The nucleobase sequences of SEQ ID Nos: 1982, 2359, 2436, 2513, 2590, 2969, 3047, and 3124 are complementary to nucleobases 82,848-82,874 of SEQ ID NO: 2.

In certain embodiments, modified oligonucleotides complementary to nucleobases 82,848-82,874 of SEQ ID NO: 2 achieve at least 57% reduction of ATXN2 RNA in vitro in the standard cell assay.

22. Nucleobases 83,784-83,813 of SEQ ID NO: 2

In certain embodiments, nucleobases 83,784-83,813 of SEQ ID NO: 2 comprise a hotspot region. In certain embodiments, modified oligonucleotides are complementary to nucleobases 83,784-83,813 of SEQ ID NO: 2. In certain embodiments, modified oligonucleotides are 20 nucleobases in length. In certain embodiments, modified oligonucleotides are gapmers. In certain embodiments, the gapmers are 5-10-5 MOE gapmers. In certain embodiments, the internucleoside linkages of the modified oligonucleotides are phosphodiester ("o") and phosphorothioate ("s") internucleoside linkages. In certain embodiments, the phosphodiester ("o") and phosphorothioate ("s") internucleoside linkages are arranged in order from 5' to 3': soooosssssssssooss.

The nucleobase sequences of SEQ ID Nos: 849, 2361, 2438, 2515, 2592, 2668, 2744, 2971, 3049, 3126, and 3203 are complementary to nucleobases 83,784-83,813 of SEQ ID NO: 2.

In certain embodiments, modified oligonucleotides complementary to nucleobases 83,784-83,813 of SEQ ID NO: 2 achieve at least 76% reduction of ATXN2 RNA in vitro in the standard cell assay.

23. Nucleobases 84,743-84,782 of SEQ ID NO: 2

In certain embodiments, nucleobases 84,743-84,782 of SEQ ID NO: 2 comprise a hotspot region. In certain embodiments, modified oligonucleotides are complementary to nucleobases 84,743-84,782 of SEQ ID NO: 2. In certain embodiments, modified oligonucleotides are 20 nucleobases in length. In certain embodiments, modified oligonucleotides are gapmers. In certain embodiments, the gapmers are 5-10-5 MOE gapmers. In certain embodiments, the internucleoside linkages of the modified oligonucleotides are phosphodiester ("o") and phosphorothioate ("s") internucleoside linkages. In certain embodiments, the phosphodiester ("o") and phosphorothioate ("s") internucleoside linkages are arranged in order from 5' to 3': soooosssssssssooss.

The nucleobase sequences of SEQ ID Nos: 2210, 2441, 2518, 2595, 2671, 2747, 2823, 2899, 2975, 3052, 3129, and 3206 are complementary to nucleobases 84,743-84,782 of SEQ ID NO: 2.

In certain embodiments, modified oligonucleotides complementary to nucleobases 84,743-84,782 of SEQ ID NO: 2 achieve at least 58% reduction of ATXN2 RNA in vitro in the standard cell assay.

24. Nucleobases 84,813-84,839 of SEQ ID NO: 2

In certain embodiments, nucleobases 84,813-84,839 of SEQ ID NO: 2 comprise a hotspot region. In certain embodiments, modified oligonucleotides are complementary to nucleobases 84,813-84,839 of SEQ ID NO: 2. In certain embodiments, modified oligonucleotides are 20 nucleobases in length. In certain embodiments, modified oligonucleotides are gapmers. In certain embodiments, the gapmers are 5-10-5 MOE gapmers. In certain embodiments, the internucleoside linkages of the modified oligonucleotides are phosphodiester ("o") and phosphorothioate ("s") internucleoside linkages. In certain embodiments, the phosphodiester ("o") and phosphorothioate ("s") internucleoside linkages are arranged in order from 5' to 3': soooosssssssssooss.

The nucleobase sequences of SEQ ID Nos: 542, 2286, 2672, 2748, 2824, 2900, 3130, and 3207 are complementary to nucleobases 84,813-84,839 of SEQ ID NO: 2.

In certain embodiments, modified oligonucleotides complementary to nucleobases 84,813-84,839 of SEQ ID NO: 2 achieve at least 69% reduction of ATXN2 RNA in vitro in the standard cell assay.

25. Nucleobases 85,051-85,076 of SEQ ID NO: 2

In certain embodiments, nucleobases 85,051-85,076 of SEQ ID NO: 2 comprise a hotspot region. In certain embodiments, modified oligonucleotides are complementary to nucleobases 85,051-85,076 of SEQ ID NO: 2. In certain embodiments, modified oligonucleotides are 20 nucleobases in length. In certain embodiments, modified oligonucleotides are gapmers. In certain embodiments, the gapmers are 5-10-5 MOE gapmers. In certain embodiments, the internucleoside linkages of the modified oligonucleotides are phosphodiester ("o") and phosphorothioate ("s") internucleoside linkages. In certain embodiments, the phosphodiester ("o") and phosphorothioate ("s") internucleoside linkages are arranged in order from 5' to 3': soooosssssssssooss.

The nucleobase sequences of SEQ ID Nos: 773, 850, 2673, 2749, 2825, 3131, and 3208 are complementary to nucleobases 85,051-85,076 of SEQ ID NO: 2.

In certain embodiments, modified oligonucleotides complementary to nucleobases 85,051-85,076 of SEQ ID NO: 2 achieve at least 57% reduction of ATXN2 RNA in vitro in the standard cell assay.

26. Nucleobases 97,618-97,643 of SEQ ID NO: 2

In certain embodiments, nucleobases 97,618-97,643 of SEQ ID NO: 2 comprise a hotspot region. In certain embodiments, modified oligonucleotides are complementary to nucleobases 97,618-97,643 of SEQ ID NO: 2. In certain embodiments, modified oligonucleotides are 20 nucleobases in length. In certain embodiments, modified oligonucleotides are gapmers. In certain embodiments, the gapmers are 5-10-5 MOE gapmers. In certain embodiments, the internucleoside linkages of the modified oligonucleotides are phosphodiester ("o") and phosphorothioate ("s") internucleoside linkages. In certain embodiments, the phosphodiester ("o") and phosphorothioate ("s") internucleoside linkages are arranged in order from 5' to 3': soooosssssssssooss.

The nucleobase sequences of SEQ ID Nos: 1839, 2370, 2447, 2524, 2904, 2980, and 3058 are complementary to nucleobases 97,618-97,643 of SEQ ID NO: 2.

In certain embodiments, modified oligonucleotides complementary to nucleobases 97,618-97,643 of SEQ ID NO: 2 achieve at least 72% reduction of ATXN2 RNA in vitro in the standard cell assay.

27. Nucleobases 119,023-119,048 of SEQ ID NO: 2

In certain embodiments, nucleobases 119,023-119,048 of SEQ ID NO: 2 comprise a hotspot region. In certain embodiments, modified oligonucleotides are complementary to nucleobases 119,023-119,048 of SEQ ID NO: 2. In certain embodiments, modified oligonucleotides are 20 nucleobases in length. In certain embodiments, modified oligonucleotides are gapmers. In certain embodiments, the gapmers are 5-10-5 MOE gapmers. In certain embodiments, the internucleoside linkages of the modified oligonucleotides are phosphodiester ("o") and phosphorothioate ("s") internucleoside linkages. In certain embodiments, the phosphodiester ("o") and phosphorothioate ("s") internucleoside linkages are arranged in order from 5' to 3': soooosssssssssooss.

The nucleobase sequences of SEQ ID Nos: 2072, 2606, 2682, 2758, 2834, 3140, and 3217 are complementary to nucleobases 119,023-119,048 of SEQ ID NO: 2.

In certain embodiments, modified oligonucleotides complementary to nucleobases 119,023-119,048 of SEQ ID NO: 2 achieve at least 69% reduction of ATXN2 RNA in vitro in the standard cell assay.

28. Nucleobases 132,161-132,195 of SEQ ID NO: 2

In certain embodiments, nucleobases 132,161-132,195 of SEQ ID NO: 2 comprise a hotspot region. In certain embodiments, modified oligonucleotides are complementary to nucleobases 132,161-132,195 of SEQ ID NO: 2. In certain embodiments, modified oligonucleotides are 20 nucleobases in length. In certain embodiments, modified oligonucleotides are gapmers. In certain embodiments, the gapmers are 5-10-5 MOE gapmers. In certain embodiments, the internucleoside linkages of the modified oligonucleotides are phosphodiester ("o") and phosphorothioate ("s") internucleoside linkages. In certain embodiments, the phosphodiester ("o") and phosphorothioate ("s") internucleoside linkages are arranged in order from 5' to 3': soooosssssssssooss.

The nucleobase sequences of SEQ ID Nos: 1927, 2002, 2381, 2458, 2763, 2839, 2915, and 2991 are complementary to nucleobases 132,161-132,195 of SEQ ID NO: 2.

In certain embodiments, modified oligonucleotides complementary to nucleobases 132,161-132,195 of SEQ ID NO: 2 achieve at least 78% reduction of ATXN2 RNA in vitro in the standard cell assay.

29. Nucleobases 139,271-139,303 of SEQ ID NO: 2

In certain embodiments, nucleobases 139,271-139,303 of SEQ ID NO: 2 comprise a hotspot region. In certain embodiments, modified oligonucleotides are complementary to nucleobases 139,271-139,303 of SEQ ID NO: 2. In certain embodiments, modified oligonucleotides are 20 nucleobases in length. In certain embodiments, modified oligonucleotides are gapmers. In certain embodiments, the gapmers are 5-10-5 MOE gapmers. In certain embodiments, the internucleoside linkages of the modified oligonucleotides are phosphodiester ("o") and phosphorothioate ("s") internucleoside linkages. In certain embodiments, the phosphodiester ("o") and phosphorothioate ("s") internucleoside linkages are arranged in order from 5' to 3': soooosssssssssooss.

The nucleobase sequences of SEQ ID Nos: 795, 872, 2540, 2617, 3074, and 3151 are complementary to nucleobases 139,271-139,303 of SEQ ID NO: 2.

In certain embodiments, modified oligonucleotides complementary to nucleobases 139,271-139,303 of SEQ ID NO: 2 achieve at least 61% reduction of ATXN2 RNA in vitro in the standard cell assay.

30. Nucleobases 1,075-1,146 of SEQ ID NO: 1

In certain embodiments, nucleobases 1,075-1,146 of SEQ ID NO: 1 comprise a hotspot region. In certain embodiments, modified oligonucleotides are complementary to nucleobases 1,075-1,146 of SEQ ID NO: 1. In certain embodiments, modified oligonucleotides are 20 nucleobases in length. In certain embodiments, modified oligonucleotides are gapmers. In certain embodiments, the gapmers are 5-10-5 MOE gapmers. In certain embodiments, the gapmers are 6-10-4 MOE gapmers. In certain embodiments, the internucleoside linkages of the modified oligonucleotides are phosphodiester ("o") and phosphorothioate ("s") internucleoside linkages. In certain embodiments, the phosphodiester ("o") and phosphorothioate ("s") internucleoside linkages are arranged in order from 5' to 3': soooosssssssssooss. In certain embodiments, the phosphodiester ("o") and phosphorothioate ("s") internucleoside linkages are arranged in order from 5' to 3': In certain embodiments, the phosphodiester ("o") and phosphorothioate ("s") internucleoside linkages are arranged in order from 5' to 3': soooosssssssssooss.

The nucleobase sequences of SEQ ID Nos: 33, 1485, 1561, 1637, 1714, 1788, 1861, 1936, 2013, 2088, 2164, 2467, 2544, 3001, 3232, 3233, 3234, 3235, 3237, 3238, 3239, 3298, 3299, 3300, and 3301 are complementary to nucleobases 1,075-1,146 of SEQ ID NO: 1.

In certain embodiments, modified oligonucleotides complementary to nucleobases 1,075-1,146 of SEQ ID NO: 1 achieve at least 49% reduction of ATXN2 mRNA in vitro in the standard cell assay.

Nonlimiting Disclosure and Incorporation by Reference

Each of the literature and patent publications listed herein is incorporated by reference in its entirety.

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH in place of one 2'-H of DNA) or as an RNA having a modified base (thymine (methylated uracil) in place of a uracil of RNA). Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified nucleobases, such as "AT$^m$CGAUCG," wherein mC indicates a cytosine base comprising a methyl group at the 5-position.

Certain compounds described herein (e.g., modified oligonucleotides) have one or more asymmetric center and thus give rise to enantiomers, diastereomers, and other stereoisomeric configurations that may be defined, in terms of absolute stereochemistry, as (R) or (S), as α or β such as for sugar anomers, or as (D) or (L), such as for amino acids, etc. Compounds provided herein that are drawn or described as having certain stereoisomeric configurations include only the indicated compounds. Compounds provided herein that are drawn or described with undefined stereochemistry include all such possible isomers, including their stereorandom and optically pure forms, unless specified otherwise. Likewise, tautomeric forms of the compounds herein are also included unless otherwise indicated. Unless otherwise indicated, compounds described herein are intended to include corresponding salt forms.

The compounds described herein include variations in which one or more atoms are replaced with a non-radioactive isotope or radioactive isotope of the indicated element. For example, compounds herein that comprise hydrogen atoms encompass all possible deuterium substitutions for each of the $^1$H hydrogen atoms. Isotopic substitutions encompassed by the compounds herein include but are not limited to: $^2$H or $^3$H in place of $^1$H, $^{13}$C or $^{14}$C in place of $^{12}$C, $^{15}$N in place of $^{14}$N, $^{17}$O or $^{18}$O in place of $^{16}$O, and $^{33}$S, $^{34}$S, $^{35}$S, or $^{36}$S in place of $^{32}$S. In certain embodiments, non-radioactive isotopic substitutions may impart new properties on the oligomeric compound that are beneficial for use as a therapeutic or research tool. In certain embodiments, radioactive isotopic substitutions may make the compound suitable for research or diagnostic purposes such as imaging.

EXAMPLES

The following examples illustrate certain embodiments of the present disclosure and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif. And, for example, where a particular high-affinity modification appears at a particular position, other high-affinity modifications at the same position are considered suitable, unless otherwise indicated.

Example 1: Effect of 5-10-5 MOE Gapmers with Mixed Internucleoside Linkages on Human ATXN2 RNA In Vitro, Single Dose Modified oligonucleotides complementary to a human ATXN2 nucleic acid were designed and tested for their effect on ATXN2 RNA in SCA2-04 cells. SCA2-04 is a patient fibroblast cell line with 34 CAG repeats. The modified oligonucleotides were tested in a series of experiments that had similar culture conditions.

Cultured SCA2-04 cells at a density of 20,000 cells per well were transfected using electroporation with 2,000 or 7,000 nM concentration of modified oligonucleotide, as indicated in the tables below, or no modified oligonucleotide for untreated controls. After approximately 24 hours, RNA was isolated from the cells and ATXN2 RNA levels were measured by quantitative real-time PCR Human primer probe set hAtaxin_LTS01321 (forward sequence ATATGGACTCCAGTTATGCAAAAAGA, designated herein as SEQ ID NO: 10; reverse sequence TCGCCATTCACTTTAGCACTGA, designated herein as SEQ ID NO: 11; probe sequence ATGCTTTTACTGACTCTGC, designated herein as SEQ ID: 12) was used to measure RNA levels. ATXN2 RNA levels were adjusted according to total RNA content, as measured by RIBOGREEN®. Results are presented in the tables below as percent ATXN2 RNA levels relative to untreated control cells.

The modified oligonucleotides marked with an asterisk (*) target the amplicon region of the primer probe set. Additional assays may be used to measure the potency and efficacy of oligonucleotides targeting the amplicon region.

The modified oligonucleotides in the tables below are 5-10-5 MOE gapmers. The gapmers are 20 nucleobases in length, wherein the central gap segment comprises ten 2'-deoxynucleosides and is flanked by wing segments on both the 5' end and on the 3' end comprising five 2'-MOE nucleosides. The sugar motif for the gapmers is (from 5' to 3'): eeeeedddddddddeeeee; wherein 'd' represents a 2'-deoxyribose sugar and 'e' represents a 2'-MOE modified sugar. The internucleoside linkages are mixed phosphodiester and phosphorothioate internucleoside linkages. The internucleoside linkage motif for the gapmers is (from 5' to 3'): sooooossssssssssooss; wherein 'o' represents a phosphodiester internucleoside linkage and 's' represents a phosphorothioate internucleoside linkage. Each cytosine residue is a 5-methyl cytosine. "Start Site" indicates the 5'-most nucleoside to which the gapmer is complementary in the human nucleic acid sequence. "Stop Site" indicates the 3'-most nucleoside to which the gapmer is complementary in the human nucleic acid sequence.

Each modified oligonucleotide listed in the Tables below is complementary to human ATXN2 nucleic acid sequences SEQ ID NO: 1 or SEQ ID NO: 2, as indicated. 'N/A' indicates that the modified oligonucleotide is not complementary to that particular nucleic acid with 100% complementarity. As shown below, modified oligonucleotides complementary to the nucleobase sequence of human ATXN2 reduced the amount of human ATXN2 RNA.

TABLE 1

Percent control of human ATXN2 RNA with 5-10-5 MOE gapmers with mixed internucleoside linkages at 7,000 nM concentration

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % Control | SEQ ID NO |
|---|---|---|---|---|---|---|---|
| 708134 | 929 | 948 | N/A | N/A | GATTCCATCAAAAGAAATCG | 16 | 30 |

TABLE 1-continued

Percent control of human ATXN2 RNA with 5-10-5 MOE gapmers with mixed internucleoside linkages at 7,000 nM concentration

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % Control | SEQ ID NO |
|---|---|---|---|---|---|---|---|
| 708155 | 1094 | 1113 | 49268 | 49287 | CGAACTGGATTCTGTACTTT | 14 | 31 |
| 708199 | 1477 | 1496 | 81637 | 81656 | GCTAACTGGTTTGCCCTTGC | 10 | 32 |
| 755233 | 1123 | 1142 | 49297 | 49316 | CTCTCCATTATTTCTTCACG | 7 | 33 |
| 756933 | 717 | 736 | 2707 | 2726 | CGGGCGGCGGCTGCTGCTGC | 20 | 34 |
| 756934 | 723 | 742 | 2713 | 2732 | CAGCCGCGGGCGGCGGCTGC | 89 | 35 |
| 756935 | 729 | 748 | 2719 | 2738 | CATTGGCAGCCGCGGGCGGC | 33 | 36 |
| 756936 | 735 | 754 | 2725 | 2744 | TGCGGACATTGGCAGCCGCG | 51 | 37 |
| 756937 | 741 | 760 | 2731 | 2750 | CGGGCTTGCGGACATTGGCA | 15 | 38 |
| 756938 | 747 | 766 | 2737 | 2756 | TGCCGCCGGGCTTGCGGACA | 27 | 39 |
| 756939 | 759 | 778 | 2749 | 2768 | CTAGAAGGCCGCTGCCGCCG | 50 | 40 |
| 756940 | 778 | 797 | 2768 | 2787 | GGCGCGGCGGCGGGCGACGC | 13 | 41 |
| 756941 | 784 | 803 | 2774 | 2793 | GGCGAAGGCGCGGCGGCGGG | 49 | 42 |
| 756942 | 790 | 809 | 2780 | 2799 | GAGGACGGCGAAGGCGCGGC | 16 | 43 |
| 756943 | 796 | 815 | 2786 | 2805 | GAGGACGAGGACGGCGAAGG | 25 | 44 |
| 756944 | 802 | 821 | 2792 | 2811 | GAGACCGAGGACGAGGACGG | 34 | 45 |
| 756945 | 808 | 827 | 2798 | 2817 | GACGAGGAGACCGAGGACGA | 19 | 46 |
| 756946 | 814 | 833 | 2804 | 2823 | GCCGAGGACGAGGAGACCGA | 13 | 47 |
| 756947 | 820 | 839 | 2810 | 2829 | GCCGTGGCCGAGGACGAGGA | 23 | 48 |
| 756948 | 826 | 845 | 2816 | 2835 | GAGGGAGCCGTGGCCGAGGA | 36 | 49 |
| 756949 | 832 | 851 | 2822 | 2841 | ACCGAGGAGGGAGCCGTGGC | 47 | 50 |
| 756950 | 838 | 857 | 2828 | 2847 | GCGACCACCGAGGAGGGAGC | 51 | 51 |
| 756951 | 844 | 863 | 2834 | 2853 | GTCGCCGCGACCACCGAGGA | 20 | 52 |
| 756952 | 850 | 869 | 2840 | 2859 | CCGGAGGTCGCCGCGACCAC | 25 | 53 |
| 756953 | 856 | 875 | 2846 | 2865 | CCGCCGCCGGAGGTCGCCGC | 15 | 54 |
| 756954 | 862 | 881 | 2852 | 2871 | GGCCTCCCGCCGCCGGAGGT | 61 | 55 |
| 756955 | 868 | 887 | 2858 | 2877 | AGGCCGGGCCTCCCGCCGCC | 33 | 56 |
| 756956 | 874 | 893 | 2864 | 2883 | CTGCCCAGGCCGGGCCTCCC | 34 | 57 |
| 756957 | 880 | 899 | N/A | N/A | CGACCTCTGCCCAGGCCGGG | 31 | 58 |
| 756958 | 886 | 905 | N/A | N/A | CTGTTTCGACCTCTGCCCAG | 28 | 59 |
| 756959 | 892 | 911 | 45746 | 45765 | TTGTTACTGTTTCGACCTCT | 6 | 60 |
| 756960 | 898 | 917 | 45752 | 45771 | AGTCCTTTGTTACTGTTTCG | 9 | 61 |
| 756961 | 904 | 923 | 45758 | 45777 | TGAGGCAGTCCTTTGTTACT | 14 | 62 |
| 756962 | 910 | 929 | 45764 | 45783 | GTAGACTGAGGCAGTCCTTT | 17 | 63 |
| 756963 | 930 | 949 | 47449 | 47468 | AGATTCCATCAAAAGAAATC | 16 | 64 |
| 756964 | 932 | 951 | 47451 | 47470 | ATAGATTCCATCAAAAGAAA | 19 | 65 |
| 756965 | 934 | 953 | 47453 | 47472 | GCATAGATTCCATCAAAAGA | 22 | 66 |

TABLE 1-continued

Percent control of human ATXN2 RNA with 5-10-5 MOE gapmers
with mixed internucleoside linkages at 7,000 nM concentration

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % Control | SEQ ID NO |
| --- | --- | --- | --- | --- | --- | --- | --- |
| 756966 | 935 | 954 | 47454 | 47473 | TGCATAGATTCCATCAAAAG | 18 | 67 |
| 756967 | 936 | 955 | 47455 | 47474 | TTGCATAGATTCCATCAAAA | 21 | 68 |
| 756968 | 938 | 957 | 47457 | 47476 | ATTTGCATAGATTCCATCAA | 23 | 69 |
| 756969 | 940 | 959 | 47459 | 47478 | ATATTTGCATAGATTCCATC | 13 | 70 |
| 756970 | 941 | 960 | 47460 | 47479 | CATATTTGCATAGATTCCAT | 13 | 71 |
| 756971 | 947 | 966 | 47466 | 47485 | CATCCTCATATTTGCATAGA | 31 | 72 |
| 756972 | 953 | 972 | 47472 | 47491 | ATGAACCATCCTCATATTTG | 15 | 73 |
| 756973 | 959 | 978 | 47478 | 47497 | AAGTATATGAACCATCCTCA | 17 | 74 |
| 756974 | 965 | 984 | 47484 | 47503 | TGATGTAAGTATATGAACCA | 33 | 75 |
| 756975 | 971 | 990 | 47490 | 47509 | AACAACTGATGTAAGTATAT | 16 | 76 |
| 756976 | 979 | 998 | N/A | N/A | TTGGAGCCAACAACTGATGT | 28 | 77 |
| 756977 | 986 | 1005 | N/A | N/A | TTCACATTTGGAGCCAACAA | 17 | 78 |
| 756978 | 992 | 1011 | 48691 | 48710 | TTGTACTTCACATTTGGAGC | 8 | 79 |
| 756979 | 998 | 1017 | 48697 | 48716 | TTTCACTTGTACTTCACATT | 20 | 80 |
| 756980 | 1004 | 1023 | 48703 | 48722 | TCCATTTTTCACTTGTACTT | 9 | 81 |
| 756981 | 1010 | 1029 | 48709 | 48728 | TATACCTCCATTTTTCACTT | 11 | 82 |
| 756982 | 1016 | 1035 | 48715 | 48734 | TTCATATATACCTCCATTTT | 33 | 83 |
| 756983 | 1022 | 1041 | 48721 | 48740 | AACTCCTTCATATATACCTC | 11 | 84 |
| 756984 | 1028 | 1047 | 48727 | 48746 | TTTAAAAACTCCTTCATATA | 39 | 85 |
| 756985 | 1034 | 1053 | 48733 | 48752 | GTAAGTTTTAAAAACTCCTT | 8 | 86 |
| 756986 | 1040 | 1059 | 48739 | 48758 | CGGACTGTAAGTTTTAAAAA | 12 | 87 |
| 756987 | 1046 | 1065 | N/A | N/A | ACACTTCGGACTGTAAGTTT | 14 | 88 |
| 756988 | 1052 | 1071 | N/A | N/A | CAAATCACACTTCGGACTGT | 18 | 89 |
| 756989 | 1058 | 1077 | N/A | N/A | AAGTACCAAATCACACTTCG | 9 | 90 |
| 756990 | 1064 | 1083 | 49238 | 49257 | GGCATCAAGTACCAAATCAC | 20 | 91 |
| 756991 | 1070 | 1089 | 49244 | 49263 | ATGTGCGGCATCAAGTACCA | 9 | 92 |
| 756992 | 1076 | 1095 | 49250 | 49269 | TTTCTCATGTGCGGCATCAA | 19 | 93 |
| 756993 | 1082 | 1101 | 49256 | 49275 | TGTACTTTTCTCATGTGCGG | 5 | 94 |
| 756994 | 1088 | 1107 | 49262 | 49281 | GGATTCTGTACTTTTCTCAT | 37 | 95 |
| 756995 | 1100 | 1119 | 49274 | 49293 | CGGCCCCGAACTGGATTCTG | 17 | 96 |
| 756996 | 1124 | 1143 | 49298 | 49317 | ACTCTCCATTATTTCTTCAC | 7 | 97 |
| 756997 | 1126 | 1145 | 49300 | 49319 | ATACTCTCCATTATTTCTTC | 4 | 98 |
| 756998 | 1128 | 1147 | 49302 | 49321 | AAATACTCTCCATTATTTCT | 13 | 99 |
| 756999 | 1129 | 1148 | 49303 | 49322 | AAAATACTCTCCATTATTTC | 34 | 100 |
| 757000 | 1135 | 1154 | 49309 | 49328 | TTGAACAAAATACTCTCCAT | 9 | 101 |
| 757001 | 1141 | 1160 | 49315 | 49334 | GAACATTTGAACAAAATACT | 38 | 102 |

TABLE 1-continued

Percent control of human ATXN2 RNA with 5-10-5 MOE gapmers
with mixed internucleoside linkages at 7,000 nM concentration

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % Control | SEQ ID NO |
|---|---|---|---|---|---|---|---|
| 757002 | 1147 | 1166 | 49321 | 49340 | AAGTCTGAACATTTGAACAA | 12 | 103 |
| 757003 | 1153 | 1172 | 49327 | 49346 | ACAACAAAGTCTGAACATTT | 24 | 104 |
| 757004 | 1159 | 1178 | 49333 | 49352 | TGTACCACAACAAAGTCTGA | 30 | 105 |
| 757005* | 1171 | 1190 | 49345 | 49364 | ATATCTTTAAACTGTACCAC | 7 | 106 |
| 757006* | 1177 | 1196 | 49351 | 49370 | GAGTCCATATCTTTAAACTG | 17 | 107 |

TABLE 2

Percent control of human ATXN2 RNA with 5-10-5 MOE gapmers
with mixed internucleoside linkages at 2,000 nM concentration

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 708199 | 1477 | 1496 | 81637 | 81656 | GCTAACTGGTTTGCCCTTGC | 1 | 32 |
| 708200 | 1478 | 1497 | 81638 | 81657 | TGCTAACTGGTTTGCCCTTG | 14 | 108 |
| 708201 | 1480 | 1499 | 81640 | 81659 | TCTGCTAACTGGTTTGCCCT | 7 | 109 |
| 708203 | 1482 | 1501 | 81642 | 81661 | CTTCTGCTAACTGGTTTGCC | 6 | 110 |
| 755237 | 1562 | 1581 | 81722 | 81741 | TGCTGTGTATTTTTCTTCCT | 4 | 111 |
| 755240 | 1693 | 1712 | 83304 | 83323 | CCCATACGCGGTGAATTCTG | 24 | 112 |
| 757007* | 1183 | 1202 | 49357 | 49376 | TAACTGGAGTCCATATCTTT | 11 | 113 |
| 757008* | 1189 | 1208 | 49363 | 49382 | TTTGCATAACTGGAGTCCAT | 1 | 114 |
| 757009* | 1195 | 1214 | N/A | N/A | TCTCTTTTTGCATAACTGGA | 0 | 115 |
| 757010* | 1201 | 1220 | N/A | N/A | AAAGCATCTCTTTTTGCATA | 10 | 116 |
| 757011* | 1207 | 1226 | N/A | N/A | TCAGTAAAAGCATCTCTTTT | 16 | 117 |
| 757012* | 1213 | 1232 | 76350 | 76369 | GCAGAGTCAGTAAAAGCATC | 3 | 118 |
| 757013* | 1219 | 1238 | 76356 | 76375 | CTGATAGCAGAGTCAGTAAA | 10 | 119 |
| 757014* | 1225 | 1244 | 76362 | 76381 | TTAGCACTGATAGCAGAGTC | 0 | 120 |
| 757015* | 1231 | 1250 | 76368 | 76387 | TTCACTTTAGCACTGATAGC | 3 | 121 |
| 757016* | 1237 | 1256 | 76374 | 76393 | TCGCCATTCACTTTAGCACT | 0 | 122 |
| 757017 | 1258 | 1277 | 76395 | 76414 | TCCAGGTCCTTCTCTTTGTG | 45 | 123 |
| 757018 | 1264 | 1283 | 76401 | 76420 | CAGGGCTCCAGGTCCTTCTC | 17 | 124 |
| 757019 | 1270 | 1289 | 76407 | 76426 | GCATCCCAGGGCTCCAGGTC | 24 | 125 |
| 757020 | 1276 | 1295 | 76413 | 76432 | TCACCTGCATCCCAGGGCTC | 9 | 126 |
| 757021 | 1282 | 1301 | 76419 | 76438 | GTGAGTTCACCTGCATCCCA | 6 | 127 |
| 757022 | 1288 | 1307 | 76425 | 76444 | TTGGCTGTGAGTTCACCTGC | 9 | 128 |
| 757023 | 1294 | 1313 | 76431 | 76450 | TCCTCATTGGCTGTGAGTTC | 14 | 129 |
| 757024 | 1300 | 1319 | 76437 | 76456 | TCAAGTTCCTCATTGGCTGT | 17 | 130 |

TABLE 2-continued

Percent control of human ATXN2 RNA with 5-10-5 MOE gapmers with mixed internucleoside linkages at 2,000 nM concentration

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 757025 | 1312 | 1331 | 76449 | 76468 | TTTTCCAAAGCCTCAAGTTC | 65 | 131 |
| 757026 | 1335 | 1354 | N/A | N/A | GATCCCATCCATTAGATACG | 8 | 132 |
| 757027 | 1350 | 1369 | 80705 | 80724 | GAAACATATCATTGGGATCC | 13 | 133 |
| 757028 | 1356 | 1375 | 80711 | 80730 | TATATCGAAACATATCATTG | 6 | 134 |
| 757029 | 1362 | 1381 | 80717 | 80736 | CTTCATTATATCGAAACATA | 22 | 135 |
| 757030 | 1368 | 1387 | 80723 | 80742 | AATTTTCTTCATTATATCGA | 56 | 136 |
| 757031 | 1374 | 1393 | 80729 | 80748 | CACCATAATTTTCTTCATTA | 14 | 137 |
| 757032 | 1380 | 1399 | 80735 | 80754 | ACACTACACCATAATTTTCT | 20 | 138 |
| 757033 | 1412 | 1431 | N/A | N/A | TGTATACGAAGATAAACTGC | 21 | 139 |
| 757034 | 1430 | 1449 | N/A | N/A | ATCTCTTTCTAAGGGCACTG | 5 | 140 |
| 757035 | 1442 | 1461 | 81602 | 81621 | TTCTTCTGAGTTATCTCTTT | 18 | 141 |
| 757036 | 1448 | 1467 | 81608 | 81627 | TAAAAATTCTTCTGAGTTAT | 80 | 142 |
| 757037 | 1454 | 1473 | 81614 | 81633 | CCGTTTTAAAAATTCTTCTG | 5 | 143 |
| 757038 | 1460 | 1479 | 81620 | 81639 | TGCTTCCCGTTTTAAAAATT | 23 | 144 |
| 757039 | 1466 | 1485 | 81626 | 81645 | TGCCCTTGCTTCCCGTTTTA | 25 | 145 |
| 757040 | 1472 | 1491 | 81632 | 81651 | CTGGTTTGCCCTTGCTTCCC | 6 | 146 |
| 757041 | 1474 | 1493 | 81634 | 81653 | AACTGGTTTGCCCTTGCTTC | 16 | 147 |
| 757042 | 1476 | 1495 | 81636 | 81655 | CTAACTGGTTTGCCCTTGCT | 16 | 148 |
| 757043 | 1484 | 1503 | 81644 | 81663 | TTCTTCTGCTAACTGGTTTG | 21 | 149 |
| 757044 | 1490 | 1509 | 81650 | 81669 | CTCAATTTCTTCTGCTAACT | 35 | 150 |
| 757045 | 1496 | 1515 | 81656 | 81675 | ACTTGACTCAATTTCTTCTG | 4 | 151 |
| 757046 | 1502 | 1521 | 81662 | 81681 | CTGGGCACTTGACTCAATTT | 14 | 152 |
| 757047 | 1508 | 1527 | 81668 | 81687 | TTTGTACTGGGCACTTGACT | 21 | 153 |
| 757048 | 1514 | 1533 | 81674 | 81693 | TCGAGCTTTGTACTGGGCAC | 10 | 154 |
| 757049 | 1520 | 1539 | 81680 | 81699 | GGCCACTCGAGCTTTGTACT | 13 | 155 |
| 757050 | 1526 | 1545 | 81686 | 81705 | TTCCAGGGCCACTCGAGCTT | 8 | 156 |
| 757051 | 1532 | 1551 | 81692 | 81711 | ATCATTTTCCAGGGCCACTC | 14 | 157 |
| 757052 | 1538 | 1557 | 81698 | 81717 | CCTATCATCATTTTCCAGGG | 2 | 158 |
| 757053 | 1544 | 1563 | 81704 | 81723 | CTCACTCCTATCATCATTTT | 13 | 159 |
| 757054 | 1550 | 1569 | 81710 | 81729 | TTCTTCCTCACTCCTATCAT | 61 | 160 |
| 757055 | 1556 | 1575 | 81716 | 81735 | GTATTTTCTTCCTCACTCC | 2 | 161 |
| 757056 | 1568 | 1587 | 81728 | 81747 | CTGAACTGCTGTGTATTTTT | 13 | 162 |
| 757057 | 1574 | 1593 | 81734 | 81753 | ATTTCTCTGAACTGCTGTGT | 2 | 163 |
| 757058 | 1580 | 1599 | 81740 | 81759 | ACTGGAATTTCTCTGAACTG | 10 | 164 |
| 757059 | 1603 | 1622 | 81763 | 81782 | TTTATGCTGTGCCCCTCACG | 42 | 165 |
| 757060 | 1609 | 1628 | 81769 | 81788 | CTAGTGTTTATGCTGTGCCC | 10 | 166 |

TABLE 2-continued

Percent control of human ATXN2 RNA with 5-10-5 MOE gapmers with mixed internucleoside linkages at 2,000 nM concentration

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 757061 | 1615 | 1634 | N/A | N/A | TTTTCCCTAGTGTTTATGCT | 39 | 167 |
| 757062 | 1621 | 1640 | N/A | N/A | TATTTATTTTCCCTAGTGTT | 33 | 168 |
| 757063 | 1633 | 1652 | 83244 | 83263 | CCAGGAGGAATATATTTATT | 16 | 169 |
| 757064 | 1639 | 1658 | 83250 | 83269 | CTTTGTCCAGGAGGAATATA | 19 | 170 |
| 757065 | 1645 | 1664 | 83256 | 83275 | CTATTTCTTTGTCCAGGAGG | 7 | 171 |
| 757066 | 1651 | 1670 | 83262 | 83281 | ACTTCTCTATTTCTTTGTCC | 0 | 172 |
| 757067 | 1657 | 1676 | 83268 | 83287 | GATATGACTTCTCTATTTCT | 13 | 173 |
| 757068 | 1663 | 1682 | 83274 | 83293 | CCCCAGGATATGACTTCTCT | 16 | 174 |
| 757069 | 1669 | 1688 | 83280 | 83299 | CCACTTCCCCAGGATATGAC | 31 | 175 |
| 757070 | 1675 | 1694 | 83286 | 83305 | TGTCTCCCACTTCCCCAGGA | 10 | 176 |
| 757071 | 1681 | 1700 | 83292 | 83311 | GAATTCTGTCTCCCACTTCC | 24 | 177 |
| 757072 | 1687 | 1706 | 83298 | 83317 | CGCGGTGAATTCTGTCTCCC | 3 | 178 |
| 757073 | 1688 | 1707 | 83299 | 83318 | ACGCGGTGAATTCTGTCTCC | 5 | 179 |
| 757074 | 1690 | 1709 | 83301 | 83320 | ATACGCGGTGAATTCTGTCT | 7 | 180 |
| 757075 | 1692 | 1711 | 83303 | 83322 | CCATACGCGGTGAATTCTGT | 6 | 181 |
| 757076 | 1694 | 1713 | 83305 | 83324 | GCCCATACGCGGTGAATTCT | 11 | 182 |
| 757077 | 1696 | 1715 | 83307 | 83326 | TGGCCCATACGCGGTGAATT | 15 | 183 |
| 757078 | 1698 | 1717 | 83309 | 83328 | GCTGGCCCATACGCGGTGAA | 21 | 184 |

TABLE 3

Percent control of human ATXN2 RNA with 5-10-5 MOE gapmers with mixed internucleoside linkages at 2,000 nM concentration

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 708199 | 1477 | 1496 | 81637 | 81656 | GCTAACTGGTTTGCCCTTGC | 8 | 32 |
| 708237 | 1783 | 1802 | 83394 | 83413 | TTAACTACTCTTTGGTCTGA | 36 | 185 |
| 708247 | 1903 | 1922 | 85399 | 85418 | CTGGAGGGCGGCCGTGTAGG | 26 | 186 |
| 708248 | 1957 | 1976 | 85453 | 85472 | GGAGAACCATGAGCAGAGGG | 41 | 187 |
| 755234 | 1963 | 1982 | 85459 | 85478 | GGAGCTGGAGAACCATGAGC | 17 | 188 |
| 755236 | 1969 | 1988 | 85465 | 85484 | GAGACAGGAGCTGGAGAACC | 40 | 189 |
| 755239 | 2099 | 2118 | 88209 | 88228 | GTGGGATACAAATTCTAGGC | 4 | 190 |
| 757079 | 1699 | 1718 | 83310 | 83329 | GGCTGGCCCATACGCGGTGA | 11 | 191 |
| 757080 | 1705 | 1724 | 83316 | 83335 | GATCCAGGCTGGCCCATACG | 42 | 192 |
| 757081 | 1711 | 1730 | 83322 | 83341 | GAGCCCGATCCAGGCTGGCC | 53 | 193 |
| 757082 | 1717 | 1736 | 83328 | 83347 | GGCATGGAGCCCGATCCAGG | 31 | 194 |
| 757083 | 1723 | 1742 | 83334 | 83353 | CTTGATGGCATGGAGCCCGA | 64 | 195 |

TABLE 3-continued

Percent control of human ATXN2 RNA with 5-10-5 MOE gapmers with mixed internucleoside linkages at 2,000 nM concentration

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 757084 | 1729 | 1748 | 83340 | 83359 | GTGGATCTTGATGGCATGGA | 23 | 196 |
| 757085 | 1735 | 1754 | 83346 | 83365 | TGAGAAGTGGATCTTGATGG | 58 | 197 |
| 757086 | 1741 | 1760 | 83352 | 83371 | GAAGTGTGAGAAGTGGATCT | 49 | 198 |
| 757087 | 1747 | 1766 | 83358 | 83377 | AAATCTGAAGTGTGAGAAGT | 71 | 199 |
| 757088 | 1753 | 1772 | 83364 | 83383 | GGGTTGAAATCTGAAGTGTG | 24 | 200 |
| 757089 | 1765 | 1784 | 83376 | 83395 | GAACCAGAATTCGGGTTGAA | 8 | 201 |
| 757090 | 1771 | 1790 | 83382 | 83401 | TGGTCTGAACCAGAATTCGG | 31 | 202 |
| 757091 | 1777 | 1796 | 83388 | 83407 | ACTCTTTGGTCTGAACCAGA | 47 | 203 |
| 757092 | 1789 | 1808 | 83400 | 83419 | CCTCCATTAACTACTCTTTG | 19 | 204 |
| 757093 | 1795 | 1814 | N/A | N/A | GGAACACCTCCATTAACTAC | 34 | 205 |
| 757094 | 1807 | 1826 | 85303 | 85322 | GGCGATGGCCAGGGAACACC | 3 | 206 |
| 757095 | 1814 | 1833 | 85310 | 85329 | TGGGCAAGGCGATGGCCAGG | 58 | 207 |
| 757096 | 1820 | 1839 | 85316 | 85335 | AGGAGATGGGCAAGGCGATG | 60 | 208 |
| 757097 | 1826 | 1845 | 85322 | 85341 | AGAGGAAGGAGATGGGCAAG | 51 | 209 |
| 757098 | 1832 | 1851 | 85328 | 85347 | TGGGCGAGAGGAAGGAGATG | 37 | 210 |
| 757099 | 1838 | 1857 | 85334 | 85353 | AGAAGGTGGGCGAGAGGAAG | 130 | 211 |
| 757100 | 1844 | 1863 | 85340 | 85359 | GTAGCGAGAAGGTGGGCGAG | 35 | 212 |
| 757101 | 1850 | 1869 | 85346 | 85365 | TGACTGGTAGCGAGAAGGTG | 65 | 213 |
| 757102 | 1856 | 1875 | 85352 | 85371 | GGGACCTGACTGGTAGCGAG | 39 | 214 |
| 757103 | 1862 | 1881 | 85358 | 85377 | AGAGTTGGGACCTGACTGGT | 28 | 215 |
| 757104 | 1868 | 1887 | 85364 | 85383 | TGGAAGAGAGTTGGGACCTG | 10 | 216 |
| 757105 | 1874 | 1893 | 85370 | 85389 | CCGAGGTGGAAGAGAGTTGG | 153 | 217 |
| 757106 | 1880 | 1899 | 85376 | 85395 | GGCTGCCCGAGGTGGAAGAG | 12 | 218 |
| 757107 | 1927 | 1946 | 85423 | 85442 | GGTCTGGATGGCCGCGAGGG | 20 | 219 |
| 757108 | 1958 | 1977 | 85454 | 85473 | TGGAGAACCATGAGCAGAGG | 26 | 220 |
| 757109 | 1960 | 1979 | 85456 | 85475 | GCTGGAGAACCATGAGCAGA | 24 | 221 |
| 757110 | 1962 | 1981 | 85458 | 85477 | GAGCTGGAGAACCATGAGCA | 34 | 222 |
| 757111 | 1964 | 1983 | 85460 | 85479 | AGGAGCTGGAGAACCATGAG | 26 | 223 |
| 757112 | 1966 | 1985 | 85462 | 85481 | ACAGGAGCTGGAGAACCATG | 26 | 224 |
| 757113 | 1968 | 1987 | 85464 | 85483 | AGACAGGAGCTGGAGAACCA | 12 | 225 |
| 757114 | 1975 | 1994 | 85471 | 85490 | ATAGTAGAGACAGGAGCTGG | 42 | 226 |
| 757115 | 1981 | 2000 | 85477 | 85496 | TTAGGCATAGTAGAGACAGG | 66 | 227 |
| 757116 | 2002 | 2021 | N/A | N/A | GGCCCTTCTGAAGACATGCG | 9 | 228 |
| 757117 | 2008 | 2027 | N/A | N/A | CTTGGAGGCCCTTCTGAAGA | 105 | 229 |
| 757118 | 2014 | 2033 | N/A | N/A | GACATCCTTGGAGGCCCTTC | 29 | 230 |
| 757119 | 2035 | 2054 | 88145 | 88164 | GGATGTCGCTGGGCCTTTGG | 48 | 231 |

TABLE 3-continued

Percent control of human ATXN2 RNA with 5-10-5 MOE gapmers with mixed internucleoside linkages at 2,000 nM concentration

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 757120 | 2041 | 2060 | 88151 | 88170 | TTTCGAGGATGTCGCTGGGC | 28 | 232 |
| 757121 | 2047 | 2066 | 88157 | 88176 | CTGTGATTTCGAGGATGTCG | 40 | 233 |
| 757122 | 2053 | 2072 | 88163 | 88182 | GAAACTCTGTGATTTCGAGG | 28 | 234 |
| 757123 | 2059 | 2078 | 88169 | 88188 | CCAGCAGAAACTCTGTGATT | 49 | 235 |
| 757124 | 2065 | 2084 | 88175 | 88194 | CCCCTCCCAGCAGAAACTCT | 20 | 236 |
| 757125 | 2071 | 2090 | 88181 | 88200 | ATGGAACCCCTCCCAGCAGA | 31 | 237 |
| 757126 | 2077 | 2096 | 88187 | 88206 | CTGGATATGGAACCCCTCCC | 26 | 238 |
| 757127 | 2083 | 2102 | 88193 | 88212 | AGGCCACTGGATATGGAACC | 5 | 239 |
| 757128 | 2089 | 2108 | 88199 | 88218 | AATTCTAGGCCACTGGATAT | 38 | 240 |
| 757129 | 2094 | 2113 | 88204 | 88223 | ATACAAATTCTAGGCCACTG | 9 | 241 |
| 757130 | 2096 | 2115 | 88206 | 88225 | GGATACAAATTCTAGGCCAC | 5 | 242 |
| 757131 | 2098 | 2117 | 88208 | 88227 | TGGGATACAAATTCTAGGCC | 4 | 243 |
| 757132 | 2100 | 2119 | 88210 | 88229 | TGTGGGATACAAATTCTAGG | 31 | 244 |
| 757133 | 2102 | 2121 | 88212 | 88231 | GTTGTGGGATACAAATTCTA | 39 | 245 |
| 757134 | 2122 | 2141 | 88232 | 88251 | GTAGCTGCTTCACTGGGTGG | 53 | 246 |
| 757135 | 2128 | 2147 | 88238 | 88257 | GGAGGAGTAGCTGCTTCACT | 15 | 247 |
| 757136 | 2134 | 2153 | 88244 | 88263 | GCTACTGGAGGAGTAGCTGC | 50 | 248 |
| 757137 | 2140 | 2159 | 88250 | 88269 | GTCCTTGCTACTGGAGGAGT | 35 | 249 |
| 757138 | 2146 | 2165 | 88256 | 88275 | GGACTGGTCCTTGCTACTGG | 18 | 250 |
| 757139 | 2152 | 2171 | 88262 | 88281 | CCCGAGGGACTGGTCCTTGC | 18 | 251 |
| 757140 | 2158 | 2177 | 88268 | 88287 | GTTCCCCCCGAGGGACTGGT | 33 | 252 |
| 757141 | 2177 | 2196 | 88287 | 88306 | ACTGACCACTGATGACCACG | 34 | 253 |
| 757142 | 2183 | 2202 | N/A | N/A | AACCCCACTGACCACTGATG | 85 | 254 |
| 757143 | 2189 | 2208 | N/A | N/A | TCTTGGAACCCCACTGACCA | 62 | 255 |
| 757144 | 2195 | 2214 | N/A | N/A | GGATAATCTTGGAACCCCAC | 51 | 256 |
| 757145 | 2215 | 2234 | 91099 | 91118 | CTGGGTCTATGAGTTTTAGG | 28 | 257 |
| 757146 | 2221 | 2240 | 91105 | 91124 | GGAGACCTGGGTCTATGAGT | 17 | 258 |
| 757147 | 2231 | 2250 | 91115 | 91134 | GTTCTGTCTGGGAGACCTGG | 13 | 259 |
| 757148 | 2237 | 2256 | 91121 | 91140 | AATACTGTTCTGTCTGGGAG | 25 | 260 |
| 757149 | 2243 | 2262 | 91127 | 91146 | ATTTCCAATACTGTTCTGTC | 18 | 261 |

TABLE 4

Percent control of human ATXN2 RNA with 5-10-5 MOE gapmers with mixed internucleoside linkages at 2,000 nM concentration

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 708199 | 1477 | 1496 | 81637 | 81656 | GCTAACTGGTTTGCCCTTGC | 26 | 32 |
| 757150 | 2266 | 2285 | 91150 | 91169 | GCAAGAACTGGCCCACTGGG | 90 | 262 |
| 757151 | 2272 | 2291 | 91156 | 91175 | GGAGAAGCAAGAACTGGCCC | 73 | 263 |
| 757152 | 2291 | 2310 | 91175 | 91194 | TGGAATAATACCAGCTTGGG | 39 | 264 |
| 757153 | 2297 | 2316 | 91181 | 91200 | TTCAGTTGGAATAATACCAG | 105 | 265 |
| 757154 | 2303 | 2322 | 91187 | 91206 | AACAGCTTCAGTTGGAATAA | 59 | 266 |
| 757155 | 2309 | 2328 | 91193 | 91212 | CATGGCAACAGCTTCAGTTG | 66 | 267 |
| 757156 | 2315 | 2334 | 91199 | 91218 | AATAGGCATGGCAACAGCTT | 44 | 268 |
| 757157 | 2321 | 2340 | 91205 | 91224 | AGCTGGAATAGGCATGGCAA | 32 | 269 |
| 757158 | 2327 | 2346 | 91211 | 91230 | AGATGCAGCTGGAATAGGCA | 129 | 270 |
| 757159 | 2333 | 2352 | 91217 | 91236 | CGTAGGAGATGCAGCTGGAA | 32 | 271 |
| 757160 | 2351 | 2370 | 91235 | 91254 | CGATGCAGGACTAGCAGGCG | 26 | 272 |
| 757161 | 2357 | 2376 | 91241 | 91260 | TCTGTTCGATGCAGGACTAG | 23 | 273 |
| 757162 | 2363 | 2382 | 91247 | 91266 | AACAGCTCTGTTCGATGCAG | 23 | 274 |
| 757163 | 2391 | 2410 | N/A | N/A | TGGAATCTTTAGCCTCACTA | 67 | 275 |
| 757164 | 2397 | 2416 | N/A | N/A | GAAGCCTGGAATCTTTAGCC | 59 | 276 |
| 757165 | 2403 | 2422 | 91673 | 91692 | GATCTTGAAGCCTGGAATCT | 67 | 277 |
| 757166 | 2409 | 2428 | 91679 | 91698 | GCCTCTGATCTTGAAGCCTG | 56 | 278 |
| 757167 | 2415 | 2434 | 91685 | 91704 | AGTTCTGCCTCTGATCTTGA | 80 | 279 |
| 757168 | 2421 | 2440 | 91691 | 91710 | CAGGAGAGTTCTGCCTCTGA | 131 | 280 |
| 757169 | 2427 | 2446 | 91697 | 91716 | TCCCTGCAGGAGAGTTCTGC | 59 | 281 |
| 757170 | 2433 | 2452 | 91703 | 91722 | CTTTATTCCCTGCAGGAGAG | 79 | 282 |
| 757171 | 2439 | 2458 | 91709 | 91728 | TATTTTCTTTATTCCCTGCA | 56 | 283 |
| 757172 | 2445 | 2464 | 91715 | 91734 | GTTTAATATTTTCTTTATTC | 89 | 284 |
| 757173 | 2451 | 2470 | 91721 | 91740 | CATTGGGTTTAATATTTTCT | 54 | 285 |
| 757174 | 2457 | 2476 | 91727 | 91746 | ATGTTTCATTGGGTTTAATA | 39 | 286 |
| 757175 | 2463 | 2482 | 91733 | 91752 | TAGGTGATGTTTCATTGGGT | 23 | 287 |
| 757176 | 2469 | 2488 | 91739 | 91758 | AGAAGCTAGGTGATGTTTCA | 81 | 288 |
| 757177 | 2475 | 2494 | 91745 | 91764 | CTTTTGAGAAGCTAGGTGAT | 90 | 289 |
| 757178 | 2481 | 2500 | 91751 | 91770 | TTTCAGCTTTTGAGAAGCTA | 61 | 290 |
| 757179 | 2487 | 2506 | 91757 | 91776 | CTTTGTTTTCAGCTTTTGAG | 35 | 291 |
| 757180 | 2493 | 2512 | N/A | N/A | ATATACCTTTGTTTTCAGCT | 31 | 292 |
| 757181 | 2499 | 2518 | N/A | N/A | CTGGTGATATACCTTTGTTT | 42 | 293 |
| 757182 | 2505 | 2524 | 92046 | 92065 | AAACAACTGGTGATATACCT | 132 | 294 |
| 757183 | 2511 | 2530 | 92052 | 92071 | GTTCAGAAACAACTGGTGAT | 39 | 295 |
| 757184 | 2517 | 2536 | 92058 | 92077 | TTCTATGTTCAGAAACAACT | 37 | 296 |

TABLE 4-continued

Percent control of human ATXN2 RNA with 5-10-5 MOE gapmers with mixed internucleoside linkages at 2,000 nM concentration

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 757185 | 2523 | 2542 | 92064 | 92083 | TCTGTTTTCTATGTTCAGAA | 58 | 297 |
| 757186 | 2529 | 2548 | 92070 | 92089 | CATCAATCTGTTTTCTATGT | 38 | 298 |
| 757187 | 2535 | 2554 | 92076 | 92095 | TTAAATCATCAATCTGTTTT | 122 | 299 |
| 757188 | 2541 | 2560 | 92082 | 92101 | ATTTCTTTAAATCATCAATC | 86 | 300 |
| 757189 | 2547 | 2566 | 92088 | 92107 | TCTTAAATTTCTTTAAATCA | 128 | 301 |
| 757190 | 2553 | 2572 | 92094 | 92113 | AATCATTCTTAAATTTCTTT | 55 | 302 |
| 757191 | 2559 | 2578 | N/A | N/A | ACCTAAAATCATTCTTAAAT | 141 | 303 |
| 757192 | 2565 | 2584 | N/A | N/A | GCTGTAACCTAAAATCATTC | 64 | 304 |
| 757193 | 2571 | 2590 | N/A | N/A | AACTTGGCTGTAACCTAAAA | 84 | 305 |
| 757194 | 2577 | 2596 | 112886 | 112905 | AAGTAGAACTTGGCTGTAAC | 59 | 306 |
| 757195 | 2583 | 2602 | 112892 | 112911 | ATTCAGAAGTAGAACTTGGC | 82 | 307 |
| 757196 | 2589 | 2608 | 112898 | 112917 | CCATAGATTCAGAAGTAGAA | 63 | 308 |
| 757197 | 2595 | 2614 | 112904 | 112923 | GTTGATCCATAGATTCAGAA | 61 | 309 |
| 757198 | 2601 | 2620 | 112910 | 112929 | TTAGTAGTTGATCCATAGAT | 50 | 310 |
| 757199 | 2607 | 2626 | 112916 | 112935 | TTTTGTTTAGTAGTTGATCC | 104 | 311 |
| 757200 | 2613 | 2632 | 112922 | 112941 | CTCTATTTTGTTTAGTAGT | 26 | 312 |
| 757201 | 2619 | 2638 | 112928 | 112947 | CTCCCTCTCTATTTTGTTT | 57 | 313 |
| 757202 | 2625 | 2644 | 112934 | 112953 | ATTTTTCTCCCTCTCTATTT | 115 | 314 |
| 757203 | 2631 | 2650 | 112940 | 112959 | CTCTTGATTTTTCTCCCTCT | 39 | 315 |
| 757204 | 2637 | 2656 | 112946 | 112965 | TCAAATCTCTTGATTTTTCT | 49 | 316 |
| 757205 | 2643 | 2662 | 112952 | 112971 | CTTTGATCAAATCTCTTGAT | 59 | 317 |
| 757206 | 2649 | 2668 | 112958 | 112977 | TTTTGTCTTTGATCAAATCT | 60 | 318 |
| 757207 | 2655 | 2674 | 112964 | 112983 | GTTCAATTTTGTCTTTGATC | 33 | 319 |
| 757208 | 2661 | 2680 | 112970 | 112989 | CACTTGGTTCAATTTTGTCT | 31 | 320 |
| 757209 | 2667 | 2686 | 112976 | 112995 | CCTTAGCACTTGGTTCAATT | 20 | 321 |
| 757210 | 2673 | 2692 | 112982 | 113001 | AAGAATCCTTAGCACTTGGT | 20 | 322 |
| 757211 | 2679 | 2698 | 112988 | 113007 | CAATGAAAGAATCCTTAGCA | 28 | 323 |
| 757212 | 2685 | 2704 | 112994 | 113013 | TATTTTCAATGAAAGAATCC | 83 | 324 |
| 757213 | 2691 | 2710 | 113000 | 113019 | TGCTGCTATTTTCAATGAAA | 20 | 325 |
| 757214 | 2697 | 2716 | 113006 | 113025 | AGTTGCTGCTGCTATTTTCA | 37 | 326 |
| 757215 | 2699 | 2718 | 113008 | 113027 | ACAGTTGCTGCTGCTATTTT | 50 | 327 |
| 757216 | 2701 | 2720 | 113010 | 113029 | GTACAGTTGCTGCTGCTATT | 36 | 328 |
| 757217 | 2703 | 2722 | 113012 | 113031 | TGGTACAGTTGCTGCTGCTA | 50 | 329 |
| 757218 | 2704 | 2723 | 113013 | 113032 | CTGGTACAGTTGCTGCTGCT | 17 | 330 |
| 757219 | 2705 | 2724 | 113014 | 113033 | ACTGGTACAGTTGCTGCTGC | 21 | 331 |
| 757220 | 2707 | 2726 | 113016 | 113035 | CCACTGGTACAGTTGCTGCT | 43 | 332 |

TABLE 4-continued

Percent control of human ATXN2 RNA with 5-10-5 MOE gapmers with mixed internucleoside linkages at 2,000 nM concentration

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 757221 | 2709 | 2728 | 113018 | 113037 | TGCCACTGGTACAGTTGCTG | 54 | 333 |
| 757222 | 2715 | 2734 | 113024 | 113043 | TGCTGCTGCCACTGGTACAG | 55 | 334 |
| 757223 | 2721 | 2740 | 113030 | 113049 | TCGGCTTGCTGCTGCCACTG | 37 | 335 |
| 757224 | 2727 | 2746 | 113036 | 113055 | GGCTATTCGGCTTGCTGCTG | 29 | 336 |
| 757225 | 2757 | 2776 | 113066 | 113085 | TGTTACTAAGTATTGAAGGG | 54 | 337 |
| 757226 | 2763 | 2782 | 113072 | 113091 | GCTCCGTGTTACTAAGTATT | 22 | 338 |

TABLE 5

Percent control of human ATXN2 RNA with 5-10-5 MOE gapmers with mixed internucleoside linkages at 2,000 nM concentration

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 708199 | 1477 | 1496 | 81637 | 81656 | GCTAACTGGTTTGCCCTTGC | 29 | 32 |
| 757227 | 2769 | 2788 | 113078 | 113097 | TCTTGTGCTCCGTGTTACTA | 48 | 339 |
| 757228 | 2775 | 2794 | 113084 | 113103 | GTCCCTCTTGTGCTCCGTG | 28 | 340 |
| 757229 | 2781 | 2800 | 113090 | 113109 | CCTCAGGTCCCTCTTGTGC | 66 | 341 |
| 757230 | 2787 | 2806 | 113096 | 113115 | AAGTGACCTCAGGTCCCCTC | 116 | 342 |
| 757231 | 2793 | 2812 | 113102 | 113121 | CTTGGGAAGTGACCTCAGGT | 37 | 343 |
| 757232 | 2799 | 2818 | 113108 | 113127 | GAACCCCTTGGGAAGTGACC | 39 | 344 |
| 757233 | 2805 | 2824 | 113114 | 113133 | AAGTCTGAACCCCTTGGGAA | 47 | 345 |
| 757234 | 2811 | 2830 | 113120 | 113139 | GGCTGGAAGTCTGAACCCCT | 28 | 346 |
| 757235 | 2817 | 2836 | 113126 | 113145 | ATGCTGGGCTGGAAGTCTGA | 63 | 347 |
| 757236 | 2823 | 2842 | 113132 | 113151 | GTTTACATGCTGGGCTGGAA | 31 | 348 |
| 757237 | 2829 | 2848 | 113138 | 113157 | TCTCTTGTTTACATGCTGGG | 47 | 349 |
| 757238 | 2835 | 2854 | 113144 | 113163 | CGTCTTTCTCTTGTTTACAT | 33 | 350 |
| 757239 | 2853 | 2872 | 113162 | 113181 | CTTTCTTCTCTTCCTTATCG | 74 | 351 |
| 757240 | 2874 | 2893 | N/A | N/A | TCCTAACTTGCTCAGCTGCG | 36 | 352 |
| 757241 | 2882 | 2901 | N/A | N/A | TGTTGATTTCCTAACTTGCT | 64 | 353 |
| 757242 | 2888 | 2907 | 114848 | 114867 | ATTCAATGTTGATTTCCTAA | 52 | 354 |
| 757243 | 2897 | 2916 | 114857 | 114876 | TGCATTGGGATTCAATGTTG | 41 | 355 |
| 757244 | 2913 | 2932 | 114873 | 114892 | GTGGGTTGAACTCCTTTGCA | 89 | 356 |
| 757245 | 2932 | 2951 | N/A | N/A | TTTGGCTGAGAGAAGGAACG | 79 | 357 |
| 757246 | 2938 | 2957 | N/A | N/A | GAAGGCTTTGGCTGAGAGAA | 88 | 358 |
| 757247 | 2944 | 2963 | N/A | N/A | GTAGTAGAAGGCTTTGGCTG | 58 | 359 |
| 757248 | 2964 | 2983 | 115819 | 115838 | GAGGCCGAGGTGAAGTTGGG | 50 | 360 |
| 757249 | 2970 | 2989 | 115825 | 115844 | GTGCTTGAGGCCGAGGTGAA | 49 | 361 |

TABLE 5-continued

Percent control of human ATXN2 RNA with 5-10-5 MOE gapmers with mixed internucleoside linkages at 2,000 nM concentration

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 757250 | 2976 | 2995 | 115831 | 115850 | TAGGTTGTGCTTGAGGCCGA | 29 | 362 |
| 757251 | 2982 | 3001 | 115837 | 115856 | ATGGGCTAGGTTGTGCTTGA | 48 | 363 |
| 757252 | 2988 | 3007 | 115843 | 115862 | CCATAGATGGGCTAGGTTGT | 84 | 364 |
| 757253 | 2994 | 3013 | 115849 | 115868 | GACCCACCATAGATGGGCTA | 87 | 365 |
| 757254 | 3000 | 3019 | 115855 | 115874 | GTTGATGACCCACCATAGAT | 88 | 366 |
| 757255 | 3006 | 3025 | 115861 | 115880 | TTGGCTGTTGATGACCCACC | 91 | 367 |
| 757256 | 3012 | 3031 | 115867 | 115886 | CTGGAGTTGGCTGTTGATGA | 101 | 368 |
| 757257 | 3018 | 3037 | 115873 | 115892 | TATAAACTGGAGTTGGCTGT | 84 | 369 |
| 757258 | 3024 | 3043 | 115879 | 115898 | GCTGAGTATAAACTGGAGTT | 52 | 370 |
| 757259 | 3030 | 3049 | 115885 | 115904 | AAACAGGCTGAGTATAAACT | 114 | 371 |
| 757260 | 3036 | 3055 | 115891 | 115910 | CAAAACAAACAGGCTGAGTA | 53 | 372 |
| 757261 | 3042 | 3061 | 115897 | 115916 | TTGGTGCAAAACAAACAGGC | 75 | 373 |
| 757262 | 3048 | 3067 | 115903 | 115922 | TCATATTTGGTGCAAAACAA | 74 | 374 |
| 757263 | 3054 | 3073 | 115909 | 115928 | GATACATCATATTTGGTGCA | 32 | 375 |
| 757264 | 3060 | 3079 | 115915 | 115934 | GGACTGGATACATCATATTT | 94 | 376 |
| 757265 | 3066 | 3085 | 115921 | 115940 | TCACTGGGACTGGATACATC | 83 | 377 |
| 757266 | 3079 | 3098 | 115934 | 115953 | TGCACGCCTGGGCTCACTGG | 70 | 378 |
| 757267 | 3085 | 3104 | N/A | N/A | AAAGGTTGCACGCCTGGGCT | 27 | 379 |
| 757268 | 3091 | 3110 | N/A | N/A | GGGTATAAAGGTTGCACGCC | 97 | 380 |
| 757269 | 3097 | 3116 | N/A | N/A | GGTATTGGGTATAAAGGTTG | 32 | 381 |
| 757270 | 3103 | 3122 | 116339 | 116358 | GTCATAGGTATTGGGTATAA | 60 | 382 |
| 757271 | 3122 | 3141 | 116358 | 116377 | TTGATTCACTGGCATGGGCG | 78 | 383 |
| 757272 | 3128 | 3147 | 116364 | 116383 | CTTGGCTTGATTCACTGGCA | 30 | 384 |
| 757273 | 3134 | 3153 | 116370 | 116389 | ATATGTCTTGGCTTGATTCA | 68 | 385 |
| 757274 | 3140 | 3159 | 116376 | 116395 | TGCTCTATATGTCTTGGCTT | 51 | 386 |
| 757275 | 3146 | 3165 | N/A | N/A | TGGTACTGCTCTATATGTCT | 42 | 387 |
| 757276 | 3152 | 3171 | N/A | N/A | CATATTTGGTACTGCTCTAT | 105 | 388 |
| 757277 | 3173 | 3192 | 130937 | 130956 | CTGGTCTTGCCGCTGTTGGG | 48 | 389 |
| 757278 | 3179 | 3198 | 130943 | 130962 | ATGATGCTGGTCTTGCCGCT | 49 | 390 |
| 757279 | 3185 | 3204 | 130949 | 130968 | ACTCTGATGATGCTGGTCTT | 98 | 391 |
| 757280 | 3191 | 3210 | 130955 | 130974 | CATGGCACTCTGATGATGCT | 120 | 392 |
| 757281 | 3197 | 3216 | 130961 | 130980 | GTGCATCATGGCACTCTGAT | 42 | 393 |
| 757282 | 3203 | 3222 | 130967 | 130986 | CGCTGGGTGCATCATGGCAC | 37 | 394 |
| 757283 | 3220 | 3239 | 130984 | 131003 | GGTGGGCCCGCTGCTGACGC | 60 | 395 |
| 757284 | 3226 | 3245 | 130990 | 131009 | GCAATCGGTGGGCCCGCTGC | 62 | 396 |
| 757285 | 3232 | 3251 | 130996 | 131015 | GTGGCTGCAATCGGTGGGCC | 57 | 397 |

TABLE 5-continued

Percent control of human ATXN2 RNA with 5-10-5 MOE gapmers with mixed internucleoside linkages at 2,000 nM concentration

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 757286 | 3269 | 3288 | 131033 | 131052 | ACTGTAGGCAACATATTGCG | 108 | 398 |
| 757287 | 3275 | 3294 | 131039 | 131058 | CTGAGGACTGTAGGCAACAT | 48 | 399 |
| 757288 | 3311 | 3330 | 131075 | 131094 | TGGCACATGCTGAACAAGGG | 32 | 400 |
| 757289 | 3317 | 3336 | 131081 | 131100 | ATAATGTGGCACATGCTGAA | 138 | 401 |
| 757290 | 3323 | 3342 | 131087 | 131106 | AGACTGATAATGTGGCACAT | 64 | 402 |
| 757291 | 3329 | 3348 | N/A | N/A | ATGCTGAGACTGATAATGTG | 77 | 403 |
| 757292 | 3335 | 3354 | N/A | N/A | ATGAGGATGCTGAGACTGAT | 81 | 404 |
| 757293 | 3341 | 3360 | N/A | N/A | ATAGACATGAGGATGCTGAG | 85 | 405 |
| 757294 | 3347 | 3366 | 131428 | 131447 | AGGACTATAGACATGAGGAT | 25 | 406 |
| 757295 | 3353 | 3372 | 131434 | 131453 | TATTACAGGACTATAGACAT | 58 | 407 |
| 757296 | 3359 | 3378 | 131440 | 131459 | ACCCTGTATTACAGGACTAT | 81 | 408 |
| 757297 | 3365 | 3384 | 131446 | 131465 | AGCATTACCCTGTATTACAG | 45 | 409 |
| 757298 | 3371 | 3390 | 131452 | 131471 | CATTCTAGCATTACCCTGTA | 90 | 410 |
| 757299 | 3377 | 3396 | 131458 | 131477 | TGCCATCATTCTAGCATTAC | 73 | 411 |
| 757300 | 3383 | 3402 | 131464 | 131483 | TGGTGGTGCCATCATTCTAG | 51 | 412 |
| 757301 | 3408 | 3427 | 131489 | 131508 | ATACTAAACCAGGCTGGGCG | 85 | 413 |
| 757302 | 3414 | 3433 | 131495 | 131514 | AAGAAGATACTAAACCAGGC | 41 | 414 |
| 757303 | 3420 | 3439 | 131501 | 131520 | TTGCTGAAGAAGATACTAAA | 81 | 415 |

TABLE 6

Percent control of human ATXN2 RNA with 5-10-5 MOE gapmers with mixed internucleoside linkages at 2,000 nM concentration

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 708199 | 1477 | 1496 | 81637 | 81656 | GCTAACTGGTTTGCCCTTGC | 19 | 32 |
| 708398 | 3476 | 3495 | N/A | N/A | TGGTAATTTGGGACATGCAT | 45 | 416 |
| 708400 | 3494 | 3513 | 136967 147866 | 136986 147885 | GCTTGTCTCCTTGTTGTATG | 49 | 417 |
| 708435 | 3897 | 3916 | N/A | N/A | GTACATGAGCCTGAGGTACG | 112 | 418 |
| 708440 | 3951 | 3970 | N/A | N/A | TCATTAGCATCATTGGCGCA | 49 | 419 |
| 757304 | 3426 | 3445 | 131507 | 131526 | ACTGAGTTGCTGAAGAAGAT | 85 | 420 |
| 757305 | 3432 | 3451 | 131513 | 131532 | CCCCGTACTGAGTTGCTGAA | 63 | 421 |
| 757306 | 3438 | 3457 | 131519 | 131538 | CATGAGCCCCGTACTGAGTT | 79 | 422 |
| 757307 | 3444 | 3463 | 131525 | 131544 | TCTGCTCATGAGCCCCGTAC | 70 | 423 |
| 757308 | 3464 | 3483 | N/A | N/A | ACATGCATACATCGCATGCG | 98 | 424 |
| 757309 | 3470 | 3489 | N/A | N/A | TTTGGGACATGCATACATCG | 111 | 425 |

TABLE 6-continued

Percent control of human ATXN2 RNA with 5-10-5 MOE gapmers with mixed internucleoside linkages at 2,000 nM concentration

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
| --- | --- | --- | --- | --- | --- | --- | --- |
| 757310 | 3482 | 3501 | 136955 | 136974 | GTTGTATGGTAATTTGGGAC | 56 | 426 |
| 757311 | 3488 | 3507 | 136961 | 136980 | CTCCTTGTTGTATGGTAATT | 32 | 427 |
| 757312 | 3500 | 3519 | 136973 | 136992 | AGAAGGGCTTGTCTCCTTGT | 63 | 428 |
| 757313 | 3506 | 3525 | 136979 | 136998 | GTAGAAAGAAGGGCTTGTCT | 70 | 429 |
| 757314 | 3512 | 3531 | 136985 | 137004 | GGCAAAGTAGAAAGAAGGGC | 54 | 430 |
| 757315 | 3518 | 3537 | N/A | N/A | GGAAATGGCAAAGTAGAAAG | 97 | 431 |
| 757316 | 3524 | 3543 | N/A | N/A | GCCCGTGGAAATGGCAAAGT | 97 | 432 |
| 757317 | 3530 | 3549 | N/A | N/A | AAGGGAGCCCGTGGAAATGG | 74 | 433 |
| 757318 | 3536 | 3555 | 144311 | 144330 | CTGAGCAAGGGAGCCCGTGG | 82 | 434 |
| 757319 | 3542 | 3561 | 144317 | 144336 | ATACTGCTGAGCAAGGGAGC | 54 | 435 |
| 757320 | 3548 | 3567 | 144323 | 144342 | GTGCGCATACTGCTGAGCAA | 61 | 436 |
| 757321 | 3554 | 3573 | 144329 | 144348 | GTTAGGGTGCGCATACTGCT | 52 | 437 |
| 757322 | 3579 | 3598 | 144354 | 144373 | GTGGAGTATGTGGGTGCAGG | 89 | 438 |
| 757323 | 3586 | 3605 | 144361 | 144380 | TGAGGGTGTGGAGTATGTGG | 94 | 439 |
| 757324 | 3592 | 3611 | 144367 | 144386 | GAAGGCTGAGGGTGTGGAGT | 85 | 440 |
| 757325 | 3598 | 3617 | 144373 | 144392 | GTAGCTGAAGGCTGAGGGTG | 70 | 441 |
| 757326 | 3619 | 3638 | 144394 | 144413 | CTTTGCTGCTGTCCAGTGGG | 43 | 442 |
| 757327 | 3625 | 3644 | 144400 | 144419 | TGTTGGCTTTGCTGCTGTCC | 55 | 443 |
| 757328 | 3631 | 3650 | 144406 | 144425 | CCACCATGTTGGCTTTGCTG | 60 | 444 |
| 757329 | 3637 | 3656 | 144412 | 144431 | TGACTTCCACCATGTTGGCT | 64 | 445 |
| 757330 | 3643 | 3662 | 144418 | 144437 | GCAGGATGACTTCCACCATG | 62 | 446 |
| 757331 | 3649 | 3668 | 144424 | 144443 | CTGGGTGCAGGATGACTTCC | 61 | 447 |
| 757332 | 3656 | 3675 | 144431 | 144450 | AACAGGACTGGGTGCAGGAT | 80 | 448 |
| 757333 | 3666 | 3685 | N/A | N/A | GATGGTGCTGAACAGGACTG | 67 | 449 |
| 757334 | 3672 | 3691 | N/A | N/A | GGTGCTGATGGTGCTGAACA | 64 | 450 |
| 757335 | 3678 | 3697 | 145410 | 145429 | CGGCCTGGTGCTGATGGTGC | 50 | 451 |
| 757336 | 3684 | 3703 | 145416 | 145435 | CCTGGGCGGCCTGGTGCTGA | 64 | 452 |
| 757337 | 3690 | 3709 | 145422 | 145441 | GGAGAGCCTGGGCGGCCTGG | 74 | 453 |
| 757338 | 3696 | 3715 | 145428 | 145447 | CCAGATGGAGAGCCTGGGCG | 81 | 454 |
| 757339 | 3702 | 3721 | 145434 | 145453 | GACTGGCCAGATGGAGAGCC | 82 | 455 |
| 757340 | 3708 | 3727 | 145440 | 145459 | GCTGTGGACTGGCCAGATGG | 84 | 456 |
| 757341 | 3714 | 3733 | 145446 | 145465 | ACTGCTGCTGTGGACTGGCC | 62 | 457 |
| 757342 | 3720 | 3739 | 145452 | 145471 | TGGCTGACTGCTGCTGTGGA | 42 | 458 |
| 757343 | 3726 | 3745 | 145458 | 145477 | GGTAAATGGCTGACTGCTGC | 54 | 459 |
| 757344 | 3747 | 3766 | 145479 | 145498 | GAGTTGGCGCAAGCCCCGCG | 62 | 460 |
| 757345 | 3753 | 3772 | 145485 | 145504 | AGGGTGGAGTTGGCGCAAGC | 88 | 461 |

TABLE 6-continued

Percent control of human ATXN2 RNA with 5-10-5 MOE gapmers with mixed internucleoside linkages at 2,000 nM concentration

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 757346 | 3759 | 3778 | 145491 | 145510 | TCATGGAGGGTGGAGTTGGC | 97 | 462 |
| 757347 | 3765 | 3784 | 145497 | 145516 | CAGGTGTCATGGAGGGTGGA | 103 | 463 |
| 757348 | 3771 | 3790 | 145503 | 145522 | TGGAGGCAGGTGTCATGGAG | 111 | 464 |
| 757349 | 3794 | 3813 | 145526 | 145545 | ACTATTCTGTGGCGACTGCG | 57 | 465 |
| 757350 | 3800 | 3819 | 145532 | 145551 | TGGGAAACTATTCTGTGGCG | 61 | 466 |
| 757351 | 3806 | 3825 | 145538 | 145557 | TGCTGCTGGGAAACTATTCT | 71 | 467 |
| 757352 | 3812 | 3831 | 145544 | 145563 | CTGTTGTGCTGCTGGGAAAC | 57 | 468 |
| 757353 | 3818 | 3837 | 145550 | 145569 | GACAGTCTGTTGTGCTGCTG | 67 | 469 |
| 757354 | 3824 | 3843 | 145556 | 145575 | CGTAAAGACAGTCTGTTGTG | 61 | 470 |
| 757355 | 3858 | 3877 | 145590 | 145609 | TGGTATACGCCGGCTGAACG | 57 | 471 |
| 757356 | 3864 | 3883 | 145596 | 145615 | GTGGGTTGGTATACGCCGGC | 75 | 472 |
| 757357 | 3903 | 3922 | 147818 | 147837 | CTGACTGTACATGAGCCTGA | 77 | 473 |
| 757358 | 3909 | 3928 | 147824 | 147843 | CCATTCCTGACTGTACATGA | 53 | 474 |
| 757359 | 3915 | 3934 | 147830 | 147849 | AAGGAACCATTCCTGACTGT | 63 | 475 |
| 757360 | 3921 | 3940 | 147836 | 147855 | GATGAGAAGGAACCATTCCT | 64 | 476 |
| 757361 | 3927 | 3946 | 147842 | 147861 | CAGTTGGATGAGAAGGAACC | 77 | 477 |
| 757362 | 3933 | 3952 | 147848 | 147867 | CATGGGCAGTTGGATGAGAA | 71 | 478 |
| 757363 | 3939 | 3958 | 147854 | 147873 | TTGGCGCATGGGCAGTTGGA | 75 | 479 |
| 757364 | 3945 | 3964 | 147860 | 147879 | GCATCATTGGCGCATGGGCA | 39 | 480 |
| 757365 | 3971 | 3990 | 147886 | 147905 | ACCGCCGGGTGGCTGTGTCG | 79 | 481 |
| 757366 | 3993 | 4012 | 147908 | 147927 | TTTGAGCGAGGGCGGCCTGG | 105 | 482 |
| 757367 | 3999 | 4018 | 147914 | 147933 | GTGCACTTTGAGCGAGGGCG | 80 | 483 |
| 757368 | 4011 | 4030 | 147926 | 147945 | GAATGGGCTGTAGTGCACTT | 44 | 484 |
| 757369 | 4017 | 4036 | 147932 | 147951 | AGACTGGAATGGGCTGTAGT | 67 | 485 |
| 757370 | 4023 | 4042 | 147938 | 147957 | TTGTCGAGACTGGAATGGGC | 61 | 486 |
| 757371 | 4029 | 4048 | 147944 | 147963 | GCGCTGTTGTCGAGACTGGA | 42 | 487 |
| 757372 | 4035 | 4054 | 147950 | 147969 | GGAAATGCGCTGTTGTCGAG | 35 | 488 |
| 757373 | 4064 | 4083 | N/A | N/A | GGCTTGTACTGAAGGGTGCG | 90 | 489 |
| 757374 | 4070 | 4089 | N/A | N/A | GTGGTGGGCTTGTACTGAAG | 69 | 490 |
| 757375 | 4076 | 4095 | 148827 | 148846 | CTGTTGGTGGTGGGCTTGTA | 90 | 491 |
| 757376 | 4082 | 4101 | 148833 | 148852 | CAACTGCTGTTGGTGGTGGG | 79 | 492 |

Example 2: Effect of 5-10-5 MOE Gapmers with Mixed Internucleoside Linkages on Human ATXN2 RNA Expression In Vitro, Single Dose Modified oligonucleotides complementary to a human ATXN2 nucleic acid were designed and tested for their effect on ATXN2 RNA in vitro.

Cultured A431 cells at a density of 10,000 cells per well were transfected via free uptake with 5,000 nM concentration of modified oligonucleotide or no modified oligonucleotide for untreated controls. After approximately 24 hours, RNA was isolated from the cells and ATXN2 RNA levels were measured by quantitative real-time PCR Human primer probe set RTS5049 (forward sequence CTA- CAGTCCTCAGCAGTTCC, designated herein as SEQ ID NO: 13; reverse sequence GCCATCATTCTAGCATTACCCT, designated herein as SEQ ID NO: 14; probe sequence ATCAGCCCCTTGTTCAGCATGTG, designated herein as SEQ ID: 15) was used to measure RNA levels. ATXN2 RNA levels were adjusted according to total RNA content, as measured by RIBOGREEN®. Results are presented in the tables below as percent control ATXN2 RNA levels relative to untreated control cells.

The modified oligonucleotides in the tables below are 5-10-5 MOE gapmers. The gapmers are 20 nucleobases in length, wherein the central gap segment comprises ten 2'-deoxynucleosides and is flanked by wing segments on both the 5' end and on the 3' end comprising five 2'-MOE nucleosides. The sugar motif for the gapmers is (from 5' to 3'): eeeeedddddddddddeeeee; wherein 'd' represents a 2'-deoxyribose sugar and 'e' represents a 2'-MOE modified sugar. The internucleoside linkages are mixed phosphodiester and phosphorothioate linkages. The internucleoside linkage motif for the gapmers is (from 5' to 3'): soooosssssssssssooss; wherein 'o' represents a phosphodiester internucleoside linkage and 's' represents a phosphorothioate internucleoside linkage. Each cytosine residue is a 5-methyl cytosine. "Start Site" indicates the 5'-most nucleoside to which the gapmer is complementary in the human nucleic acid sequence. "Stop Site" indicates the 3'-most nucleoside to which the gapmer is complementary in the human nucleic acid sequence.

Each modified oligonucleotide listed in the tables below is complementary to human ATXN2 nucleic acid sequences SEQ ID NO: 1 or SEQ ID NO: 2, as indicated. 'N/A' indicates that the modified oligonucleotide is not complementary to that particular nucleic acid with 100% complementarity. As shown below, modified oligonucleotides complementary to the nucleobase sequence of human ATXN2 RNA reduced the amount of human ATXN2 RNA.

TABLE 8

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 708199 | 1477 | 1496 | 81637 | 708199 | GCTAACTGGTTTGCCCTTGC | 29 | 32 |
| 874154 | 5 | 24 | 1995 | 874154 | GCGCTGGGTTGCTTTCTCGG | 104 | 493 |
| 874178 | 246 | 265 | 2236 | 874178 | CCGGCCGCTGGAGCGAGCGC | 85 | 494 |
| 874202 | 469 | 488 | 2459 | 874202 | AGAAGGAGGACGACGAAGGG | 89 | 495 |
| 874224 | 1305 | 1324 | 76442 | 874224 | AAGCCTCAAGTTCCTCATTG | 110 | 496 |
| 874247 | 1561 | 1580 | 81721 | 874247 | GCTGTGTATTTTTCTTCCTC | 24 | 497 |
| 874271 | 2358 | 2377 | 91242 | 874271 | CTCTGTTCGATGCAGGACTA | 86 | 498 |
| 874295 | 2672 | 2691 | 112981 | 874295 | AGAATCCTTAGCACTTGGTT | 45 | 499 |
| 874319 | 3127 | 3146 | 116363 | 874319 | TTGGCTTGATTCACTGGCAT | 89 | 500 |
| 874341 | 4116 | 4135 | 148867 | 874341 | AATTTGGCCTTTCGGTTCCT | 64 | 501 |
| 874365 | 4272 | 4291 | 149023 | 874365 | TGCCTCTACTCGGTCCAAGT | 74 | 502 |
| 874389 | 4422 | 4441 | 149173 | 874389 | TCTTGTTACTTCTTTTGCTA | 63 | 503 |
| 874412 | 4603 | 4622 | 149354 | 874412 | CTTAACTTAAAAGTTGAACC | 118 | 504 |
| 874436 | N/A | N/A | 146563 | 874436 | TCTAGCCCACACCTTGCCAG | 114 | 505 |
| 874484 | N/A | N/A | 3698 | 874484 | CGAACAGCAATGCGGATCGG | 97 | 506 |
| 874508 | N/A | N/A | 5223 | 874508 | GAATTTCCAGACTTTCAAGC | 48 | 507 |
| 874532 | N/A | N/A | 7785 | 874532 | TAACAAAGGATGATGCCATT | 67 | 508 |
| 874556 | N/A | N/A | 9958 | 874556 | TTGGGCAAGTCCCCTAATCT | 115 | 509 |
| 874580 | N/A | N/A | 13708 | 874580 | ACCAGCATGTTAGGAGGCCT | 95 | 510 |
| 874604 | N/A | N/A | 16563 | 874604 | TACTTCTTTGGGAGATATAA | 83 | 511 |
| 874628 | N/A | N/A | 18790 | 874628 | CAGGGTTTCCCCATGTTAGG | 98 | 512 |
| 874652 | N/A | N/A | 20571 | 874652 | AAGGAGCCAAGATTGCCCCA | 116 | 513 |
| 874676 | N/A | N/A | 25034 | 874676 | ACTGAGACTGTAGATGAGCC | 121 | 514 |
| 874700 | N/A | N/A | 28108 | 874700 | AAGCAATGGAACAGTTATTA | 46 | 515 |
| 874724 | N/A | N/A | 30929 | 874724 | CAGTCCCCTCCCAGTGCTAC | 78 | 516 |

TABLE 8-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 874748 | N/A | N/A | 32488 | 874748 | GTTCAAATTCCGGCTCCATC | 32 | 517 |
| 874772 | N/A | N/A | 34639 | 874772 | TGTGGTAAAAAAGCAAGAGA | 70 | 518 |
| 874796 | N/A | N/A | 37016 | 874796 | AAATCAAGCAGAGCCAGGTG | 97 | 519 |
| 874820 | N/A | N/A | 38400 | 874820 | TCTTGGACAGAGGGAGTAAA | 93 | 520 |
| 874844 | N/A | N/A | 41510 | 874844 | AAAGCTCCACGGAAAACAAT | 108 | 521 |
| 874868 | N/A | N/A | 43617 | 874868 | TACATCTTTGACTAATAAAA | 95 | 522 |
| 874892 | N/A | N/A | 44608 | 874892 | ATTATAGAATATAATACAAC | 98 | 523 |
| 874916 | N/A | N/A | 46490 | 874916 | AAAAGCACATTAATTCAAAA | 89 | 524 |
| 874940 | N/A | N/A | 48167 | 874940 | TGTAAATTGTCATACTGTAT | 50 | 525 |
| 874964 | N/A | N/A | 50706 | 874964 | CTACAATTTACAACAGAATT | 79 | 526 |
| 874988 | N/A | N/A | 52791 | 874988 | GATTATAGACATGTGCCATC | 88 | 527 |
| 875012 | N/A | N/A | 55320 | 875012 | TTCTGTAAAGAGACAGTCAA | 100 | 528 |
| 875036 | N/A | N/A | 57881 | 875036 | AAACTGTGAACACCATGAAA | 102 | 529 |
| 875060 | N/A | N/A | 60512 | 875060 | GTTTTGTTTAATCACAGTTT | 32 | 530 |
| 875084 | N/A | N/A | 62556 | 875084 | CATTTTCTCCATTAGGCTTC | 84 | 531 |
| 875108 | N/A | N/A | 64420 | 875108 | AAAGAAAGAAGTACTAATAC | 108 | 532 |
| 875132 | N/A | N/A | 67160 | 875132 | ATATACTAGACACCATGGTT | 78 | 533 |
| 875156 | N/A | N/A | 69694 | 875156 | CTGTTGGCATAGTAACATAC | 74 | 534 |
| 875180 | N/A | N/A | 71679 | 875180 | TAACCATTTCTTCTCAACTA | 116 | 535 |
| 875204 | N/A | N/A | 73162 | 875204 | GTTGTGTTAAGAGGGCATTA | 86 | 536 |
| 875228 | N/A | N/A | 74868 | 875228 | TTTTGTTTTTAACTTTCCAT | 107 | 537 |
| 875252 | N/A | N/A | 77333 | 875252 | GATATGTTACAAATTCTCTT | 40 | 538 |
| 875276 | N/A | N/A | 79712 | 875276 | CTAATGTTTCAACTCCTTTT | 73 | 539 |
| 875300 | N/A | N/A | 81860 | 875300 | AAAGGAAGAGGAAATATAAT | 104 | 540 |
| 875324 | N/A | N/A | 83038 | 875324 | GTCCCTTCCCTTAGATTCTG | 49 | 541 |
| 875348 | N/A | N/A | 84816 | 875348 | CTGGTTCCTTACAATTATCT | 25 | 542 |
| 875372 | N/A | N/A | 86229 | 875372 | TTTGATATGTGGCAATGATG | 54 | 543 |
| 875396 | N/A | N/A | 89279 | 875396 | AACAAAGCACTAAGGACTGA | 73 | 544 |
| 875420 | N/A | N/A | 91499 | 875420 | ACCAATAATTTTATTTATGT | 107 | 545 |
| 875444 | N/A | N/A | 93243 | 875444 | TTGTATGTGTTAACTATTGT | 56 | 546 |
| 875468 | N/A | N/A | 96231 | 875468 | CAGAACAGGAGAAAACATTT | 101 | 547 |
| 875492 | N/A | N/A | 98219 | 875492 | GTTAGACAAGATTTAACATA | 70 | 548 |
| 875516 | N/A | N/A | 99997 | 875516 | GGTATTTATGTGGGCACACT | 65 | 549 |
| 875540 | N/A | N/A | 102876 | 875540 | AAATGAACAAAACGGGAGGA | 122 | 550 |
| 875564 | N/A | N/A | 106246 | 875564 | AACAATATTCCATGCAAATG | 123 | 551 |
| 875588 | N/A | N/A | 109670 | 875588 | ACTGAAAGTAAAGACCCAGT | 111 | 552 |

TABLE 8-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 875612 | N/A | N/A | 111907 | 875612 | GTGATACCCTGTCTCATTTA | 68 | 553 |
| 875636 | N/A | N/A | 113969 | 875636 | CAACTCCTAACCTCAAGTAA | 98 | 554 |
| 875660 | N/A | N/A | 116228 | 875660 | CTAGGCATGAGAAGGTTTCC | 114 | 555 |
| 875684 | N/A | N/A | 119113 | 875684 | GTTAGAATGTGACTCTCCCA | 50 | 556 |
| 875708 | N/A | N/A | 121999 | 875708 | CTGGGACGGCTTTGAATGTG | 76 | 557 |
| 875732 | N/A | N/A | 125533 | 875732 | CAAATTTTTAAATTGTTTTG | 111 | 558 |
| 875756 | N/A | N/A | 128616 | 875756 | TGAGGCTGACACAGGCAGAC | 103 | 559 |
| 875780 | N/A | N/A | 130619 | 875780 | CTTGATCAAGTCCCTGTAAC | 72 | 560 |
| 875804 | N/A | N/A | 132522 | 875804 | ATGTAGTTACATGTAACCAT | 37 | 561 |
| 875828 | N/A | N/A | 134584 | 875828 | GCAGATTTAATGAAGAACAT | 109 | 562 |
| 875852 | N/A | N/A | 137143 | 875852 | TCCATTTTAAAAACTGAATT | 86 | 563 |
| 875876 | N/A | N/A | 139105 | 875876 | AATAAAAGGCAACTTGACCA | 75 | 564 |
| 875900 | N/A | N/A | 141644 | 875900 | ACTGCACCCGGCCTAAAAAT | 101 | 565 |
| 875924 | N/A | N/A | 143719 | 875924 | ATCTCCCATCTTTGCTTTAT | 85 | 566 |
| 875948 | N/A | N/A | 145875 | 875948 | CATTCCAGAGTCAAAGATAT | 99 | 567 |
| 875972 | N/A | N/A | 147334 | 875972 | CACAGTCAAGTATGTGAATT | 96 | 568 |

TABLE 9

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 708199 | 1477 | 1496 | 81637 | 81656 | GCTAACTGGTTTGCCCTTGC | 58 | 32 |
| 874155 | 10 | 29 | 2000 | 2019 | GCGGCGCGCTGGGTTGCTTT | 90 | 569 |
| 874179 | 251 | 270 | 2241 | 2260 | CCGCGCCGGCCGCTGGAGCG | 134 | 570 |
| 874203 | 511 | 530 | 2501 | 2520 | CGGGTTGGCGCGGCCGGAGG | 118 | 571 |
| 874225 | 1317 | 1336 | 76454 | 76473 | CGTCATTTTCCAAAGCCTCA | 60 | 572 |
| 874248 | 1585 | 1604 | 81745 | 81764 | CGTTCACTGGAATTTCTCTG | 61 | 573 |
| 874272 | 2360 | 2379 | 91244 | 91263 | AGCTCTGTTCGATGCAGGAC | 54 | 574 |
| 874296 | 2674 | 2693 | 112983 | 113002 | AAAGAATCCTTAGCACTTGG | 75 | 575 |
| 874320 | 3129 | 3148 | 116365 | 116384 | TCTTGGCTTGATTCACTGGC | 90 | 576 |
| 874342 | 4121 | 4140 | 148872 | 148891 | GAGGGAATTTGGCCTTTCGG | 97 | 577 |
| 874366 | 4277 | 4296 | 149028 | 149047 | CTAAATGCCTCTACTCGGTC | 68 | 578 |
| 874390 | 4440 | 4459 | 149191 | 149210 | AATAGCAGCAAGAATCACTC | 84 | 579 |
| 874413 | 4608 | 4627 | 149359 | 149378 | TTTCCCTTAACTTAAAAGTT | 81 | 580 |

TABLE 9-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 874437 | N/A | N/A | 146568 | 146587 | GCATCTCTAGCCCACACCTT | 82 | 581 |
| 874461 | N/A | N/A | 3425 | 3444 | GGGAGAGAGCCCCGACAGAC | 114 | 582 |
| 874485 | N/A | N/A | 3703 | 3722 | GGCCTCGAACAGCAATGCGG | 84 | 583 |
| 874509 | N/A | N/A | 5239 | 5258 | TTCTTAAAGCAGATGTGAAT | 103 | 584 |
| 874533 | N/A | N/A | 7805 | 7824 | TCAATGTGCACATAAAAGAA | 113 | 585 |
| 874557 | N/A | N/A | 9975 | 9994 | ATCCTACAAATATTGCTTTG | 88 | 586 |
| 874581 | N/A | N/A | 13824 | 13843 | TTACAAAGACTTCATTATAG | 84 | 587 |
| 874605 | N/A | N/A | 16684 | 16703 | TTTCAATAATGCAATGCATC | 96 | 588 |
| 874629 | N/A | N/A | 18946 | 18965 | GTCGCCCAGCAGGCTGGAGT | 108 | 589 |
| 874653 | N/A | N/A | 20901 | 20920 | GAAAAAATAAAAAGGAGAGA | 92 | 590 |
| 874677 | N/A | N/A | 25039 | 25058 | GAGTCACTGAGACTGTAGAT | 98 | 591 |
| 874701 | N/A | N/A | 28112 | 28131 | TTAGAAGCAATGGAACAGTT | 95 | 592 |
| 874725 | N/A | N/A | 30931 | 30950 | GGCAGTCCCCTCCCAGTGCT | 73 | 593 |
| 874749 | N/A | N/A | 32518 | 32537 | CAAGAACTAATATCAGCATT | 71 | 594 |
| 874773 | N/A | N/A | 34663 | 34682 | TTCAGTAGAGCAAGTAACTG | 89 | 595 |
| 874797 | N/A | N/A | 37036 | 37055 | AACAGCAATACAACAATTAA | 102 | 596 |
| 874821 | N/A | N/A | 38419 | 38438 | GTAACAATCCTGGATTGGTT | 87 | 597 |
| 874845 | N/A | N/A | 41559 | 41578 | CAAAGAAGCGCAAATTTGAT | 117 | 598 |
| 874869 | N/A | N/A | 43662 | 43681 | TCCCCTTTAAATAAGTCACA | 103 | 599 |
| 874893 | N/A | N/A | 44669 | 44688 | AGAAAAGATGCAGTACACAA | 91 | 600 |
| 874917 | N/A | N/A | 46497 | 46516 | GCAGAAAAAAAGCACATTAA | 89 | 601 |
| 874941 | N/A | N/A | 48294 | 48313 | CGAATTACATAATACTTAAG | 87 | 602 |
| 874965 | N/A | N/A | 50719 | 50738 | AAATTGTACTGAACTACAAT | 92 | 603 |
| 874989 | N/A | N/A | 52916 | 52935 | GAAAATAAAGCACAAATTCT | 108 | 604 |
| 875013 | N/A | N/A | 55467 | 55486 | AATCAAAGCATGCAATTAGT | 84 | 605 |
| 875037 | N/A | N/A | 57947 | 57966 | GCTTTGCTATCTCTAACTCT | 94 | 606 |
| 875061 | N/A | N/A | 60556 | 60575 | AATTAAACAAATTCACAGAT | 127 | 607 |
| 875085 | N/A | N/A | 62584 | 62603 | TACTGTTTATGGGTGAACAT | 81 | 608 |
| 875109 | N/A | N/A | 64468 | 64487 | AAATGTAGTGTACCTGTGTA | 110 | 609 |
| 875133 | N/A | N/A | 67289 | 67308 | ATCACCACACTCCAACCTCA | 122 | 610 |
| 875157 | N/A | N/A | 69719 | 69738 | TGCAGTTATCAAAAACTAAA | 116 | 611 |
| 875181 | N/A | N/A | 71692 | 71711 | CAAAATCCTCAGCTAACCAT | 128 | 612 |
| 875205 | N/A | N/A | 73171 | 73190 | AGAATTTAGGTTGTGTTAAG | 93 | 613 |
| 875229 | N/A | N/A | 75201 | 75220 | CAGACCGGAGTGCAGTGACA | 108 | 614 |
| 875253 | N/A | N/A | 77463 | 77482 | GAATTAATGACATGTTGCCT | 94 | 615 |
| 875277 | N/A | N/A | 79953 | 79972 | GTAACTCCACAATTCTACGA | 110 | 616 |

TABLE 9-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 875301 | N/A | N/A | 81905 | 81924 | AGATCTTAAACCAATTCTAC | 110 | 617 |
| 875325 | N/A | N/A | 83430 | 83449 | TGATATTGACAAGTCTGGTC | 56 | 618 |
| 875349 | N/A | N/A | 84836 | 84855 | ATTATATCCAATTAGAAATG | 98 | 619 |
| 875373 | N/A | N/A | 86281 | 86300 | ATATGGGTGGCATTTAAATT | 111 | 620 |
| 875397 | N/A | N/A | 89309 | 89328 | TTGTAAGCTCTTGCTTACCA | 95 | 621 |
| 875421 | N/A | N/A | 91828 | 91847 | GTATGGGCATGAAATTAGAC | 66 | 622 |
| 875445 | N/A | N/A | 93318 | 93337 | TTAACTGTGTTAGAATGCTT | 36 | 623 |
| 875469 | N/A | N/A | 96243 | 96262 | AAAGACAACCAACAGAACAG | 76 | 624 |
| 875493 | N/A | N/A | 98273 | 98292 | CAAGCTGCCTAATATACACA | 100 | 625 |
| 875517 | N/A | N/A | 100105 | 100124 | GCTCTTGGTGTCATGGCAAA | 101 | 626 |
| 875541 | N/A | N/A | 102894 | 102913 | CAAAAGCCATACTGAGCAAA | 96 | 627 |
| 875565 | N/A | N/A | 106257 | 106276 | AAGAGCTGGAAAACAATATT | 97 | 628 |
| 875589 | N/A | N/A | 109713 | 109732 | CAGCATTTCTAGACACACCC | 88 | 629 |
| 875613 | N/A | N/A | 112340 | 112359 | CACATAAAACAATAGCACCA | 85 | 630 |
| 875637 | N/A | N/A | 114253 | 114272 | AAAGACAGTAGCTACTTATG | 73 | 631 |
| 875661 | N/A | N/A | 116230 | 116249 | AGCTAGGCATGAGAAGGTTT | 77 | 632 |
| 875685 | N/A | N/A | 119136 | 119155 | TTAAAAAGACAGTACCTCCT | 100 | 633 |
| 875709 | N/A | N/A | 122055 | 122074 | TACACTGTTTAGGACACACA | 78 | 634 |
| 875733 | N/A | N/A | 125689 | 125708 | CACACACTTTAAATACAGGG | 47 | 635 |
| 875757 | N/A | N/A | 128698 | 128717 | TCATTTCTTCTCAAGTTAAT | 100 | 636 |
| 875781 | N/A | N/A | 130627 | 130646 | CCCTCAGACTTGATCAAGTC | 119 | 637 |
| 875805 | N/A | N/A | 132529 | 132548 | AATGCCCATGTAGTTACATG | 54 | 638 |
| 875829 | N/A | N/A | 134590 | 134609 | ATCACTGCAGATTTAATGAA | 94 | 639 |
| 875853 | N/A | N/A | 137205 | 137224 | AAAAATTGATTTCTGAAACA | 108 | 640 |
| 875877 | N/A | N/A | 139231 | 139250 | GCACAAGTCATAAGAGATCA | 45 | 641 |
| 875901 | N/A | N/A | 141780 | 141799 | GGGATTACCTGGCTAATTTT | 75 | 642 |
| 875925 | N/A | N/A | 143835 | 143854 | TATGGTATGTGGCAAGGCCA | 103 | 643 |
| 875949 | N/A | N/A | 145895 | 145914 | AGGAAAGAAGGACTGGGTTG | 112 | 644 |
| 875973 | N/A | N/A | 147394 | 147413 | TTTTGCAGATAACATCCCTT | 68 | 645 |

Example 3: Effect of 5-10-5 MOE Gapmers with Mixed Internucleoside Linkages on Human ATXN2 RNA Expression In Vitro, Single Dose Modified oligonucleotides complementary to a human ATXN2 nucleic acid were designed and tested for their effect on ATXN2 RNA in vitro.

Cultured A431 cells at a density of 10,000 cells per well were transfected using electroporation with 6,000 nM concentration of modified oligonucleotide or no modified oligonucleotide for untreated controls. After approximately 24 hours, RNA was isolated from the cells and ATXN2 RNA levels were measured by quantitative real-time PCR as described in Example 2. Results are presented in the tables below as percent ATXN2 RNA levels relative to untreated control cells. The modified oligonucleotides marked with an asterisk (*) target the amplicon region of the primer probe set. Additional assays may be used to measure the potency and efficacy of oligonucleotides targeting the amplicon region.

The modified oligonucleotides in the tables below are 5-10-5 MOE gapmers. The gapmers are 20 nucleobases in length, wherein the central gap segment comprises ten 2'-deoxynucleosides and is flanked by wing segments on both the 5' end and on the 3' end comprising five 2'-MOE nucleosides. The sugar motif for the gapmers is (from 5' to 3'): eeeeedddddddddddeeeee; wherein 'd' represents a 2'-deoxyribose sugar and 'e' represents a 2'-MOE modified sugar. The internucleoside linkages are mixed phosphodiester and phosphorothioate linkages. The internucleoside linkage motif for the gapmers is (from 5' to 3'): sooooossssssssssooss; wherein 'o' represents a phosphodiester internucleoside linkage and 's' represents a phosphorothioate internucleoside linkage. Each cytosine residue is a 5-methyl cytosine. "Start Site" indicates the 5'-most nucleoside to which the gapmer is complementary in the human nucleic acid sequence. "Stop Site" indicates the 3'-most nucleoside to which the gapmer is complementary in the human nucleic acid sequence.

Each modified oligonucleotide listed in the tables below is complementary to human ATXN2 nucleic acid sequences SEQ ID NO: 1 or SEQ ID NO: 2, as indicated. 'N/A' indicates that the modified oligonucleotide is not complementary to that particular nucleic acid with 100% complementarity. As shown below, modified oligonucleotides complementary to the nucleobase sequence of human ATXN2 reduced the amount of human ATXN2 RNA.

TABLE 10

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 708199 | 1477 | 1496 | 81637 | 81656 | GCTAACTGGTTTGCCCTTGC | 28 | 32 |
| 874156 | 18 | 37 | 2008 | 2027 | AGGAGCGGGCGGCGCGCTGG | 94 | 646 |
| 874180 | 256 | 275 | 2246 | 2265 | CTCCGCCGCGCCGGCCGCTG | 91 | 647 |
| 874204 | 516 | 535 | 2506 | 2525 | AGGCGCGGGTTGGCGCGGCC | 132 | 648 |
| 874226 | 1385 | 1404 | 80740 | 80759 | CGTAGACACTACACCATAAT | 52 | 649 |
| 874249 | 1646 | 1665 | 83257 | 83276 | TCTATTTCTTTGTCCAGGAG | 20 | 650 |
| 874273 | 2361 | 2380 | 91245 | 91264 | CAGCTCTGTTCGATGCAGGA | 36 | 651 |
| 874297 | 2675 | 2694 | 112984 | 113003 | GAAAGAATCCTTAGCACTTG | 41 | 652 |
| 874321 | 3130 | 3149 | 116366 | 116385 | GTCTTGGCTTGATTCACTGG | 49 | 653 |
| 874343 | 4137 | 4156 | 148888 | 148907 | AAGCAGTAGAAGGGAGGAGG | 93 | 654 |
| 874367 | 4282 | 4301 | 149033 | 149052 | AGTTCCTAAATGCCTCTACT | 49 | 655 |
| 874391 | 4445 | 4464 | 149196 | 149215 | GCAGTAATAGCAGCAAGAAT | 93 | 656 |
| 874414 | 4613 | 4632 | 149364 | 149383 | AAGTTTTTCCCTTAACTTAA | 73 | 657 |
| 874438 | N/A | N/A | 146573 | 146592 | GAGTCGCATCTCTAGCCCAC | 58 | 658 |
| 874462 | N/A | N/A | 3475 | 3494 | CACTTGTCTCCACCCCGTCC | 100 | 659 |
| 874486 | N/A | N/A | 3714 | 3733 | TTCTCCACTGCGGCCTCGAA | 45 | 660 |
| 874510 | N/A | N/A | 5251 | 5270 | ATTATGAAATGTTTCTTAAA | 73 | 661 |
| 874534 | N/A | N/A | 7835 | 7854 | TTTTTGGTCTAACTTCAGAG | 44 | 662 |
| 874558 | N/A | N/A | 9990 | 10009 | GAGAGGTGTAATAAAATCCT | 53 | 663 |
| 874582 | N/A | N/A | 13950 | 13969 | TGTTCAATAAAGCCTCTCAA | 65 | 664 |
| 874606 | N/A | N/A | 16689 | 16708 | AATTATTTCAATAATGCAAT | 88 | 665 |
| 874630 | N/A | N/A | 19022 | 19041 | AACAGAAAATATTAAGACTT | 133 | 666 |
| 874654 | N/A | N/A | 21088 | 21107 | CAGCTACTAAGGAGGCAGAA | 104 | 667 |
| 874678 | N/A | N/A | 25040 | 25059 | TGAGTCACTGAGACTGTAGA | 125 | 668 |
| 874702 | N/A | N/A | 28494 | 28513 | CCGGATTGTTTTCTTCATTA | 15 | 669 |
| 874726 | N/A | N/A | 30965 | 30984 | ATTTTGAAGCCCTTTTTCTT | 86 | 670 |
| 874750 | N/A | N/A | 32534 | 32553 | ACAATTACCATTCACACAAG | 108 | 671 |
| 874774 | N/A | N/A | 34867 | 34886 | CGCCCGCCACCACATCCCCG | 81 | 672 |

TABLE 10-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 874798 | N/A | N/A | 37079 | 37098 | GTTTGCCCATCCTCACACTG | 78 | 673 |
| 874822 | N/A | N/A | 38436 | 38455 | ATACATGATAACCGAAGGTA | 44 | 674 |
| 874846 | N/A | N/A | 41631 | 41650 | GGAAAGAGAGCTGGGAGGAC | 71 | 675 |
| 874870 | N/A | N/A | 43690 | 43709 | AAGCTATATAAAAGACTTAA | 96 | 676 |
| 874894 | N/A | N/A | 44693 | 44712 | CTTTCCTTGCCAACTCTCTC | 138 | 677 |
| 874918 | N/A | N/A | 46532 | 46551 | TAAGACCAGAAAGCCAAAGG | 71 | 678 |
| 874942 | N/A | N/A | 48314 | 48333 | CCAGGACCTCCTTCAGATAC | 59 | 679 |
| 874966 | N/A | N/A | 50832 | 50851 | CTCCTAAGTCTAAGAGAAAG | 84 | 680 |
| 874990 | N/A | N/A | 53025 | 53044 | AACACTCTATCTATCCATTC | 71 | 681 |
| 875014 | N/A | N/A | 55577 | 55596 | TGATTTTTCACTAAATGTGA | 97 | 682 |
| 875038 | N/A | N/A | 58068 | 58087 | CACACCAGCACACCAGGCTA | 100 | 683 |
| 875062 | N/A | N/A | 60580 | 60599 | CTTATAAAGTCCTTCTCCAC | 127 | 684 |
| 875086 | N/A | N/A | 62923 | 62942 | TTTAGAAATGGTATCAGTTA | 69 | 685 |
| 875110 | N/A | N/A | 64474 | 64493 | TAAACAAAATGTAGTGTACC | 104 | 686 |
| 875134 | N/A | N/A | 67636 | 67655 | AAAAAACAGTTATTCCCTGG | 78 | 687 |
| 875158 | N/A | N/A | 69783 | 69802 | ATTCAGAATGTACTTAAATT | 91 | 688 |
| 875182 | N/A | N/A | 71785 | 71804 | TAAAAACTATAAAATGACAT | 94 | 689 |
| 875206 | N/A | N/A | 73172 | 73191 | CAGAATTTAGGTTGTGTTAA | 46 | 690 |
| 875230 | N/A | N/A | 75224 | 75243 | GAGATGGAGCTTGCTCTTTC | 80 | 691 |
| 875254 | N/A | N/A | 77472 | 77491 | AAAGTTTGAGAATTAATGAC | 85 | 692 |
| 875278 | N/A | N/A | 80006 | 80025 | CTCAGAAGTGGCAACTCTGG | 133 | 693 |
| 875302 | N/A | N/A | 81907 | 81926 | ACAGATCTTAAACCAATTCT | 67 | 694 |
| 875326 | N/A | N/A | 83480 | 83499 | TATGTAAACTATTTTAAGTA | 162 | 695 |
| 875350 | N/A | N/A | 84936 | 84955 | GATAATTTCACATAATAAAT | 98 | 696 |
| 875374 | N/A | N/A | 86298 | 86317 | GAAAACAGGTTTTTAATATA | 85 | 697 |
| 875398 | N/A | N/A | 89332 | 89351 | TGTTTGTTTGTTTTAAGTAT | 14 | 698 |
| 875422 | N/A | N/A | 92190 | 92209 | ACTGTATACATAACGCATTT | 80 | 699 |
| 875446 | N/A | N/A | 93885 | 93904 | CGTCTGTGGAGAAAGAAGTA | 102 | 700 |
| 875470 | N/A | N/A | 96308 | 96327 | AAAATCAGATAAATTGGACT | 67 | 701 |
| 875494 | N/A | N/A | 98278 | 98297 | TTGCCCAAGCTGCCTAATAT | 90 | 702 |
| 875518 | N/A | N/A | 100258 | 100277 | TTAGGACAACGGACCTAAGC | 103 | 703 |
| 875542 | N/A | N/A | 102896 | 102915 | AGCAAAAGCCATACTGAGCA | 71 | 704 |
| 875566 | N/A | N/A | 106280 | 106299 | AAATCACACATAGACTAAAA | 89 | 705 |
| 875590 | N/A | N/A | 109774 | 109793 | TCAGCCCCAGTACAATAAAG | 84 | 706 |
| 875614 | N/A | N/A | 112397 | 112416 | TAAGTAAAAGGAAGAGTATG | 98 | 707 |
| 875638 | N/A | N/A | 114258 | 114277 | GCTGAAAAGACAGTAGCTAC | 71 | 708 |

TABLE 10-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 875662 | N/A | N/A | 116237 | 116256 | GCTAGAGAGCTAGGCATGAG | 47 | 709 |
| 875686 | N/A | N/A | 119146 | 119165 | ATCATTTCTATTAAAAAGAC | 90 | 710 |
| 875710 | N/A | N/A | 122060 | 122079 | ATTACTACACTGTTTAGGAC | 55 | 711 |
| 875734 | N/A | N/A | 125791 | 125810 | CACAAAAAGACACTTGTTAT | 86 | 712 |
| 875758 | N/A | N/A | 129116 | 129135 | AAAAAATGTACAAAACCTTA | 99 | 713 |
| 875782 | N/A | N/A | 130691 | 130710 | ATTCTGCTTCATCCTTCAGG | 54 | 714 |
| 875806 | N/A | N/A | 132608 | 132627 | GTTCAGGACATCTAAACTTA | 61 | 715 |
| 875830 | N/A | N/A | 134620 | 134639 | AAGGCTTTGAAAGTCTAATA | 46 | 716 |
| 875854 | N/A | N/A | 137343 137421 | 137362 137440 | ATACCAAGCTTGTGGCTTGG | 128 | 717 |
| 875878 | N/A | N/A | 139233 | 139252 | ATGCACAAGTCATAAGAGAT | 90 | 718 |
| 875902 | N/A | N/A | 142200 | 142219 | TTGTTTAATTTTTGACAGAG | 67 | 719 |
| 875926 | N/A | N/A | 143901 | 143920 | TGGAGCAATGTCCTGAGGGC | 66 | 720 |
| 875950 | N/A | N/A | 145923 | 145942 | ATATAGACATAGCAAAGCAG | 107 | 721 |
| 875974 | N/A | N/A | 147433 | 147452 | ATGCTTCAGAATCAGGCTGC | 64 | 722 |

TABLE 11

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 708199 | 1477 | 1496 | 81637 | 81656 | GCTAACTGGTTTGCCCTTGC | 32 | 32 |
| 874157 | 89 | 108 | 2079 | 2098 | CTTTACCGGAAGTCGGAGGG | 121 | 723 |
| 874181 | 261 | 280 | 2251 | 2270 | GCCCGCTCCGCCGCGCCGGC | 115 | 724 |
| 874205 | 572 | 591 | 2562 | 2581 | CGGGCGCGCCAAGGAGACGC | 95 | 725 |
| 874227 | 1417 | 1436 | N/A | N/A | GGCACTGTATACGAAGATAA | 67 | 726 |
| 874250 | 1648 | 1667 | 83259 | 83278 | TCTCTATTTCTTTGTCCAGG | 20 | 727 |
| 874274 | 2362 | 2381 | 91246 | 91265 | ACAGCTCTGTTCGATGCAGG | 37 | 728 |
| 874298 | 2676 | 2695 | 112985 | 113004 | TGAAAGAATCCTTAGCACTT | 51 | 729 |
| 874322 | 3131 | 3150 | 116367 | 116386 | TGTCTTGGCTTGATTCACTG | 72 | 730 |
| 874344 | 4142 | 4161 | 148893 | 148912 | GGTAGAAGCAGTAGAAGGGA | 45 | 731 |
| 874368 | 4287 | 4306 | 149038 | 149057 | CCCCAAGTTCCTAAATGCCT | 69 | 732 |
| 874392 | 4450 | 4469 | 149201 | 149220 | TTTTAGCAGTAATAGCAGCA | 65 | 733 |
| 874415 | 4618 | 4637 | 149369 | 149388 | AGTAAAGTTTTTCCCTTAA | 35 | 734 |
| 874439 | N/A | N/A | 146578 | 146597 | CAACTGAGTCGCATCTCTAG | 88 | 735 |
| 874463 | N/A | N/A | 3480 | 3499 | AGGCCCACTTGTCTCCACCC | 109 | 736 |

TABLE 11-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 874487 | N/A | N/A | 3719 | 3738 | GCGCCTTCTCCACTGCGGCC | 138 | 737 |
| 874511 | N/A | N/A | 5358 | 5377 | TTATCTTTCCTAAAACAGCC | 62 | 738 |
| 874535 | N/A | N/A | 7849 | 7868 | AATGTCAATTAACTTTTTG | 72 | 739 |
| 874559 | N/A | N/A | 10080 | 10099 | GACAGGAGAAATGCTTGGCC | 134 | 740 |
| 874583 | N/A | N/A | 13962 | 13981 | CATTGGCAACACTGTTCAAT | 66 | 741 |
| 874607 | N/A | N/A | 16692 | 16711 | AACAATTATTTCAATAATGC | 129 | 742 |
| 874631 | N/A | N/A | 19028 | 19047 | CATAAAAACAGAAAATATTA | 86 | 743 |
| 874655 | N/A | N/A | 21122 | 21141 | AAGATGACAACGGAACGGGA | 58 | 744 |
| 874679 | N/A | N/A | 25252 | 25271 | CTGCACGCCACTGTACTCCA | 59 | 745 |
| 874703 | N/A | N/A | 28507 | 28526 | CTGACAATAATCACCGGATT | 32 | 746 |
| 874727 | N/A | N/A | 30982 | 31001 | CCATCTCAACTCTCATTATT | 74 | 747 |
| 874751 | N/A | N/A | 32580 | 32599 | GCCAGATTAATCCGGTCATA | 73 | 748 |
| 874775 | N/A | N/A | 35179 | 35198 | ATTCTGTAAGGCTACTACTG | 60 | 749 |
| 874799 | N/A | N/A | 37218 | 37237 | TGATTTTTATGTTCCTCAAG | 35 | 750 |
| 874823 | N/A | N/A | 38567 | 38586 | ATCTGAATCTAATCATAAGG | 142 | 751 |
| 874847 | N/A | N/A | 41643 | 41662 | GGCCAGAACTAGGGAAAGAG | 69 | 752 |
| 874871 | N/A | N/A | 43726 | 43745 | CACGAACTGTCCTTAAACTC | 64 | 753 |
| 874895 | N/A | N/A | 44805 | 44824 | TCATATGATTACAACTGCAG | 74 | 754 |
| 874919 | N/A | N/A | 46547 | 46566 | TAACATTCCAAAATTTAAGA | 76 | 755 |
| 874943 | N/A | N/A | 48522 | 48541 | ACAATACACTGAACTCTTGA | 69 | 756 |
| 874967 | N/A | N/A | 50878 | 50897 | AATACCCAGTACTGTTAGCC | 81 | 757 |
| 874991 | N/A | N/A | 53104 | 53123 | TGAAATCAATTCATATCTTT | 91 | 758 |
| 875015 | N/A | N/A | 55614 | 55633 | ATGGAGATCTTTTCCATTAA | 88 | 759 |
| 875039 | N/A | N/A | 58233 | 58252 | TACTAAAATCTACACAATTC | 128 | 760 |
| 875063 | N/A | N/A | 60587 | 60606 | AGTCATGCTTATAAAGTCCT | 30 | 761 |
| 875087 | N/A | N/A | 62947 | 62966 | ACTTAAAATTTGAACTGAAA | 119 | 762 |
| 875111 | N/A | N/A | 64571 | 64590 | ACCCGGCCCACACAAAAACT | 96 | 763 |
| 875135 | N/A | N/A | 68028 | 68047 | GGTTCAAGCAAATTGCTTGT | 77 | 764 |
| 875159 | N/A | N/A | 69889 | 69908 | GTATGATGACAAAAGAGGAC | 86 | 765 |
| 875183 | N/A | N/A | 71861 | 71880 | TTTTAAAGGGCCAGAATAAT | 100 | 766 |
| 875207 | N/A | N/A | 73177 | 73196 | CTGACCAGAATTTAGGTTGT | 146 | 767 |
| 875231 | N/A | N/A | 75227 | 75246 | TTTGAGATGGAGCTTGCTCT | 117 | 768 |
| 875255 | N/A | N/A | 77500 | 77519 | CATTATATTAGGTTATATAT | 137 | 769 |
| 875279 | N/A | N/A | 80036 | 80055 | AAATGGTTTTACCATTAGCA | 80 | 770 |
| 875303 | N/A | N/A | 81936 | 81955 | TTTCCAAGATCACCATAACC | 76 | 771 |
| 875327 | N/A | N/A | 83758 | 83777 | TATGTCTAAAAAATTTTATT | 87 | 772 |

TABLE 11-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 875351 | N/A | N/A | 85054 | 85073 | AGGGTTAATTAGGATCTATA | 27 | 773 |
| 875375 | N/A | N/A | 86537 | 86556 | AACTTGCTCTTCAAGGTTAG | 79 | 774 |
| 875399 | N/A | N/A | 89386 | 89405 | TTTTAAAGGTTCTCTGGACT | 56 | 775 |
| 875423 | N/A | N/A | 92208 | 92227 | TATGGTTTGATGTTTCTGAC | 38 | 776 |
| 875447 | N/A | N/A | 95006 | 95025 | CCCTCCCCCTCCTTCTCCTT | 110 | 777 |
| 875471 | N/A | N/A | 96438 | 96457 | AAAGAAAAAAAAGTTGCTC | 90 | 778 |
| 875495 | N/A | N/A | 98289 | 98308 | TTAACTTCTCTTTGCCCAAG | 82 | 779 |
| 875519 | N/A | N/A | 100293 | 100312 | AGTACAAGCAACAAAAACAG | 95 | 780 |
| 875543 | N/A | N/A | 102900 | 102919 | AAAGAGCAAAAGCCATACTG | 93 | 781 |
| 875567 | N/A | N/A | 106296 | 106315 | ACACACTTTACCTATAAAAT | 96 | 782 |
| 875591 | N/A | N/A | 109890 | 109909 | TGTGCCAGCTTCAGATATGA | 72 | 783 |
| 875615 | N/A | N/A | 112404 | 112423 | AATAGTCTAAGTAAAAGGAA | 106 | 784 |
| 875639 | N/A | N/A | 114281 | 114300 | CTGGCCAATCAACAAACACT | 76 | 785 |
| 875663 | N/A | N/A | 116247 | 116266 | GTTTTATATTGCTAGAGAGC | 65 | 786 |
| 875687 | N/A | N/A | 119697 | 119716 | TGCTCCCAGCCTCATATGAA | 109 | 787 |
| 875711 | N/A | N/A | 122603 | 122622 | TTAAAAAAATGAAATATGCA | 83 | 788 |
| 875735 | N/A | N/A | 125807 | 125826 | CAGAAACAAATTCAACCACA | 76 | 789 |
| 875759 | N/A | N/A | 129144 | 129163 | AAAAGAACCTACCTAAGGCA | 121 | 790 |
| 875783* | N/A | N/A | 131147 | 131166 | TATTAAAAGTTTTTTTATAT | 93 | 791 |
| 875807 | N/A | N/A | 132969 | 132988 | CCAGAAATCTGTAAATTCTT | 33 | 792 |
| 875831 | N/A | N/A | 134653 | 134672 | TGTACTTCAAATTTTGTTTA | 28 | 793 |
| 875855 | N/A | N/A | 137344 137422 | 137363 137441 | TATACCAAGCTTGTGGCTTG | 146 | 794 |
| 875879 | N/A | N/A | 139271 | 139290 | GTTTAATTTGTAACTAGGTT | 22 | 795 |
| 875903 | N/A | N/A | 142210 | 142229 | ATGTATTTATTTGTTTAATT | 95 | 796 |
| 875927 | N/A | N/A | 143971 | 143990 | CAAGTGCATTTTAGGTGCAC | 92 | 797 |
| 875951 | N/A | N/A | 145925 | 145944 | CTATATAGACATAGCAAAGC | 80 | 798 |
| 875975 | N/A | N/A | 147453 | 147472 | ATATCATACAAGATTCAATG | 86 | 799 |

TABLE 12

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 (% control) | SEQ ID NO |
|---|---|---|---|---|---|---|---|
| 708199 | 1477 | 1496 | 81637 | 81656 | GCTAACTGGTTTGCCCTTGC | 41 | 32 |
| 874158 | 94 | 113 | 2084 | 2103 | GGACTCTTTACCGGAAGTCG | 92 | 800 |

TABLE 12-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 (% control) | SEQ ID NO |
|---|---|---|---|---|---|---|---|
| 874182 | 266 | 285 | 2256 | 2275 | GCCCCGCCCGCTCCGCCGCG | 55 | 801 |
| 874206 | 577 | 596 | 2567 | 2586 | GGAGCCGGGCGCGCCAAGGA | 114 | 802 |
| 874228 | 1467 | 1486 | 81627 | 81646 | TTGCCCTTGCTTCCCGTTTT | 48 | 803 |
| 874251 | 1649 | 1668 | 83260 | 83279 | TTCTCTATTTCTTTGTCCAG | 39 | 804 |
| 874275 | 2364 | 2383 | 91248 | 91267 | TAACAGCTCTGTTCGATGCA | 53 | 805 |
| 874299 | 2678 | 2697 | 112987 | 113006 | AATGAAAGAATCCTTAGCAC | 65 | 806 |
| 874323 | 3133 | 3152 | 116369 | 116388 | TATGTCTTGGCTTGATTCAC | 73 | 807 |
| 874345 | 4147 | 4166 | 148898 | 148917 | CAGTTGGTAGAAGCAGTAGA | 53 | 808 |
| 874369 | 4292 | 4311 | 149043 | 149062 | ATAGCCCCCAAGTTCCTAAA | 45 | 809 |
| 874393 | 4455 | 4474 | 149206 | 149225 | TTTTTTTTTAGCAGTAATAG | 118 | 810 |
| 874416 | 4623 | 4642 | 149374 | 149393 | TACAAAGTAAAAGTTTTTCC | 132 | 811 |
| 874440 | N/A | N/A | 146583 | 146602 | AGATCCAACTGAGTCGCATC | 62 | 812 |
| 874464 | N/A | N/A | 3512 | 3531 | TCGGACACGAACGCAGAGGG | 46 | 813 |
| 874488 | N/A | N/A | 5403 | 5422 | TTCGACCTCGATGTTCCACA | 85 | 814 |
| 874512 | N/A | N/A | 7908 | 7927 | CAAAATTAGATTACAGTAAA | 96 | 815 |
| 874536 | N/A | N/A | 10350 | 10369 | AACAAAACATGTCTCTTTGG | 100 | 816 |
| 874560 | N/A | N/A | 13986 | 14005 | CAGCATGATCTTGTGTATAT | 23 | 817 |
| 874584 | N/A | N/A | 16725 | 16744 | AAGGAAATTTAAAAAAAAAC | 93 | 818 |
| 874608 | N/A | N/A | 19049 | 19068 | CCTCGGCAACTAAGAGCGAA | 125 | 819 |
| 874632 | N/A | N/A | 21273 | 21292 | TCCCATCTCAAAAAATAAAT | 118 | 820 |
| 874656 | N/A | N/A | 25454 | 25473 | AGGTACTCAGCAAGCTGAGG | 93 | 821 |
| 874680 | N/A | N/A | 28537 | 28556 | GCCACTTTGGAAGGTCGAGG | 63 | 822 |
| 874704 | N/A | N/A | 31297 | 31316 | AAAGCATGGTTGATTGAAGA | 48 | 823 |
| 874728 | N/A | N/A | 32795 | 32814 | CTAAAGCTGAGTGACAGGTA | 46 | 824 |
| 874752 | N/A | N/A | 35188 | 35207 | CTTGTTGTTGTTTACATTAT | 23 | 825 |
| 874776 | N/A | N/A | 37309 | 37328 | AAGAAATACATTCTGTAAGG | 64 | 826 |
| 874800 | N/A | N/A | 38708 | 38727 | AAACTTTCCATTTCAAAGCT | 88 | 827 |
| 874824 | N/A | N/A | 41669 | 41688 | AACTTAGTAGACACAACTCT | 104 | 828 |
| 874848 | N/A | N/A | 43780 | 43799 | GCTAAATTGTAGTTGTCTAG | 57 | 829 |
| 874872 | N/A | N/A | 44818 | 44837 | TCTGGTATCCTGGTGGCTGC | 85 | 830 |
| 874896 | N/A | N/A | 45132 | 45151 | AAAGAAAAACAGGTCATATG | 68 | 831 |
| 874920 | N/A | N/A | 46580 | 46599 | TTCTGCCCTTCATGTCCGGT | 80 | 832 |
| 874944 | N/A | N/A | 48569 | 48588 | ATATTAGGTATTCACTAACA | 66 | 833 |
| 874968 | N/A | N/A | 50978 | 50997 | GGCCTCTTAAGACAAAAAGT | 83 | 834 |
| 874992 | N/A | N/A | 53114 | 53133 | AGCTCAGAAATGAAATCAAT | 71 | 835 |
| 875016 | N/A | N/A | 55889 | 55908 | ACCAGCCTGTGCAATACAGG | 120 | 836 |

TABLE 12-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 (% control) | SEQ ID NO |
|---|---|---|---|---|---|---|---|
| 875040 | N/A | N/A | 58283 | 58302 | TATTTCTCACTGTTCTCTAA | 135 | 837 |
| 875064 | N/A | N/A | 60616 | 60635 | CTTTTACTTCATGATTTTTT | 67 | 838 |
| 875088 | N/A | N/A | 62995 | 63014 | AGTAATTTTATGTTTTTAAA | 101 | 839 |
| 875112 | N/A | N/A | 64881 | 64900 | TCCACACGCAGTTTTTTTTT | 77 | 840 |
| 875136 | N/A | N/A | 68147 | 68166 | TTTCCCATATAATTTTTTTT | 105 | 841 |
| 875160 | N/A | N/A | 69928 | 69947 | CAGGTGGAGCCACGCTCCTC | 95 | 842 |
| 875184 | N/A | N/A | 71978 | 71997 | GGGTATCCCCAGCCCCATAC | 98 | 843 |
| 875208 | N/A | N/A | 73487 | 73506 | TAGAAGCTCAGTATTAAAAA | 72 | 844 |
| 875232 | N/A | N/A | 75614 | 75633 | GTAATTACTCTGCATGTCTC | 60 | 845 |
| 875256 | N/A | N/A | 77522 | 77541 | CGTGATGTACAGACTTGAGA | 50 | 846 |
| 875280 | N/A | N/A | 80042 | 80061 | CTTTAGAAATGGTTTTACCA | 139 | 847 |
| 875304 | N/A | N/A | 82011 | 82030 | GCTCTTCAAGATCTTGGATT | 57 | 848 |
| 875328 | N/A | N/A | 83789 | 83808 | TTGCACATAGGTTAGAATTT | 10 | 849 |
| 875352 | N/A | N/A | 85056 | 85075 | AAAGGGTTAATTAGGATCTA | 43 | 850 |
| 875376 | N/A | N/A | 86832 | 86851 | TCTTTAGAAGAATGCTAATG | 82 | 851 |
| 875400 | N/A | N/A | 89401 | 89420 | GGCCGATCTTGTTTCTTTTA | 107 | 852 |
| 875424 | N/A | N/A | 92295 | 92314 | TATTGTTGTTACCAAATCTC | 63 | 853 |
| 875448 | N/A | N/A | 95058 | 95077 | GGAAGAATACCTACAGCAAG | 75 | 854 |
| 875472 | N/A | N/A | 96869 | 96888 | CTGAGCACCAAGTCACTCTC | 118 | 855 |
| 875496 | N/A | N/A | 98388 | 98407 | TGCACTATGCATTAGTTACT | 73 | 856 |
| 875520 | N/A | N/A | 100334 | 100353 | CAAAAGAAAGAAAACAGGAA | 77 | 857 |
| 875544 | N/A | N/A | 102911 | 102930 | CAAAAGGCCCAAAAGAGCAA | 70 | 858 |
| 875568 | N/A | N/A | 106734 | 106753 | TAACAAAATGGTAGTAGTTA | 144 | 859 |
| 875592 | N/A | N/A | 110018 | 110037 | CTAGACATATTCTGGACCAG | 68 | 860 |
| 875616 | N/A | N/A | 112411 | 112430 | GATGGAGAATAGTCTAAGTA | 76 | 861 |
| 875640 | N/A | N/A | 114357 | 114376 | TGGCCACGCTGACCTTAAGT | 88 | 862 |
| 875664 | N/A | N/A | 116254 | 116273 | ACTCTTAGTTTTATATTGCT | 66 | 863 |
| 875688 | N/A | N/A | 119897 | 119916 | GTTCAAGCGATTCTGATGCT | 51 | 864 |
| 875712 | N/A | N/A | 122950 | 122969 | CTTATTAATTGAAATATGTA | 144 | 865 |
| 875736 | N/A | N/A | 125972 | 125991 | GTTGGTTTTAAAAAGGCAAC | 86 | 866 |
| 875760 | N/A | N/A | 129173 | 129192 | GAGAAGTCCCTGGGTTACAC | 47 | 867 |
| 875784* | N/A | N/A | 131173 | 131192 | AATTATAAAGGAAAATCCCT | 102 | 868 |
| 875808 | N/A | N/A | 133004 | 133023 | TATGAAAAGTAGTAATGTCT | 60 | 869 |
| 875832 | N/A | N/A | 134730 | 134749 | TTATAAAATATAAATTGTTC | 120 | 870 |
| 875856 | N/A | N/A | 137345 137423 | 137364 137442 | TTATACCAAGCTTGTGGCTT | 89 | 871 |

TABLE 12-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 (% control) | SEQ ID NO |
|---|---|---|---|---|---|---|---|
| 875880 | N/A | N/A | 139284 | 139303 | CAGAAAGCTGTGTGTTTAAT | 39 | 872 |
| 875904 | N/A | N/A | 142258 | 142277 | CGAACCTGAGTTTGTTGTAC | 40 | 873 |
| 875928 | N/A | N/A | 144009 | 144028 | AAAAGGCAACTTGAAGGCAT | 73 | 874 |
| 875952 | N/A | N/A | 145950 | 145969 | TGTACACATATATATAGTAG | 65 | 875 |
| 875976 | N/A | N/A | 147460 | 147479 | CAACTTAATATCATACAAGA | 95 | 876 |

TABLE 13

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 708199 | 1477 | 1496 | 81637 | 81656 | GCTAACTGGTTTGCCCTTGC | 31 | 32 |
| 874159 | 99 | 118 | 2089 | 2108 | GATAGGGACTCTTTACCGGA | 109 | 877 |
| 874183 | 271 | 290 | 2261 | 2280 | CCGCCGCCCCGCCCGCTCCG | 118 | 878 |
| 874207 | 752 | 771 | 2742 | 2761 | GCCGCTGCCGCCGGGCTTGC | 157 | 879 |
| 874229 | 1469 | 1488 | 81629 | 81648 | GTTTGCCCTTGCTTCCCGTT | 30 | 880 |
| 874252 | 1650 | 1669 | 83261 | 83280 | CTTCTCTATTTCTTTGTCCA | 44 | 881 |
| 874276 | 2365 | 2384 | 91249 | 91268 | GTAACAGCTCTGTTCGATGC | 34 | 882 |
| 874300 | 2758 | 2777 | 113067 | 113086 | GTGTTACTAAGTATTGAAGG | 32 | 883 |
| 874324* | 3388 | 3407 | 131469 | 131488 | TGTGTTGGTGGTGCCATCAT | 254 | 884 |
| 874346 | 4152 | 4171 | 148903 | 148922 | GCTTCCAGTTGGTAGAAGCA | 115 | 885 |
| 874370 | 4297 | 4316 | 149048 | 149067 | ATGGAATAGCCCCCAAGTTC | 57 | 886 |
| 874394 | 4476 | 4495 | 149227 | 149246 | AAGTCTTGATTTTTTTTTTT | 106 | 887 |
| 874417 | 4628 | 4647 | 149379 | 149398 | TTATCTACAAAGTAAAAGTT | 77 | 888 |
| 874441 | N/A | N/A | 146588 | 146607 | GAGATAGATCCAACTGAGTC | 60 | 889 |
| 874465 | N/A | N/A | 3517 | 3536 | CCGCCTCGGACACGAACGCA | 81 | 890 |
| 874489 | N/A | N/A | N/A | N/A | ACTGTTTCGACCTCGATGTT | 121 | 891 |
| 874513 | N/A | N/A | 5527 | 5546 | ATGAACCCAGGAGACAGAGA | 62 | 892 |
| 874537 | N/A | N/A | 7982 | 8001 | AAAAAGTTTATTTTCTCCAC | 53 | 893 |
| 874561 | N/A | N/A | 10665 | 10684 | GGTTTCATGCCATTCTCTTG | 66 | 894 |
| 874585 | N/A | N/A | 14245 | 14264 | TAATTAAAGCACTTTGGGAA | 71 | 895 |
| 874609 | N/A | N/A | 17106 | 17125 | ATTCTTGGCAGCTGGGTGCA | 60 | 896 |
| 874633 | N/A | N/A | 19342 | 19361 | ATGATGGCACACACATGTGG | 74 | 897 |
| 874657 | N/A | N/A | 21336 | 21355 | CTCCGAAAAATTAAAAATAA | 82 | 898 |
| 874681 | N/A | N/A | 25995 | 26014 | TTATTCACTACTGTATTCCC | 51 | 899 |
| 874705 | N/A | N/A | 28864 | 28883 | CCAGACTTTGCAGCCTACCA | 65 | 900 |

TABLE 13-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 874729 | N/A | N/A | 31541 | 31560 | TTCCCATCTTCTCGAGTTCT | 78 | 901 |
| 874753 | N/A | N/A | 32803 | 32822 | TCAGACTTCTTGTTGTTGTT | 19 | 902 |
| 874777 | N/A | N/A | 35267 | 35286 | GAGATAGCATGCCACTGCAC | 51 | 903 |
| 874801 | N/A | N/A | 37352 | 37371 | AACAGCCCAATCAGAACAAG | 58 | 904 |
| 874825 | N/A | N/A | 38727 | 38746 | AATAACTTTATAGTGAAGAA | 71 | 905 |
| 874849 | N/A | N/A | 41776 | 41795 | AAAAACTCACAATCTCTTCC | 68 | 906 |
| 874873 | N/A | N/A | 43784 | 43803 | ATGATCTGGTATCCTGGTGG | 39 | 907 |
| 874897 | N/A | N/A | 45158 | 45177 | CTTCCCATATTTCTCCCCCA | 77 | 908 |
| 874921 | N/A | N/A | 46603 | 46622 | TTCCATCATGTGGGACTTAT | 51 | 909 |
| 874945 | N/A | N/A | 48588 | 48607 | CCTCATCAGGCTTCATTCAA | 72 | 910 |
| 874969 | N/A | N/A | 51035 | 51054 | ATCAACTCCAAAGGTAGCAG | 26 | 911 |
| 874993 | N/A | N/A | 53450 | 53469 | AACAAACAAACATTAATTCG | 85 | 912 |
| 875017 | N/A | N/A | 56035 | 56054 | AGTCAAGGGCATGATTGAAG | 63 | 913 |
| 875041 | N/A | N/A | 58308 | 58327 | CAGAATAAAACAATCTGTAG | 97 | 914 |
| 875065 | N/A | N/A | 60652 | 60671 | TAAATCTTTAATCTCTTTAT | 60 | 915 |
| 875089 | N/A | N/A | 63006 | 63025 | TGTACCCAGCCAGTAATTTT | 67 | 916 |
| 875113 | N/A | N/A | 65073 | 65092 | AAATCAGCCTGTGCAACAGT | 106 | 917 |
| 875137 | N/A | N/A | 68347 | 68366 | CCCTAGGGATACCAAAATCC | 111 | 918 |
| 875161 | N/A | N/A | 69938 | 69957 | ACCAAGGGCACAGGTGGAGC | 73 | 919 |
| 875185 | N/A | N/A | 72025 | 72044 | GCTGGTGGTCATAAAGAAAT | 128 | 920 |
| 875209 | N/A | N/A | 73728 | 73747 | TTTCAAGAATGTAAAATGTT | 92 | 921 |
| 875233 | N/A | N/A | 75640 | 75659 | ACATAATTCATTAAATTATA | 122 | 922 |
| 875257 | N/A | N/A | 77573 | 77592 | ACCAATAGTGTAAAAGAAGT | 104 | 923 |
| 875281 | N/A | N/A | 80384 | 80403 | CTGTAAAAGCCACCTTTCAG | 103 | 924 |
| 875305 | N/A | N/A | 82014 | 82033 | CAAGCTCTTCAAGATCTTGG | 90 | 925 |
| 875329 | N/A | N/A | 83868 | 83887 | TAAGTTACCTCAGATCCTTT | 52 | 926 |
| 875353 | N/A | N/A | 85058 | 85077 | CCAAAGGGTTAATTAGGATC | 52 | 927 |
| 875377 | N/A | N/A | 86878 | 86897 | TAGCCACCATGCCTGGCTTC | 98 | 928 |
| 875401 | N/A | N/A | 89788 | 89807 | CAATTACATGAATGTGCATC | 36 | 929 |
| 875425 | N/A | N/A | 92341 | 92360 | ATGGTGGTTTCAAATGTCAG | 39 | 930 |
| 875449 | N/A | N/A | 95227 95287 | 95246 95306 | TATATATGTAAATTATATCT | 128 | 931 |
| 875473 | N/A | N/A | 96913 | 96932 | TTGAACCCCACCTTATGCTA | 60 | 932 |
| 875497 | N/A | N/A | 98445 | 98464 | GGGCTATGAGCATGTCATGA | 71 | 933 |
| 875521 | N/A | N/A | 100335 | 100354 | ACAAAAGAAAGAAAACAGGA | 135 | 934 |
| 875545 | N/A | N/A | 103117 | 103136 | TATAATGACAACTTTAAAAC | 106 | 935 |

TABLE 13-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 875569 | N/A | N/A | 106756 | 106775 | TACAAAACAACCAGATAATA | 86 | 936 |
| 875593 | N/A | N/A | 110045 | 110064 | CTAGGCCATAGCTCCCAGAT | 99 | 937 |
| 875617 | N/A | N/A | 112430 | 112449 | AGTTTAGGAAAGGTGTTGGG | 128 | 938 |
| 875641 | N/A | N/A | 114754 | 114773 | CAATTTAAAAAAATTGCTA | 111 | 939 |
| 875665 | N/A | N/A | 116291 | 116310 | ACATTAGGCACCTATGATAA | 74 | 940 |
| 875689 | N/A | N/A | 119970 | 119989 | TTGAGACTCACTCTTTCACT | 71 | 941 |
| 875713 | N/A | N/A | 123039 | 123058 | GGCAAGGATGCAGAACACAT | 46 | 942 |
| 875737 | N/A | N/A | 125996 | 126015 | AGCCAAGATATATTTTAAAG | 84 | 943 |
| 875761 | N/A | N/A | 129221 | 129240 | CTTCATATATGGTACTTCAT | 46 | 944 |
| 875785* | N/A | N/A | 131273 | 131292 | TTTCCTCTGAACCTCTTACA | 77 | 945 |
| 875809 | N/A | N/A | 133039 | 133058 | TTAAAACTTTTATTCTTCAA | 87 | 946 |
| 875833 | N/A | N/A | 134752 | 134771 | TATTACAATATATTTAATAT | 79 | 947 |
| 875857 | N/A | N/A | 137346 137424 | 137365 137443 | TTTATACCAAGCTTGTGGCT | 98 | 948 |
| 875881 | N/A | N/A | 139301 | 139320 | CTGAAGCAAATTAAGTACAG | 65 | 949 |
| 875905 | N/A | N/A | 142335 | 142354 | CATACTCATTAAGTTTACTT | 60 | 950 |
| 875929 | N/A | N/A | 144073 | 144092 | TCTACATATGATATTAAAAT | 97 | 951 |
| 875953 | N/A | N/A | 146067 | 146086 | ACTCATGTGAGTAACAATCA | 65 | 952 |
| 875977 | N/A | N/A | 147547 | 147566 | TAACCCTTGACATTTCTGAT | 65 | 953 |

TABLE 14

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 708199 | 1477 | 1496 | 81637 | 81656 | GCTAACTGGTTTGCCCTTGC | 45 | 32 |
| 708399 | 3483 | 3502 | 136956 | 136975 | TGTTGTATGGTAATTTGGGA | 29 | 954 |
| 874160 | 104 | 123 | 2094 | 2113 | GTGCGGATAGGGACTCTTTA | 98 | 955 |
| 874184 | 276 | 295 | 2266 | 2285 | CGCCACCGCCGCCCCGCCCG | 120 | 956 |
| 874208 | 987 | 1006 | N/A | N/A | CTTCACATTTGGAGCCAACA | 62 | 957 |
| 874230 | 1470 | 1489 | 81630 | 81649 | GGTTTGCCCTTGCTTCCCGT | 72 | 958 |
| 874253 | 1652 | 1671 | 83263 | 83282 | GACTTCTCTATTTCTTTGTC | 62 | 959 |
| 874277 | 2366 | 2385 | 91250 | 91269 | GGTAACAGCTCTGTTCGATG | 36 | 960 |
| 874301 | 2760 | 2779 | 113069 | 113088 | CCGTGTTACTAAGTATTGAA | 48 | 961 |
| 874347 | 4157 | 4176 | 148908 | 148927 | TCTGTGCTTCCAGTTGGTAG | 61 | 962 |
| 874371 | 4311 | 4330 | 149062 | 149081 | CAGCATATGGAATTATGGAA | 44 | 963 |

TABLE 14-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 874395 | 4481 | 4500 | 149232 | 149251 | GTTCCAAGTCTTGATTTTTT | 50 | 964 |
| 874418 | 4633 | 4652 | 149384 | 149403 | TTATATTATCTACAAAGTAA | 76 | 965 |
| 874442 | N/A | N/A | 146593 | 146612 | TCTGAGAGATAGATCCAACT | 62 | 966 |
| 874466 | N/A | N/A | 3522 | 3541 | CGCCGCCGCCTCGGACACGA | 79 | 967 |
| 874490 | N/A | N/A | 2936 | 2955 | GGACGGCGGCGCGGGCCGCG | 96 | 968 |
| 874514 | N/A | N/A | 5531 | 5550 | TTAAATGAACCCAGGAGACA | 106 | 969 |
| 874538 | N/A | N/A | 7992 | 8011 | GCCCAAACTTAAAAAGTTTA | 84 | 970 |
| 874562 | N/A | N/A | 10678 | 10697 | GCTCTGCCTCCCGGGTTTCA | 71 | 971 |
| 874586 | N/A | N/A | 14320 | 14339 | CATGACTTTAAAAAGCAATA | 59 | 972 |
| 874610 | N/A | N/A | 17158 | 17177 | TTTGAATTACAATGCGGTAT | 19 | 973 |
| 874634 | N/A | N/A | 19549 | 19568 | CAAGGCAAGAGGAGTACTTG | 87 | 974 |
| 874658 | N/A | N/A | 21350 | 21369 | GAGCAAGATCCTATCTCCGA | 67 | 975 |
| 874682 | N/A | N/A | 26160 | 26179 | TGTTTTCCTCTTCATCTAAA | 35 | 976 |
| 874706 | N/A | N/A | 28889 | 28908 | AGTCTTGTTCAGTGTCCTTC | 19 | 977 |
| 874730 | N/A | N/A | 31622 | 31641 | GAAATATTTAAATTTTAATC | 100 | 978 |
| 874754 | N/A | N/A | 32817 | 32836 | TTGTTCTTCCAATTTCAGAC | 12 | 979 |
| 874778 | N/A | N/A | 35640 | 35659 | AAAATTACTTCTCATTGACA | 67 | 980 |
| 874802 | N/A | N/A | 37398 | 37417 | GAATCATGCCTCATATGATA | 127 | 981 |
| 874826 | N/A | N/A | 38826 | 38845 | TCCACAGAAGCTAAATATAG | 113 | 982 |
| 874850 | N/A | N/A | 41826 | 41845 | AAATTGTTAAAATGGTATAT | 118 | 983 |
| 874874 | N/A | N/A | 43788 | 43807 | AACGATGATCTGGTATCCTG | 25 | 984 |
| 874898 | N/A | N/A | 45195 | 45214 | CTTGATTTAACCAACACAGA | 77 | 985 |
| 874922 | N/A | N/A | 46632 | 46651 | AAAATTTGTGATAGCTTCTC | 45 | 986 |
| 874946 | N/A | N/A | 48678 | 48697 | TTGGAGCCCTAAAAACATAT | 106 | 987 |
| 874970 | N/A | N/A | 51088 | 51107 | AATATTTCAATAGTATAAGT | 94 | 988 |
| 874994 | N/A | N/A | 53501 | 53520 | CACGCCACTGTACCCAGCCT | 107 | 989 |
| 875018 | N/A | N/A | 56070 | 56089 | GAAAAAGAGAACAAGGAGGT | 86 | 990 |
| 875042 | N/A | N/A | 58395 | 58414 | GAAGAGATCCCTGTTTGTTA | 78 | 991 |
| 875066 | N/A | N/A | 61057 | 61076 | CCACCTTTTCATACATTCAC | 71 | 992 |
| 875090 | N/A | N/A | 63149 | 63168 | TACCACCGTGTCTGGCTACT | 135 | 993 |
| 875114 | N/A | N/A | 65095 | 65114 | TGATACAGCCACTATGCCCA | 64 | 994 |
| 875138 | N/A | N/A | 68412 | 68431 | AATAAATTATTCCAACACAC | 88 | 995 |
| 875162 | N/A | N/A | 70035 | 70054 | ATATTAAAGACTATAATACT | 89 | 996 |
| 875186 | N/A | N/A | 72033 | 72052 | TGCCACCTGCTGGTGGTCAT | 95 | 997 |
| 875210 | N/A | N/A | 73774 | 73793 | TAAAGTTATGTGGATTGCTG | 82 | 998 |
| 875234 | N/A | N/A | 76018 | 76037 | CAGATGACTATCAGTAAAGG | 65 | 999 |

TABLE 14-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 875258 | N/A | N/A | 77592 | 77611 | CTATCAATTTATCCACCTCA | 84 | 1000 |
| 875282 | N/A | N/A | 80426 | 80445 | CATAAAATAGCCTTCAGATC | 83 | 1001 |
| 875306 | N/A | N/A | 82128 | 82147 | CTAGCTCCTCCTCATTCTGT | 59 | 1002 |
| 875330 | N/A | N/A | 83955 | 83974 | CCTTAGACTAAGGGTTGTTT | 75 | 1003 |
| 875354 | N/A | N/A | 85060 | 85079 | TCCCAAAGGGTTAATTAGGA | 52 | 1004 |
| 875378 | N/A | N/A | 87195 | 87214 | TCCTCACTCTCTCACCCGGC | 116 | 1005 |
| 875402 | N/A | N/A | 90101 | 90120 | CCTCCCGGGTCCTGGTTCAA | 68 | 1006 |
| 875426 | N/A | N/A | 92344 | 92363 | GCTATGGTGGTTTCAAATGT | 42 | 1007 |
| 875450 | N/A | N/A | 95228 95288 | 95247 95307 | TTATATATGTAAATTATATC | 103 | 1008 |
| 875474 | N/A | N/A | 96950 | 96969 | GTCAATTAGAAATAAAAAAT | 144 | 1009 |
| 875498 | N/A | N/A | 98617 | 98636 | CTAAAACCCACATTATTAAC | 87 | 1010 |
| 875522 | N/A | N/A | 100343 | 100362 | CATCCTCTACAAAAGAAAGA | 83 | 1011 |
| 875546 | N/A | N/A | 103265 | 103284 | TACAAAAATCAACACACAAA | 87 | 1012 |
| 875570 | N/A | N/A | 106843 | 106862 | AAAATCACTTTCAAAACAAG | 102 | 1013 |
| 875594 | N/A | N/A | 110104 | 110123 | TGGATACTAGTTCAGCCACA | 73 | 1014 |
| 875618 | N/A | N/A | 112541 | 112560 | TCAGACACTTCACAATAAAA | 96 | 1015 |
| 875642 | N/A | N/A | 114895 | 114914 | AAACCTACCTGAGAGAAGGA | 92 | 1016 |
| 875666 | N/A | N/A | 116299 | 116318 | AAAAATTAACATTAGGCACC | 108 | 1017 |
| 875690 | N/A | N/A | 120054 | 120073 | GTTTGGCAGTTCCATCACAG | 75 | 1018 |
| 875714 | N/A | N/A | 123199 | 123218 | TTACTAAAAAAAGGTTGACA | 101 | 1019 |
| 875738 | N/A | N/A | 126191 | 126210 | TTATTGTAAAAAGATTTATC | 95 | 1020 |
| 875762 | N/A | N/A | 129249 | 129268 | TAAAAACTAACATATAAACA | 94 | 1021 |
| 875786* | N/A | N/A | 131299 | 131318 | GTAAACTCTCAAATCTTTCT | 88 | 1022 |
| 875810 | N/A | N/A | 133116 | 133135 | GCATAAGCTGTGGGTTACAG | 41 | 1023 |
| 875834 | N/A | N/A | 134776 | 134795 | GTATTTGGTTCCTTTGAGAA | 33 | 1024 |
| 875858 | N/A | N/A | 137508 | 137527 | CTTAGTATTTCATCAATCCT | 41 | 1025 |
| 875882 | N/A | N/A | 139406 | 139425 | AGTGTTCCTTGACATAAATA | 56 | 1026 |
| 875906 | N/A | N/A | 142354 | 142373 | ACAGGCCCTCCATCATCATC | 71 | 1027 |
| 875930 | N/A | N/A | 144074 | 144093 | CTCTACATATGATATTAAAA | 89 | 1028 |
| 875954 | N/A | N/A | 146116 | 146135 | AGCAGATATATGGATAACCA | 29 | 1029 |
| 875978 | N/A | N/A | 147750 | 147769 | CATGTCAACTGTGTTCCTTT | 37 | 1030 |

TABLE 15

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 708199 | 1477 | 1496 | 81637 | 81656 | GCTAACTGGTTTGCCCTTGC | 48 | 32 |
| 708490 | 4500 | 4519 | 149251 | 149270 | TCAAGTTTAGTAAAAGGGCG | 74 | 1031 |
| 874161 | 109 | 128 | 2099 | 2118 | CGGAGGTGCGGATAGGGACT | 78 | 1032 |
| 874185 | 281 | 300 | 2271 | 2290 | GGCCGCGCCACCGCCGCCCC | 91 | 1033 |
| 874209 | 989 | 1008 | N/A | N/A | TACTTCACATTTGGAGCCAA | 60 | 1034 |
| 874231 | 1471 | 1490 | 81631 | 81650 | TGGTTTGCCCTTGCTTCCCG | 65 | 1035 |
| 874254 | 1654 | 1673 | 83265 | 83284 | ATGACTTCTCTATTTCTTTG | 35 | 1036 |
| 874278 | 2385 | 2404 | N/A | N/A | CTTTAGCCTCACTAGAAGGG | 73 | 1037 |
| 874302 | 2761 | 2780 | 113070 | 113089 | TCCGTGTTACTAAGTATTGA | 64 | 1038 |
| 874325 | 3485 | 3504 | 136958 | 136977 | CTTGTTGTATGGTAATTTGG | 40 | 1039 |
| 874348 | 4171 | 4190 | 148922 | 148941 | TGAAATTCTAGTTTTCTGTG | 44 | 1040 |
| 874372 | 4316 | 4335 | 149067 | 149086 | TGAAACAGCATATGGAATTA | 69 | 1041 |
| 874419 | 4638 | 4657 | 149389 | 149408 | TTATTTTATATTATCTACAA | 91 | 1042 |
| 874443 | N/A | N/A | 146598 | 146617 | AGCCTTCTGAGAGATAGATC | 73 | 1043 |
| 874467 | N/A | N/A | 3527 | 3546 | GCCCCCGCCGCCGCCTCGGA | 73 | 1044 |
| 874491 | N/A | N/A | 2984 | 3003 | CTGCCGGCCCCCAGCCCACC | 106 | 1045 |
| 874515 | N/A | N/A | 5633 | 5652 | TGGCAAAATCCCGTCCTCAC | 139 | 1046 |
| 874539 | N/A | N/A | 8091 | 8110 | CACTGTTTCAGAATGTGGAA | 125 | 1047 |
| 874563 | N/A | N/A | 10828 | 10847 | GCATATAGCAAGAGATGTAG | 89 | 1048 |
| 874587 | N/A | N/A | 14339 | 14358 | ATTATTAAGAATATTTTAAC | 141 | 1049 |
| 874611 | N/A | N/A | 17212 | 17231 | GCAGAGCAGGACTAGTCCAT | 91 | 1050 |
| 874635 | N/A | N/A | 19575 | 19594 | GCCTTAATTTCAATACTTTG | 65 | 1051 |
| 874659 | N/A | N/A | 21398 | 21417 | GCAAGAGTTTCACTTGAGCC | 112 | 1052 |
| 874683 | N/A | N/A | 26226 | 26245 | CCCATTTCAGCCTCCCCATG | 115 | 1053 |
| 874707 | N/A | N/A | 28898 | 28917 | TACTGCTGAAGTCTTGTTCA | 98 | 1054 |
| 874731 | N/A | N/A | 31654 | 31673 | ACTTGAAATACGATTAGTAT | 67 | 1055 |
| 874755 | N/A | N/A | 32836 | 32855 | CTCACTTAGGTGAGTCATTT | 87 | 1056 |
| 874779 | N/A | N/A | 35967 | 35986 | TGAGATATAACAATATTGAA | 84 | 1057 |
| 874803 | N/A | N/A | 37400 | 37419 | AGGAATCATGCCTCATATGA | 85 | 1058 |
| 874827 | N/A | N/A | 39445 | 39464 | GCAGAAGGACCACTTAAGAC | 78 | 1059 |
| 874851 | N/A | N/A | 42179 | 42198 | AATACATATAAAAGCAATGC | 57 | 1060 |
| 874875 | N/A | N/A | 43912 | 43931 | TACCTCGCCTAACAAAAATT | 103 | 1061 |
| 874899 | N/A | N/A | 45357 | 45376 | ACCAGAGTCCAGGAGTCTGA | 125 | 1062 |
| 874923 | N/A | N/A | 46639 | 46658 | AGTCTCAAAAATTTGTGATA | 82 | 1063 |
| 874947 | N/A | N/A | 48833 | 48852 | ATCATTCAAAGTGGCTTTAA | 41 | 1064 |
| 874971 | N/A | N/A | 51100 | 51119 | TTATAACAGAGGAATATTTC | 107 | 1065 |

TABLE 15-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 874995 | N/A | N/A | 53763 | 53782 | ATCCTTTAACAACCATGGAA | 79 | 1066 |
| 875019 | N/A | N/A | 56364 | 56383 | GGTATAAAAGAGCAAGGAGA | 100 | 1067 |
| 875043 | N/A | N/A | 58428 | 58447 | CCGTAAACAGCTTTTCTAAT | 82 | 1068 |
| 875067 | N/A | N/A | 61071 | 61090 | ACAAGTGAGGAGGGCCACCT | 99 | 1069 |
| 875091 | N/A | N/A | 63212 | 63231 | ATCTCCCTGCGCTCAGATGA | 95 | 1070 |
| 875115 | N/A | N/A | 65108 65149 | 65127 65168 | TAGGATTGTAAAATGATACA | 61 | 1071 |
| 875139 | N/A | N/A | 68476 | 68495 | ATGGAACAGAACTTAGGAGG | 59 | 1072 |
| 875163 | N/A | N/A | 70051 | 70070 | ATGTATTATACAGATTATAT | 74 | 1073 |
| 875187 | N/A | N/A | 72064 | 72083 | GGGCAGAAACTTAGTCATTT | 82 | 1074 |
| 875211 | N/A | N/A | 73872 | 73891 | TCTTACCAACACCTCATCTT | 87 | 1075 |
| 875235 | N/A | N/A | 76039 | 76058 | TTAATTTAGCAAATGGAATC | 117 | 1076 |
| 875259 | N/A | N/A | 77632 | 77651 | AAATTTTGATTAGCATTGCC | 60 | 1077 |
| 875283 | N/A | N/A | 80616 | 80635 | GTTATAACCAACATCTATAT | 97 | 1078 |
| 875307 | N/A | N/A | 82190 | 82209 | CTATTATCTTATCACAAAAT | 108 | 1079 |
| 875331 | N/A | N/A | 83977 | 83996 | GTTGCTAAACTGTAACATCC | 91 | 1080 |
| 875355 | N/A | N/A | 85061 | 85080 | TTCCCAAAGGGTTAATTAGG | 63 | 1081 |
| 875379 | N/A | N/A | 87247 | 87266 | GCCTACTGGTGTTAACACCA | 89 | 1082 |
| 875403 | N/A | N/A | 90168 | 90187 | AATGGAGTCTCACTCTATAG | 72 | 1083 |
| 875427 | N/A | N/A | 92352 | 92371 | TAAGCTGTGCTATGGTGGTT | 27 | 1084 |
| 875451 | N/A | N/A | 95230 95290 | 95249 95309 | ATTTATATATGTAAATTATA | 140 | 1085 |
| 875475 | N/A | N/A | 96989 | 97008 | ACTTACACAGTAAAAATGGT | 70 | 1086 |
| 875499 | N/A | N/A | 98735 | 98754 | ACACTATGAAGCAGGTTCTA | 66 | 1087 |
| 875523 | N/A | N/A | 100418 | 100437 | TAAGTGATGAGGTTTTTAAG | 80 | 1088 |
| 875547 | N/A | N/A | 103306 | 103325 | ACCTATTAGAACTGACAAAC | 122 | 1089 |
| 875571 | N/A | N/A | 107260 | 107279 | GGGTTATAAAATGTTATTTG | 35 | 1090 |
| 875595 | N/A | N/A | 110110 | 110129 | GCAATGTGGATACTAGTTCA | 52 | 1091 |
| 875619 | N/A | N/A | 112569 | 112588 | TCCTCTTATACTTGTCATTT | 126 | 1092 |
| 875643 | N/A | N/A | 114953 | 114972 | AGGACTATTACTAATAATTT | 72 | 1093 |
| 875667 | N/A | N/A | 116631 | 116650 | CACACCAGGCCTCCAATTAC | 85 | 1094 |
| 875691 | N/A | N/A | 120228 | 120247 | GGGCACGATCTCAAAACAAT | 70 | 1095 |
| 875715 | N/A | N/A | 123671 | 123690 | TGCAAAGACAGGGTTTTGTC | 86 | 1096 |
| 875739 | N/A | N/A | 126238 | 126257 | AAACAAATCCAAATTGCAAG | 54 | 1097 |
| 875763 | N/A | N/A | 129540 | 129559 | TACAAAAATATTAGCCAGCT | 83 | 1098 |
| 875787* | N/A | N/A | 131307 | 131326 | AAACAGCTGTAAACTCTCAA | 81 | 1099 |
| 875811 | N/A | N/A | 133194 | 133213 | AAACTAAACACCTTTGATCA | 80 | 1100 |

TABLE 15-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 875835 | N/A | N/A | 134893 | 134912 | AAAAGGTGACATAAAATTGT | 119 | 1101 |
| 875859 | N/A | N/A | 137537 | 137556 | AGCCATGCACAGGACTGAAA | 104 | 1102 |
| 875883 | N/A | N/A | 139441 | 139460 | CTTTGGTCCAGACCTAGTCC | 63 | 1103 |
| 875907 | N/A | N/A | 142390 | 142409 | AAGACAGTCCTTTTTTCTA | 52 | 1104 |
| 875931 | N/A | N/A | 144082 | 144101 | TAATACAGCTCTACATATGA | 95 | 1105 |
| 875955 | N/A | N/A | 146118 | 146137 | AAAGCAGATATATGGATAAC | 94 | 1106 |
| 875979 | N/A | N/A | 147776 | 147795 | ACAGGCAACATCTCCGGCTT | 86 | 1107 |

TABLE 16

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 708199 | 1477 | 1496 | 81637 | 81656 | GCTAACTGGTTTGCCCTTGC | 26 | 32 |
| 874162 | 114 | 133 | 2104 | 2123 | GGGAGCGGAGGTGCGGATAG | 114 | 1108 |
| 874186 | 301 | 320 | 2291 | 2310 | GCGGAGGGATACGGTCCCGG | 119 | 1109 |
| 874210 | 990 | 1009 | N/A | N/A | GTACTTCACATTTGGAGCCA | 46 | 1110 |
| 874232 | 1473 | 1492 | 81633 | 81652 | ACTGGTTTGCCCTTGCTTCC | 90 | 1111 |
| 874255 | 1656 | 1675 | 83267 | 83286 | ATATGACTTCTCTATTTCTT | 48 | 1112 |
| 874279 | 2458 | 2477 | 91728 | 91747 | GATGTTTCATTGGGTTTAAT | 25 | 1113 |
| 874303 | 2762 | 2781 | 113071 | 113090 | CTCCGTGTTACTAAGTATTG | 73 | 1114 |
| 874326 | 3486 | 3505 | 136959 | 136978 | CCTTGTTGTATGGTAATTTG | 45 | 1115 |
| 874349 | 4176 | 4195 | 148927 | 148946 | ATAAATGAAATTCTAGTTTT | 150 | 1116 |
| 874373 | 4321 | 4340 | 149072 | 149091 | GACTCTGAAACAGCATATGG | 82 | 1117 |
| 874396 | 4505 | 4524 | 149256 | 149275 | CTTTGTCAAGTTTAGTAAAA | 78 | 1118 |
| 874420 | 4643 | 4662 | 149394 | 149413 | AGTTTTTATTTTATATTATC | 95 | 1119 |
| 874444 | N/A | N/A | 146603 | 146622 | AAGGTAGCCTTCTGAGAGAT | 60 | 1120 |
| 874468 | N/A | N/A | 3532 | 3551 | CGGGAGCCCCCGCCGCCGCC | 92 | 1121 |
| 874492 | N/A | N/A | 2996 | 3015 | GTCTCCCCCGCGCTGCCGGC | 89 | 1122 |
| 874516 | N/A | N/A | 5636 | 5655 | ACATGGCAAAATCCCGTCCT | 96 | 1123 |
| 874540 | N/A | N/A | 8113 | 8132 | ACCATGACTGATCCCATGTT | 78 | 1124 |
| 874564 | N/A | N/A | 10830 | 10849 | CTGCATATAGCAAGAGATGT | 68 | 1125 |
| 874588 | N/A | N/A | 14371 | 14390 | AATTATAATCAAGATTAATT | 89 | 1126 |
| 874612 | N/A | N/A | 17241 | 17260 | AAAAATTCATTGAACTGTTG | 70 | 1127 |
| 874636 | N/A | N/A | 19633 | 19652 | CTACTATGTGCCAAGAACAG | 90 | 1128 |
| 874660 | N/A | N/A | 21433 | 21452 | GCCTGTAATCCCTCCCAACA | 134 | 1129 |

TABLE 16-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 874684 | N/A | N/A | 26574 | 26593 | TGTTTCCCTCCCTTTTTAAT | 71 | 1130 |
| 874708 | N/A | N/A | 29092 | 29111 | AACAGCAAAAGGTAGGCTAG | 66 | 1131 |
| 874732 | N/A | N/A | 31705 | 31724 | TATGTCATGCTGTCCAATAT | 86 | 1132 |
| 874756 | N/A | N/A | 32845 | 32864 | TAAGGTTAACTCACTTAGGT | 68 | 1133 |
| 874780 | N/A | N/A | 35982 | 36001 | TGCCTCTCTATTCCCTGAGA | 68 | 1134 |
| 874804 | N/A | N/A | 37534 | 37553 | AAGGCACATTGTGTGGCCAA | 104 | 1135 |
| 874828 | N/A | N/A | 39544 | 39563 | CCCGGCCTCGAGACTCCACC | 81 | 1136 |
| 874852 | N/A | N/A | 42204 | 42223 | TAGGAGGAGAACTTATGAAT | 56 | 1137 |
| 874876 | N/A | N/A | 44007 | 44026 | AGCTGGTATTTAAACCAGGT | 128 | 1138 |
| 874900 | N/A | N/A | 45369 | 45388 | TGAGGCAGGATCACCAGAGT | 46 | 1139 |
| 874924 | N/A | N/A | 46715 | 46734 | CAACCACACTACTCCATATT | 85 | 1140 |
| 874948 | N/A | N/A | 48866 | 48885 | TAAAATAATCAGTATTTGAA | 87 | 1141 |
| 874972 | N/A | N/A | 51110 | 51129 | ATTTTTGAATTTATAACAGA | 134 | 1142 |
| 874996 | N/A | N/A | 54214 | 54233 | AGGTTTCCCTGGCTGGGCGC | 79 | 1143 |
| 875020 | N/A | N/A | 56850 | 56869 | GGACCTGGCAGTTAGAGGTT | 90 | 1144 |
| 875044 | N/A | N/A | 58517 | 58536 | CTGGCCTCAATAAGTGCCAC | 90 | 1145 |
| 875068 | N/A | N/A | 61079 | 61098 | AAATCATTACAAGTGAGGAG | 47 | 1146 |
| 875092 | N/A | N/A | 63237 | 63256 | TCTCACTTGGCTCACTGCAG | 69 | 1147 |
| 875116 | N/A | N/A | 65143 | 65162 | TGTAAAATGATACAGCTACG | 81 | 1148 |
| 875140 | N/A | N/A | 68607 | 68626 | AGAAGTGTAAAGTTTATAGC | 112 | 1149 |
| 875164 | N/A | N/A | 70065 | 70084 | TATACTACTACACCATGTAT | 159 | 1150 |
| 875212 | N/A | N/A | 73918 | 73937 | TGAATTTTGGAAAATCTCTC | 94 | 1151 |
| 875236 | N/A | N/A | 76149 | 76168 | AGACCAATGCACTATAATAA | 117 | 1152 |
| 875284 | N/A | N/A | 80623 | 80642 | TCATTCAGTTATAACCAACA | 60 | 1153 |
| 875308 | N/A | N/A | 82230 | 82249 | ATAAACTCTTCTCCCAACTC | 68 | 1154 |
| 875332 | N/A | N/A | 84070 | 84089 | AAAGATCCACAACCTACAAG | 87 | 1155 |
| 875356 | N/A | N/A | 85062 | 85081 | GTTCCCAAAGGGTTAATTAG | 177 | 1156 |
| 875380 | N/A | N/A | 87346 | 87365 | CTGCCATGCCACTAGTGACT | 73 | 1157 |
| 875404 | N/A | N/A | 90195 | 90214 | GAAGCAGATTTTTTTTTTTT | 27 | 1158 |
| 875428 | N/A | N/A | 92385 | 92404 | TCACTGAACAAAGTACAAAT | 68 | 1159 |
| 875452 | N/A | N/A | 95260 95320 | 95279 95339 | AACCACTGATTTATACACTT | 20 | 1160 |
| 875476 | N/A | N/A | 97064 | 97083 | TGCCTGGCCAAGAATAGTCT | 100 | 1161 |
| 875500 | N/A | N/A | 98816 | 98835 | GAACATGTATTGAATACATA | 55 | 1162 |
| 875524 | N/A | N/A | 100442 | 100461 | CAGAAGACAAAGATATTAGC | 128 | 1163 |
| 875548 | N/A | N/A | 104013 | 104032 | ATATTATTTATACTGTGTAT | 50 | 1164 |

TABLE 16-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 875572 | N/A | N/A | 107323 | 107342 | GTTTTCTCTTTGCTTGCTTG | 23 | 1165 |
| 875596 | N/A | N/A | 110114 | 110133 | TCTTGCAATGTGGATACTAG | 79 | 1166 |
| 875620 | N/A | N/A | 112575 | 112594 | TTTCTATCCTCTTATACTTG | 71 | 1167 |
| 875644 | N/A | N/A | 114990 | 115009 | CACACTAAAACAAAATTCAG | 96 | 1168 |
| 875668 | N/A | N/A | 117316 | 117335 | GCTCTCGAACTCATGGGTTC | 144 | 1169 |
| 875692 | N/A | N/A | 120399 | 120418 | AGCCTGGGAAGCACGGAGAA | 83 | 1170 |
| 875716 | N/A | N/A | 123804 | 123823 | ATCACCCCTCCATCGCCCTC | 93 | 1171 |
| 875740 | N/A | N/A | 126330 | 126349 | TAGGTGACAGAGCCAAGATT | 110 | 1172 |
| 875764 | N/A | N/A | 129790 | 129809 | TGTTACTTATTACCTTCCTG | 30 | 1173 |
| 875788* | N/A | N/A | 131325 | 131344 | TGGTTTCCAGATTTCCAGAA | 75 | 1174 |
| 875812 | N/A | N/A | 133282 | 133301 | CACAATTTTTTATTTAAAAT | 195 | 1175 |
| 875836 | N/A | N/A | 134901 | 134920 | TGAATGAGAAAAGGTGACAT | 101 | 1176 |
| 875860 | N/A | N/A | 137712 | 137731 | GCCAGCATGCATGGCTGATT | 97 | 1177 |
| 875884 | N/A | N/A | 139457 | 139476 | TCAAAGACATATGCTTCTTT | 70 | 1178 |
| 875908 | N/A | N/A | 142421 | 142440 | CTTCCTGAGCTTCACAGTCC | 61 | 1179 |
| 875932 | N/A | N/A | 144151 | 144170 | ATTTAAACCATCCATTGTCT | 70 | 1180 |
| 875956 | N/A | N/A | 146131 | 146150 | ACAACTTATGGTCAAAGCAG | 29 | 1181 |
| 875980 | N/A | N/A | 147793 | 147812 | AGAGCTCTTTTACGCATACA | 71 | 1182 |

TABLE 17

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 708199 | 1477 | 1496 | 81637 | 81656 | GCTAACTGGTTTGCCCTTGC | 26 | 32 |
| 874163 | 153 | 172 | 2143 | 2162 | CTGAGCGCATCGGAGGGCGG | 113 | 1183 |
| 874187 | 353 | 372 | 2343 | 2362 | AGGCGAGCTCTGCCGGGAGG | 83 | 1184 |
| 874211 | 991 | 1010 | 48690 | 48709 | TGTACTTCACATTTGGAGCC | 25 | 1185 |
| 874233 | 1475 | 1494 | 81635 | 81654 | TAACTGGTTTGCCCTTGCTT | 65 | 1186 |
| 874256 | 1758 | 1777 | 83369 | 83388 | AATTCGGGTTGAAATCTGAA | 81 | 1187 |
| 874280 | 2460 | 2479 | 91730 | 91749 | GTGATGTTTCATTGGGTTTA | 6 | 1188 |
| 874304 | 2764 | 2783 | 113073 | 113092 | TGCTCCGTGTTACTAAGTAT | 48 | 1189 |
| 874327 | 3487 | 3506 | 136960 | 136979 | TCCTTGTTGTATGGTAATTT | 23 | 1190 |
| 874350 | 4181 | 4200 | 148932 | 148951 | ACAAAATAAATGAAATTCTA | 80 | 1191 |
| 874397 | 4510 | 4529 | 149261 | 149280 | TGAAACTTTGTCAAGTTTAG | 74 | 1192 |
| 874421 | 4648 | 4667 | 149399 | 149418 | TTTTAAGTTTTTATTTTATA | 82 | 1193 |

TABLE 17-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 874469 | N/A | N/A | 3537 | 3556 | GAGTTCGGGAGCCCCGCCG | 85 | 1194 |
| 874493 | N/A | N/A | 3003 | 3022 | CGAGCGAGTCTCCCCCGCGC | 98 | 1195 |
| 874517 | N/A | N/A | 5901 | 5920 | AAAAGCAAAATAAGAATTA | 77 | 1196 |
| 874541 | N/A | N/A | 8117 | 8136 | GAACACCATGACTGATCCCA | 23 | 1197 |
| 874565 | N/A | N/A | 10902 | 10921 | TAGCACCTGAGCCCCACCTG | 70 | 1198 |
| 874589 | N/A | N/A | 14504 | 14523 | CTTCAATTCCTGATTTCGAA | 74 | 1199 |
| 874613 | N/A | N/A | 17561 | 17580 | AAAAAAAATTTTTGGCTAGG | 78 | 1200 |
| 874637 | N/A | N/A | 19886 | 19905 | TTTCAAGTCTATCAACAGAT | 63 | 1201 |
| 874661 | N/A | N/A | 21470 | 21489 | AATGGGAAGAAAGAGGAGGC | 78 | 1202 |
| 874685 | N/A | N/A | 26678 | 26697 | GAGGACAGGATAACAGATTA | 31 | 1203 |
| 874709 | N/A | N/A | 29104 | 29123 | GAGTTGAAGTCTAACAGCAA | 44 | 1204 |
| 874733 | N/A | N/A | 31730 | 31749 | ACTTTGTACAATGATGAAGA | 87 | 1205 |
| 874757 | N/A | N/A | 32856 | 32875 | GTTCCACCTCTTAAGGTTAA | 59 | 1206 |
| 874781 | N/A | N/A | 36132 36238 | 36151 36257 | TTATAGTAATCTGTAATCAG | 56 | 1207 |
| 874805 | N/A | N/A | 37550 | 37569 | ATAGATATAGCCCCCAAAGG | 165 | 1208 |
| 874829 | N/A | N/A | 39845 | 39864 | GCAAGACTCCGTCTTTCTGT | 93 | 1209 |
| 874853 | N/A | N/A | 42212 | 42231 | AAACATCATAGGAGGAGAAC | 108 | 1210 |
| 874877 | N/A | N/A | 44056 | 44075 | CTCAGCAGTCAAGTATCTTG | 68 | 1211 |
| 874901 | N/A | N/A | 45525 | 45544 | AGAAGGAAGCAAACTAGAAA | 74 | 1212 |
| 874925 | N/A | N/A | 46792 | 46811 | CAGGTCATACCTTCATAGAA | 62 | 1213 |
| 874949 | N/A | N/A | 48877 | 48896 | AAACCAGTCTATAAAATAAT | 92 | 1214 |
| 874973 | N/A | N/A | 51139 | 51158 | TTCAACTAAAATTTTATCTT | 182 | 1215 |
| 874997 | N/A | N/A | 54231 | 54250 | ACTCCGCCTCAAAATAAAGG | 79 | 1216 |
| 875021 | N/A | N/A | 56853 | 56872 | AAAGGACCTGGCAGTTAGAG | 93 | 1217 |
| 875045 | N/A | N/A | 58639 | 58658 | TAATAAACATGTAATGCTTT | 100 | 1218 |
| 875069 | N/A | N/A | 61085 | 61104 | TTTCTTAAATCATTACAAGT | 81 | 1219 |
| 875093 | N/A | N/A | 63247 | 63266 | GAAACCAGGGTCTCACTTGG | 95 | 1220 |
| 875117 | N/A | N/A | 65191 | 65210 | GGTGAGGATGTGAAAAACAT | 119 | 1221 |
| 875141 | N/A | N/A | 68674 | 68693 | GATTAGGAGTAGACAGAGTT | 90 | 1222 |
| 875165 | N/A | N/A | 70194 | 70213 | TGTATAAACATTTTCTGAAT | 67 | 1223 |
| 875189 | N/A | N/A | 72110 | 72129 | GCTACCCCACAGCAGTGGG | 90 | 1224 |
| 875213 | N/A | N/A | 73928 | 73947 | TAGAAATGGCTGAATTTTGG | 69 | 1225 |
| 875237 | N/A | N/A | 76502 | 76521 | GTCATACTGACCAGAGTCTA | 158 | 1226 |
| 875285 | N/A | N/A | 80645 | 80664 | ATGTCAAAGTAGTTGTTCCC | 103 | 1227 |
| 875309 | N/A | N/A | 82340 | 82359 | TGCTGCACCTGACACAGATC | 93 | 1228 |

TABLE 17-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 875333 | N/A | N/A | 84072 | 84091 | GAAAAGATCCACAACCTACA | 63 | 1229 |
| 875357 | N/A | N/A | 85116 | 85135 | AATTCACATTTTACTTTAAC | 101 | 1230 |
| 875405 | N/A | N/A | 90206 | 90225 | ACAGAATAGCTGAAGCAGAT | 34 | 1231 |
| 875429 | N/A | N/A | 92388 | 92407 | GCTTCACTGAACAAAGTACA | 80 | 1232 |
| 875453 | N/A | N/A | 95293 | 95312 | TTGATTTATATATGTAAATT | 101 | 1233 |
| 875477 | N/A | N/A | 97173 | 97192 | GACATGCGGTTTCACCATTT | 28 | 1234 |
| 875501 | N/A | N/A | 98850 | 98869 | AATACTGGGTCATCTATATT | 108 | 1235 |
| 875525 | N/A | N/A | 100484 | 100503 | ACCTTTAAAGTAGACTGCAA | 60 | 1236 |
| 875549 | N/A | N/A | 104018 | 104037 | TATATATATTATTTATACTG | 104 | 1237 |
| 875573 | N/A | N/A | 107414 | 107433 | ACTACAGTTTTTTAAGACAT | 63 | 1238 |
| 875597 | N/A | N/A | 110197 | 110216 | GAGTGCTTGTGCCAGCCTTC | 117 | 1239 |
| 875621 | N/A | N/A | 112598 | 112617 | TGGGTGAGAAAAATATGAAA | 108 | 1240 |
| 875645 | N/A | N/A | 114996 | 115015 | GTTCAGCACACTAAAACAAA | 68 | 1241 |
| 875669 | N/A | N/A | 117334 | 117353 | CACTATATTGCCCATGCTGC | 135 | 1242 |
| 875693 | N/A | N/A | 120627 | 120646 | ACCTATAGTCAGGGCATGGT | 70 | 1243 |
| 875717 | N/A | N/A | 123819 | 123838 | CTCACTGCAACCTCGATCAC | 87 | 1244 |
| 875741 | N/A | N/A | 126725 | 126744 | AAAATACAAGGCCGGGCGCA | 352 | 1245 |
| 875765 | N/A | N/A | 129856 | 129875 | ACTTTTATCAAATGAAAGTT | 139 | 1246 |
| 875789* | N/A | N/A | 131417 | 131436 | CATGAGGATGCTGTGTTCAA | 67 | 1247 |
| 875813 | N/A | N/A | 133329 | 133348 | TACGGATGGGCCTCTTGAAA | 41 | 1248 |
| 875837 | N/A | N/A | 134997 | 135016 | CATACTAAAAATTTAAAAAC | 80 | 1249 |
| 875861 | N/A | N/A | 137893 | 137912 | TTAAGCTCAAGATATCCTGA | 37 | 1250 |
| 875885 | N/A | N/A | 139585 | 139604 | CATTCTGGCTAAAGATCCCA | 96 | 1251 |
| 875933 | N/A | N/A | 144213 | 144232 | TGAACTTTCTTGATGGTTAC | 64 | 1252 |
| 875957 | N/A | N/A | 146218 | 146237 | TGCTCTTAAAGAAAAATGGG | 66 | 1253 |
| 875981 | N/A | N/A | 147796 | 147815 | CAGAGAGCTCTTTTACGCAT | 51 | 1254 |

TABLE 18

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 708199 | 1477 | 1496 | 81637 | 81656 | GCTAACTGGTTTGCCCTTGC | 28 | 32 |
| 760782 | 1479 | 1498 | 81639 | 81658 | CTGCTAACTGGTTTGCCCTT | 55 | 1255 |
| 874164 | 158 | 177 | 2148 | 2167 | GGCCGCTGAGCGCATCGGAG | 104 | 1256 |
| 874188 | 358 | 377 | 2348 | 2367 | GAGGGAGGCGAGCTCTGCCG | 94 | 1257 |

TABLE 18-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 874212 | 993 | 1012 | 48692 | 48711 | CTTGTACTTCACATTTGGAG | 27 | 1258 |
| 874257 | 1760 | 1779 | 83371 | 83390 | AGAATTCGGGTTGAAATCTG | 57 | 1259 |
| 874281 | 2461 | 2480 | 91731 | 91750 | GGTGATGTTTCATTGGGTTT | 22 | 1260 |
| 874305 | 2765 | 2784 | 113074 | 113093 | GTGCTCCGTGTTACTAAGTA | 64 | 1261 |
| 874328 | 3489 | 3508 | 136962 | 136981 | TCTCCTTGTTGTATGGTAAT | 42 | 1262 |
| 874351 | 4186 | 4205 | 148937 | 148956 | TAAAAACAAAATAAATGAAA | 100 | 1263 |
| 874375 | 4331 | 4350 | 149082 | 149101 | GTACCTGCGGGACTCTGAAA | 81 | 1264 |
| 874398 | 4515 | 4534 | 149266 | 149285 | TTTACTGAAACTTTGTCAAG | 69 | 1265 |
| 874422 | 4653 | 4672 | 149404 | 149423 | ATTTTTTTTAAGTTTTTATT | 128 | 1266 |
| 874470 | N/A | N/A | 3557 | 3576 | GGAGCCCCACGATTTCAGGG | 65 | 1267 |
| 874494 | N/A | N/A | 3037 | 3056 | CTGCGCCCACCGGCCGAGCC | 93 | 1268 |
| 874518 | N/A | N/A | 6371 | 6390 | AAAAATGTTCACTGCACCAC | 67 | 1269 |
| 874542 | N/A | N/A | 8121 | 8140 | AAAGGAACACCATGACTGAT | 66 | 1270 |
| 874566 | N/A | N/A | 10936 | 10955 | GAACCAGACTGCACAACAGG | 82 | 1271 |
| 874590 | N/A | N/A | 14650 | 14669 | GCTAAAGCAGGAGGACAGTT | 111 | 1272 |
| 874614 | N/A | N/A | 17582 | 17601 | ATATCAATAAAAAATTACTT | 71 | 1273 |
| 874638 | N/A | N/A | 19928 | 19947 | ATCATTACGACCATTCTGCT | 61 | 1274 |
| 874662 | N/A | N/A | 21807 | 21826 | AGGAGCGCGCCACCGTGCCT | 98 | 1275 |
| 874686 | N/A | N/A | 26733 | 26752 | GAATTTGAATAGGTCATTTA | 89 | 1276 |
| 874710 | N/A | N/A | 29848 | 29867 | CTGAGATCAGGAGACCAGCC | 125 | 1277 |
| 874734 | N/A | N/A | 31806 | 31825 | CCTAGACACACCAAAAAATC | 119 | 1278 |
| 874758 | N/A | N/A | 32891 | 32910 | ATCAGTTAGACAATTAACTA | 80 | 1279 |
| 874782 | N/A | N/A | 36313 | 36332 | TGCTCTCTTTGCGCCTGTGT | 31 | 1280 |
| 874806 | N/A | N/A | 37712 | 37731 | TGTCATATACCCACTACTCA | 37 | 1281 |
| 874830 | N/A | N/A | 40133 | 40152 | CATAAAATTAAAATACTACA | 77 | 1282 |
| 874854 | N/A | N/A | 42262 | 42281 | ACCACGCCCGGCCAAAGATG | 117 | 1283 |
| 874878 | N/A | N/A | 44068 | 44087 | AGGAAACTGAACCTCAGCAG | 112 | 1284 |
| 874902 | N/A | N/A | 45563 | 45582 | CACTGCTTGCCTGGAGACCC | 125 | 1285 |
| 874926 | N/A | N/A | 46840 | 46859 | GAAATGTACCCTAAGAAGGG | 111 | 1286 |
| 874950 | N/A | N/A | 49008 | 49027 | TCTTAAGTACATTAATAATA | 115 | 1287 |
| 874974 | N/A | N/A | 51158 | 51177 | CAGAGTGCTATGTATTAAAT | 52 | 1288 |
| 874998 | N/A | N/A | 54550 | 54569 | GAACTTAAAAGTCACACTGA | 134 | 1289 |
| 875022 | N/A | N/A | 56884 | 56903 | AAGTGCAGCAATAAAGACAG | 95 | 1290 |
| 875046 | N/A | N/A | 58702 | 58721 | ATTTCTATATACTCTAAAAA | 86 | 1291 |
| 875070 | N/A | N/A | 61108 | 61127 | CAATAAAATAAAAATAAACT | 87 | 1292 |
| 875094 | N/A | N/A | 63266 | 63285 | TAGTAACCTTTTTTTTTTTG | 73 | 1293 |

TABLE 18-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 875118 | N/A | N/A | 65226 | 65245 | GGGTATAATCAAAGAGACAG | 85 | 1294 |
| 875142 | N/A | N/A | 68733 | 68752 | TACATTCCTAACTAATCAGC | 137 | 1295 |
| 875166 | N/A | N/A | 70825 | 70844 | AAAAACAAAAAAATGTGTAT | 135 | 1296 |
| 875190 | N/A | N/A | 72135 | 72154 | TCCAGCCCCTGTATCCCACC | 70 | 1297 |
| 875214 | N/A | N/A | 74077 | 74096 | GGAATAAAAGCATTAATCCA | 148 | 1298 |
| 875238 | N/A | N/A | 76541 | 76560 | CAACAAAAGCACATTTAAAT | 75 | 1299 |
| 875262 | N/A | N/A | 77753 | 77772 | TCTGCAGAAAAAGAAAAAAA | 117 | 1300 |
| 875286 | N/A | N/A | 80664 | 80683 | ATGAAGCTTGTTTTTCAAAA | 98 | 1301 |
| 875310 | N/A | N/A | 82410 | 82429 | CCAACAGGGTGCTCTTTAGC | 52 | 1302 |
| 875334 | N/A | N/A | 84147 | 84166 | AAGTTAGTAACATACTATTG | 64 | 1303 |
| 875358 | N/A | N/A | 85131 | 85150 | AACTTAACTGACATAAATTC | 73 | 1304 |
| 875382 | N/A | N/A | 87622 | 87641 | ACACCCCGATACCACTAAAA | 112 | 1305 |
| 875406 | N/A | N/A | 90234 | 90253 | AGACCATCTAAGTAATGTCA | 43 | 1306 |
| 875430 | N/A | N/A | 92407 | 92426 | CTTGCTCTACTAATATCTAG | 83 | 1307 |
| 875454 | N/A | N/A | 95304 | 95323 | ACTTTAAATGGTTGATTTAT | 66 | 1308 |
| 875478 | N/A | N/A | 97379 | 97398 | ATGTGAAGATAATTCAATGG | 71 | 1309 |
| 875502 | N/A | N/A | 98921 | 98940 | AGCAGAAAACTGAAATTCTT | 64 | 1310 |
| 875526 | N/A | N/A | 101064 | 101083 | AATTTTAAAGGCCGGGCACG | 125 | 1311 |
| 875550 | N/A | N/A | 104158 | 104177 | CGAATTCAGTAACACATTAA | 78 | 1312 |
| 875574 | N/A | N/A | 108028 | 108047 | AAGAACTACAATTTTTTTTT | 82 | 1313 |
| 875598 | N/A | N/A | 110258 | 110277 | TCATAGTCAGTGGACTTGGG | 79 | 1314 |
| 875622 | N/A | N/A | 112622 | 112641 | CCACATGTCAGAAATTGTGC | 71 | 1315 |
| 875646 | N/A | N/A | 115026 | 115045 | ATGGCCATGTAAAAAAAAGA | 82 | 1316 |
| 875670 | N/A | N/A | 117477 | 117496 | GTAGGTATATATAAAGCAAG | 34 | 1317 |
| 875694 | N/A | N/A | 120644 | 120663 | AAGCAAGTAAAAAGATAACC | 136 | 1318 |
| 875718 | N/A | N/A | 123915 | 123934 | TCACAGTAAGAAAAGAAACA | 86 | 1319 |
| 875742 | N/A | N/A | 127208 | 127227 | GACAAGACAAGAAAAGAAAA | 142 | 1320 |
| 875766 | N/A | N/A | 129887 | 129906 | TAAACAAAAAAGCCACTGAA | 103 | 1321 |
| 875790* | N/A | N/A | 131421 | 131440 | TAGACATGAGGATGCTGTGT | 81 | 1322 |
| 875814 | N/A | N/A | 133409 | 133428 | AACTAAAGACAAGTCAAATG | 89 | 1323 |
| 875838 | N/A | N/A | 135021 | 135040 | TAATGTTAGCATATGTGTAT | 51 | 1324 |
| 875862 | N/A | N/A | 137974 | 137993 | CTATTTCTGTACTTTTTGCC | 42 | 1325 |
| 875886 | N/A | N/A | 139601 | 139620 | TTTTGTTATATATGCTCATT | 37 | 1326 |
| 875910 | N/A | N/A | 142529 | 142548 | TGCCAGAATATTTTAACAAG | 61 | 1327 |
| 875934 | N/A | N/A | 144707 | 144726 | AGTTTCACAGTGTTCGCCAG | 55 | 1328 |

TABLE 18-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 875958 | N/A | N/A | 146252 | 146271 | ACACTGGAGGTGAGCTCCAA | 112 | 1329 |
| 875982 | N/A | N/A | 147991 | 148010 | CCTGCACACACACGCCTCAC | 135 | 1330 |

TABLE 19

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 708199 | 1477 | 1496 | 81637 | 81656 | GCTAACTGGTTTGCCCTTGC | 45 | 32 |
| 874165 | 163 | 182 | 2153 | 2172 | GCTGCGGCCGCTGAGCGCAT | 111 | 1331 |
| 874189 | 363 | 382 | 2353 | 2372 | AGGCGGAGGGAGGCGAGCTC | 100 | 1332 |
| 874213 | 994 | 1013 | 48693 | 48712 | ACTTGTACTTCACATTTGGA | 49 | 1333 |
| 874234 | 1533 | 1552 | 81693 | 81712 | CATCATTTTCCAGGGCCACT | 53 | 1334 |
| 874258 | 1762 | 1781 | 83373 | 83392 | CCAGAATTCGGGTTGAAATC | 42 | 1335 |
| 874282 | 2462 | 2481 | 91732 | 91751 | AGGTGATGTTTCATTGGGTT | 16 | 1336 |
| 874306 | 2766 | 2785 | 113075 | 113094 | TGTGCTCCGTGTTACTAAGT | 71 | 1337 |
| 874329 | 3491 | 3510 | 136964 | 136983 | TGTCTCCTTGTTGTATGGTA | 49 | 1338 |
| 874352 | 4191 | 4210 | 148942 | 148961 | TATTTTAAAAACAAAATAAA | 88 | 1339 |
| 874376 | 4351 | 4370 | 149102 | 149121 | TTTCGGCAAGCAGAGCTGGG | 100 | 1340 |
| 874399 | 4520 | 4539 | 149271 | 149290 | AAGAATTTACTGAAACTTTG | 54 | 1341 |
| 874423 | 4658 | 4677 | 149409 | 149428 | TTTAAATTTTTTTTAAGTTT | 103 | 1342 |
| 874471 | N/A | N/A | 3562 | 3581 | CACATGGAGCCCCACGATTT | 102 | 1343 |
| 874495 | N/A | N/A | 3082 | 3101 | TGCTGCGGGAGGCTGGACAG | 121 | 1344 |
| 874519 | N/A | N/A | 6400 | 6419 | AATAATTACACTGAAGCAAA | 60 | 1345 |
| 874543 | N/A | N/A | 8244 | 8263 | TCCTTTAAGTCAAAATATAT | 81 | 1346 |
| 874567 | N/A | N/A | 10956 | 10975 | AAAAAAAACAGGCCTGTTAG | 103 | 1347 |
| 874591 | N/A | N/A | 14654 | 14673 | AGAGGCTAAAGCAGGAGGAC | 39 | 1348 |
| 874615 | N/A | N/A | 17664 | 17683 | CCTAGCTTAGATATAACCTC | 42 | 1349 |
| 874639 | N/A | N/A | 19930 | 19949 | GCATCATTACGACCATTCTG | 16 | 1350 |
| 874663 | N/A | N/A | 22432 | 22451 | AATCATATGTTCACACAAAA | 73 | 1351 |
| 874687 | N/A | N/A | 26823 | 26842 | AATAACATTTTTAATACCA | 80 | 1352 |
| 874711 | N/A | N/A | 29958 | 29977 | CATGGCTTAAAGCTCAGAAT | 119 | 1353 |
| 874735 | N/A | N/A | 31839 | 31858 | CTTGGTCATGAAGCCATGAA | 81 | 1354 |
| 874759 | N/A | N/A | 32915 | 32934 | ACTTAAGTAACTAATATTTA | 95 | 1355 |
| 874783 | N/A | N/A | 36363 | 36382 | GGAACCCCGAGTCGGGCAA | 94 | 1356 |

TABLE 19-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 874807 | N/A | N/A | 37726 | 37745 | ATTACTAGTGTATCTGTCAT | 47 | 1357 |
| 874831 | N/A | N/A | 40160 | 40179 | AAACCTCCGTCTCAAAGAAA | 89 | 1358 |
| 874855 | N/A | N/A | 42417 | 42436 | GCTAGGACTACAGGTACGCG | 87 | 1359 |
| 874879 | N/A | N/A | 44193 | 44212 | AAATTCCTGAAGTCTAAGGA | 148 | 1360 |
| 874903 | N/A | N/A | 45566 | 45585 | ATGCACTGCTTGCCTGGAGA | 40 | 1361 |
| 874927 | N/A | N/A | 46912 | 46931 | GCAATGAAACTGTTCTATTA | 61 | 1362 |
| 874951 | N/A | N/A | 49059 | 49078 | TCCATCATTTAAAAATCCTC | 37 | 1363 |
| 874975 | N/A | N/A | 51367 | 51386 | AGTAATAAAAATTTAATGAC | 70 | 1364 |
| 874999 | N/A | N/A | 54561 | 54580 | GTTAGCATCAAGAACTTAAA | 30 | 1365 |
| 875023 | N/A | N/A | 56886 | 56905 | TCAAGTGCAGCAATAAAGAC | 78 | 1366 |
| 875047 | N/A | N/A | 58785 | 58804 | TTTTATGCTAGAGGTTTTTA | 92 | 1367 |
| 875071 | N/A | N/A | 61109 | 61128 | ACAATAAAATAAAAATAAAC | 71 | 1368 |
| 875095 | N/A | N/A | 63285 | 63304 | AGATAAAAGGCACTGCAATT | 147 | 1369 |
| 875119 | N/A | N/A | 65276 | 65295 | GAAAAAAAAAATCTACAGTG | 95 | 1370 |
| 875143 | N/A | N/A | 68890 | 68909 | CTGACAAGCAGGAAGAAAGA | 83 | 1371 |
| 875167 | N/A | N/A | 71122 | 71141 | CGTGTATAGCTGGGAGCGGT | 84 | 1372 |
| 875191 | N/A | N/A | 72378 | 72397 | AAAGAATATTAATTTTCCAT | 83 | 1373 |
| 875215 | N/A | N/A | 74178 | 74197 | CCAGCAAATTTAAGCATGGA | 82 | 1374 |
| 875239 | N/A | N/A | 76560 | 76579 | CTCACTACAATAACAACAAC | 98 | 1375 |
| 875263 | N/A | N/A | 78033 | 78052 | GCTTGGAAAGCTGAGGCAGT | 98 | 1376 |
| 875287 | N/A | N/A | 80668 | 80687 | GAAAATGAAGCTTGTTTTTC | 137 | 1377 |
| 875311 | N/A | N/A | 82443 | 82462 | CAATGCCCCAGGGTTTATTC | 80 | 1378 |
| 875335 | N/A | N/A | 84195 | 84214 | CTTTCCAAATTTAAATAGCT | 133 | 1379 |
| 875359 | N/A | N/A | 85140 | 85159 | TTTTAGCATAACTTAACTGA | 133 | 1380 |
| 875383 | N/A | N/A | 87736 | 87755 | CATGATAAAATATTTTTAAC | 97 | 1381 |
| 875407 | N/A | N/A | 90262 | 90281 | AATCATGTTATTCTCAAAAT | 73 | 1382 |
| 875431 | N/A | N/A | 92462 | 92481 | ACACCAGAGTCCAGTACATC | 80 | 1383 |
| 875455 | N/A | N/A | 95328 | 95347 | ATTTTAAAAACCACTGATTT | 73 | 1384 |
| 875479 | N/A | N/A | 97386 | 97405 | AACAAGCATGTGAAGATAAT | 106 | 1385 |
| 875503 | N/A | N/A | 99111 | 99130 | CTCCTGCCTCAGTCTTGCGA | 96 | 1386 |
| 875527 | N/A | N/A | 101077 | 101096 | AATGATTTAAAATAATTTTA | 166 | 1387 |
| 875551 | N/A | N/A | 104161 | 104180 | AACCGAATTCAGTAACACAT | 59 | 1388 |
| 875575 | N/A | N/A | 108060 | 108079 | CAGGAAGAATAAAAAATGAA | 95 | 1389 |
| 875599 | N/A | N/A | 110294 | 110313 | TGCAATTCCTGGACAAGTCA | 69 | 1390 |
| 875623 | N/A | N/A | 112683 | 112702 | CACAGTCACCAAAGCACTCA | 142 | 1391 |
| 875647 | N/A | N/A | 115093 | 115112 | GCCCAAGATCACATCTAATT | 85 | 1392 |

TABLE 19-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 875671 | N/A | N/A | 117483 | 117502 | ATAACTGTAGGTATATATAA | 134 | 1393 |
| 875695 | N/A | N/A | 120698 | 120717 | ACAGATAAATTGAACTTCAT | 94 | 1394 |
| 875719 | N/A | N/A | 123938 | 123957 | TACTAAAAGTAGTAACTTTA | 82 | 1395 |
| 875743 | N/A | N/A | 127331 | 127350 | AGGCTGAGGTAGAAAGATAA | 128 | 1396 |
| 875767 | N/A | N/A | 129897 | 129916 | CTCCTTCTGGTAAACAAAAA | 108 | 1397 |
| 875791 | N/A | N/A | 131573 | 131592 | CACACTGGAAGAGACAAACA | 106 | 1398 |
| 875815 | N/A | N/A | 133419 | 133438 | CCGTTAAGACAACTAAAGAC | 101 | 1399 |
| 875839 | N/A | N/A | 135123 | 135142 | AGGTTTTTGACAAAAGCCCT | 104 | 1400 |
| 875863 | N/A | N/A | 137991 | 138010 | TCTCCATGAAGGAGCAACTA | 92 | 1401 |
| 875887 | N/A | N/A | 139982 | 140001 | AGACAAAAAAGGAACCAGGG | 106 | 1402 |
| 875911 | N/A | N/A | 142611 | 142630 | TTCCTTCATATCCAGTTTAG | 114 | 1403 |
| 875935 | N/A | N/A | 144712 | 144731 | GACGGAGTTTCACAGTGTTC | 87 | 1404 |
| 875959 | N/A | N/A | 146275 | 146294 | ACACCTTTCACCTGTAGCAG | 45 | 1405 |
| 875983 | N/A | N/A | 148054 | 148073 | AGCACTGGCCCTGCCTGCCA | 115 | 1406 |

TABLE 20

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 708199 | 1477 | 1496 | 81637 | 81656 | GCTAACTGGTTTGCCCTTGC | 41 | 32 |
| 874166 | 168 | 187 | 2158 | 2177 | GAGGAGCTGCGGCCGCTGAG | 110 | 1407 |
| 874190 | 368 | 387 | 2358 | 2377 | GTCTGAGGCGGAGGGAGGCG | 91 | 1408 |
| 874214 | 995 | 1014 | 48694 | 48713 | CACTTGTACTTCACATTTGG | 62 | 1409 |
| 874235 | 1535 | 1554 | 81695 | 81714 | ATCATCATTTTCCAGGGCCA | 71 | 1410 |
| 874259 | 1763 | 1782 | 83374 | 83393 | ACCAGAATTCGGGTTGAAAT | 60 | 1411 |
| 874283 | 2464 | 2483 | 91734 | 91753 | CTAGGTGATGTTTCATTGGG | 30 | 1412 |
| 874307 | 2768 | 2787 | 113077 | 113096 | CTTGTGCTCCGTGTTACTAA | 37 | 1413 |
| 874330 | 3493 | 3512 | 136966 | 136985 | CTTGTCTCCTTGTTGTATGG | 45 | 1414 |
| 874353 | 4196 | 4215 | 148947 | 148966 | ATATATATTTTAAAAACAAA | 123 | 1415 |
| 874377 | 4356 | 4375 | 149107 | 149126 | TCCAGTTTCGGCAAGCAGAG | 52 | 1416 |
| 874400 | 4525 | 4544 | 149276 | 149295 | ACGGTAAGAATTTACTGAAA | 90 | 1417 |
| 874424 | 4671 | 4690 | 149422 | 149441 | ACTTTTTTTATTTTTTAAAT | 95 | 1418 |
| 874472 | N/A | N/A | 3567 | 3586 | GAGGCCACATGGAGCCCCAC | 97 | 1419 |
| 874496 | N/A | N/A | 3396 | 3415 | TCCGGAGGAGCCCGGTGCCT | 70 | 1420 |
| 874520 | N/A | N/A | 6521 | 6540 | TTCTTGACACTGGAAGTAAT | 70 | 1421 |

TABLE 20-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 874544 | N/A | N/A | 8253 | 8272 | TTGAGATCCTCCTTTAAGTC | 41 | 1422 |
| 874568 | N/A | N/A | 11322 | 11341 | GCCAAAATCAAGGTTACAAA | 36 | 1423 |
| 874592 | N/A | N/A | 14673 | 14692 | ATAAAGAACTCTCCAGACCA | 90 | 1424 |
| 874616 | N/A | N/A | 17714 | 17733 | ATTCAAATTTAACTGAGTGT | 85 | 1425 |
| 874640 | N/A | N/A | 20042 | 20061 | GCATTGGCCTACTCCGTGAA | 45 | 1426 |
| 874664 | N/A | N/A | 22447 | 22466 | AACCAAGAGAAATAAAATCA | 107 | 1427 |
| 874688 | N/A | N/A | 26863 | 26882 | GCTAGTGACTCAAGTTCCTG | 56 | 1428 |
| 874712 | N/A | N/A | 30034 | 30053 | AGTTAATGGGAAACATGATC | 84 | 1429 |
| 874736 | N/A | N/A | 31851 | 31870 | AGGGATAAAAGGCTTGGTCA | 72 | 1430 |
| 874760 | N/A | N/A | 32983 | 33002 | TGAAAGAAGCCTTCTCAAAC | 93 | 1431 |
| 874784 | N/A | N/A | 36387 | 36406 | ATTTTTGACAAGCTGACCGT | 103 | 1432 |
| 874808 | N/A | N/A | 37739 | 37758 | GATCTGTATTATAATTACTA | 79 | 1433 |
| 874832 | N/A | N/A | 40698 | 40717 | CGCCCTGACTCACGCCTGTA | 99 | 1434 |
| 874856 | N/A | N/A | 42555 | 42574 | ATCCAGAATGCAGTAAATGC | 27 | 1435 |
| 874880 | N/A | N/A | 44286 | 44305 | AAACAATGGACTTGAATTAA | 68 | 1436 |
| 874904 | N/A | N/A | 45671 | 45690 | ATTTCCAAACTTAAAATATA | 76 | 1437 |
| 874928 | N/A | N/A | 46982 | 47001 | GATGGAAGACAAATCAATGG | 71 | 1438 |
| 874952 | N/A | N/A | 49152 | 49171 | AGCTCATCAAGGTACCAGTT | 20 | 1439 |
| 874976 | N/A | N/A | 51385 | 51404 | GAAATGAAGATCTAATAAAG | 127 | 1440 |
| 875000 | N/A | N/A | 54588 | 54607 | CTTTTAAACTTTATTGAAAT | 85 | 1441 |
| 875024 | N/A | N/A | 56983 | 57002 | TGAAGGAAAAGAAGCCCAGG | 83 | 1442 |
| 875048 | N/A | N/A | 59243 | 59262 | ATTTTTAGTAGAGCCATGTC | 65 | 1443 |
| 875072 | N/A | N/A | 61124 | 61143 | AATTTCTTTAAAAATACAAT | 91 | 1444 |
| 875096 | N/A | N/A | 63309 | 63328 | TAGTTTGACTAAGCCCATTA | 53 | 1445 |
| 875120 | N/A | N/A | 65378 | 65397 | ACCACACTTATTTTCTATTT | 48 | 1446 |
| 875144 | N/A | N/A | 68973 | 68992 | TCCAAGGTCATCAATGCCCT | 106 | 1447 |
| 875168 | N/A | N/A | 71142 | 71161 | CTGGAGTGGCATTAAAAATA | 85 | 1448 |
| 875192 | N/A | N/A | 72380 | 72399 | TCAAAGAATATTAATTTTCC | 64 | 1449 |
| 875216 | N/A | N/A | 74198 | 74217 | GCCAAAATAAGAAATCTGAG | 55 | 1450 |
| 875240 | N/A | N/A | 76565 | 76584 | ATACACTCACTACAATAACA | 81 | 1451 |
| 875264 | N/A | N/A | 78448 | 78467 | TTGCAGTGTGACAGAGCAAG | 80 | 1452 |
| 875288 | N/A | N/A | 80812 | 80831 | ATCAAAGACAAATGCACTAA | 103 | 1453 |
| 875312 | N/A | N/A | 82491 | 82510 | TTGAACTATTTCAGTGCACT | 79 | 1454 |
| 875336 | N/A | N/A | 84211 | 84230 | CTCTATTTTCATCTAACTTT | 52 | 1455 |
| 875360 | N/A | N/A | 85184 | 85203 | GTACATTTTAACCCTTTGAG | 24 | 1456 |
| 875384 | N/A | N/A | 87737 | 87756 | ACATGATAAAATATTTTTAA | 144 | 1457 |

TABLE 20-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 875408 | N/A | N/A | 90294 | 90313 | CTCCAAAACTATGCTTATAC | 60 | 1458 |
| 875432 | N/A | N/A | 92496 | 92515 | TGTGTACAAAGTATAAATCT | 72 | 1459 |
| 875456 | N/A | N/A | 95417 | 95436 | CGACTGCTAAACTGGGCACG | 70 | 1460 |
| 875480 | N/A | N/A | 97390 | 97409 | TTCCAACAAGCATGTGAAGA | 116 | 1461 |
| 875504 | N/A | N/A | 99262 | 99281 | TCCTCTCTGCACTATACTAA | 90 | 1462 |
| 875528 | N/A | N/A | 101138 | 101157 | AATTTAGAAAGAACGAATAA | 92 | 1463 |
| 875552 | N/A | N/A | 104251 | 104270 | TACAAAACCAAAGGACACAT | 102 | 1464 |
| 875576 | N/A | N/A | 108123 | 108142 | AGAAAAATACAGAATATTGT | 100 | 1465 |
| 875600 | N/A | N/A | 110667 | 110686 | GGCACTATGGTCTGTAATCC | 73 | 1466 |
| 875624 | N/A | N/A | 112840 | 112859 | ATATCTTAAATAACTTTAGT | 89 | 1467 |
| 875648 | N/A | N/A | 115157 | 115176 | ATAAACCTGACAGCCTAGCT | 85 | 1468 |
| 875672 | N/A | N/A | 117704 | 117723 | GGCTAAGATTTCTATTTTTT | 62 | 1469 |
| 875696 | N/A | N/A | 120718 | 120737 | AGCAACAAAAGAAAAACAA | 86 | 1470 |
| 875720 | N/A | N/A | 124032 | 124051 | GGCTCTTCAAAAAAAACCGC | 96 | 1471 |
| 875744 | N/A | N/A | 127393 | 127412 | CTGGGTGTGATGGCTCATCC | 106 | 1472 |
| 875768 | N/A | N/A | 129900 | 129919 | CACCTCCTTCTGGTAAACAA | 87 | 1473 |
| 875792 | N/A | N/A | 131617 | 131636 | TAGATAGAGTATGTTTTCAG | 52 | 1474 |
| 875816 | N/A | N/A | 133430 | 133449 | ATATTCAGTCCCCGTTAAGA | 68 | 1475 |
| 875840 | N/A | N/A | 136211 | 136230 | GGTAAAAGCATCACCATAAA | 43 | 1476 |
| 875864 | N/A | N/A | 137994 | 138013 | CTTTCTCCATGAAGGAGCAA | 157 | 1477 |
| 875888 | N/A | N/A | 140040 | 140059 | AAGCAGGGTAGGAAGAAAAT | 106 | 1478 |
| 875912 | N/A | N/A | 142660 | 142679 | TCTAGGATCACCTGTGCATC | 60 | 1479 |
| 875936 | N/A | N/A | 144926 | 144945 | TCAACATGTATCTTAAATGT | 79 | 1480 |
| 875960 | N/A | N/A | 146301 | 146320 | AGACAGCAACCACTGAGATG | 93 | 1481 |
| 875984 | N/A | N/A | 148158 | 148177 | CTCGGCTCCCGGAAGCCTCA | 79 | 1482 |

TABLE 21

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 708199 | 1477 | 1496 | 81637 | 81656 | GCTAACTGGTTTGCCCTTGC | 34 | 32 |
| 874167 | 173 | 192 | 2163 | 2182 | ACTCCGAGGAGCTGCGGCCG | 100 | 1483 |
| 874191 | 373 | 392 | 2363 | 2382 | AAACAGTCTGAGGCGGAGGG | 83 | 1484 |
| 874215 | 1077 | 1096 | 49251 | 49270 | TTTTCTCATGTGCGGCATCA | 49 | 1485 |

TABLE 21-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 874236 | 1536 | 1555 | 81696 | 81715 | TATCATCATTTTCCAGGGCC | 60 | 1486 |
| 874260 | 1764 | 1783 | 83375 | 83394 | AACCAGAATTCGGGTTGAAA | 58 | 1487 |
| 874284 | 2465 | 2484 | 91735 | 91754 | GCTAGGTGATGTTTCATTGG | 50 | 1488 |
| 874308 | 2806 | 2825 | 113115 | 113134 | GAAGTCTGAACCCCTTGGGA | 104 | 1489 |
| 874331 | 3940 | 3959 | 147855 | 147874 | ATTGGCGCATGGGCAGTTGG | 62 | 1490 |
| 874354 | 4201 | 4220 | 148952 | 148971 | TCAACATATATATTTTAAAA | 104 | 1491 |
| 874378 | 4361 | 4380 | 149112 | 149131 | TAACTTCCAGTTTCGGCAAG | 47 | 1492 |
| 874401 | 4530 | 4549 | 149281 | 149300 | GTTTGACGGTAAGAATTTAC | 86 | 1493 |
| 874425 | 4679 | 4698 | 149430 | 149449 | TTTTTAAAACTTTTTTTATT | 87 | 1494 |
| 874473 | N/A | N/A | 3572 | 3591 | TGCCGGAGGCCACATGGAGC | 93 | 1495 |
| 874497 | N/A | N/A | 3410 | 3429 | CAGACCCTGATGATTCCGGA | 56 | 1496 |
| 874521 | N/A | N/A | 6751 | 6770 | AACCAAGTACCCTCATTAAT | 110 | 1497 |
| 874545 | N/A | N/A | 8481 | 8500 | CCGCACTCATTGCAACCTCC | 100 | 1498 |
| 874569 | N/A | N/A | 11435 | 11454 | CAAAATAAATAAATAACCAA | 90 | 1499 |
| 874593 | N/A | N/A | 14692 | 14711 | AAAAGTTCTCAAAGAGGCCA | 72 | 1500 |
| 874617 | N/A | N/A | 17725 | 17744 | GTTCATCAAAAATTCAAATT | 140 | 1501 |
| 874641 | N/A | N/A | 20069 | 20088 | ATGAACTCCTGCTGCCTGGG | 55 | 1502 |
| 874665 | N/A | N/A | 22469 | 22488 | CAATCTCATTTCTATGCATT | 53 | 1503 |
| 874689 | N/A | N/A | 27130 | 27149 | CCTGGGTTTAAGTGACCCTC | 88 | 1504 |
| 874713 | N/A | N/A | 30201 | 30220 | TTAGTTTCATGGAAAATTTG | 78 | 1505 |
| 874737 | N/A | N/A | 31871 | 31890 | CCTTGAGTCCCTCTAGAGAA | 81 | 1506 |
| 874761 | N/A | N/A | 32994 | 33013 | ATGTCACCTCCTGAAAGAAG | 54 | 1507 |
| 874785 | N/A | N/A | 36430 | 36449 | TCATTTATTCTGCTTTGCT | 34 | 1508 |
| 874809 | N/A | N/A | 37849 | 37868 | AATAATACTTAATCCTACTC | 87 | 1509 |
| 874833 | N/A | N/A | 40743 | 40762 | AGAAACCATAATTAATGCA | 99 | 1510 |
| 874857 | N/A | N/A | 42595 | 42614 | GAATATATTAACTGATACCA | 50 | 1511 |
| 874881 | N/A | N/A | 44316 | 44335 | ACTTTTCCTCACTTTCTTCT | 95 | 1512 |
| 874905 | N/A | N/A | 45694 | 45713 | ACAGGCTAAATAAGCTGAAA | 93 | 1513 |
| 874929 | N/A | N/A | 47002 | 47021 | GGAAGGACACAAACCGTAAG | 62 | 1514 |
| 874953 | N/A | N/A | 49157 | 49176 | TCTTTAGCTCATCAAGGTAC | 75 | 1515 |
| 874977 | N/A | N/A | 51885 | 51904 | GTTTTGAAATAAGATACCTG | 78 | 1516 |
| 875001 | N/A | N/A | 54602 | 54621 | ATGCATGAATATAACTTTTA | 68 | 1517 |
| 875025 | N/A | N/A | 57059 | 57078 | AGCTGGCAGTGTGTGTCATG | 79 | 1518 |
| 875049 | N/A | N/A | 59277 | 59296 | CAGGTGCCCGTCACCTCGCC | 87 | 1519 |
| 875073 | N/A | N/A | 61226 | 61245 | TGTTTTGCAACTCCCTCAGT | 93 | 1520 |
| 875097 | N/A | N/A | 63380 | 63399 | GTGAGAGGTACAAATTGGAT | 58 | 1521 |

TABLE 21-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 875121 | N/A | N/A | 65409 | 65428 | ACAATATTTGCCTTGGTGGA | 74 | 1522 |
| 875145 | N/A | N/A | 68996 | 69015 | ATAAAGATGTAAATTTCTCT | 96 | 1523 |
| 875169 | N/A | N/A | 71146 | 71165 | TAGACTGGAGTGGCATTAAA | 103 | 1524 |
| 875193 | N/A | N/A | 72393 | 72412 | CCAATGCCATAAGTCAAAGA | 130 | 1525 |
| 875217 | N/A | N/A | 74384 | 74403 | CTCTGCTGAGGAATATAAGC | 129 | 1526 |
| 875241 | N/A | N/A | 76650 | 76669 | CCCCTACAAGTAAAATGACA | 122 | 1527 |
| 875265 | N/A | N/A | 78696 | 78715 | GGCAATAAGAATATGAACAG | 66 | 1528 |
| 875289 | N/A | N/A | 80842 | 80861 | ATTTATTCATCATAAATTAA | 103 | 1529 |
| 875313 | N/A | N/A | 82494 | 82513 | CAGTTGAACTATTTCAGTGC | 54 | 1530 |
| 875337 | N/A | N/A | 84223 | 84242 | AAACTTAGTGTTCTCTATTT | 88 | 1531 |
| 875361 | N/A | N/A | 85272 | 85291 | ATGATATGAAGGAAAGTATA | 84 | 1532 |
| 875385 | N/A | N/A | 87771 | 87790 | TTTGTAAAGAAATATGTTAC | 85 | 1533 |
| 875409 | N/A | N/A | 90317 | 90336 | CTATAATGCTATTCTGAGTG | 54 | 1534 |
| 875433 | N/A | N/A | 92571 | 92590 | AAGGAGAGATGTTAAGTAAA | 73 | 1535 |
| 875457 | N/A | N/A | 95441 | 95460 | GAAGGGCTGGAGGCAAATGT | 83 | 1536 |
| 875481 | N/A | N/A | 97406 | 97425 | TTTGTAGTCAACAGACTTCC | 89 | 1537 |
| 875505 | N/A | N/A | 99283 99341 | 99302 99360 | AATATAGCACTCTGCTGTAT | 109 | 1538 |
| 875529 | N/A | N/A | 101178 | 101197 | GGAGAAGAAGGGAAATGAGG | 87 | 1539 |
| 875553 | N/A | N/A | 104262 | 104281 | CTATTACCCTATACAAAACC | 82 | 1540 |
| 875577 | N/A | N/A | 108143 | 108162 | CTCACTGGTAACAAGTACAC | 66 | 1541 |
| 875601 | N/A | N/A | 110953 | 110972 | AAGGAAAAAGACACCAAAAA | 135 | 1542 |
| 875625 | N/A | N/A | 112860 | 112879 | AAGGAAACAATTATACTTAA | 83 | 1543 |
| 875649 | N/A | N/A | 115236 | 115255 | AGATTATCCTAACTATGTTT | 90 | 1544 |
| 875673 | N/A | N/A | 117770 | 117789 | TTTCAATTGATCCTCCCACC | 133 | 1545 |
| 875697 | N/A | N/A | 120786 | 120805 | TTCATAGGAGTAAATCTCTG | 53 | 1546 |
| 875721 | N/A | N/A | 124051 | 124070 | CATTAAAATTAACAATACTG | 128 | 1547 |
| 875745 | N/A | N/A | 127761 | 127780 | GTGGGAAAAAAATACAAGAC | 72 | 1548 |
| 875769 | N/A | N/A | 129981 | 130000 | GTTACATATTATTTTATCTA | 91 | 1549 |
| 875793 | N/A | N/A | 131634 | 131653 | AAAGGTCAGGTTATTCTTAG | 46 | 1550 |
| 875817 | N/A | N/A | 133534 | 133553 | CATAATGAACTTTTAACCTA | 65 | 1551 |
| 875841 | N/A | N/A | 136265 | 136284 | TCTTCCTAATGGCTCTAGTT | 60 | 1552 |
| 875865 | N/A | N/A | 138252 | 138271 | GGAACTCTTGTGCCTCCGCC | 87 | 1553 |
| 875889 | N/A | N/A | 140074 | 140093 | TTCCTTGATAGGCCAGTTAA | 72 | 1554 |
| 875913 | N/A | N/A | 142681 | 142700 | AGGGCAAGGCAAAGAGCCAG | 165 | 1555 |
| 875937 | N/A | N/A | 144941 | 144960 | CCAATCACCTTATTATCAAC | 60 | 1556 |

TABLE 21-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
| --- | --- | --- | --- | --- | --- | --- | --- |
| 875961 | N/A | N/A | 146302 | 146321 | CAGACAGCAACCACTGAGAT | 71 | 1557 |
| 875985 | N/A | N/A | 148184 | 148203 | CTGTATACCATCAGAACACA | 81 | 1558 |

TABLE 22

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
| --- | --- | --- | --- | --- | --- | --- | --- |
| 708199 | 1477 | 1496 | 81637 | 81656 | GCTAACTGGTTTGCCCTTGC | 33 | 32 |
| 874168 | 178 | 197 | 2168 | 2187 | GCGGGACTCCGAGGAGCTGC | 163 | 1559 |
| 874192 | 378 | 397 | 2368 | 2387 | TACCAAAACAGTCTGAGGCG | 74 | 1560 |
| 874216 | 1079 | 1098 | 49253 | 49272 | ACTTTTCTCATGTGCGGCAT | 31 | 1561 |
| 874237 | 1537 | 1556 | 81697 | 81716 | CTATCATCATTTTCCAGGGC | 42 | 1562 |
| 874261 | 1766 | 1785 | 83377 | 83396 | TGAACCAGAATTCGGGTTGA | 73 | 1563 |
| 874285 | 2466 | 2485 | 91736 | 91755 | AGCTAGGTGATGTTTCATTG | 62 | 1564 |
| 874309 | 2808 | 2827 | 113117 | 113136 | TGGAAGTCTGAACCCCTTGG | 68 | 1565 |
| 874332 | 3942 | 3961 | 147857 | 147876 | TCATTGGCGCATGGGCAGTT | 79 | 1566 |
| 874355 | 4206 | 4225 | 148957 | 148976 | AGAAATCAACATATATATTT | 67 | 1567 |
| 874379 | 4372 | 4391 | 149123 | 149142 | TAAAAAATAAATAACTTCCA | 106 | 1568 |
| 874402 | 4535 | 4554 | 149286 | 149305 | CGTCAGTTTGACGGTAAGAA | 81 | 1569 |
| 874426 | 4684 | 4703 | N/A | N/A | TTCAGTTTTTAAAACTTTTT | 79 | 1570 |
| 874474 | N/A | N/A | 3606 | 3625 | CCTTCCCTTCCCCAGGTGGG | 101 | 1571 |
| 874498 | N/A | N/A | 3852 | 3871 | CTCCTAGCATTTCCGAAATT | 88 | 1572 |
| 874522 | N/A | N/A | 6805 | 6824 | TTCCTCAGGAATTTCATTCC | 89 | 1573 |
| 874546 | N/A | N/A | 8491 | 8510 | ACTGCAACCTCCGCACTCAT | 97 | 1574 |
| 874570 | N/A | N/A | 11884 | 11903 | AAAAATTTTGCTGGGCATAG | 70 | 1575 |
| 874594 | N/A | N/A | 14775 | 14794 | ATCTGCCTCTGAAAACATTG | 51 | 1576 |
| 874618 | N/A | N/A | 17808 | 17827 | GATGCTCAGTTAAATTTCAA | 90 | 1577 |
| 874642 | N/A | N/A | 20074 | 20093 | ACTTCATGAACTCCTGCTGC | 73 | 1578 |
| 874666 | N/A | N/A | 22506 | 22525 | GTACCCTGGAAAAATAAACA | 88 | 1579 |
| 874690 | N/A | N/A | 27138 | 27157 | CTCCAATTCCTGGGTTTAAG | 89 | 1580 |
| 874714 | N/A | N/A | 30240 | 30259 | ACAAAGTTAAGTTCTACAGG | 62 | 1581 |
| 874738 | N/A | N/A | 31884 | 31903 | CAGTGCCTTTACCCCTTGAG | 22 | 1582 |
| 874762 | N/A | N/A | 33100 | 33119 | CATAAGGGTACCACATACCT | 66 | 1583 |
| 874786 | N/A | N/A | 36460 | 36479 | GTGTACATGTGATGGCAATA | 63 | 1584 |

TABLE 22-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 874810 | N/A | N/A | 37868 | 37887 | TCCAAGGCATTTTTTAAATA | 77 | 1585 |
| 874834 | N/A | N/A | 40754 | 40773 | TTAAGAACGAAAGAAAACCA | 121 | 1586 |
| 874858 | N/A | N/A | 42680 | 42699 | CACCTTCTGCTTCTGATGTG | 51 | 1587 |
| 874882 | N/A | N/A | 44355 | 44374 | CATTCTGAGGCCAGTCCTAG | 78 | 1588 |
| 874906 | N/A | N/A | 45805 | 45824 | CTACTAATTTTCCCCAATAA | 111 | 1589 |
| 874930 | N/A | N/A | 47049 | 47068 | TTGACTAAACATGACATAAA | 118 | 1590 |
| 874954 | N/A | N/A | 49184 | 49203 | CTTTACAAAATAAAATTTGT | 81 | 1591 |
| 874978 | N/A | N/A | 51901 | 51920 | CACTAAACCACTGTAAGTTT | 81 | 1592 |
| 875002 | N/A | N/A | 54673 | 54692 | GAGACCAAAGGAAACTTATT | 121 | 1593 |
| 875026 | N/A | N/A | 57092 | 57111 | TACACACATGATAGGAGGGA | 43 | 1594 |
| 875050 | N/A | N/A | 59367 | 59386 | AGTGCAGCACCACCATCTCG | 90 | 1595 |
| 875074 | N/A | N/A | 61380 | 61399 | GATAGTAAGTATATTAGCAT | 91 | 1596 |
| 875098 | N/A | N/A | 63430 | 63449 | TTTAAGTAATAAAAAGCAGT | 81 | 1597 |
| 875122 | N/A | N/A | 65449 | 65468 | AAATGAGAAATCTGGAAGAC | 76 | 1598 |
| 875146 | N/A | N/A | 69021 | 69040 | AAATTTCACTTGAAGGTTAG | 70 | 1599 |
| 875170 | N/A | N/A | 71153 | 71172 | TCCAACATAGACTGGAGTGG | 86 | 1600 |
| 875194 | N/A | N/A | 72435 | 72454 | TCTAATCTACAGGCAACTGT | 101 | 1601 |
| 875218 | N/A | N/A | 74386 | 74405 | GGCTCTGCTGAGGAATATAA | 145 | 1602 |
| 875242 | N/A | N/A | 76793 | 76812 | CTTATTTGGCTGGGTGTTAA | 70 | 1603 |
| 875266 | N/A | N/A | 79338 | 79357 | AACTACTATTAAGAGTTCTG | 66 | 1604 |
| 875290 | N/A | N/A | 80898 | 80917 | TTGGTAATAAGAGAAAAATT | 97 | 1605 |
| 875314 | N/A | N/A | 82601 | 82620 | AACTTGCTCCATGTTTCCTC | 51 | 1606 |
| 875338 | N/A | N/A | 84232 | 84251 | TGAAATTGGAAACTTAGTGT | 62 | 1607 |
| 875362 | N/A | N/A | 85722 | 85741 | GATAAACCCCCTTTTTAACA | 106 | 1608 |
| 875386 | N/A | N/A | 87885 | 87904 | TTATTATTTCCCTTTATTTT | 138 | 1609 |
| 875410 | N/A | N/A | 90318 | 90337 | TCTATAATGCTATTCTGAGT | 60 | 1610 |
| 875434 | N/A | N/A | 92599 | 92618 | TAACATGCAAAAGAATGAAA | 83 | 1611 |
| 875458 | N/A | N/A | 95478 | 95497 | GATTAACGGTTGCTTAGGGT | 10 | 1612 |
| 875482 | N/A | N/A | 97440 | 97459 | AGGACAATTCAGAGTCCAGT | 75 | 1613 |
| 875506 | N/A | N/A | 99284 99342 | 99303 99361 | GAATATAGCACTCTGCTGTA | 58 | 1614 |
| 875530 | N/A | N/A | 101219 | 101238 | GAGATAGCAGAATGGTTACC | 112 | 1615 |
| 875554 | N/A | N/A | 104868 | 104887 | AAAAAGTGGAAAAACTTCA | 88 | 1616 |
| 875578 | N/A | N/A | 108258 | 108277 | AGGCTGGTAACAGAGCATGA | 81 | 1617 |
| 875602 | N/A | N/A | 110997 | 111016 | AAAATTAGGTAAGCGATCAC | 72 | 1618 |
| 875626 | N/A | N/A | 112866 | 112885 | TAAATAAAGGAAACAATTAT | 111 | 1619 |
| 875650 | N/A | N/A | 115247 | 115266 | GTGTTCAGTATAGATTATCC | 28 | 1620 |

TABLE 22-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 875674 | N/A | N/A | 117793 | 117812 | TCCCTGCAGCCTGGACCTTC | 87 | 1621 |
| 875698 | N/A | N/A | 120810 | 120829 | AAATCATAGGAGTTTTATAG | 102 | 1622 |
| 875722 | N/A | N/A | 124664 | 124683 | CAAAGATCAATACAACAAAA | 91 | 1623 |
| 875746 | N/A | N/A | 127802 | 127821 | TTAAATATCAACACAGGGAT | 73 | 1624 |
| 875770 | N/A | N/A | 129995 | 130014 | ATTTGGGAGAGCTAGTTACA | 67 | 1625 |
| 875794 | N/A | N/A | 131763 | 131782 | TAGTTAAAGCAGGAAAGAGA | 108 | 1626 |
| 875818 | N/A | N/A | 133541 | 133560 | AAACAATCATAATGAACTTT | 112 | 1627 |
| 875842 | N/A | N/A | 136401 | 136420 | AAAATGTTAAAAGGCAGTTG | 69 | 1628 |
| 875866 | N/A | N/A | 138269 | 138288 | CCACCTCCAGGGTTCATGGA | 83 | 1629 |
| 875890 | N/A | N/A | 140774 | 140793 | TAATCTATAGCTAATTTGCA | 80 | 1630 |
| 875914 | N/A | N/A | 142798 | 142817 | TTAGGCTAGGCACATGGAGC | 33 | 1631 |
| 875938 | N/A | N/A | 144978 | 144997 | ATTTGATTTTTCATTACTGC | 57 | 1632 |
| 875962 | N/A | N/A | 146349 | 146368 | CAATCCCCTGGGCCCTGGAG | 127 | 1633 |
| 875986 | N/A | N/A | 148191 | 148210 | CCAAATCCTGTATACCATCA | 61 | 1634 |

TABLE 23

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 708199 | 1477 | 1496 | 81637 | 81656 | GCTAACTGGTTTGCCCTTGC | 37 | 32 |
| 874169 | 183 | 202 | 2173 | 2192 | CCACCGCGGGACTCCGAGGA | 151 | 1635 |
| 874193 | 383 | 402 | 2373 | 2392 | GTTGCTACCAAAACAGTCTG | 94 | 1636 |
| 874217 | 1080 | 1099 | 49254 | 49273 | TACTTTTCTCATGTGCGGCA | 24 | 1637 |
| 874238 | 1539 | 1558 | 81699 | 81718 | TCCTATCATCATTTTCCAGG | 36 | 1638 |
| 874262 | 1767 | 1786 | 83378 | 83397 | CTGAACCAGAATTCGGGTTG | 100 | 1639 |
| 874286 | 2468 | 2487 | 91738 | 91757 | GAAGCTAGGTGATGTTTCAT | 89 | 1640 |
| 874310 | 2809 | 2828 | 113118 | 113137 | CTGGAAGTCTGAACCCCTTG | 70 | 1641 |
| 874333 | 3943 | 3962 | 147858 | 147877 | ATCATTGGCGCATGGGCAGT | 65 | 1642 |
| 874356 | 4211 | 4230 | 148962 | 148981 | TTACAAGAAATCAACATATA | 110 | 1643 |
| 874380 | 4377 | 4396 | 149128 | 149147 | GTTATTAAAAAATAAATAAC | 110 | 1644 |
| 874403 | 4540 | 4559 | 149291 | 149310 | TAATCCGTCAGTTTGACGGT | 80 | 1645 |
| 874427 | 4689 | 4708 | N/A | N/A | TTTTTTTCAGTTTTTAAAAC | 91 | 1646 |
| 874475 | N/A | N/A | 3611 | 3630 | CCACCCCTTCCCTTCCCCAG | 103 | 1647 |
| 874499 | N/A | N/A | 3916 | 3935 | CGCTAGTAAACACCCGCCTT | 69 | 1648 |

TABLE 23-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 874523 | N/A | N/A | 7056 | 7075 | CCTGTATCCCAAGCAATTCT | 51 | 1649 |
| 874547 | N/A | N/A | 8814 | 8833 | TTACATCTCCGTTGAAGTTG | 28 | 1650 |
| 874571 | N/A | N/A | 11970 | 11989 | ATGAGAATCATTTGAACGCA | 36 | 1651 |
| 874595 | N/A | N/A | 14959 | 14978 | TTTCTGTTTTTCAGTAGAGA | 70 | 1652 |
| 874619 | N/A | N/A | 17836 | 17855 | TAGACTGGAGTTGCCAGATA | 87 | 1653 |
| 874643 | N/A | N/A | 20097 | 20116 | CGTCTGGTCCCTGTTCAACA | 36 | 1654 |
| 874667 | N/A | N/A | 23044 | 23063 | ATCACCGAAAAAATTTCTCA | 111 | 1655 |
| 874691 | N/A | N/A | 27274 | 27293 | CTAAATTCCCTGAATTCCGT | 74 | 1656 |
| 874715 | N/A | N/A | 30281 | 30300 | ATAGTAAGCTACTACTGAAT | 82 | 1657 |
| 874739 | N/A | N/A | 32055 | 32074 | TACAGTTCCAGTTACTTGGG | 54 | 1658 |
| 874763 | N/A | N/A | 33174 | 33193 | TATAATCAAAATATTTCATT | 84 | 1659 |
| 874787 | N/A | N/A | 36472 | 36491 | CGTATTTTACTAGTGTACAT | 67 | 1660 |
| 874811 | N/A | N/A | 37919 | 37938 | TTAATTGGAGACTATAAGTG | 110 | 1661 |
| 874835 | N/A | N/A | 40848 | 40867 | ACCCACTGGAAAAAGAAGTA | 126 | 1662 |
| 874859 | N/A | N/A | 42797 | 42816 | TAAATCAAACAAGAATGGTA | 88 | 1663 |
| 874883 | N/A | N/A | 44372 | 44391 | TAGAAGAGTACTCTTAACAT | 103 | 1664 |
| 874907 | N/A | N/A | 45893 | 45912 | TTAAACAGTCAAGTTATCTA | 70 | 1665 |
| 874931 | N/A | N/A | 47058 | 47077 | AATGGTGTTTTGACTAAACA | 75 | 1666 |
| 874955 | N/A | N/A | 49371 | 49390 | CACCTCTTTTTGCATAACTG | 50 | 1667 |
| 874979 | N/A | N/A | 51931 | 51950 | ATACTACGCACTGGACGCAA | 97 | 1668 |
| 875003 | N/A | N/A | 54952 | 54971 | ATCAAGTAAAAAACAAGCAG | 82 | 1669 |
| 875027 | N/A | N/A | 57111 | 57130 | CATGGTATAAGGGCAATGAT | 102 | 1670 |
| 875051 | N/A | N/A | 59425 | 59444 | CATGTCCTATGCTTATTTTT | 105 | 1671 |
| 875075 | N/A | N/A | 61670 | 61689 | AATTCCAATTCTTACAGCTG | 57 | 1672 |
| 875099 | N/A | N/A | 63477 | 63496 | AGTGAGATAAAATAGAAAAA | 98 | 1673 |
| 875123 | N/A | N/A | 65509 | 65528 | GATGATCTAATAAAAGCAAT | 81 | 1674 |
| 875147 | N/A | N/A | 69082 | 69101 | ATAAATACTGCTAATACTAC | 94 | 1675 |
| 875171 | N/A | N/A | 71209 | 71228 | CTGATCTAGGCCTTCAAGAA | 109 | 1676 |
| 875195 | N/A | N/A | 72501 | 72520 | TGTTGGTAGTAAATAGTACA | 104 | 1677 |
| 875219 | N/A | N/A | 74397 | 74416 | TCTGCTGATCTGGCTCTGCT | 125 | 1678 |
| 875243 | N/A | N/A | 76838 | 76857 | CTCTAGGTGAAGTCAACAAT | 72 | 1679 |
| 875267 | N/A | N/A | 79378 | 79397 | AGTAAAAAGTAAATGTCTTC | 92 | 1680 |
| 875291 | N/A | N/A | 81016 | 81035 | ACAGCGAGATTCCCTCTCAA | 75 | 1681 |
| 875315 | N/A | N/A | 82626 | 82645 | AACGGAGTCACTGTTTTTCC | 45 | 1682 |
| 875339 | N/A | N/A | 84273 | 84292 | TTTGGAGAGGAATTCTGGAG | 120 | 1683 |
| 875363 | N/A | N/A | 85730 | 85749 | CAGGCAGAGATAAACCCCCT | 70 | 1684 |

TABLE 23-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 875387 | N/A | N/A | 88403 | 88422 | ATTTTTAACATATACATACT | 102 | 1685 |
| 875411 | N/A | N/A | 90320 | 90339 | AATCTATAATGCTATTCTGA | 78 | 1686 |
| 875435 | N/A | N/A | 92716 | 92735 | CCTTTAATTCAGCTACTTTT | 63 | 1687 |
| 875459 | N/A | N/A | 95503 | 95522 | AGCCCATCCATAGAGACAGA | 130 | 1688 |
| 875483 | N/A | N/A | 97464 | 97483 | GGATAAGACATAGAGATTCA | 82 | 1689 |
| 875507 | N/A | N/A | 99309 | 99328 | TTCTAATGCTATATTGCTAT | 129 | 1690 |
| 875531 | N/A | N/A | 101479 | 101498 | TACGGCACTATATACACAAC | 60 | 1691 |
| 875555 | N/A | N/A | 104920 | 104939 | TACAGTAAAAGCAACAATAA | 123 | 1692 |
| 875579 | N/A | N/A | 108451 | 108470 | TCACCCTGAGGTCAGGAGCT | 131 | 1693 |
| 875603 | N/A | N/A | 111034 | 111053 | CAACTATCCACACAAGAAAG | 95 | 1694 |
| 875627 | N/A | N/A | 112878 | 112897 | CTTGGCTGTAACTAAATAAA | 81 | 1695 |
| 875651 | N/A | N/A | 115321 | 115340 | TTATTTATAATACCTAAAAC | 91 | 1696 |
| 875675 | N/A | N/A | 117891 | 117910 | CTCCCTAATTTTAATGCAGA | 75 | 1697 |
| 875699 | N/A | N/A | 120877 | 120896 | CTCATCTCATACACAAAAAT | 158 | 1698 |
| 875723 | N/A | N/A | 124851 | 124870 | TATTTCTCCCAGAACTGATA | 94 | 1699 |
| 875747 | N/A | N/A | 127963 | 127982 | CTCACTGACTACTCCTATCA | 90 | 1700 |
| 875771 | N/A | N/A | 130056 | 130075 | AAGAACTGATTATATAATTA | 82 | 1701 |
| 875795 | N/A | N/A | 131935 | 131954 | AAGTAGTGAAGCAAAATGTT | 68 | 1702 |
| 875819 | N/A | N/A | 133588 | 133607 | ATGTTCTTTCCACTTGTTAA | 68 | 1703 |
| 875843 | N/A | N/A | 136489 | 136508 | ACATGAATATTATTTCTTAT | 116 | 1704 |
| 875867 | N/A | N/A | 138357 | 138376 | CCTTATTTTTATTTTTATT | 138 | 1705 |
| 875891 | N/A | N/A | 140799 | 140818 | ATTTAAAGACTATAATACGG | 77 | 1706 |
| 875915 | N/A | N/A | 142869 | 142888 | GGTAGGCAAGGCTGCCGAGT | 83 | 1707 |
| 875939 | N/A | N/A | 145137 | 145156 | TACTGCCCCAGGGAACTGAT | 81 | 1708 |
| 875963 | N/A | N/A | 146696 | 146715 | AAAGCAAATCAACTGCAGTG | 72 | 1709 |
| 875987 | N/A | N/A | 148256 | 148275 | GAAGGCCAACTGAGTCCTAG | 77 | 1710 |

TABLE 24

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 708199 | 1477 | 1496 | 81637 | 81656 | GCTAACTGGTTTGCCCTTGC | 31 | 32 |
| 708439 | 3944 | 3963 | 147859 | 147878 | CATCATTGGCGCATGGGCAG | 99 | 1711 |
| 874170 | 188 | 207 | 2178 | 2197 | GGTGGCCACCGCGGGACTCC | 87 | 1712 |
| 874194 | 397 | 416 | 2387 | 2406 | CCGCCGCCGTTGCCGTTGCT | 83 | 1713 |

TABLE 24-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 874218 | 1081 | 1100 | 49255 | 49274 | GTACTTTTCTCATGTGCGGC | 42 | 1714 |
| 874239 | 1540 | 1559 | 81700 | 81719 | CTCCTATCATCATTTTCCAG | 65 | 1715 |
| 874263 | 1768 | 1787 | 83379 | 83398 | TCTGAACCAGAATTCGGGTT | 92 | 1716 |
| 874287 | 2662 | 2681 | 112971 | 112990 | GCACTTGGTTCAATTTTGTC | 53 | 1717 |
| 874311 | 2810 | 2829 | 113119 | 113138 | GCTGGAAGTCTGAACCCCTT | 47 | 1718 |
| 874357 | 4216 | 4235 | 148967 | 148986 | GGATGTTACAAGAAATCAAC | 43 | 1719 |
| 874381 | 4382 | 4401 | 149133 | 149152 | CAAGGGTTATTAAAAAATAA | 85 | 1720 |
| 874404 | 4545 | 4564 | 149296 | 149315 | AATAATAATCCGTCAGTTTG | 117 | 1721 |
| 874476 | N/A | N/A | 3616 | 3635 | ACTCCCCACCCCTTCCCTTC | 84 | 1722 |
| 874500 | N/A | N/A | 3958 | 3977 | CCCCCAGCCCCTACTACAAC | 96 | 1723 |
| 874524 | N/A | N/A | 7091 | 7110 | ATCACTAAAAGAAAAATATT | 87 | 1724 |
| 874548 | N/A | N/A | 8823 | 8842 | ATAAACTGTTTACATCTCCG | 29 | 1725 |
| 874572 | N/A | N/A | 12217 | 12236 | AAGGCCATCCTGGGCAACAG | 79 | 1726 |
| 874596 | N/A | N/A | 15407 | 15426 | GAGTCTCACTCTGCTCTGTG | 64 | 1727 |
| 874620 | N/A | N/A | 17861 | 17880 | AAAACAGTGAACCATGATTC | 56 | 1728 |
| 874644 | N/A | N/A | 20157 | 20176 | TGCTCCCCAATGTCCACCG | 90 | 1729 |
| 874668 | N/A | N/A | 23193 | 23212 | TTATGTTACATCTGCCAACA | 60 | 1730 |
| 874692 | N/A | N/A | 27712 | 27731 | TTTTCTGAAATGTTTTATAT | 126 | 1731 |
| 874716 | N/A | N/A | 30303 | 30322 | AATCTTTTTATTCTTGTAAT | 54 | 1732 |
| 874740 | N/A | N/A | 32095 | 32114 | AGAAAGTTTTAAAAATTAGG | 82 | 1733 |
| 874764 | N/A | N/A | 33231 | 33250 | TGTCCTTCAGTAGTTTCTAA | 38 | 1734 |
| 874788 | N/A | N/A | 36528 | 36547 | TTTAAGTAATGCTTTATATT | 126 | 1735 |
| 874812 | N/A | N/A | 37937 | 37956 | TGTTTAAGTAAAATGTTTTT | 119 | 1736 |
| 874836 | N/A | N/A | 40941 | 40960 | TGAGGTATCCAGAGTTACTA | 45 | 1737 |
| 874860 | N/A | N/A | 42836 | 42855 | AAATAATAATAATACAGAAG | 90 | 1738 |
| 874884 | N/A | N/A | 44389 | 44408 | CACGACTGGTCGATCCCTAG | 51 | 1739 |
| 874908 | N/A | N/A | 45927 | 45946 | TCATTAAAAAAACACATATA | 99 | 1740 |
| 874932 | N/A | N/A | 47502 | 47521 | CTAATAACTTACAACAACTG | 102 | 1741 |
| 874956 | N/A | N/A | 49373 | 49392 | CCCACCTCTTTTTGCATAAC | 85 | 1742 |
| 874980 | N/A | N/A | 52015 | 52034 | TATAGAAGAGGGCAATTTCT | 86 | 1743 |
| 875004 | N/A | N/A | 54998 | 55017 | GAAGGAAAAAAATAGAGGAG | 89 | 1744 |
| 875028 | N/A | N/A | 57198 | 57217 | AATAATAAAGACAGTATCAC | 86 | 1745 |
| 875052 | N/A | N/A | 59519 | 59538 | AATAATTCCATTCAAAGTAT | 81 | 1746 |
| 875076 | N/A | N/A | 61682 | 61701 | TAAAATGAAATTAATTCCAA | 117 | 1747 |
| 875100 | N/A | N/A | 63482 | 63501 | GATAAAGTGAGATAAAATAG | 103 | 1748 |
| 875124 | N/A | N/A | 66333 | 66352 | TAAATCCAGGAGTAAAAGAA | 81 | 1749 |

TABLE 24-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 875148 | N/A | N/A | 69107 | 69126 | ACTGAGTTCTATAGGTGCTT | 31 | 1750 |
| 875172 | N/A | N/A | 71274 | 71293 | CAAAGTTCTAAGGAACAAAA | 113 | 1751 |
| 875196 | N/A | N/A | 72792 | 72811 | GCAAGATCTGGGTATCCATT | 40 | 1752 |
| 875220 | N/A | N/A | 74536 | 74555 | CTCTAGTTGGGAGTTAGACT | 109 | 1753 |
| 875244 | N/A | N/A | 76866 | 76885 | GGCTTAAAATGTCCTACTTC | 90 | 1754 |
| 875268 | N/A | N/A | 79384 | 79403 | ACATCCAGTAAAAAGTAAAT | 78 | 1755 |
| 875292 | N/A | N/A | 81142 | 81161 | ATGGGCATGGTAGCACGCGC | 80 | 1756 |
| 875316 | N/A | N/A | 82640 | 82659 | CAATTAGCTGCACAAACGGA | 104 | 1757 |
| 875340 | N/A | N/A | 84332 | 84351 | CAGTGAGCAAAGAAATTTCA | 118 | 1758 |
| 875364 | N/A | N/A | 85737 | 85756 | TAATTATCAGGCAGAGATAA | 79 | 1759 |
| 875388 | N/A | N/A | 88525 | 88544 | ACACTTTACTCACTGCGAAA | 41 | 1760 |
| 875412 | N/A | N/A | 90352 | 90371 | AACTGCCATTTTTCCAATTA | 49 | 1761 |
| 875436 | N/A | N/A | 92751 | 92770 | TGAGGAAAGGCTACCTTTGC | 87 | 1762 |
| 875460 | N/A | N/A | 95519 | 95538 | GAATTTGCCCCAAATAAGCC | 85 | 1763 |
| 875484 | N/A | N/A | 97532 | 97551 | GCTAACTGAAAAAGTACAGC | 89 | 1764 |
| 875508 | N/A | N/A | 99312 | 99331 | TTGTTCTAATGCTATATTGC | 36 | 1765 |
| 875532 | N/A | N/A | 101681 | 101700 | GCTGGTAACGATGTGGATAA | 52 | 1766 |
| 875556 | N/A | N/A | 105449 | 105468 | AGTTAAAATCATATCAACTA | 94 | 1767 |
| 875580 | N/A | N/A | 108631 | 108650 | AAAGTGGAAAAATTCAATTG | 117 | 1768 |
| 875604 | N/A | N/A | 111039 | 111058 | TTGAACAACTATCCACACAA | 119 | 1769 |
| 875628 | N/A | N/A | 113298 | 113317 | TAAGGGCAATGTATAAAGTA | 82 | 1770 |
| 875652 | N/A | N/A | 115440 | 115459 | GTTACAGTACCCTGTGAAGA | 75 | 1771 |
| 875676 | N/A | N/A | 118364 | 118383 | AAAATGAAAACTTTATGTCA | 87 | 1772 |
| 875700 | N/A | N/A | 120891 | 120910 | CCTGGACCACTACTCTCATC | 77 | 1773 |
| 875724 | N/A | N/A | 124961 | 124980 | AGCAGGCACAAAACTGATAC | 58 | 1774 |
| 875748 | N/A | N/A | 128029 | 128048 | ACACACCAAAAAAATTAAGG | 97 | 1775 |
| 875772 | N/A | N/A | 130077 | 130096 | AGAACTTGTTCATAAAATCC | 57 | 1776 |
| 875796 | N/A | N/A | 131945 | 131964 | CCCTCAGATCAAGTAGTGAA | 69 | 1777 |
| 875820 | N/A | N/A | 133661 | 133680 | GCAATGGAAATTTTAGCTTA | 39 | 1778 |
| 875844 | N/A | N/A | 136534 | 136553 | ATCTAGTAATGGATCCAAAA | 80 | 1779 |
| 875868 | N/A | N/A | 138482 | 138501 | AATCCTTAATATCCTCTAGA | 48 | 1780 |
| 875892 | N/A | N/A | 140856 | 140875 | TGAAATATTTTTACTATGCA | 57 | 1781 |
| 875916 | N/A | N/A | 142990 | 143009 | ATTCCAAAATAGTTCCCCAC | 79 | 1782 |
| 875940 | N/A | N/A | 145153 | 145172 | TAAAGTCAAAAAAGACTACT | 115 | 1783 |

TABLE 24-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 875964 | N/A | N/A | 146768 | 146787 | CTCTTATGAAGCTGACTCCA | 82 | 1784 |
| 875988 | N/A | N/A | 148406 | 148425 | TACACTCAAAGCCAGTCCAT | 87 | 1785 |

TABLE 25

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 708199 | 1477 | 1496 | 81637 | 81656 | GCTAACTGGTTTGCCCTTGC | 27 | 32 |
| 874171 | 193 | 212 | 2183 | 2202 | GACTCGGTGGCCACCGCGGG | 80 | 1786 |
| 874195 | 402 | 421 | 2392 | 2411 | ACGCGCCGCCGCCGTTGCCG | 92 | 1787 |
| 874219 | 1083 | 1102 | 49257 | 49276 | CTGTACTTTTCTCATGTGCG | 44 | 1788 |
| 874240 | 1541 | 1560 | 81701 | 81720 | ACTCCTATCATCATTTTCCA | 85 | 1789 |
| 874264 | 1770 | 1789 | 83381 | 83400 | GGTCTGAACCAGAATTCGGG | 59 | 1790 |
| 874288 | 2664 | 2683 | 112973 | 112992 | TAGCACTTGGTTCAATTTTG | 26 | 1791 |
| 874312 | 2812 | 2831 | 113121 | 113140 | GGGCTGGAAGTCTGAACCCC | 120 | 1792 |
| 874334 | 3946 | 3965 | 147861 | 147880 | AGCATCATTGGCGCATGGGC | 24 | 1793 |
| 874358 | 4230 | 4249 | 148981 | 149000 | TTAGCATTCCTATTGGATGT | 70 | 1794 |
| 874382 | 4387 | 4406 | 149138 | 149157 | ACTTTCAAGGGTTATTAAAA | 54 | 1795 |
| 874405 | 4556 | 4575 | 149307 | 149326 | CTTGATTTATAAATAATAAT | 90 | 1796 |
| 874477 | N/A | N/A | 3621 | 3640 | CGGGCACTCCCCACCCCTTC | 71 | 1797 |
| 874501 | N/A | N/A | 4095 | 4114 | CGTTTCCTTCTCCCTTTGAA | 20 | 1798 |
| 874525 | N/A | N/A | 7401 | 7420 | TAGGCCCTTCTACAAGATAT | 79 | 1799 |
| 874549 | N/A | N/A | 9003 | 9022 | TGGTGGTGTGCGCATGTAGA | 47 | 1800 |
| 874573 | N/A | N/A | 12222 | 12241 | AATTCAAGGCCATCCTGGGC | 73 | 1801 |
| 874597 | N/A | N/A | 15438 | 15457 | TCTTCCAAACTTTTTTTTTT | 48 | 1802 |
| 874621 | N/A | N/A | 18178 | 18197 | GAAGAGTGAACCATGGCCAG | 69 | 1803 |
| 874645 | N/A | N/A | 20304 | 20323 | AGCAACCCGACCACAGCTGG | 86 | 1804 |
| 874669 | N/A | N/A | 23253 | 23272 | GCTGTATTTTTACTCACCTT | 18 | 1805 |
| 874693 | N/A | N/A | 27825 | 27844 | AATGTTCATCTTTTCACATC | 42 | 1806 |
| 874717 | N/A | N/A | 30442 | 30461 | TCATAATCTCAAATGCAAGC | 39 | 1807 |
| 874741 | N/A | N/A | 32163 | 32182 | CTGGGAGGCCAAGGTGAGTC | 71 | 1808 |
| 874765 | N/A | N/A | 33310 | 33329 | ATAATTATAGAGCTTCATGT | 42 | 1809 |
| 874789 | N/A | N/A | 36607 | 36626 | AACTGCTGGATAGCATTAAA | 73 | 1810 |
| 874813 | N/A | N/A | 37953 | 37972 | TAAAAGTCTAAAATTATGTT | 85 | 1811 |

TABLE 25-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 874837 | N/A | N/A | 41033 | 41052 | GGGAAGAAGGATAGAACACT | 53 | 1812 |
| 874861 | N/A | N/A | 42880 | 42899 | GCATTGGTGACAGAGCAAAA | 81 | 1813 |
| 874885 | N/A | N/A | 44413 | 44432 | ATTCAGATCCAAAAAGTCTA | 107 | 1814 |
| 874909 | N/A | N/A | 45945 | 45964 | TGTACATTTTATACAGAGTC | 38 | 1815 |
| 874933 | N/A | N/A | 47521 | 47540 | GCAGTTTATCCCCAATAATC | 35 | 1816 |
| 874957 | N/A | N/A | 49426 | 49445 | ATCTTTGCTTGAATAAATCT | 66 | 1817 |
| 874981 | N/A | N/A | 52019 | 52038 | CTTTTATAGAAGAGGGCAAT | 76 | 1818 |
| 875005 | N/A | N/A | 55002 | 55021 | AAATGAAGGAAAAAAATAGA | 85 | 1819 |
| 875029 | N/A | N/A | 57201 | 57220 | ATAAATAATAAAGACAGTAT | 112 | 1820 |
| 875053 | N/A | N/A | 59564 | 59583 | TCTTTAGAGATTTATTTGAG | 67 | 1821 |
| 875077 | N/A | N/A | 61729 | 61748 | TCAAACCTATGGCAAAAGTG | 71 | 1822 |
| 875101 | N/A | N/A | 63615 | 63634 | TTATGGTGAGCTACGATGGC | 72 | 1823 |
| 875125 | N/A | N/A | 66398 | 66417 | GTGGGCTTGGTTTTGAAAAA | 67 | 1824 |
| 875149 | N/A | N/A | 69151 | 69170 | AATAATAATTTGAGATACCC | 77 | 1825 |
| 875173 | N/A | N/A | 71317 | 71336 | CTTTTAGAATCGAATACAAT | 83 | 1826 |
| 875197 | N/A | N/A | 72817 | 72836 | CATTGCATCATTAGCTAGAA | 67 | 1827 |
| 875221 | N/A | N/A | 74550 | 74569 | GCACAGGAAATTTTCTCTAG | 54 | 1828 |
| 875245 | N/A | N/A | 76887 | 76906 | CAACCTTTTCTTCAGACAAG | 120 | 1829 |
| 875269 | N/A | N/A | 79445 | 79464 | TTACTTAAGTAATGTATGCC | 105 | 1830 |
| 875293 | N/A | N/A | 81388 | 81407 | TTCTGTTACCTTTTCTCCAG | 60 | 1831 |
| 875317 | N/A | N/A | 82821 | 82840 | ACCTCAAACTGAACCGCCAG | 73 | 1832 |
| 875341 | N/A | N/A | 84407 | 84426 | GTATCATATATTTCTCAGCC | 23 | 1833 |
| 875365 | N/A | N/A | 85746 | 85765 | AAAGAAGCATAATTATCAGG | 65 | 1834 |
| 875389 | N/A | N/A | 88528 | 88547 | TTAACACTTTACTCACTGCG | 33 | 1835 |
| 875413 | N/A | N/A | 90523 | 90542 | GTTTGTATCCCATATGACTT | 42 | 1836 |
| 875437 | N/A | N/A | 92768 | 92787 | AAAGCTAAAACACAGGCTGA | 79 | 1837 |
| 875461 | N/A | N/A | 95659 | 95678 | TCAAGGAATATTAGTCAGTC | 70 | 1838 |
| 875485 | N/A | N/A | 97621 | 97640 | AAGACTTTTTATGTTGCTCC | 15 | 1839 |
| 875509 | N/A | N/A | 99383 | 99402 | TATTGCCATCTTACAAATAG | 100 | 1840 |
| 875533 | N/A | N/A | 102082 | 102101 | TGGTGGCAGGAGGCAGGAGA | 72 | 1841 |
| 875557 | N/A | N/A | 105635 | 105654 | ATGTGACGGCATGTGCCTGT | 141 | 1842 |
| 875581 | N/A | N/A | 108635 | 108654 | TCCCAAAGTGGAAAAATTCA | 83 | 1843 |
| 875605 | N/A | N/A | 111085 | 111104 | GCCAAACAGAACCTTCCAGT | 81 | 1844 |
| 875629 | N/A | N/A | 113410 | 113429 | CTTGTTTTTCTAGCCCTGGG | 82 | 1845 |
| 875653 | N/A | N/A | 115560 | 115579 | CAGCTATTTTTAAGAAACTG | 74 | 1846 |
| 875677 | N/A | N/A | 118824 | 118843 | TTCCAAGGCTAAAAAAAAAA | 116 | 1847 |

TABLE 25-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 875701 | N/A | N/A | 120923 | 120942 | GGACAACGGATATCCACAAG | 86 | 1848 |
| 875725 | N/A | N/A | 125020 | 125039 | TTAAAATATAACTCACAACA | 87 | 1849 |
| 875749 | N/A | N/A | 128050 | 128069 | ATCATCAATGGCTGCTAAAA | 51 | 1850 |
| 875773 | N/A | N/A | 130117 | 130136 | GAATGACTGCTTACAACTAG | 50 | 1851 |
| 875797 | N/A | N/A | 131959 | 131978 | TGTAATGCCAGTGACCCTCA | 54 | 1852 |
| 875821 | N/A | N/A | 133854 | 133873 | TGAAAATCATCTGTACCTCA | 58 | 1853 |
| 875845 | N/A | N/A | 136627 | 136646 | GTACCAAAATAAAACTATTT | 81 | 1854 |
| 875869 | N/A | N/A | 138721 | 138740 | TTTCCTAGCACCAAATAAAT | 85 | 1855 |
| 875893 | N/A | N/A | 141020 | 141039 | TTTGAAATTTCACTTTTAAA | 86 | 1856 |
| 875917 | N/A | N/A | 143008 | 143027 | AGCCCATACACAGAAATGAT | 77 | 1857 |
| 875941 | N/A | N/A | 145161 | 145180 | ATACATACTAAAGTCAAAAA | 79 | 1858 |
| 875965 | N/A | N/A | 146830 | 146849 | TACATGTAAGTTCACATGCC | 129 | 1859 |
| 875989 | N/A | N/A | 148687 | 148706 | ATTCGCTTTTCCCCCTCCCA | 75 | 1860 |

TABLE 26

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 708152 | 1085 | 1104 | 49259 | 49278 | TTCTGTACTTTTCTCATGTG | 50 | 1861 |
| 708199 | 1477 | 1496 | 81637 | 81656 | GCTAACTGGTTTGCCCTTGC | 31 | 32 |
| 874172 | 198 | 217 | 2188 | 2207 | GGCGAGACTCGGTGGCCACC | 90 | 1862 |
| 874196 | 407 | 426 | 2397 | 2416 | CCGAAACGCGCCGCCGCCGT | 88 | 1863 |
| 874241 | 1553 | 1572 | 81713 | 81732 | TTTTTCTTCCTCACTCCTAT | 70 | 1864 |
| 874265 | 1800 | 1819 | N/A | N/A | GCCAGGGAACACCTCCATTA | 80 | 1865 |
| 874289 | 2665 | 2684 | 112974 | 112993 | TTAGCACTTGGTTCAATTTT | 55 | 1866 |
| 874313 | 2813 | 2832 | 113122 | 113141 | TGGGCTGGAAGTCTGAACCC | 88 | 1867 |
| 874335 | 3947 | 3966 | 147862 | 147881 | TAGCATCATTGGCGCATGGG | 29 | 1868 |
| 874359 | 4235 | 4254 | 148986 | 149005 | AACTGTTAGCATTCCTATTG | 32 | 1869 |
| 874383 | 4392 | 4411 | 149143 | 149162 | TCATGACTTTCAAGGGTTAT | 46 | 1870 |
| 874406 | 4561 | 4580 | 149312 | 149331 | TCAAACTTGATTTATAAATA | 94 | 1871 |
| 874478 | N/A | N/A | 3644 | 3663 | AAGGAGGAAGGCCGGGACGG | 90 | 1872 |
| 874502 | N/A | N/A | 4159 | 4178 | TGGTAAGCTCTGGCGGCACT | 50 | 1873 |
| 874526 | N/A | N/A | 7402 | 7421 | TTAGGCCCTTCTACAAGATA | 59 | 1874 |
| 874550 | N/A | N/A | 9185 | 9204 | AAAAACACAAGTACTTTCAT | 78 | 1875 |
| 874574 | N/A | N/A | 12346 | 12365 | AAGATCCTGCAACACACACA | 62 | 1876 |

TABLE 26-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 874598 | N/A | N/A | 15441 | 15460 | CAGTCTTCCAAACTTTTTT | 47 | 1877 |
| 874622 | N/A | N/A | 18202 | 18221 | CATAGAGCTTAAATTTTAGT | 57 | 1878 |
| 874646 | N/A | N/A | 20308 | 20327 | CCCCAGCAACCCGACCACAG | 94 | 1879 |
| 874670 | N/A | N/A | 23345 | 23364 | ACTGATAAATGACTCATCCC | 48 | 1880 |
| 874694 | N/A | N/A | 27838 | 27857 | ATTACCTAAATAAAATGTTC | 88 | 1881 |
| 874718 | N/A | N/A | 30485 | 30504 | TAATTGTAAAGTCCCTGCTC | 115 | 1882 |
| 874742 | N/A | N/A | 32207 | 32226 | AAAAAAGGCCAGTCGCAGTG | 73 | 1883 |
| 874766 | N/A | N/A | 33314 | 33333 | CAATATAATTATAGAGCTTC | 48 | 1884 |
| 874790 | N/A | N/A | 36647 | 36666 | GCATAAGACACCATGCCTAG | 89 | 1885 |
| 874814 | N/A | N/A | 38116 | 38135 | TCATGTCTCTCATATGTTTA | 67 | 1886 |
| 874838 | N/A | N/A | 41106 | 41125 | TAGAGTGATGGTAGGCATAC | 64 | 1887 |
| 874862 | N/A | N/A | 42969 | 42988 | CCCCGCTACTTGGTAGGGTG | 89 | 1888 |
| 874886 | N/A | N/A | 44472 | 44491 | TTTTAATAAAATAATCACAA | 90 | 1889 |
| 874910 | N/A | N/A | 46039 | 46058 | GCATGAGTCAATTAAACCTC | 39 | 1890 |
| 874934 | N/A | N/A | 47558 | 47577 | TTTTAACTTCATGGAATTAC | 72 | 1891 |
| 874958 | N/A | N/A | 49453 | 49472 | AAAAAAGTTTGTAAGATCAC | 87 | 1892 |
| 874982 | N/A | N/A | 52064 | 52083 | TGGTTTTCTCCATACTGATA | 43 | 1893 |
| 875006 | N/A | N/A | 55055 | 55074 | GTTGGAGTAAAGAGGAAAAC | 88 | 1894 |
| 875030 | N/A | N/A | 57279 | 57298 | GGCACTGAATTTCATTTATT | 43 | 1895 |
| 875054 | N/A | N/A | 59820 | 59839 | CGGCTGGAGTGCAATCTCAG | 82 | 1896 |
| 875078 | N/A | N/A | 61798 | 61817 | ACAGAATTTAGGAATTGAAA | 91 | 1897 |
| 875102 | N/A | N/A | 63893 | 63912 | AAAATGTAAATTGATTGTAG | 111 | 1898 |
| 875126 | N/A | N/A | 66456 | 66475 | AATAAAAACAAACCACAATG | 100 | 1899 |
| 875150 | N/A | N/A | 69170 | 69189 | CAAAAATATATATACATAAA | 103 | 1900 |
| 875174 | N/A | N/A | 71392 | 71411 | ATACAATTCCCAGCATTTCC | 78 | 1901 |
| 875198 | N/A | N/A | 72868 | 72887 | CATCAGGATGCTGAGAAAAT | 90 | 1902 |
| 875222 | N/A | N/A | 74610 | 74629 | AGTACTGACTTATGAAAGCA | 85 | 1903 |
| 875246 | N/A | N/A | 76925 | 76944 | CTTTAATTCCAATGTAACCT | 42 | 1904 |
| 875270 | N/A | N/A | 79474 | 79493 | AATCACACTTACTTATGGAG | 75 | 1905 |
| 875294 | N/A | N/A | 81536 | 81555 | TTTAAAGCCACAGTTTATGT | 49 | 1906 |
| 875318 | N/A | N/A | 82842 | 82861 | AATATCGGCAATGCTGATGA | 84 | 1907 |
| 875342 | N/A | N/A | 84409 | 84428 | AAGTATCATATATTTCTCAG | 50 | 1908 |
| 875366 | N/A | N/A | 85841 | 85860 | TTCAAGACTGGCTGAAGAAA | 86 | 1909 |
| 875390 | N/A | N/A | 88618 | 88637 | ACAAAACTTTATAGTTTTAC | 99 | 1910 |
| 875414 | N/A | N/A | 90912 | 90931 | GGAATTTGCTGGCAATCAAA | 31 | 1911 |
| 875438 | N/A | N/A | 92803 | 92822 | AATAAGTCAAGAATGAAGCT | 79 | 1912 |

TABLE 26-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 875462 | N/A | N/A | 95679 | 95698 | AAAATGTGGTATTATCCACA | 119 | 1913 |
| 875486 | N/A | N/A | 97661 | 97680 | AGGCACCTAAAAGTAGTAAG | 45 | 1914 |
| 875510 | N/A | N/A | 99409 | 99428 | ACAGCCCTATTTGATGTAGA | 48 | 1915 |
| 875534 | N/A | N/A | 102327 | 102346 | AATATAAAAGGCACTCAAGC | 95 | 1916 |
| 875558 | N/A | N/A | 105640 | 105659 | GCCATATGTGACGGCATGTG | 92 | 1917 |
| 875582 | N/A | N/A | 108837 | 108856 | CCTCACCAAATGAACTAAAA | 105 | 1918 |
| 875606 | N/A | N/A | 111160 | 111179 | ATATTGGTCAGTTAGACATT | 85 | 1919 |
| 875630 | N/A | N/A | 113616 | 113635 | ACATTAACTAAAACACAGTT | 76 | 1920 |
| 875654 | N/A | N/A | 115601 | 115620 | AACTTAAAACTTTGTCAATT | 97 | 1921 |
| 875678 | N/A | N/A | 118878 | 118897 | CTCTATAATTTGATTACATT | 70 | 1922 |
| 875702 | N/A | N/A | 120942 | 120961 | TTTTCAACAAATGAGGTGGG | 87 | 1923 |
| 875726 | N/A | N/A | 125029 | 125048 | TGAAAGTTTTTAAAATATAA | 93 | 1924 |
| 875750 | N/A | N/A | 128051 | 128070 | TATCATCAATGGCTGCTAAA | 57 | 1925 |
| 875774 | N/A | N/A | 130162 | 130181 | TTTCTGGTGTGGCATTAACC | 68 | 1926 |
| 875798 | N/A | N/A | 132162 | 132181 | TGCTTATTATTCTCACATAT | 22 | 1927 |
| 875822 | N/A | N/A | 133992 | 134011 | GTTCATTCCAGATTTCACTG | 34 | 1928 |
| 875846 | N/A | N/A | 136702 | 136721 | AGTAAAAGGAATAAAATCAT | 98 | 1929 |
| 875870 | N/A | N/A | 138751 | 138770 | AGAGCATCTATTAAAGGATT | 76 | 1930 |
| 875894 | N/A | N/A | 141087 | 141106 | CGGAATCTCAGAGGTTTTTG | 52 | 1931 |
| 875918 | N/A | N/A | 143022 | 143041 | CCCTCAAGATAATAAGCCCA | 87 | 1932 |
| 875942 | N/A | N/A | 145277 | 145296 | GTACAGGAGAATGTACAGGG | 83 | 1933 |
| 875966 | N/A | N/A | 146947 | 146966 | AATGCCGTTTTTACTCTCAC | 18 | 1934 |
| 875990 | N/A | N/A | 148704 | 148723 | ACAAAACTCAAAATTGAATT | 103 | 1935 |

TABLE 27

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 708153 | 1087 | 1106 | 49261 | 49280 | GATTCTGTACTTTTCTCATG | 45 | 1936 |
| 708199 | 1477 | 1496 | 81637 | 81656 | GCTAACTGGTTTGCCCTTGC | 29 | 32 |
| 874173 | 203 | 222 | 2193 | 2212 | GAAGCGGCGAGACTCGGTGG | 96 | 1937 |
| 874197 | 412 | 431 | 2402 | 2421 | CCGGGCCGAAACGCGCCGCC | 109 | 1938 |
| 874242 | 1554 | 1573 | 81714 | 81733 | ATTTTTCTTCCTCACTCCTA | 64 | 1939 |
| 874266 | 2091 | 2110 | 88201 | 88220 | CAAATTCTAGGCCACTGGAT | 91 | 1940 |

TABLE 27-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 874290 | 2666 | 2685 | 112975 | 112994 | CTTAGCACTTGGTTCAATTT | 45 | 1941 |
| 874314 | 2814 | 2833 | 113123 | 113142 | CTGGGCTGGAAGTCTGAACC | 92 | 1942 |
| 874336 | 3948 | 3967 | 147863 | 147882 | TTAGCATCATTGGCGCATGG | 52 | 1943 |
| 874360 | 4240 | 4259 | 148991 | 149010 | AAGTGAACTGTTAGCATTCC | 34 | 1944 |
| 874384 | 4397 | 4416 | 149148 | 149167 | TGTGTTCATGACTTTCAAGG | 18 | 1945 |
| 874407 | 4566 | 4585 | 149317 | 149336 | CCTCATCAAACTTGATTTAT | 52 | 1946 |
| 874479 | N/A | N/A | 3666 | 3685 | CGCCGGAGAGGTCTGGCGGG | 91 | 1947 |
| 874503 | N/A | N/A | 4530 | 4549 | AAGTAGTGTTTGGGATGCTT | 12 | 1948 |
| 874527 | N/A | N/A | 7453 | 7472 | AAACCCCATGTACATAGATG | 71 | 1949 |
| 874551 | N/A | N/A | 9771 | 9790 | TTCGAGATGAGCCTAACCAA | 78 | 1950 |
| 874575 | N/A | N/A | 12824 | 12843 | TACTTAAAATGCATAAAAAA | 86 | 1951 |
| 874599 | N/A | N/A | 15653 | 15672 | TAAGTGAACCACCTGCCTCA | 98 | 1952 |
| 874623 | N/A | N/A | 18210 | 18229 | CCTGCTTTCATAGAGCTTAA | 65 | 1953 |
| 874647 | N/A | N/A | 20402 | 20421 | ATTTCTTCACCCGTAAATAG | 60 | 1954 |
| 874671 | N/A | N/A | 23871 | 23890 | CATTGGTCAACAGTTCACAA | 42 | 1955 |
| 874695 | N/A | N/A | 27880 | 27899 | CTAATAGGCACACAATAAAT | 61 | 1956 |
| 874719 | N/A | N/A | 30635 | 30654 | TTATTACTTGCCAGGCATTG | 40 | 1957 |
| 874743 | N/A | N/A | 32289 | 32308 | TATGTTATTAAGTGTTTAAT | 89 | 1958 |
| 874767 | N/A | N/A | 33325 | 33344 | CTGTCACCATACAATATAAT | 67 | 1959 |
| 874791 | N/A | N/A | 36798 | 36817 | CTGCTAGACAAATTCTGTAA | 77 | 1960 |
| 874815 | N/A | N/A | 38215 | 38234 | TTATTAATTTCCTTATTTTG | 91 | 1961 |
| 874839 | N/A | N/A | 41127 | 41146 | ATGCCAAAATCACTGTGATT | 87 | 1962 |
| 874863 | N/A | N/A | 43158 | 43177 | GTCAAATTAATATAAAGAAA | 95 | 1963 |
| 874887 | N/A | N/A | 44512 | 44531 | TCTCATAAACATTAGTCATG | 43 | 1964 |
| 874911 | N/A | N/A | 46136 | 46155 | CAGCACTTCTCTCTCCTGTC | 39 | 1965 |
| 874935 | N/A | N/A | 47663 | 47682 | AATGAATTATATTAGACTGG | 51 | 1966 |
| 874959 | N/A | N/A | 49459 | 49478 | TCTTTAAAAAAGTTTGTAA | 109 | 1967 |
| 874983 | N/A | N/A | 52103 | 52122 | AAAAAAAGAAGGAAACCATG | 98 | 1968 |
| 875007 | N/A | N/A | 55092 | 55111 | CAATGGAATAAGGAAACAGA | 102 | 1969 |
| 875031 | N/A | N/A | 57429 | 57448 | TTGTATTTCTCCGTACTGTC | 40 | 1970 |
| 875055 | N/A | N/A | 59830 | 59849 | TGGAGTCACCCGGCTGGAGT | 86 | 1971 |
| 875079 | N/A | N/A | 61810 | 61829 | AAGAATCAAAAACAGAATT | 95 | 1972 |
| 875103 | N/A | N/A | 63905 | 63924 | TTCAGGGTGATGAAAATGTA | 82 | 1973 |
| 875127 | N/A | N/A | 66510 | 66529 | CATACAAACATAAATTAATT | 112 | 1974 |
| 875151 | N/A | N/A | 69174 | 69193 | ATCTCAAAAATATATATACA | 102 | 1975 |
| 875175 | N/A | N/A | 71435 | 71454 | TGCACTCATAAGTCTGGACG | 79 | 1976 |

TABLE 27-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 875199 | N/A | N/A | 72897 | 72916 | TGGAGAGTTAGCACGAAATG | 106 | 1977 |
| 875223 | N/A | N/A | 74624 | 74643 | TAATGTTATTGAAGAGTACT | 107 | 1978 |
| 875247 | N/A | N/A | 76941 | 76960 | AGAAATTTATGTAATGCTTT | 80 | 1979 |
| 875271 | N/A | N/A | 79484 | 79503 | ATGGGCAGGAAATCACACTT | 79 | 1980 |
| 875295 | N/A | N/A | 81537 | 81556 | CTTTAAAGCCACAGTTTATG | 89 | 1981 |
| 875319 | N/A | N/A | 82852 | 82871 | TCATGGCTCCAATATCGGCA | 16 | 1982 |
| 875343 | N/A | N/A | 84424 | 84443 | GGGTTCCACACACTTAAGTA | 49 | 1983 |
| 875367 | N/A | N/A | 85857 | 85876 | GTAAAATGAACCTAAGTTCA | 77 | 1984 |
| 875391 | N/A | N/A | 88635 | 88654 | TATTAGAGAGGTACTTTACA | 84 | 1985 |
| 875415 | N/A | N/A | 90965 | 90984 | CCTCTCTAGCCCTTACCCTT | 84 | 1986 |
| 875439 | N/A | N/A | 92861 | 92880 | AGCTGAATAGATACATGTGC | 75 | 1987 |
| 875463 | N/A | N/A | 95779 | 95798 | ACGAGAAAAAAACTGCACAC | 95 | 1988 |
| 875487 | N/A | N/A | 97686 | 97705 | GGCTAAATAATACATTTGGT | 54 | 1989 |
| 875511 | N/A | N/A | 99731 | 99750 | GGTCTGACTCCGTTGCCCAG | 84 | 1990 |
| 875535 | N/A | N/A | 102493 | 102512 | ATACCCCAAAAGTACAGGCA | 97 | 1991 |
| 875559 | N/A | N/A | 105649 | 105668 | AAAATATCAGCCATATGTGA | 95 | 1992 |
| 875583 | N/A | N/A | 108869 | 108888 | CACAAGCATCAAGGCCATCT | 85 | 1993 |
| 875607 | N/A | N/A | 111262 | 111281 | TTAGGATGTGGAGGGACCGT | 85 | 1994 |
| 875631 | N/A | N/A | 113671 | 113690 | TCCATTTAATTAATATACTG | 79 | 1995 |
| 875655 | N/A | N/A | 115613 | 115632 | TGTTTCAGTAGGAACTTAAA | 84 | 1996 |
| 875679 | N/A | N/A | 118886 | 118905 | AGATTAAACTCTATAATTTG | 93 | 1997 |
| 875703 | N/A | N/A | 121448 | 121467 | ATTTGTCAAAACTCATTAAA | 73 | 1998 |
| 875727 | N/A | N/A | 125164 | 125183 | CAACATGGTGATTAGATCAT | 73 | 1999 |
| 875751 | N/A | N/A | 128148 | 128167 | AGAAATATTCCAGGCAATAA | 74 | 2000 |
| 875775 | N/A | N/A | 130284 | 130303 | GAATTCAGCTCAACTGTCAT | 91 | 2001 |
| 875799 | N/A | N/A | 132176 | 132195 | AAGATGGGTTTTTTGCTTA | 21 | 2002 |
| 875823 | N/A | N/A | 134012 | 134031 | AGAACCGGCTCTAATGACTA | 72 | 2003 |
| 875847 | N/A | N/A | 136768 | 136787 | GGACTAAACCGGAAGACACT | 64 | 2004 |
| 875871 | N/A | N/A | 138796 | 138815 | GTTTCCCCTTTAATAGTATA | 48 | 2005 |
| 875895 | N/A | N/A | 141093 | 141112 | ACAGTACGGAATCTCAGAGG | 35 | 2006 |
| 875919 | N/A | N/A | 143144 | 143163 | GACAGCACACCGATGATAAA | 85 | 2007 |
| 875943 | N/A | N/A | 145320 | 145339 | CTAAGCTTTGCACACTTGGG | 80 | 2008 |
| 875967 | N/A | N/A | 146952 | 146971 | GATGAAATGCCGTTTTTACT | 39 | 2009 |
| 875991 | N/A | N/A | 148739 | 148758 | AGCACATGATTGTAAACTAT | 35 | 2010 |

TABLE 28

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 708199 | 1477 | 1496 | 81637 | 81656 | GCTAACTGGTTTGCCCTTGC | 29 | 32 |
| 874174 | 208 | 227 | 2198 | 2217 | GCGGCGAAGCGGCGAGACTC | 107 | 2011 |
| 874198 | 428 | 447 | 2418 | 2437 | AAGGAGCCGCCGGGAGCCGG | 87 | 2012 |
| 874220 | 1105 | 1124 | 49279 | 49298 | CGTTTCGGCCCCGAACTGGA | 51 | 2013 |
| 874243 | 1555 | 1574 | 81715 | 81734 | TATTTTTCTTCCTCACTCCT | 70 | 2014 |
| 874267 | 2093 | 2112 | 88203 | 88222 | TACAAATTCTAGGCCACTGG | 62 | 2015 |
| 874291 | 2668 | 2687 | 112977 | 112996 | TCCTTAGCACTTGGTTCAAT | 53 | 2016 |
| 874315 | 2816 | 2835 | 113125 | 113144 | TGCTGGGCTGGAAGTCTGAA | 88 | 2017 |
| 874337 | 3950 | 3969 | 147865 | 147884 | CATTAGCATCATTGGCGCAT | 81 | 2018 |
| 874361 | 4245 | 4264 | 148996 | 149015 | ACTGCAAGTGAACTGTTAGC | 87 | 2019 |
| 874385 | 4402 | 4421 | 149153 | 149172 | GCTGATGTGTTCATGACTTT | 35 | 2020 |
| 874408 | 4571 | 4590 | 149322 | 149341 | GATCACCTCATCAAACTTGA | 52 | 2021 |
| 874480 | N/A | N/A | 3671 | 3690 | CCGCGCGCCGGAGAGGTCTG | 90 | 2022 |
| 874504 | N/A | N/A | 4591 | 4610 | AAAGGGAAACTGAAGTTACC | 155 | 2023 |
| 874528 | N/A | N/A | 7600 | 7619 | CCTTTAATCTGCTTTCTTCT | 103 | 2024 |
| 874552 | N/A | N/A | 9851 | 9870 | GTAGGCTGCGCACGGTGGCT | 90 | 2025 |
| 874576 | N/A | N/A | 12944 | 12963 | AAACCAGGCCGGACGCGGTG | 146 | 2026 |
| 874600 | N/A | N/A | 15789 | 15808 | CTTGTGTCTGTTTTTTAGTA | 69 | 2027 |
| 874624 | N/A | N/A | 18211 | 18230 | TCCTGCTTTCATAGAGCTTA | 81 | 2028 |
| 874648 | N/A | N/A | 20415 | 20434 | CCTCTTGGTCTCAATTTCTT | 74 | 2029 |
| 874672 | N/A | N/A | 23931 | 23950 | GGTCAGAGGTTAAAAGTCTT | 79 | 2030 |
| 874696 | N/A | N/A | 27902 | 27921 | CTTGGCACAGCTCTCCTGAA | 126 | 2031 |
| 874720 | N/A | N/A | 30661 | 30680 | AAGAACAGCTAAAAGTTACT | 89 | 2032 |
| 874744 | N/A | N/A | 32321 | 32340 | ATACAGATCGCATAGCTTAA | 68 | 2033 |
| 874768 | N/A | N/A | 33334 | 33353 | CTATTGGTACTGTCACCATA | 82 | 2034 |
| 874792 | N/A | N/A | 36850 | 36869 | ATCAGTATTTACTACTTCTG | 34 | 2035 |
| 874816 | N/A | N/A | 38219 | 38238 | ACAATTATTAATTTCCTTAT | 114 | 2036 |
| 874840 | N/A | N/A | 41151 | 41170 | ACAGTCAGGAAAAGAGACAA | 96 | 2037 |
| 874864 | N/A | N/A | 43345 | 43364 | AAACCAAATATTTTACTATT | 89 | 2038 |
| 874888 | N/A | N/A | 44523 | 44542 | AATGTTATATTTCTCATAAA | 94 | 2039 |
| 874912 | N/A | N/A | 46218 | 46237 | GTTTCCCCTACGCTGCTCTC | 51 | 2040 |
| 874936 | N/A | N/A | 47696 | 47715 | CCCACAGATGCAGAGGACCA | 76 | 2041 |
| 874960 | N/A | N/A | 49471 | 49490 | AGCCCAGATATTTCTTTAAA | 99 | 2042 |
| 874984 | N/A | N/A | 52289 | 52308 | GTACTAAGAATACAAACAAA | 87 | 2043 |
| 875008 | N/A | N/A | 55163 | 55182 | TTTGCTGACCCCTATCATCT | 82 | 2044 |
| 875032 | N/A | N/A | 57470 | 57489 | ACAGTTTCACTAGGTTCTCA | 24 | 2045 |

TABLE 28-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 875056 | N/A | N/A | 59886 | 59905 | TTTCTACAAAAACGGATATA | 92 | 2046 |
| 875080 | N/A | N/A | 61853 | 61872 | CTGTAGAAGAACTAAGACAA | 81 | 2047 |
| 875104 | N/A | N/A | 64010 | 64029 | TGTCCAGAATGGGCAAACCT | 81 | 2048 |
| 875128 | N/A | N/A | 66875 | 66894 | TGTTTTAACTAAGAGTCAGC | 75 | 2049 |
| 875152 | N/A | N/A | 69497 | 69516 | GGCCAGAGCGGATACCATAT | 88 | 2050 |
| 875176 | N/A | N/A | 71472 | 71491 | TATTTAGTCATTTTTAGCAC | 87 | 2051 |
| 875200 | N/A | N/A | 72951 | 72970 | AAAAGTAGCTCTTTCTAAAG | 87 | 2052 |
| 875224 | N/A | N/A | 74662 | 74681 | ATTAACACACTCTCACTTTG | 64 | 2053 |
| 875248 | N/A | N/A | 76949 | 76968 | TAAGACCAAGAAATTTATGT | 104 | 2054 |
| 875272 | N/A | N/A | 79499 | 79518 | CCTTTTGCCAAACACATGGG | 90 | 2055 |
| 875296 | N/A | N/A | 81540 | 81559 | GTCCTTTAAAGCCACAGTTT | 99 | 2056 |
| 875320 | N/A | N/A | 82893 | 82912 | TTCTCTGAGATCTCTTCTCT | 98 | 2057 |
| 875344 | N/A | N/A | 84594 | 84613 | ACAGTTAAACACTTATCTAA | 88 | 2058 |
| 875368 | N/A | N/A | 85860 | 85879 | GCTGTAAAATGAACCTAAGT | 61 | 2059 |
| 875392 | N/A | N/A | 88725 | 88744 | ATGTTTATAGAATGTACTGA | 60 | 2060 |
| 875416 | N/A | N/A | 91284 | 91303 | CAGAAGCCCTTTGTTACATA | 40 | 2061 |
| 875440 | N/A | N/A | 92863 | 92882 | AAAGCTGAATAGATACATGT | 95 | 2062 |
| 875464 | N/A | N/A | 96003 | 96022 | ACACTTCACACCCACAAGGA | 95 | 2063 |
| 875488 | N/A | N/A | 97870 | 97889 | TAGGGTTTCGCCATGTTATC | 43 | 2064 |
| 875512 | N/A | N/A | 99818 | 99837 | ACTTTTGGTGTTGCTTTTTC | 40 | 2065 |
| 875536 | N/A | N/A | 102497 | 102516 | AGTAATACCCCAAAAGTACA | 151 | 2066 |
| 875560 | N/A | N/A | 105876 | 105895 | CAGCTATAGAATACACATTC | 93 | 2067 |
| 875584 | N/A | N/A | 109381 | 109400 | GATACCTCTACAGAGTCACA | 81 | 2068 |
| 875608 | N/A | N/A | 111328 | 111347 | GGCAGATTTATAGTTCAGAA | 46 | 2069 |
| 875632 | N/A | N/A | 113780 | 113799 | CCCCAATTTATCAATAAGCT | 85 | 2070 |
| 875656 | N/A | N/A | 115778 | 115797 | AAAAACAACAATAAATTCAA | 98 | 2071 |
| 875680 | N/A | N/A | 119028 | 119047 | AAGTTCCCATTGCATTGTTT | 21 | 2072 |
| 875704 | N/A | N/A | 121520 | 121539 | GGACAGAGAAGAGGAACAGG | 83 | 2073 |
| 875728 | N/A | N/A | 125171 | 125190 | AAAACACCAACATGGTGATT | 95 | 2074 |
| 875752 | N/A | N/A | 128189 | 128208 | AGGGTAACCAAACAGCTGGA | 59 | 2075 |
| 875776 | N/A | N/A | 130418 | 130437 | AGTATAACACAGCACCATGT | 78 | 2076 |
| 875800 | N/A | N/A | 132257 | 132276 | ACAGTGAAAAATCTATTATT | 92 | 2077 |
| 875824 | N/A | N/A | 134106 | 134125 | AGCCTGCCTCCATACAGACA | 91 | 2078 |
| 875848 | N/A | N/A | 136819 | 136838 | TCATAAGAGATGACAAGCAC | 66 | 2079 |
| 875872 | N/A | N/A | 138832 | 138851 | ACCTACTATCTTTTACACAC | 84 | 2080 |
| 875896 | N/A | N/A | 141120 | 141139 | ATTCTGTTCATGGAGGTTCA | 41 | 2081 |

TABLE 28-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 875920 | N/A | N/A | 143153 | 143172 | GTGACTATGGACAGCACACC | 77 | 2082 |
| 875944 | N/A | N/A | 145386 | 145405 | AAGCGACAGGAAAGAATTGA | 129 | 2083 |
| 875968 | N/A | N/A | 147009 | 147028 | GAGCCCTTGTTTCCTTTTTC | 109 | 2084 |
| 875992 | N/A | N/A | 148775 | 148794 | AACTGGCAACACCACACATC | 152 | 2085 |

TABLE 29

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 708199 | 1477 | 1496 | 81637 | 81656 | GCTAACTGGTTTGCCCTTGC | 30 | 32 |
| 874175 | 213 | 232 | 2203 | 2222 | TGGCTGCGGCGAAGCGGCGA | 94 | 2086 |
| 874199 | 433 | 452 | 2423 | 2442 | AGACCAAGGAGCCGCCGGGA | 64 | 2087 |
| 874221 | 1125 | 1144 | 49299 | 49318 | TACTCTCCATTATTTCTTCA | 46 | 2088 |
| 874244 | 1557 | 1576 | 81717 | 81736 | TGTATTTTTCTTCCTCACTC | 38 | 2089 |
| 874268 | 2095 | 2114 | 88205 | 88224 | GATACAAATTCTAGGCCACT | 51 | 2090 |
| 874292 | 2669 | 2688 | 112978 | 112997 | ATCCTTAGCACTTGGTTCAA | 87 | 2091 |
| 874316 | 3123 | 3142 | 116359 | 116378 | CTTGATTCACTGGCATGGGC | 52 | 2092 |
| 874338 | 4093 | 4112 | 148844 | 148863 | GGGCAGCCTTACAACTGCTG | 88 | 2093 |
| 874362 | 4257 | 4276 | 149008 | 149027 | CAAGTATCTTCCACTGCAAG | 70 | 2094 |
| 874386 | 4407 | 4426 | 149158 | 149177 | TGCTAGCTGATGTGTTCATG | 66 | 2095 |
| 874409 | 4576 | 4595 | 149327 | 149346 | ACAGTGATCACCTCATCAAA | 83 | 2096 |
| 874433 | N/A | N/A | 146548 | 146567 | GCCAGAGCCTCACTGGCGCA | 122 | 2097 |
| 874481 | N/A | N/A | 3676 | 3695 | ACCACCCGCGCGCCGGAGAG | 89 | 2098 |
| 874505 | N/A | N/A | 4702 | 4721 | GAATTATCTGCCAAATCTCT | 56 | 2099 |
| 874529 | N/A | N/A | 7648 | 7667 | CCAATCCATTTAAAATTGTA | 83 | 2100 |
| 874553 | N/A | N/A | 9909 | 9928 | TTTAAGATTTAGGATTTTTT | 81 | 2101 |
| 874577 | N/A | N/A | 13311 | 13330 | CACAAATAATTACCAGCAAA | 62 | 2102 |
| 874601 | N/A | N/A | 15978 | 15997 | GACCAATATCTGTACTCCCA | 41 | 2103 |
| 874625 | N/A | N/A | 18215 | 18234 | AAGTTCCTGCTTTCATAGAG | 49 | 2104 |
| 874649 | N/A | N/A | 20447 | 20466 | GCAGCCAATGATGAGATACT | 43 | 2105 |
| 874673 | N/A | N/A | 24094 | 24113 | CGGGCCCGGCCCGCATGTTT | 83 | 2106 |
| 874697 | N/A | N/A | 27956 | 27975 | ACCAGCCTGACAGGCTGGGC | 106 | 2107 |
| 874721 | N/A | N/A | 30733 | 30752 | CCAAGCCCATCAATACCACT | 80 | 2108 |
| 874745 | N/A | N/A | 32329 | 32348 | AATATTCCATACAGATCGCA | 30 | 2109 |
| 874769 | N/A | N/A | 33336 | 33355 | CTCTATTGGTACTGTCACCA | 42 | 2110 |

TABLE 29-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 874793 | N/A | N/A | 36881 | 36900 | GAAAGATAAAGTTGTTTATT | 125 | 2111 |
| 874817 | N/A | N/A | 38303 | 38322 | TACTGGTTCTTGACCAGAAA | 91 | 2112 |
| 874841 | N/A | N/A | 41190 | 41209 | CAGCATCACCTAGTAATTAG | 47 | 2113 |
| 874865 | N/A | N/A | 43373 | 43392 | TTACTTTTAATCTTTTCATT | 79 | 2114 |
| 874889 | N/A | N/A | 44532 | 44551 | TTAAAGTGAAATGTTATATT | 99 | 2115 |
| 874913 | N/A | N/A | 46464 | 46483 | GCATAAAGAACTCTGCAGAC | 72 | 2116 |
| 874937 | N/A | N/A | 48095 | 48114 | AACCATGCCTCTTTTTCTC | 30 | 2117 |
| 874961 | N/A | N/A | 49914 | 49933 | TACAAACTAATTTTTTAAGA | 117 | 2118 |
| 874985 | N/A | N/A | 52437 | 52456 | TTGATTAAACCATACCTTCC | 136 | 2119 |
| 875009 | N/A | N/A | 55244 | 55263 | AGCCATCAAAACAGCCATAG | 65 | 2120 |
| 875033 | N/A | N/A | 57471 | 57490 | CACAGTTTCACTAGGTTCTC | 51 | 2121 |
| 875057 | N/A | N/A | 59915 | 59934 | TCTAATAAGCTTTAGAATCA | 78 | 2122 |
| 875081 | N/A | N/A | 61874 | 61893 | AGAAAAAAGAAGAAAATGAT | 96 | 2123 |
| 875105 | N/A | N/A | 64054 | 64073 | AGAAAAAAAAAGGCTATATA | 119 | 2124 |
| 875129 | N/A | N/A | 66933 | 66952 | GGAAAGTGGAGTAAGTAGGG | 68 | 2125 |
| 875153 | N/A | N/A | 69604 | 69623 | GTGATGAACATACATAATAA | 59 | 2126 |
| 875177 | N/A | N/A | 71587 | 71606 | CCTGCGGCACTTTCAACAAC | 94 | 2127 |
| 875201 | N/A | N/A | 72955 | 72974 | CACCAAAAGTAGCTCTTTCT | 71 | 2128 |
| 875225 | N/A | N/A | 74767 | 74786 | TCCCAGAACCCACTTCTTCA | 132 | 2129 |
| 875249 | N/A | N/A | 77066 | 77085 | CAGCATACCCAGCTAAGCAC | 124 | 2130 |
| 875273 | N/A | N/A | 79530 | 79549 | ACTATAATGTAAGTCTACCA | 136 | 2131 |
| 875297 | N/A | N/A | 81557 | 81576 | AAAGAAAAGCAAATGAGTC | 77 | 2132 |
| 875321 | N/A | N/A | 82937 | 82956 | CTATCTTCACAACATTTTTT | 93 | 2133 |
| 875345 | N/A | N/A | 84688 | 84707 | CTGTGAGTATCAAATGATAA | 56 | 2134 |
| 875369 | N/A | N/A | 85954 | 85973 | TCAGCTACATGGGCTGTCGC | 121 | 2135 |
| 875393 | N/A | N/A | 88766 | 88785 | CAGATGCTATAGAAACACAC | 40 | 2136 |
| 875417 | N/A | N/A | 91311 | 91330 | TCAATTTCACAGCTGAGATT | 72 | 2137 |
| 875441 | N/A | N/A | 92866 | 92885 | ATTAAAGCTGAATAGATACA | 120 | 2138 |
| 875465 | N/A | N/A | 96065 | 96084 | ACAAAGATGTTCAACATCA | 125 | 2139 |
| 875489 | N/A | N/A | 98062 | 98081 | ATATTTTTTTTTCCACTCT | 32 | 2140 |
| 875513 | N/A | N/A | 99836 | 99855 | AGTGAAGGCAAAAATCAGAC | 83 | 2141 |
| 875537 | N/A | N/A | 102822 | 102841 | TGGCATGGTACTGGCATAAA | 55 | 2142 |
| 875561 | N/A | N/A | 106019 | 106038 | CTCAGTAACAGTCGGAAACT | 103 | 2143 |
| 875585 | N/A | N/A | 109417 | 109436 | GGAATTCTCCCAGATCTTCC | 83 | 2144 |
| 875609 | N/A | N/A | 111754 | 111773 | ATAAGGAACTTAAAAGCTA | 90 | 2145 |
| 875633 | N/A | N/A | 113815 | 113834 | TAAAAAAAAATTGCCTCAAA | 109 | 2146 |

TABLE 29-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 875657 | N/A | N/A | 115792 | 115811 | AAGGCTTTGGCTACAAAAAC | 94 | 2147 |
| 875681 | N/A | N/A | 119037 | 119056 | GACAACAAAAAGTTCCCATT | 38 | 2148 |
| 875705 | N/A | N/A | 121526 | 121545 | ACAGTTGGACAGAGAAGAGG | 76 | 2149 |
| 875729 | N/A | N/A | 125288 | 125307 | CTAACTGTATGCTTAATAGT | 133 | 2150 |
| 875753 | N/A | N/A | 128252 | 128271 | GACTGCCTTAAAAAGGGAAA | 151 | 2151 |
| 875777 | N/A | N/A | 130493 | 130512 | CCAACACTAACTTTCTATCT | 144 | 2152 |
| 875801 | N/A | N/A | 132282 | 132301 | ATGGACATTTTATTTTAAAT | 83 | 2153 |
| 875825 | N/A | N/A | 134120 | 134139 | ACAGCCTTGCTCCTAGCCTG | 75 | 2154 |
| 875849 | N/A | N/A | 136822 | 136841 | TTTTCATAAGAGATGACAAG | 84 | 2155 |
| 875873 | N/A | N/A | 138868 | 138887 | ACATTTGAGACCTCAAATTG | 101 | 2156 |
| 875897 | N/A | N/A | 141190 | 141209 | CCCAGCCTCTTAAAAATGTC | 86 | 2157 |
| 875921 | N/A | N/A | 143195 | 143214 | GTTGAGAATCAGAAGCAGAG | 58 | 2158 |
| 875945 | N/A | N/A | 145674 | 145693 | ATAACCTTCACATTCTACTT | 85 | 2159 |
| 875969 | N/A | N/A | 147105 | 147124 | TCAACCTGGTCTCACTCACT | 69 | 2160 |
| 875993 | N/A | N/A | 148785 | 148804 | TGAAACAGAAAACTGGCAAC | 87 | 2161 |

TABLE 30

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 708199 | 1477 | 1496 | 81637 | 81656 | GCTAACTGGTTTGCCCTTGC | 27 | 32 |
| 874176 | 223 | 242 | 2213 | 2232 | CCGGGCCACCTGGCTGCGGC | 76 | 2162 |
| 874200 | 438 | 457 | 2428 | 2447 | CGCCGAGACCAAGGAGCCGC | 100 | 2163 |
| 874222 | 1127 | 1146 | 49301 | 49320 | AATACTCTCCATTATTTCTT | 42 | 2164 |
| 874245 | 1558 | 1577 | 81718 | 81737 | GTGTATTTTTCTTCCTCACT | 41 | 2165 |
| 874269 | 2097 | 2116 | 88207 | 88226 | GGGATACAAATTCTAGGCCA | 59 | 2166 |
| 874293 | 2670 | 2689 | 112979 | 112998 | AATCCTTAGCACTTGGTTCA | 53 | 2167 |
| 874317 | 3125 | 3144 | 116361 | 116380 | GGCTTGATTCACTGGCATGG | 74 | 2168 |
| 874339 | 4098 | 4117 | 148849 | 148868 | CTCCAGGGCAGCCTTACAAC | 166 | 2169 |
| 874363 | 4262 | 4281 | 149013 | 149032 | CGGTCCAAGTATCTTCCACT | 39 | 2170 |
| 874387 | 4412 | 4431 | 149163 | 149182 | TCTTTTGCTAGCTGATGTGT | 61 | 2171 |
| 874410 | 4586 | 4605 | 149337 | 149356 | ACCACTGTAGACAGTGATCA | 85 | 2172 |
| 874434 | N/A | N/A | 146553 | 146572 | ACCTTGCCAGAGCCTCACTG | 73 | 2173 |
| 874482 | N/A | N/A | 3688 | 3707 | TGCGGATCGGCCACCACCCG | 88 | 2174 |

TABLE 30-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 874506 | N/A | N/A | 4749 | 4768 | TGCAACTTAATAACCTTAGT | 15 | 2175 |
| 874530 | N/A | N/A | 7734 | 7753 | GACTAATTAACCTAGATAAA | 94 | 2176 |
| 874554 | N/A | N/A | 9932 | 9951 | GCTTAGAGTTTTTGCCTTCC | 10 | 2177 |
| 874578 | N/A | N/A | 13355 | 13374 | CTTTAAATGTTAATGAGAAT | 92 | 2178 |
| 874602 | N/A | N/A | 16423 | 16442 | CTCCCAGGCCGGGAGTGGTG | 77 | 2179 |
| 874626 | N/A | N/A | 18328 | 18347 | TAAATAAACTAAGCCTGAGA | 85 | 2180 |
| 874650 | N/A | N/A | 20475 | 20494 | AAGTACATCAGATTCTAATG | 49 | 2181 |
| 874674 | N/A | N/A | 24497 | 24516 | AAACACTTGTTCCTACTGTC | 36 | 2182 |
| 874698 | N/A | N/A | 27969 | 27988 | CAGATATGGCACTACCAGCC | 81 | 2183 |
| 874722 | N/A | N/A | 30818 | 30837 | GTCTGACAGCATCAAATGTG | 79 | 2184 |
| 874746 | N/A | N/A | 32340 | 32359 | GGAAATTAAGTAATATTCCA | 92 | 2185 |
| 874770 | N/A | N/A | 33607 | 33626 | ATCTGAGGTCAGGAACTCAA | 76 | 2186 |
| 874794 | N/A | N/A | 36935 | 36954 | CAGGAATTAAAGGCCAGTCT | 64 | 2187 |
| 874818 | N/A | N/A | 38320 | 38339 | TGTAGAATATACATATTTAC | 100 | 2188 |
| 874842 | N/A | N/A | 41277 | 41296 | TATGAGGGACTAGAGCATCC | 37 | 2189 |
| 874866 | N/A | N/A | 43499 | 43518 | CTAATTTCCACTGATCTATG | 60 | 2190 |
| 874890 | N/A | N/A | 44538 | 44557 | ACATCATTAAAGTGAAATGT | 75 | 2191 |
| 874914 | N/A | N/A | 46468 | 46487 | AAAAGCATAAAGAACTCTGC | 62 | 2192 |
| 874938 | N/A | N/A | 48098 | 48117 | CGCAACCATGCCTCTTTTTT | 90 | 2193 |
| 874962 | N/A | N/A | 50020 | 50039 | CACATGCCCACTTATAAACT | 105 | 2194 |
| 874986 | N/A | N/A | 52556 | 52575 | ACACCCTGACTGTCCAGAGC | 96 | 2195 |
| 875010 | N/A | N/A | 55256 | 55275 | CTCTATGGCTACAGCCATCA | 149 | 2196 |
| 875034 | N/A | N/A | 57481 | 57500 | TCACTAGGTACACAGTTTCA | 64 | 2197 |
| 875058 | N/A | N/A | 59957 | 59976 | TGTGGAAAAAAATTTCCAAA | 90 | 2198 |
| 875082 | N/A | N/A | 62377 | 62396 | GCTCAGGAGTTCAAGACAGC | 99 | 2199 |
| 875106 | N/A | N/A | 64118 | 64137 | CTGCAATCATGCCACTGCGC | 84 | 2200 |
| 875130 | N/A | N/A | 66996 | 67015 | ACTGGTTCTCCAACTGTACT | 101 | 2201 |
| 875154 | N/A | N/A | 69659 | 69678 | GCATTAAATATTAAGATCCA | 92 | 2202 |
| 875178 | N/A | N/A | 71639 | 71658 | TCAAAGTTCCATATAAACCT | 69 | 2203 |
| 875202 | N/A | N/A | 72957 | 72976 | TTCACCAAAAGTAGCTCTTT | 68 | 2204 |
| 875226 | N/A | N/A | 74790 | 74809 | GCCATTCTAAGTGGTTTAAC | 76 | 2205 |
| 875250 | N/A | N/A | 77268 | 77287 | TAACACTCATTTTTGGCAAG | 58 | 2206 |
| 875274 | N/A | N/A | 79564 | 79583 | TAACCTTGGGTCCTCCTGTG | 103 | 2207 |
| 875298 | N/A | N/A | 81589 | 81608 | TCTCTTTCTAAGGGCACTCT | 80 | 2208 |
| 875322 | N/A | N/A | 82976 | 82995 | CCACTTGACCTCTCTATGGC | 132 | 2209 |
| 875346 | N/A | N/A | 84758 | 84777 | GTTTGGAATCTTATTAAGCA | 19 | 2210 |

TABLE 30-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 875370 | N/A | N/A | 86008 | 86027 | TTCTTCTGGCATTCTAAAAA | 74 | 2211 |
| 875394 | N/A | N/A | 88861 | 88880 | ATATTCCTTATGCTAATCAC | 47 | 2212 |
| 875418 | N/A | N/A | 91332 | 91351 | TATAATATCACCCTCTAACA | 95 | 2213 |
| 875442 | N/A | N/A | 92879 | 92898 | AACTGTTAATAGCATTAAAG | 93 | 2214 |
| 875466 | N/A | N/A | 96102 | 96121 | CATCAATCCAAAGAAGATAT | 90 | 2215 |
| 875490 | N/A | N/A | 98063 | 98082 | CATATTTTTTTTTCCACTC | 31 | 2216 |
| 875514 | N/A | N/A | 99918 | 99937 | CTTTAGTAGAGGCGATCCAC | 67 | 2217 |
| 875538 | N/A | N/A | 102856 | 102875 | ATCATTATCTGACTTCAAAT | 82 | 2218 |
| 875562 | N/A | N/A | 106022 | 106041 | GACCTCAGTAACAGTCGGAA | 93 | 2219 |
| 875586 | N/A | N/A | 109466 | 109485 | CATTTGTTTGGAGAAATGTA | 116 | 2220 |
| 875610 | N/A | N/A | 111768 | 111787 | AAAGGAATATGACAATAAAG | 94 | 2221 |
| 875634 | N/A | N/A | 113841 | 113860 | GACATACCTGGAAAAAGTCA | 94 | 2222 |
| 875658 | N/A | N/A | 115994 | 116013 | CTTGGTGTCAGATACAAACA | 62 | 2223 |
| 875682 | N/A | N/A | 119087 | 119106 | AGCCAAACTGTCATGCTTGC | 57 | 2224 |
| 875706 | N/A | N/A | 121576 | 121595 | TAGTAAAAGAAGGCAGATTA | 89 | 2225 |
| 875730 | N/A | N/A | 125327 | 125346 | AACAAACCCACCTCTGCAAA | 66 | 2226 |
| 875754 | N/A | N/A | 128289 | 128308 | TTTGGAGGATAACAGAAAAC | 84 | 2227 |
| 875778 | N/A | N/A | 130500 | 130519 | AACAGATCCAACACTAACTT | 80 | 2228 |
| 875802 | N/A | N/A | 132362 | 132381 | AATGAAATCAGTACTATTTA | 85 | 2229 |
| 875826 | N/A | N/A | 134239 | 134258 | CCTCCCCAAGTTCTTGGATT | 97 | 2230 |
| 875850 | N/A | N/A | 136826 | 136845 | TTCATTTTCATAAGAGATGA | 89 | 2231 |
| 875874 | N/A | N/A | 138983 | 139002 | GGGAAGTTGTGCTAAGGCAA | 45 | 2232 |
| 875898 | N/A | N/A | 141431 | 141450 | GACTACAGGCGCGCCTGGCT | 86 | 2233 |
| 875922 | N/A | N/A | 143582 | 143601 | GAACTGAAAGCCAGTTCTTT | 83 | 2234 |
| 875946 | N/A | N/A | 145831 | 145850 | AAAGGACTGACCAATCAGCA | 51 | 2235 |
| 875970 | N/A | N/A | 147296 | 147315 | TTGCCTCTCTCCCTCTGCTT | 77 | 2236 |
| 875994 | N/A | N/A | 148798 | 148817 | GAAAAGCGAACATTGAAACA | 119 | 2237 |

TABLE 31

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 708199 | 1477 | 1496 | 81637 | 81656 | GCTAACTGGTTTGCCCTTGC | 25 | 32 |
| 874177 | 228 | 247 | 2218 | 2237 | GCCACCCGGGCCACCTGGCT | 104 | 2238 |
| 874201 | 443 | 462 | 2433 | 2452 | AGGCCCGCCGAGACCAAGGA | 111 | 2239 |

TABLE 31-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 874223 | 1131 | 1150 | 49305 | 49324 | ACAAAATACTCTCCATTATT | 69 | 2240 |
| 874246 | 1559 | 1578 | 81719 | 81738 | TGTGTATTTTTCTTCCTCAC | 29 | 2241 |
| 874270 | 2103 | 2122 | 88213 | 88232 | GGTTGTGGGATACAAATTCT | 53 | 2242 |
| 874294 | 2671 | 2690 | 112980 | 112999 | GAATCCTTAGCACTTGGTTC | 59 | 2243 |
| 874318 | 3126 | 3145 | 116362 | 116381 | TGGCTTGATTCACTGGCATG | 82 | 2244 |
| 874340 | 4111 | 4130 | 148862 | 148881 | GGCCTTTCGGTTCCTCCAGG | 68 | 2245 |
| 874364 | 4267 | 4286 | 149018 | 149037 | CTACTCGGTCCAAGTATCTT | 44 | 2246 |
| 874388 | 4417 | 4436 | 149168 | 149187 | TTACTTCTTTTGCTAGCTGA | 31 | 2247 |
| 874411 | 4598 | 4617 | 149349 | 149368 | CTTAAAAGTTGAACCACTGT | 96 | 2248 |
| 874435 | N/A | N/A | 146558 | 146577 | CCCACACCTTGCCAGAGCCT | 74 | 2249 |
| 874483 | N/A | N/A | 3693 | 3712 | AGCAATGCGGATCGGCCACC | 83 | 2250 |
| 874507 | N/A | N/A | 4848 | 4867 | AAAGACCTTGTGGTACTAAA | 53 | 2251 |
| 874531 | N/A | N/A | 7757 | 7776 | ATAAATTACTAATGAAGCCA | 43 | 2252 |
| 874555 | N/A | N/A | 9936 | 9955 | CAAAGCTTAGAGTTTTTGCC | 63 | 2253 |
| 874579 | N/A | N/A | 13511 | 13530 | TATTTGCAACACTGCACTCC | 117 | 2254 |
| 874603 | N/A | N/A | 16532 | 16551 | ACCTGGTGTTATGAGTCACC | 74 | 2255 |
| 874627 | N/A | N/A | 18680 | 18699 | AGTATCTCAGTTTTTTTTTT | 17 | 2256 |
| 874651 | N/A | N/A | 20482 | 20501 | GAAATAAAAGTACATCAGAT | 63 | 2257 |
| 874675 | N/A | N/A | 24888 | 24907 | CCATCCCAGATAACACGGCG | 133 | 2258 |
| 874699 | N/A | N/A | 28082 | 28101 | AAAGACTTTGAAATCTCACA | 21 | 2259 |
| 874723 | N/A | N/A | 30895 | 30914 | TGCATGCCTGCCTTCTCTAC | 74 | 2260 |
| 874747 | N/A | N/A | 32353 | 32372 | TTCATAAGGTTGTGGAAATT | 93 | 2261 |
| 874771 | N/A | N/A | 33816 | 33835 | CGTATGTTTGTCTGTCTTAT | 8 | 2262 |
| 874795 | N/A | N/A | 36992 | 37011 | GGTGCAGCCTGTAGTCTCAG | 69 | 2263 |
| 874819 | N/A | N/A | 38371 | 38390 | TCCACATATATATGTAGAAT | 85 | 2264 |
| 874843 | N/A | N/A | 41450 | 41469 | AATCACTCGAGATTAAAAAC | 67 | 2265 |
| 874867 | N/A | N/A | 43533 | 43552 | TATAAAAAAACAGTACAGTA | 70 | 2266 |
| 874891 | N/A | N/A | 44605 | 44624 | ATAGAATATAATACAACCTA | 70 | 2267 |
| 874915 | N/A | N/A | 46475 | 46494 | CAAAATAAAAGCATAAAGA | 124 | 2268 |
| 874939 | N/A | N/A | 48160 | 48179 | TGTCATACTGTATTGTTTTA | 16 | 2269 |
| 874963 | N/A | N/A | 50170 | 50189 | CTCAAAACCTTGTCTCATAC | 54 | 2270 |
| 874987 | N/A | N/A | 52570 | 52589 | GAAACCCATAGCTCACACCC | 120 | 2271 |
| 875011 | N/A | N/A | 55273 | 55292 | CAGCTACAACTACTCAACTC | 78 | 2272 |
| 875035 | N/A | N/A | 57555 | 57574 | AAAATTAATTTTTAAAGAA | 95 | 2273 |
| 875059 | N/A | N/A | 60014 | 60033 | ACAAGTTATGTTTTAATTCT | 99 | 2274 |
| 875083 | N/A | N/A | 62546 | 62565 | ATTAGGCTTCTGGATCAGGA | 30 | 2275 |

TABLE 31-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 875107 | N/A | N/A | 64341 | 64360 | AGATGCGGTGGCTCATGGCT | 71 | 2276 |
| 875131 | N/A | N/A | 67056 | 67075 | GGTAAAAAAGACACTACATA | 79 | 2277 |
| 875155 | N/A | N/A | 69693 | 69712 | TGTTGGCATAGTAACATACA | 55 | 2278 |
| 875179 | N/A | N/A | 71660 | 71679 | AAATCAGCCTTTTCTCAAAC | 78 | 2279 |
| 875203 | N/A | N/A | 72969 | 72988 | TGGTTTTAAAATTTCACCAA | 115 | 2280 |
| 875227 | N/A | N/A | 74793 | 74812 | GAAGCCATTCTAAGTGGTTT | 84 | 2281 |
| 875251 | N/A | N/A | 77332 | 77351 | ATATGTTACAAATTCTCTTT | 73 | 2282 |
| 875275 | N/A | N/A | 79658 | 79677 | TAAAGGTTGTAATCCATCCC | 46 | 2283 |
| 875299 | N/A | N/A | 81847 | 81866 | ATATAATAACAATACACCGT | 66 | 2284 |
| 875323 | N/A | N/A | 83010 | 83029 | CACAAAGTTTAACAGATGCG | 47 | 2285 |
| 875347 | N/A | N/A | 84815 | 84834 | TGGTTCCTTACAATTATCTA | 26 | 2286 |
| 875371 | N/A | N/A | 86056 | 86075 | TAAGATTGCAAAGCTAACTT | 65 | 2287 |
| 875395 | N/A | N/A | 88869 | 88888 | CTGTCAGCATATTCCTTATG | 62 | 2288 |
| 875419 | N/A | N/A | 91453 | 91472 | CCTTTGTAACACAGACACTA | 43 | 2289 |
| 875443 | N/A | N/A | 93030 | 93049 | TCTATTTTTGGTCAAGACAG | 74 | 2290 |
| 875467 | N/A | N/A | 96143 | 96162 | AAGACAACTCAATTTTTAAA | 167 | 2291 |
| 875491 | N/A | N/A | 98116 | 98135 | TTAGAAAGTTCACTCTTTTA | 87 | 2292 |
| 875515 | N/A | N/A | 99926 | 99945 | ACAAAAATCTTTAGTAGAGG | 88 | 2293 |
| 875539 | N/A | N/A | 102868 | 102887 | AAAACGGGAGGAATCATTAT | 113 | 2294 |
| 875563 | N/A | N/A | 106187 | 106206 | ATAGATTTTGAGACAAAGTC | 103 | 2295 |
| 875587 | N/A | N/A | 109530 | 109549 | GGCCATGGCAGTGCTTGTGT | 103 | 2296 |
| 875611 | N/A | N/A | 111837 | 111856 | AAGCACCAATGGCTGGACCA | 89 | 2297 |
| 875635 | N/A | N/A | 113885 | 113904 | TATTCTAGCATGCAGTAATT | 62 | 2298 |
| 875659 | N/A | N/A | 116005 | 116024 | CCTAAAGAGTGCTTGGTGTC | 68 | 2299 |
| 875683 | N/A | N/A | 119112 | 119131 | TTAGAATGTGACTCTCCCAT | 55 | 2300 |
| 875707 | N/A | N/A | 121601 | 121620 | ATCTAAAGAGGATAAATCTA | 114 | 2301 |
| 875731 | N/A | N/A | 125371 | 125390 | AAGTATTTGAACATAATCCA | 51 | 2302 |
| 875755 | N/A | N/A | 128357 | 128376 | AAAAAAAATTCCAGAAGTTT | 81 | 2303 |
| 875779 | N/A | N/A | 130588 | 130607 | GCATTATGAAATCGCTTCTC | 45 | 2304 |
| 875803 | N/A | N/A | 132506 | 132525 | CCATAATCTCATTCTCATAG | 31 | 2305 |
| 875827 | N/A | N/A | 134571 | 134590 | AGAACATGCTTAAGCAGATT | 59 | 2306 |
| 875851 | N/A | N/A | 137089 | 137108 | GGCACAAGGAAAATATTGTT | 53 | 2307 |
| 875875 | N/A | N/A | 139090 | 139109 | GACCAAACCATCATAAAATG | 64 | 2308 |
| 875899 | N/A | N/A | 141630 | 141649 | AAAAATTTATTTTTGAATAA | 98 | 2309 |
| 875923 | N/A | N/A | 143668 | 143687 | GAGTGCCCCAGCCCTTTGGA | 106 | 2310 |
| 875947 | N/A | N/A | 145860 | 145879 | GATATTTTTAAGGTCTCAGT | 37 | 2311 |

TABLE 31-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 875971 | N/A | N/A | 147316 | 147335 | TTACTTGGACCTCTGTTCAT | 84 | 2312 |
| 875995 | N/A | N/A | 148812 | 148831 | TTGTACTGTAAAAGAAAAG | 104 | 2313 |

TABLE 32

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 708199 | 1477 | 1496 | 81637 | 81656 | GCTAACTGGTTTGCCCTTGC | 15 | 32 |
| 937361 | 893 | 912 | 45747 | 45766 | TTTGTTACTGTTTCGACCTC | 56 | 2314 |
| 937371 | 2359 | 2378 | 91243 | 91262 | GCTCTGTTCGATGCAGGACT | 43 | 2315 |
| 937383 | 4394 | 4413 | 149145 | 149164 | GTTCATGACTTTCAAGGGTT | 10 | 2316 |
| 937394 | 4414 | 4433 | 149165 | 149184 | CTTCTTTTGCTAGCTGATGT | 32 | 2317 |
| 937418 | N/A | N/A | 4092 | 4111 | TTCCTTCTCCCTTTGAACAC | 59 | 2318 |
| 937430 | N/A | N/A | 4535 | 4554 | TGGCTAAGTAGTGTTTGGGA | 4 | 2319 |
| 937442 | N/A | N/A | 4776 | 4795 | AATCTAATTTTTAAGCCTAG | 65 | 2320 |
| 937454 | N/A | N/A | 6855 | 6874 | CTTTCAGATGAAAAGAAAG | 99 | 2321 |
| 937466 | N/A | N/A | 9235 | 9254 | GGTAACAGTAACATCATAGA | 13 | 2322 |
| 937478 | N/A | N/A | 10346 | 10365 | ATGATCTTGTGTATATATTA | 9 | 2323 |
| 937490 | N/A | N/A | 11385 | 11404 | CGTAAGTACAGAACCACATA | 34 | 2324 |
| 937502 | N/A | N/A | 16613 | 16632 | CTAATGTGTTTCACAATCTA | 58 | 2325 |
| 937514 | N/A | N/A | 17511 | 17530 | TTCTGGACACCAAGGTGGGT | 80 | 2326 |
| 937526 | N/A | N/A | 19926 | 19945 | CATTACGACCATTCTGCTCA | 31 | 2327 |
| 937538 | N/A | N/A | 21223 | 21242 | GAATTCGAGGTTACACAGTT | 45 | 2328 |
| 937550 | N/A | N/A | 23395 | 23414 | TTGTCTACAGTAGCATACAG | 47 | 2329 |
| 937562 | N/A | N/A | 27188 | 27207 | CTCTGTCGCCTGGGATGGTA | 89 | 2330 |
| 937574 | N/A | N/A | 28086 | 28105 | AAGCAAAGACTTTGAAATCT | 38 | 2331 |
| 937586 | N/A | N/A | 28814 | 28833 | AGTGAGTTCCATACTCTAAT | 73 | 2332 |
| 937598 | N/A | N/A | 29042 | 29061 | CAGTAATTAAGAATAAAATG | 134 | 2333 |
| 937610 | N/A | N/A | 32328 | 32347 | ATATTCCATACAGATCGCAT | 19 | 2334 |
| 937622 | N/A | N/A | 32798 | 32817 | CTTCTTGTTGTTGTTTACAT | 22 | 2335 |
| 937634 | N/A | N/A | 32811 | 32830 | TTCCAATTTCAGACTTCTTG | 15 | 2336 |
| 937646 | N/A | N/A | 33812 | 33831 | TGTTTGTCTGTCTTATTCAC | 31 | 2337 |
| 937658 | N/A | N/A | 36314 | 36333 | GTGCTCTCTTTGCGCCTGTG | 22 | 2338 |
| 937670 | N/A | N/A | 36853 | 36872 | TGAATCAGTATTTACTACTT | 37 | 2339 |

TABLE 32-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 937682 | N/A | N/A | 38658 | 38677 | AATGGGATAAATATATACAA | 75 | 2340 |
| 937694 | N/A | N/A | 41726 | 41745 | AAGAGTTAATGATGCTTTCA | 29 | 2341 |
| 937706 | N/A | N/A | 45475 | 45494 | AAGTAAAATAGCCTACTGGA | 78 | 2342 |
| 937718 | N/A | N/A | 48284 | 48303 | AATACTTAAGTCACTTACAT | 92 | 2343 |
| 937730 | N/A | N/A | 49049 | 49068 | AAAAATCCTCATATCTAAAT | 98 | 2344 |
| 937742 | N/A | N/A | 49167 | 49186 | TGTTAGGAATTCTTTAGCTC | 24 | 2345 |
| 937754 | N/A | N/A | 50792 | 50811 | TCCAAGTAACAGTGTAGAAG | 4 | 2346 |
| 937766 | N/A | N/A | 52956 | 52975 | CAGTTGCCAATTCTGAGACA | 73 | 2347 |
| 937778 | N/A | N/A | 55537 | 55556 | AGTAATTCTTCAGACTAAAT | 103 | 2348 |
| 937790 | N/A | N/A | 57468 | 57487 | AGTTTCACTAGGTTCTCAAA | 41 | 2349 |
| 937802 | N/A | N/A | 58557 | 58576 | TCTTTCTTTTAATCTCAATA | 50 | 2350 |
| 937814 | N/A | N/A | 60511 | 60530 | TTTTGTTTAATCACAGTTTT | 65 | 2351 |
| 937826 | N/A | N/A | 63945 | 63964 | AACAAACAGAGAGGAACTGC | 68 | 2352 |
| 937838 | N/A | N/A | 68930 | 68949 | AGAATCCACAGATCCAGGTG | 46 | 2353 |
| 937850 | N/A | N/A | 69823 | 69842 | ATGGGCCCCTTCAATATTTT | 75 | 2354 |
| 937862 | N/A | N/A | 73009 | 73028 | GAAAACACAGAAGTGTGATT | 100 | 2355 |
| 937874 | N/A | N/A | 74344 | 74363 | CAGTACTGTAAGTTGCCACT | 78 | 2356 |
| 937886 | N/A | N/A | 81784 | 81803 | ATTTCCTTTAAATACCTAGT | 55 | 2357 |
| 937898 | N/A | N/A | 82355 | 82374 | ACTATCAACTGCCACTGCTG | 77 | 2358 |
| 937910 | N/A | N/A | 82849 | 82868 | TGGCTCCAATATCGGCAATG | 43 | 2359 |
| 937922 | N/A | N/A | 82961 | 82980 | ATGGCTGATTCCATCAATCT | 76 | 2360 |
| 937934 | N/A | N/A | 83785 | 83804 | ACATAGGTTAGAATTTTCCA | 10 | 2361 |
| 937946 | N/A | N/A | 83992 | 84011 | GTTTCTTTTACTTAAGTTGC | 21 | 2362 |
| 937958 | N/A | N/A | 84403 | 84422 | CATATATTTCTCAGCCCCCT | 54 | 2363 |
| 937970 | N/A | N/A | 84703 | 84722 | TAGAGTTTGTGACTCCTGTG | 83 | 2364 |
| 937982 | N/A | N/A | 84773 | 84792 | TGAACCCAGAACTCAGTTTG | 74 | 2365 |
| 937994 | N/A | N/A | 84921 | 84940 | TAAATCACAATAATTCCTAC | 100 | 2366 |
| 938006 | N/A | N/A | 85155 | 85174 | TTGATTTGTGATAAGTTTTA | 45 | 2367 |
| 938018 | N/A | N/A | 85199 | 85218 | CAAAAATGATTTCTTGTACA | 74 | 2368 |
| 938030 | N/A | N/A | 95476 | 95495 | TTAACGGTTGCTTAGGGTTG | 24 | 2369 |
| 938042 | N/A | N/A | 97620 | 97639 | AGACTTTTTATGTTGCTCCT | 15 | 2370 |
| 938054 | N/A | N/A | 98577 | 98596 | AGCAATTCTTACACAAATAA | 67 | 2371 |
| 938066 | N/A | N/A | 100145 | 100164 | TCAGTATAGGCAAACCAATT | 82 | 2372 |
| 938078 | N/A | N/A | 107363 | 107382 | AAGTTAAAAAGCGGGCAGAT | 64 | 2373 |
| 938090 | N/A | N/A | 111222 | 111241 | CTGGGCCTAGTCAGCTTGGA | 92 | 2374 |
| 938102 | N/A | N/A | 118404 | 118423 | ACCCAAAAAAACACATTGAG | 83 | 2375 |

TABLE 32-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 938114 | N/A | N/A | 119032 | 119051 | CAAAAAGTTCCCATTGCATT | 50 | 2376 |
| 938126 | N/A | N/A | 123992 | 124011 | CAATATTCTGAGAAAGGACT | 53 | 2377 |
| 938138 | N/A | N/A | 125932 | 125951 | TAATTATAGAGTTCATATGG | 54 | 2378 |
| 938150 | N/A | N/A | 129788 | 129807 | TTACTTATTACCTTCCTGTA | 61 | 2379 |
| 938162 | N/A | N/A | 130897 | 130916 | AAAAAAGCAGACTGCCTATT | 107 | 2380 |
| 938174 | N/A | N/A | 132166 | 132185 | TTTTTGCTTATTATTCTCAC | 11 | 2381 |
| 938186 | N/A | N/A | 132523 | 132542 | CATGTAGTTACATGTAACCA | 40 | 2382 |
| 938198 | N/A | N/A | 133814 | 133833 | GGCTGTTTCAAAACCAATGA | 42 | 2383 |
| 938210 | N/A | N/A | 135083 | 135102 | GGTCAAGGTCAATACTTTTT | 7 | 2384 |
| 938222 | N/A | N/A | 137933 | 137952 | GCTGTCCAAGATAATGACCT | 82 | 2385 |
| 938234 | N/A | N/A | 139269 | 139288 | TTAATTTGTAACTAGGTTTT | 73 | 2386 |
| 938246 | N/A | N/A | 141230 | 141249 | CCCCTACTGTTAAACCATTA | 112 | 2387 |
| 938258 | N/A | N/A | 144253 | 144272 | ATGTCTGACAACCTCCATCG | 92 | 2388 |
| 938270 | N/A | N/A | 146666 | 146685 | CAGAACCTAAACTTTGCAGG | 57 | 2389 |

TABLE 33

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 708199 | 1477 | 1496 | 81637 | 81656 | GCTAACTGGTTTGCCCTTGC | 18 | 32 |
| 937362 | 894 | 913 | 45748 | 45767 | CTTTGTTACTGTTTCGACCT | 36 | 2390 |
| 937372 | 2455 | 2474 | 91725 | 91744 | GTTTCATTGGGTTTAATATT | 21 | 2391 |
| 937384 | 4395 | 4414 | 149146 | 149165 | TGTTCATGACTTTCAAGGGT | 18 | 2392 |
| 937395 | 4415 | 4434 | 149166 | 149185 | ACTTCTTTTGCTAGCTGATG | 21 | 2393 |
| 937407 | N/A | N/A | 3132 | 3151 | GGGAGGCCGCCCGCTCCCTC | 108 | 2394 |
| 937419 | N/A | N/A | 4093 | 4112 | TTTCCTTCTCCCTTTGAACA | 50 | 2395 |
| 937431 | N/A | N/A | 4652 | 4671 | ACATCCTTTTCTATAAAAGT | 53 | 2396 |
| 937443 | N/A | N/A | 4898 | 4917 | GAAAAATCTAAATTAACCTT | 97 | 2397 |
| 937455 | N/A | N/A | 6965 | 6984 | GGAATGTAGAAGAAGAAGAG | 72 | 2398 |
| 937467 | N/A | N/A | 9927 | 9946 | GAGTTTTGCCTTCCATTTT | 12 | 2399 |
| 937479 | N/A | N/A | 10347 | 10366 | CATGATCTTGTGTATATATT | 13 | 2400 |
| 937491 | N/A | N/A | 12994 | 13013 | ACAGCTGTGACAAGTTTTCA | 63 | 2401 |
| 937503 | N/A | N/A | 16634 | 16653 | AAAAATGCTTGTCATAATCC | 44 | 2402 |
| 937515 | N/A | N/A | 18265 | 18284 | AAGTGCCAACCATTCAAGAA | 31 | 2403 |
| 937527 | N/A | N/A | 19927 | 19946 | TCATTACGACCATTCTGCTC | 70 | 2404 |

TABLE 33-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 937539 | N/A | N/A | 21520 | 21539 | TGACCAATGCTCCTCTCTGC | 53 | 2405 |
| 937551 | N/A | N/A | 24044 | 24063 | AACCAGTAAGTTAAGGTAAA | 65 | 2406 |
| 937563 | N/A | N/A | 27762 | 27781 | CCAGAAAAAATGGCCACTAC | 58 | 2407 |
| 937575 | N/A | N/A | 28087 | 28106 | AAAGCAAAGACTTTGAAATC | 90 | 2408 |
| 937587 | N/A | N/A | 28884 | 28903 | TGTTCAGTGTCCTTCTAGCC | 41 | 2409 |
| 937599 | N/A | N/A | 30084 | 30103 | CAGTGAGGAAGGAGACCATC | 51 | 2410 |
| 937611 | N/A | N/A | 32330 | 32349 | TAATATTCCATACAGATCGC | 12 | 2411 |
| 937623 | N/A | N/A | 32799 | 32818 | ACTTCTTGTTGTTGTTTACA | 24 | 2412 |
| 937635 | N/A | N/A | 32812 | 32831 | CTTCCAATTTCAGACTTCTT | 20 | 2413 |
| 937647 | N/A | N/A | 33813 | 33832 | ATGTTTGTCTGTCTTATTCA | 22 | 2414 |
| 937659 | N/A | N/A | 36315 | 36334 | TGTGCTCTCTTTGCGCCTGT | 27 | 2415 |
| 937671 | N/A | N/A | 36854 | 36873 | ATGAATCAGTATTTACTACT | 42 | 2416 |
| 937683 | N/A | N/A | 38876 | 38895 | GCATCACTACTTGGTAACAC | 15 | 2417 |
| 937695 | N/A | N/A | 42730 | 42749 | TTTACCATTCTGTCTACTTT | 70 | 2418 |
| 937707 | N/A | N/A | 45616 | 45635 | AGAGCTCACCTAATATTAAG | 105 | 2419 |
| 937719 | N/A | N/A | 48304 | 48323 | CTTCAGATACCGAATTACAT | 61 | 2420 |
| 937731 | N/A | N/A | 49069 | 49088 | TATTATCCATTCCATCATTT | 55 | 2421 |
| 937743 | N/A | N/A | 49174 | 49193 | TAAAATTGTTAGGAATTCT | 87 | 2422 |
| 937755 | N/A | N/A | 50918 | 50937 | AGAACACTGTGCTTTCATCA | 38 | 2423 |
| 937767 | N/A | N/A | 52985 | 53004 | CAAATGATAACAGCAGAGAC | 100 | 2424 |
| 937779 | N/A | N/A | 55654 | 55673 | AGAAGATAAATTTGTAGATA | 82 | 2425 |
| 937791 | N/A | N/A | 57469 | 57488 | CAGTTTCACTAGGTTCTCAA | 14 | 2426 |
| 937803 | N/A | N/A | 58599 | 58618 | ATTCTGTTTAGCTTTCCATT | 37 | 2427 |
| 937815 | N/A | N/A | 61017 | 61036 | TTTCTACTTTTCCCAGTTTG | 63 | 2428 |
| 937827 | N/A | N/A | 64531 | 64550 | CAGGATTATGTATAAATCAA | 41 | 2429 |
| 937839 | N/A | N/A | 68933 | 68952 | TTGAGAATCCACAGATCCAG | 78 | 2430 |
| 937851 | N/A | N/A | 69849 | 69868 | GGGATTCTTAGCCTTTTTCT | 73 | 2431 |
| 937863 | N/A | N/A | 73122 | 73141 | AATGCTACATTTTAATCTTA | 71 | 2432 |
| 937875 | N/A | N/A | 74437 | 74456 | CCCATAGGGTACCACCTACT | 95 | 2433 |
| 937887 | N/A | N/A | 81832 | 81851 | ACCGTCTCACACAGACCTTG | 66 | 2434 |
| 937899 | N/A | N/A | 82395 | 82414 | TTAGCATGACATGCCAAGTC | 58 | 2435 |
| 937911 | N/A | N/A | 82850 | 82869 | ATGGCTCCAATATCGGCAAT | 39 | 2436 |
| 937923 | N/A | N/A | 82991 | 83010 | GTGCTCATTCTCATCCCACT | 29 | 2437 |
| 937935 | N/A | N/A | 83786 | 83805 | CACATAGGTTAGAATTTTCC | 24 | 2438 |
| 937947 | N/A | N/A | 84055 | 84074 | ACAAGATATATTCAACCTAG | 35 | 2439 |
| 937959 | N/A | N/A | 84404 | 84423 | TCATATATTTCTCAGCCCCC | 51 | 2440 |

TABLE 33-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 937971 | N/A | N/A | 84743 | 84762 | AAGCAAGTCCCATTTAAGTA | 26 | 2441 |
| 937983 | N/A | N/A | 84800 | 84819 | ATCTATGATTTTCATCAGGT | 6 | 2442 |
| 937995 | N/A | N/A | 84951 | 84970 | ATATAACATACACTAGATAA | 99 | 2443 |
| 938007 | N/A | N/A | 85169 | 85188 | TTGAGGACAGTCATTTGATT | 57 | 2444 |
| 938019 | N/A | N/A | 85287 | 85306 | CACCTGACAGAACAAATGAT | 103 | 2445 |
| 938031 | N/A | N/A | 95719 | 95738 | AGAACACCACAAATAGCTAC | 67 | 2446 |
| 938043 | N/A | N/A | 97622 | 97641 | TAAGACTTTTTATGTTGCTC | 6 | 2447 |
| 938055 | N/A | N/A | 98657 | 98676 | ATGTATAGAGGCCAACATTC | 85 | 2448 |
| 938067 | N/A | N/A | 100218 | 100237 | AACAAGCTAAAGAGAAACCT | 114 | 2449 |
| 938079 | N/A | N/A | 108591 | 108610 | GTCTCTCAATAGCAGAAATG | 89 | 2450 |
| 938091 | N/A | N/A | 111368 | 111387 | TGGGCAGTCTATACGGAATT | 52 | 2451 |
| 938103 | N/A | N/A | 118784 | 118803 | CGAAAATTAAGAGTTTTAGT | 83 | 2452 |
| 938115 | N/A | N/A | 119033 | 119052 | ACAAAAAGTTCCCATTGCAT | 56 | 2453 |
| 938127 | N/A | N/A | 124091 | 124110 | AAGCATGAACCTTAAGAGAA | 58 | 2454 |
| 938139 | N/A | N/A | 126290 | 126309 | AAAAGTTACCACAATATGAA | 86 | 2455 |
| 938151 | N/A | N/A | 129789 | 129808 | GTTACTTATTACCTTCCTGT | 14 | 2456 |
| 938163 | N/A | N/A | 131674 | 131693 | GTTCATCTTTTCCTTCAGAT | 10 | 2457 |
| 938175 | N/A | N/A | 132167 | 132186 | TTTTTTGCTTATTATTCTCA | 19 | 2458 |
| 938187 | N/A | N/A | 132524 | 132543 | CCATGTAGTTACATGTAACC | 48 | 2459 |
| 938199 | N/A | N/A | 133894 | 133913 | CCCACTGCTCTTCAAATGGA | 68 | 2460 |
| 938211 | N/A | N/A | 136171 | 136190 | AGAGTAGATGTGAGGCTGGG | 105 | 2461 |
| 938223 | N/A | N/A | 137934 | 137953 | TGCTGTCCAAGATAATGACC | 85 | 2462 |
| 938235 | N/A | N/A | 139270 | 139289 | TTTAATTTGTAACTAGGTTT | 42 | 2463 |
| 938247 | N/A | N/A | 141590 | 141609 | AAGTAGCTAATACGGTGGAC | 30 | 2464 |
| 938259 | N/A | N/A | 144271 | 144290 | GGAGCATGTACACAACCGAT | 108 | 2465 |
| 938271 | N/A | N/A | 146726 | 146745 | GACCAAACCGGCTTCCCTCC | 94 | 2466 |

TABLE 34

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 708199 | 1477 | 1496 | 81637 | 81656 | GCTAACTGGTTTGCCCTTGC | 21 | 32 |
| 937363 | 1075 | 1094 | 49249 | 49268 | TTCTCATGTGCGGCATCAAG | 35 | 2467 |
| 937373 | 2456 | 2475 | 91726 | 91745 | TGTTTCATTGGGTTTAATAT | 33 | 2468 |

TABLE 34-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 937385 | 4396 | 4415 | 149147 | 149166 | GTGTTCATGACTTTCAAGGG | 11 | 2469 |
| 937396 | 4416 | 4435 | 149167 | 149186 | TACTTCTTTTGCTAGCTGAT | 23 | 2470 |
| 937408 | N/A | N/A | 3161 | 3180 | CGAGAACCCCTCCCAACACG | 128 | 2471 |
| 937420 | N/A | N/A | 4094 | 4113 | GTTTCCTTCTCCCTTTGAAC | 14 | 2472 |
| 937432 | N/A | N/A | 4744 | 4763 | CTTAATAACCTTAGTTTTAA | 102 | 2473 |
| 937444 | N/A | N/A | 5108 | 5127 | TAAGTGAGGAGATTCTAGAA | 56 | 2474 |
| 937456 | N/A | N/A | 7006 | 7025 | GTAACAATTGTAAATCCATA | 10 | 2475 |
| 937468 | N/A | N/A | 9928 | 9947 | AGAGTTTTGCCTTCCATTT | 9 | 2476 |
| 937480 | N/A | N/A | 10348 | 10367 | GCATGATCTTGTGTATATAT | 8 | 2477 |
| 937492 | N/A | N/A | 13405 | 13424 | TCACTTGACACAACTTCAGG | 58 | 2478 |
| 937504 | N/A | N/A | 17153 | 17172 | ATTACAATGCGGTATATATA | 32 | 2479 |
| 937516 | N/A | N/A | 18278 | 18297 | TGACCAAGCAGTTAAGTGCC | 45 | 2480 |
| 937528 | N/A | N/A | 19929 | 19948 | CATCATTACGACCATTCTGC | 42 | 2481 |
| 937540 | N/A | N/A | 22556 | 22575 | ACAGTTTAGCAATTACTTTT | 23 | 2482 |
| 937552 | N/A | N/A | 24447 | 24466 | GCAAATATTTCCAAACAAGT | 13 | 2483 |
| 937564 | N/A | N/A | 28019 | 28038 | AAAGGCAATTTCCTTAATTT | 47 | 2484 |
| 937576 | N/A | N/A | 28162 | 28181 | GCTCCCAGCCTTCTTCACTG | 76 | 2485 |
| 937588 | N/A | N/A | 28885 | 28904 | TTGTTCAGTGTCCTTCTAGC | 24 | 2486 |
| 937600 | N/A | N/A | 30151 | 30170 | CTCGAATGGCAGAACAATGA | 57 | 2487 |
| 937612 | N/A | N/A | 32331 | 32350 | GTAATATTCCATACAGATCG | 33 | 2488 |
| 937624 | N/A | N/A | 32800 | 32819 | GACTTCTTGTTGTTGTTTAC | 21 | 2489 |
| 937636 | N/A | N/A | 32813 | 32832 | TCTTCCAATTTCAGACTTCT | 24 | 2490 |
| 937648 | N/A | N/A | 33814 | 33833 | TATGTTTGTCTGTCTTATTC | 32 | 2491 |
| 937660 | N/A | N/A | 36316 | 36335 | ATGTGCTCTCTTTGCGCCTG | 41 | 2492 |
| 937672 | N/A | N/A | 36855 | 36874 | CATGAATCAGTATTTACTAC | 35 | 2493 |
| 937684 | N/A | N/A | 41272 | 41291 | GGGACTAGAGCATCCATAAA | 52 | 2494 |
| 937696 | N/A | N/A | 43208 | 43227 | TGCTTTTAATAGTTGCCAAA | 43 | 2495 |
| 937708 | N/A | N/A | 47531 | 47550 | TACCCCCAAGGCAGTTTATC | 109 | 2496 |
| 937720 | N/A | N/A | 48512 | 48531 | GAACTCTTGAAATTCTTCAG | 37 | 2497 |
| 937732 | N/A | N/A | 49142 | 49161 | GGTACCAGTTCTTATATGCC | 67 | 2498 |
| 937744 | N/A | N/A | 49194 | 49213 | TACTCCAAACCTTTACAAAA | 94 | 2499 |
| 937756 | N/A | N/A | 50938 | 50957 | ATTTGAGAAGATTCAAAAAC | 84 | 2500 |
| 937768 | N/A | N/A | 53154 | 53173 | CTTAATAATTTGACAGACTA | 64 | 2501 |
| 937780 | N/A | N/A | 55995 | 56014 | ACTAAAACCAGAGGAAAAAT | 89 | 2502 |
| 937792 | N/A | N/A | 57472 | 57491 | ACACAGTTTCACTAGGTTCT | 11 | 2503 |
| 937804 | N/A | N/A | 58742 | 58761 | AGTTATTGTTCTGACTTTGG | 14 | 2504 |

TABLE 34-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 937816 | N/A | N/A | 61164 | 61183 | GCAAGCTGATAGACAATCAT | 71 | 2505 |
| 937828 | N/A | N/A | 65549 | 65568 | TAAACAACAGTGGCCACTGA | 92 | 2506 |
| 937840 | N/A | N/A | 69102 | 69121 | GTTCTATAGGTGCTTAAGTC | 38 | 2507 |
| 937852 | N/A | N/A | 69978 | 69997 | CACAGTTAAGGGTGCAGGAT | 45 | 2508 |
| 937864 | N/A | N/A | 73447 | 73466 | AAATTAAAGCTCGAAGCAGC | 92 | 2509 |
| 937876 | N/A | N/A | 74496 | 74515 | GGGCAATGATGGCACTAGGA | 51 | 2510 |
| 937888 | N/A | N/A | 81875 | 81894 | TACCTAAGCTATATTAAAGG | 96 | 2511 |
| 937900 | N/A | N/A | 82425 | 82444 | TCACCCCATCTCCTTCCAAC | 86 | 2512 |
| 937912 | N/A | N/A | 82851 | 82870 | CATGGCTCCAATATCGGCAA | 35 | 2513 |
| 937924 | N/A | N/A | 83053 | 83072 | TCTAACCTCTGGACTGTCCC | 68 | 2514 |
| 937936 | N/A | N/A | 83787 | 83806 | GCACATAGGTTAGAATTTTC | 4 | 2515 |
| 937948 | N/A | N/A | 84087 | 84106 | TATCCCTGATTTATGGAAAA | 79 | 2516 |
| 937960 | N/A | N/A | 84405 | 84424 | ATCATATATTTCTCAGCCCC | 39 | 2517 |
| 937972 | N/A | N/A | 84753 | 84772 | GAATCTTATTAAGCAAGTCC | 8 | 2518 |
| 937984 | N/A | N/A | 84810 | 84829 | CCTTACAATTATCTATGATT | 48 | 2519 |
| 937996 | N/A | N/A | 85039 | 85058 | CTATACACACTATTGAAGAA | 58 | 2520 |
| 938008 | N/A | N/A | 85179 | 85198 | TTTTAACCCTTTGAGGACAG | 51 | 2521 |
| 938020 | N/A | N/A | 85288 | 85307 | ACACCTGACAGAACAAATGA | 91 | 2522 |
| 938032 | N/A | N/A | 95819 | 95838 | CAACTCCTAGGTAGGTACAC | 41 | 2523 |
| 938044 | N/A | N/A | 97623 | 97642 | ATAAGACTTTTTATGTTGCT | 18 | 2524 |
| 938056 | N/A | N/A | 98775 | 98794 | AAACACTTTATAGGCAATAT | 56 | 2525 |
| 938068 | N/A | N/A | 101519 | 101538 | AATCAGTTTATTGAAGGAAT | 88 | 2526 |
| 938080 | N/A | N/A | 108675 | 108694 | GAGACTGCAATAATTATTAG | 85 | 2527 |
| 938092 | N/A | N/A | 112470 | 112489 | GTTTCTCAGTAAAGTGTCAG | 86 | 2528 |
| 938104 | N/A | N/A | 118926 | 118945 | ACCCACTTTCTTCTCAGAAT | 87 | 2529 |
| 938116 | N/A | N/A | 119657 | 119676 | CAAAAGCATTACTCATTGCC | 61 | 2530 |
| 938128 | N/A | N/A | 124624 | 124643 | ATACAATACAGTCAACTGAA | 112 | 2531 |
| 938140 | N/A | N/A | 127721 | 127740 | AAAAACTAAGGGAAAAACTG | 85 | 2532 |
| 938152 | N/A | N/A | 129791 | 129810 | TTGTTACTTATTACCTTCCT | 27 | 2533 |
| 938164 | N/A | N/A | 131723 | 131742 | GTAGAAACTATTTGCCAAAA | 44 | 2534 |
| 938176 | N/A | N/A | 132216 | 132235 | AAGTTGATCTACACAAATTT | 69 | 2535 |
| 938188 | N/A | N/A | 132525 | 132544 | CCCATGTAGTTACATGTAAC | 46 | 2536 |
| 938200 | N/A | N/A | 133952 | 133971 | GTTTTGTTTGCAACATTTCC | 50 | 2537 |
| 938212 | N/A | N/A | 136441 | 136460 | TATTTGAGTGTATTTAAATA | 91 | 2538 |
| 938224 | N/A | N/A | 138034 | 138053 | TACCTTAAAAGTTCATTTCC | 64 | 2539 |
| 938236 | N/A | N/A | 139272 | 139291 | TGTTTAATTTGTAACTAGGT | 20 | 2540 |

TABLE 34-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 938248 | N/A | N/A | 142489 | 142508 | TCTGAATGTTTTTAAGAGTA | 37 | 2541 |
| 938260 | N/A | N/A | 145644 | 145663 | GAAAGTTGGCTAAAGCTGGT | 84 | 2542 |
| 938272 | N/A | N/A | 146738 | 146757 | CTGGCCCACACGGACCAAAC | 100 | 2543 |

TABLE 35

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 708151 | 1084 | 1103 | 49258 | 49277 | TCTGTACTTTTCTCATGTGC | 50 | 2544 |
| 708199 | 1477 | 1496 | 81637 | 81656 | GCTAACTGGTTTGCCCTTGC | 32 | 32 |
| 937375 | 2467 | 2486 | 91737 | 91756 | AAGCTAGGTGATGTTTCATT | 55 | 2545 |
| 937387 | 4399 | 4418 | 149150 | 149169 | GATGTGTTCATGACTTTCAA | 36 | 2546 |
| 937398 | 4419 | 4438 | 149170 | 149189 | TGTTACTTCTTTTGCTAGCT | 49 | 2547 |
| 937410 | N/A | N/A | 3453 | 3472 | CGATCTTTCCCAGGACTCGG | 87 | 2548 |
| 937422 | N/A | N/A | 4526 | 4545 | AGTGTTTGGGATGCTTCAGA | 6 | 2549 |
| 937434 | N/A | N/A | 4746 | 4765 | AACTTAATAACCTTAGTTTT | 86 | 2550 |
| 937446 | N/A | N/A | 5301 | 5320 | CACTTCTGAAAGTCATGAAA | 53 | 2551 |
| 937458 | N/A | N/A | 7351 | 7370 | AATTTAAATGGAAGCATGAT | 82 | 2552 |
| 937470 | N/A | N/A | 9930 | 9949 | TTAGAGTTTTTGCCTTCCAT | 5 | 2553 |
| 937482 | N/A | N/A | 10351 | 10370 | ACAGCATGATCTTGTGTATA | 30 | 2554 |
| 937494 | N/A | N/A | 13774 | 13793 | GTTAGCTATTAATCATGGCA | 20 | 2555 |
| 937506 | N/A | N/A | 17155 | 17174 | GAATTACAATGCGGTATATA | 22 | 2556 |
| 937518 | N/A | N/A | 18682 | 18701 | CCAGTATCTCAGTTTTTTTT | 35 | 2557 |
| 937530 | N/A | N/A | 19932 | 19951 | GCGCATCATTACGACCATTC | 50 | 2558 |
| 937542 | N/A | N/A | 23248 | 23267 | ATTTTTACTCACCTTTTCTA | 80 | 2559 |
| 937554 | N/A | N/A | 24984 | 25003 | ATAAACACAGGGTAGGCCAG | 96 | 2560 |
| 937566 | N/A | N/A | 28077 | 28096 | CTTTGAAATCTCACAAGGTT | 60 | 2561 |
| 937578 | N/A | N/A | 28492 | 28511 | GGATTGTTTTCTTCATTATT | 16 | 2562 |
| 937590 | N/A | N/A | 28887 | 28906 | TCTTGTTCAGTGTCCTTCTA | 21 | 2563 |
| 937602 | N/A | N/A | 30535 | 30554 | AAATAACTTGCCTTACATCA | 62 | 2564 |
| 937614 | N/A | N/A | 32333 | 32352 | AAGTAATATTCCATACAGAT | 34 | 2565 |
| 937626 | N/A | N/A | 32802 | 32821 | CAGACTTCTTGTTGTTGTTT | 28 | 2566 |
| 937638 | N/A | N/A | 32815 | 32834 | GTTCTTCCAATTTCAGACTT | 34 | 2567 |
| 937650 | N/A | N/A | 35590 | 35609 | AAATGTTTTCATAACTGCTA | 54 | 2568 |
| 937662 | N/A | N/A | 36318 | 36337 | ACATGTGCTCTCTTTGCGCC | 76 | 2569 |

TABLE 35-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 937674 | N/A | N/A | 37450 | 37469 | AACAACCAAGCTTGGCAAAA | 67 | 2570 |
| 937686 | N/A | N/A | 41274 | 41293 | GAGGGACTAGAGCATCCATA | 53 | 2571 |
| 937698 | N/A | N/A | 43423 | 43442 | CCACTGAAGTCTAAATTCTT | 82 | 2572 |
| 937710 | N/A | N/A | 47568 | 47587 | TTTATCCACATTTTAACTTC | 74 | 2573 |
| 937722 | N/A | N/A | 48559 | 48578 | TTCACTAACAAAACAATAAA | 97 | 2574 |
| 937734 | N/A | N/A | 49148 | 49167 | CATCAAGGTACCAGTTCTTA | 22 | 2575 |
| 937746 | N/A | N/A | 49874 | 49893 | ATTTTTCTCTAAAGTTCTAA | 76 | 2576 |
| 937758 | N/A | N/A | 51327 | 51346 | AGGAATGGACTATCACAAAC | 40 | 2577 |
| 937770 | N/A | N/A | 54510 | 54529 | TTCCCCAGCAGCCGAGTGTG | 83 | 2578 |
| 937782 | N/A | N/A | 56810 | 56829 | TAATGGCTAGAAGAATTCAG | 83 | 2579 |
| 937794 | N/A | N/A | 57474 | 57493 | GTACACAGTTTCACTAGGTT | 4 | 2580 |
| 937806 | N/A | N/A | 58825 | 58844 | CACACAGTATTTTTTATCG | 72 | 2581 |
| 937818 | N/A | N/A | 61266 | 61285 | CTACTTGTTTTACTTAAACC | 86 | 2582 |
| 937830 | N/A | N/A | 67096 | 67115 | TCCAGAAAAGTTTAATGCAT | 94 | 2583 |
| 937842 | N/A | N/A | 69104 | 69123 | GAGTTCTATAGGTGCTTAAG | 30 | 2584 |
| 937854 | N/A | N/A | 71512 | 71531 | CTATATAAAGTATCAGTATA | 153 | 2585 |
| 937866 | N/A | N/A | 73688 | 73707 | AACCTACCTTAAGATCCTGA | 86 | 2586 |
| 937878 | N/A | N/A | 74727 | 74746 | AAGTTCAGGCCCTACAGTAT | 87 | 2587 |
| 937890 | N/A | N/A | 81996 | 82015 | GGATTGCTCACCGTGATATA | 30 | 2588 |
| 937902 | N/A | N/A | 82458 | 82477 | GTCTCAGCCAGTCCTCAATG | 39 | 2589 |
| 937914 | N/A | N/A | 82854 | 82873 | TTTCATGGCTCCAATATCGG | 39 | 2590 |
| 937926 | N/A | N/A | 83415 | 83434 | TGGTCAAAATACTTGCCTCC | 95 | 2591 |
| 937938 | N/A | N/A | 83790 | 83809 | GTTGCACATAGGTTAGAATT | 12 | 2592 |
| 937950 | N/A | N/A | 84162 | 84181 | CACTCTTTTCCCACAAAGTT | 57 | 2593 |
| 937962 | N/A | N/A | 84408 | 84427 | AGTATCATATATTTCTCAGC | 20 | 2594 |
| 937974 | N/A | N/A | 84755 | 84774 | TGGAATCTTATTAAGCAAGT | 28 | 2595 |
| 937986 | N/A | N/A | 84812 | 84831 | TTCCTTACAATTATCTATGA | 56 | 2596 |
| 937998 | N/A | N/A | 85050 | 85069 | TTAATTAGGATCTATACACA | 75 | 2597 |
| 938010 | N/A | N/A | 85181 | 85200 | CATTTTAACCCTTTGAGGAC | 83 | 2598 |
| 938022 | N/A | N/A | 92150 | 92169 | AGTAATGCTTATTTTCTAAA | 40 | 2599 |
| 938034 | N/A | N/A | 96348 | 96367 | AAACAGTATTTTCTTAGATA | 104 | 2600 |
| 938046 | N/A | N/A | 97625 | 97644 | AGATAAGACTTTTTATGTTG | 58 | 2601 |
| 938058 | N/A | N/A | 99151 | 99170 | TTAACTCATGGCAACCACCG | 86 | 2602 |
| 938070 | N/A | N/A | 104058 | 104077 | TACATCTTAACAGAATAAAA | 95 | 2603 |
| 938082 | N/A | N/A | 109341 | 109360 | CCCTCTAATGCATGTATGGC | 76 | 2604 |
| 938094 | N/A | N/A | 112723 | 112742 | ACTATAAACTAACAATAACA | 88 | 2605 |

TABLE 35-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 938106 | N/A | N/A | 119023 | 119042 | CCCATTGCATTGTTTTAAGT | 30 | 2606 |
| 938118 | N/A | N/A | 120014 | 120033 | TGAAAATCTAAGGCCACATG | 87 | 2607 |
| 938130 | N/A | N/A | 124891 | 124910 | AGTATATGATGACCTCAATG | 36 | 2608 |
| 938142 | N/A | N/A | 127923 | 127942 | ACTCCTCACTGAAAGTACAC | 76 | 2609 |
| 938154 | N/A | N/A | 129793 | 129812 | CTTTGTTACTTATTACCTTC | 40 | 2610 |
| 938166 | N/A | N/A | 132157 | 132176 | ATTATTCTCACATATAAATA | 118 | 2611 |
| 938178 | N/A | N/A | 132322 | 132341 | TTTGAAGCAATCCATTAATT | 67 | 2612 |
| 938190 | N/A | N/A | 132527 | 132546 | TGCCCATGTAGTTACATGTA | 64 | 2613 |
| 938202 | N/A | N/A | 134160 | 134179 | AAGGGAATCTTGATTAACTA | 48 | 2614 |
| 938214 | N/A | N/A | 136587 | 136606 | CACACAATTTTGCAAAAACA | 77 | 2615 |
| 938226 | N/A | N/A | 138442 | 138461 | TGACAATATTAATGGCACAA | 23 | 2616 |
| 938238 | N/A | N/A | 139274 | 139293 | TGTGTTTAATTTGTAACTAG | 21 | 2617 |
| 938250 | N/A | N/A | 142909 | 142928 | AGCACAGCTTTGGGAAGAGG | 44 | 2618 |
| 938262 | N/A | N/A | 145801 | 145820 | TCCCATGACAAAACCACACA | 81 | 2619 |
| 938274 | N/A | N/A | 146800 | 146819 | CCAGCCTCTGGTAGACACCT | 68 | 2620 |

TABLE 36

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 708199 | 1477 | 1496 | 81637 | 81656 | GCTAACTGGTTTGCCCTTGC | 20 | 32 |
| 937366 | 1563 | 1582 | 81723 | 81742 | CTGCTGTGTATTTTTCTTCC | 21 | 2621 |
| 937378 | 3492 | 3511 | 136965 | 136984 | TTGTCTCCTTGTTGTATGGT | 14 | 2622 |
| 937390 | 4403 | 4422 | 149154 | 149173 | AGCTGATGTGTTCATGACTT | 29 | 2623 |
| 937413 | N/A | N/A | 3946 | 3965 | ACTACAACCCCGGCTTAGGA | 65 | 2624 |
| 937425 | N/A | N/A | 4529 | 4548 | AGTAGTGTTTGGGATGCTTC | 14 | 2625 |
| 937437 | N/A | N/A | 4750 | 4769 | ATGCAACTTAATAACCTTAG | 12 | 2626 |
| 937449 | N/A | N/A | 6321 | 6340 | CCCAACAATAGAATGGTTAA | 87 | 2627 |
| 937461 | N/A | N/A | 7550 | 7569 | TAGGCTGGTAATTTAATGTC | 40 | 2628 |
| 937473 | N/A | N/A | 9934 | 9953 | AAGCTTAGAGTTTTTGCCTT | 38 | 2629 |
| 937485 | N/A | N/A | 10354 | 10373 | TACACAGCATGATCTTGTGT | 85 | 2630 |
| 937497 | N/A | N/A | 14749 | 14768 | TACTTGCTGCCAATATGTAC | 83 | 2631 |
| 937509 | N/A | N/A | 17159 | 17178 | TTTTGAATTACAATGCGGTA | 14 | 2632 |
| 937521 | N/A | N/A | 18685 | 18704 | CGGCCAGTATCTCAGTTTTT | 90 | 2633 |

TABLE 36-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 937533 | N/A | N/A | 19935 | 19954 | TGTGCGCATCATTACGACCA | 79 | 2634 |
| 937545 | N/A | N/A | 23252 | 23271 | CTGTATTTTACTCACCTTT | 32 | 2635 |
| 937557 | N/A | N/A | 26110 | 26129 | AGTAAACATCAGCATCTCAA | 30 | 2636 |
| 937569 | N/A | N/A | 28080 | 28099 | AGACTTTGAAATCTCACAAG | 45 | 2637 |
| 937581 | N/A | N/A | 28496 | 28515 | CACCGGATTGTTTTCTTCAT | 33 | 2638 |
| 937593 | N/A | N/A | 28891 | 28910 | GAAGTCTTGTTCAGTGTCCT | 8 | 2639 |
| 937605 | N/A | N/A | 31491 | 31510 | TTCATATCACCTCTGACTTA | 76 | 2640 |
| 937617 | N/A | N/A | 32745 | 32764 | TGAATATTTTCTCCCTAAAA | 72 | 2641 |
| 937629 | N/A | N/A | 32806 | 32825 | ATTTCAGACTTCTTGTTGTT | 44 | 2642 |
| 937641 | N/A | N/A | 32819 | 32838 | TTTTGTTCTTCCAATTTCAG | 40 | 2643 |
| 937653 | N/A | N/A | 36308 | 36327 | TCTTTGCGCCTGTGTCACAT | 31 | 2644 |
| 937665 | N/A | N/A | 36847 | 36866 | AGTATTTACTACTTCTGCAT | 34 | 2645 |
| 937677 | N/A | N/A | 37662 | 37681 | TGAAAATCAGAAAATGATGC | 80 | 2646 |
| 937689 | N/A | N/A | 41279 | 41298 | TTTATGAGGGACTAGAGCAT | 68 | 2647 |
| 937701 | N/A | N/A | 44118 | 44137 | AAGTACTTCACATGCAACAT | 48 | 2648 |
| 937713 | N/A | N/A | 47686 | 47705 | CAGAGGACCAACTGTACTTT | 49 | 2649 |
| 937725 | N/A | N/A | 48823 | 48842 | GTGGCTTTAAAAACTAGGTA | 13 | 2650 |
| 937737 | N/A | N/A | 49151 | 49170 | GCTCATCAAGGTACCAGTTC | 15 | 2651 |
| 937749 | N/A | N/A | 50060 | 50079 | TCTTCCTTAGCCTTATACTT | 71 | 2652 |
| 937761 | N/A | N/A | 51975 | 51994 | AGAGACCTGATGTCCTAAAC | 53 | 2653 |
| 937773 | N/A | N/A | 55203 | 55222 | ATAGCTATGCTACAATAAAA | 97 | 2654 |
| 937785 | N/A | N/A | 57319 | 57338 | ATTCTTTCCATAAAATAATG | 96 | 2655 |
| 937797 | N/A | N/A | 58028 | 58047 | ACAATTATTTGCATCGCTGA | 61 | 2656 |
| 937809 | N/A | N/A | 60472 | 60491 | TTATTTATCAGTGTGAAGTA | 67 | 2657 |
| 937821 | N/A | N/A | 61630 | 61649 | CCCTGGCAAATATGTAAAAC | 88 | 2658 |
| 937833 | N/A | N/A | 67676 | 67695 | TTTAATCATTGTCTATGGTA | 83 | 2659 |
| 937845 | N/A | N/A | 69108 | 69127 | AACTGAGTTCTATAGGTGCT | 42 | 2660 |
| 937857 | N/A | N/A | 71901 | 71920 | ATAATGCCTCTGAAAAATCA | 107 | 2661 |
| 937869 | N/A | N/A | 73968 | 73987 | GAGCAGCAGGACTCAGCTGG | 95 | 2662 |
| 937881 | N/A | N/A | 75978 | 75997 | TTAAGCCACACGAAGCATTT | 72 | 2663 |
| 937893 | N/A | N/A | 82143 | 82162 | ACTCTACAGGTTATGCTAGC | 66 | 2664 |
| 937905 | N/A | N/A | 82586 | 82605 | TCCTCTCTCTCTTACCAGTA | 50 | 2665 |
| 937917 | N/A | N/A | 82857 | 82876 | GTTTTTCATGGCTCCAATAT | 38 | 2666 |
| 937929 | N/A | N/A | 83495 | 83514 | CACATTCATATCAGTTATGT | 25 | 2667 |
| 937941 | N/A | N/A | 83793 | 83812 | AGTGTTGCACATAGGTTAGA | 17 | 2668 |
| 937953 | N/A | N/A | 84288 | 84307 | ACTCAAGAGTGTCCATTTGG | 41 | 2669 |

TABLE 36-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 937965 | N/A | N/A | 84412 | 84431 | CTTAAGTATCATATATTTCT | 78 | 2670 |
| 937977 | N/A | N/A | 84759 | 84778 | AGTTTGGAATCTTATTAAGC | 37 | 2671 |
| 937989 | N/A | N/A | 84817 | 84836 | GCTGGTTCCTTACAATTATC | 10 | 2672 |
| 938001 | N/A | N/A | 85053 | 85072 | GGGTTAATTAGGATCTATAC | 23 | 2673 |
| 938013 | N/A | N/A | 85185 | 85204 | TGTACATTTTAACCCTTTGA | 61 | 2674 |
| 938025 | N/A | N/A | 92639 | 92658 | ATTGGTTGGTCTCAAAATCT | 34 | 2675 |
| 938037 | N/A | N/A | 97581 | 97600 | CATTAATGAAGGTTTACAGA | 58 | 2676 |
| 938049 | N/A | N/A | 98156 | 98175 | AAACATAAGAGAATAACATT | 94 | 2677 |
| 938061 | N/A | N/A | 99778 | 99797 | GCATTCTTACTATGGGTTG | 28 | 2678 |
| 938073 | N/A | N/A | 105409 | 105428 | ATAACACTAGAGGCCGGGCA | 85 | 2679 |
| 938085 | N/A | N/A | 109978 | 109997 | AGGGAAATACCTAGTCCTAG | 71 | 2680 |
| 938097 | N/A | N/A | 117276 | 117295 | TATCAGGCATGGAGCCACTG | 71 | 2681 |
| 938109 | N/A | N/A | 119026 | 119045 | GTTCCCATTGCATTGTTTTA | 28 | 2682 |
| 938121 | N/A | N/A | 122563 | 122582 | CCAATTCTAGGTATTTAACT | 56 | 2683 |
| 938133 | N/A | N/A | 125211 | 125230 | AGTAATGCACCAGTACAATA | 36 | 2684 |
| 938145 | N/A | N/A | 129289 | 129308 | CCAATACCTCAAAGGATTGG | 132 | 2685 |
| 938157 | N/A | N/A | 130202 | 130221 | TTCCTCACACATTTCTTACA | 75 | 2686 |
| 938169 | N/A | N/A | 132160 | 132179 | CTTATTATTCTCACATATAA | 61 | 2687 |
| 938181 | N/A | N/A | 132517 | 132536 | GTTACATGTAACCATAATCT | 51 | 2688 |
| 938193 | N/A | N/A | 133242 | 133261 | TTGAAAGTGATAATGTGGAA | 40 | 2689 |
| 938205 | N/A | N/A | 134816 | 134835 | ATGATGTAGCTTAAAAAGAA | 86 | 2690 |
| 938217 | N/A | N/A | 137025 | 137044 | ACTGTACAATTAAAAATTAG | 93 | 2691 |
| 938229 | N/A | N/A | 138943 | 138962 | ATTAAGGACCTTAGCTACTT | 93 | 2692 |
| 938241 | N/A | N/A | 139366 | 139385 | ATCAGTCAAAAATCCTTAAT | 60 | 2693 |
| 938253 | N/A | N/A | 143542 | 143561 | AACCTTGGTACAAAACCAT | 77 | 2694 |
| 938265 | N/A | N/A | 146161 | 146180 | CAATGTCCAAGGCCAAGCCC | 99 | 2695 |
| 938277 | N/A | N/A | 147075 | 147094 | AAAGGTGATTTTAGTCAGCC | 43 | 2696 |

TABLE 37

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 708199 | 1477 | 1496 | 81637 | 81656 | GCTAACTGGTTTGCCCTTGC | 20 | 32 |
| 760800 | 4404 | 4423 | 149155 | 149174 | TAGCTGATGTGTTCATGACT | 36 | 2697 |
| 937367 | 1564 | 1583 | 81724 | 81743 | ACTGCTGTGTATTTTCTTC | 32 | 2698 |

TABLE 37-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 937379 | 3941 | 3960 | 147856 | 147875 | CATTGGCGCATGGGCAGTTG | 62 | 2699 |
| 937414 | N/A | N/A | 4008 | 4027 | TGCACAAACACACCCTCGAG | 85 | 2700 |
| 937426 | N/A | N/A | 4531 | 4550 | TAAGTAGTGTTTGGGATGCT | 18 | 2701 |
| 937438 | N/A | N/A | 4751 | 4770 | AATGCAACTTAATAACCTTA | 30 | 2702 |
| 937450 | N/A | N/A | 6450 | 6469 | CTGAAGCCCTCTGAACTAGT | 63 | 2703 |
| 937462 | N/A | N/A | 8171 | 8190 | CATTGCTAATTAGAGTAACA | 45 | 2704 |
| 937474 | N/A | N/A | 9935 | 9954 | AAAGCTTAGAGTTTTTGCCT | 16 | 2705 |
| 937486 | N/A | N/A | 10355 | 10374 | ATACACAGCATGATCTTGTG | 62 | 2706 |
| 937498 | N/A | N/A | 14825 | 14844 | GTCTTTCAACTTTCTATCAC | 45 | 2707 |
| 937510 | N/A | N/A | 17160 | 17179 | ATTTTGAATTACAATGCGGT | 13 | 2708 |
| 937522 | N/A | N/A | 19099 | 19118 | AATAAGCCATGATCACAATA | 68 | 2709 |
| 937534 | N/A | N/A | 19980 | 19999 | GGCCTATGCCTTTACCGCCA | 51 | 2710 |
| 937546 | N/A | N/A | 23254 | 23273 | CGCTGTATTTTTACTCACCT | 14 | 2711 |
| 937558 | N/A | N/A | 26524 | 26543 | TCAGAAAGCTTCTCAAACAT | 52 | 2712 |
| 937570 | N/A | N/A | 28081 | 28100 | AAGACTTTGAAATCTCACAA | 27 | 2713 |
| 937582 | N/A | N/A | 28497 | 28516 | TCACCGGATTGTTTTCTTCA | 24 | 2714 |
| 937594 | N/A | N/A | 28892 | 28911 | TGAAGTCTTGTTCAGTGTCC | 23 | 2715 |
| 937606 | N/A | N/A | 32324 | 32343 | TCCATACAGATCGCATAGCT | 33 | 2716 |
| 937618 | N/A | N/A | 32792 | 32811 | GTTGTTGTTTACATTATTAT | 9 | 2717 |
| 937630 | N/A | N/A | 32807 | 32826 | AATTTCAGACTTCTTGTTGT | 42 | 2718 |
| 937642 | N/A | N/A | 32820 | 32839 | ATTTTGTTCTTCCAATTTCA | 46 | 2719 |
| 937654 | N/A | N/A | 36309 | 36328 | CTCTTTGCGCCTGTGTCACA | 31 | 2720 |
| 937666 | N/A | N/A | 36848 | 36867 | CAGTATTTACTACTTCTGCA | 15 | 2721 |
| 937678 | N/A | N/A | 37789 | 37808 | TTCGATTATCTCAATCAAAT | 63 | 2722 |
| 937690 | N/A | N/A | 41280 | 41299 | TTTTATGAGGGACTAGAGCA | 52 | 2723 |
| 937702 | N/A | N/A | 44143 | 44162 | TTACTACAAAACCAGACACC | 91 | 2724 |
| 937714 | N/A | N/A | 47706 | 47725 | GAATATGGAACCCACAGATG | 71 | 2725 |
| 937726 | N/A | N/A | 48843 | 48862 | GAGAAGTAAAATCATTCAAA | 56 | 2726 |
| 937738 | N/A | N/A | 49153 | 49172 | TAGCTCATCAAGGTACCAGT | 8 | 2727 |
| 937750 | N/A | N/A | 50130 | 50149 | GTATGTTCTACTTCTTCACC | 27 | 2728 |
| 937762 | N/A | N/A | 52329 | 52348 | GAAAACCATGCGGCCTGGCC | 87 | 2729 |
| 937774 | N/A | N/A | 55204 | 55223 | CATAGCTATGCTACAATAAA | 77 | 2730 |
| 937786 | N/A | N/A | 57389 | 57408 | GGAACACATCCCAGAGCTCT | 45 | 2731 |
| 937798 | N/A | N/A | 58348 | 58367 | AAGACCAAAAAGACAACCAT | 122 | 2732 |
| 937810 | N/A | N/A | 60507 | 60526 | GTTTAATCACAGTTTTCTCA | 24 | 2733 |
| 937822 | N/A | N/A | 62506 | 62525 | GGAGGAAAAGCTAGCTACCT | 99 | 2734 |

TABLE 37-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 937834 | N/A | N/A | 68516 | 68535 | AAAGCAGGATGCTACAACGC | 104 | 2735 |
| 937846 | N/A | N/A | 69109 | 69128 | TAACTGAGTTCTATAGGTGC | 48 | 2736 |
| 937858 | N/A | N/A | 71938 | 71957 | TCAGCTTCTCAATCTTTCCT | 45 | 2737 |
| 937870 | N/A | N/A | 74037 | 74056 | CTCCACCAGCAGCACTACTC | 91 | 2738 |
| 937882 | N/A | N/A | 76079 | 76098 | TACGGAATATATAGTATTCA | 115 | 2739 |
| 937894 | N/A | N/A | 82205 | 82224 | TAAGTGTCAAAGACCCTATT | 111 | 2740 |
| 937906 | N/A | N/A | 82655 | 82674 | ACAAGCCCACATATGCAATT | 55 | 2741 |
| 937918 | N/A | N/A | 82867 | 82886 | CTGTTCTTTGGTTTTTCATG | 16 | 2742 |
| 937930 | N/A | N/A | 83743 | 83762 | TTATTATCCAGTGTTTTTAA | 39 | 2743 |
| 937942 | N/A | N/A | 83794 | 83813 | CAGTGTTGCACATAGGTTAG | 14 | 2744 |
| 937954 | N/A | N/A | 84317 | 84336 | TTTCACCCCCAATATTAAGT | 33 | 2745 |
| 937966 | N/A | N/A | 84439 | 84458 | GGTCTCCTCTCCATAGGGTT | 69 | 2746 |
| 937978 | N/A | N/A | 84760 | 84779 | CAGTTTGGAATCTTATTAAG | 38 | 2747 |
| 937990 | N/A | N/A | 84818 | 84837 | TGCTGGTTCCTTACAATTAT | 23 | 2748 |
| 938002 | N/A | N/A | 85055 | 85074 | AAGGGTTAATTAGGATCTAT | 23 | 2749 |
| 938014 | N/A | N/A | 85186 | 85205 | TTGTACATTTTAACCCTTTG | 24 | 2750 |
| 938026 | N/A | N/A | 92676 | 92695 | ATTTTCCTTTCTAAGAAGCT | 109 | 2751 |
| 938038 | N/A | N/A | 97616 | 97635 | TTTTTATGTTGCTCCTTCTT | 60 | 2752 |
| 938050 | N/A | N/A | 98179 | 98198 | TGGTACACAGGAAATACGCA | 51 | 2753 |
| 938062 | N/A | N/A | 99876 | 99895 | TGCCAAGGACTTCGGAGTTT | 41 | 2754 |
| 938074 | N/A | N/A | 105836 | 105855 | GCTCTCAAAGATAGACCCTA | 47 | 2755 |
| 938086 | N/A | N/A | 110157 | 110176 | GCTCACAGCTCTGGGAGGAG | 76 | 2756 |
| 938098 | N/A | N/A | 117437 | 117456 | ATCTAGCAAACCCTCTTCTT | 84 | 2757 |
| 938110 | N/A | N/A | 119027 | 119046 | AGTTCCCATTGCATTGTTTT | 25 | 2758 |
| 938122 | N/A | N/A | 122999 | 123018 | ATCAGTTGGAATGTAAAATG | 42 | 2759 |
| 938134 | N/A | N/A | 125248 | 125267 | TAAAAATGGGAGCATGGCAA | 72 | 2760 |
| 938146 | N/A | N/A | 129750 | 129769 | AAAGCTAGTCAAGTATACTA | 78 | 2761 |
| 938158 | N/A | N/A | 130244 | 130263 | CCAGTTCCTCCAGCACGAGC | 60 | 2762 |
| 938170 | N/A | N/A | 132161 | 132180 | GCTTATTATTCTCACATATA | 8 | 2763 |
| 938182 | N/A | N/A | 132518 | 132537 | AGTTACATGTAACCATAATC | 41 | 2764 |
| 938194 | N/A | N/A | 133369 | 133388 | ATAAACCAAGTTAGTTTGTC | 35 | 2765 |
| 938206 | N/A | N/A | 134853 | 134872 | TTCTTCTGTTTGCATTAAAT | 53 | 2766 |
| 938218 | N/A | N/A | 137049 | 137068 | CATGTAT CCTTTAAAAGTG | 72 | 2767 |
| 938230 | N/A | N/A | 139050 | 139069 | AAGCAGCAGATTAAATTAGC | 70 | 2768 |
| 938242 | N/A | N/A | 139497 | 139516 | AAAACTTTAGTCTTCATAAA | 110 | 2769 |
| 938254 | N/A | N/A | 143622 | 143641 | GGACAACATGATGGGCCAGT | 62 | 2770 |

TABLE 37-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 938266 | N/A | N/A | 146188 | 146207 | TGCTTCCAGCTTCTAGTTAC | 55 | 2771 |
| 938278 | N/A | N/A | 147266 | 147285 | CACCAGGCAGTGAAAAGAGA | 93 | 2772 |

TABLE 38

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 708199 | 1477 | 1496 | 81637 | 81656 | GCTAACTGGTTTGCCCTTGC | 19 | 32 |
| 937368 | 1565 | 1584 | 81725 | 81744 | AACTGCTGTGTATTTTCTT | 45 | 2773 |
| 937380 | 3949 | 3968 | 147864 | 147883 | ATTAGCATCATTGGCGCATG | 54 | 2774 |
| 937391 | 4405 | 4424 | 149156 | 149175 | CTAGCTGATGTGTTCATGAC | 48 | 2775 |
| 937415 | N/A | N/A | 4045 | 4064 | GAACTGACAACCGCCCGCCA | 30 | 2776 |
| 937427 | N/A | N/A | 4532 | 4551 | CTAAGTAGTGTTTGGGATGC | 21 | 2777 |
| 937439 | N/A | N/A | 4752 | 4771 | CAATGCAACTTAATAACCTT | 28 | 2778 |
| 937451 | N/A | N/A | 6471 | 6490 | CTAGCAAGAGCCATAAAAAT | 78 | 2779 |
| 937463 | N/A | N/A | 8194 | 8213 | ATCCCTTATGTAGAAGTATA | 40 | 2780 |
| 937475 | N/A | N/A | 9937 | 9956 | TCAAAGCTTAGAGTTTTTGC | 38 | 2781 |
| 937487 | N/A | N/A | 10383 | 10402 | TAAAAAGGTTGAGGACCATT | 62 | 2782 |
| 937499 | N/A | N/A | 15807 | 15826 | TGGTATACTTGTTGAGCTCT | 36 | 2783 |
| 937511 | N/A | N/A | 17161 | 17180 | CATTTTGAATTACAATGCGG | 19 | 2784 |
| 937523 | N/A | N/A | 19683 | 19702 | ACCAGAGCCATTCCAACTCC | 60 | 2785 |
| 937535 | N/A | N/A | 19992 | 20011 | GATCAGGGCCCAGGCCTATG | 75 | 2786 |
| 937547 | N/A | N/A | 23255 | 23274 | ACGCTGTATTTTTACTCACC | 8 | 2787 |
| 937559 | N/A | N/A | 26624 | 26643 | TGTATGCCCTGGGAGAATAA | 67 | 2788 |
| 937571 | N/A | N/A | 28083 | 28102 | CAAAGACTTTGAAATCTCAC | 35 | 2789 |
| 937583 | N/A | N/A | 28498 | 28517 | ATCACCGGATTGTTTCTTC | 25 | 2790 |
| 937595 | N/A | N/A | 28893 | 28912 | CTGAAGTCTTGTTCAGTGTC | 21 | 2791 |
| 937607 | N/A | N/A | 32325 | 32344 | TTCCATACAGATCGCATAGC | 46 | 2792 |
| 937619 | N/A | N/A | 32793 | 32812 | TGTTGTTGTTTACATTATTA | 9 | 2793 |
| 937631 | N/A | N/A | 32808 | 32827 | CAATTTCAGACTTCTTGTTG | 44 | 2794 |
| 937643 | N/A | N/A | 33044 | 33063 | CCCTCCAGCTATTCACATGG | 87 | 2795 |
| 937655 | N/A | N/A | 36310 | 36329 | TCTCTTTGCGCCTGTGTCAC | 26 | 2796 |
| 937667 | N/A | N/A | 36849 | 36868 | TCAGTATTTACTACTTCTGC | 28 | 2797 |
| 937679 | N/A | N/A | 37799 | 37818 | GAAGTCTTCCTTCGATTATC | 32 | 2798 |

TABLE 38-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 937691 | N/A | N/A | 41281 | 41300 | ATTTTATGAGGGACTAGAGC | 44 | 2799 |
| 937703 | N/A | N/A | 44743 | 44762 | TCATTTCTAAATAATATGCG | 90 | 2800 |
| 937715 | N/A | N/A | 48108 | 48127 | TTGGTTCAGACGCAACCATG | 129 | 2801 |
| 937727 | N/A | N/A | 48856 | 48875 | AGTATTTGAAACTGAGAAGT | 66 | 2802 |
| 937739 | N/A | N/A | 49154 | 49173 | TTAGCTCATCAAGGTACCAG | 15 | 2803 |
| 937751 | N/A | N/A | 50210 | 50229 | GACTAAATTTTAATATAAC | 88 | 2804 |
| 937763 | N/A | N/A | 52397 | 52416 | AGTAAGTCTCTAATAAAAAA | 96 | 2805 |
| 937775 | N/A | N/A | 55360 | 55379 | GCAGCGGAAAATATGATTTA | 64 | 2806 |
| 937787 | N/A | N/A | 57465 | 57484 | TTCACTAGGTTCTCAAAAGG | 84 | 2807 |
| 937799 | N/A | N/A | 58355 | 58374 | CACTATCAAGACCAAAAAGA | 113 | 2808 |
| 937811 | N/A | N/A | 60508 | 60527 | TGTTTAATCACAGTTTTCTC | 51 | 2809 |
| 937823 | N/A | N/A | 62624 | 62643 | AAGATCAAAAGAAGTTTTAG | 89 | 2810 |
| 937835 | N/A | N/A | 68567 | 68586 | AAAAGCATTCTGGAAGAGAA | 98 | 2811 |
| 937847 | N/A | N/A | 69110 | 69129 | TTAACTGAGTTCTATAGGTG | 53 | 2812 |
| 937859 | N/A | N/A | 72175 | 72194 | TAGCAGGCGATGTTGGAGGA | 131 | 2813 |
| 937871 | N/A | N/A | 74117 | 74136 | TAGGTGTGGGTAGGTATGAG | 86 | 2814 |
| 937883 | N/A | N/A | 76109 | 76128 | TATGTGAAGATAAACTGCTA | 73 | 2815 |
| 937895 | N/A | N/A | 82215 | 82234 | AACTCTTCTCTAAGTGTCAA | 79 | 2816 |
| 937907 | N/A | N/A | 82806 | 82825 | GCCAGTCTCACAGTGTCAAC | 27 | 2817 |
| 937919 | N/A | N/A | 82878 | 82897 | TCTCTCACTGGCTGTTCTTT | 64 | 2818 |
| 937931 | N/A | N/A | 83773 | 83792 | ATTTTCCATATAAATTATGT | 94 | 2819 |
| 937943 | N/A | N/A | 83804 | 83823 | ATATTAACCACAGTGTTGCA | 41 | 2820 |
| 937955 | N/A | N/A | 84347 | 84366 | ACTAAAATCTTTCCTCAGTG | 70 | 2821 |
| 937967 | N/A | N/A | 84579 | 84598 | TCTAAGCGACTGCTTAATAA | 78 | 2822 |
| 937979 | N/A | N/A | 84761 | 84780 | TCAGTTTGGAATCTTATTAA | 33 | 2823 |
| 937991 | N/A | N/A | 84819 | 84838 | ATGCTGGTTCCTTACAATTA | 19 | 2824 |
| 938003 | N/A | N/A | 85057 | 85076 | CAAAGGGTTAATTAGGATCT | 33 | 2825 |
| 938015 | N/A | N/A | 85187 | 85206 | CTTGTACATTTTAACCCTTT | 22 | 2826 |
| 938027 | N/A | N/A | 95247 | 95266 | TACACTTTAAACGGTTTATT | 54 | 2827 |
| 938039 | N/A | N/A | 97617 | 97636 | CTTTTTATGTTGCTCCTTCT | 45 | 2828 |
| 938051 | N/A | N/A | 98329 | 98348 | GCCCTCTTACTTACTAGCCA | 67 | 2829 |
| 938063 | N/A | N/A | 99878 | 99897 | ATTGCCAAGGACTTCGGAGT | 55 | 2830 |
| 938075 | N/A | N/A | 105916 | 105935 | CAAATAGGCCCAATACATAT | 93 | 2831 |
| 938087 | N/A | N/A | 110707 | 110726 | AATTGTCCATCCCAGTGATT | 98 | 2832 |
| 938099 | N/A | N/A | 117523 | 117542 | GTTGCCCCTCTGCTTCAAAA | 57 | 2833 |
| 938111 | N/A | N/A | 119029 | 119048 | AAAGTTCCCATTGCATTGTT | 31 | 2834 |

TABLE 38-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 938123 | N/A | N/A | 123079 | 123098 | GACCTGTTGAAATTAAAAAG | 91 | 2835 |
| 938135 | N/A | N/A | 125729 | 125748 | GAATTACATTATTATCTATC | 50 | 2836 |
| 938147 | N/A | N/A | 129785 | 129804 | CTTATTACCTTCCTGTATAT | 117 | 2837 |
| 938159 | N/A | N/A | 130324 | 130343 | TCTGCATGTAAGGGCCTCGC | 53 | 2838 |
| 938171 | N/A | N/A | 132163 | 132182 | TTGCTTATTATTCTCACATA | 19 | 2839 |
| 938183 | N/A | N/A | 132519 | 132538 | TAGTTACATGTAACCATAAT | 54 | 2840 |
| 938195 | N/A | N/A | 133470 | 133489 | ATAAAAGCCAGCATGATAAA | 64 | 2841 |
| 938207 | N/A | N/A | 134941 | 134960 | CTATGTTTTCAATGCCTTTG | 21 | 2842 |
| 938219 | N/A | N/A | 137245 | 137264 | AAAATATTAGGCATTTCCCA | 44 | 2843 |
| 938231 | N/A | N/A | 139266 | 139285 | ATTTGTAACTAGGTTTTGTC | 74 | 2844 |
| 938243 | N/A | N/A | 139545 | 139564 | AATTTTATTTGTAATACTGA | 121 | 2845 |
| 938255 | N/A | N/A | 143628 | 143647 | TTCAAAGGACAACATGATGG | 82 | 2846 |
| 938267 | N/A | N/A | 146379 | 146398 | CTTCAGTGCAGCTCCTTCTC | 55 | 2847 |
| 938279 | N/A | N/A | 147364 | 147383 | AAACAGATTACATTAATAAG | 86 | 2848 |

TABLE 39

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 708199 | 1477 | 1496 | 81637 | 81656 | GCTAACTGGTTTGCCCTTGC | 17 | 32 |
| 937369 | 1566 | 1585 | 81726 | 81745 | GAACTGCTGTGTATTTTTCT | 28 | 2849 |
| 937381 | 3952 | 3971 | 147867 | 147886 | GTCATTAGCATCATTGGCGC | 87 | 2850 |
| 937392 | 4406 | 4425 | 149157 | 149176 | GCTAGCTGATGTGTTCATGA | 60 | 2851 |
| 937416 | N/A | N/A | 4090 | 4109 | CCTTCTCCCTTTGAACACTA | 37 | 2852 |
| 937428 | N/A | N/A | 4533 | 4552 | GCTAAGTAGTGTTTGGGATG | 14 | 2853 |
| 937440 | N/A | N/A | 4753 | 4772 | TCAATGCAACTTAATAACCT | 55 | 2854 |
| 937452 | N/A | N/A | 6571 | 6590 | CCCACAATATTTGACAAACT | 70 | 2855 |
| 937464 | N/A | N/A | 8607 | 8626 | GCTGTAGCTATTTAGGACAA | 24 | 2856 |
| 937476 | N/A | N/A | 10130 | 10149 | ATGTTAGCCAGCTGGTGTAC | 97 | 2857 |
| 937488 | N/A | N/A | 10400 | 10419 | AAACCGGTCCCTAGTGTTAA | 91 | 2858 |
| 937500 | N/A | N/A | 16473 | 16492 | AGTAATGCCCTTAGGGCCTA | 76 | 2859 |
| 937512 | N/A | N/A | 17162 | 17181 | ACATTTGAATTACAATGCG | 19 | 2860 |
| 937524 | N/A | N/A | 19836 | 19855 | CCCGTGATCTGATTCCCATG | 71 | 2861 |
| 937536 | N/A | N/A | 20207 | 20226 | ATGCTCAAGGAGGAGCAAGA | 104 | 2862 |
| 937548 | N/A | N/A | 23256 | 23275 | TACGCTGTATTTTACTCAC | 36 | 2863 |

TABLE 39-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 937560 | N/A | N/A | 26628 | 26647 | ATTATGTATGCCCTGGGAGA | 58 | 2864 |
| 937572 | N/A | N/A | 28084 | 28103 | GCAAAGACTTTGAAATCTCA | 11 | 2865 |
| 937584 | N/A | N/A | 28499 | 28518 | AATCACCGGATTGTTTTCTT | 28 | 2866 |
| 937596 | N/A | N/A | 28894 | 28913 | GCTGAAGTCTTGTTCAGTGT | 66 | 2867 |
| 937608 | N/A | N/A | 32326 | 32345 | ATTCCATACAGATCGCATAG | 37 | 2868 |
| 937620 | N/A | N/A | 32796 | 32815 | TCTTGTTGTTGTTTACATTA | 11 | 2869 |
| 937632 | N/A | N/A | 32809 | 32828 | CCAATTTCAGACTTCTTGTT | 28 | 2870 |
| 937644 | N/A | N/A | 33050 | 33069 | GCTCTTCCCTCCAGCTATTC | 44 | 2871 |
| 937656 | N/A | N/A | 36311 | 36330 | CTCTCTTTGCGCCTGTGTCA | 24 | 2872 |
| 937668 | N/A | N/A | 36851 | 36870 | AATCAGTATTTACTACTTCT | 25 | 2873 |
| 937680 | N/A | N/A | 38003 | 38022 | TACAGGTGAGATATATAGGA | 9 | 2874 |
| 937692 | N/A | N/A | 41282 | 41301 | CATTTTATGAGGGACTAGAG | 63 | 2875 |
| 937704 | N/A | N/A | 45245 | 45264 | ACCAATCACTGTTATAAAGA | 42 | 2876 |
| 937716 | N/A | N/A | 48164 | 48183 | AAATTGTCATACTGTATTGT | 60 | 2877 |
| 937728 | N/A | N/A | 48887 | 48906 | CTGATTACACAAACCAGTCT | 73 | 2878 |
| 937740 | N/A | N/A | 49155 | 49174 | TTTAGCTCATCAAGGTACCA | 64 | 2879 |
| 937752 | N/A | N/A | 50666 | 50685 | TGGCATATACAAATAAATAA | 57 | 2880 |
| 937764 | N/A | N/A | 52516 | 52535 | TTAAACCAGGATCCCTAGAA | 93 | 2881 |
| 937776 | N/A | N/A | 55427 | 55446 | CACATTCTGTTACTTCACCA | 57 | 2882 |
| 937788 | N/A | N/A | 57466 | 57485 | TTTCACTAGGTTCTCAAAAG | 93 | 2883 |
| 937800 | N/A | N/A | 58468 | 58487 | ACACATATCTGTGTCTTAAT | 67 | 2884 |
| 937812 | N/A | N/A | 60509 | 60528 | TTGTTTAATCACAGTTTTCT | 49 | 2885 |
| 937824 | N/A | N/A | 63522 | 63541 | CTCCCTATCTCAAATGAATG | 105 | 2886 |
| 937836 | N/A | N/A | 68773 | 68792 | TGCTGAACTCTTCTGAGGCT | 98 | 2887 |
| 937848 | N/A | N/A | 69111 | 69130 | ATTAACTGAGTTCTATAGGT | 51 | 2888 |
| 937860 | N/A | N/A | 72338 | 72357 | AAAAGCATTGTAACAACAAG | 77 | 2889 |
| 937872 | N/A | N/A | 74138 | 74157 | TAACCTCTTCTTATCCCAAA | 97 | 2890 |
| 937884 | N/A | N/A | 76189 | 76208 | GAAACATTTATTGAACATAA | 78 | 2891 |
| 937896 | N/A | N/A | 82245 | 82264 | GCTTTTCATCAGGTGATAAA | 70 | 2892 |
| 937908 | N/A | N/A | 82847 | 82866 | GCTCCAATATCGGCAATGCT | 59 | 2893 |
| 937920 | N/A | N/A | 82922 | 82941 | TTTTTGTCCTTCACTTTCTC | 53 | 2894 |
| 937932 | N/A | N/A | 83774 | 83793 | AATTTTCCATATAAATTATG | 145 | 2895 |
| 937944 | N/A | N/A | 83853 | 83872 | CCTTTCTTGAAGTAAGCATA | 29 | 2896 |
| 937956 | N/A | N/A | 84392 | 84411 | CAGCCCCCTTCAGGTTTTTT | 59 | 2897 |
| 937968 | N/A | N/A | 84609 | 84628 | TTCTAAATAATTTATACAGT | 81 | 2898 |
| 937980 | N/A | N/A | 84762 | 84781 | CTCAGTTTGGAATCTTATTA | 35 | 2899 |

TABLE 39-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 937992 | N/A | N/A | 84820 | 84839 | AATGCTGGTTCCTTACAATT | 31 | 2900 |
| 938004 | N/A | N/A | 85059 | 85078 | CCCAAAGGGTTAATTAGGAT | 7 | 2901 |
| 938016 | N/A | N/A | 85188 | 85207 | TCTTGTACATTTTAACCCTT | 29 | 2902 |
| 938028 | N/A | N/A | 95368 | 95387 | TTAAAATCAACTGAGAAGAC | 95 | 2903 |
| 938040 | N/A | N/A | 97618 | 97637 | ACTTTTTATGTTGCTCCTTC | 28 | 2904 |
| 938052 | N/A | N/A | 98348 | 98367 | CTTAAACACCAGATGGTCAG | 74 | 2905 |
| 938064 | N/A | N/A | 100037 | 100056 | ATAGCTAAAGAGTCAAGTGG | 65 | 2906 |
| 938076 | N/A | N/A | 106796 | 106815 | AGAGGAAGTAAAAAAGAAGG | 91 | 2907 |
| 938088 | N/A | N/A | 110913 | 110932 | AACTGCCCCTCCAACACCCC | 84 | 2908 |
| 938100 | N/A | N/A | 117931 | 117950 | AGCACAGAATACTAGTTTAT | 55 | 2909 |
| 938112 | N/A | N/A | 119030 | 119049 | AAAAGTTCCCATTGCATTGT | 45 | 2910 |
| 938124 | N/A | N/A | 123159 | 123178 | TGATGAGGTGCTCCTGGATC | 60 | 2911 |
| 938136 | N/A | N/A | 125751 | 125770 | ATCAGTTTGTATGACCATAA | 9 | 2912 |
| 938148 | N/A | N/A | 129786 | 129805 | ACTTATTACCTTCCTGTATA | 69 | 2913 |
| 938160 | N/A | N/A | 130548 | 130567 | GGCACTGCATTCATTTTGAG | 64 | 2914 |
| 938172 | N/A | N/A | 132164 | 132183 | TTTGCTTATTATTCTCACAT | 12 | 2915 |
| 938184 | N/A | N/A | 132520 | 132539 | GTAGTTACATGTAACCATAA | 27 | 2916 |
| 938196 | N/A | N/A | 133494 | 133513 | ATTGTTAAAATATATACAAG | 100 | 2917 |
| 938208 | N/A | N/A | 134957 | 134976 | GCAGTCATTAGTGGTCCTAT | 21 | 2918 |
| 938220 | N/A | N/A | 137464 | 137483 | ATAAATTTCATCTTATCAGA | 97 | 2919 |
| 938232 | N/A | N/A | 139267 | 139286 | AATTTGTAACTAGGTTTTGT | 79 | 2920 |
| 938244 | N/A | N/A | 140114 | 140133 | TATACTTTAAATCAATACTA | 81 | 2921 |
| 938256 | N/A | N/A | 143759 | 143778 | CTTCTGCCACTCAGTTTACT | 87 | 2922 |
| 938268 | N/A | N/A | 146518 | 146537 | GGAAATGGAATTCATTGTGG | 33 | 2923 |
| 938280 | N/A | N/A | 147490 | 147509 | ATTAGACACTGGATCCAAGG | 53 | 2924 |

TABLE 40

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 708199 | 1477 | 1496 | 81637 | 81656 | GCTAACTGGTTTGCCCTTGC | 20 | 32 |
| 937370 | 2356 | 2375 | 91240 | 91259 | CTGTTCGATGCAGGACTAGC | 49 | 2925 |
| 937382 | 4393 | 4412 | 149144 | 149163 | TTCATGACTTTCAAGGGTTA | 27 | 2926 |
| 937393 | 4413 | 4432 | 149164 | 149183 | TTCTTTTGCTAGCTGATGTG | 31 | 2927 |

TABLE 40-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 937417 | N/A | N/A | 4091 | 4110 | TCCTTCTCCCTTTGAACACT | 23 | 2928 |
| 937429 | N/A | N/A | 4534 | 4553 | GGCTAAGTAGTGTTTGGGAT | 4 | 2929 |
| 937441 | N/A | N/A | 4754 | 4773 | GTCAATGCAACTTAATAACC | 18 | 2930 |
| 937453 | N/A | N/A | 6585 | 6604 | TCCTTTAAAAATTCCCCACA | 73 | 2931 |
| 937465 | N/A | N/A | 8764 | 8783 | AATAGGGTTTTGTTCATGCT | 4 | 2932 |
| 937477 | N/A | N/A | 10345 | 10364 | TGATCTTGTGTATATATTAC | 11 | 2933 |
| 937489 | N/A | N/A | 11272 | 11291 | GACTGTATTCCATAAAACAA | 48 | 2934 |
| 937501 | N/A | N/A | 16482 | 16501 | CTATAAAACAGTAATGCCCT | 91 | 2935 |
| 937513 | N/A | N/A | 17163 | 17182 | TACATTTTGAATTACAATGC | 25 | 2936 |
| 937525 | N/A | N/A | 19925 | 19944 | ATTACGACCATTCTGCTCAG | 39 | 2937 |
| 937537 | N/A | N/A | 20254 | 20273 | CAAACCTCTTCACTCCTGCC | 66 | 2938 |
| 937549 | N/A | N/A | 23257 | 23276 | TTACGCTGTATTTTTACTCA | 23 | 2939 |
| 937561 | N/A | N/A | 26913 | 26932 | TTTCTTTTCCGTTTTTCATA | 21 | 2940 |
| 937573 | N/A | N/A | 28085 | 28104 | AGCAAAGACTTTGAAATCTC | 19 | 2941 |
| 937585 | N/A | N/A | 28587 | 28606 | TATAAACAAACTTTTTGATT | 104 | 2942 |
| 937597 | N/A | N/A | 28948 | 28967 | GGAATTATTCTCTCAACTAT | 89 | 2943 |
| 937609 | N/A | N/A | 32327 | 32346 | TATTCCATACAGATCGCATA | 52 | 2944 |
| 937621 | N/A | N/A | 32797 | 32816 | TTCTTGTTGTTGTTTACATT | 12 | 2945 |
| 937633 | N/A | N/A | 32810 | 32829 | TCCAATTTCAGACTTCTTGT | 10 | 2946 |
| 937645 | N/A | N/A | 33766 | 33785 | AATATACACAAACAATCTAA | 90 | 2947 |
| 937657 | N/A | N/A | 36312 | 36331 | GCTCTCTTTGCGCCTGTGTC | 20 | 2948 |
| 937669 | N/A | N/A | 36852 | 36871 | GAATCAGTATTTACTACTTC | 21 | 2949 |
| 937681 | N/A | N/A | 38517 | 38536 | GTCTACAAAATAACCTGTAA | 54 | 2950 |
| 937693 | N/A | N/A | 41719 | 41738 | AATGATGCTTTCAAAGGCAC | 90 | 2951 |
| 937705 | N/A | N/A | 45419 | 45438 | TTATAGCCAGGCATGTGGCA | 73 | 2952 |
| 937717 | N/A | N/A | 48165 | 48184 | TAAATTGTCATACTGTATTG | 55 | 2953 |
| 937729 | N/A | N/A | 49018 | 49037 | CTATGGTTTGTCTTAAGTAC | 46 | 2954 |
| 937741 | N/A | N/A | 49156 | 49175 | CTTTAGCTCATCAAGGTACC | 67 | 2955 |
| 937753 | N/A | N/A | 50759 | 50778 | ATAAAAACAGCTTTTGGTAT | 75 | 2956 |
| 937765 | N/A | N/A | 52610 | 52629 | AAGGCCACAGAACAGAGCCA | 110 | 2957 |
| 937777 | N/A | N/A | 55507 | 55526 | TGGTCATGAATAAGAATCGC | 77 | 2958 |
| 937789 | N/A | N/A | 57467 | 57486 | GTTTCACTAGGTTCTCAAAA | 32 | 2959 |
| 937801 | N/A | N/A | 58477 | 58496 | CCAGAATGAACACATATCTG | 95 | 2960 |
| 937813 | N/A | N/A | 60510 | 60529 | TTTGTTTAATCACAGTTTTC | 60 | 2961 |
| 937825 | N/A | N/A | 63655 | 63674 | AGGAGGCTAAGGTGAATCAC | 66 | 2962 |
| 937837 | N/A | N/A | 68850 | 68869 | AAATAGGTGAGGGACTGGAA | 80 | 2963 |

TABLE 40-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 937849 | N/A | N/A | 69112 | 69131 | AATTAACTGAGTTCTATAGG | 85 | 2964 |
| 937861 | N/A | N/A | 72541 | 72560 | ACTATGCCCAGCAAGTCTGG | 118 | 2965 |
| 937873 | N/A | N/A | 74238 | 74257 | CTTCTATAACTGTCATTGTC | 66 | 2966 |
| 937885 | N/A | N/A | 76310 | 76329 | GAAAGTTTATATAATCTGGC | 96 | 2967 |
| 937897 | N/A | N/A | 82325 | 82344 | AGATCCTGTGTTCCAGACAC | 39 | 2968 |
| 937909 | N/A | N/A | 82848 | 82867 | GGCTCCAATATCGGCAATGC | 34 | 2969 |
| 937921 | N/A | N/A | 82952 | 82971 | TCCATCAATCTTGGTCTATC | 26 | 2970 |
| 937933 | N/A | N/A | 83784 | 83803 | CATAGGTTAGAATTTTCCAT | 14 | 2971 |
| 937945 | N/A | N/A | 83883 | 83902 | TCATGTCTTGTATTATAAGT | 57 | 2972 |
| 937957 | N/A | N/A | 84402 | 84421 | ATATATTTCTCAGCCCCCTT | 61 | 2973 |
| 937969 | N/A | N/A | 84673 | 84692 | GATAATATTCATTGCTATTT | 23 | 2974 |
| 937981 | N/A | N/A | 84763 | 84782 | ACTCAGTTTGGAATCTTATT | 34 | 2975 |
| 937993 | N/A | N/A | 84821 | 84840 | AAATGCTGGTTCCTTACAAT | 50 | 2976 |
| 938005 | N/A | N/A | 85101 | 85120 | TTAACCTCCTTAAGATTAAG | 89 | 2977 |
| 938017 | N/A | N/A | 85189 | 85208 | TTCTTGTACATTTTAACCCT | 27 | 2978 |
| 938029 | N/A | N/A | 95475 | 95494 | TAACGGTTGCTTAGGGTTGG | 36 | 2979 |
| 938041 | N/A | N/A | 97619 | 97638 | GACTTTTTATGTTGCTCCTT | 15 | 2980 |
| 938053 | N/A | N/A | 98485 | 98504 | AAATGAAGGACTACAGATAT | 89 | 2981 |
| 938065 | N/A | N/A | 100065 | 100084 | GCATCGCAAGCTTTACTGCA | 74 | 2982 |
| 938077 | N/A | N/A | 106803 | 106822 | GGAGCGAAGAGGAAGTAAAA | 138 | 2983 |
| 938089 | N/A | N/A | 111200 | 111219 | GTCATTAAGTAGGTGAATTC | 70 | 2984 |
| 938101 | N/A | N/A | 118324 | 118343 | TGAGAAATGTCTTTTCTGTA | 36 | 2985 |
| 938113 | N/A | N/A | 119031 | 119050 | AAAAAGTTCCCATTGCATTG | 46 | 2986 |
| 938125 | N/A | N/A | 123631 | 123650 | AAACTGTTGGCTCAAATGAT | 79 | 2987 |
| 938137 | N/A | N/A | 125847 | 125866 | AAGGTAGTCCTATTAGATTA | 53 | 2988 |
| 938149 | N/A | N/A | 129787 | 129806 | TACTTATTACCTTCCTGTAT | 72 | 2989 |
| 938161 | N/A | N/A | 130731 | 130750 | CTCAGCCTCAAACACCAGTT | 66 | 2990 |
| 938173 | N/A | N/A | 132165 | 132184 | TTTTGCTTATTATTCTCACA | 11 | 2991 |
| 938185 | N/A | N/A | 132521 | 132540 | TGTAGTTACATGTAACCATA | 25 | 2992 |
| 938197 | N/A | N/A | 133701 | 133720 | GTCTCAAAAGCATGCATACA | 36 | 2993 |
| 938209 | N/A | N/A | 135061 | 135080 | GAATAAAATAATTATCCTAT | 110 | 2994 |
| 938221 | N/A | N/A | 137468 | 137487 | AGGCATAAATTTCATCTTAT | 8 | 2995 |
| 938233 | N/A | N/A | 139268 | 139287 | TAATTTGTAACTAGGTTTTG | 89 | 2996 |
| 938245 | N/A | N/A | 140734 | 140753 | GCTGAGTGAATGTACATAGG | 21 | 2997 |

TABLE 40-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 938257 | N/A | N/A | 143795 | 143814 | AAGGACCACAGTCTCTCTCA | 73 | 2998 |
| 938269 | N/A | N/A | 146633 | 146652 | AACTTCCCAGAGCTGTGGAA | 79 | 2999 |
| 938281 | N/A | N/A | 147720 | 147739 | GGACTCTCAGGAAAGGGCAA | 62 | 3000 |

TABLE 41

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 708199 | 1477 | 1496 | 81637 | 81656 | GCTAACTGGTTTGCCCTTGC | 22 | 32 |
| 937364 | 1078 | 1097 | 49252 | 49271 | CTTTTCTCATGTGCGGCATC | 26 | 3001 |
| 937374 | 2459 | 2478 | 91729 | 91748 | TGATGTTTCATTGGGTTTAA | 13 | 3002 |
| 937386 | 4398 | 4417 | 149149 | 149168 | ATGTGTTCATGACTTTCAAG | 18 | 3003 |
| 937397 | 4418 | 4437 | 149169 | 149188 | GTTACTTCTTTTGCTAGCTG | 16 | 3004 |
| 937409 | N/A | N/A | 3346 | 3365 | CTAACTTCTCCCCTCCAGAG | 69 | 3005 |
| 937421 | N/A | N/A | 4525 | 4544 | GTGTTTGGGATGCTTCAGAC | 8 | 3006 |
| 937433 | N/A | N/A | 4745 | 4764 | ACTTAATAACCTTAGTTTTA | 83 | 3007 |
| 937445 | N/A | N/A | 5173 | 5192 | GAATGCTGCATTTTTTTTCA | 42 | 3008 |
| 937457 | N/A | N/A | 7141 | 7160 | TAAGTTGCAATGCCTCAAGA | 44 | 3009 |
| 937469 | N/A | N/A | 9929 | 9948 | TAGAGTTTTTGCCTTCCATT | 5 | 3010 |
| 937481 | N/A | N/A | 10349 | 10368 | AGCATGATCTTGTGTATATA | 5 | 3011 |
| 937493 | N/A | N/A | 13758 | 13777 | GGCACGAAACTGACATTTTC | 20 | 3012 |
| 937505 | N/A | N/A | 17154 | 17173 | AATTACAATGCGGTATATAT | 29 | 3013 |
| 937517 | N/A | N/A | 18681 | 18700 | CAGTATCTCAGTTTTTTTTT | 22 | 3014 |
| 937529 | N/A | N/A | 19931 | 19950 | CGCATCATTACGACCATTCT | 26 | 3015 |
| 937541 | N/A | N/A | 22994 | 23013 | AACATAGTTTCTCATCACCA | 26 | 3016 |
| 937553 | N/A | N/A | 24547 | 24566 | CTGGCCACGACAAGTTAATT | 88 | 3017 |
| 937565 | N/A | N/A | 28032 | 28051 | ATCTCTTTGACCTAAAGGCA | 49 | 3018 |
| 937577 | N/A | N/A | 28491 | 28510 | GATTGTTTTCTTCATTATTG | 23 | 3019 |
| 937589 | N/A | N/A | 28886 | 28905 | CTTGTTCAGTGTCCTTCTAG | 25 | 3020 |
| 937601 | N/A | N/A | 30392 | 30411 | GGGATTAGGATGCCAAATAG | 18 | 3021 |
| 937613 | N/A | N/A | 32332 | 32351 | AGTAATATTCCATACAGATC | 32 | 3022 |
| 937625 | N/A | N/A | 32801 | 32820 | AGACTTCTTGTTGTTGTTTA | 28 | 3023 |
| 937637 | N/A | N/A | 32814 | 32833 | TTCTTCCAATTTCAGACTTC | 34 | 3024 |
| 937649 | N/A | N/A | 34713 | 34732 | ACCAGGAAATTGCTTCTAAT | 55 | 3025 |

TABLE 41-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 937661 | N/A | N/A | 36317 | 36336 | CATGTGCTCTCTTTGCGCCT | 60 | 3026 |
| 937673 | N/A | N/A | 37129 | 37148 | ATATGGCCCTAGAGCCTAAA | 105 | 3027 |
| 937685 | N/A | N/A | 41273 | 41292 | AGGGACTAGAGCATCCATAA | 41 | 3028 |
| 937697 | N/A | N/A | 43295 | 43314 | AACAAAGGCCAAGAGCATAT | 49 | 3029 |
| 937709 | N/A | N/A | 47548 | 47567 | ATGGAATTACTTTATTCTAC | 64 | 3030 |
| 937721 | N/A | N/A | 48532 | 48551 | CAAAACATTAACAATACACT | 89 | 3031 |
| 937733 | N/A | N/A | 49147 | 49166 | ATCAAGGTACCAGTTCTTAT | 21 | 3032 |
| 937745 | N/A | N/A | 49228 | 49247 | ACCAAATCACACTAAAATGA | 99 | 3033 |
| 937757 | N/A | N/A | 51198 | 51217 | AGTAGGGAACCTTTTTTTTT | 45 | 3034 |
| 937769 | N/A | N/A | 53410 | 53429 | ACAACAAACCAAACCACATA | 82 | 3035 |
| 937781 | N/A | N/A | 56404 | 56423 | CTAGAAAGGCAGATGTTGAA | 98 | 3036 |
| 937793 | N/A | N/A | 57473 | 57492 | TACACAGTTTCACTAGGTTC | 33 | 3037 |
| 937805 | N/A | N/A | 58745 | 58764 | TGAAGTTATTGTTCTGACTT | 42 | 3038 |
| 937817 | N/A | N/A | 61186 | 61205 | TTTCTCACATTTACCATTCA | 84 | 3039 |
| 937829 | N/A | N/A | 66835 | 66854 | AAAAAACTGACCTATTCTAT | 87 | 3040 |
| 937841 | N/A | N/A | 69103 | 69122 | AGTTCTATAGGTGCTTAAGT | 32 | 3041 |
| 937853 | N/A | N/A | 70105 | 70124 | GAATACTCATCTGTTCTAAC | 74 | 3042 |
| 937865 | N/A | N/A | 73527 | 73546 | TGAAAAGCACACATTTAAGT | 78 | 3043 |
| 937877 | N/A | N/A | 74702 | 74721 | GTCTCAGAAAGTTCAGGTAG | 76 | 3044 |
| 937889 | N/A | N/A | 81890 | 81909 | TCTACTTGCATTCTCTACCT | 70 | 3045 |
| 937901 | N/A | N/A | 82428 | 82447 | TATTCACCCCATCTCCTTCC | 78 | 3046 |
| 937913 | N/A | N/A | 82853 | 82872 | TTCATGGCTCCAATATCGGC | 36 | 3047 |
| 937925 | N/A | N/A | 83229 | 83248 | TTATTTTCCCTGAAAATGAG | 109 | 3048 |
| 937937 | N/A | N/A | 83788 | 83807 | TGCACATAGGTTAGAATTTT | 14 | 3049 |
| 937949 | N/A | N/A | 84132 | 84151 | TATTGCTATTACTATTTCCA | 49 | 3050 |
| 937961 | N/A | N/A | 84406 | 84425 | TATCATATATTTCTCAGCCC | 31 | 3051 |
| 937973 | N/A | N/A | 84754 | 84773 | GGAATCTTATTAAGCAAGTC | 4 | 3052 |
| 937985 | N/A | N/A | 84811 | 84830 | TCCTTACAATTATCTATGAT | 57 | 3053 |
| 937997 | N/A | N/A | 85049 | 85068 | TAATTAGGATCTATACACAC | 70 | 3054 |
| 938009 | N/A | N/A | 85180 | 85199 | ATTTTAACCCTTTGAGGACA | 88 | 3055 |
| 938021 | N/A | N/A | 92134 | 92153 | TAAAACTCAAATTCATCAGT | 95 | 3056 |
| 938033 | N/A | N/A | 96191 | 96210 | GGACTTGTACACACAATATA | 74 | 3057 |
| 938045 | N/A | N/A | 97624 | 97643 | GATAAGACTTTTTATGTTGC | 13 | 3058 |
| 938057 | N/A | N/A | 98776 | 98795 | TAAACACTTTATAGGCAATA | 69 | 3059 |
| 938069 | N/A | N/A | 102537 | 102556 | TTAAACTCCCAGGGACATTA | 85 | 3060 |
| 938081 | N/A | N/A | 108797 | 108816 | ATTCCCAAGTGATAAGAGAT | 94 | 3061 |

TABLE 41-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 938093 | N/A | N/A | 112501 | 112520 | CTATAGAAAAGCAACCTAT | 115 | 3062 |
| 938105 | N/A | N/A | 118988 | 119007 | CTACACCTGCTGGTGATACA | 79 | 3063 |
| 938117 | N/A | N/A | 120010 | 120029 | AATCTAAGGCCACATGAAAA | 86 | 3064 |
| 938129 | N/A | N/A | 124704 | 124723 | AGTAACAGCAATAAAGAGAG | 78 | 3065 |
| 938141 | N/A | N/A | 127842 | 127861 | ACTATCAGTTTACAAAGATT | 75 | 3066 |
| 938153 | N/A | N/A | 129792 | 129811 | TTTGTTACTTATTACCTTCC | 57 | 3067 |
| 938165 | N/A | N/A | 131803 | 131822 | TCCACAAAGATGCTTTGCCA | 93 | 3068 |
| 938177 | N/A | N/A | 132217 | 132236 | TAAGTTGATCTACACAAATT | 88 | 3069 |
| 938189 | N/A | N/A | 132526 | 132545 | GCCCATGTAGTTACATGTAA | 46 | 3070 |
| 938201 | N/A | N/A | 134052 | 134071 | GTAGTTCAGATTTGGCTGAG | 22 | 3071 |
| 938213 | N/A | N/A | 136574 | 136593 | AAAAACATTACTAATGGAAA | 100 | 3072 |
| 938225 | N/A | N/A | 138397 | 138416 | TAGTACTCCTTCCTATTTAA | 49 | 3073 |
| 938237 | N/A | N/A | 139273 | 139292 | GTGTTTAATTTGTAACTAGG | 9 | 3074 |
| 938249 | N/A | N/A | 142569 | 142588 | ATACACTGGGAAAATTTTCC | 56 | 3075 |
| 938261 | N/A | N/A | 145704 | 145723 | CTAGCTGGGAGAGCCTCTAG | 81 | 3076 |
| 938273 | N/A | N/A | 146798 | 146817 | AGCCTCTGGTAGACACCTAC | 52 | 3077 |

TABLE 42

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 708199 | 1477 | 1496 | 81637 | 81656 | GCTAACTGGTTTGCCCTTGC | 10 | 32 |
| 708202 | 1481 | 1500 | 81641 | 81660 | TTCTGCTAACTGGTTTGCCC | 36 | 3078 |
| 937376 | 3484 | 3503 | 136957 | 136976 | TTGTTGTATGGTAATTTGGG | 16 | 3079 |
| 937388 | 4400 | 4419 | 149151 | 149170 | TGATGTGTTCATGACTTTCA | 17 | 3080 |
| 937399 | 4420 | 4439 | 149171 | 149190 | TTGTTACTTCTTTTGCTAGC | 83 | 3081 |
| 937411 | N/A | N/A | 3769 | 3788 | ATCTCCAGGGTCCAGCCTGG | 85 | 3082 |
| 937423 | N/A | N/A | 4527 | 4546 | TAGTGTTTGGGATGCTTCAG | 8 | 3083 |
| 937435 | N/A | N/A | 4747 | 4766 | CAACTTAATAACCTTAGTTT | 62 | 3084 |
| 937447 | N/A | N/A | 5308 | 5327 | AATAAATCACTTCTGAAAGT | 95 | 3085 |
| 937459 | N/A | N/A | 7503 | 7522 | GTAAACTCCAAAAGGACAAT | 39 | 3086 |
| 937471 | N/A | N/A | 9931 | 9950 | CTTAGAGTTTTGCCTTCCA | 2 | 3087 |
| 937483 | N/A | N/A | 10352 | 10371 | CACAGCATGATCTTGTGTAT | 102 | 3088 |
| 937495 | N/A | N/A | 13900 | 13919 | AGTTCTGATACAGTTAATAA | 40 | 3089 |
| 937507 | N/A | N/A | 17156 | 17175 | TGAATTACAATGCGGTATAT | 16 | 3090 |

TABLE 42-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 937519 | N/A | N/A | 18683 | 18702 | GCCAGTATCTCAGTTTTTTT | 30 | 3091 |
| 937531 | N/A | N/A | 19933 | 19952 | TGCGCATCATTACGACCATT | 64 | 3092 |
| 937543 | N/A | N/A | 23250 | 23269 | GTATTTTTACTCACCTTTTC | 43 | 3093 |
| 937555 | N/A | N/A | 25504 | 25523 | AAACCAAACCAATAGTCTGG | 59 | 3094 |
| 937567 | N/A | N/A | 28078 | 28097 | ACTTTGAAATCTCACAAGGT | 73 | 3095 |
| 937579 | N/A | N/A | 28493 | 28512 | CGGATTGTTTTCTTCATTAT | 6 | 3096 |
| 937591 | N/A | N/A | 28888 | 28907 | GTCTTGTTCAGTGTCCTTCT | 4 | 3097 |
| 937603 | N/A | N/A | 30585 | 30604 | AATCCTCTTCCATCCCCTTT | 34 | 3098 |
| 937615 | N/A | N/A | 32334 | 32353 | TAAGTAATATTCCATACAGA | 52 | 3099 |
| 937627 | N/A | N/A | 32804 | 32823 | TTCAGACTTCTTGTTGTTGT | 16 | 3100 |
| 937639 | N/A | N/A | 32816 | 32835 | TGTTCTTCCAATTTCAGACT | 8 | 3101 |
| 937651 | N/A | N/A | 36032 | 36051 | GTTATGACTACTCCACGAAC | 36 | 3102 |
| 937663 | N/A | N/A | 36845 | 36864 | TATTTACTACTTCTGCATGG | 31 | 3103 |
| 937675 | N/A | N/A | 37484 | 37503 | ACTTGGTCAGGAACTCTTGG | 53 | 3104 |
| 937687 | N/A | N/A | 41275 | 41294 | TGAGGGACTAGAGCATCCAT | 46 | 3105 |
| 937699 | N/A | N/A | 43449 | 43468 | CATATCGAAGCAGTATTCTC | 35 | 3106 |
| 937711 | N/A | N/A | 47653 | 47672 | ATTAGACTGGATAAAAGGAG | 46 | 3107 |
| 937723 | N/A | N/A | 48598 | 48617 | ACTTTTTATACCTCATCAGG | 42 | 3108 |
| 937735 | N/A | N/A | 49149 | 49168 | TCATCAAGGTACCAGTTCTT | 31 | 3109 |
| 937747 | N/A | N/A | 49954 | 49973 | ATCAGTAGCATTCTTGACCA | 37 | 3110 |
| 937759 | N/A | N/A | 51425 | 51444 | GTATTTTCTTGCCTTTCTAT | 18 | 3111 |
| 937771 | N/A | N/A | 54713 | 54732 | GTTTCTCAGTAAATCAAACT | 78 | 3112 |
| 937783 | N/A | N/A | 56926 | 56945 | ATACAGAAGAGGAAATTCTG | 112 | 3113 |
| 937795 | N/A | N/A | 57475 | 57494 | GGTACACAGTTTCACTAGGT | 4 | 3114 |
| 937807 | N/A | N/A | 59465 | 59484 | TCTCCTTCAGCTGTGTCTTC | 34 | 3115 |
| 937819 | N/A | N/A | 61340 | 61359 | CAGTCTTACTGAAAATGTCC | 83 | 3116 |
| 937831 | N/A | N/A | 67200 | 67219 | ATATATATGTTGAACACCTG | 70 | 3117 |
| 937843 | N/A | N/A | 69105 | 69124 | TGAGTTCTATAGGTGCTTAA | 54 | 3118 |
| 937855 | N/A | N/A | 71732 | 71751 | TAACATCACAAACCCTCAAA | 73 | 3119 |
| 937867 | N/A | N/A | 73814 | 73833 | TTTGATACTAACCTGAATCA | 102 | 3120 |
| 937879 | N/A | N/A | 74908 | 74927 | AGATATACCTTCGGAGTACT | 50 | 3121 |
| 937891 | N/A | N/A | 82029 | 82048 | AGATAACTATTTTAACAAGC | 50 | 3122 |
| 937903 | N/A | N/A | 82476 | 82495 | GCACTAACTGTTCTCTGTGT | 51 | 3123 |
| 937915 | N/A | N/A | 82855 | 82874 | TTTTCATGGCTCCAATATCG | 33 | 3124 |
| 937927 | N/A | N/A | 83445 | 83464 | AAACTATTTTATCAATGATA | 108 | 3125 |
| 937939 | N/A | N/A | 83791 | 83810 | TGTTGCACATAGGTTAGAAT | 5 | 3126 |

TABLE 42-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 937951 | N/A | N/A | 84180 | 84199 | TAGCTAAAATTGAATGTCCA | 40 | 3127 |
| 937963 | N/A | N/A | 84410 | 84429 | TAAGTATCATATATTTCTCA | 41 | 3128 |
| 937975 | N/A | N/A | 84756 | 84775 | TTGGAATCTTATTAAGCAAG | 15 | 3129 |
| 937987 | N/A | N/A | 84813 | 84832 | GTTCCTTACAATTATCTATG | 8 | 3130 |
| 937999 | N/A | N/A | 85051 | 85070 | GTTAATTAGGATCTATACAC | 40 | 3131 |
| 938011 | N/A | N/A | 85182 | 85201 | ACATTTTAACCCTTTGAGGA | 49 | 3132 |
| 938023 | N/A | N/A | 92248 | 92267 | TAGGCAAAGACCACTTTAAA | 64 | 3133 |
| 938035 | N/A | N/A | 96398 | 96417 | ATGTAATTCTTAAAAAACC | 86 | 3134 |
| 938047 | N/A | N/A | 97626 | 97645 | GAGATAAGACTTTTTATGTT | 27 | 3135 |
| 938059 | N/A | N/A | 99449 | 99468 | GTTCTAAACTATTTATAGAC | 98 | 3136 |
| 938071 | N/A | N/A | 104201 | 104220 | TGAAGAACATTATGCAAAAA | 77 | 3137 |
| 938083 | N/A | N/A | 109630 | 109649 | ACTGACTAAAGCACCCTTGG | 76 | 3138 |
| 938095 | N/A | N/A | 116416 | 116435 | ACTACAAGCAAACACAGGCA | 72 | 3139 |
| 938107 | N/A | N/A | 119024 | 119043 | TCCCATTGCATTGTTTTAAG | 16 | 3140 |
| 938119 | N/A | N/A | 120188 | 120207 | AATGACACTTCATAACCACT | 34 | 3141 |
| 938131 | N/A | N/A | 124921 | 124940 | GGTGAAACTTAAGACTTAAA | 16 | 3142 |
| 938143 | N/A | N/A | 128091 | 128110 | TACAACCCCTAAGGAAATAA | 57 | 3143 |
| 938155 | N/A | N/A | 129794 | 129813 | ACTTTGTTACTTATTACCTT | 23 | 3144 |
| 938167 | N/A | N/A | 132158 | 132177 | TATTATTCTCACATATAAAT | 84 | 3145 |
| 938179 | N/A | N/A | 132402 | 132421 | ACTACGGTAGTTCTCAGAAA | 38 | 3146 |
| 938191 | N/A | N/A | 132648 | 132667 | TATAAATTCTTAAATAACTC | 97 | 3147 |
| 938203 | N/A | N/A | 134199 | 134218 | CCAGCTCCTAGTGTCCTTTT | 52 | 3148 |
| 938215 | N/A | N/A | 136866 | 136885 | GGTTGACATATTAGTAATTT | 27 | 3149 |
| 938227 | N/A | N/A | 138522 | 138541 | CACCCCAAAATAACTCAAAA | 71 | 3150 |
| 938239 | N/A | N/A | 139275 | 139294 | GTGTGTTTAATTTGTAACTA | 14 | 3151 |
| 938251 | N/A | N/A | 142950 | 142969 | GCAAACACAGACATATGCAG | 65 | 3152 |
| 938263 | N/A | N/A | 145980 | 145999 | TTCCAAGGTAAGTGTGTAGG | 41 | 3153 |
| 938275 | N/A | N/A | 146860 | 146879 | AACAGAGTGAGGTTTTAGGG | 20 | 3154 |

TABLE 43

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 708199 | 1477 | 1496 | 81637 | 81656 | GCTAACTGGTTTGCCCTTGC | 17 | 32 |
| 937365 | 1560 | 1579 | 81720 | 81739 | CTGTGTATTTTCTTCCTCA | 6 | 3155 |
| 937377 | 3490 | 3509 | 136963 | 136982 | GTCTCCTTGTTGTATGGTAA | 21 | 3156 |
| 937389 | 4401 | 4420 | 149152 | 149171 | CTGATGTGTTCATGACTTTC | 15 | 3157 |
| 937400 | 4421 | 4440 | 149172 | 149191 | CTTGTTACTTCTTTTGCTAG | 30 | 3158 |
| 937412 | N/A | N/A | 3802 | 3821 | GCCCGCCCCTGCCACCAGC | 60 | 3159 |
| 937424 | N/A | N/A | 4528 | 4547 | GTAGTGTTTGGGATGCTTCA | 8 | 3160 |
| 937436 | N/A | N/A | 4748 | 4767 | GCAACTTAATAACCTTAGTT | 7 | 3161 |
| 937448 | N/A | N/A | 5951 | 5970 | CTACAAAATAACATACACAA | 77 | 3162 |
| 937460 | N/A | N/A | 7520 | 7539 | CCTAGTCACATTAGAATGTA | 95 | 3163 |
| 937472 | N/A | N/A | 9933 | 9952 | AGCTTAGAGTTTTTGCCTTC | 15 | 3164 |
| 937484 | N/A | N/A | 10353 | 10372 | ACACAGCATGATCTTGTGTA | 94 | 3165 |
| 937496 | N/A | N/A | 14454 | 14473 | CACAAAGTCCACAGCAAATG | 51 | 3166 |
| 937508 | N/A | N/A | 17157 | 17176 | TTGAATTACAATGCGGTATA | 9 | 3167 |
| 937520 | N/A | N/A | 18684 | 18703 | GGCCAGTATCTCAGTTTTTT | 91 | 3168 |
| 937532 | N/A | N/A | 19934 | 19953 | GTGCGCATCATTACGACCAT | 49 | 3169 |
| 937544 | N/A | N/A | 23251 | 23270 | TGTATTTTACTCACCTTTT | 35 | 3170 |
| 937556 | N/A | N/A | 26045 | 26064 | CTAGTCTATACTACCACATA | 81 | 3171 |
| 937568 | N/A | N/A | 28079 | 28098 | GACTTTGAAATCTCACAAGG | 29 | 3172 |
| 937580 | N/A | N/A | 28495 | 28514 | ACCGGATTGTTTTCTTCATT | 15 | 3173 |
| 937592 | N/A | N/A | 28890 | 28909 | AAGTCTTGTTCAGTGTCCTT | 10 | 3174 |
| 937604 | N/A | N/A | 31032 | 31051 | TCCTCCTCTCTTCATGGCCT | 85 | 3175 |
| 937616 | N/A | N/A | 32403 | 32422 | GAAATGAAGATGAAAATAGT | 88 | 3176 |
| 937628 | N/A | N/A | 32805 | 32824 | TTTCAGACTTCTTGTTGTTG | 20 | 3177 |
| 937640 | N/A | N/A | 32818 | 32837 | TTTGTTCTTCCAATTTCAGA | 35 | 3178 |
| 937652 | N/A | N/A | 36188 | 36207 | AGAAAAGATTGTATTTTACA | 70 | 3179 |
| 937664 | N/A | N/A | 36846 | 36865 | GTATTTACTACTTCTGCATG | 30 | 3180 |
| 937676 | N/A | N/A | 37600 | 37619 | GGTCGGCAAGCAGTGTCTTT | 37 | 3181 |
| 937688 | N/A | N/A | 41278 | 41297 | TTATGAGGGACTAGAGCATC | 41 | 3182 |
| 937700 | N/A | N/A | 43838 | 43857 | GTGTACTTATAGTCTGTACA | 70 | 3183 |
| 937712 | N/A | N/A | 47673 | 47692 | GTACTTTTACAATGAATTAT | 44 | 3184 |
| 937724 | N/A | N/A | 48749 | 48768 | AAATTACCTTCGGACTGTAA | 76 | 3185 |
| 937736 | N/A | N/A | 49150 | 49169 | CTCATCAAGGTACCAGTTCT | 30 | 3186 |
| 937748 | N/A | N/A | 49980 | 49999 | GGACAAGAAATTTTCAGTTG | 11 | 3187 |
| 937760 | N/A | N/A | 51971 | 51990 | ACCTGATGTCCTAAACACAT | 65 | 3188 |
| 937772 | N/A | N/A | 54912 | 54931 | AGATACACGAATACAGAGCC | 77 | 3189 |

TABLE 43-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 937784 | N/A | N/A | 57158 | 57177 | AGAGCTCAAACTGTAACAGG | 51 | 3190 |
| 937796 | N/A | N/A | 57987 | 58006 | ATGCAGTACAACATTCCATT | 10 | 3191 |
| 937808 | N/A | N/A | 59479 | 59498 | AATCTACTTTTATGTCTCCT | 20 | 3192 |
| 937820 | N/A | N/A | 61420 | 61439 | AAACCATCCAAGACAAGAGA | 51 | 3193 |
| 937832 | N/A | N/A | 67596 | 67615 | TCTAGTGAGTATAAAAATAT | 55 | 3194 |
| 937844 | N/A | N/A | 69106 | 69125 | CTGAGTTCTATAGGTGCTTA | 69 | 3195 |
| 937856 | N/A | N/A | 71745 | 71764 | TTAACATCAGATTTAACATC | 66 | 3196 |
| 937868 | N/A | N/A | 73832 | 73851 | ACTAGAAATCTGACCTTATT | 71 | 3197 |
| 937880 | N/A | N/A | 75267 | 75286 | TATCAATCCATCAAAAATAT | 72 | 3198 |
| 937892 | N/A | N/A | 82113 | 82132 | TCTGTATGTTCCTAGTACTT | 42 | 3199 |
| 937904 | N/A | N/A | 82509 | 82528 | GTTACCAAATTCTCACAGTT | 27 | 3200 |
| 937916 | N/A | N/A | 82856 | 82875 | TTTTTCATGGCTCCAATATC | 58 | 3201 |
| 937928 | N/A | N/A | 83465 | 83484 | AAGTATTTTAAGTATTTAGA | 94 | 3202 |
| 937940 | N/A | N/A | 83792 | 83811 | GTGTTGCACATAGGTTAGAA | 7 | 3203 |
| 937952 | N/A | N/A | 84258 | 84277 | TGGAGAAAAGACTCAATGAA | 58 | 3204 |
| 937964 | N/A | N/A | 84411 | 84430 | TTAAGTATCATATATTTCTC | 62 | 3205 |
| 937976 | N/A | N/A | 84757 | 84776 | TTTGGAATCTTATTAAGCAA | 42 | 3206 |
| 937988 | N/A | N/A | 84814 | 84833 | GGTTCCTTACAATTATCTAT | 18 | 3207 |
| 938000 | N/A | N/A | 85052 | 85071 | GGTTAATTAGGATCTATACA | 19 | 3208 |
| 938012 | N/A | N/A | 85183 | 85202 | TACATTTTAACCCTTTGAGG | 43 | 3209 |
| 938024 | N/A | N/A | 92255 | 92274 | TAAAGGATAGGCAAAGACCA | 51 | 3210 |
| 938036 | N/A | N/A | 97572 | 97591 | AGGTTTACAGAAAGTTGTGC | 22 | 3211 |
| 938048 | N/A | N/A | 97726 | 97745 | TCCTGGTATGCCCCTATGGA | 58 | 3212 |
| 938060 | N/A | N/A | 99771 | 99790 | TTACTATGGGTTGGACACTT | 61 | 3213 |
| 938072 | N/A | N/A | 104211 | 104230 | CCAGTGTCTCTGAAGAACAT | 50 | 3214 |
| 938084 | N/A | N/A | 109930 | 109949 | CCCTTGTGCCTTGAATAAAA | 79 | 3215 |
| 938096 | N/A | N/A | 116591 | 116610 | TATAATCACAACTGATGGGC | 28 | 3216 |
| 938108 | N/A | N/A | 119025 | 119044 | TTCCCATTGCATTGTTTTAA | 25 | 3217 |
| 938120 | N/A | N/A | 122100 | 122119 | CAAACAAAAGGAATAAGCT | 76 | 3218 |
| 938132 | N/A | N/A | 125124 | 125143 | AAGGGCTGCCAGAAACAGTG | 44 | 3219 |
| 938144 | N/A | N/A | 128108 | 128127 | AAAGAATGTCACCATTTTAC | 44 | 3220 |
| 938156 | N/A | N/A | 129795 | 129814 | TACTTTGTTACTTATTACCT | 65 | 3221 |
| 938168 | N/A | N/A | 132159 | 132178 | TTATTATTCTCACATATAAA | 90 | 3222 |
| 938180 | N/A | N/A | 132466 | 132485 | TGAATAAACCAAAATTATCC | 71 | 3223 |
| 938192 | N/A | N/A | 133234 | 133253 | GATAATGTGGAAAATTAAGA | 75 | 3224 |
| 938204 | N/A | N/A | 134531 | 134550 | ATAGAACAAAACAATTCTTT | 90 | 3225 |

TABLE 43-continued

Percent control of human ATXN2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | ATXN2 % control | SEQ ID NO |
|---|---|---|---|---|---|---|---|
| 938216 | N/A | N/A | 136915 | 136934 | AAAGGTAAATTAGCCTTTTG | 88 | 3226 |
| 938228 | N/A | N/A | 138908 | 138927 | CCAAACTACTAACAGAGACA | 73 | 3227 |
| 938240 | N/A | N/A | 139341 | 139360 | TAACCACATTCCAGAACTAG | 81 | 3228 |
| 938252 | N/A | N/A | 143062 | 143081 | TATAGTTCCCAGCCCTCTCT | 63 | 3229 |
| 938264 | N/A | N/A | 146037 | 146056 | CCCCGGTAGTCACTTCGGAG | 86 | 3230 |
| 938276 | N/A | N/A | 146917 | 146936 | GGGCACATGGCAAATTTGAG | 32 | 3231 |

Example 4: Effect of 5-10-5 MOE Gapmers with Mixed Internucleoside Linkages on Human ATXN2 RNA Expression In Vitro, Multiple Doses Modified oligonucleotides selected from the examples above were tested at various doses in SCA2-04 cells. Cells were plated at a density of 20,000 cells per well and transfected using electroporation with 31.25 nM, 125.00 nM, 500.00 nM, and 2,000.00 nM concentrations of modified oligonucleotide, as specified in the tables below. After a treatment period of approximately 24 hours, total RNA was isolated from the cells and ATXN2 RNA levels were measured by quantitative real-time PCR. Human ATXN2 primer probe set hAtaxin_LTS01321 (described hereinabove in Example 1) was used to measure RNA levels. ATXN2 RNA levels were adjusted according to total RNA content, as measured by RIBOGREEN®. Results are presented in the tables below as percent ATXN2 RNA expression relative to untreated control cells. As illustrated in the tables below, ATXN2 RNA levels were reduced in a dose-dependent manner in modified oligonucleotide-treated cells. $IC_{50}$ was calculated using the "log(inhibitor) vs. response–variable slope (4 parameters)" formula using Prism6 software.

TABLE 44

Dose-dependent reduction of human ATXN2 RNA expression in SCA2-04 cells

| Compound Number | ATXN2 expression (% control) | | | | $IC_{50}$ (µM) |
|---|---|---|---|---|---|
| | 31.25 nM | 125.00 nM | 500.00 nM | 2,000.00 nM | |
| 708199 | 126 | 94 | 59 | 30 | 0.8 |
| 755233 | 119 | 113 | 93 | 41 | >2.0 |
| 756959 | 132 | 118 | 89 | 32 | 1.5 |
| 756960 | 106 | 103 | 90 | 36 | 2.0 |
| 756978 | 106 | 105 | 56 | 20 | 0.7 |
| 756980 | 128 | 126 | 83 | 35 | 2.0 |
| 756981 | 98 | 95 | 72 | 38 | 1.6 |
| 756985 | 98 | 517 | 84 | 33 | 1.5 |
| 756989 | 134 | 137 | 87 | 52 | >2.0 |
| 756991 | 117 | 204 | 77 | 37 | 1.4 |
| 756993 | 137 | 138 | 67 | 21 | 1.0 |
| 756996 | 128 | 104 | 81 | 33 | 1.3 |
| 756997 | 120 | 111 | 82 | 24 | 1.1 |
| 757000 | 122 | 114 | 86 | 32 | 1.5 |
| 757052 | 85 | 77 | 43 | 15 | 0.3 |
| 757055 | 92 | 86 | 58 | 27 | 0.7 |

TABLE 44-continued

Dose-dependent reduction of human ATXN2 RNA expression in SCA2-04 cells

| Compound Number | ATXN2 expression (% control) | | | | $IC_{50}$ (µM) |
|---|---|---|---|---|---|
| | 31.25 nM | 125.00 nM | 500.00 nM | 2,000.00 nM | |
| 757057 | 133 | 127 | 87 | 42 | 2.0 |
| 757066 | 91 | 81 | 59 | 19 | 0.5 |
| 757072 | 151 | 125 | 88 | 39 | 1.7 |

TABLE 45

Dose-dependent reduction of human ATXN2 RNA expression in SCA2-04 cells

| Compound Number | ATXN2 expression (% control) | | | | $IC_{50}$ (µM) |
|---|---|---|---|---|---|
| | 31.25 nM | 125.00 nM | 500.00 nM | 2,000.00 nM | |
| 708199 | 113 | 111 | 64 | 21 | 0.8 |
| 755237 | 159 | 151 | 97 | 38 | 1.9 |
| 755239 | 69 | 82 | 43 | 25 | 0.4 |
| 757028 | 110 | 158 | 145 | 53 | >2.0 |
| 757034 | 125 | 125 | 105 | 35 | 1.6 |
| 757037 | 142 | 151 | 117 | 49 | >2.0 |
| 757040 | 117 | 103 | 81 | 21 | 0.9 |
| 757045 | 254 | 153 | 113 | 35 | 1.6 |
| 757073 | 163 | 141 | 116 | 55 | >2.0 |
| 757075 | 120 | 102 | 81 | 48 | >2.0 |
| 757089 | 101 | 90 | 62 | 27 | 0.8 |
| 757094 | 202 | 161 | 86 | 34 | 1.3 |
| 757104 | 140 | 182 | 151 | 72 | >2.0 |
| 757116 | 100 | 93 | 69 | 42 | 1.5 |
| 757127 | 98 | 94 | 67 | 34 | 1.1 |
| 757129 | 89 | 83 | 67 | 37 | 1.2 |
| 757130 | 109 | 85 | 50 | 22 | 0.5 |
| 757131 | 152 | 103 | 66 | 30 | 0.9 |
| 757218 | 131 | 123 | 113 | 53 | >2.0 |

TABLE 46

Dose-dependent reduction of human ATXN2 RNA expression in SCA2-04 cells

| Compound Number | ATXN2 expression (% control) | | | | IC$_{50}$ (μM) |
|---|---|---|---|---|---|
| | 31.25 nM | 125.00 nM | 500.00 nM | 2,000.00 nM | |
| 708199 | 95 | 54 | 28 | 17 | 0.2 |
| 757161 | 100 | 95 | 61 | 32 | 0.9 |
| 757162 | 97 | 83 | 51 | 19 | 0.5 |
| 757175 | 101 | 84 | 60 | 25 | 0.7 |
| 757209 | 102 | 77 | 69 | 27 | 0.8 |
| 757210 | 112 | 95 | 51 | 30 | 0.7 |
| 757213 | 105 | 102 | 63 | 31 | 1.0 |
| 757219 | 112 | 89 | 67 | 37 | 1.1 |
| 757226 | 102 | 84 | 55 | 31 | 0.7 |
| 757228 | 92 | 104 | 65 | 36 | 1.3 |
| 757234 | 96 | 94 | 58 | 29 | 0.8 |
| 757250 | 85 | 92 | 64 | 46 | 2.0 |
| 757267 | 108 | 92 | 60 | 40 | 1.1 |
| 757272 | 95 | 88 | 48 | 35 | 0.7 |
| 757294 | 98 | 101 | 73 | 47 | >2.0 |
| 757311 | 91 | 62 | 55 | 24 | 0.4 |
| 757364 | 98 | 76 | 53 | 31 | 0.6 |
| 757371 | 107 | 97 | 73 | 38 | 1.4 |
| 757372 | 64 | 94 | 74 | 45 | 1.6 |

Example 5: Effect of 5-10-5 MOE Gapmers with Mixed Internucleoside Linkages on Human ATXN2 RNA Expression In Vitro, Multiple Doses Modified oligonucleotides selected from the examples above were tested at various doses in A431 cells. Cells were plated at a density of 10,000 cells per well and transfected by free uptake with 0.44 μM, 1.33 μM, 4.00 μM, and 12.00 μM concentrations of modified oligonucleotide, as specified in the tables below. After a treatment period of approximately 24 hours, total RNA was isolated from the cells and ATXN2 RNA levels were measured by quantitative real-time PCR Human ATXN2 primer probe set RTS5049 (described hereinabove in Example 2) was used to measure RNA levels. ATXN2 RNA levels were adjusted according to total RNA content, as measured by RIBOGREEN®. Results are presented in the tables below as percent ATXN2 RNA expression relative to untreated control. As illustrated in the tables below, ATXN2 RNA levels were reduced in a dose-dependent manner in modified oligonucleotide-treated cells. IC$_{50}$ was calculated using the "log(inhibitor) vs. response-variable slope (4 parameters)" formula using Prism6 software.

TABLE 47

Dose-dependent reduction of human ATXN2 RNA expression in A431 cells

| Compound Number | ATXN2 expression (% control) | | | | IC$_{50}$ (μM) |
|---|---|---|---|---|---|
| | 0.44 μM | 1.33 μM | 4.00 μM | 12.00 μM | |
| 708199 | 65 | 45 | 36 | 23 | 1.2 |
| 874225 | 89 | 72 | 64 | 52 | >12.0 |
| 874247 | 50 | 37 | 22 | 13 | <0.4 |
| 874248 | 67 | 54 | 45 | 32 | 2.2 |
| 874249 | 67 | 56 | 32 | 27 | 1.6 |
| 874272 | 64 | 51 | 35 | 27 | 1.4 |
| 874273 | 53 | 50 | 34 | 32 | 0.8 |
| 874702 | 34 | 25 | 16 | 13 | <0.4 |
| 874748 | 50 | 44 | 28 | 16 | 0.6 |
| 875060 | 63 | 44 | 27 | 14 | 1.0 |
| 875252 | 65 | 61 | 37 | 25 | 1.8 |
| 875325 | 105 | 80 | 61 | 46 | 8.4 |
| 875348 | 58 | 41 | 26 | 21 | 0.7 |
| 875398 | 54 | 33 | 20 | 11 | 0.5 |
| 875445 | 65 | 55 | 39 | 24 | 1.7 |
| 875733 | 65 | 54 | 41 | 33 | 1.9 |
| 875804 | 57 | 34 | 27 | 13 | 0.6 |
| 875805 | 83 | 70 | 58 | 45 | 7.6 |
| 875877 | 88 | 68 | 59 | 46 | 8.1 |

TABLE 48

Dose-dependent reduction of human ATXN2 RNA expression in A431 cells

| Compound Number | ATXN2 expression (% control) | | | | IC$_{50}$ (μM) |
|---|---|---|---|---|---|
| | 0.44 μM | 1.33 μM | 4.00 μM | 12.00 μM | |
| 708199 | 57 | 46 | 35 | 24 | 0.9 |
| 874250 | 60 | 51 | 33 | 21 | 1.1 |
| 874251 | 67 | 49 | 41 | 32 | 1.8 |
| 874297 | 82 | 82 | 69 | 53 | >12.0 |
| 874369 | 78 | 64 | 49 | 36 | 4.0 |
| 874415 | 62 | 56 | 38 | 26 | 1.6 |
| 874560 | 44 | 26 | 16 | 10 | <0.4 |
| 874703 | 75 | 59 | 47 | 24 | 2.5 |
| 874752 | 43 | 26 | 18 | 11 | <0.4 |
| 874799 | 70 | 63 | 43 | 28 | 2.5 |
| 875063 | 68 | 58 | 41 | 26 | 2.0 |
| 875328 | 27 | 15 | 9 | 7 | <0.4 |
| 875351 | 54 | 39 | 30 | 20 | 0.5 |
| 875352 | 80 | 66 | 52 | 40 | 5.1 |
| 875807 | 68 | 45 | 38 | 27 | 1.4 |
| 875831 | 61 | 50 | 44 | 36 | 1.7 |
| 875879 | 50 | 41 | 31 | 22 | 0.4 |
| 875880 | 61 | 50 | 37 | 30 | 1.3 |
| 875904 | 69 | 53 | 49 | 33 | 2.5 |

TABLE 49

Dose-dependent reduction of human ATXN2 RNA expression in A431 cells

| Compound Number | ATXN2 expression (% control) | | | | IC$_{50}$ (μM) |
|---|---|---|---|---|---|
| | 0.44 μM | 1.33 μM | 4.00 μM | 12.00 μM | |
| 708199 | 66 | 53 | 35 | 28 | 1.6 |
| 708399 | 87 | 77 | 55 | 33 | 5.1 |
| 874229 | 72 | 62 | 45 | 72 | >12.0 |
| 874254 | 72 | 63 | 49 | 35 | 3.5 |
| 874276 | 78 | 67 | 57 | 39 | 5.5 |
| 874277 | 60 | 48 | 46 | 41 | 1.8 |
| 874300 | 80 | 64 | 41 | 30 | 3.0 |
| 874610 | 58 | 45 | 24 | 13 | 0.8 |
| 874682 | 79 | 59 | 44 | 31 | 2.9 |
| 874706 | 57 | 39 | 26 | 13 | 0.7 |
| 874753 | 41 | 37 | 25 | 12 | <0.4 |
| 874754 | 52 | 40 | 24 | 11 | 0.5 |
| 874874 | 67 | 50 | 35 | 21 | 1.4 |
| 874969 | 74 | 55 | 36 | 17 | 1.8 |
| 875401 | 91 | 83 | 68 | 39 | 8.7 |
| 875427 | 74 | 49 | 38 | 23 | 1.8 |
| 875571 | 72 | 62 | 40 | 27 | 2.3 |
| 875834 | 69 | 58 | 45 | 37 | 3.0 |
| 875954 | 73 | 53 | 46 | 31 | 2.5 |

TABLE 50

Dose-dependent reduction of human ATXN2 RNA expression in A431 cells

| Compound Number | ATXN2 expression (% control) | | | | IC$_{50}$ (μM) |
|---|---|---|---|---|---|
| | 0.44 μM | 1.33 μM | 4.00 μM | 12.00 μM | |
| 708199 | 70 | 43 | 34 | 23 | 1.3 |
| 874211 | 65 | 50 | 39 | 33 | 1.7 |
| 874212 | 64 | 51 | 37 | 24 | 1.4 |
| 874279 | 68 | 54 | 39 | 20 | 1.6 |
| 874280 | 32 | 20 | 13 | 8 | <0.4 |
| 874281 | 48 | 39 | 22 | 14 | <0.4 |
| 874325 | 70 | 65 | 50 | 39 | 4.2 |
| 874327 | 55 | 36 | 32 | 25 | 0.5 |
| 874348 | 55 | 10 | 109 | 52 | >12.0 |
| 874541 | 3 | 3 | 31743 | 32 | <0.4 |
| 874685 | 81 | 78 | 56 | 46 | 8.6 |
| 874947 | 93 | 73 | 60 | 35 | 5.6 |
| 875404 | 61 | 54 | 39 | 22 | 1.4 |
| 875405 | 92 | 72 | 57 | 36 | 5.5 |
| 875452 | 62 | 42 | 26 | 14 | 0.9 |
| 875477 | 61 | 57 | 44 | 34 | 2.0 |
| 875572 | 44 | 36 | 29 | 72 | <0.4 |
| 875764 | 49 | 40 | 23 | 14 | <0.4 |
| 875956 | 75 | 55 | 50 | 45 | 4.8 |

TABLE 51

Dose-dependent reduction of human ATXN2 RNA expression in A431 cells

| Compound Number | ATXN2 expression (% control) | | | | IC$_{50}$ (μM) |
|---|---|---|---|---|---|
| | 0.44 μM | 1.33 μM | 4.00 μM | 12.00 μM | |
| 708199 | 80 | 49 | 37 | 23 | 2.0 |
| 874258 | 74 | 67 | 45 | 52 | >12.0 |
| 874282 | 41 | 36 | 21 | 13 | <0.4 |
| 874283 | 73 | 44 | 33 | 24 | 1.5 |
| 874591 | 79 | 66 | 53 | 50 | 8.4 |
| 874615 | 74 | 64 | 45 | 33 | 3.1 |
| 874639 | 46 | 30 | 17 | 10 | <0.4 |
| 874782 | 57 | 46 | 36 | 26 | 0.9 |
| 874806 | 84 | 84 | 61 | 47 | 11.1 |
| 874807 | 76 | 61 | 53 | 38 | 4.3 |
| 874856 | 78 | 59 | 34 | 28 | 2.3 |
| 874903 | 67 | 59 | 40 | 33 | 2.2 |
| 874951 | 72 | 61 | 52 | 42 | 4.8 |
| 874952 | 60 | 43 | 27 | 19 | 0.9 |
| 874999 | 93 | 77 | 55 | 29 | 4.6 |
| 875360 | 61 | 42 | 29 | 22 | 0.8 |
| 875670 | 84 | 63 | 49 | 28 | 3.3 |
| 875886 | 76 | 60 | 42 | 25 | 2.4 |
| 875959 | 75 | 58 | 41 | 37 | 2.9 |

TABLE 52

Dose-dependent reduction of human ATXN2 RNA expression in A431 cells

| Compound Number | ATXN2 expression (% control) | | | | IC$_{50}$ (μM) |
|---|---|---|---|---|---|
| | 0.44 μM | 1.33 μM | 4.00 μM | 12.00 μM | |
| 708199 | 74 | 44 | 32 | 25 | 1.5 |
| 874216 | 81 | 55 | n.d. | 16 | 2.0 |
| 874217 | 51 | 40 | 29 | 26 | <0.4 |
| 874237 | 66 | 59 | 43 | 30 | 2.2 |
| 874238 | 86 | 58 | 42 | 37 | 3.4 |
| 874307 | 173 | 64 | 64 | 68 | >12.0 |
| 874544 | 92 | 78 | 71 | 54 | >12.0 |
| 874547 | 80 | 59 | 46 | 34 | 3.3 |
| 874568 | 77 | 59 | 42 | 32 | 2.8 |
| 874571 | 106 | 79 | 55 | 38 | 5.9 |
| 874643 | 85 | 62 | 40 | 35 | 3.3 |
| 874738 | 65 | 46 | 37 | 25 | 1.3 |
| 874785 | 71 | 58 | 38 | 25 | 2.0 |
| 874858 | 93 | 86 | 65 | 66 | >12.0 |
| 875458 | 42 | 28 | 19 | 12 | <0.4 |
| 875650 | 63 | 46 | 31 | 19 | 1.1 |
| 875793 | 89 | 93 | 78 | 64 | >12.0 |
| 875840 | 97 | 81 | 79 | 48 | >12.0 |
| 875914 | 60 | 48 | 42 | 38 | 1.5 |

TABLE 53

Dose-dependent reduction of human ATXN2 RNA expression in A431 cells

| Compound Number | ATXN2 expression (% control) | | | | IC$_{50}$ (μM) |
|---|---|---|---|---|---|
| | 0.44 μM | 1.33 μM | 4.00 μM | 12.00 μM | |
| 708199 | 59 | 44 | 29 | 21 | 0.8 |
| 874288 | 64 | 40 | n.d. | 16 | 0.9 |
| 874334 | 57 | 38 | 29 | 28 | 0.6 |
| 874335 | 56 | 37 | 32 | 27 | 0.6 |
| 874430 | 60 | 49 | 32 | 25 | 1.1 |
| 874501 | 54 | 41 | 33 | 21 | 0.6 |
| 874548 | 68 | 49 | 34 | 23 | 1.4 |
| 874669 | 40 | 20 | 12 | 10 | <0.4 |
| 874764 | 77 | 53 | 51 | 33 | 3.1 |
| 875148 | 60 | 43 | 39 | 26 | 1.0 |
| 875196 | 84 | 85 | 64 | 38 | 7.8 |
| 875315 | 63 | 54 | 36 | 31 | 1.6 |
| 875341 | 62 | 40 | 30 | 20 | 0.9 |
| 875389 | 66 | 56 | 38 | 29 | 1.8 |
| 875485 | 52 | 23 | 16 | 13 | <0.4 |
| 875508 | 63 | 57 | 48 | 33 | 2.4 |
| 875798 | 59 | 42 | 31 | 17 | 0.8 |
| 875820 | 72 | 67 | 45 | 35 | 3.4 |
| 875966 | 45 | 31 | 24 | 19 | <0.4 |

TABLE 54

Dose-dependent reduction of human ATXN2 RNA expression in A431 cells

| Compound Number | ATXN2 expression (% control) | | | | IC$_{50}$ (μM) |
|---|---|---|---|---|---|
| | 0.44 μM | 1.33 μM | 4.00 μM | 12.00 μM | |
| 708199 | 59 | 47 | 28 | 20 | 0.9 |
| 874359 | 84 | 65 | n.d. | 16 | 6.1 |
| 874360 | 75 | 62 | 43 | 38 | 3.3 |
| 874384 | 50 | 47 | 34 | 32 | <0.4 |
| 874385 | 50 | 35 | 29 | 31 | <0.4 |
| 874503 | 32 | 21 | 14 | 6 | <0.4 |
| 874745 | 65 | 41 | 27 | 16 | 1.0 |
| 874792 | 58 | 39 | 26 | 19 | 0.7 |
| 874937 | 64 | 55 | 30 | 22 | 1.4 |
| 875032 | 35 | 21 | 11 | 6 | <0.4 |
| 875319 | 53 | 36 | 22 | 15 | 0.5 |
| 875414 | 68 | 59 | 42 | 28 | 2.2 |
| 875416 | 74 | 58 | 48 | 35 | 3.3 |
| 875512 | 68 | 57 | 42 | 31 | 2.2 |
| 875680 | 47 | 32 | 22 | 15 | <0.4 |
| 875799 | 49 | 39 | 26 | 14 | <0.4 |
| 875822 | 62 | 53 | 39 | 27 | 1.5 |
| 875895 | 76 | 52 | 41 | 33 | 2.4 |
| 875991 | 65 | 48 | 40 | 27 | 1.5 |

TABLE 55

Dose-dependent reduction of human ATXN2 RNA expression in A431 cells

| Compound Number | ATXN2 expression (% control) | | | | $IC_{50}$ (µM) |
|---|---|---|---|---|---|
| | 0.44 µM | 1.33 µM | 4.00 µM | 12.00 µM | |
| 708199 | 56 | 50 | 36 | 23 | 1.0 |
| 874244 | 85 | 82 | n.d. | 16 | >12.0 |
| 874246 | 53 | 40 | 30 | 23 | 0.5 |
| 874388 | 54 | 51 | 41 | 29 | 1.0 |
| 874506 | 44 | 24 | 17 | 8 | <0.4 |
| 874554 | 30 | 17 | 10 | 4 | <0.4 |
| 874627 | 33 | 28 | 17 | 10 | <0.4 |
| 874674 | 83 | 75 | 62 | 45 | 9.4 |
| 874699 | 60 | 39 | 23 | 17 | 0.7 |
| 874771 | 28 | 19 | 10 | 7 | <0.4 |
| 874842 | 60 | 44 | 29 | 20 | 0.9 |
| 874939 | 45 | 34 | 21 | 15 | <0.4 |
| 875083 | 74 | 57 | 46 | 26 | 2.4 |
| 875346 | 55 | 52 | 38 | 26 | 1.0 |
| 875347 | 47 | 35 | 39 | 26 | <0.4 |
| 875489 | 75 | 71 | 45 | 37 | 3.9 |
| 875490 | 76 | 68 | 52 | 31 | 3.7 |
| 875681 | 81 | 76 | 61 | 39 | 7.0 |
| 875803 | 63 | 53 | 38 | 22 | 1.4 |

Example 6: Effect of 5-10-5 MOE Gapmers with Mixed Internucleoside Linkages on Human ATXN2 In Vitro, Multiple Doses Modified oligonucleotides selected from the examples above were tested at various doses in A431 cells. Cells were plated at a density of 10,000 cells per well and transfected by free uptake with 0.094, 0.375, 1.500, and 6.000 µM concentrations of modified oligonucleotide, as specified in the tables below. After a treatment period of approximately 24 hours, total RNA was isolated from the cells and ATXN2 RNA levels were measured by quantitative real-time PCR. Human ATXN2 primer probe set RTS5049 (described hereinabove in Example 2) was used to measure RNA levels. ATXN2 RNA levels were adjusted according to total RNA content, as measured by RIBOGREEN®. Results are presented in the tables below as percent ATXN2 RNA expression relative to untreated control cells. As illustrated in the tables below, ATXN2 RNA levels were reduced in a dose-dependent manner in modified oligonucleotide-treated cells. $IC_{50}$ was calculated using the "log(inhibitor) vs. response–variable slope (4 parameters)" formula using Prism6 software.

TABLE 56

Dose-dependent reduction of human ATXN2 RNA expression in A431 cells

| Compound Number | ATXN2 expression (% control) | | | | $IC_{50}$ (µM) |
|---|---|---|---|---|---|
| | 0.094 µM | 0.375 µM | 1.500 µM | 6.000 µM | |
| 708199 | 72 | 52 | 28 | 14 | 0.4 |
| 937383 | 52 | 26 | n.d. | 16 | <0.1 |
| 937430 | 60 | 24 | 10 | 4 | 0.1 |
| 937466 | 85 | 62 | 34 | 19 | 0.7 |
| 937467 | 74 | 52 | 26 | 12 | 0.4 |
| 937478 | 66 | 44 | 23 | 12 | 0.3 |
| 937479 | 66 | 35 | 17 | 9 | 0.2 |
| 937611 | 79 | 54 | 31 | 15 | 0.5 |
| 937634 | 76 | 51 | 24 | 11 | 0.4 |
| 937754 | 73 | 34 | 10 | 3 | 0.2 |
| 937791 | 77 | 47 | 22 | 10 | 0.4 |
| 937934 | 65 | 37 | 16 | 8 | 0.2 |
| 937983 | 69 | 34 | 14 | 5 | 0.2 |
| 938042 | 91 | 58 | 27 | 17 | 0.7 |
| 938043 | 55 | 28 | 13 | 5 | 0.1 |
| 938151 | 70 | 48 | 27 | 12 | 0.3 |
| 938163 | 67 | 38 | 15 | 6 | 0.2 |
| 938174 | 97 | 67 | 31 | 15 | 0.9 |
| 938210 | 65 | 33 | 14 | 8 | 0.2 |

TABLE 57

Dose-dependent reduction of human ATXN2 RNA expression in A431 cells

| Compound Number | ATXN2 expression (% control) | | | | $IC_{50}$ (µM) |
|---|---|---|---|---|---|
| | 0.094 µM | 0.375 µM | 1.500 µM | 6.000 µM | |
| 708199 | 79 | 51 | 26 | 15 | 0.5 |
| 937385 | 33 | 15 | n.d. | 16 | <0.1 |
| 937420 | 68 | 38 | 20 | 10 | 0.2 |
| 937422 | 55 | 24 | 9 | 5 | <0.1 |
| 937456 | 76 | 51 | 21 | 8 | 0.4 |
| 937468 | 52 | 21 | 8 | 3 | <0.1 |
| 937470 | 51 | 25 | 9 | 3 | <0.1 |
| 937480 | 41 | 22 | 9 | 5 | <0.1 |
| 937494 | 85 | 64 | 34 | 16 | 0.7 |
| 937552 | 76 | 41 | 19 | 7 | 0.3 |
| 937578 | 76 | 39 | 23 | 10 | 0.3 |
| 937683 | 73 | 46 | 24 | 14 | 0.4 |
| 937792 | 73 | 39 | 21 | 9 | 0.3 |
| 937794 | 35 | 9 | 4 | 2 | <0.1 |
| 937804 | 68 | 42 | 19 | 7 | 0.3 |
| 937936 | 49 | 19 | 6 | 2 | <0.1 |
| 937938 | 63 | 31 | 15 | 11 | 0.1 |
| 937972 | 55 | 32 | 15 | 5 | 0.1 |
| 938044 | 66 | 39 | 24 | 10 | 0.2 |

TABLE 58

Dose-dependent reduction of human ATXN2 RNA expression in A431 cells

| Compound Number | ATXN2 expression (% control) | | | | $IC_{50}$ (µM) |
|---|---|---|---|---|---|
| | 0.094 µM | 0.375 µM | 1.500 µM | 6.000 µM | |
| 708199 | 77 | 45 | 27 | 16 | 0.4 |
| 937365 | 63 | 36 | n.d. | 16 | 0.2 |
| 937423 | 81 | 41 | 20 | 11 | 0.4 |
| 937424 | 67 | 37 | 19 | 11 | 0.2 |
| 937436 | 82 | 39 | 15 | 5 | 0.3 |
| 937471 | 57 | 20 | 7 | 2 | <0.1 |
| 937508 | 78 | 52 | 23 | 8 | 0.4 |
| 937579 | 61 | 35 | 14 | 7 | 0.2 |
| 937591 | 50 | 28 | 9 | 4 | <0.1 |
| 937592 | 67 | 35 | 15 | 6 | 0.2 |
| 937639 | 64 | 39 | 15 | 7 | 0.2 |
| 937748 | 83 | 55 | 21 | 10 | 0.5 |
| 937795 | 60 | 28 | 11 | 6 | 0.1 |
| 937796 | 76 | 55 | 23 | 11 | 0.4 |
| 937939 | 39 | 20 | 10 | 5 | <0.1 |
| 937940 | 63 | 28 | 12 | 6 | 0.1 |
| 937962 | 90 | 62 | 32 | 13 | 0.7 |
| 937987 | 77 | 46 | 24 | 14 | 0.4 |
| 938238 | 87 | 55 | 40 | 20 | 0.8 |

TABLE 59

Dose-dependent reduction of human ATXN2 RNA expression in A431 cells

| Compound Number | ATXN2 expression (% control) | | | | $IC_{50}$ ($\mu$M) |
|---|---|---|---|---|---|
| | 0.094 $\mu$M | 0.375 $\mu$M | 1.500 $\mu$M | 6.000 $\mu$M | |
| 708199 | 80 | 46 | 29 | 13 | 0.4 |
| 937378 | 66 | 37 | n.d. | 16 | 0.2 |
| 937389 | 64 | 38 | 19 | 15 | 0.2 |
| 937425 | 63 | 40 | 18 | 9 | 0.2 |
| 937437 | 82 | 53 | 19 | 7 | 0.4 |
| 937472 | 86 | 52 | 34 | 16 | 0.6 |
| 937509 | 86 | 53 | 28 | 12 | 0.6 |
| 937510 | 76 | 51 | 21 | 8 | 0.4 |
| 937546 | 73 | 43 | 20 | 9 | 0.3 |
| 937580 | 68 | 40 | 20 | 12 | 0.2 |
| 937593 | 68 | 39 | 15 | 5 | 0.2 |
| 937618 | 50 | 24 | 13 | 6 | <0.1 |
| 937725 | 84 | 48 | 24 | 12 | 0.5 |
| 937737 | 70 | 38 | 20 | 12 | 0.2 |
| 937738 | 62 | 35 | 15 | 6 | 0.2 |
| 937941 | 73 | 53 | 29 | 13 | 0.4 |
| 937942 | 67 | 45 | 19 | 10 | 0.3 |
| 937989 | 65 | 42 | 16 | 8 | 0.2 |
| 938170 | 53 | 23 | 10 | 4 | <0.1 |

TABLE 60

Dose-dependent reduction of human ATXN2 RNA expression in A431 cells

| Compound Number | ATXN2 expression (% control) | | | | $IC_{50}$ ($\mu$M) |
|---|---|---|---|---|---|
| | 0.094 $\mu$M | 0.375 $\mu$M | 1.500 $\mu$M | 6.000 $\mu$M | |
| 708199 | 74 | 45 | 24 | 15 | 0.4 |
| 937426 | 84 | 63 | n.d. | 16 | 0.6 |
| 937428 | 63 | 41 | 20 | 10 | 0.2 |
| 937474 | 74 | 42 | 19 | 9 | 0.3 |
| 937511 | 82 | 51 | 24 | 18 | 0.5 |
| 937547 | 67 | 41 | 14 | 5 | 0.2 |
| 937572 | 74 | 46 | 21 | 9 | 0.3 |
| 937595 | 95 | 66 | 39 | 16 | 0.9 |
| 937619 | 63 | 39 | 14 | 7 | 0.2 |
| 937620 | 61 | 37 | 18 | 10 | 0.2 |
| 937666 | 79 | 41 | 23 | 13 | 0.4 |
| 937680 | 70 | 38 | 17 | 7 | 0.3 |
| 937739 | 86 | 49 | 22 | 10 | 0.5 |
| 937918 | 73 | 41 | 21 | 12 | 0.3 |
| 937991 | 75 | 49 | 20 | 12 | 0.4 |
| 938004 | 51 | 20 | 10 | 4 | <0.1 |
| 938136 | 68 | 38 | 20 | 7 | 0.2 |
| 938171 | 83 | 54 | 28 | 11 | 0.5 |
| 938172 | 78 | 44 | 20 | 9 | 0.4 |

TABLE 61

Dose-dependent reduction of human ATXN2 RNA expression in A431 cells

| Compound Number | ATXN2 expression (% control) | | | | $IC_{50}$ ($\mu$M) |
|---|---|---|---|---|---|
| | 0.094 $\mu$M | 0.375 $\mu$M | 1.500 $\mu$M | 6.000 $\mu$M | |
| 708199 | 80 | 48 | 30 | 14 | 0.5 |
| 937374 | 78 | 42 | n.d. | 16 | 0.4 |
| 937397 | 52 | 27 | 18 | 13 | <0.1 |
| 937421 | 72 | 35 | 13 | 5 | 0.2 |
| 937429 | 43 | 15 | 5 | 3 | <0.1 |
| 937465 | 41 | 14 | 6 | 3 | <0.1 |
| 937469 | 62 | 28 | 9 | 3 | 0.1 |
| 937477 | 75 | 49 | 21 | 10 | 0.4 |
| 937481 | 48 | 18 | 7 | 3 | <0.1 |
| 937621 | 69 | 45 | 24 | 12 | 0.3 |
| 937633 | 68 | 41 | 19 | 7 | 0.3 |
| 937933 | 93 | 42 | 23 | 12 | 0.5 |
| 937937 | 71 | 42 | 23 | 12 | 0.3 |
| 937973 | 53 | 22 | 7 | 3 | <0.1 |
| 938041 | 77 | 49 | 24 | 9 | 0.4 |
| 938045 | 73 | 50 | 27 | 11 | 0.4 |
| 938173 | 78 | 45 | 21 | 8 | 0.4 |
| 938221 | 58 | 26 | 14 | 7 | 0.1 |
| 938237 | 54 | 23 | 11 | 7 | <0.1 |

Example 7: Design of Gapmers with Mixed Internucleoside Linkages Complementary to Human ATXN2 RNA Modified oligonucleotides complementary to a human ATXN2 nucleic acid were designed. The modified oligonucleotides in the table below are gapmers. The gapmers have a central gap segment that comprises 2'-deoxynucleosides and is flanked by wing segments on both the 5' end on the 3' end comprising 2'-MOE nucleosides. The internucleoside linkages are mixed phosphodiester internucleoside linkages and phosphorothioate internucleoside linkages. Each cytosine residue is a 5-methyl cytosine. The sequence and chemical notation column specifies the sequence, including 5-methyl cytosines, sugar chemistry, and the internucleoside linkage chemistry, wherein subscript 'd' represents a 2'-deoxyribose sugar; subscript 'e' represents a 2'-MOE modified sugar; subscript 'o' represents a phosphodiester internucleoside linkage; subscript 's' represents a phosphorothioate internucleoside linkage; and a 'm' superscript before the cytosine residue indicates a 5-methyl cytosine. "Start Site" indicates the 5'-most nucleoside to which the gapmer is complementary in the human nucleic acid sequence. "Stop Site" indicates the 3'-most nucleoside to which the gapmer is complementary in the human nucleic acid sequence.

Each modified oligonucleotide listed in the table below is complementary to human ATXN2 nucleic acid sequence SEQ ID NO: 1 or SEQ ID NO: 2, as indicated. 'N/A' indicates that the modified oligonucleotide is not complementary to that particular nucleic acid with 100% complementarity.

TABLE 62

Modified oligonucleotides complementary to human ATXN2 RNA

| Compound Number | Gapmer motif | Sequence and chemistry notation (5' to 3') | SEQ ID NO: 1 Start Site | SEQ ID NO: 1 Stop Site | SEQ ID NO: 2 Start Site | SEQ ID NO: 2 Stop Site | SEQ ID NO: |
|---|---|---|---|---|---|---|---|
| 702063 | 5-10-5 | $^{m}C_{es} T_{eo}\ ^{m}C_{eo} T_{eo}\ ^{m}C_{es}\ ^{m}C_{ds} A_{ds} T_{ds} T_{ds} A_{ds} T_{ds}$ $T_{ds} T_{ds}\ ^{m}C_{ds} T_{ds} T_{eo}\ ^{m}C_{eo} A_{es}\ ^{m}C_{es} G_{e}$ | 1123 | 1142 | 49297 | 49316 | 33 |

TABLE 62-continued

Modified oligonucleotides complementary to human ATXN2 RNA

| Compound Number | Gapmer motif | Sequence and chemistry notation (5' to 3') | SEQ ID NO: 1 Start Site | SEQ ID NO: 1 Stop Site | SEQ ID NO: 2 Start Site | SEQ ID NO: 2 Stop Site | SEQ ID NO: |
|---|---|---|---|---|---|---|---|
| 708154 | 5-10-5 | $T_{es} G_{eo} G_{eo} A_{eo} T_{eo} T_{ds} {}^mC_{ds} T_{ds} G_{ds} T_{ds} A_{ds} {}^mC_{ds} T_{ds} T_{ds} T_{ds} T_{eo} {}^mC_{eo} T_{es} {}^mC_{es} A_e$ | 1089 | 1108 | 49263 | 49282 | 3235 |
| 755235 | 5-10-5 | ${}^mC_{es} T_{eo} G_{eo} G_{eo} A_{eo} T_{ds} T_{ds} {}^mC_{ds} T_{ds} G_{ds} T_{ds} A_{ds} {}^mC_{ds} T_{ds} T_{ds} T_{eo} T_{eo} {}^mC_{es} T_{es} {}^mC_e$ | 1090 | 1109 | 49264 | 49283 | 3234 |
| 760771 | 5-8-5 | $T_{es} G_{eo} {}^mC_{eo} {}^mC_{eo} T_{es} {}^mC_{ds} T_{ds} A_{ds} {}^mC_{ds} T_{ds} {}^mC_{ds} G_{ds} T_{eo} {}^mC_{eo} {}^mC_{es} A_{es} A_e$ | 4274 | 4291 | 149025 | 149042 | 3292 |
| 874430 | 5-10-5 | $G_{es} T_{eo} T_{eo} A_{eo} {}^mC_{eo} T_{ds} G_{ds} T_{ds} T_{ds} T_{ds} {}^mC_{ds} G_{ds} A_{ds} {}^mC_{ds} {}^mC_{ds} T_{eo} {}^mC_{eo} G_{es} G_{es} A_e$ | N/A | N/A | N/A | N/A | 3293 |
| 1008800 | 5-8-5 | $T_{es} G_{eo} T_{eo} A_{eo} {}^mC_{es} T_{ds} T_{ds} T_{ds} T_{ds} {}^mC_{ds} T_{ds} {}^mC_{ds} A_{ds} T_{eo} G_{eo} T_{es} G_{es} {}^mC_e$ | 1084 | 1101 | 49258 | 49275 | 3232 |
| 1008806 | 5-8-5 | $G_{es} G_{eo} A_{eo} T_{eo} T_{es} {}^mC_{ds} T_{ds} G_{ds} T_{ds} A_{ds} {}^mC_{ds} T_{ds} T_{ds} T_{eo} T_{eo} {}^mC_{es} T_{es} {}^mC_e$ | 1090 | 1107 | 49264 | 49281 | 3233 |
| 1008845 | 4-10-6 | $T_{es} A_{eo} {}^mC_{eo} T_{eo} T_{ds} T_{ds} T_{ds} {}^mC_{ds} T_{ds} {}^mC_{ds} A_{ds} T_{ds} G_{ds} T_{ds} G_{eo} {}^mC_{eo} G_{eo} G_{es} {}^mC_{es} A_e$ | 1080 | 1099 | 49254 | 49273 | 1637 |
| 1008852 | 4-10-6 | ${}^mC_{es} T_{eo} G_{eo} G_{eo} A_{ds} T_{ds} T_{ds} {}^mC_{ds} T_{ds} G_{ds} T_{ds} A_{ds} {}^mC_{ds} T_{ds} T_{eo} T_{eo} T_{eo} {}^mC_{es} T_{es} {}^mC_e$ | 1090 | 1109 | 49264 | 49283 | 3234 |
| 1008854 | 4-10-6 | ${}^mC_{es} T_{eo} G_{eo} {}^mC_{eo} T_{ds} A_{ds} A_{ds} {}^mC_{ds} T_{ds} G_{ds} G_{ds} T_{ds} T_{ds} T_{ds} G_{eo} {}^mC_{eo} {}^mC_{eo} {}^mC_{es} T_{es} T_e$ | 1479 | 1498 | 81639 | 81658 | 1255 |
| 1008858 | 6-10-4 | ${}^mC_{es} T_{eo} T_{eo} A_{eo} G_{eo} A_{eo} G_{ds} T_{ds} T_{ds} T_{ds} T_{ds} G_{ds} {}^mC_{ds} {}^mC_{ds} T_{ds} T_{eo} {}^mC_{es} {}^mC_{es} A_e$ | N/A | N/A | 9931 | 9950 | 3087 |
| 1008859 | 6-10-4 | $G_{es} {}^mC_{eo} T_{eo} T_{eo} A_{eo} G_{eo} A_{ds} G_{ds} T_{ds} T_{ds} T_{ds} T_{ds} T_{ds} G_{ds} {}^mC_{ds} {}^mC_{ds} T_{eo} {}^mC_{es} {}^mC_e$ | N/A | N/A | 9932 | 9951 | 2177 |
| 1008860 | 6-10-4 | $A_{es} G_{eo} {}^mC_{eo} T_{eo} T_{eo} A_{eo} G_{ds} A_{ds} G_{ds} T_{ds} T_{ds} T_{ds} T_{ds} T_{ds} G_{ds} {}^mC_{ds} {}^mC_{eo} T_{es} T_{es} {}^mC_e$ | N/A | N/A | 9933 | 9952 | 3164 |
| 1008861 | 6-10-4 | ${}^mC_{es} G_{eo} T_{eo} A_{eo} T_{eo} G_{eo} T_{ds} T_{ds} T_{ds} G_{ds} T_{ds} {}^mC_{ds} G_{ds} G_{ds} T_{ds} {}^mC_e T_{eo} A_{es} T_e$ | N/A | N/A | 33816 | 33835 | 2262 |
| 1008862 | 6-10-4 | $T_{es} G_{eo} T_{eo} A_{eo} {}^mC_{eo} T_{eo} T_{ds} {}^mC_{ds} A_{ds} {}^mC_{ds} A_{ds} T_{ds} T_{ds} T_{ds} G_{ds} G_{ds} A_{eo} G_{es} {}^mC_{es} {}^mC_e$ | 991 | 1010 | 48690 | 48709 | 1185 |
| 1008863 | 6-10-4 | $A_{es} {}^mC_{eo} T_{eo} T_{eo} T_{eo} T_{eo} {}^mC_{ds} T_{ds} {}^mC_{ds} A_{ds} T_{ds} G_{ds} T_{ds} G_{ds} {}^mC_{ds} G_{ds} G_{eo} {}^mC_e A_{es} T_e$ | 1079 | 1098 | 49253 | 49272 | 1561 |
| 1008864 | 6-10-4 | $T_{es} A_{eo} {}^mC_{eo} T_{eo} T_{eo} T_{eo} T_{ds} {}^mC_{ds} T_{ds} {}^mC_{ds} A_{ds} T_{ds} G_{ds} T_{ds} G_{ds} {}^mC_{ds} G_{eo} G_{es} {}^mC_e A_e$ | 1080 | 1099 | 49254 | 49273 | 1637 |
| 1008865 | 6-10-4 | $T_{es} {}^mC_{eo} T_{eo} G_{eo} T_{eo} A_{eo} {}^mC_{ds} T_{ds} T_{ds} T_{ds} T_{ds} {}^mC_{ds} T_{ds} {}^mC_{ds} A_{ds} T_{ds} G_{eo} T_{es} G_{es} {}^mC_e$ | 1084 | 1103 | 49258 | 49277 | 2544 |
| 1008866 | 6-10-4 | $T_{es} T_{eo} {}^mC_{eo} T_{eo} {}^mC_{eo} T_{eo} A_{ds} T_{ds} T_{ds} T_{ds} {}^mC_{ds} T_{ds} T_{ds} G_{ds} T_{ds} {}^mC_{eo} {}^mC_{es} A_{es} G_e$ | 1649 | 1668 | 83260 | 83279 | 804 |
| 1008867 | 6-10-4 | $A_{es} {}^mC_{eo} A_{eo} {}^mC_{eo} A_{eo} G_{eo} T_{ds} T_{ds} T_{ds} {}^mC_{ds} A_{ds} {}^mC_{ds} T_{ds} A_{ds} G_{ds} G_{ds} T_{eo} T_{es} {}^mC_{es} T_e$ | N/A | N/A | 57472 | 57491 | 2503 |
| 1008868 | 6-10-4 | $T_{es} G_{eo} G_{eo} G_{eo} G_{eo} G_{eo} T_{ds} G_{ds} G_{ds} T_{ds} G_{ds} {}^mC_{ds} {}^mC_{ds} A_{ds} T_{ds} G_{ds} T_{eo} A_{es} G_{es} A_e$ | N/A | N/A | 9003 | 9022 | 1800 |
| 1008869 | 6-10-4 | $G_{es} T_{eo} T_{eo} A_{eo} {}^mC_{eo} T_{eo} G_{ds} T_{ds} T_{ds} T_{ds} {}^mC_{ds} G_{ds} A_{ds} {}^mC_{ds} {}^mC_{ds} T_{ds} {}^mC_{eo} T_{es} G_{es} A_e$ | N/A | N/A | 45744 | 45763 | 3291 |
| 1008870 | 6-10-4 | $T_{es} G_{eo} G_{eo} A_{eo} T_{eo} T_{eo} {}^mC_{ds} T_{ds} G_{ds} T_{ds} A_{ds} {}^mC_{ds} T_{ds} T_{ds} T_{ds} T_{ds} {}^mC_{eo} T_{es} {}^mC_{es} A_e$ | 1089 | 1108 | 49263 | 49282 | 3235 |
| 1008871 | 6-10-4 | ${}^mC_{es} T_{eo} G_{eo} G_{eo} A_{eo} T_{eo} T_{ds} {}^mC_{ds} T_{ds} G_{ds} T_{ds} A_{ds} {}^mC_{ds} T_{ds} T_{ds} T_{ds} T_{eo} {}^mC_{es} T_{es} {}^mC_e$ | 1090 | 1109 | 49264 | 49283 | 3234 |
| 1008872 | 6-10-4 | ${}^mC_{es} T_{eo} {}^mC_{eo} T_{eo} {}^mC_{eo} {}^mC_{eo} A_{ds} T_{ds} T_{ds} A_{ds} {}^mC_{ds} T_{ds} T_{ds} {}^mC_{ds} A_{ds} {}^mC_{eo} A_{es} {}^mC_{es} G_e$ | 1123 | 1142 | 49297 | 49316 | 33 |
| 1008873 | 6-10-4 | ${}^mC_{es} T_{eo} G_{eo} {}^mC_{eo} T_{eo} A_{eo} A_{ds} {}^mC_{ds} T_{ds} G_{ds} G_{ds} T_{ds} T_{ds} T_{ds} G_{ds} {}^mC_{ds} {}^mC_{eo} {}^mC_{es} T_{es} T_e$ | 1479 | 1498 | 81639 | 81658 | 1255 |
| 1008874 | 6-10-4 | ${}^mC_{es} {}^mC_{eo} T_{eo} T_{eo} A_{eo} T_{eo} {}^mC_{eo} A_{ds} T_{ds} {}^mC_{ds} A_{ds} T_{ds} T_{ds} T_{ds} {}^mC_{ds} {}^mC_{ds} A_{eo} G_{es} G_{es} G_e$ | 1538 | 1557 | 81698 | 81717 | 158 |
| 1008875 | 6-10-4 | $A_{es} {}^mC_{eo} T_{eo} T_{eo} {}^mC_{eo} T_{eo} {}^mC_{ds} T_{ds} A_{ds} T_{ds} T_{ds} T_{ds} {}^mC_{ds} T_{ds} T_{ds} T_{ds} G_{eo} T_{es} {}^mC_{es} {}^mC_e$ | 1651 | 1670 | 83262 | 83281 | 172 |
| 1008876 | 6-10-4 | $G_{es} T_{eo} G_{eo} A_{eo} T_{eo} G_{eo} T_{ds} T_{ds} T_{ds} {}^mC_{ds} A_{ds} T_{ds} T_{ds} G_{ds} G_{ds} G_{ds} T_{eo} T_{es} T_{es} A_e$ | 2460 | 2479 | 91730 | 91749 | 1188 |
| 1008877 | 5-10-5 | $G_{es} T_{eo} A_{eo} T_{eo} G_{eo} T_{ds} T_{ds} T_{ds} T_{ds} G_{ds} T_{ds} {}^mC_{ds} T_{ds} G_{ds} T_{ds} {}^mC_{ds} T_{eo} T_{eo} A_{es} T_{es} T_e$ | N/A | N/A | 33815 | 33834 | 3294 |
| 1008878 | 5-10-5 | $T_{es} {}^mC_{eo} G_{eo} T_{eo} A_{eo} T_{ds} G_{ds} T_{ds} T_{ds} T_{ds} G_{ds} T_{ds} {}^mC_{ds} T_{ds} G_{ds} T_{eo} {}^mC_{eo} T_{es} T_{es} A_e$ | N/A | N/A | 33817 | 33836 | 3295 |
| 1008879 | 5-10-5 | $A_{es} {}^mC_{eo} T_{eo} T_{eo} {}^mC_{eo} A_{ds} T_{ds} {}^mC_{ds} A_{ds} A_{ds} T_{ds} T_{ds} T_{ds} G_{ds} G_{ds} A_{ds} G_{ds} {}^mC_{eo} {}^mC_{eo} {}^mC_{es} T_{es} A_e$ | N/A | N/A | 48687 | 48706 | 3296 |
| 1008880 | 5-10-5 | $T_{es} A_{eo} {}^mC_{eo} T_{eo} T_{eo} {}^mC_{ds} A_{ds} T_{ds} {}^mC_{ds} A_{ds} T_{ds} T_{ds} T_{ds} T_{ds} G_{ds} G_{ds} A_{ds} G_{eo} {}^mC_{eo} {}^mC_{es} {}^mC_{es} T_e$ | N/A | N/A | 48688 | 48707 | 3297 |
| 1008881 | 5-10-5 | $G_{es} T_{eo} A_{eo} {}^mC_{eo} T_{eo} T_{ds} {}^mC_{ds} A_{ds} {}^mC_{ds} A_{ds} T_{ds} T_{ds} T_{ds} G_{ds} G_{ds} A_{eo} G_{eo} {}^mC_{es} {}^mC_{es} {}^mC_e$ | N/A | N/A | 48689 | 48708 | 3236 |
| 1008882 | 5-10-5 | $A_{es} T_{eo} A_{eo} T_{eo} {}^mC_{eo} G_{ds} T_{ds} A_{ds} A_{ds} {}^mC_{ds} T_{ds} T_{ds} T_{ds} {}^mC_{ds} T_{ds} {}^mC_{eo} A_{eo} T_{es} G_{es} T_e$ | 1086 | 1105 | 49260 | 49279 | 3298 |
| 1008883 | 5-10-5 | $G_{es} T_{eo} T_{eo} A_{eo} {}^mC_{eo} T_{ds} G_{ds} T_{ds} T_{ds} T_{ds} {}^mC_{ds} G_{ds} A_{ds} {}^mC_{ds} {}^mC_{ds} T_{eo} {}^mC_{eo} T_{es} G_{es} A_e$ | N/A | N/A | 45744 | 45763 | 3291 |
| 1008884 | 5-10-5 | $A_{es} {}^mC_{eo} T_{eo} G_{eo} G_{eo} A_{ds} T_{ds} T_{ds} {}^mC_{ds} T_{ds} G_{ds} T_{ds} A_{ds} {}^mC_{ds} T_{ds} T_{eo} T_{eo} T_{es} {}^mC_{es} T_e$ | 1091 | 1110 | 49265 | 49284 | 3237 |

TABLE 62-continued

Modified oligonucleotides complementary to human ATXN2 RNA

| Compound Number | Gapmer motif | Sequence and chemistry notation (5' to 3') | SEQ ID NO: 1 Start Site | SEQ ID NO: 1 Stop Site | SEQ ID NO: 2 Start Site | SEQ ID NO: 2 Stop Site | SEQ ID NO: |
|---|---|---|---|---|---|---|---|
| 1008885 | 5-10-5 | $A_{es} A_{eo} {}^mC_{eo} T_{eo} G_{eo} G_{ds} A_{ds} T_{ds} T_{ds} {}^mC_{ds} T_{ds} G_{ds} T_{ds} A_{ds} {}^mC_{ds} T_{eo} T_{eo} T_{es} T_{es} {}^mC_e$ | 1092 | 1111 | 49266 | 49285 | 3299 |
| 1008886 | 5-10-5 | $G_{es} A_{eo} A_{eo} {}^mC_{eo} T_{eo} G_{ds} G_{ds} A_{ds} T_{ds} T_{ds} {}^mC_{ds} T_{ds} G_{ds} T_{ds} A_{ds} {}^mC_{eo} T_{eo} T_{es} T_{es} T_e$ | 1093 | 1112 | 49267 | 49286 | 3300 |
| 1008887 | 5-10-5 | $T_{es} {}^mC_{eo} {}^mC_{eo} A_{eo} T_{eo} T_{ds} A_{ds} T_{ds} T_{ds} T_{ds} {}^mC_{ds} T_{ds} T_{ds} {}^mC_{ds} A_{ds} {}^mC_{eo} G_{eo} T_{es} T_{es} T_e$ | 1120 | 1139 | 49294 | 49313 | 3301 |
| 1008888 | 5-10-5 | ${}^mC_{es} T_{eo} {}^mC_{eo} {}^mC_{eo} A_{eo} T_{ds} T_{ds} A_{ds} T_{ds} T_{ds} T_{ds} {}^mC_{ds} T_{ds} T_{ds} {}^mC_{ds} A_{eo} {}^mC_{eo} G_{es} T_{es} T_e$ | 1121 | 1140 | 49295 | 49314 | 3238 |
| 1008889 | 5-10-5 | $T_{es} {}^mC_{eo} T_{eo} {}^mC_{eo} {}^mC_{eo} A_{ds} T_{ds} T_{ds} A_{ds} T_{ds} T_{ds} T_{ds} {}^mC_{ds} T_{ds} T_{ds} {}^mC_{ds} A_{eo} {}^mC_{es} G_{es} T_e$ | 1122 | 1141 | 49296 | 49315 | 3239 |
| 1008890 | 5-10-5 | ${}^mC_{es} T_{eo} {}^mC_{eo} T_{eo} A_{eo} T_{ds} T_{ds} T_{ds} {}^mC_{ds} T_{ds} T_{ds} T_{ds} G_{ds} T_{ds} {}^mC_{ds} {}^mC_{eo} A_{eo} G_{es} G_{es} A_e$ | 1647 | 1666 | 83258 | 83277 | 3302 |
| 1008891 | 5-10-5 | $G_{es} T_{eo} G_{eo} G_{eo} T_{eo} G_{ds} T_{ds} G_{ds} {}^mC_{ds} G_{ds} {}^mC_{ds} A_{ds} T_{ds} G_{ds} T_{ds} A_{eo} G_{eo} A_{es} {}^mC_{es} {}^mC_e$ | N/A | N/A | 9001 | 9020 | 3303 |
| 1008892 | 5-10-5 | $G_{es} G_{eo} T_{eo} G_{eo} G_{eo} T_{ds} G_{ds} T_{ds} G_{ds} {}^mC_{ds} G_{ds} {}^mC_{ds} A_{ds} T_{ds} G_{ds} T_{eo} A_{eo} G_{es} A_{es} {}^mC_e$ | N/A | N/A | 9002 | 9021 | 3304 |
| 1008893 | 5-10-5 | $G_{es} T_{eo} G_{eo} G_{eo} T_{eo} G_{ds} G_{ds} T_{ds} G_{ds} T_{ds} G_{ds} {}^mC_{ds} G_{ds} {}^mC_{ds} A_{ds} T_{eo} G_{eo} T_{es} A_{es} G_e$ | N/A | N/A | 9004 | 9023 | 3305 |
| 1008894 | 5-10-5 | ${}^mC_{es} G_{eo} T_{eo} G_{eo} G_{eo} T_{ds} G_{ds} G_{ds} T_{ds} G_{ds} T_{ds} G_{ds} {}^mC_{ds} G_{ds} {}^mC_{ds} A_{eo} T_{eo} G_{es} T_{es} A_e$ | N/A | N/A | 9005 | 9024 | 3306 |
| 1008895 | 5-10-5 | $A_{es} G_{eo} T_{eo} T_{eo} {}^mC_{es} A_{ds} {}^mC_{ds} {}^mC_{ds} T_{ds} G_{ds} {}^mC_{ds} A_{ds} T_{ds} {}^mC_{ds} {}^mC_{ds} {}^mC_{eo} A_{eo} G_{es} G_e G_e$ | 1279 | 1298 | 76416 | 76435 | 3307 |
| 1008896 | 5-10-5 | $G_{es} A_{eo} G_{eo} T_{eo} T_{eo} {}^mC_{ds} A_{ds} {}^mC_{ds} {}^mC_{ds} T_{ds} G_{ds} {}^mC_{ds} A_{ds} T_{ds} {}^mC_{ds} {}^mC_{eo} {}^mC_{eo} A_{es} G_{es} G_e$ | 1280 | 1299 | 76417 | 76436 | 3308 |
| 1008897 | 5-10-5 | $T_{es} G_{eo} A_{eo} G_{eo} T_{eo} T_{ds} {}^mC_{ds} A_{ds} {}^mC_{ds} {}^mC_{ds} T_{ds} G_{ds} {}^mC_{ds} A_{ds} T_{ds} {}^mC_{eo} {}^mC_{eo} {}^mC_{es} A_{es} G_e$ | 1281 | 1300 | 76418 | 76437 | 3309 |
| 1008898 | 5-10-5 | $T_{es} G_{eo} T_{eo} G_{eo} A_{eo} G_{ds} T_{ds} T_{ds} {}^mC_{ds} A_{ds} {}^mC_{ds} {}^mC_{ds} T_{ds} G_{ds} {}^mC_{ds} A_{eo} T_{eo} {}^mC_{es} {}^mC_{es} {}^mC_e$ | 1283 | 1302 | 76420 | 76439 | 3310 |
| 1008899 | 5-10-5 | ${}^mC_{es} T_{eo} G_{eo} T_{eo} G_{eo} A_{ds} G_{ds} T_{ds} T_{ds} {}^mC_{ds} A_{ds} {}^mC_{ds} {}^mC_{ds} T_{ds} G_{ds} {}^mC_{eo} A_{eo} T_{es} {}^mC_{es} {}^mC_e$ | 1284 | 1303 | 76421 | 76440 | 3311 |
| 1008900 | 5-10-5 | $G_{es} {}^mC_{eo} T_{eo} G_{eo} T_{eo} G_{ds} A_{ds} G_{ds} T_{ds} T_{ds} {}^mC_{ds} A_{ds} {}^mC_{ds} {}^mC_{ds} T_{ds} G_{eo} {}^mC_{eo} A_{es} T_{es} {}^mC_e$ | 1285 | 1304 | 76422 | 76441 | 3312 |
| 1008901 | 5-10-5 | $G_{es} {}^mC_{eo} G_{eo} G_{eo} T_{eo} G_{ds} A_{ds} A_{ds} T_{ds} T_{ds} {}^mC_{ds} T_{ds} G_{ds} T_{ds} {}^mC_{ds} T_{eo} {}^mC_{eo} {}^mC_{es} {}^mC_{es} A_e$ | 1686 | 1705 | 83297 | 83316 | 3313 |
| 1008902 | 5-10-5 | $T_{es} A_{eo} {}^mC_{eo} G_{eo} {}^mC_{eo} G_{ds} G_{ds} T_{ds} G_{ds} A_{ds} A_{ds} T_{ds} T_{ds} {}^mC_{ds} T_{ds} G_{eo} T_{eo} {}^mC_{es} T_{es} {}^mC_e$ | 1689 | 1708 | 83300 | 83319 | 3314 |
| 1008903 | 5-10-5 | ${}^mC_{es} A_{eo} T_{eo} A_{eo} {}^mC_{eo} G_{ds} {}^mC_{ds} G_{ds} G_{ds} T_{ds} G_{ds} A_{ds} A_{ds} T_{ds} T_{ds} {}^mC_{eo} T_{eo} G_{es} T_{es} {}^mC_e$ | 1691 | 1710 | 83302 | 83321 | 3315 |
| 1008904 | 5-10-5 | $A_{es} {}^mC_{eo} T_{eo} G_{eo} T_{eo} T_{ds} T_{ds} {}^mC_{ds} G_{ds} A_{ds} {}^mC_{ds} {}^mC_{ds} T_{ds} {}^mC_{ds} T_{ds} G_{eo} A_{eo} A_{es} A_{es} A_e$ | N/A | N/A | 45741 | 45760 | 3316 |
| 1008905 | 5-10-5 | $T_{es} A_{eo} {}^mC_{eo} T_{eo} G_{eo} T_{ds} T_{ds} T_{ds} {}^mC_{ds} G_{ds} A_{ds} {}^mC_{ds} {}^mC_{ds} T_{ds} {}^mC_{ds} T_{eo} G_{eo} A_{es} A_{es} A_e$ | N/A | N/A | 45742 | 45761 | 3317 |
| 1008906 | 5-10-5 | $T_{es} T_{eo} A_{eo} {}^mC_{eo} T_{eo} G_{ds} T_{ds} T_{ds} T_{ds} {}^mC_{ds} G_{ds} A_{ds} {}^mC_{ds} {}^mC_{ds} T_{ds} {}^mC_{eo} T_{eo} G_{es} A_{es} A_e$ | N/A | N/A | 45743 | 45762 | 3318 |
| 1008907 | 5-10-5 | $T_{es} G_{eo} T_{eo} T_{eo} A_{eo} {}^mC_{ds} T_{ds} G_{ds} T_{ds} T_{ds} T_{ds} {}^mC_{ds} G_{ds} A_{ds} {}^mC_{ds} {}^mC_{eo} T_{eo} {}^mC_{es} T_{es} G_e$ | 891 | 910 | 45745 | 45764 | 3319 |
| 1008908 | 5-10-5 | $T_{es} G_{eo} T_{eo} A_{eo} {}^mC_{es} T_{ds} T_{ds} {}^mC_{ds} A_{ds} {}^mC_{ds} A_{ds} T_{ds} T_{ds} T_{ds} G_{ds} G_{eo} A_{eo} G_{es} {}^mC_{es} {}^mC_e$ | 991 | 1010 | 48690 | 48709 | 1185 |
| 1008909 | 5-10-5 | $T_{es} G_{eo} T_{eo} A_{es} {}^mC_{es} T_{ds} T_{ds} {}^mC_{ds} A_{ds} {}^mC_{ds} A_{ds} T_{ds} T_{ds} T_{ds} G_{ds} G_{eo} A_{eo} G_{es} {}^mC_{es} {}^mC_e$ | 991 | 1010 | 48690 | 48709 | 1185 |
| 1008910 | 5-10-5 | $T_{es} {}^mC_{eo} T_{eo} G_{eo} T_{es} A_{ds} {}^mC_{ds} T_{ds} T_{ds} T_{ds} T_{ds} {}^mC_{ds} T_{ds} {}^mC_{ds} A_{ds} T_{eo} G_{eo} T_{es} G_{es} {}^mC_e$ | 1084 | 1103 | 49258 | 49277 | 2544 |
| 1008911 | 5-10-5 | $T_{es} {}^mC_{eo} T_{eo} G_{es} T_{es} A_{ds} {}^mC_{ds} T_{ds} T_{ds} T_{ds} T_{ds} {}^mC_{ds} T_{ds} {}^mC_{ds} A_{ds} T_{eo} G_{eo} T_{es} G_{es} {}^mC_e$ | 1084 | 1103 | 49258 | 49277 | 2544 |
| 1008912 | 5-10-5 | ${}^mC_{es} A_{eo} {}^mC_{eo} A_{eo} G_{es} T_{ds} T_{ds} T_{ds} {}^mC_{ds} A_{ds} {}^mC_{ds} T_{ds} A_{ds} G_{ds} G_{ds} T_{eo} T_{eo} {}^mC_{es} T_{es} {}^mC_e$ | N/A | N/A | 57471 | 57490 | 2121 |
| 1008913 | 5-10-5 | ${}^mC_{es} A_{eo} {}^mC_{eo} A_{es} G_{es} T_{ds} T_{ds} T_{ds} {}^mC_{ds} A_{ds} {}^mC_{ds} T_{ds} A_{ds} G_{ds} G_{ds} T_{eo} T_{eo} {}^mC_{es} T_{es} {}^mC_e$ | N/A | N/A | 57471 | 57490 | 2121 |
| 1008914 | 5-10-5 | $A_{es} {}^mC_{eo} A_{eo} {}^mC_{eo} A_{es} G_{ds} T_{ds} T_{ds} T_{ds} {}^mC_{ds} A_{ds} {}^mC_{ds} T_{ds} A_{ds} G_{ds} G_{eo} T_{eo} T_{es} {}^mC_{es} T_e$ | N/A | N/A | 57472 | 57491 | 2503 |
| 1008915 | 5-10-5 | $A_{es} {}^mC_{eo} A_{eo} {}^mC_{es} A_{es} G_{ds} T_{ds} T_{ds} T_{ds} {}^mC_{ds} A_{ds} {}^mC_{ds} T_{ds} A_{ds} G_{ds} G_{eo} T_{eo} T_{es} {}^mC_{es} T_e$ | N/A | N/A | 57472 | 57491 | 2503 |
| 1008916 | 5-10-5 | $T_{es} T_{eo} {}^mC_{eo} T_{eo} {}^mC_{es} T_{ds} A_{ds} T_{ds} T_{ds} T_{ds} {}^mC_{ds} T_{ds} T_{ds} T_{ds} G_{ds} T_{eo} {}^mC_{eo} {}^mC_{es} A_{es} G_e$ | 1649 | 1668 | 83260 | 83279 | 804 |
| 1008917 | 5-10-5 | $T_{es} T_{eo} {}^mC_{eo} T_{es} {}^mC_{es} T_{ds} A_{ds} T_{ds} T_{ds} T_{ds} {}^mC_{ds} T_{ds} T_{ds} T_{ds} G_{ds} T_{eo} {}^mC_{eo} {}^mC_{es} A_{es} G_e$ | 1649 | 1668 | 83260 | 83279 | 804 |

Example 8: Effect of MOE Gapmers with Mixed Internucleoside Linkages on Human ATXN2 In Vitro, Multiple Doses Modified oligonucleotides selected from the examples above were tested at various doses in A431 cells. Cells were plated at a density of 11,000 cells per well and transfected by free uptake with 0.023, 0.094, 0.375, 1.500 or 6.000 µM concentrations of modified oligonucleotide, as specified in the tables below. After a treatment period of approximately 48 hours, total RNA was isolated from the cells and ATXN2 RNA levels were measured by quantitative real-time PCR Human ATXN2 primer probe set RTS5051 (forward sequence TCCAGTAGCAAGGACCAGT, designated herein as SEQ ID NO: 16; reverse sequence CAATACTGTTCTGTCTGGGAGA, designated herein as SEQ ID NO: 17; probe sequence ACTGACCACT-GATGACCACGTTCC, designated herein as SEQ ID: 18) was used to measure RNA levels. ATXN2 RNA levels were adjusted according to total RNA content, as measured by RIBOGREEN®. Results are presented in the tables below as percent ATXN2 RNA expression relative to untreated control cells. As illustrated in the tables below, ATXN2 RNA levels were reduced in a dose-dependent manner in modified oligonucleotide-treated cells. $IC_{50}$ was calculated using the "log(inhibitor) vs. response–variable slope (4 parameters)" formula u sing Prism6 software.

TABLE 63

Dose-dependent reduction of human ATXN2 RNA expression in A431 cells

| Compound Number | ATXN2 expression (% control) | | | | | $IC_{50}$ (µM) |
|---|---|---|---|---|---|---|
| | 0.023 µM | 0.094 µM | 0.375 µM | 1.500 µM | 6.000 µM | |
| 756993 | 88 | 83 | 59 | 37 | 22 | 0.8 |
| 874218 | 99 | 83 | 56 | 37 | 22 | 0.7 |
| 1008800 | 99 | 86 | 57 | 34 | 22 | 0.7 |
| 1008806 | 90 | 84 | 67 | 41 | 32 | 1.2 |
| 1008845 | 94 | 74 | 54 | 32 | 24 | 0.6 |
| 1008852 | 90 | 70 | 39 | 19 | 10 | 0.3 |
| 1008854 | 97 | 83 | 71 | 54 | 43 | 2.7 |
| 1008862 | 105 | 82 | 79 | 40 | 29 | 1.3 |
| 1008865 | 95 | 56 | 36 | 17 | 8 | 0.2 |
| 1008870 | 95 | 73 | 46 | 24 | 14 | 0.4 |
| 1008871 | 95 | 83 | 63 | 40 | 26 | 0.9 |
| 1008872 | 90 | 78 | 69 | 49 | 36 | 1.6 |
| 1008874 | 94 | 78 | 54 | 36 | 26 | 0.7 |
| 1008875 | 83 | 69 | 40 | 24 | 13 | 0.3 |
| 1008881 | 91 | 71 | 61 | 57 | 43 | 2.4 |

TABLE 63-continued

Dose-dependent reduction of human ATXN2 RNA expression in A431 cells

| Compound Number | ATXN2 expression (% control) | | | | | $IC_{50}$ (µM) |
|---|---|---|---|---|---|---|
| | 0.023 µM | 0.094 µM | 0.375 µM | 1.500 µM | 6.000 µM | |
| 1008884 | 86 | 116 | 40 | 22 | 14 | 0.3 |
| 1008888 | 84 | 62 | 39 | 20 | 12 | 0.2 |
| 1008889 | 84 | 60 | 31 | 18 | 10 | 0.2 |
| 1008910 | 90 | 77 | 49 | 23 | 14 | 0.4 |

Example 9: Effect of Modified Oligonucleotides on Human ATXN2 In Vitro, Multiple Doses Modified oligonucleotides selected from the examples above were tested at various doses in SH-SY5Y cells. Cells were plated at a density of 35,000 cells per well and transfected by free uptake with 0.023, 0.094, 0.375, 1.500, or 6.000 µM concentrations of modified oligonucleotide, as specified in the tables below. After a treatment period of approximately 24 hours, total RNA was isolated from the cells and ATXN2 RNA levels were measured by quantitative real-time PCR Human ATXN2 primer probe set RTS5051 (described herein in Example 8) was used to measure RNA levels. ATXN2 RNA levels were adjusted according to total RNA content, as measured by RIBOGREEN®. Results are presented in the tables below as percent ATXN2 RNA relative to untreated control. As illustrated in the tables below, ATXN2 RNA levels were reduced in a dose-dependent manner in modified oligonucleotide-treated cells. $IC_{50}$ was calculated using the "log(inhibitor) vs. response–variable slope (4 parameters)" formula u sing Prism6 software.

TABLE 64

Dose-dependent reduction of human ATXN2 RNA expression in SH-SY5Y cells

| Compound Number | ATXN2 expression (% control) | | | | | $IC_{50}$ (µM) |
|---|---|---|---|---|---|---|
| | 0.023 µM | 0.094 µM | 0.375 µM | 1.500 µM | 6.000 µM | |
| 756993 | 131 | 98 | 73 | 37 | 15 | 1.0 |
| 874218 | 111 | 89 | 62 | 26 | 15 | 0.7 |
| 1008800 | 96 | 89 | 64 | 45 | 19 | 1.0 |
| 1008806 | 102 | 99 | 74 | 55 | 34 | 2.1 |
| 1008854 | 90 | 86 | 75 | 56 | 31 | 1.9 |
| 1008862 | 114 | 107 | 78 | 50 | 21 | 1.5 |

TABLE 65

Dose-dependent reduction of human ATXN2 RNA expression in SH-SY5Y cells

| Compound Number | ATXN2 expression (% control) | | | | | $IC_{50}$ (µM) |
|---|---|---|---|---|---|---|
| | 0.023 µM | 0.094 µM | 0.375 µM | 1.500 µM | 6.000 µM | |
| 1008865 | 108 | 97 | 74 | 35 | 16 | 1.0 |
| 1008870 | 109 | 99 | 90 | 52 | 24 | 1.7 |
| 1008874 | 98 | 90 | 75 | 42 | 27 | 1.3 |

TABLE 65-continued

Dose-dependent reduction of human ATXN2 RNA expression in SH-SY5Y cells

| Compound Number | ATXN2 expression (% control) | | | | | $IC_{50}$ ($\mu M$) |
|---|---|---|---|---|---|---|
| | 0.023 $\mu M$ | 0.094 $\mu M$ | 0.375 $\mu M$ | 1.500 $\mu M$ | 6.000 $\mu M$ | |
| 1008888 | 100 | 95 | 72 | 43 | 30 | 1.4 |
| 1008889 | 91 | 86 | 58 | 36 | 15 | 0.7 |
| 1008910 | 106 | 106 | 85 | 50 | 23 | 1.6 |

Example 10: Effect of Modified Oligonucleotides on Rhesus Monkey ATXN2 RNA Expression In Vitro, Multiple Doses Modified oligonucleotides selected from the examples above, which are also complementary to rhesus monkey ATXN2, were tested at various doses in LLC-MK2 monkey cells. Cells were plated at a density of 20,000 cells per well and transfected by free uptake with 0.023, 0.094, 0.375, 1.500, or 6.000 μM concentrations of modified oligonucleotide, as specified in the tables below. After a treatment period of approximately 24 hours, total RNA was isolated from the cells and ATXN2 RNA levels were measured by quantitative real-time PCR Human ATXN2 primer probe set RTS5051 (described herein in Example 8) was used to measure RNA levels. ATXN2 RNA levels were adjusted according to total RNA content, as measured by RIBOGREEN®. Results are presented in the tables below as percent ATXN2 RNA expression relative to untreated control cells. As illustrated in the tables below, ATXN2 RNA levels were reduced in a dose-dependent manner in modified oligonucleotide-treated cells. $IC_{50}$ was calculated using the "log(inhibitor) vs. response–variable slope (4 parameters)" formula u sing Prism6 software.

TABLE 66

Dose-dependent reduction of human ATXN2 RNA expression in LLC-MK2 rhesus monkey cells

| Compound Number | ATXN2 expression (% control) | | | | | $IC_{50}$ ($\mu M$) |
|---|---|---|---|---|---|---|
| | 0.023 $\mu M$ | 0.094 $\mu M$ | 0.375 $\mu M$ | 1.500 $\mu M$ | 6.000 $\mu M$ | |
| 756993* | 140 | 124 | 107 | 69 | 26 | 2.8 |
| 874218* | 114 | 97 | 83 | 50 | 21 | 1.5 |
| 1008800 | 106 | 108 | 85 | 57 | 31 | 2.2 |
| 1008806 | 102 | 103 | 97 | 84 | 50 | 7.3 |
| 1008854 | 87 | 88 | 78 | 59 | 34 | 2.3 |
| 1008862 | 97 | 99 | 87 | 58 | 29 | 2.2 |

*Oligos contain one mismatch to rhesus monkey

TABLE 67

Dose-dependent reduction of human ATXN2 RNA expression in LLC-MK2 rhesus monkey cells

| Compound Number | ATXN2 expression (% control) | | | | | $IC_{50}$ ($\mu M$) |
|---|---|---|---|---|---|---|
| | 0.023 $\mu M$ | 0.094 $\mu M$ | 0.375 $\mu M$ | 1.500 $\mu M$ | 6.000 $\mu M$ | |
| 1008865 | 114 | 105 | 101 | 56 | 22 | 2.1 |
| 1008870 | 107 | 87 | 76 | 58 | 26 | 1.7 |
| 1008874 | 90 | 82 | 66 | 39 | 18 | 0.7 |
| 1008888 | 91 | 85 | 82 | 53 | 24 | 1.7 |
| 1008889 | 75 | 78 | 68 | 36 | 15 | 0.9 |
| 1008910 | 86 | 94 | 79 | 72 | 31 | 2.7 |

Example 11: Design of 5-8-5 MOE Gapmers with Mixed Internucleoside Linkages Complementary to Human ATXN2 RNA Modified oligonucleotides complementary to a human ATXN2 nucleic acid were designed. The modified oligonucleotides in the table below are 5-8-5 MOE gapmers. The gapmers are 18 nucleobases in length, wherein the central gap segment comprises eight 2'-deoxynucleosides and is flanked by wing segments on both the 5' end and on the 3' end comprising five 2'-MOE nucleosides. The sugar motif for the gapmers is (from 5' to 3'): eeeeedddddddeeeee; wherein 'd' represents a 2'-deoxyribose sugar and 'e' represents a 2'-MOE modified sugar. The internucleoside linkages are mixed phosphodiester and phosphorothioate linkages. The internucleoside linkage motif for the gapmers is (from 5' to 3'): sooosssssssssooss; wherein 'o' represents a phosphodiester internucleoside linkage and 's' represents a phosphorothioate internucleoside linkage. Each cytosine residue is a 5-methyl cytosine. "Start Site" indicates the 5'-most nucleoside to which the gapmer is complementary in the human nucleic acid sequence. "Stop Site" indicates the 3'-most nucleoside to which the gapmer is complementary in the human nucleic acid sequence.

Each modified oligonucleotide listed in the table below is complementary to human ATXN2 nucleic acid sequence SEQ ID NO: 1 or SEQ ID NO: 2, as indicated. 'N/A' indicates that the modified oligonucleotide is not complementary to that particular nucleic acid with 100% complementarity.

TABLE 68

5-8-5 MOE gapmers with mixed internucleoside linkages complementary to human ATXN2 RNA

| Compound Number | Sequence (5' to 3') | SEQ ID NO: 1 Start Site | SEQ ID NO: 1 Stop Site | SEQ ID NO: 2 Start Site | SEQ ID NO: 2 Stop Site | SEQ ID NO: |
|---|---|---|---|---|---|---|
| 1008786 | TTAGAGTTTTTGCCTTCC | N/A | N/A | 9932 | 9949 | 3240 |
| 1008787 | CTTAGAGTTTTTGCCTTC | N/A | N/A | 9933 | 9950 | 3241 |
| 1008788 | GCTTAGAGTTTTTGCCTT | N/A | N/A | 9934 | 9951 | 3242 |
| 1008789 | TATGTTTGTCTGTCTTAT | N/A | N/A | 33816 | 33833 | 3243 |
| 1008790 | GTATGTTTGTCTGTCTTA | N/A | N/A | 33817 | 33834 | 3244 |
| 1008791 | CGTATGTTTGTCTGTCTT | N/A | N/A | 33818 | 33835 | 3245 |
| 1008792 | TACTTCACATTTGGAGCC | 991 | 1008 | 48690 | 48707 | 3246 |
| 1008793 | GTACTTCACATTTGGAGC | 992 | 1009 | 48691 | 48708 | 3247 |
| 1008794 | TGTACTTCACATTTGGAG | 993 | 1010 | 48692 | 48709 | 3248 |
| 1008795 | TTTTCTCATGTGCGGCAT | 1079 | 1096 | 49253 | 49270 | 3249 |
| 1008796 | CTTTTCTCATGTGCGGCA | 1080 | 1097 | 49254 | 49271 | 3250 |
| 1008797 | ACTTTTCTCATGTGCGGC | 1081 | 1098 | 49255 | 49272 | 3251 |
| 1008798 | TACTTTTCTCATGTGCGG | 1082 | 1099 | 49256 | 49273 | 3252 |
| 1008799 | GTACTTTTCTCATGTGCG | 1083 | 1100 | 49257 | 49274 | 3253 |
| 1008801 | CTGTACTTTTCTCATGTG | 1085 | 1102 | 49259 | 49276 | 3254 |
| 1008802 | TCTGTACTTTTCTCATGT | 1086 | 1103 | 49260 | 49277 | 3255 |
| 1008803 | TTCTGTACTTTTCTCATG | 1087 | 1104 | 49261 | 49278 | 3256 |
| 1008804 | ATTCTGTACTTTTCTCAT | 1088 | 1105 | 49262 | 49279 | 3257 |
| 1008805 | GATTCTGTACTTTTCTCA | 1089 | 1106 | 49263 | 49280 | 3258 |
| 1008807 | TGGATTCTGTACTTTTCT | 1091 | 1108 | 49265 | 49282 | 3259 |
| 1008808 | CTGGATTCTGTACTTTTC | 1092 | 1109 | 49266 | 49283 | 3260 |
| 1008809 | CTCCATTATTTCTTCACG | 1123 | 1140 | 49297 | 49314 | 3261 |
| 1008810 | TCTCCATTATTTCTTCAC | 1124 | 1141 | 49298 | 49315 | 3262 |
| 1008811 | CTCTCCATTATTTCTTCA | 1125 | 1142 | 49299 | 49316 | 3263 |
| 1008812 | TAACTGGTTTGCCCTTGC | 1477 | 1494 | 81637 | 81654 | 3264 |
| 1008813 | CTAACTGGTTTGCCCTTG | 1478 | 1495 | 81638 | 81655 | 3265 |

TABLE 68-continued 5-8-5 MOE gapmers with mixed internucleoside linkages complementary to human ATXN2 RNA

| Compound Number | Sequence (5' to 3') | SEQ ID NO: 1 Start Site | SEQ ID NO: 1 Stop Site | SEQ ID NO: 2 Start Site | SEQ ID NO: 2 Stop Site | SEQ ID NO: |
|---|---|---|---|---|---|---|
| 1008814 | GCTAACTGGTTTGCCCTT | 1479 | 1496 | 81639 | 81656 | 3266 |
| 1008815 | TGCTAACTGGTTTGCCCT | 1480 | 1497 | 81640 | 81657 | 3267 |
| 1008816 | CTGCTAACTGGTTTGCCC | 1481 | 1498 | 81641 | 81658 | 3268 |
| 1008817 | TCTGCTAACTGGTTTGCC | 1482 | 1499 | 81642 | 81659 | 3269 |
| 1008818 | TTCTGCTAACTGGTTTGC | 1483 | 1500 | 81643 | 81660 | 3270 |
| 1008819 | TCATCATTTTCCAGGGCC | 1536 | 1553 | 81696 | 81713 | 3271 |
| 1008820 | ATCATCATTTTCCAGGGC | 1537 | 1554 | 81697 | 81714 | 3272 |
| 1008821 | TATCATCATTTTCCAGGG | 1538 | 1555 | 81698 | 81715 | 3273 |
| 1008822 | CTATCATCATTTTCCAGG | 1539 | 1556 | 81699 | 81716 | 3274 |
| 1008823 | CCTATCATCATTTTCCAG | 1540 | 1557 | 81700 | 81717 | 3275 |
| 1008824 | TCCTATCATCATTTTCCA | 1541 | 1558 | 81701 | 81718 | 3276 |
| 1008825 | CTCCTATCATCATTTTCC | 1542 | 1559 | 81702 | 81719 | 3277 |
| 1008826 | CTATTTCTTTGTCCAGGA | 1647 | 1664 | 83258 | 83275 | 3278 |
| 1008827 | TCTATTTCTTTGTCCAGG | 1648 | 1665 | 83259 | 83276 | 3279 |
| 1008828 | CTCTATTTCTTTGTCCAG | 1649 | 1666 | 83260 | 83277 | 3280 |
| 1008829 | TCTCTATTTCTTTGTCCA | 1650 | 1667 | 83261 | 83278 | 3281 |
| 1008830 | TTCTCTATTTCTTTGTCC | 1651 | 1668 | 83262 | 83279 | 3282 |
| 1008831 | CTTCTCTATTTCTTTGTC | 1652 | 1669 | 83263 | 83280 | 3283 |
| 1008832 | ACTTCTCTATTTCTTTGT | 1653 | 1670 | 83264 | 83281 | 3284 |
| 1008833 | GTGGTGTGCGCATGTAGA | N/A | N/A | 9003 | 9020 | 3285 |
| 1008834 | GGTGGTGTGCGCATGTAG | N/A | N/A | 9004 | 9021 | 3286 |
| 1008835 | TGGTGGTGTGCGCATGTA | N/A | N/A | 9005 | 9022 | 3287 |
| 1008836 | TACTGTTTCGACCTCTGA | N/A | N/A | 45744 | 45761 | 3288 |
| 1008837 | TTACTGTTTCGACCTCTG | 891 | 908 | 45745 | 45762 | 3289 |
| 1008838 | GTTACTGTTTCGACCTCT | 892 | 909 | 45746 | 45763 | 3290 |

Example 12: Design of 4-10-6 MOE Gapmers with Mixed Internucleoside Linkages Complementary to Human ATXN2 RNA Modified oligonucleotides complementary to a human ATXN2 nucleic acid were designed. The modified oligonucleotides in the table below are 4-10-6 MOE gapmers. The gapmers are 20 nucleobases in length, wherein the central gap segment comprises eight 2'-deoxynucleosides and is flanked by wing segments on both the 5' end and on the 3' end comprising five 2'-MOE nucleosides. The sugar motif for the gapmers is (from 5' to 3'): eeeeddddddddd-deeeeee; wherein 'd' represents a 2'-deoxyribose sugar and 'e' represents a 2'-MOE modified sugar. The internucleoside linkages are mixed phosphodiester and phosphorothioate linkages. The internucleoside linkage motif for the gapmers is (from 5' to 3'): sooosssssssssssooss; wherein 'o' represents a phosphodiester internucleoside linkage and 's' represents a phosphorothioate internucleoside linkage. Each cytosine residue is a 5-methyl cytosine. "Start Site" indicates the 5'-most nucleoside to which the gapmer is complementary in the human nucleic acid sequence. "Stop Site" indicates the 3'-most nucleoside to which the gapmer is complementary in the human nucleic acid sequence.

Each modified oligonucleotide listed in the table below is complementary to human ATXN2 nucleic acid sequence SEQ ID NO: 1 or SEQ ID NO: 2, as indicated. 'N/A' indicates that the modified oligonucleotide is not complementary to that particular nucleic acid with 100% complementarity.

TABLE 69

4-10-6 MOE gapmers with mixed internucleoside linkages complementary to human ATXN2 RNA

| Compound Number | Sequence (5' to 3') | SEQ ID NO: 1 Start Site | SEQ ID NO: 1 Stop Site | SEQ ID NO: 2 Start Site | SEQ ID NO: 2 Stop Site | SEQ ID NO: |
|---|---|---|---|---|---|---|
| 1008839 | CTTAGAGTTTTTGCCTTCCA | N/A | N/A | 9931 | 9950 | 3087 |
| 1008840 | GCTTAGAGTTTTTGCCTTCC | N/A | N/A | 9932 | 9951 | 2177 |
| 1008841 | AGCTTAGAGTTTTTGCCTTC | N/A | N/A | 9933 | 9952 | 3164 |
| 1008842 | CGTATGTTTGTCTGTCTTAT | N/A | N/A | 33816 | 33835 | 2262 |
| 1008843 | TGTACTTCACATTTGGAGCC | 991 | 1010 | 48690 | 48709 | 1185 |
| 1008844 | ACTTTTCTCATGTGCGGCAT | 1079 | 1098 | 49253 | 49272 | 1561 |
| 1008846 | TCTGTACTTTCTCATGTGC | 1084 | 1103 | 49258 | 49277 | 2544 |
| 1008847 | TTCTCTATTTCTTTGTCCAG | 1649 | 1668 | 83260 | 83279 | 804 |
| 1008848 | ACACAGTTTCACTAGGTTCT | N/A | N/A | 57472 | 57491 | 2503 |
| 1008849 | TGGTGGTGTGCGCATGTAGA | N/A | N/A | 9003 | 9022 | 1800 |
| 1008850 | GTTACTGTTTCGACCTCTGA | N/A | N/A | 45744 | 45763 | 3291 |
| 1008851 | TGGATTCTGTACTTTTCTCA | 1089 | 1108 | 49263 | 49282 | 3235 |
| 1008853 | CTCTCCATTATTTCTTCACG | 1123 | 1142 | 49297 | 49316 | 33 |
| 1008855 | CCTATCATCATTTTCCAGGG | 1538 | 1557 | 81698 | 81717 | 158 |
| 1008856 | ACTTCTCTATTTCTTTGTCC | 1651 | 1670 | 83262 | 83281 | 172 |
| 1008857 | GTGATGTTTCATTGGGTTTA | 2460 | 2479 | 91730 | 91749 | 1188 |

Example 13: Tolerability of Modified Oligonucleotides Complementary to Human ATXN2 RNA in Wild-Type Mice, 3 Hour FOB Assessment Modified oligonucleotides described above were tested in wild-type mice to assess the tolerability of the oligonucleotides. Comparator oligonucleotides 564122, 564127, 564133, 564143, 564150, 564188, 564210, 564216, described hereinabove and in WO 2015/143246, were also tested. Wild type C57/B16 mice each received a single ICV dose of 700 µg of modified oligonucleotide listed in the table below. Each treatment group consisted of 4 mice. A group of 3 mice received PBS as a negative control for each experiment (identified in separate tables below). At 3 hours post-injection, mice were evaluated according to 7 different criteria. The criteria are (1) the mouse was bright, alert, and responsive; (2) the mouse was standing or hunched without stimuli; (3) the mouse showed any movement without stimuli; (4) the mouse demonstrated forward movement after it was lifted; (5) the mouse demonstrated any movement after it was lifted; (6) the mouse responded to tail pinching; (7) regular breathing. For each of the 7 criteria, a mouse was given a subscore of 0 if it met the criteria and 1 if it did not (the functional observational battery score or FOB). After all 7 criteria were evaluated, the scores were summed for each mouse and averaged within each treatment group. Results are presented as the average score for each treatment group in the tables below.

TABLE 70

Tolerability scores in wild-type mice

| Compound Number | 3 hr FOB |
|---|---|
| 564122 | 7.00 |
| 564127 | 7.00 |
| 564133 | 7.00 |
| 564143 | 7.00 |
| 564150 | 7.00 |
| 564188 | 7.00 |
| 564210 | 7.00 |
| 564216 | 7.00 |

TABLE 71

Tolerability scores in wild-type mice

| Compound Number | 3 hr FOB |
|---|---|
| 708151 | 0 |
| 757066 | 3.00 |
| 760782 | 6.00 |
| 708154 | 5.25 |
| 757052 | 5.50 |
| 755233 | 4.00 |
| 702063 | 5.75 |
| 755235 | 5.25 |
| 756978 | 3.75 |
| 757130 | 4.00 |
| 757162 | 6.00 |
| 757089 | 3.75 |
| 757210 | 6.25 |
| 760771 | 4.00 |

TABLE 71-continued

Tolerability scores in wild-type mice

| Compound Number | 3 hr FOB |
|---|---|
| 708199 | 6.75 |
| 757055 | 3.25 |
| 757234 | 6.00 |

TABLE 72

Tolerability scores in wild-type mice

| Compound Number | 3 hr FOB |
|---|---|
| 874211 | 2.00 |
| 874251 | 3.00 |
| 874216 | 5.00 |
| 874217 | 3.75 |
| 874280 | 4.50 |
| 874249 | 6.50 |
| 874282 | 4.50 |
| 874212 | 2.25 |
| 874279 | 6.25 |
| 874288 | 6.00 |
| 874281 | 4.50 |
| 874327 | 5.00 |
| 874388 | 1.00 |
| 874384 | 4.50 |
| 874246 | 0.25 |
| 874247 | 0 |
| 874250 | 6.75 |
| 874277 | 7.00 |
| 874283 | 7.00 |
| 874334 | 5.00 |
| 874335 | 6.25 |
| 874385 | 4.50 |

TABLE 73

Tolerability scores in wild-type mice

| Compound Number | 3 hr FOB |
|---|---|
| 874771 | 6.25 |
| 874754 | 0 |
| 874702 | 1.00 |
| 874745 | 2.50 |
| 874748 | 5.25 |
| 874752 | 3.00 |
| 874753 | 2.00 |
| 874501 | 0 |
| 874503 | 6.00 |
| 874669 | 0 |
| 874706 | 5.00 |
| 874738 | 5.25 |
| 874782 | 5.00 |

TABLE 74

Tolerability scores in wild-type mice

| Compound Number | 3 hr FOB |
|---|---|
| 874785 | 2.00 |
| 874842 | 6.25 |
| 875389 | 4.50 |
| 875148 | 3.00 |
| 874939 | 5.25 |
| 875032 | 3.25 |
| 875328 | 6.50 |
| 875319 | 2.25 |
| 875341 | 2.25 |
| 875252 | 0 |

TABLE 74-continued

Tolerability scores in wild-type mice

| Compound Number | 3 hr FOB |
|---|---|
| 874969 | 6.00 |
| 875346 | 1.00 |
| 875347 | 0 |
| 874792 | 2.75 |
| 875360 | 2.50 |
| 874874 | 7.00 |
| 874903 | 5.00 |
| 874937 | 0 |
| 875063 | 3.50 |
| 875315 | 5.50 |

TABLE 75

Tolerability scores in wild-type mice

| Compound Number | 3 hr FOB |
|---|---|
| 875485 | 3.50 |
| 875680 | 6.00 |
| 875650 | 3.75 |
| 875804 | 2.00 |
| 875764 | 4.00 |
| 875427 | 6.25 |
| 875966 | 0 |
| 875803 | 2.25 |
| 875477 | 4.00 |
| 875799 | 4.00 |
| 875807 | 3.00 |
| 875822 | 4.00 |
| 875398 | 6.50 |
| 875452 | 2.50 |

TABLE 76

Tolerability scores in wild-type mice

| Compound Number | 3 hr FOB |
|---|---|
| 937471 | 4.00 |
| 937481 | 3.00 |
| 937480 | 1.00 |
| 937508 | 4.00 |
| 937468 | 3.00 |
| 937467 | 1.00 |
| 937456 | 0.75 |
| 937509 | 2.00 |
| 937383 | 2.00 |
| 937385 | 3.50 |
| 937424 | 6.00 |
| 937422 | 6.50 |
| 937478 | 6.00 |
| 937423 | 6.25 |
| 937437 | 0.25 |
| 937477 | 6.00 |
| 937436 | 0 |
| 937421 | 5.50 |
| 937465 | 3.75 |
| 937469 | 2.50 |
| 937470 | 3.50 |
| 937365 | 0 |

TABLE 77

Tolerability scores in wild-type mice

| Compound Number | 3 hr FOB |
|---|---|
| 937680 | 4.00 |
| 937639 | 0 |

TABLE 77-continued

Tolerability scores in wild-type mice

| Compound Number | 3 hr FOB |
|---|---|
| 937794 | 3.00 |
| 937792 | 0 |
| 937547 | 0 |
| 937739 | 3.75 |
| 937633 | 2.00 |
| 937754 | 4.00 |
| 937620 | 3.00 |
| 937611 | 0 |
| 937725 | 0 |
| 937795 | 4.75 |
| 937579 | 1.00 |
| 937591 | 6.00 |
| 937510 | 0 |
| 937572 | 0 |
| 937511 | 1.00 |
| 937738 | 3.00 |
| 937593 | 3.75 |
| 937592 | 4.50 |
| 937748 | 4.50 |
| 937578 | 0 |
| 937618 | 0 |
| 937619 | 0 |

TABLE 78

Tolerability scores in wild-type mice

| Compound Number | 3 hr FOB |
|---|---|
| 937936 | 4.00 |
| 937939 | 4.00 |
| 937989 | 0 |
| 937938 | 6.00 |
| 937934 | 1.00 |
| 938163 | 0 |
| 937796 | 0 |
| 937987 | 3.00 |
| 938004 | 1.00 |
| 937991 | 0 |
| 938174 | 0 |
| 938173 | 0 |
| 938237 | 4.00 |
| 937983 | 0 |
| 937940 | 6.50 |
| 937942 | 5.00 |
| 937972 | 2.50 |
| 938170 | 0 |
| 938172 | 0 |
| 938221 | 0 |
| 937973 | 4.50 |
| 938043 | 1.00 |
| 938136 | 3.00 |
| 938210 | 2.00 |

TABLE 79

Tolerability scores in wild-type mice

| Compound Number | 3 hr FOB |
|---|---|
| 874430 | 4.50 |
| 874554 | 4.00 |
| 874639 | 4.00 |
| 874272 | 4.00 |
| 874952 | 4.00 |
| 875348 | 1.00 |
| 874548 | 4.00 |
| 875060 | 2.00 |
| 874627 | 2.00 |
| 874560 | 2.25 |
| 874506 | 1.75 |

TABLE 79-continued

Tolerability scores in wild-type mice

| Compound Number | 3 hr FOB |
|---|---|
| 874610 | 3.50 |
| 874541 | 4.00 |
| 874699 | 1.00 |
| 875880 | 6.00 |
| 875798 | 0 |
| 875445 | 5.50 |
| 875404 | 3.00 |
| 874415 | 3.25 |
| 875831 | 0 |
| 875914 | 5.25 |
| 875351 | 6.00 |
| 875879 | 3.50 |
| 874273 | 6.25 |
| 875458 | 6.50 |
| 875733 | 6.50 |
| 875991 | 6.00 |

TABLE 80

Tolerability scores in wild-type mice

| Compound Number | 3 hr FOB |
|---|---|
| 874218 | 1.00 |
| 756993 | 1.00 |
| 756994 | 1.00 |
| 708202 | 2.00 |
| 757072 | 1.00 |
| 757073 | 1.00 |
| 756996 | 1.00 |
| 757021 | 2.25 |
| 708201 | 3.00 |
| 756997 | 0 |
| 874213 | 1.00 |
| 757074 | 1.00 |
| 708203 | 2.50 |
| 708152 | 4.50 |
| 708153 | 4.50 |
| 756992 | 6.00 |
| 874215 | 5.00 |
| 708200 | 7.00 |
| 757075 | 4.50 |
| 756959 | 4.25 |
| 1008838 | 6.00 |

TABLE 81

Tolerability scores in wild-type mice

| Compound Number | 3 hr FOB |
|---|---|
| 874239 | 1.00 |
| 874252 | 1.00 |
| 874219 | 1.25 |
| 874237 | 1.00 |
| 874221 | 2.25 |
| 1008793 | 1.00 |
| 1008792 | 3.25 |
| 1008794 | 3.50 |
| 937364 | 6.25 |
| 1008795 | 5.50 |
| 1008796 | 5.50 |
| 1008797 | 3.25 |
| 874236 | 4.75 |
| 874238 | 3.75 |
| 875033 | 4.25 |
| 937472 | 5.00 |
| 937473 | 4.00 |

TABLE 81-continued

Tolerability scores in wild-type mice

| Compound Number | 3 hr FOB |
|---|---|
| 1008791 | 6.00 |
| 937361 | 5.00 |
| 874549 | 6.50 |

TABLE 82

Tolerability scores in wild-type mice

| Compound Number | 3 hr FOB |
|---|---|
| 1008806 | 2.50 |
| 1008800 | 0 |
| 1008811 | 0 |
| 1008817 | 2.00 |
| 1008810 | 1.00 |
| 1008803 | 2.50 |
| 1008805 | 1.00 |
| 1008804 | 0 |
| 1008802 | 0.50 |
| 1008799 | 1.25 |
| 1008798 | 4.75 |
| 1008801 | 3.50 |
| 1008807 | 5.25 |
| 1008808 | 3.75 |
| 1008809 | 3.50 |
| 1008813 | 7.00 |
| 1008812 | 6.00 |
| 1008814 | 6.50 |
| 1008815 | 6.00 |
| 1008816 | 4.00 |

TABLE 83

Tolerability scores in wild-type mice

| Compound Number | 3 hr FOB |
|---|---|
| 1008819 | 1.00 |
| 1008829 | 1.00 |
| 1008830 | 1.00 |
| 1008825 | 0 |
| 1008818 | 1.75 |
| 1008824 | 1.00 |
| 1008822 | 1.00 |
| 1008831 | 0 |
| 1008832 | 2.00 |
| 1008821 | 1.50 |
| 1008823 | 1.00 |
| 1008820 | 4.50 |
| 1008826 | 3.25 |
| 1008827 | 5.00 |
| 1008828 | 3.50 |
| 1008836 | 4.75 |
| 1008837 | 6.00 |
| 1008834 | 7.00 |
| 1008833 | 6.75 |
| 1008835 | 6.25 |

TABLE 84

Tolerability scores in wild-type mice

| Compound Number | 3 hr FOB |
|---|---|
| 1008854 | 1.00 |
| 1008845 | 1.75 |
| 1008852 | 2.00 |
| 1008853 | 3.00 |
| 1008844 | 2.50 |

TABLE 84-continued

Tolerability scores in wild-type mice

| Compound Number | 3 hr FOB |
|---|---|
| 1008851 | 3.50 |
| 1008856 | 0 |
| 1008855 | 1.75 |
| 1008786 | 5.50 |
| 1008790 | 6.50 |
| 1008846 | 0 |
| 1008843 | 1.00 |
| 937793 | 1.00 |
| 1008787 | 6.00 |
| 1008848 | 0 |
| 1008789 | 6.00 |
| 1008788 | 4.00 |
| 1008847 | 4.00 |
| 1008839 | 5.50 |
| 1008840 | 4.00 |
| 1008841 | 4.00 |
| 1008842 | 4.00 |
| 1008857 | 6.00 |
| 1008850 | 6.50 |
| 1008849 | 6.75 |

TABLE 85

Tolerability scores in wild-type mice

| Compound Number | 3 hr FOB |
|---|---|
| 1008870 | 1.00 |
| 1008862 | 2.50 |
| 1008874 | 1.25 |
| 1008865 | 1.00 |
| 1008872 | 2.00 |
| 1008871 | 1.00 |
| 1008875 | 1.25 |
| 1008867 | 1.00 |
| 1008863 | 6.50 |
| 1008864 | 5.50 |
| 1008873 | 5.50 |
| 1008866 | 4.00 |
| 1008858 | 4.50 |
| 1008859 | 5.00 |
| 1008860 | 5.00 |
| 1008861 | 6.75 |
| 1008877 | 6.00 |
| 1008876 | 4.00 |
| 1008869 | 5.00 |
| 1008868 | 7 |

TABLE 86

Tolerability scores in wild-type mice

| Compound Number | 3 hr FOB |
|---|---|
| 1008888 | 1.00 |
| 1008889 | 0.75 |
| 1008881 | 1.00 |
| 1008884 | 2.00 |
| 1008890 | 3.50 |
| 1008887 | 1.00 |
| 1008882 | 1.00 |
| 1008879 | 5.75 |
| 1008880 | 5.25 |
| 1008885 | 4.75 |
| 1008886 | 4.00 |
| 1008895 | 5.50 |
| 1008896 | 6.00 |
| 1008897 | 5.75 |
| 1008878 | 6.25 |
| 1008883 | 6.50 |
| 1008891 | 5.50 |

TABLE 86-continued

Tolerability scores in wild-type mice

| Compound Number | 3 hr FOB |
|---|---|
| 1008892 | 7.00 |
| 1008893 | 7.00 |
| 1008894 | 6.25 |

TABLE 87

Tolerability scores in wild-type mice

| Compound Number | 3 hr FOB |
|---|---|
| 1008910 | 0 |
| 1008899 | 1.00 |
| 1008901 | 0 |
| 1008908 | 3.00 |
| 1008911 | 1.00 |
| 1008902 | 0 |
| 1008915 | 2.00 |
| 1008900 | 0 |
| 1008909 | 3.00 |
| 1008905 | 3.00 |
| 1008916 | 4.00 |
| 1008917 | 4.00 |
| 1008898 | 3.50 |
| 1008903 | 4.00 |
| 1008912 | 4.75 |
| 1008913 | 4.00 |
| 1008914 | 4.75 |
| 1008904 | 4.00 |
| 1008906 | 4.50 |
| 1008907 | 6.25 |

Example 14: Tolerability of Modified Oligonucleotides Complementary to Human ATXN2 RNA in Wild-Type Rats, FOB Assessment Modified oligonucleotides described above were tested in Sprague Dawley rats to assess the tolerability of the oligonucleotides. Sprague Dawley rats each received a single intrathecal (IT) dose of 3 mg of oligonucleotide listed in the table below. Each treatment group consisted of 4 rats. A group of 4 rats received PBS as a negative control for each experiment (identified in separate tables below). At 3 hours post-injection, movement of 7 different parts of the body were evaluated for each rat. The 7 body parts are (1) the rat's tail; (2) the rat's posterior posture; (3) the rat's hind limbs; (4) the rat's hind paws; (5) the rat's forepaws; (6) the rat's anterior posture; (7) the rat's head. For each of the 7 different body parts, each rat was given a subscore of 0 if the body part was moving or 1 if the body part was not moving (the functional observational battery score or FOB). After all 7 criteria were evaluated, the scores were summed for each rat and averaged within each treatment group. The results are presented in the tables below.

TABLE 88

Tolerability scores in wild-type rats

| Compound Number | 3 hr FOB |
|---|---|
| 708151 | 2.00 |
| 708154 | 3.00 |
| 755235 | 3.00 |

TABLE 88-continued

Tolerability scores in wild-type rats

| Compound Number | 3 hr FOB |
|---|---|
| 756978 | 3.00 |
| 757130 | 3.75 |
| 757089 | 2.00 |

TABLE 89

Tolerability scores in wild-type rats

| Compound Number | 3 hr FOB |
|---|---|
| 874211 | 2.25 |
| 874251 | 3.50 |
| 874754 | 1.50 |
| 874745 | 3.00 |
| 874785 | 1.00 |
| 874212 | 2.75 |
| 875148 | 2.50 |
| 875032 | 2.00 |
| 874753 | 3.50 |
| 875319 | 2.25 |
| 875341 | 1.00 |
| 875252 | 1.00 |
| 875485 | 1.75 |
| 874388 | 1.75 |
| 875346 | 1.25 |
| 875347 | 1.00 |
| 874792 | 2.00 |
| 875360 | 3.25 |
| 875477 | 4.00 |

TABLE 90

Tolerability scores in wild-type rats

| Compound Number | 3 hr FOB |
|---|---|
| 875650 | 4.00 |
| 875804 | 1.75 |
| 875764 | 2.00 |
| 875966 | 0.25 |
| 875803 | 1.50 |
| 875799 | 4.00 |
| 875807 | 1.50 |
| 875822 | 3.75 |

TABLE 91

Tolerability scores in wild-type rats

| Compound Number | 3 hr FOB |
|---|---|
| 937481 | 3.00 |
| 937480 | 1.25 |
| 937508 | 5.25 |
| 937468 | 2.50 |
| 937467 | 3.00 |
| 937456 | 2.50 |
| 937383 | 1.00 |
| 937385 | 2.75 |
| 937437 | 1.25 |
| 937436 | 2.25 |

TABLE 92

Tolerability scores in wild-type rats

| Compound Number | 3 hr FOB |
|---|---|
| 937680 | 4.25 |
| 937639 | 1.00 |
| 937547 | 0 |
| 937739 | 3.00 |
| 937633 | 3.00 |
| 937611 | 1.00 |
| 937725 | 0.75 |
| 937579 | 2.00 |
| 937510 | 0 |
| 937572 | 0.50 |
| 937511 | 0.75 |
| 937738 | 4.25 |
| 937593 | 2.00 |
| 937592 | 4.00 |
| 937748* | 3.67 |
| 937578 | 1.75 |
| 937618 | 0.50 |
| 937619 | 1.75 |

*This treatment group included 3 rats

TABLE 93

Tolerability scores in wild-type rats

| Compound Number | 3 hr FOB |
|---|---|
| 874218 | 2.00 |
| 756993 | 2.75 |
| 756994 | 2.75 |
| 874239 | 1.75 |
| 708202 | 2.75 |
| 757072 | 1.50 |
| 757073 | 2.50 |
| 874252 | 1.75 |
| 756996 | 0.75 |
| 757021 | 4.25 |
| 874219 | 3.00 |
| 708201 | 3.75 |
| 874237 | 2.25 |
| 756997 | 0..05 |
| 874213 | 1.00 |
| 874221 | 3.00 |
| 757074 | 1.50 |
| 708203 | 3.00 |

TABLE 94

Tolerability scores in wild-type rats

| Compound Number | 3 hr FOB |
|---|---|
| 1008806 | 1.50 |
| 1008800 | 0 |
| 1008819 | 2.00 |
| 1008829 | 1.50 |
| 1008811 | 0 |
| 1008830 | 0.25 |
| 1008825 | 0 |
| 1008817 | 0.75 |
| 1008810 | 0 |
| 1008818 | 2.00 |

TABLE 95

Tolerability scores in wild-type rats

| Compound Number | 3 hr FOB |
|---|---|
| 1008862 | 0.75 |
| 1008854 | 2.25 |
| 1008845 | 2.00 |
| 1008852 | 3.00 |
| 1008853 | 1.75 |
| 1008844 | 1.50 |
| 1008851 | 3.00 |
| 1008856 | 0.50 |
| 1008855 | 1.00 |
| 1008846 | 1.00 |
| 1008843 | 2.50 |
| 937793 | 1.00 |
| 1008848 | 1.25 |

TABLE 96

Tolerability scores in wild-type rats

| Compound Number | 3 hr FOB |
|---|---|
| 1008870 | 1.25 |
| 1008874 | 3.00 |
| 1008865 | 1.50 |
| 1008888 | 1.00 |
| 1008889 | 1.00 |
| 1008872 | 2.50 |
| 1008871 | 1.00 |
| 1008875 | 1.75 |
| 1008881 | 2.25 |
| 1008884 | 3.00 |
| 1008887 | 1.25 |
| 1008882 | 2.75 |
| 1008867 | 2.50 |

TABLE 97

Tolerability scores in wild-type rats

| Compound Number | 3 hr FOB |
|---|---|
| 1008910 | 2.25 |
| 1008899 | 2.50 |
| 1008901 | 2.00 |
| 1008908 | 2.00 |
| 1008911 | 2.75 |
| 1008902 | 2.75 |
| 1008890 | 3.25 |
| 1008915 | 2.25 |
| 1008900 | 2.00 |
| 1008909 | 3.00 |
| 1008905 | 3.25 |

Example 15: Activity of Modified Oligonucleotides Complementary to Human ATXN2 RNA in Transgenic Mice Modified oligonucleotides described above were tested in the BAC-ATXN2-Q22 transgenic mouse model which was generated by using a 169 kb human BAC (bacterial artificial chromosome), RP11-798L5, that contained the entire 150 kb human ATXN2 locus with 22 CAG repeats in the coding sequence, 16 kb of the 5' flanking genomic sequence, and 3 kb of the 3' flanking genomic sequence (Dansithong et al., PLoS Genetics, 2015).

The hATXN2 mice were divided into groups of 3-4 mice each. Two groups were tested with each compound. hATXN2 mice each received a single intracerebroventricular (ICV) dose of 350 μg of modified oligonucleotide. The PBS-injected group served as the control group to which oligonucleotide-treated groups were compared. After two weeks, mice were sacrificed and RNA was extracted from cortical brain tissue and spinal cord for real-time PCR analysis of measurement of RNA expression of human ATXN2 using primer probe set hAtaxin_LTS01321, described in Example 1 above. Results are presented as percent ATXN2 RNA expression relative to PBS control, normalized to GADPH. As shown in the table below, treatment with modified oligonucleotides resulted in significant of ATXN2 RNA in comparison to the PBS control.

TABLE 98

Reduction of human ATXN2 RNA in transgenic mice

| Compound Number | ATXN2 Expression (% control) | |
|---|---|---|
| | Spinal Cord | Cortex |
| 702063 | 17 | 34 |
| 708151 | 19 | 33 |
| 755233 | 16 | 31 |
| 755235 | 8 | 25 |
| 760771 | 85 | 87 |
| 760782 | 13 | 22 |

TABLE 99

Reduction of human ATXN2 RNA in transgenic mice

| Compound Number | ATXN2 Expression (% control) | |
|---|---|---|
| | Spinal Cord | Cortex |
| 708154 | 14 | 14 |
| 756978 | 35 | 46 |
| 757052 | 15 | 19 |
| 757066 | 16 | 15 |
| 757089 | 38 | 61 |
| 757130 | 42 | 53 |
| 757162 | 57 | 60 |
| 757210 | 66 | 75 |
| 874211 | 23 | 37 |
| 874212 | 49 | 52 |
| 874251 | 20 | 19 |
| 874388 | 71 | 75 |
| 874745 | 41 | 43 |
| 874753 | 54 | 60 |
| 874754 | 42 | 38 |
| 874785 | 49 | 48 |
| 874792 | 75 | 84 |
| 875032 | 58 | 58 |
| 875148 | 57 | 53 |
| 875252 | 61 | 67 |
| 875319 | 58 | 63 |

TABLE 100

Reduction of human ATXN2 RNA in transgenic mice

| Compound Number | ATXN2 Expression (% control) | |
|---|---|---|
| | Spinal Cord | Cortex |
| 874217 | 19 | 29 |
| 874279 | 53 | 52 |
| 874280 | 34 | 34 |
| 874281 | 68 | 62 |
| 874282 | 55 | 50 |
| 874702 | 46 | 41 |
| 874752 | 65 | 53 |
| 875341 | 66 | 67 |
| 875346 | 86 | 79 |
| 875347 | 74 | 81 |
| 875360 | 88 | 90 |
| 875477 | 89 | 94 |
| 875485 | 66 | 74 |
| 875650 | 77 | 76 |
| 875764 | 83 | 78 |
| 875799 | 100 | 100 |
| 875803 | 84 | 87 |
| 875804 | 88 | 78 |
| 875807 | 102 | 107 |
| 875822 | 109 | 108 |
| 875966 | 77 | 80 |

TABLE 101

Reduction of human ATXN2 RNA in transgenic mice

| Compound Number | ATXN2 Expression (% control) | |
|---|---|---|
| | Spinal Cord | Cortex |
| 874216 | 16 | 28 |
| 874249 | 30 | 40 |
| 874272 | 50 | 51 |
| 874288 | 48 | 57 |
| 874327 | 65 | 69 |
| 874384 | 71 | 78 |
| 874415 | 84 | 99 |
| 874430 | 19 | 35 |
| 874506 | 49 | 63 |
| 874541 | 48 | 75 |
| 874548 | 42 | 58 |
| 874554 | 32 | 36 |
| 874560 | 45 | 62 |
| 874610 | 58 | 65 |
| 874627 | 50 | 60 |
| 874639 | 39 | 39 |
| 874699 | 63 | 79 |
| 874748 | 42 | 44 |
| 874771 | 31 | 33 |
| 874842 | 45 | 50 |
| 874939 | 54 | 56 |
| 874952 | 56 | 54 |
| 874969 | 60 | 69 |
| 875060 | 60 | 59 |
| 875328 | 54 | 58 |
| 875348 | 54 | 58 |
| 875389 | 60 | 52 |
| 875427 | 70 | 78 |
| 875680 | 65 | 75 |

TABLE 102

Reduction of human ATXN2 RNA in transgenic mice

| Compound Number | ATXN2 Expression (% control) | |
|---|---|---|
| | Spinal Cord | Cortex |
| 875351 | 93 | 110 |
| 875404 | 86 | 97 |
| 875445 | 87 | 95 |
| 875798 | 73 | 90 |
| 875831 | 87 | 101 |
| 875879 | 95 | 111 |
| 875880 | 75 | 90 |
| 875914 | 94 | 104 |
| 937383 | 64 | 81 |
| 937385 | 72 | 82 |
| 937422 | 59 | 83 |
| 937423 | 67 | 92 |
| 937424 | 69 | 83 |
| 937436 | 74 | 105 |
| 937437 | 71 | 92 |
| 937456 | 58 | 77 |
| 937467 | 53 | 77 |
| 937468 | 47 | 76 |
| 937471 | 40 | 43 |
| 937477 | 75 | 97 |
| 937478 | 65 | 92 |
| 937480 | 48 | 64 |
| 937481 | 49 | 57 |
| 937508 | 56 | 66 |
| 937509 | 71 | 81 |
| 937510 | 56 | 63 |
| 937511 | 52 | 72 |
| 937547 | 44 | 47 |
| 937572 | 51 | 70 |
| 937578 | 69 | 99 |
| 937579 | 41 | 60 |
| 937591 | 58 | 63 |
| 937592 | 64 | 83 |

TABLE 103

Reduction of human ATXN2 RNA in transgenic mice

| Compound Number | ATXN2 Expression (% control) | |
|---|---|---|
| | Spinal Cord | Cortex |
| 937593 | 57 | 74 |
| 937611 | 50 | 57 |
| 937620 | 56 | 55 |
| 937633 | 50 | 54 |
| 937639 | 41 | 44 |
| 937680 | 43 | 42 |
| 937725 | 53 | 57 |
| 937738 | 65 | 73 |
| 937739 | 60 | 53 |
| 937748 | 75 | 89 |
| 937754 | 41 | 54 |
| 937792 | 37 | 46 |

TABLE 103-continued

Reduction of human ATXN2 RNA in transgenic mice

| Compound Number | ATXN2 Expression (% control) | |
|---|---|---|
| | Spinal Cord | Cortex |
| 937794 | 45 | 45 |
| 937795 | 53 | 58 |
| 937796 | 64 | 76 |
| 937934 | 68 | 72 |
| 937936 | 51 | 52 |
| 937938 | 56 | 65 |
| 937939 | 50 | 61 |
| 937940 | 69 | 86 |
| 937942 | 68 | 87 |
| 937972 | 71 | 87 |
| 937973 | 74 | 93 |
| 937983 | 61 | 84 |
| 937987 | 62 | 76 |
| 937989 | 47 | 63 |
| 937991 | 62 | 78 |
| 938004 | 61 | 77 |
| 938043 | 77 | 94 |
| 938136 | 80 | 98 |
| 938163 | 59 | 73 |
| 938170 | 77 | 88 |
| 938172 | 78 | 89 |
| 938173 | 67 | 81 |
| 938174 | 67 | 79 |
| 938210 | 94 | 110 |
| 938221 | 78 | 92 |
| 938237 | 72 | 83 |

TABLE 104

Reduction of human ATXN2 RNA in transgenic mice

| Compound Number | ATXN2 Expression (% control) | |
|---|---|---|
| | Spinal Cord | Cortex |
| 1008786 | 36 | 28 |
| 1008787 | 56 | 53 |
| 1008788 | 71 | 66 |
| 1008789 | 62 | 58 |
| 1008790 | 43 | 39 |
| 1008799 | 49 | 54 |
| 1008802 | 50 | 51 |
| 1008803 | 50 | 39 |

TABLE 104-continued

Reduction of human ATXN2 RNA in transgenic mice

| Compound Number | ATXN2 Expression (% control) | |
|---|---|---|
| | Spinal Cord | Cortex |
| 1008804 | 51 | 49 |
| 1008805 | 46 | 42 |
| 1008810 | 35 | 32 |
| 1008811 | 32 | 25 |
| 1008817 | 33 | 31 |
| 1008818 | 27 | 33 |
| 1008819 | 9 | 9 |
| 1008821 | 48 | 48 |
| 1008822 | 56 | 40 |
| 1008823 | 65 | 60 |
| 1008824 | 41 | 40 |
| 1008825 | 34 | 30 |
| 1008829 | 35 | 24 |
| 1008830 | 26 | 26 |
| 1008831 | 48 | 46 |
| 1008832 | 40 | 46 |
| 1008800 | 22 | 25 |
| 1008806 | 18 | 26 |

TABLE 105

Reduction of human ATXN2 RNA in transgenic mice

| Compound Number | ATXN2 Expression (% control) | |
|---|---|---|
| | Spinal Cord | Cortex |
| 708201 | 27 | 30 |
| 708202 | 23 | 44 |
| 708203 | 46 | 57 |
| 756994 | 12 | 16 |
| 756996 | 14 | 13 |
| 756997 | 29 | 40 |
| 757021 | 15 | 28 |
| 757072 | 24 | 36 |
| 757073 | 14 | 19 |
| 757074 | 45 | 49 |
| 874213 | 33 | 42 |
| 874219 | 21 | 20 |
| 874221 | 44 | 47 |
| 874237 | 34 | 31 |
| 874239 | 23 | 23 |
| 874252 | 23 | 14 |
| 1008793 | 64 | 69 |
| 756993 | 15 | 23 |
| 874218 | 8 | 10 |

TABLE 106

Reduction of human ATXN2 RNA in transgenic mice

| Compound Number | ATXN2 Expression (% control) | |
|---|---|---|
| | Spinal Cord | Cortex |
| 937793 | 46 | 52 |
| 1008843 | 44 | 48 |
| 1008844 | 20 | 28 |
| 1008845 | 12 | 20 |
| 1008846 | 36 | 47 |
| 1008848 | 54 | 54 |
| 1008851 | 25 | 23 |
| 1008852 | 10 | 11 |
| 1008853 | 12 | 13 |
| 1008855 | 26 | 23 |
| 1008856 | 26 | 16 |
| 1008867 | 58 | 55 |
| 1008871 | 5 | 7 |
| 1008872 | 11 | 6 |
| 1008875 | 15 | 11 |
| 1008854 | 23 | 24 |
| 1008862 | 14 | 15 |
| 1008865 | 11 | 11 |
| 1008870 | 7 | 10 |
| 1008874 | 13 | 10 |

TABLE 107

Reduction of human ATXN2 RNA in transgenic mice

| Compound Number | ATXN2 Expression (% control) | |
|---|---|---|
| | Spinal Cord | Cortex |
| 1008881 | 17 | 20 |
| 1008882 | 39 | 46 |
| 1008884 | 8 | 11 |
| 1008887 | 44 | 36 |
| 1008890 | 13 | 14 |
| 1008899 | 13 | 18 |
| 1008900 | 30 | 46 |
| 1008901 | 12 | 31 |
| 1008902 | 23 | 31 |
| 1008905 | 69 | 72 |
| 1008908 | 24 | 27 |
| 1008909 | 27 | 50 |
| 1008911 | 21 | 24 |
| 1008915 | 40 | 42 |
| 1008888 | 18 | 14 |
| 1008889 | 10 | 12 |
| 1008910 | 23 | 23 |

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11078486B2). An electronic copy of the "Sequence Listing" will also be available from the USPTO upon request and payment of the fee set forth in 37 CFR 1.19(b)(3).

The invention claimed is:
1. A modified oligonucleotide according to the following formula:
(SEQ ID NO: 3235)
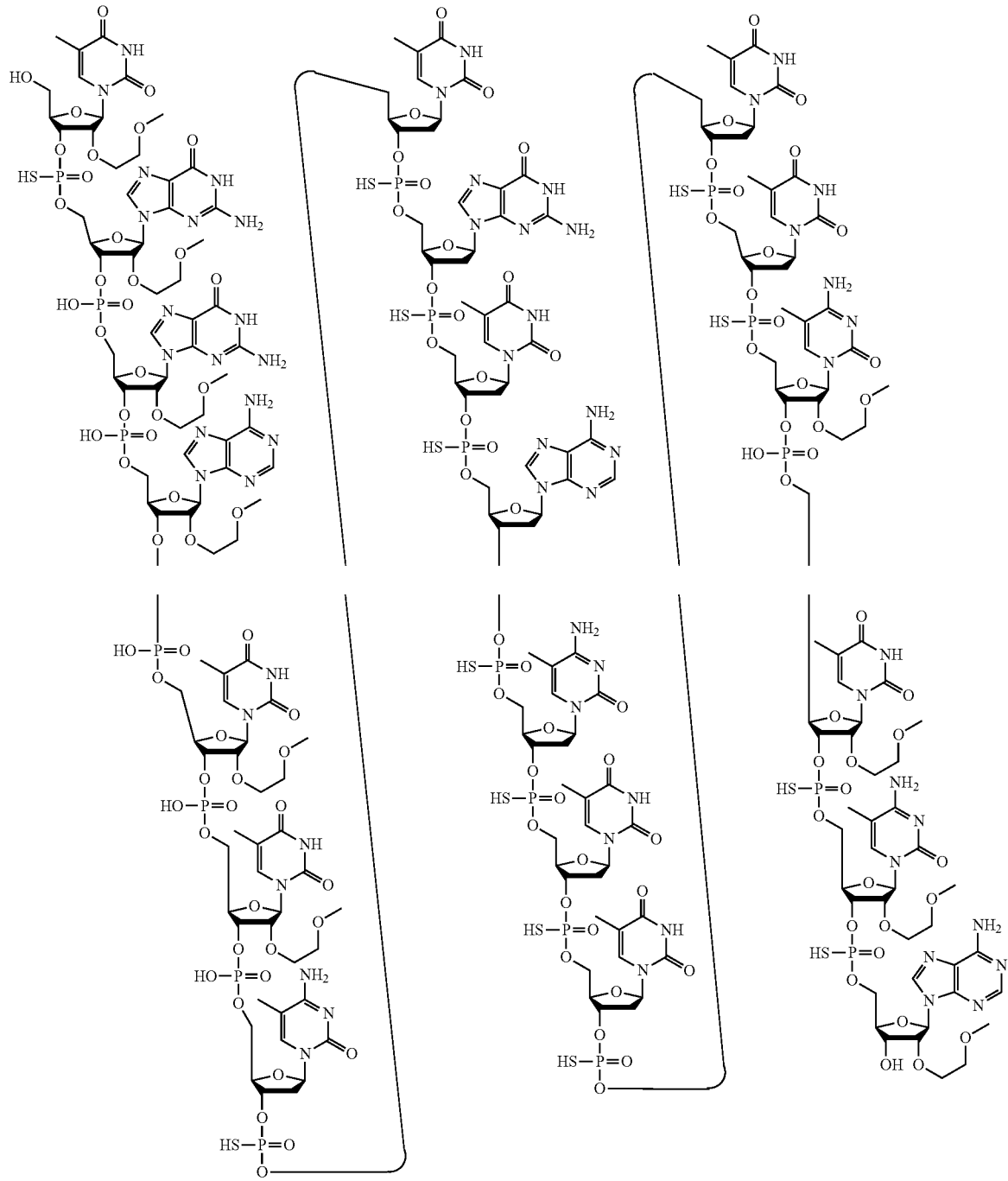
or a salt thereof.
2. The modified oligonucleotide of claim 1, which is a sodium salt or a potassium salt of the formula.
3. A modified oligonucleotide according to the following formula:

SEQ ID NO: 3235

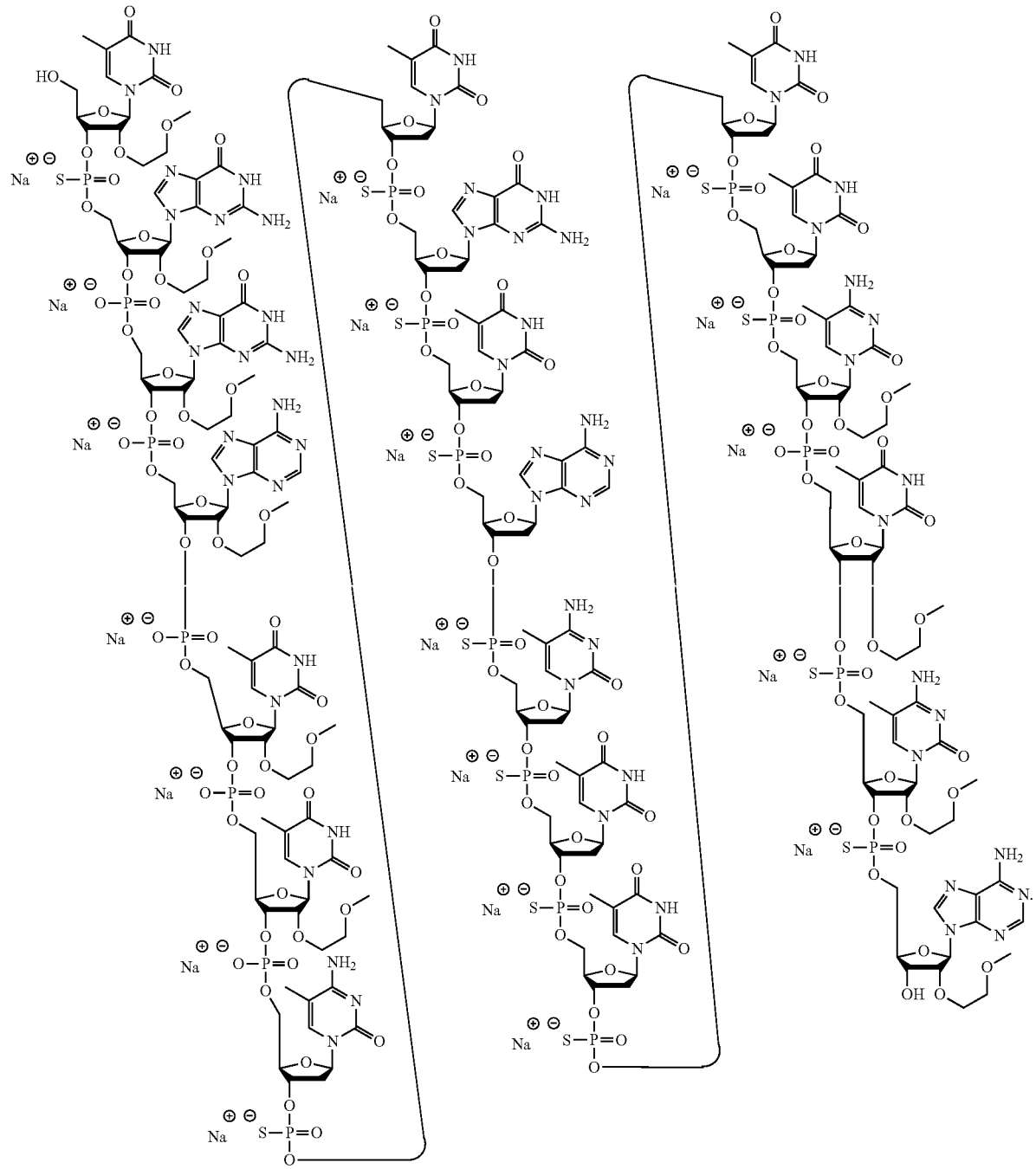

4. A chirally enriched population of modified oligonucleotides of claim 1, wherein the population is enriched for modified oligonucleotides comprising at least one particular phosphorothioate internucleoside linkage having a particular stereochemical configuration.

5. The chirally enriched population of claim 4, wherein the population is enriched for modified oligonucleotides comprising at least one particular phosphorothioate internucleoside linkage having the (Sp) configuration.

6. The chirally enriched population of claim 4, wherein the population is enriched for modified oligonucleotides comprising at least one particular phosphorothioate internucleoside linkage having the (Rp) configuration.

7. The chirally enriched population of claim 4, wherein the population is enriched for modified oligonucleotides having a particular, independently selected stereochemical configuration at each phosphorothioate internucleoside linkage.

8. The chirally enriched population of claim 7, wherein the population is enriched for modified oligonucleotides having the (Sp) configuration at each phosphorothioate internucleoside linkage.

9. The chirally enriched population of claim 7, wherein the population is enriched for modified oligonucleotides having the (Rp) configuration at each phosphorothioate internucleoside linkage.

10. The chirally enriched population of claim 4, wherein the population is enriched for modified oligonucleotides having at least 3 contiguous phosphorothioate internucleoside linkages in the Sp-Sp-Rp configuration, in the 5' to 3' direction.

11. A population of modified oligonucleotides of claim 1, wherein all of the phosphorothioate internucleoside linkages of the modified oligonucleotide are stereorandom.

12. A pharmaceutical composition comprising the modified oligonucleotide of claim 1, and a pharmaceutically acceptable diluent or carrier.

13. The pharmaceutical composition of claim 12, comprising a pharmaceutically acceptable diluent, wherein the pharmaceutically acceptable diluent is phosphate-buffered saline (PBS) or artificial cerebrospinal fluid (aCSF).

14. The pharmaceutical composition of claim 12, wherein the pharmaceutical composition consists essentially of the modified oligonucleotide and phosphate-buffered saline (PBS) or artificial cerebrospinal fluid (aCSF).

15. An oligomeric compound comprising a modified oligonucleotide according to the following formula:

$T_{es}G_{eo}G_{eo}A_{eo}T_{eo}T_{eo}{}^mC_{ds}T_{ds}G_{ds}T_{ds}A_{ds}{}^mC_{ds}T_{ds}T_{ds}T_{ds}T_{ds}{}^mC_{eo}T_{es}{}^mC_{es}A_e$ (SEQ ID NO: 3235);

wherein,
A=an adenine nucleobase,
$^mC$=a 5'-methyl cytosine nucleobase,
G=a guanine nucleobase,
T=a thymine nucleobase,
e=a 2'-MOE modified sugar,
d=a 2'-deoxyribose sugar,
s=a phosphorothioate internucleoside linkage, and
o=a phosphodiester internucleoside linkage.

16. A pharmaceutical composition comprising the chirally enriched population of modified oligonucleotides of claim 4, and a pharmaceutically acceptable diluent or carrier.

17. The oligomeric compound of claim 15, wherein the modified oligonucleotide is covalently linked to a conjugate group.

18. An oligomeric duplex comprising the modified oligonucleotide of claim 1.

19. An oligomeric duplex comprising the oligomeric compound of claim 15.

20. A pharmaceutical composition comprising the oligomeric compound of claim 15 and a pharmaceutically acceptable carrier or diluent.

21. The pharmaceutical composition of claim 20, comprising a pharmaceutically acceptable diluent, wherein the pharmaceutically acceptable diluent is phosphate-buffered saline (PBS) or artificial cerebrospinal fluid (aCSF).

22. The pharmaceutical composition of claim 20, wherein the pharmaceutical composition consists essentially of the oligomeric compound and phosphate-buffered saline (PBS) or artificial cerebrospinal fluid (aCSF).

23. A pharmaceutical composition comprising the oligomeric compound of claim 17 and a pharmaceutically acceptable carrier or diluent.

24. The pharmaceutical composition of claim 23, comprising a pharmaceutically acceptable diluent, wherein the pharmaceutically acceptable diluent is phosphate-buffered saline (PBS) or artificial cerebrospinal fluid (aCSF).

25. The pharmaceutical composition of claim 23, wherein the pharmaceutical composition consists essentially of the oligomeric compound and phosphate-buffered saline (PBS) or artificial cerebrospinal fluid (aCSF).

26. The chirally enriched population of claim 7, wherein the population is enriched for modified oligonucleotides having the (Rp) configuration at one particular phosphorothioate internucleoside linkage and the (Sp) configuration at each of the remaining phosphorothioate internucleoside linkages.

27. The modified oligonucleotide of claim 1, which is a potassium salt of the formula.

28. A pharmaceutical composition comprising the modified oligonucleotide of claim 3 and a pharmaceutically acceptable carrier or diluent.

29. The pharmaceutical composition of claim 28, comprising a pharmaceutically acceptable diluent, wherein the pharmaceutically acceptable diluent is phosphate-buffered saline (PBS) or artificial cerebrospinal fluid (aCSF).

30. The pharmaceutical composition of claim 28, wherein the pharmaceutical composition consists essentially of the modified oligonucleotide and phosphate-buffered saline (PBC) or artificial cerebrospinal fluid (aCSF).

31. A pharmaceutical composition comprising the modified oligonucleotide of claim 27 and a pharmaceutically acceptable carrier or diluent.

32. The pharmaceutical composition of claim 31, comprising a pharmaceutically acceptable diluent, wherein the pharmaceutically acceptable diluent is phosphate-buffered saline (PBS) or artificial cerebrospinal fluid (aCSF).

33. The pharmaceutical composition of claim 31, wherein the pharmaceutical composition consists essentially of the oligomeric compound and phosphate-buffered saline (PBS) or artificial cerebrospinal fluid (aCSF).

34. A pharmaceutical composition comprising the oligomeric duplex of claim 18 and a pharmaceutically acceptable carrier or diluent.

35. The pharmaceutical composition of claim 34, comprising a pharmaceutically acceptable diluent, wherein the pharmaceutically acceptable diluent is phosphate-buffered saline (PBS) or artificial cerebrospinal fluid (aCSF).

36. The pharmaceutical composition of claim 34, wherein the pharmaceutical composition consists essentially of the oligomeric duplex and phosphate-buffered saline (PBS) or artificial cerebrospinal fluid (aCSF).

* * * * *

UNITED STATES PATENT AND TRADEMARK OFFICE
CERTIFICATE OF CORRECTION

PATENT NO. : 11,078,486 B2
APPLICATION NO. : 16/522133
DATED : August 3, 2021
INVENTOR(S) : Susan M. Freier et al.

It is certified that error appears in the above-identified patent and that said Letters Patent is hereby corrected as shown below:

In the Specification

Column 38, Line 21, should read: -- mC=a 5-methyl cytosine nucleobase, --

Column 38, Line 37, should read: -- mC=a 5-methyl cytosine nucleobase, --

Column 38, Line 52, should read: -- mC=a 5-methyl cytosine nucleobase, --

Column 38, Line 67, should read: -- mC=a 5-methyl cytosine nucleobase, --

Column 39, Line 15, should read: -- mC=a 5-methyl cytosine nucleobase, --

Column 39, Line 30, should read: -- mC=a 5-methyl cytosine nucleobase, --

Signed and Sealed this
Twenty-eighth Day of December, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 11,078,486 B2

Page 2 of 3

In the Claims

Claim 1, Columns 335-336, the structure should read as follows:

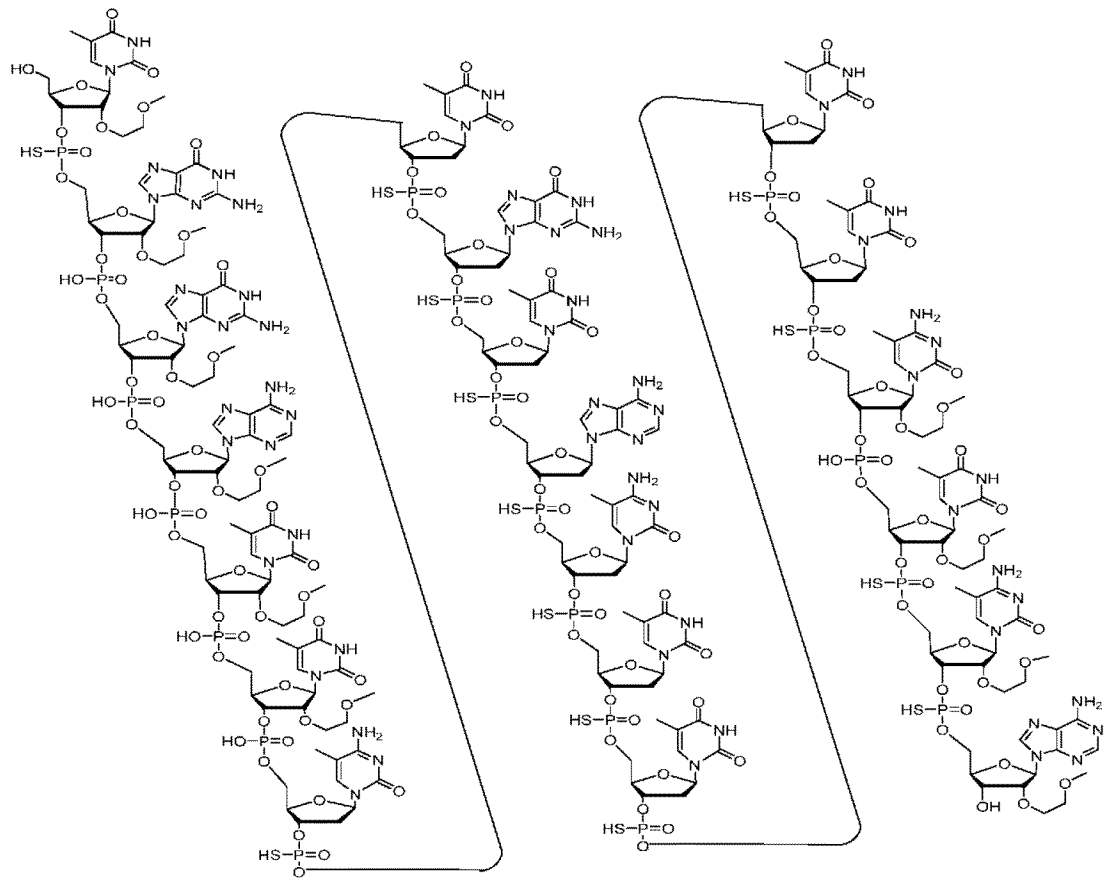

--                                                                                   --

Claim 3, Columns 337-338, the structure should read as follows:
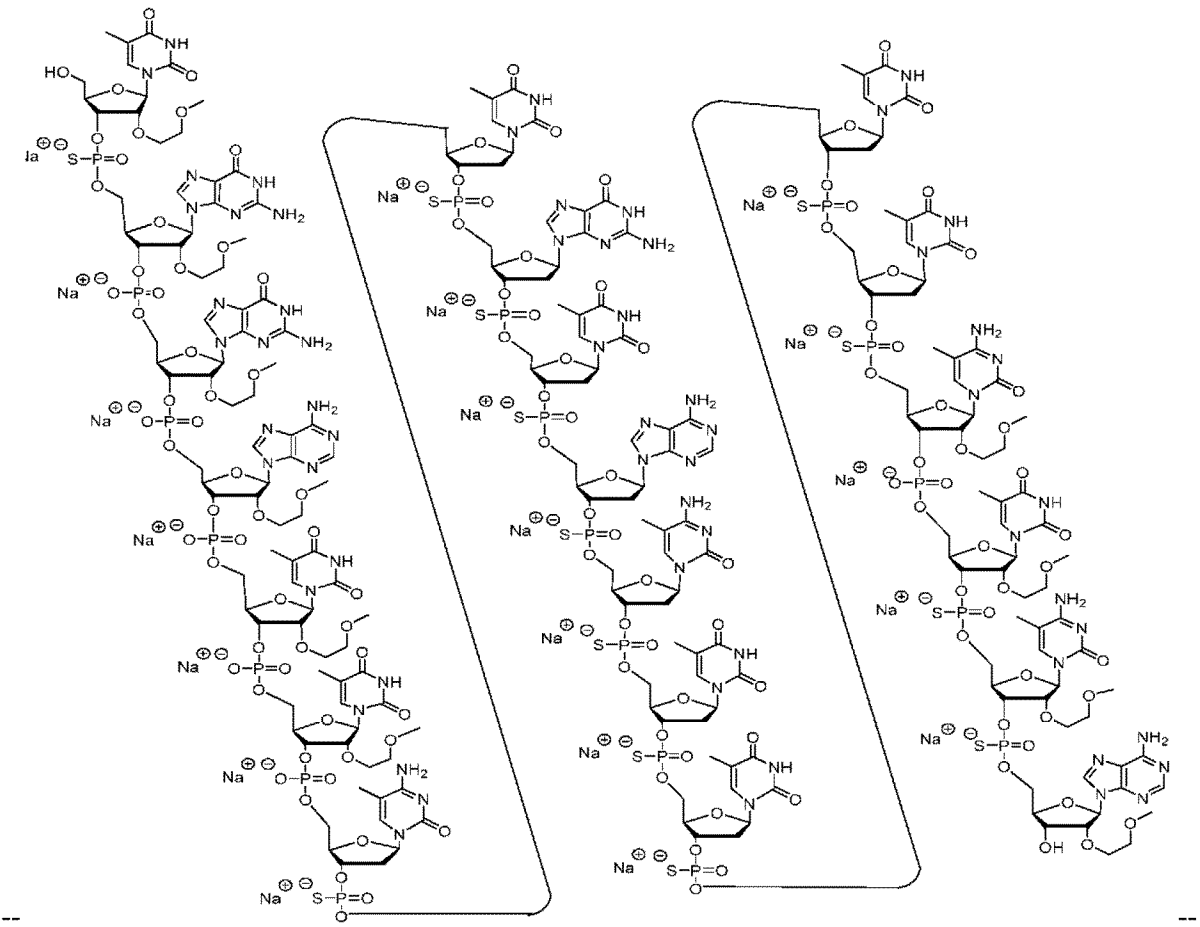
--
Claim 15, Column 339, Lines 26-27, should read:
-- $T_{es}G_{eo}G_{eo}A_{eo}T_{eo}T_{e}o^{m}C_{ds}T_{ds}G_{ds}T_{ds}A_{ds}{}^{m}C_{ds}T_{ds}T_{ds}T_{ds}T_{ds}{}^{m}C_{eo}T_{es}{}^{m}C_{es}A_{e}$ (SEQ ID NO: 3235); --
Claim 15, Column 339, Line 30, should read: -- mC=a 5-methyl cytosine nucleobase, --
Claim 30, Column 340, Line 32, should read: -- (PBS) or artificial cerebrospinal fluid (aCSF). --